US012577247B2

(12) United States Patent
Peer Mohamed et al.

(10) Patent No.: US 12,577,247 B2
(45) Date of Patent: Mar. 17, 2026

(54) DIAMINOPYRAZOLO[1,5-A]PYRIMIDINE-6-CARBONITRILE COMPOUNDS AS ADENOSINE 2A RECEPTOR AND ADENOSINE 2B RECEPTOR ANTAGONIST

(71) Applicant: BUGWORKS RESEARCH, INC., Wilmington, DE (US)

(72) Inventors: Shahul Hameed Peer Mohamed, Bengaluru (IN); Nagakumar Bharatham, Bengaluru (IN); Ranga Rao Kajipalya Ranganatha Rao, Bengaluru (IN); Radha Nandishaiah, Bengaluru (IN); Nainesh Katagihalli Math, Bengaluru (IN); Harish Kaushik Kotakonda, Bengaluru (IN); Sambasiva Reddy, Bengaluru (IN)

(73) Assignee: BUGWORKS RESEARCH, INC., Wilmington, DE (US)

( * ) Notice: Subject to any disclaimer, the term of this patent is extended or adjusted under 35 U.S.C. 154(b) by 537 days.

(21) Appl. No.: 17/921,023

(22) PCT Filed: Jan. 7, 2022

(86) PCT No.: PCT/IN2022/050018
§ 371 (c)(1),
(2) Date: Oct. 24, 2022

(87) PCT Pub. No.: WO2022/149167
PCT Pub. Date: Jul. 14, 2022

(65) Prior Publication Data

US 2023/0167119 A1 Jun. 1, 2023

(30) Foreign Application Priority Data

Jan. 9, 2021 (IN) ............................ 202141001078
Jun. 9, 2021 (IN) ............................ 202141025756

(51) Int. Cl.
*C07D 487/04* (2006.01)
*A61K 45/06* (2006.01)
*A61P 35/00* (2006.01)

(52) U.S. Cl.
CPC ............ *C07D 487/04* (2013.01); *A61K 45/06* (2013.01); *A61P 35/00* (2018.01)

(58) Field of Classification Search
CPC ........ A61P 35/00; A61K 45/06; C07D 487/04
See application file for complete search history.

(56) References Cited

U.S. PATENT DOCUMENTS

| | | | |
|---|---|---|---|
| 4,977,144 A | 12/1990 | Fujimoto et al. | |
| 6,355,653 B1 | 3/2002 | Trottmann et al. | |
| 8,591,943 B2 * | 11/2013 | Deng | A61P 35/02 514/249 |
| 2005/0090513 A1 | 4/2005 | Castelhano et al. | |
| 2018/0162874 A1 | 6/2018 | Morriello et al. | |
| 2020/0369665 A1 | 11/2020 | Bobowska (Née Witkowska) et al. | |

FOREIGN PATENT DOCUMENTS

| | | | | |
|---|---|---|---|---|
| CN | 1379777 A | 11/2002 | | |
| CN | 110809577 A | 2/2020 | | |
| EP | 0354180 A2 | 2/1990 | | |
| JP | H0269496 A | 3/1990 | | |
| JP | 2003528811 A | 9/2003 | | |
| JP | 2006160628 A | 6/2006 | | |
| WO | WO 0117999 A2 | 3/2001 | | |
| WO | WO 2004110454 A1 | 12/2004 | | |
| WO | WO-2010118207 A1 * | 10/2010 | A61P 35/02 | |
| WO | WO 2011006074 A1 | 1/2011 | | |
| WO | WO-2011068667 A1 * | 6/2011 | A61P 9/14 | |
| WO | 2020227156 A1 | 11/2020 | | |

OTHER PUBLICATIONS

Muller, Christa E., and Kenneth A. Jacobson. "Recent developments in adenosine receptor ligands and their potential as novel drugs." Biochimica et Biophysica Acta (BBA)-Biomembranes 1808, No. 5 (2011): 1290-1308. (Year: 2011).*

Braga et al. "Dealing with crystal forms (the kingdom of serendip?)." Chemistry An Asian Journal 6, No. 9 (2011): 2214-2223 (Year: 2011).*

CAS Registry No. 1251726-81-4, Entered Nov. 4, 1010. (Year: 2010).*

Qin, Xin, Michael G. Zaki, Zhicheng Chen, Elisabet Jakova, Zhi Ming, and Francisco S. Cayabyab. "Adenosine signaling and clathrin-mediated endocytosis of glutamate AMPA receptors in delayed hypoxic injury in rat hippocampus: Role of casein kinase 2." Molecular neurobiology 58 (2021): 1932-1951. (Year: 2021).*

(Continued)

*Primary Examiner* — James H Alstrum-Acevedo
*Assistant Examiner* — Carolyn L. Ladd
(74) *Attorney, Agent, or Firm* — Seed Intellectual Property Law Group LLP

(57) ABSTRACT

The present disclosure provides a compound of Formula I or its pharmaceutically acceptable salts, complexes, hydrates, solvates, tautomers, polymorphs, stereoisomers, racemates, pharmaceutically active derivatives thereof. The compounds of Formula I act as antagonists to adenosine receptors. The present disclosure also provides a process for preparation of compounds of Formula I and pharmaceutical composition thereof.

Formula I

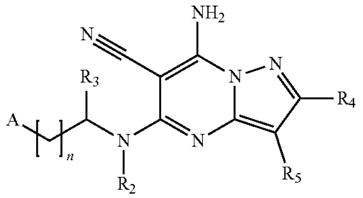

10 Claims, 1 Drawing Sheet

(56) References Cited

OTHER PUBLICATIONS

Talele, Tanaji T. "The cyclopropyl fragment is a versatile player that frequently appears in preclinical/clinical drug molecules." Journal of medicinal chemistry 59, No. 19 (2016): 8712-8756 (Year: 2016).*

Shi, Linsen, Zhaoying Wu, Ji Miao, Shangce Du, Shichao Ai, En Xu, Min Feng, Jun Song, and Wenxian Guan. "Adenosine interaction with adenosine receptor A2a promotes gastric cancer metastasis by enhancing PI3K-AKT-mTOR signaling." Molecular biology of the cell 30, No. 19 (2019): 2527-2534. (Year: 2019).*

Müller, C.E. and Jacobson, K.A., 2011. Recent developments in adenosine receptor ligands and their potential as novel drugs. Biochimica et Biophysica Acta (BBA)-Biomembranes, 1808(5), pp. 1290-1308 (Year: 2011).*

Allard et al., "The adenosine pathway in immuno-oncology," *Nature Reviews Clinical Oncology*, 2020. (19 pages).

Borea et al., "The Adenosine Receptors," *The Receptors 34*, 2018, DOI: 10.1007/978-3-319-90808-3. (603 pages).

Cheng et al., "Structures of Human A1 and A2A Adenosine Receptors with Xanthines Reveal Determinants of Selectivity," *Structure* 25:1-11.e1-e4, Aug. 1, 2017.

Hassan et al., "Synthesis and Anticancer Evaluation of Some Novel 5-Amino[1,2,4]Triazole Derivatives," *Journal of Heterocyclic Chemistry* 55(6):1450-1478, 2018.

Jacobson et al., "G protein-coupled adenosine (P1) and P2Y receptors: ligand design and receptor interactions," *Purinergic Signalling* 8:419-436, Feb. 29, 2012.

Sek et al., "Targeting Adenosine Receptor Signaling in Cancer Immunotherapy," *International Journal of Molecular Sciences* 19:1-23, Dec. 2, 2018.

Smith et al., "Pharmacokinetics and Metabolism in Drug Design," *Methods and Principles in Medicinal Chemistry*, 2006, ISBN: 3-527-31368-0. (197 pages).

Vijayan et al., "Targeting immunosuppressive adenosine in cancer," *Nature Reviews Cancer* 17:709-724, Oct. 23, 2017.

* cited by examiner

DIAMINOPYRAZOLO[1,5-A]PYRIMIDINE-6-CARBONITRILE COMPOUNDS AS ADENOSINE 2A RECEPTOR AND ADENOSINE 2B RECEPTOR ANTAGONIST

FIELD OF INVENTION

The present disclosure relates to the field of medicinal chemistry and particularly to the development of heterocyclic compounds and a process of preparation of the same. The present disclosure more particularly to the pyrazolopyrimidine compounds and in particular diaminopyrazolopyrimidine compounds which act as antagonists for adenosine receptors.

BACKGROUND

Adenosine is a purine nucleoside produced by cells for its intracellular physiological and extracellular signaling processes. It is synthesized from inosine monophosphate (IMP) as a nucleotide from adenosine monophosphate (AMP) or by the hydrolysis of adenosine triphosphate (ATP) via adenosine diphosphate (ADP) and AMP. Apart from being one of the building blocks of DNA, it is the primary energy source of cells as adenosine triphosphate (ATP) and is involved in the all-pervasive signal transduction processes as cyclic adenosine monophosphate (cAMP). Extracellular adenosine regulates inflammation, allostasis and cognitive functions in the brain, and vasodilation in the heart, lungs, and kidneys, all brought about by its binding to the adenosine receptors.

Adenosine receptors are members of the guanine nucleotide protein-coupled receptors (GPCR) family on the cell surface and consist of $A_1R$, $A_{2a}R$, $A_{2b}R$, and $A_3R$ subtypes in humans (Jacobson et al., 2012, PMID: 22371149). $A_1$ and $A_3$ receptor couple to $G\alpha_{i/o}$, in contrast, $A_{2a}$ and $A_{2b}$ receptors couple to $G\alpha_s$ to inhibit or stimulate adenylate cyclase (AC) respectively and are distributed ubiquitously throughout the body (Borea et al., 2018, DOI: 10.1007/978-3-319-90808-3; Cheng et al., 2017, PMID: 28712806). Their agonist or antagonist ligands are used as pharmacological interventions of various pro- and anti-inflammatory mediators to manage asthma, chronic pulmonary obstructive disease, heart failure, arrhythmia, diabetic kidney disease, glaucoma, stroke, sleep, anxiety, neurodegenerative disorders like Parkinson's, Alzheimer's and Huntington's diseases, epilepsy, pain, cognition and memory, and cancer (Sek et al., 2018, PMID: 30513816).

During infection, injury, hypoxia, ischemia, or seizure, extracellular adenosine is upregulated in tissues as an allostatic measure to protect tissue damage from the inflammatory responses. Similar immunosuppressive mechanisms of elevated adenosine levels (in the tumor micro-environment, TME) have been identified in tumor immune evasion. In the TME, adenosine binds to $A_{2a}R$ and $A_{2b}R$ on various immune cells and suppresses them by activating the cAMP-dependent Protein Kinase A (PKA) and blockade of the nuclear factor-kB (NF-kB) and Janus kinase (JAK)-signal transducer and activator of transcription (STAT) signaling pathway (Allard et al., 2020, PMID: 32514148). Relieving this inhibition of the $A_{2a}R$ and $A_{2b}R$ by selective antagonists can make the immune cells capable of killing tumor cells (Vijayan et al., 2017; PMID: 29162946, Allard et al., 2020, PMID: 32514148). Thus, in the present scenario of increasing proliferative disorders, or diseases or conditions, there is a huge need for antagonists of adenosine receptors. Hence there is a huge need for the antagonists of adenosine receptors, which will be useful in treating condition related to cancer or immune-related disorders mediated by these receptors.

SUMMARY OF THE INVENTION

In an aspect of the present disclosure, there is provided a compound of Formula I Formula I

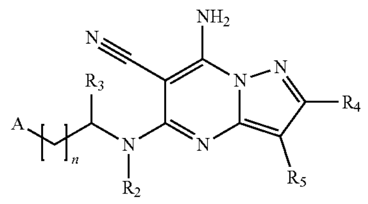

or its pharmaceutically acceptable salts, complexes, hydrates, solvates, tautomers, polymorphs, stereoisomers, racemates, pharmaceutically active derivatives thereof, wherein A is selected from $C_{5-10}$ aryl, $C_{2-10}$ heteroaryl, $C_{3-6}$ cycloalkyl, or $C_{1-10}$ heterocyclyl; wherein $C_{5-10}$ aryl, $C_{2-10}$ heteroaryl, $C_{3-6}$ cycloalkyl, or $C_{1-10}$ heterocyclyl is optionally substituted with one or more substituents selected from $R_6$, $R_7$, $R_8$, $R_9$, $R_{9a}$, or oxo;

$R_2$ is selected from hydrogen, $C_{1-6}$ alkyl, $C_{2-6}$ alkenyl, $C_{2-6}$ alkynyl, or $C_{1-6}$ haloalkyl; $R_3$ is selected from hydrogen, $C_{1-6}$ alkyl, $C_{2-6}$ alkenyl, $C_{2-6}$ alkynyl, or $C_{1-6}$ haloalkyl; wherein $C_{1-6}$ alkyl is optionally substituted with $C_{1-6}$ alkoxy;

$R_4$ and $R_5$ are independently selected from hydrogen, halogen, cyano, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ haloalkyl, $C_{1-6}$ haloalkoxy, —CO—N($R_{10}R_{11}$), $C_{4-10}$ carbocyclyl, or $C_{1-10}$ heterocyclyl, wherein $C_{1-6}$ alkyl, $C_{2-6}$ alkenyl or $C_{2-6}$ alkynyl are optionally substituted with one or more groups selected from $C_{3-6}$ cycloalkyl, $C_{1-6}$ alkoxy, or $C_{1-10}$ heterocyclyl; or $R_4$ and $R_5$ are joined together to form $C_{4-10}$ carbocyclyl, or $C_{1-10}$ heterocyclyl, wherein $C_{4-10}$ carbocyclyl or $C_{1-10}$ heterocyclyl is optionally substituted with 1 to 3 groups independently selected from halogen, $C_{1-6}$ alkyl, $C_{1-6}$ alkoxy, or $C_{1-6}$ haloalkoxy;

$R_{10}$ and $R_{11}$ are independently selected from hydrogen, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ haloalkyl, $C_{3-6}$ halocycloalkyl, $C_{4-10}$ carbocyclyl, or $C_{1-10}$ heterocyclyl;

$R_6$ is selected from hydrogen, halogen, hydroxyl, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylhydroxy, $C_{1-6}$ aminoalkyl, $C_{3-6}$ cycloalkyl, $C_{3-6}$ halocycloalkyl, —Y—O—$C_{1-6}$ alkyl, —Y—O—$C_{3-6}$ cycloalkyl, —Y—CO—NH—$R_{13}$, —Y—Z, $C_{4-10}$ carbocyclyl, or $C_{1-10}$ heterocyclyl, wherein $C_{1-6}$ alkyl, $C_{1-6}$ alkoxy, $C_{3-6}$ cycloalkyl, $C_{1-6}$ haloalkyl, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{1-6}$ alkoxy, $C_{3-6}$ cycloalkyl, $C_{1-6}$ alkylhydroxy, $C_{1-6}$ aminoalkyl, $C_{1-6}$ haloalkoxy, $C_{4-10}$ carbocyclyl, or $C_{1-10}$ heterocyclyl, wherein $C_{3-6}$ cycloalkyl, or $C_{1-6}$ aminoalkyl, is optionally further substituted with one or more groups independently selected from halogen, hydroxyl, $C_{1-6}$ alkylhydroxy, —C(O)$C_{1-6}$ alkyl, —C(O)$NH_2$, —C(O)—$C_{1-6}$alkylhydroxy, or $C_{1-10}$ heterocyclyl, and $C_{1-10}$ heterocyclyl has 1 to 4 heteroatoms independently selected from O, N or S, and optionally substituted with 1 to 3 groups independently selected from halogen, hydroxyl, $C_{1-6}$ alkyl, $C_{1-6}$ alkoxy, or $C_{1-6}$ haloalkoxy;

Y is selected from $C_{1-6}$ alkyl, $C_{2-6}$ alkenyl, $C_{2-6}$ alkynyl, $C_{3-6}$ cycloalkyl, or $C_{3-6}$ cycloalkenyl; and $C_{1-6}$ alkyl is optionally substituted with $C_{3-6}$ cycloalkyl;

Z is selected from —OH, —$NH_2$, —COOH, —$SO_2NH_2$, —$SO_2CH_3$, —$SOCH_3$, —$SCH_3$, $CH_2$—NH—($C_{1-6}$ alkyl)-$SOCH_3$, —O—P(=O)$(OH)_2$, —$CONH_2$, —CONH($C_{1-6}$ alkyl), —$SO_2$NH($C_{1-6}$ alkyl), CON($C_{1-6}$ alkyl)$_2$, —NHCO($C_{1-6}$ alkyl), $C_{4-10}$ carbocyclyl, or $C_{1-10}$ heterocyclyl, wherein $C_{1-10}$ heterocyclyl has 1 to 4 heteroatoms independently selected from O, N or S, and optionally substituted with 1 to 3 groups independently selected from halogen, $C_{1-6}$ alkyl, $C_{1-6}$ alkoxy, or $C_{1-6}$ haloalkoxy;

$R_{13}$ is selected from hydrogen, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl;

$R_7$, $R_8$, $R_9$, and $R_{9a}$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl;

and n is 0, 1, or 2.

In another aspect of the present disclosure, there is provided a process of preparation of compounds of Formula I or its pharmaceutically acceptable salts, complexes, hydrates, solvates, tautomers, polymorphs, stereoisomers, racemates, pharmaceutically active derivatives thereof, said process comprising: reacting Formula (A), and Formula (B) in the presence of a base to obtain the compounds of Formula I,

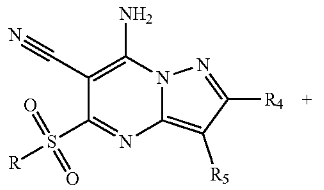

Formula (A)

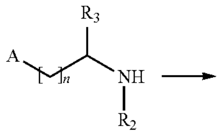

Formula (B)

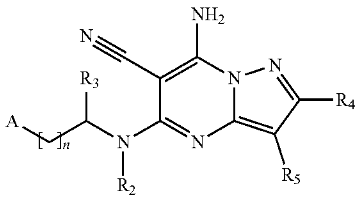

Formula (I)

wherein R is selected from $C_{1-6}$ alkyl, $C_{3-6}$ cycloalkyl, $C_{5-10}$ aryl, $C_{2-10}$ heteroaryl, or $C_{1-10}$ heterocyclyl; and the substituents are as defined above.

In one another aspect of the present disclosure, there is provided a pharmaceutical composition comprising a compound of Formula I as disclosed herein and one or more additional therapeutic agents.

In yet another aspect of the present disclosure, there is provided a method of treatment and/or prevention of a condition mediated by adenosine receptor or a proliferative disorder or cancer, comprising administering to a subject suffering from a condition mediated by adenosine receptor or a disease or proliferative disorder or cancer, a therapeutically effective amount of the compounds of Formula I as disclosed herein or the pharmaceutical composition comprising compounds of Formula I as disclosed herein and one or more additional therapeutic agent.

In further another aspect of the present disclosure, there is provided use of the compounds as disclosed herein or the pharmaceutical composition as disclosed herein for treatment of a condition mediated by adenosine receptor $A_{2a}R$, or $A_{2b}R$; treatment and/or prevention of a proliferative disorder or disease or cancer or immune-related disorder or disease or condition; or treatment of cancer together with other clinically relevant cytotoxic agents or non-cytotoxic agents.

In furthermore aspect of the present disclosure, there is provided use of the compounds as disclosed herein or the pharmaceutical composition as disclosed herein for treatment of a condition mediated by adenosine receptors $A_{2a}R$ and $A_{2b}R$; treatment and/or prevention of a proliferative disorder or disease or cancer or immune-related disorder or disease or condition; or treatment of cancer together with other clinically relevant cytotoxic agents or non-cytotoxic agents.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Figure 1:
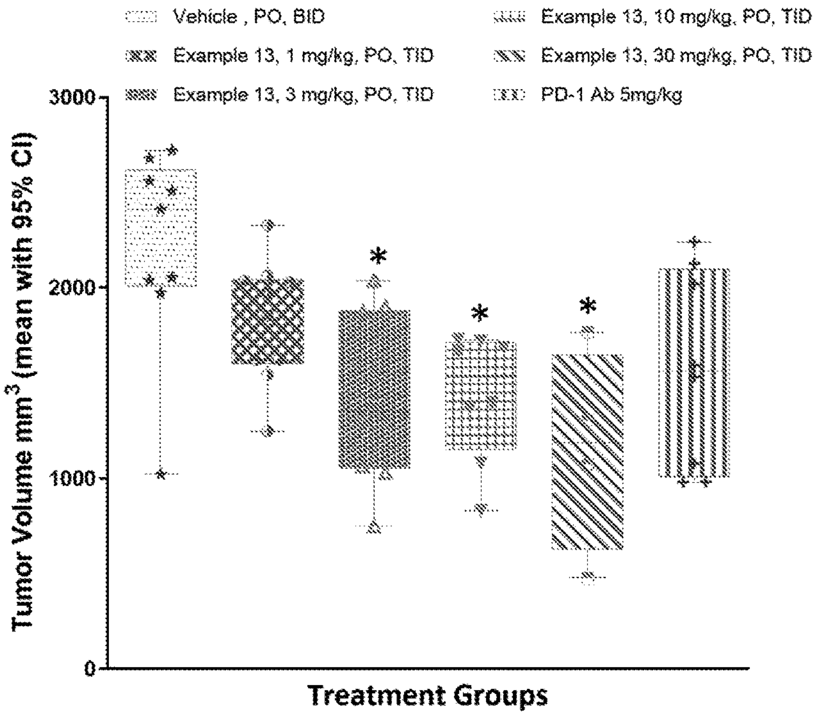
FIG. 1 depicts the in vivo efficacy effect of Example-13 on Tumor volume, in accordance with an implementation of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural Formulae given herein and throughout the present disclosure, the following terms have been indicated meaning, unless specifically stated otherwise.

In this specification, the prefix $C_{x-y}$ as used in terms such as $C_{x-y}$ alkyl and the like (where x and y are integers) indicates the numerical range of carbon atoms that are present in the group; for example, $C_{1-6}$alkyl includes $C_1$alkyl (methyl($-CH_3$), ($—CH_2—$)), $C_2$alkyl (ethyl($-C_2H_5$, $—CH_2CH_2—$)), $C_3$alkyl (propyl and isopropyl) and $C_4$alkyl (butyl, 1-methylpropyl, 2-methylpropyl, and t-butyl). Unless specifically stated, the bonding atom of a group may be any suitable atom of that group; for example, propyl includes prop-1-yl and prop-2-yl.

The term "alkyl" refers to a monoradical branched or unbranched saturated hydrocarbon chain having from 1 to 6 carbon atoms. This term is exemplified by groups such as methyl, ethyl, n-propyl, isopropyl, n-butyl, iso-butyl, t-butyl, n-hexyl, and the like. The groups may be optionally substituted.

The term "haloalkyl" as used herein refers to an alkyl group in which one or more hydrogen atoms are replaced by the same number of identical or different halogen atoms. The term "haloalkyl" is exemplified by groups such as chloromethyl, trifluoromethyl, 1-fluoroethyl, 2,2,2-trifluoroethyl, 2-fluoropropyl, 2,2-difluoropropyl, and the like. The term haloalkyl is exemplified by groups such as $CF_3$, $CHF_2$, $CH_2F$, and the like.

The term "aminoalkyl" refers to a group having an amine and an alkyl group and the amine may be primary, secondary or tertiary amine. The point of attachment may be N or C i.e amine or alkyl group. The term "aminoalkyl" and "alkylamino" may be used interchangeably. The term aminoalkyl is exemplified by groups such as $—CH(CH_3)_2NH_2$, $—CH_2CH_2NH_2$, $—CH_2CH_2NHCH_3$, $—CH_2CH(NH_2)CH_3$, $—CH_2CH_2N(CH_3)_2$, $—NHCH_3$, $—N(CH_3)_2$, $—CH_2NH_2$, $—CH_2NHCH_3$, $—CH_2NHCH_2—$, $—CH_2NHCH_2CH_2—$ and the like.

The term "alkylhydroxy" or "alkylhydroxyl" refers to an alkyl group in which one or more hydrogen atoms are replaced by a hydroxyl(-OH) group. The term alkylhydroxy is exemplified by groups such as $—CH_2CH(CH_3)_2OH$, $—CH(CH_3)_2OH$, $—CH_2OH$, $CH_2CH_2OH$ and the like.

The term "alkenyl" refers to a monoradical of a branched or unbranched unsaturated hydrocarbon group preferably having from 2, 3, 4, 5, or 6 carbon atoms and having 1, 2, or 3, double bond. The groups may be optionally substituted.

The term "alkynyl" refers to a monoradical of a branched or unbranched unsaturated hydrocarbon group preferably having from 2, 3, 4, 5, or 6 carbon atoms and having 1, 2, or 3, triple bond. The groups may be optionally substituted.

The term "cycloalkyl" refers to carbocyclic groups with 3 to 6 carbon atoms having a single cyclic ring or multiple condensed rings. Such cycloalkyl groups include, by way of example, single ring structures such as cyclopropyl, cyclobutyl, cyclopentyl, cyclopentenyl, cyclohexyl, and the like. The groups may be optionally substituted.

The term "cycloalkenyl" refers to carbocyclic groups of 3 to 6 carbon atoms having a single cyclic ring or multiple condensed rings which may be partially unsaturated.

The term "halocycloalkyl" as used herein refers to a cycloalkyl substituted with one or more halogen atoms. The halocycloalkyl refers to 3 to 6 carbon containing cycloalkyl substituted with one or more halogens.

The terms "alkoxyl" or "alkoxy" refers to an alkyl group, as defined above, having an oxygen radical attached thereto. Representative alkoxyl groups include methoxy, ethoxy, propyloxy, tert-butoxy, and the like. An "ether" is two hydrocarbons covalently linked by an oxygen. Accordingly, the substituent of an alkyl that renders an ether is or resembles an alkoxyl, such as can be represented by one of —O-alkyl, —O-alkenyl, —O-alkynyl. The alkoxy groups may be optionally substituted.

"Halo" or "Halogen", alone or in combination with any other term means halogens such as chloro (Cl), fluoro (F), bromo (Br) and iodo (I).

The term "carbocyclyl" or "carbocycle" refers to a saturated, unsaturated ring having 4 to 10 carbon atoms forming cyclic systems. Carbocyclic groups may be spiral or bridged systems, may be saturated, unsaturated or partially saturated. Carbocyclyl groups may be optionally substituted with one or more heteroatoms. Carbocyclic groups may refer to heteroaryl groups with one or more heteroatoms. Representative carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocyclyl" refers to a "carbocyclyl" as defined herein, wherein one or more carbon atoms have been replaced with a heteroatom selected from O, N, or S. The heterocyclyl group may contain 1 to 10 carbon in the ring structure, substituted with one to four heteroatoms selected from O, N, or S. The heterocyclyl may be saturated, unsaturated or partially saturated. Representative examples of heterocyclyl include oxiranyl, oxetanyl, oxolanyl, oxanyl, furanyl, dioxanyl, pyranyl, aziridinyl, piperidinyl, tetrahydropyranyl, azepinyl, oxazepinyl and the like.

The term "heteroaryl" refers to aromatic rings containing from 1 to 4 heteroatoms selected from N, O and S in the ring. "Heteroaryl" groups may be substituted with one or more substituents if so defined herein. The "$C_{2-6}$ heteroaryl" rings refers to a group having 2 or 6 carbon as ring member atoms with one to four heteroatoms.

The term "aryl" refers to aromatic ring having a specified number of carbon atoms. For example, $C_{5-10}$ aryl refers to an aryl group having 5 to 10 member atoms, or 6 member atoms. Preferred aryl groups include, without limitation, phenyl, and the like.

The term "haloalkoxy" refers to an alkoxy group as defined above further attached via halo linkage. For example, $C_{1-6}$ haloalkoxy refers to an alkoxy group having 1-6 carbon atoms further attached to one or more halogen. Preferred haloalkoxy groups include, without limitation, $—CH_2OCF_3$, $—CH_2CH_2OCF_3$, $—CH_2CH_2OCHF_2$, $—OCH_2Cl$, $—OCHCl_2$, $—CH_2OCF_3$ and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician.

The compounds described herein may contain one or more chiral centers and/or double bonds and therefore, may exist as stereoisomers, such as double-bond isomers (i.e., geometric isomers), regioisomers, enantiomers, or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form, and mixtures thereof. Accordingly, the chemical structures depicted herein encompass all possible tautomeric forms of the illustrated or identified compounds.

The term "racemates" refers to a mixture comprising a pair of optical isomers. Racemate refers to equimolar mixture of a pair of enantiomers. Racemate does not exhibit optical activity.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

Salts and solvates having non-pharmaceutically acceptable counter-ions or associated solvents are within the scope of the present disclosure, for example, for use as intermediates in the preparation of other compounds of Formula I, and their pharmaceutically acceptable salts. Thus, one embodiment of the disclosure embraces compounds of Formula I, and salts thereof. Compounds according to and Formula I contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "solvate", as used herein, refers to a crystal form of a substance which contains solvent.

The term "complexes" as used herein, can be interchangeably used as "coordination complex," or "metal coordination complex," and the like. It refers to a complex of an organic compound with a metal that can be empirically differentiated from a simple metal salt of the organic compound based on physiochemical and/or spectroscopic properties, with a coordination complex typically having enhanced covalency as compared to a salt. Without limitation "complexes" as used herein also involve a combination of coordinate covalent bonds and/or ionic bonds. As used herein, the term "complexes" also includes molecules that lack an ionic component (e.g., such as a neutral coordination complex prior to deprotonation, where pKa of the coordination complex falls within a physiologically acceptable range).

The term "hydrate" refers to a solvate wherein the solvent is water.

A term once described, the same meaning applies for it, throughout the disclosure.

As discussed in the background, there has been enormous efforts for the identification and development of new compounds acting as antagonists for adenosine receptors for treating proliferative disorders or diseases or condition or diseases related to immune depression or cancer. Heterocyclic compounds have been found to act as such antagonists and in the present disclosure there is disclosed, compounds of Formula I, their synthetic preparation methods, and their biological activity towards the adenosine receptors. The compounds of Formula I are found to be adenosine receptor antagonists, in particular adenosine $A_{2a}R$ and $A_{2b}R$ receptor antagonists. The compounds of Formula I are suitably formulated with therapeutic agents to form the pharmaceutical composition. The pharmaceutical composition and the compounds of Formula I is used for the treatment of diseases or disorders or condition mediated by the adenosine receptors.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, Formula I

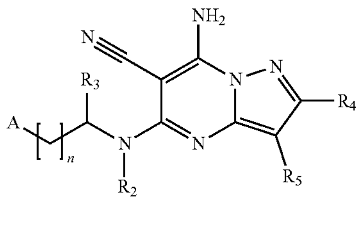

wherein A is selected from $C_{5-10}$ aryl, $C_{2-10}$ heteroaryl, $C_{3-6}$ cycloalkyl, or $C_{1-10}$ heterocyclyl; wherein $C_{5-10}$ aryl, $C_{2-10}$ heteroaryl, $C_{3-6}$ cycloalkyl, or $C_{1-10}$ heterocyclyl is optionally substituted with one or more substituents selected from $R_6$, $R_7$, $R_8$, $R_9$, $R_{9a}$, or oxo;

$R_2$ is selected from hydrogen, $C_{1-6}$ alkyl, $C_{2-6}$ alkenyl, $C_{2-6}$ alkynyl, or $C_{1-6}$ haloalkyl;

$R_3$ is selected from hydrogen, $C_{1-6}$ alkyl, $C_{2-6}$ alkenyl, $C_{2-6}$ alkynyl, or $C_{1-6}$ haloalkyl;

wherein $C_{1-6}$ alkyl is optionally substituted with $C_{1-6}$ alkoxy;

$R_4$ and $R_5$ are independently selected from hydrogen, halogen, cyano, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ haloalkyl, $C_{1-6}$ haloalkoxy, —CO—N($R_{10}$ $R_{11}$), $C_{4-10}$ carbocyclyl, or $C_{1-10}$ heterocyclyl, wherein $C_{1-6}$ alkyl, $C_{2-6}$ alkenyl or $C_{2-6}$ alkynyl are optionally substituted with one or more groups selected from $C_{3-6}$ cycloalkyl, $C_{1-6}$ alkoxy, or $C_{1-10}$ heterocyclyl; or $R_4$ and $R_5$ are joined together to form $C_{4-10}$ carbocyclyl, or $C_{1-10}$ heterocyclyl, wherein $C_{4-10}$ carbocyclyl or $C_{1-10}$ heterocyclyl is optionally substituted with 1 to 3 groups independently selected from halogen, $C_{1-6}$ alkyl, $C_{1-6}$ alkoxy, or $C_{1-6}$ haloalkoxy;

$R_{10}$ and $R_{11}$ are independently selected from hydrogen, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ haloalkyl, $C_{3-6}$ halocycloalkyl, $C_{4-10}$ carbocyclyl, or $C_{1-10}$ heterocyclyl;

$R_6$ is selected from hydrogen, halogen, hydroxyl, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylhydroxy, $C_{1-6}$ aminoalkyl, $C_{3-6}$ cycloalkyl, $C_{3-6}$ halocycloalkyl, —Y—O—$C_{1-6}$ alkyl, —Y—O—$C_{3-6}$ cycloalkyl, —Y—CO—NH—$R_{13}$, —Y—Z, $C_{4-10}$ carbocyclyl, or $C_{1-10}$ heterocyclyl, wherein $C_{1-6}$ alkyl, $C_{1-6}$ alkoxy, $C_{3-6}$ cycloalkyl, $C_{1-6}$ haloalkyl, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{1-6}$ alkoxy, $C_{3-6}$ cycloalkyl, $C_{1-6}$ alkylhydroxy, $C_{1-6}$ aminoalkyl, $C_{1-6}$ haloalkoxy, $C_{4-10}$ carbocyclyl, or $C_{1-10}$ heterocyclyl, wherein $C_{3-6}$ cycloalkyl, or $C_{1-6}$ aminoalkyl, is optionally further substituted with one or more groups independently selected from halogen, hydroxyl, $C_{1-6}$ alkylhydroxy, —C(O)$C_{1-6}$ alkyl, —C(O)$NH_2$, —C(O)—$C_{1-6}$alkylhydroxy, or $C_{1-10}$ heterocyclyl, and $C_{1-10}$ heterocyclyl is optionally substituted with 1 to 3 groups independently selected from halogen, hydroxyl, $C_{1-6}$ alkyl, $C_{1-6}$ alkoxy, or $C_{1-6}$ haloalkoxy;

Y is selected from $C_{1-6}$ alkyl, $C_{2-6}$ alkenyl, $C_{2-6}$ alkynyl, $C_{3-6}$ cycloalkyl, or $C_{3-6}$ cycloalkenyl; and $C_{1-6}$ alkyl is optionally substituted with $C_{3-6}$ cycloalkyl;

Z is selected from —OH, —$NH_2$, —COOH, —$SO_2NH_2$, —$SO_2CH_3$, —$SOCH_3$, —$SCH_3$, $CH_2$—NH—($C_{1-6}$ alkyl)—$SOCH_3$, —O—P(═O)$(OH)_2$, —$CONH_2$, —CONH($C_{1-6}$ alkyl), —$SO_2$NH($C_{1-6}$ alkyl), CON$(C_{1-6}$ alkyl$)_2$, —NHCO($C_{1-6}$ alkyl), $C_{4-10}$ carbocyclyl, or $C_{1-10}$ heterocyclyl, wherein $C_{1-10}$ heterocyclyl has 1 to 4 heteroatoms independently selected from O, N or S, and optionally substituted with 1 to 3 groups independently selected from halogen, $C_{1-6}$ alkyl, $C_{1-6}$ alkoxy, or $C_{1-6}$ haloalkoxy;

$R_{13}$ is selected from hydrogen, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl;

$R_7$, $R_8$, $R_9$, and $R_{9a}$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl;

and n is 0, 1, or 2.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, A is selected from $C_{5-10}$ aryl, $C_{2-10}$ heteroaryl, or $C_{1-10}$ heterocyclyl; $C_{5-10}$ aryl, $C_{2-10}$ heteroaryl, or $C_{1-10}$ heterocyclyl is optionally substituted with one or more substituents selected from $R_6$, $R_7$, $R_8$, $R_9$, $R_{9a}$, or oxo; $R_2$ is selected from hydrogen, $C_{1-6}$ alkyl, or $C_{1-6}$ haloalkyl; $R_3$ is selected from hydrogen, $C_{1-6}$ alkyl, or $C_{1-6}$ haloalkyl and wherein $C_{1-6}$ alkyl is optionally substituted with $C_{1-6}$ alkoxy; $R_4$ and $R_5$ are independently selected from hydrogen, halogen, cyano, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ haloalkyl, $C_{1-6}$ haloalkoxy, $C_{4-10}$ carbocyclyl, or $C_{1-10}$ heterocyclyl, wherein $C_{1-6}$ alkyl, $C_{2-6}$ alkenyl, or $C_{2-6}$ alkynyl, is optionally substituted with one or more groups selected from $C_{3-6}$ cycloalkyl, $C_{1-6}$ alkoxy, or $C_{1-10}$ heterocyclyl; wherein $C_{1-10}$ heterocyclyl has 1 to 3 heteroatoms independently selected from O, N or S, and optionally substituted with 1 to 3 groups independently selected from halogen, $C_{1-6}$ alkyl, $C_{1-6}$ alkoxy, or $C_{1-6}$ haloalkoxy; $R_6$ is selected from hydrogen, halogen, hydroxyl, $C_{1-6}$ alkyl, $C_{1-6}$ haloalkyl, $C_{1-6}$ alkoxy, $C_{1-6}$ haloalkoxy, $C_{1-6}$ alkylhydroxy, $C_{1-6}$ aminoalkyl, $C_{3-6}$ cycloalkyl, $C_{3-6}$ halocycloalkyl, —Y—O—$C_{1-6}$ alkyl, —Y—O—$C_{3-6}$ cycloalkyl, —Y—CO—NH—$R_{13}$, —Y—Z, or $C_{1-10}$ heterocyclyl, wherein $C_{1-6}$ alkyl, $C_{1-6}$ haloalkyl, $C_{1-6}$ alkoxy, $C_{1-6}$ haloalkoxy, $C_{1-6}$ alkylhydroxy, $C_{1-6}$ aminoalkyl, $C_{3-6}$ cycloalkyl, $C_{3-6}$ halocycloalkyl or $C_{1-10}$ heterocyclyl is optionally substituted with one or more groups selected from halogen, hydroxyl, amine, $C_{1-6}$ alkoxy, $C_{3-6}$ cycloalkyl, $C_{1-6}$ alkylhydroxy, $C_{1-6}$ aminoalkyl, $C_{1-6}$ haloalkoxy, or $C_{1-10}$ heterocyclyl, wherein $C_{3-6}$ cycloalkyl, or $C_{1-6}$ aminoalkyl, is optionally further substituted with one or more groups selected from halogen, hydroxyl, $C_{1-6}$ alkylhydroxy, —C(O)$C_{1-6}$ alkyl, —C(O)$NH_2$, —C(O)—$C_{1-6}$alkylhydroxy, or $C_{1-10}$ heterocyclyl; Y is selected from $C_{1-6}$ alkyl, or $C_{3-6}$ cycloalkyl; and $C_{1-6}$ alkyl is optionally substituted with $C_{3-6}$ cycloalkyl; Z is selected from —OH, —$NH_2$, —COOH, —$SO_2NH_2$, —$SO_2CH_3$, —$SOCH_3$, —$SCH_3$, $CH_2$—NH—($C_{1-6}$ alkyl)—$SOCH_3$, —O—P(═O)$(OH)_2$, —$CONH_2$, —CONH($C_{1-6}$ alkyl), —$SO_2$NH($C_{1-6}$ alkyl), CON$(C_{1-6}$ alkyl$)_2$, NHCO($C_{1-6}$alkyl), or $C_{1-10}$ heterocyclyl, wherein $C_{1-10}$ heterocyclyl has 1 to 3 heteroatoms independently selected from O, N, or S, and optionally substituted with 1 to 3 groups independently selected from halogen, $C_{1-6}$ alkyl, $C_{1-6}$ alkoxy, or $C_{1-6}$ haloalkoxy; $R_{13}$ is selected from hydrogen, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; $R_7$, $R_8$, $R_9$, and $R_{9a}$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; and n is 0, 1, or 2.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, wherein A is selected from

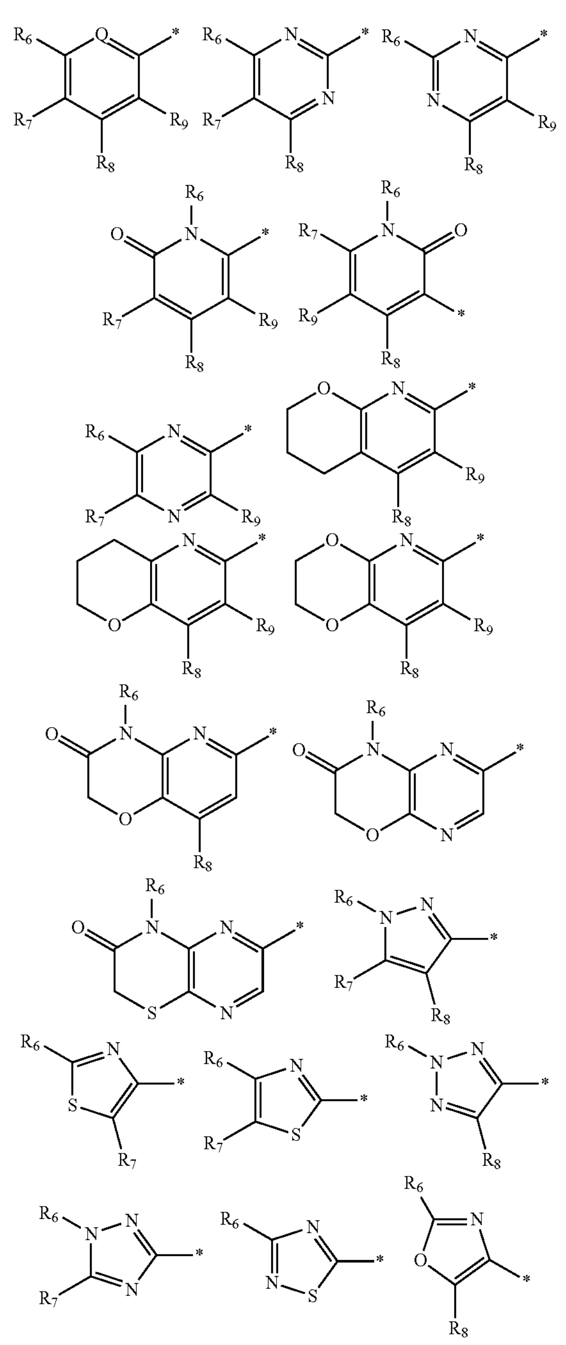

-continued

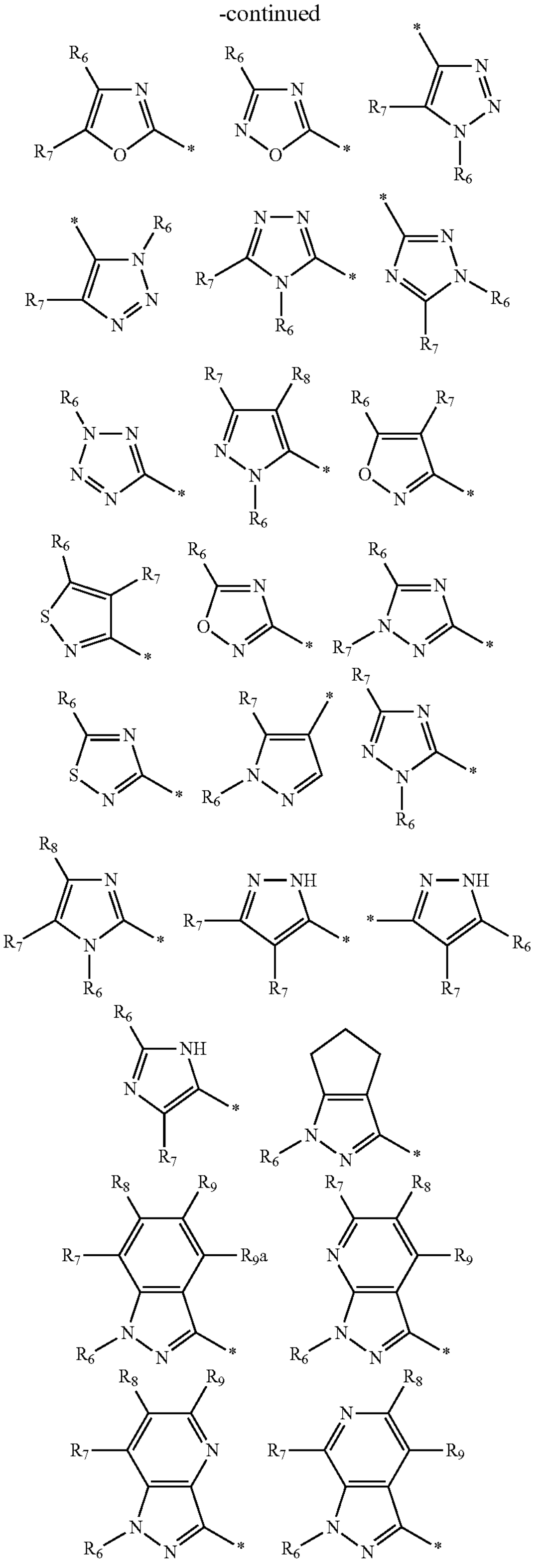

* is the point of attachment.

wherein Q is N or $CR_1$; and $R_1$ is selected from cyano, hydrogen, halogen, $C_{1-6}$ alkyl, $C_{2-6}$ alkenyl, $C_{2-6}$ alkynyl $C_{1-6}$ alkoxy, $C_{1-6}$ haloalkyl, or $C_{1-6}$ haloalkoxy; and $C_{1-6}$ alkyl, $C_{2-6}$ alkenyl, or $C_{2-6}$ alkynyl is optionally substituted with $C_{1-6}$ alkoxy.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, wherein A is selected from

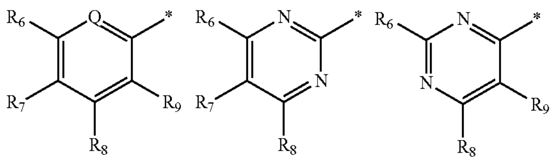
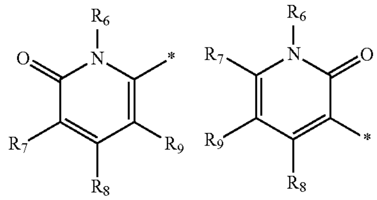
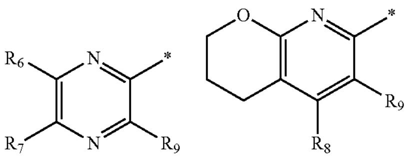
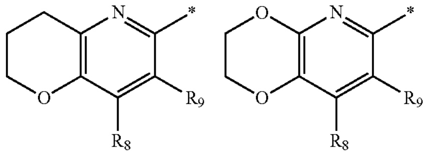
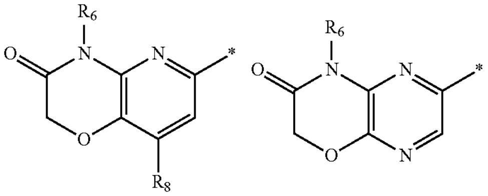
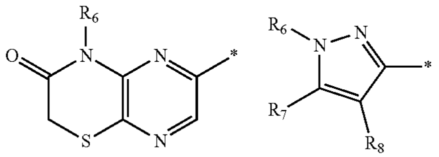
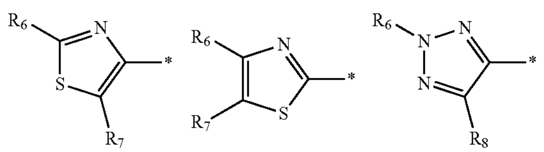
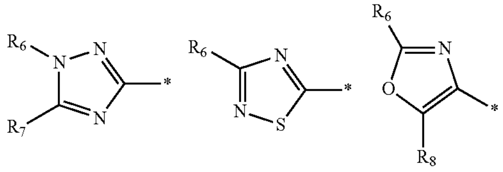
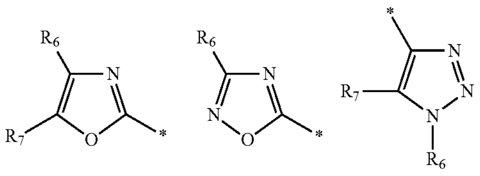

-continued

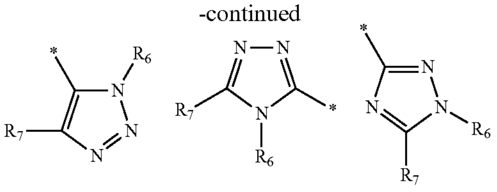
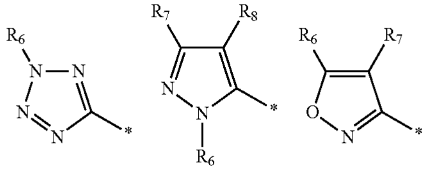
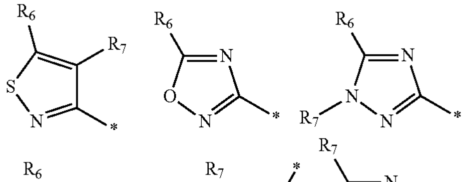
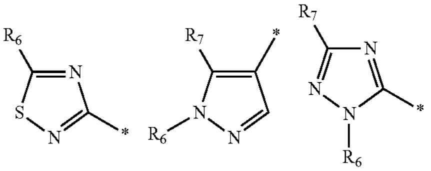
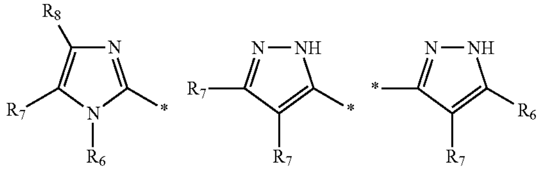
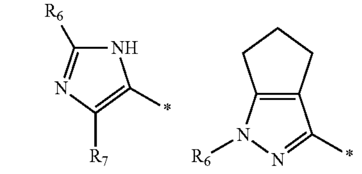
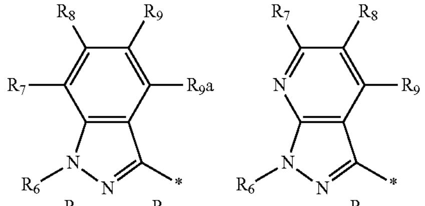
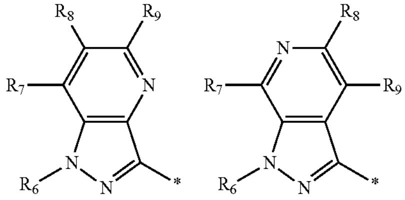

* is the point of attachment.

Q is N or $CR_1$;

$R_1$ is selected from cyano, hydrogen, halogen, $C_{1-6}$ alkyl, $C_{1-6}$ alkoxy, $C_{1-6}$ haloalkyl, or $C_{1-6}$ haloalkoxy; $R_2$ is hydrogen or $C_{1-6}$ alkyl; $R_3$ is hydrogen or $C_{1-6}$ alkyl; wherein $C_{1-6}$ alkyl is optionally substituted with $C_{1-6}$ alkoxy; $R_4$ and $R_5$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, $C_{1-10}$ heterocyclyl; wherein $C_{1-6}$ alkyl is optionally substituted with one or more groups selected from $C_{3-6}$ cycloalkyl, $C_{1-6}$ alkoxy, or $C_{1-10}$ heterocyclyl, wherein $C_{1-10}$ heterocyclyl has 1 to 3 heteroatoms independently selected from O, N or S and optionally substituted with 1 to 3 groups independently selected from halogen, $C_{1-6}$ alkyl, $C_{1-6}$ alkoxy, or $C_{1-6}$ haloalkoxy; $R_6$ is selected from hydrogen, $C_{1-6}$ alkyl, $C_{3-6}$ cycloalkyl, $C_{1-6}$ haloalkyl, $C_{1-6}$ alkoxy, $C_{1-6}$ alkylhydroxy, $C_{1-6}$ aminoalkyl, —Y—CO—NH—$R_{13}$, —Y—Z, or $C_{1-10}$ heterocyclyl, wherein $C_{1-6}$ alkyl, $C_{3-6}$ cycloalkyl, $C_{1-6}$ haloalkyl, $C_{1-6}$ alkoxy, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{3-6}$ cycloalkyl, $C_{1-6}$ alkoxy, $C_{1-6}$ alkylhydroxy, $C_{1-6}$ aminoalkyl, $C_{1-6}$ haloalkoxy, or $C_{1-10}$ heterocyclyl having 1 to 4 heteroatoms independently selected from O, N or S, wherein $C_{3-6}$ cycloalkyl, or $C_{1-6}$ aminoalkyl optionally substituted with 1 to 3 groups independently selected from halogen, hydroxyl, $C_{1-6}$ alkyl, $C_{1-6}$ alkoxy, $C_{1-6}$ haloalkoxy, $C_{1-6}$ alkylhydroxy, —C(O)$C_{1-6}$ alkyl, —C(O)$NH_2$, —C(O)—$C_{1-6}$alkylhydroxy, or $C_{1-10}$ heterocyclyl; Y is $C_{1-6}$ alkyl or $C_{3-6}$ cycloalkyl, wherein $C_{1-6}$ alkyl optionally substituted with $C_{3-6}$ cycloalkyl; Z is selected from —OH, —$NH_2$, —COOH, —$SO_2NH_2$, —$SO_2CH_3$, —S(═O)$CH_3$, —$SCH_3$, $CH_2$—NH—($C_{1-6}$ alkyl)—$SOCH_3$, —O—P(═O)$(OH)_2$, $CONH_2$, CON($C_{1-6}$ alkyl)$_2$-CONH($C_{1-6}$ alkyl), —$SO_2$NH($C_{1-6}$ alkyl), or —NHCO($C_{1-6}$ alkyl); $R_{13}$ is selected from hydrogen, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; $R_7$, $R_8$, $R_9$, and $R_{9a}$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; and n is 0, 1 or 2.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, wherein A is selected from

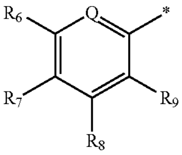
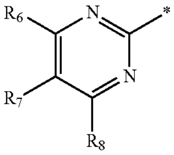
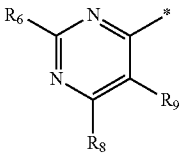
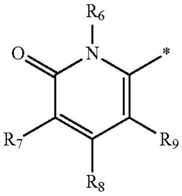
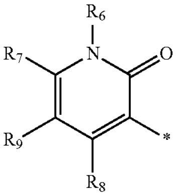
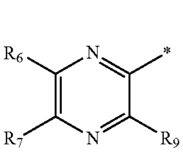
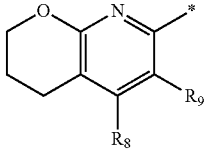
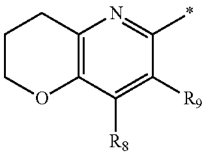
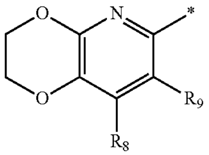

-continued

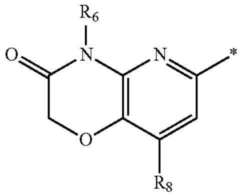
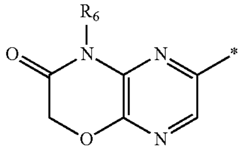
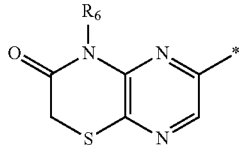
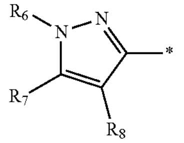
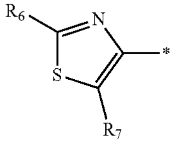
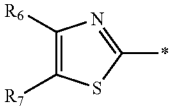
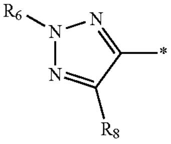
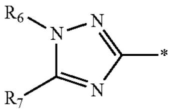
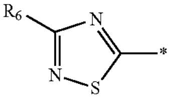
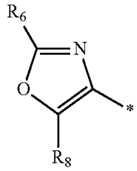
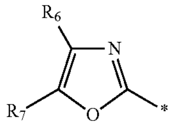
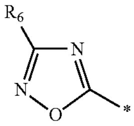
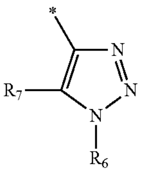
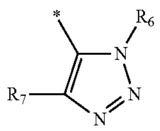
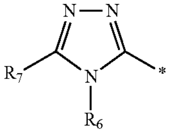
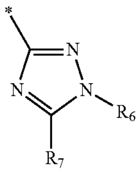
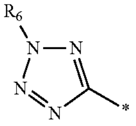
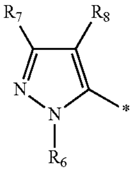
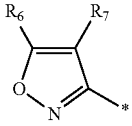
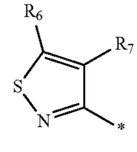
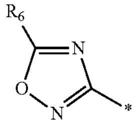
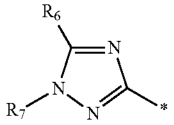
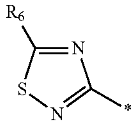
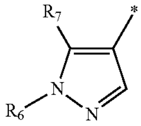
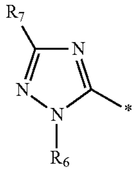
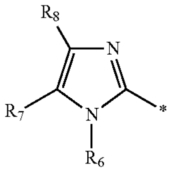
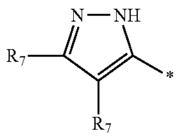
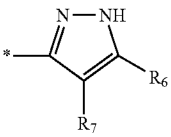

-continued

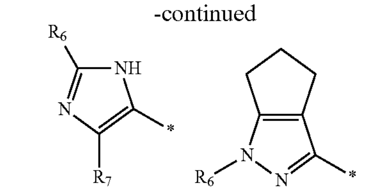
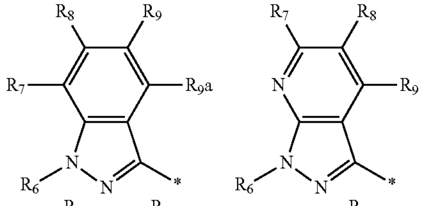
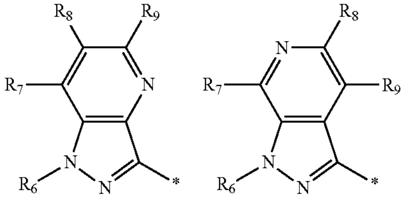

* is the point of attachment, wherein Q is N or $CR_1$; $R_1$ is selected from cyano, hydrogen, halogen, $C_{1-6}$ alkyl, $C_{1-6}$ alkoxy, $C_{1-6}$ haloalkyl, or $C_{1-6}$ haloalkoxy; $R_2$ is hydrogen or $C_{1-6}$ alkyl; $R_3$ is hydrogen or $C_{1-6}$ alkyl and wherein $C_{1-6}$ alkyl is optionally substituted with $C_{1-6}$ alkoxy; $R_4$ and $R_5$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, —CO—$N(R_{10}R_{11})$, $C_{1-10}$ heterocyclyl, wherein $C_{1-6}$ alkyl optionally substituted with one or more groups selected from $C_{3-6}$ cycloalkyl, $C_{1-6}$ alkoxy, or $C_{1-10}$ heterocyclyl, wherein the $C_{1-10}$ heterocyclyl has 1 to 4 heteroatoms independently selected from O, N or S and optionally substituted with 1 to 3 groups independently selected from halogen, $C_{1-6}$ alkyl, $C_{1-6}$ alkoxy, or $C_{1-6}$ haloalkoxy; $R_{10}$ is hydrogen or $C_{1-6}$ alkyl; $R_{11}$ is selected from hydrogen, $C_{1-6}$ alkyl, or $C_{1-10}$ heterocyclyl, wherein $C_{1-6}$ alkyl is optionally substituted with one or more groups selected from halogen, $C_{3-6}$ cycloalkyl or $C_{1-10}$ heterocyclyl; $C_{1-10}$ heterocyclyl has 1 to 4 heteroatoms independently selected from O, N or S, and optionally substituted with 1 to 3 groups independently selected from halogen, $C_{1-6}$ alkyl, $C_{1-6}$ alkoxy, $C_{1-6}$ haloalkoxy,

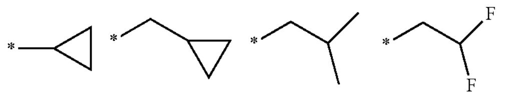
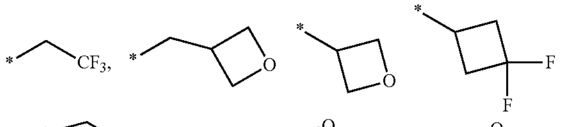
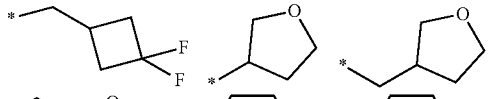
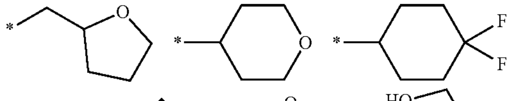
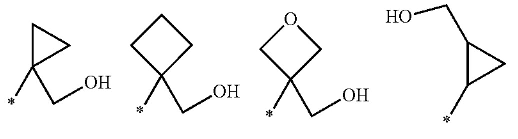

-continued

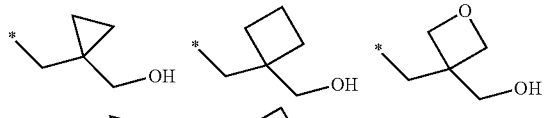
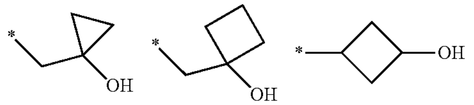
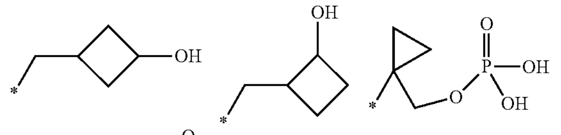
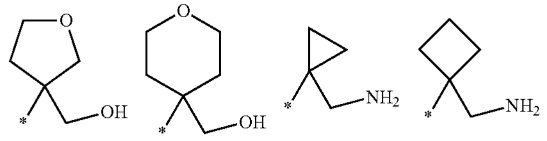
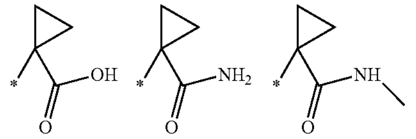

$R_6$ is selected from hydrogen, $C_{1-6}$ alkyl, $C_{3-6}$ cycloalkyl, $C_{1-6}$ haloalkyl, $C_{1-6}$ alkoxy, $C_{1-6}$ alkylhydroxy, $C_{1-6}$ aminoalkyl, —Y—CO—NH—$R_{13}$, —Y—Z, or $C_{1-10}$ heterocyclyl, wherein $C_{1-6}$ alkyl, $C_{3-6}$ cycloalkyl, $C_{1-6}$ haloalkyl, $C_{1-6}$ alkoxy, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{3-6}$ cycloalkyl, $C_{1-6}$ alkoxy, $C_{1-6}$ alkylhydroxy, $C_{1-6}$ aminoalkyl, $C_{1-6}$ haloalkoxy, $C_{1-10}$ heterocyclyl having 1 to 4 heteroatoms independently selected from O, N or S; wherein $C_{3-6}$ cycloalkyl, or $C_{1-6}$ aminoalkyl is optionally further substituted with one or more groups selected from halogen, hydroxyl, $C_{1-6}$ alkyl, $C_{1-6}$ alkoxy, $C_{1-6}$ haloalkoxy, $C_{1-6}$ alkylhydroxy, —C(O)$C_{1-6}$ alkyl, —C(O)$NH_2$, —C(O)—$C_{1-6}$ alkylhydroxy, $C_{1-10}$ heterocyclyl, cyclopropyl, cyclobutyl, $CH_2CF_3$, $CH_2CHFCH_3$, $CH_2CF_2CH_3$, $CH_2C(CH_3)_2OH$, $C(CH_3)_2OH$, $C(CD_3)_2OH$, $CH_2OH$, $CH_2OCH_3$, $CH_2OCF_3$, $C(CH_3CF_3)OH$, $CH_2CH_2OH$, $CH_2CH_2OCH_3$, $CH_2CH(OCH_3)CH_3$, $C(CH_3)_2NH_2$, $CH_2NH_2$, $CH_2CH_2NH_2$, $CH_2CH_2NHCH_3$, $CH_2CH(NH_2)CH_3$, $CH_2CH_2N(CH_3)_2$, $CH_2CHFCH_2NH_2$, $OCH_3$, $OCF_3$, $OCH_2CF_3$, $OCH_2CH_2OCH_3$, $OCH_2CH_2OCHCF_2$, $OCH_2CH_2OH$, $OCH_2CH_2OCF_3$, $CH_2CF_2CH_2OH$, $CH_2C(CH_3)_2CH_2OH$, $CHCF_3OH$, $CHOHCH_2OH$, $CHOHCH_2OCH_3$, $CH_2CH_2CH_2OH$, $CH_2CH_2NHCH_2CH_2OH$, $CH_2NHCH_2CH_2OH$, $CH_2CH_2NHCOCH_3$, $CH_2CH_2S(=O)CH_3$, $CH_2CH_2CH_2S(=O)CH_3$,

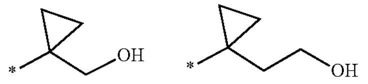
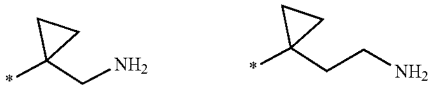
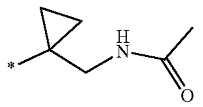

-continued

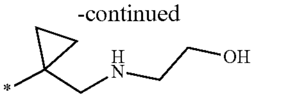
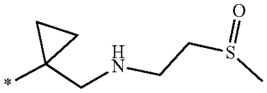
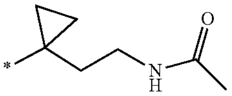
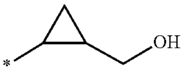
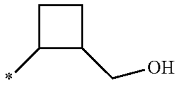
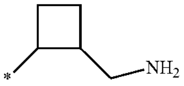
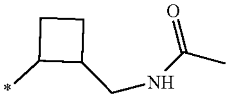
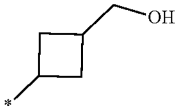
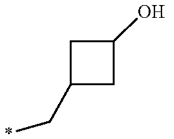
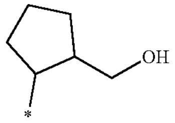
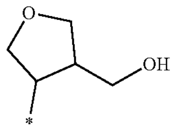
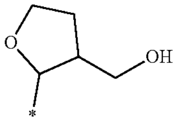
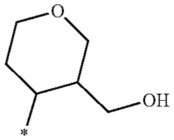
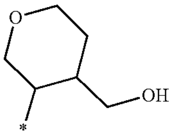
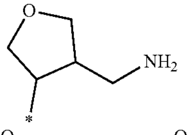
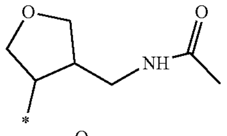
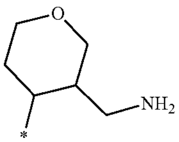
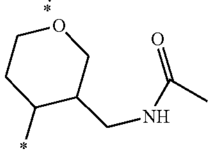 ;

Y is $C_{1-6}$ alkyl or $C_{3-6}$ cycloalkyl, wherein $C_{1-6}$ alkyl optionally substituted with $C_{3-6}$ cycloalkyl; Z is selected from —OH, —$NH_2$, —COOH, —$SO_2NH_2$, —$SO_2CH_3$, —S(═O)$CH_3$, —$SCH_3$, $CH_2$—NH—($C_{1-6}$ alkyl)—$SOCH_3$, —O—P(═O)$(OH)_2$, $CONH_2$, CON($C_{1-6}$ alkyl)$_2$-CONH($C_{1-6}$ alkyl), —$SO_2NH$($C_{1-6}$ alkyl), or —NHCO($C_{1-6}$ alkyl); and $R_{13}$ is selected from hydrogen, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; $R_7$, $R_8$, $R_9$, and $R_{9a}$ are independently selected from hydrogen, halogen, cyano, $C_{1-6}$ alkyl, $C_{3-6}$ cycloalkyl, $C_{1-6}$ alkoxy, $C_{1-6}$ haloalkyl, $C_{1-6}$ haloalkoxy, or $C_{3-6}$ halocycloalkyl; and n is 0, 1 or 2.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, wherein A is selected from

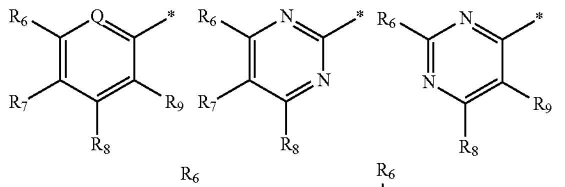
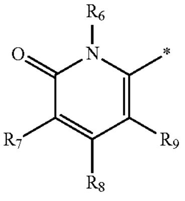
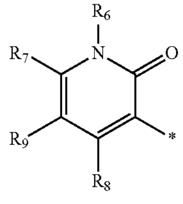
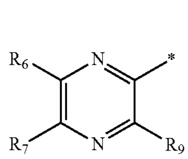
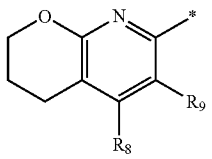
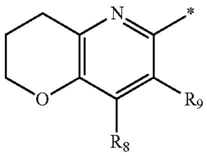
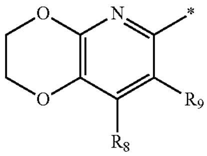
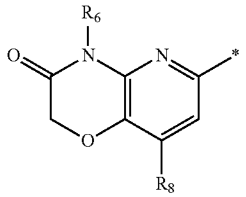
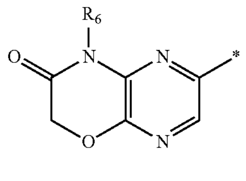
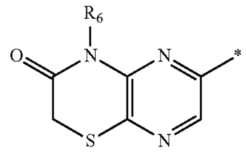
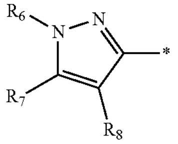
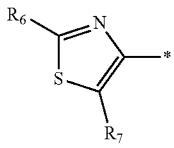
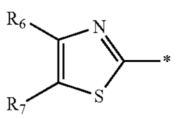
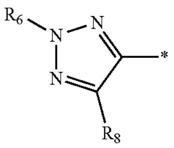
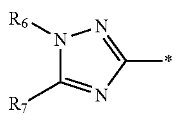
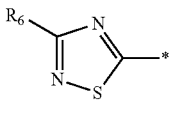
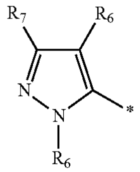

Q is N or $CR_1$; $R_1$ is selected from cyano, hydrogen, halogen, $C_{1-6}$ alkyl, or $C_{1-6}$ alkoxy; $R_2$ is hydrogen or $C_{1-6}$ alkyl; $R_3$ is hydrogen or $C_{1-6}$ alkyl; $R_4$ and $R_5$ are independently selected from hydrogen, halogen, cyano, $C_{1-6}$ alkyl, $C_{3-6}$ cycloalkyl, $C_{1-6}$ alkoxy, $C_{1-6}$ haloalkyl, or $C_{1-6}$ haloalkoxy; wherein $C_{1-6}$ alkyl optionally substituted with one or more groups selected from $C_{3-6}$ cycloalkyl, or $C_{1-6}$ alkoxy; $R_6$ is selected from hydrogen, $C_{1-6}$ alkyl, $C_{3-6}$ cycloalkyl, $C_{1-6}$ haloalkyl, $C_{1-6}$ alkoxy, $C_{1-6}$ alkylhydroxy, $C_{1-6}$ aminoalkyl, —Y—CO—NH—$R_{13}$, —Y—Z, or $C_{1-10}$ heterocyclyl, wherein $C_{1-6}$ alkyl, $C_{3-6}$ cycloalkyl, $C_{1-6}$ haloalkyl, $C_{1-6}$ alkoxy, $C_{1-6}$ aminoalkyl, $C_{1-6}$ alkylhydroxy, or $C_{1-10}$ heterocyclyl is optionally substituted with one or more groups independently selected from halogen, hydroxyl, $C_{3-6}$ cycloalkyl, $C_{1-6}$ alkoxy, $C_{1-6}$ alkylhydroxy, $C_{1-6}$ aminoalkyl, $C_{1-6}$ haloalkoxy, $C_{1-10}$ heterocyclyl, wherein $C_{3-6}$ cycloalkyl, or $C_{1-6}$ aminoalkyl is optionally further substituted with one or more groups independently selected from halogen, hydroxyl, $C_{1-6}$ alkylhydroxy, —C(O)$C_{1-6}$ alkyl, —C(O)$NH_2$, or —C(O)—$C_{1-6}$alkylhydroxy; Y is $C_{1-6}$ alkyl or $C_{3-6}$ cycloalkyl; Z is selected from —OH, —$NH_2$, —COOH, —$SO_2NH_2$, —$SO_2CH_3$, —$SOCH_3$, —$SCH_3$, $CH_2$—NH—($C_{1-6}$ alkyl)—$SOCH_3$, —$CONH_2$, —CONH($C_{1-6}$ alkyl), —$SO_2$NH($C_{1-6}$ alkyl), CON($C_{1-6}$ alkyl)$_2$, or —NHCO($C_{1-6}$ alkyl); $R_{13}$ is selected from hydrogen, $C_{1-6}$ alkyl, or $C_{3-6}$ cycloalkyl; $R_7$, $R_8$, $R_9$, and $R_{9a}$ are independently selected from hydrogen, halogen, cyano, $C_{1-6}$ alkyl, $C_{3-6}$ cycloalkyl, or $C_{1-6}$ alkoxy; and n is 0, 1, or 2.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, wherein A is selected from

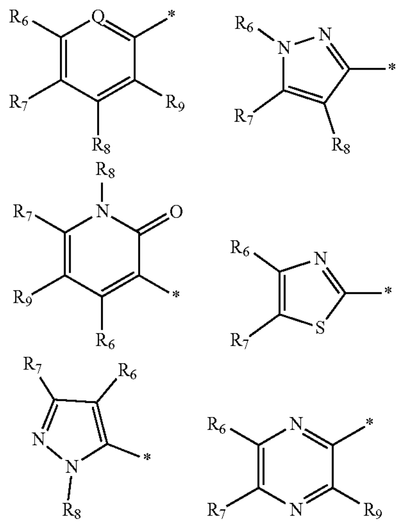

Q is N;

$R_2$ is hydrogen or $C_{1-6}$ alkyl; $R_3$ is hydrogen or $C_{1-6}$ alkyl; $R_4$ and $R_5$ are independently selected from halogen, $C_{1-6}$ alkyl, $C_{3-6}$ cycloalkyl or $C_{1-6}$ haloalkyl; wherein $C_{1-6}$ alkyl is optionally substituted with $C_{3-6}$ cycloalkyl; $R_6$ is selected from hydrogen, $C_{1-6}$ alkyl, $C_{1-6}$ haloalkyl, $C_{3-6}$ cycloalkyl, $C_{1-6}$ alkoxy, $C_{1-6}$ alkylhydroxy, $C_{1-6}$ aminoalkyl, —Y—CO—NH—$R_{13}$, —Y—Z, or $C_{1-10}$ heterocyclyl, wherein $C_{1-6}$ alkyl, $C_{1-6}$ alkoxy, $C_{3-6}$ cycloalkyl, $C_{1-6}$ haloalkyl, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{1-6}$ alkoxy, $C_{3-6}$ cycloalkyl, $C_{1-6}$ alkylhydroxy, $C_{1-6}$ aminoalkyl, or $C_{1-10}$ heterocyclyl; wherein $C_{3-6}$ cycloalkyl, or $C_{1-6}$ aminoalkyl, is optionally further substituted with one or more groups independently selected from halogen, hydroxyl, $C_{1-6}$ alkylhydroxy, —C(O)$C_{1-6}$ alkyl, —C(O)$NH_2$, or —C(O)—$C_{1-6}$alkylhydroxy; Y is $C_{1-6}$ alkyl, or $C_{3-6}$ cycloalkyl;

Z is selected from —$SOCH_3$, —$SCH_3$, $CH_2$—NH—($C_{1-6}$ alkyl)—$SOCH_3$, or —NHCO($C_{1-6}$ alkyl); $R_{13}$ is selected from hydrogen, $C_{1-6}$ alkyl, or $C_{3-6}$ cycloalkyl; $R_7$, $R_8$, $R_9$, and $R_{9a}$ are independently selected from hydrogen, halogen, cyano, $C_{1-6}$ alkyl or $C_{1-6}$ alkoxy; and n is 0, or 1.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, is selected from a group consisting of:

1. 7-amino-2,3-dimethyl-5-{[1-(6-methylpyridin-2-yl)ethyl]amino}pyrazolo[1,5-a]pyrimidine-6-carbonitrile;

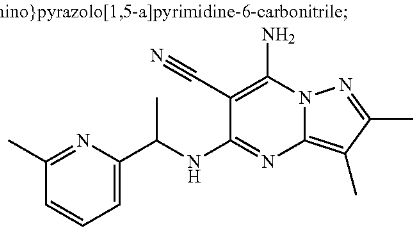

2. 7-amino-2,3-dimethyl-5-{[(1S)-1-(6-methylpyridin-2-yl)ethyl]amino}pyrazolo[1,5-a]pyrimidine-6-carbonitrile;

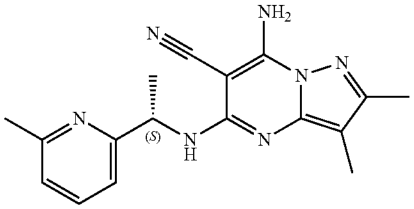

3. (R)-7-Amino-3-ethyl-2-methyl-5-((1-(pyridin-2-yl)ethyl) amino) pyrazolo[1,5-a] pyrimidine-6-carbonitrile;

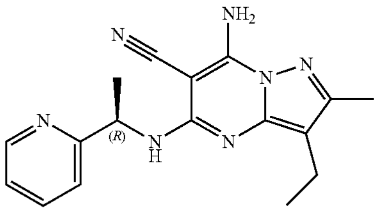

4. (S)-7-Amino-3-ethyl-2-methyl-5-((1-(pyridin-2-yl)ethyl) amino) pyrazolo[1,5-a] pyrimidine-6-carbonitrile;

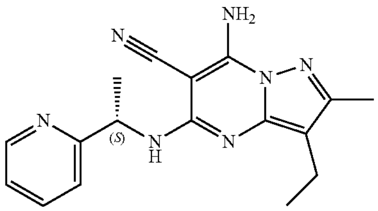

5. (S)-7-Amino-3-ethyl-2-methyl-5-((1-(6-methylpyridin-2-yl)ethyl) amino) pyrazolo [1,5-a] pyrimidine-6-carbonitrile;

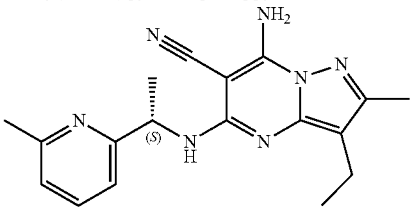

-continued 6. 7-amino-2,3-dimethyl-5-{[(6-methylpyridin-2-yl) methyl]amino}pyrazolo[1,5-a]pyrimidine-6-carbonitrile;

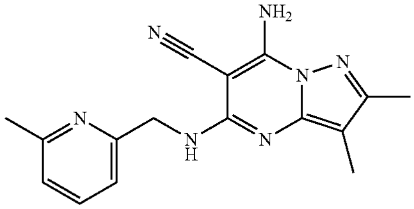

7. 7-amino-5-{[(6-ethylpyridin-2-yl)methyl]amino}-2,3-dimethylpyrazolo[1,5-a]pyrimidine-6-carbonitrile;

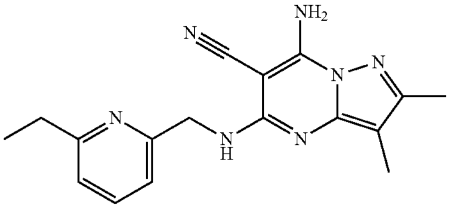

8. 7-amino-2,3-dimethyl-5-{methyl[(6-methylpyridin-2-yl) methyl]amino}pyrazolo[1,5-a]pyrimidine-6-carbonitrile;

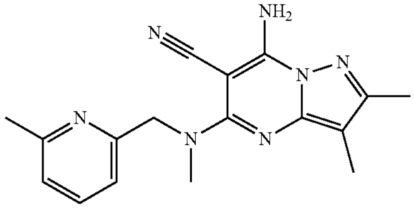

9. 7-amino-5-({[6-(2-hydroxypropan-2-yl)pyridin-2-yl]methyl} amino)-2,3-dimethylpyrazolo[1,5-a]pyrimidine-6-carbonitrile;

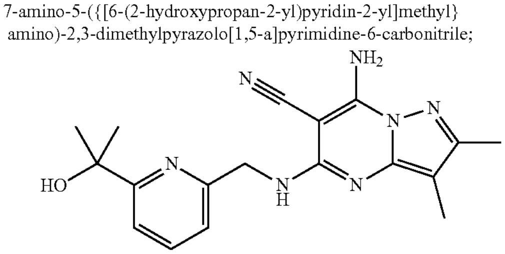

10. 7-Amino-2,3-dimethyl-5-((2-(5-methylpyridin-2-yl) ethyl) amino) pyrazolo[1,5-a] pyrimidine-6-carbonitrile;

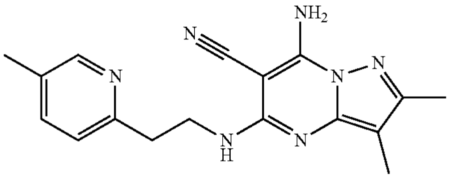

11. 7-amino-5-((2-(5-fluoropyridin-2-yl)ethyl)amino)-2,3-dimethylpyrazolo[1,5-a] pyrimidine-6-carbonitrile;

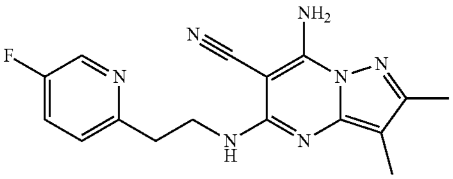

12. 7-amino-5-((2-(6-methoxypyridin-2-yl)ethyl)amino)-2,3-dimethylpyrazolo[1,5-a] pyrimidine-6-carbonitrile;

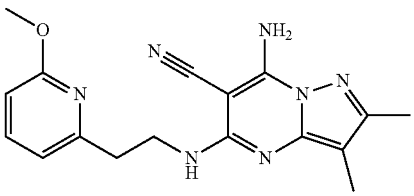

-continued 13. 7-amino-5-((2-(6-methylpyridin-2-yl)ethyl)amino)-2,3-dimethylpyrazolo[1,5-a] pyrimidine-6-carbonitrile;

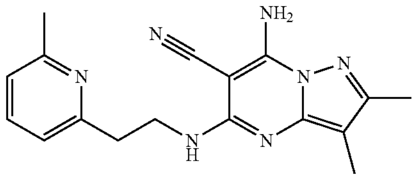

14. Chiral 7-amino-2,3-dimethyl-5-{[1-(6-methylpyridin-2-yl) propan-2-yl]amino}pyrazolo[1,5-a] pyrimidine-6-carbonitrile (Isomer 1);

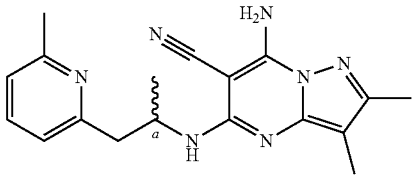

15. Chiral 7-amino-2,3-dimethyl-5-{[1-(6-methylpyridin-2-yl) propan-2-yl]amino}pyrazolo[1,5-a]pyrimidine-6-carbonitrile (Isomer2);

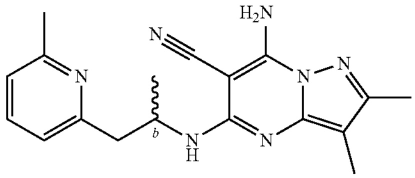

16. 7-amino-5-({2-[6-(2-hydroxypropan-2-yl)pyridin-2-yl]ethyl}amino)-2,3-dimethylpyrazolo [1,5-a]pyrimidine-6-carbonitrile;

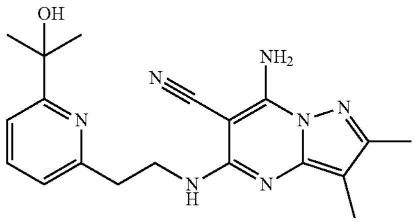

17. 7-Amino-3-ethyl-2-methyl-5-((2-(6-methylpyridin-2-yl) ethyl) amino) pyrazolo[1,5-a] pyrimidine-6-carbonitrile;

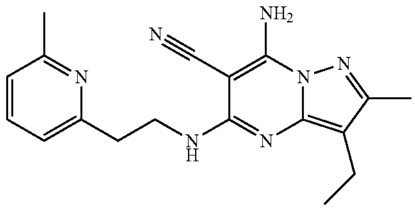

18. 7-Amino-3-ethyl-2-methyl-5-((2-(5-methylpyridin-2-yl) ethyl) amino) pyrazolo[1,5-a] pyrimidine-6-carbonitrile;

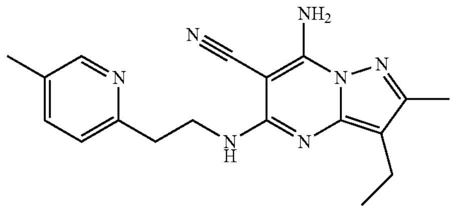

-continued 19. 7-Amino-3-ethyl-5-((2-(5-methoxypyridin-2-yl) ethyl) amino)-2-methylpyrazolo [1,5-a] pyrimidine-6-carbonitrile;

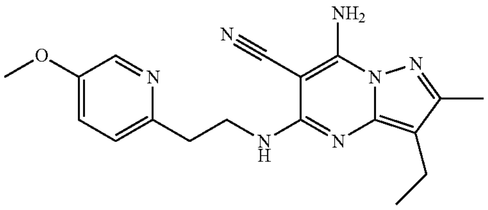

20. 7-Amino-3-ethyl-5-((2-(6-methoxypyridin-2-yl) ethyl) amino)-2-methylpyrazolo [1,5-a] pyrimidine-6-carbonitrile;

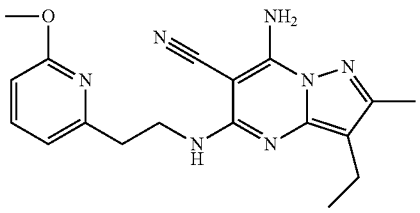

21. 7-Amino-3-ethyl-5-((2-(5-fluoropyridin-2-yl) ethyl) amino)-2-methylpyrazolo[1,5-a] pyrimidine-6-carbonitrile;

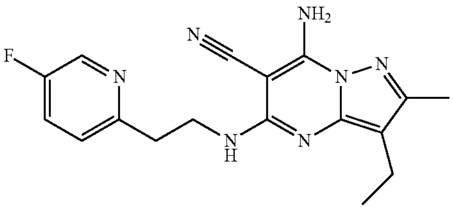

22. Chiral 7-Amino-3-ethyl-2-methyl-5-((1-(pyridin-2-yl) propan-2-yl) amino) pyrazolo[1,5-a] pyrimidine-6-carbonitrile (isomer 1);

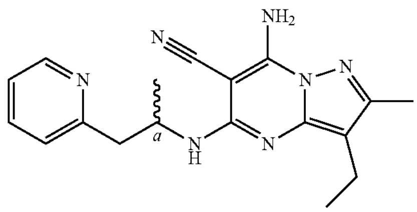

23. Chiral 7-Amino-3-ethyl-2-methyl-5-((1-(pyridin-2-yl) propan-2-yl) amino) pyrazolo[1,5-a] pyrimidine-6-carbonitrile (isomer 2);

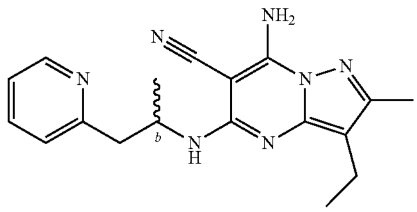

24. 7-Amino-3-ethyl-2-methyl-5-((1-(6-methylpyridin-2-yl) propan-2-yl) amino) pyrazolo[1,5-a] pyrimidine-6-carbonitrile;

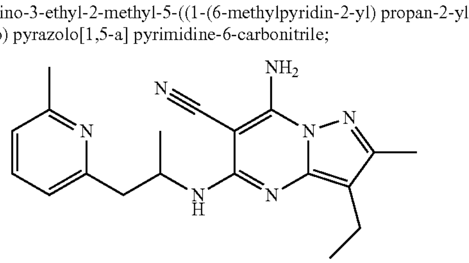

-continued 25. 7-amino-3-ethyl-5-({2-[6-(2-hydroxypropan-2-yl)pyridin-2-yl]ethyl}amino)-2-methylpyrazolo[1,5-a]pyrimidine-6-carbonitrile;

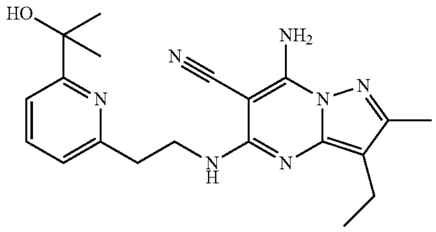

26. 7-amino-3-(cyclopropylmethyl)-2-methyl-5-((2-(6-methylpyridin-2-yl)ethyl) amino) pyrazolo[1,5-a]pyrimidine-6-carbonitrile;

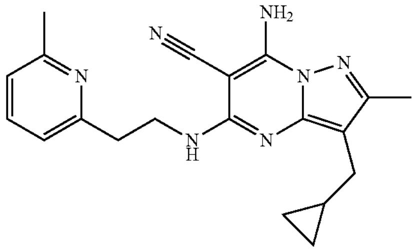

27. 7-amino-3-(isopropylmethyl)-2-methyl-5-((2-(6-methylpyridin-2-yl)ethyl) amino) pyrazolo[1,5-a]pyrimidine-6-carbonitrile;

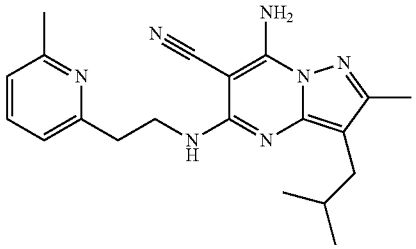

28. 7-amino-3-(isopropyl)-2-methyl-5-((2-(6-methylpyridin-2-yl) ethyl) amino) pyrazolo[1,5-a]pyrimidine-6-carbonitrile;

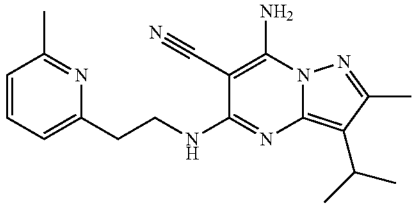

29. 7-amino-5-{[2-(1-ethyl-1H-pyrazol-3-yl)ethyl]amino}-2,3-dimethylpyrazolo[1,5-a]pyrimidine-6-carbonitrile;

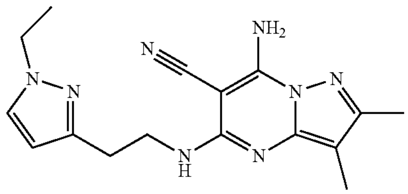

30. 7-amino-3-ethyl-5-{[2-(1-ethyl-1H-pyrazol-3-yl)ethyl]amino)-2-methylpyrazolo[1,5-a]pyrimidine-6-carbonitrile;

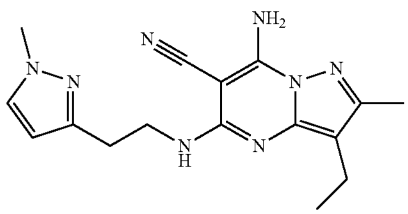

-continued 31. 7-amino-5-({2-[1-(1-hydroxy-2-methylpropan-2-yl)-1H-pyrazol-3-yl]ethyl}amino)-2,3-dimethylpyrazolo[1,5-a] pyrimidine-6-carbonitrile;

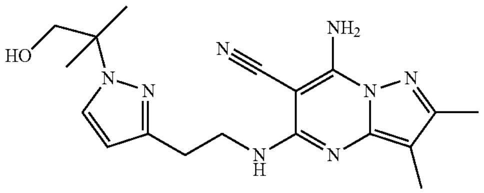

32. 7-amino-3-ethyl-5-((2-(1-hydroxy-2-methylpropan-2-yl)-1H-pyrazol-3-yl) ethyl) amino)-2-methylpyrazolo[1,5-a] pyrimidine-6-carbonitrile;

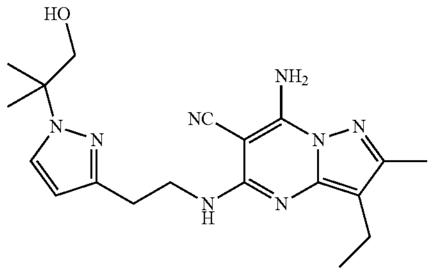

33. 7-amino-3-chloro-5-((2-(6-hydroxymethykl) pyridin-2-yl) ethyl) amino(-2-methylpyrazolo[1,5-a] pyrimidine-6-carbonitrile;

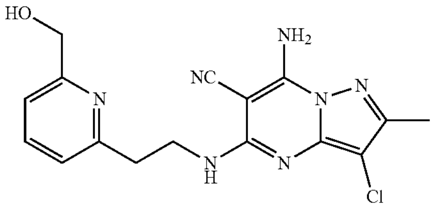

34. 7-amino-3-chloro-5-((2-(6-(1-(hydroxymethyl) cyclopropyl) pyridin-2-yl) ethyl) amino)-2-methylprazolo[1,5-a] pyrimidine-6-carbonitrile;

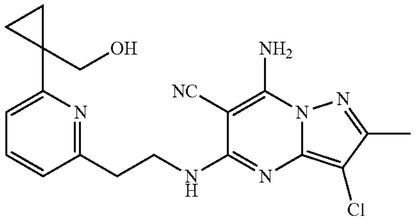

35. 7-amino-3-chloro-5-((2-(1-(2-hydroxyethyl)-1H-pyrazol-3-yl) ethyl) amino)-2-methylpyrazolo[1,5-a] pyrimidine-6-carbonitrile;

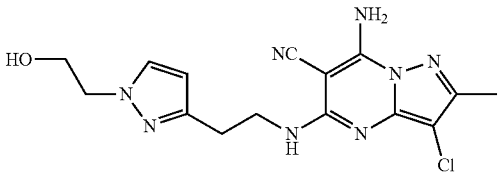

36. 7-amino-3-chloro-5-((2-(1-(1-hydroxy-2-methylpropan-2-yl)-1H-pyrazol-3-yl) ethyl) amino)-2-methylpyrazolo[1,5-a] pyrimidine-6-carbonitrile;

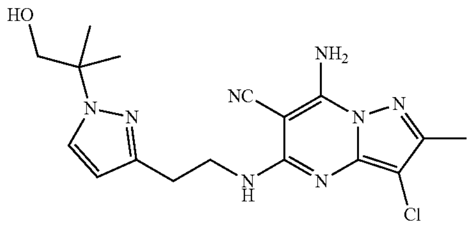

-continued 37. 7-amino-3-chloro-5-((2-(1-(1-(hydroxymethyl) cyclopropyl)-1H-pyrazol-3-yl) ethyl) amino)-2-methylpyrazolo[1,5-a] pyrimidine-6-carbonitrile;

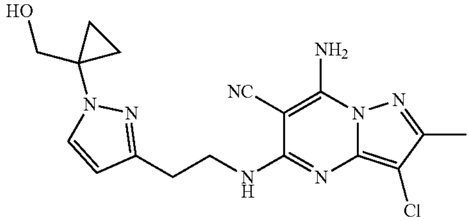

38. 7-amino-3-chloro-5-((2-(6-(2-(hydroxymethyl) cyclopropyl) pyridin-2-yl) ethyl) amino)-2-methylpyrazolo[1,5-a] pyrimidine-6-carbonitrile;

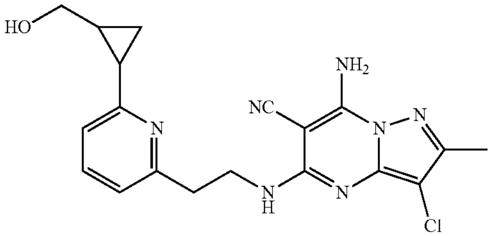

39. 7-amino-3-ethyl-5-((2-(1-(1-(hydroxymethyl) cyclopropyl)-1H-pyrazol-3-yl) ethyl) amino)-2-methylpyrazolo[1,5-a] pyrimidine-6-carbonitrile.

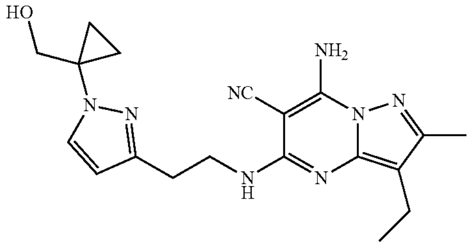

40. amino-5-((2-(6-ethylpyridin-2-yl) ethyl) amino)-2,3-dimethylpyrazolo[1,5-a] pyrimidine-6-carbonitrile;

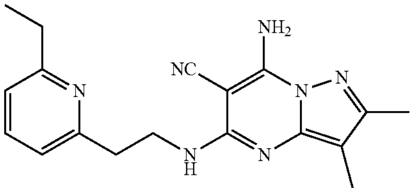

41. 7-amino-5-((2-(3-fluoro-6-methylpyridin-2-yl) ethyl) amino)-2,3-dimethylpyrazolo[1,5-a]pyrimidine-6-carbonitrile;

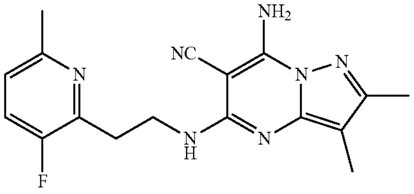

42. 7-amino-2-ethyl-3-methyl-5-((2-(6-methylpyridin-2-yl) ethyl) amino)pyrazolo[1,5-a]pyrimidine-6-carbonitrile;

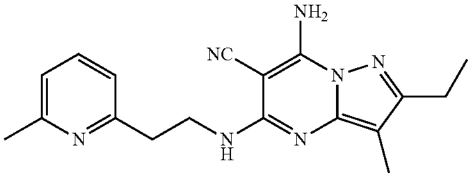

-continued 43. 7-amino-2-ethyl-5-((2-(6-(2-hydroxypropan-2-yl) pyridin-2-yl)ethyl)amino)-3-methylpyrazolo[1,5-a]pyrimidine-6-carbonitrile;

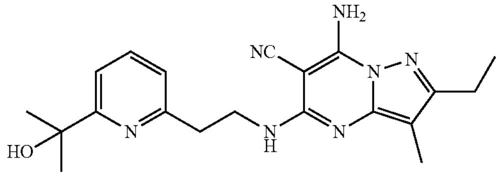

44. 7-amino-5-((2-(6-(hydroxymethyl) pyridin-2-yl) ethyl) amino)-2,3-dimethylpyrazolo [1,5-a] pyrimidine-6-carbonitrile;

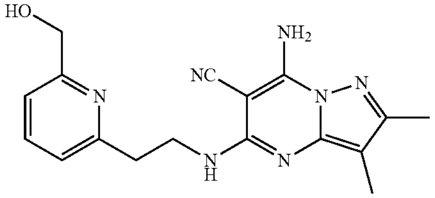

45. 7-amino-3-ethyl-5-((2-(6-(hydroxymethyl) pyridin-2-yl) ethyl) amino)-2-methylpyrazolo[1,5-a]pyrimidine-6-carbonitrile;

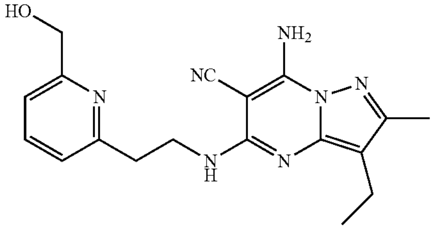

46. 7-amino-3-(cyclopropyl methyl)-5-((2-(6-(hydroxymethyl) pyridin-2-yl) ethyl)amino)-2-methylpyrazolo [1.5-a]pyrimidine-6-carbonitrile;

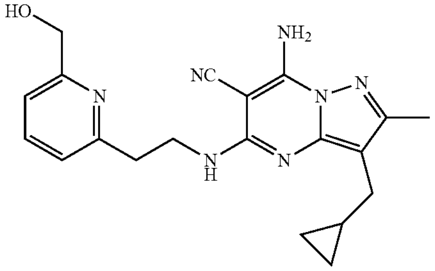

47. 7-amino-2-cyclopropyl-5-((2-(6-(2-hydroxypropan-2-yl) pyridine-2-yl) ethyl)amino)-3-methylpyrazolo [1,5-a]pyrimidine-6-carbonitrile;

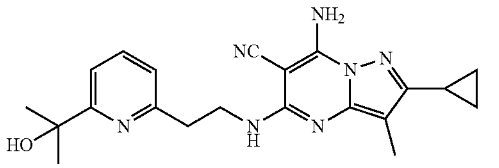

48. 7-amino-2-(difluoromethyl)-3-ethyl-5-((2-(1-(1-hydroxy-2-methylpropan-2-yl)-1H-pyrazol-3-yl) ethyl) amino) pyrazolo [1,5-a]pyrimidine-6-carbonitrile;

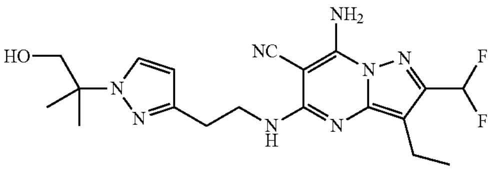

-continued 49. 7-amino-5-((2-(6-(1-(hydroxymethyl) cyclopropyl) pyridin-2-yl) ethyl)amino)-2,3-dimethylpyrazolo[1,5-a]pyrimidine-6-carbonitrile;

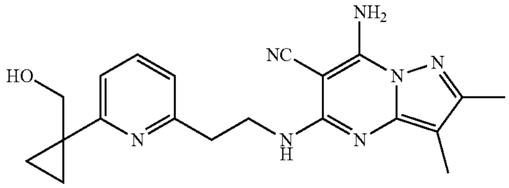

50. 7-amino-3-ethyl-5-((2-(6-(1-(hydroxymethyl) cyclopropyl) pyridin-2-yl)ethyl)amino)-2-methylpyrazolo[1,5-a] pyrimidine-6-carbonitrile;

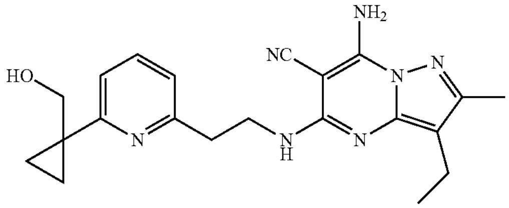

51. 7-amino-5-((2-(6-(2-(hydroxymethyl) cyclopropyl) pyridin-2-yl) ethyl)amino)-2,3-dimethylpyrazolo[1,5-a] pyrimidine-6-carbonitrile;

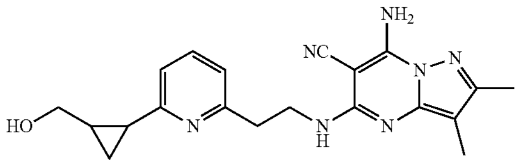

52. 7-amino-3-ethyl-5-((2-(6-(1-hydroxy-2-methylpropan-2-yl) pyridin-2-yl)ethyl) amino)-2-methylpyrazolo[1,5-a] pyrimidine-6-carbonitrile;

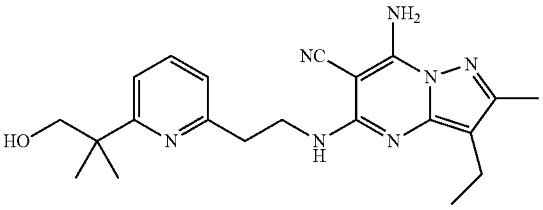

53. 7-amino-5-((2-(6-(1-hydroxy-2-methylpropan-2-yl) pyridin-2-yl) ethyl)amino)-2,3-dimethylpyrazolo[1,5-a] pyrimidine-6-carbonitrile;

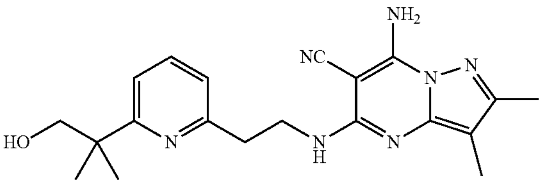

54. 7-amino-3-ethyl-5-((2-(1-(2-hydroxyethyl)-1H-pyrazol-3-yl) ethyl) amino)-2-methylpyrazolo [1,5-a] pyrimidine-6-carbonitrile;

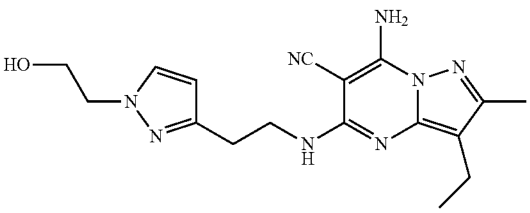

-continued 55. 7-amino-5-((2-(1-(1-(hydroxymethyl) cyclorpopyl)-1H-pyrazol-3-yl)ethyl) amino)-2,3-dimethylpyrazolo[1,5-a] pyrimidine-6-carbonitrile;

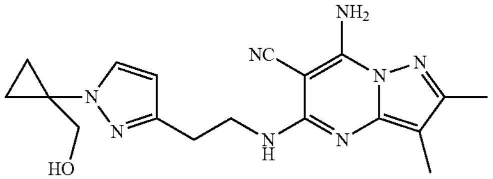

56. 7-amino-2-(difluoro methyl)-3-ethyl-5-((2-(6-hydroxymethyl) pyridin-2-yl) ethyl) amino) pyrazolo[1,5-a] pyrimidine-6-carbonitrile;

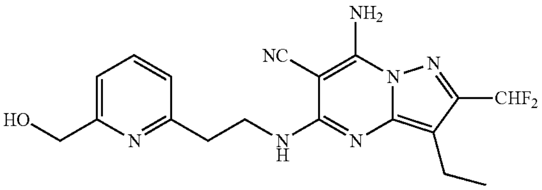

57. 7-amino-5-(((1-(1-hydroxy-2-methylpropan-2-yl)-1H-pyrazol-3-yl)methyl) amino)-2,3-dimethylpyrazolo[1,5-a] pyrimidine-6-carbonitrile;

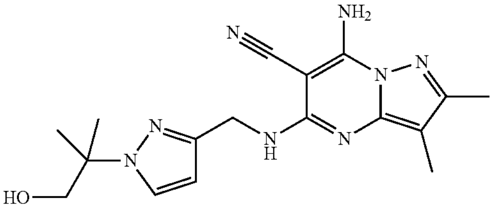

58. 7-amino-2-(difluoro methyl)-3-ethyl-5-((2-(1-(1-(hydroxymethyl) cyclopropyl)-1H-pyrazol-3-yl) ethyl) amino) pyrazolo[1,5-a] pyrimidine-6-carbonitrile;

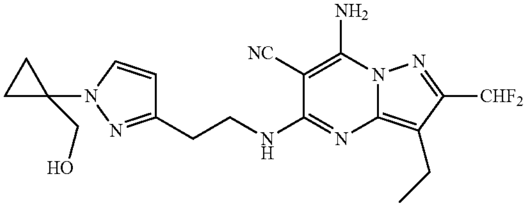

59. 7-amino-2-(difluoro methyl)-3-ethyl-5-((2-(6-(2-(hydroxymethyl) cyclopropyl) pyridin-2-yl) ethyl) amino) pyrazolo[1,5-a] pyrimidine-6-carboonitrile;

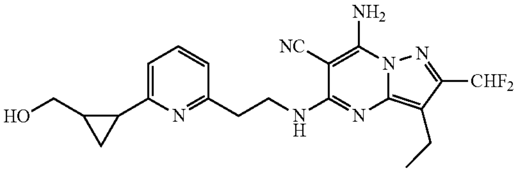

60. 7-amino-3-ethyl-5-((2-(6-(2-(hydroxymethyl) cyclopropyl) pyridin-2-yl) ethyl) amino)-2-methylpyrazolo[1,5-a] pyrimidine-6-carbonitrile;

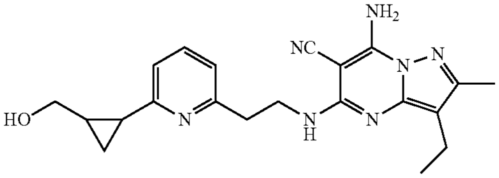

-continued 61. 7-amino-3-chloro-5-((2-(4-(1-(hydroxymethyl) cyclopropyl) thiazol-2-yl) ethyl) amino)-2-methylpyrazolo[1,5-a] pyrimidine-6-carbonitrile;

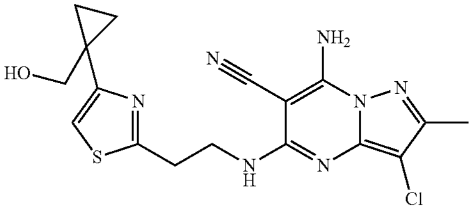

62. 7-amino-3-ethyl-5-((2-(4-fluoro-1-(1-hydroxy-2-methylpropan-2-yl)-1H-pyrazol-3-yl) ethyl) amino)-2-methylpyrazolo[1,5-a] pyrimidine-6-carbonitrile;

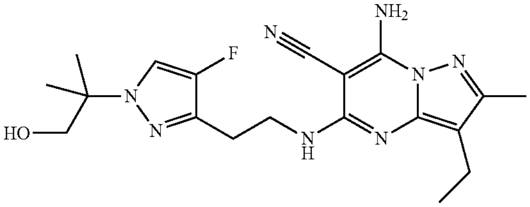

63. 7-amino-3-ethyl-5-((2-(1-((-(hydroxymethyl) cyclopropyl) methyl)-1H-pyrazol-3-yl) ethyl) amino)-2-methylpyrazolo [1,5-a] pyrimidine-6-carbonitrile;

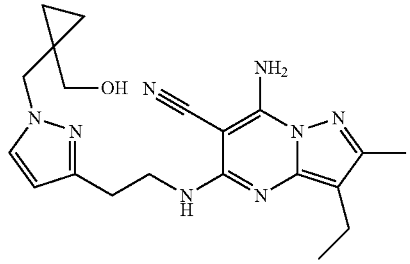

64. 7-amino-3-chloro-5-((2-(6-(1,1-difluoro-2-hydroxyethyl) pyridin-2-yl)ethyl) amino)-2-methylpyrazolo[1,5-a] pyrimidine-6-carbonitrile;

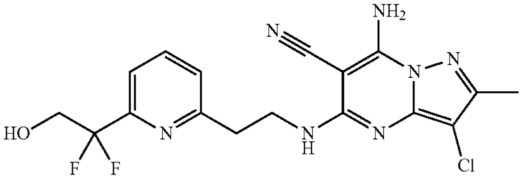

65. 7-amino-3-chloro-5-((2-(6-(1-hydroxy-2-methylpropan-2-yl) pyridin-2-yl) ethyl) amino)-2-methylpyrazolo[1,5-a] pyrimidine-6-carbonitrile;

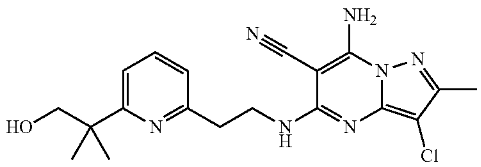

66. 7-amino-3-ethyl-5-((2-(4-(1-(hydroxymethyl) cyclopropyl) thiazol-2-yl) ethyl) amino)-2-methylpyrazolo[1,5-a] pyrimidine-6-carbonitrile;

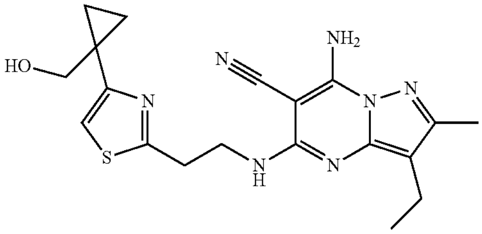

-continued 67. 7-amino-3-chlor-5-((2-(1-(2-(hydroxymethyl) cyclobutyl)-1H-pyrazol-3-yl) ethyl) amino)-2-methylpyrazolo[1,5-a] pyrimidine-6-carbonitrile;

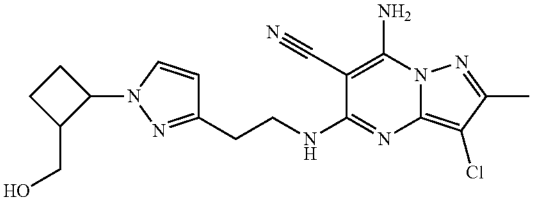

68. 7-amino-5-((2-(1-(1-(amino methyl) cyclopropyl)-1H-pyrazol-3-yl) ethyl)amino)-3-chloro-2-methylpyrazolo [1,5-a] pyrimidine-6-carbonitrile;

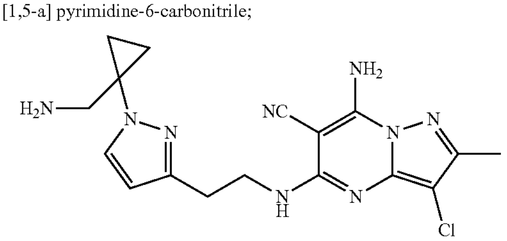

69. 7-amino-3-bromo-5-((2-(1-(1-(hydroxymethyl) cyclopropyl)-1H-pyrazol-3-yl) ethyl) amino)-2-methylpyrazolo[1,5-a] pyrimidine-6-carbonitrile;

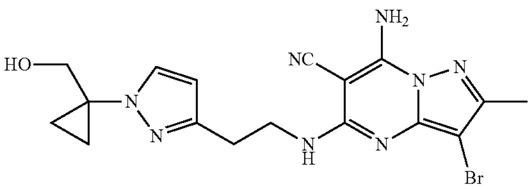

70. 7-amino-3-chloro-5-((2-(1-ethyl-2-oxo-1,2-dihydropyridin-3-yl) ethyl) amino)-2-methylpyrazolo[1,5-a]pyrimidine-6-carbonitrile;

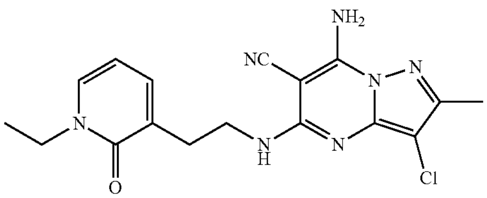

71. 7-amino-3-ethyl-5-((2-(1-(1-(hydroxymethyl) cyclopropyl)-1H-pyrazol-3-yl)ethyl) amino) pyrazolo[1,5-a] pyrimidine-6-carbonitrile;

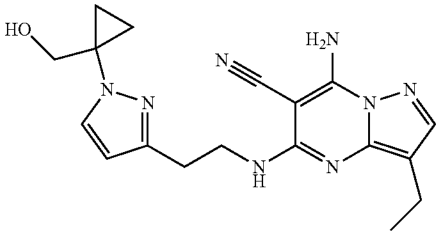

72. 7-amino-3-bromo-5-((2-(6-(hydroxymethyl) pyridine-2-yl) ethyl) amino)-2-methylpyrazolo[1,5-a] pyrimidine-6-carbonitrile;

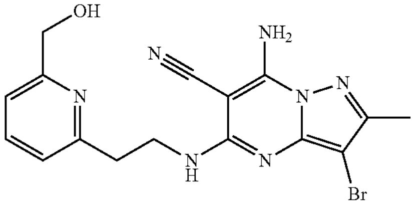

-continued 73. 7-amino-3-chloro-5-((2-(1-(1-(hydroxymethyl) cyclorpopyl)-1H-pyrazol-4-yl)ethyl) amino)-2-methylpyrazolo[1,5-a] pyrimidine-6-carbonitrile;

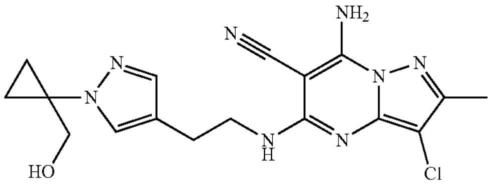

74. 7-amino-3-(cyclopropyl methyl)-5-((2-(1-(1-(hydroxymethyl) cyclopropyl)-1H-pyrazol-3-yl) ethyl) amino)-2-methylpyrazolo [1,5-a] pyrimidine-6-carbonitrile;

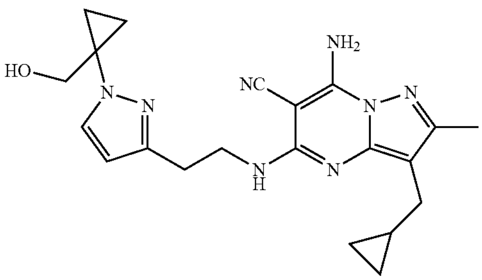

75. 7-amino-3-chloro-5-((2-(1-(1-(hydroxymethyl) cyclopropyl)-5-methyl-1H-pyrazol-3-yl) ethyl) amino)-2-methylpyrazolo [1,5-a] pyrimidine-6-carbonitrile;

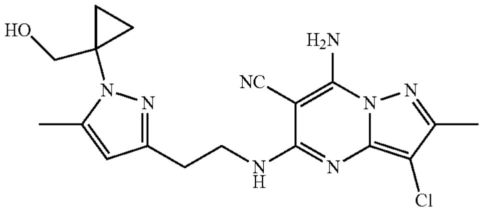

76. 7-amino-3-ethyl-5-((2-(1-(1-(hydroxymethyl)cyclopropyl)-5-methyl-1H-pyrazol-3-yl) ethyl) amino)-2-methylpyrazolo [1,5-a] pyrimidine-6-carbonitrile;

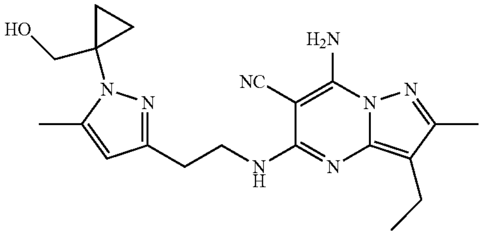

77. N-((1-(3-(2-((7-amino-3-chloro-6-cyano-2-methylpyrazolo [1,5-a] pyrimidin-5-yl) amino) ethyl)-1H-pyrazol-1-yl) cyclopropyl) methyl) acetamide;

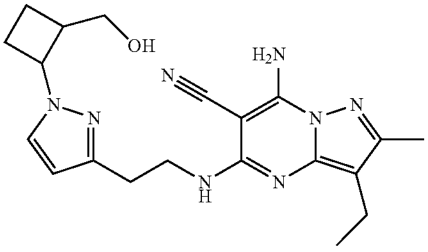

-continued 78. (+)- 7-amino-3-ethyl-5-((2-(1-(2-(hydroxymethyl)cyclobutyl)-1H-pyrazol-3-yl)ethyl)amino)-2-methylpyrazolo[1,5-a] pyrimidine-6-carbonitrile;

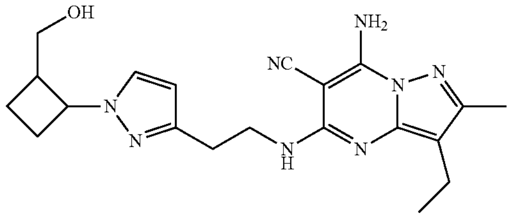

Example 78; dextro(+) rotatory 79. (-)- 7-amino -3ethyl-5-((2-(1-(2-(hydroxymethyl)cyclobutyl)-1H-pyrazol-3-yl)ethyl) amino)-2-methypyrazolo[1,5-a]pyrimidine-6-carbonitrile;

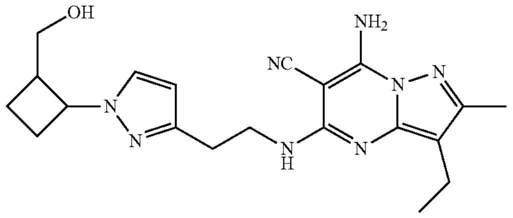

Example 79; leavo(-) rotatory 80. 7-amino-3-ethyl-5-((2-(1-(1-(hydroxymethyl) cyclopropyl)-5-1H-pyrazol-3-yl) ethyl) amino) pyrazolo[1,5-a] pyrimidine-6-carbonitrile;

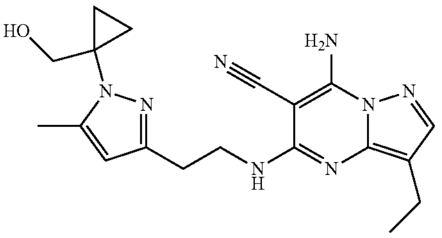

81. 7-amino-3-ethyl-5-((2-(1-(1-hydroxypropan-2-yl)-1H-pyrazol-3-yl) ethyl)amino)-2-methylpyrazolo[1,5-a] pyrimidine-6-carbonitrile;

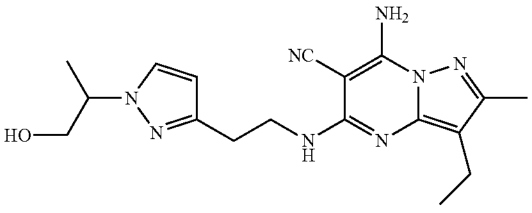

82. (+-)- 7-amino-3-chloro-5-((2-(1-((3-hydroxycyclobutyl) methyl)-1H-pyrazol-3-yl) ethyl) amino)-2-methylpyrazolo[1,5-a] pyrimidine-6-carbonitrile;

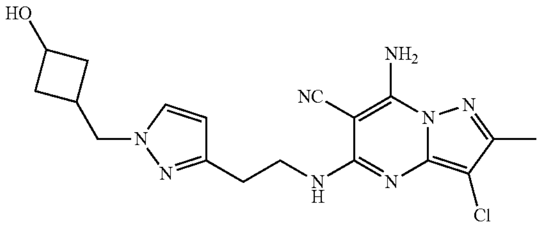

-continued 83. (+)- 7-amino-3-chloro-5-((2-(1-((3-hydroxycyclobutyl) methyl-1H-pyrazol-3-yl) ethyl) amino)-2-methylpyrazolo[1,5-a] pyrimidine-6-carbonitrile;

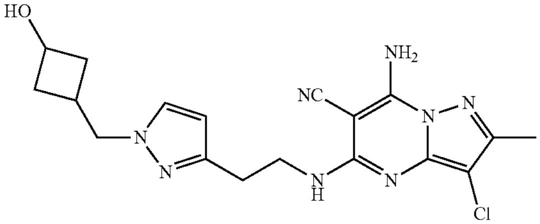

84. (-)- 7-amino-3-chloro-5-((2-(1-((3-hydroxycyclobutyl) methyl-1H-pyrazol-3-yl) ethyl) amino)-2-methylpyrazolo[1,5-a] pyrimidine-6-carbonitrile(83b);

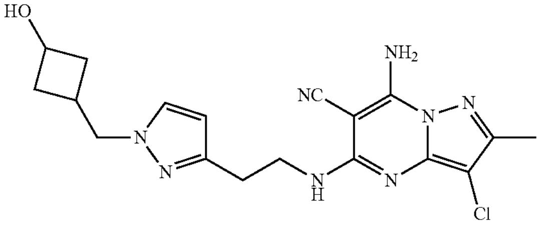

85. 7-amino-3-ethyl-5-((2-(1-((3-hydroxycyclobutyl) methyl)-1H-pyrazol-3-yl) ethyl) amino-2-methylpyrazolo[1,5-a] pyrimidine-6-carbonitrile;

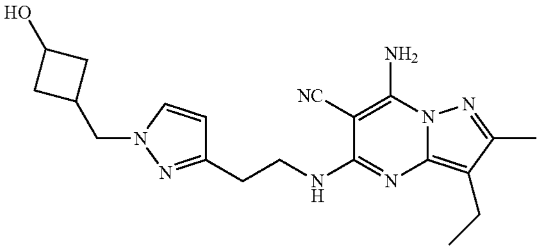

86. 7-amino-5-((2-(1-(1-(hydroxy methyl) cyclopropyl)-5-methyl-1H-pyrazol-3-yl) ethyl) amino)-2,3-dimethylpyrazolo[1,5-a] pyrimidine-6-carbonitrile;

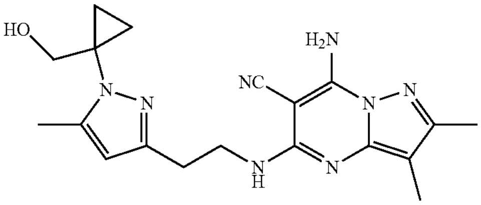

87. 7-amino-3-chloro-2-methyl-5-((2-(1-methyl-2-oxo-1,2-dihydropyridin 3-yl) ethyl) amino) pyrazolo[1,5-a] pyrimidine-6-carbonitrile;

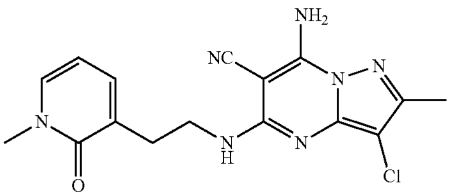

-continued 88. 7-amino-3-ethyl-2-methyl-5-((2-(methyl-2-oxo-1,2-oxo-1,2-dihydropyridin-3-yl) ethyl) amino) pyrazolo[1,5-a] pyrimidine-6-carbonitrile;

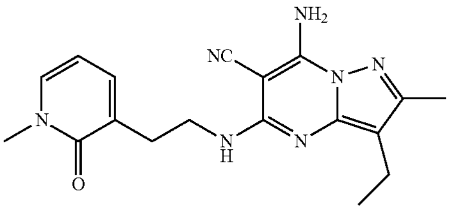

89. 7-amino-3-bromo-5-((2-(1-(1-(hydroxymethyl) cyclopropyl)-5-methyl-1H-pyrazol-3-yl) ethyl) amino)-2-methypyrazolo[1,5-a] pyrimidine-6-carbonitrile;

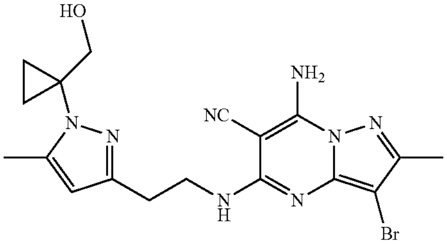

90. 7-amino-3-chloro-5-((2-(6-(((2-hydroxyethyl) amino) methyl) pyridin-2-yl) ethyl) amino)-2-methylpyrazolo[1,5-a] pyrimidine-6-carbonitrile;

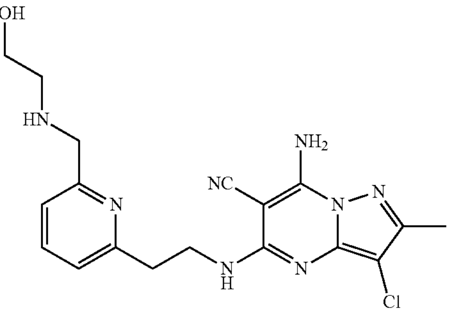

91. 7-amino-3-ethyl-5-((2-(5-fluoro-6-(hydroxymethyl)46yridine-2-yl) ethyl) amino)-2-methylpyrazolo[1,5-a] pyrimidine-6-carbonitrile;

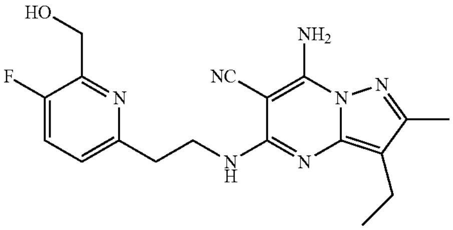

92. 7-amino-3-chloro-5-((2-(1-(2-methoxyethyl)-2-oxo-1,2-dihydropyridin-3-yl) ethyl) amino-2-methylpyrazolo[1,5-a] pyrimidine-6-carbonitrile;

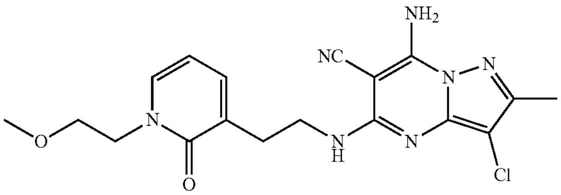

-continued 93. 7-amino-3-chloro-5-((2-(1-(2-hydroxyethyl)-2-oxo-1,2-dihydropyridin-3-yl) ethyl) amino)-2-methylpyrazolo[1,5-a] pyrimidine-6-carbonitrile;

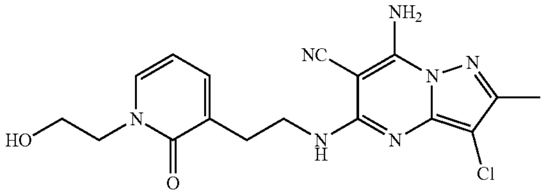

94. 7-amino-5-((2-(1-(1-(hydroxymethyl) cyclopropyl)-1H-pyrazol-3-yl) ethyl) amino)-2-methyl-3-(trifluoromethyl)pyrazolo [1,5-a] pyrimidine-6-carbonitrile;

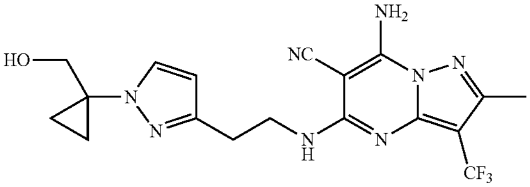

95. 7-amino-5-((2-(1-(2-(amino methyl) cyclobutyl)-1H-pyrazol-3-yl) ethyl) amino)-3-chloro-2-methylpyrazolo[1,5-a] pyrimidine-6-carbonitrile;

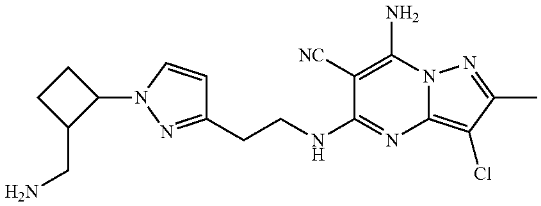

96. 7-amino-3-ethyl-5-((2-(6-(((2-methoxyethyl) amino) methyl) 47yridine-2-yl) ethyl) amino)-2-methylpyrazolo[1,5-a] pyrimidine-6-carbonitrile;

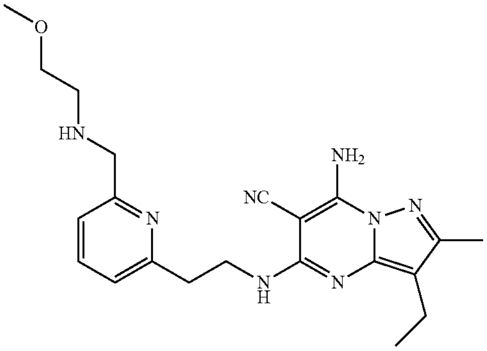

97. 7-amino-3-ethyl-5-((2-(6-(((2-hydroxyethyl) amino) methyl) pyridine-2-yl) ethyl) amino)-2-methylpyrazolo[1,5-a]pyrimidine-6-carbonitrile;

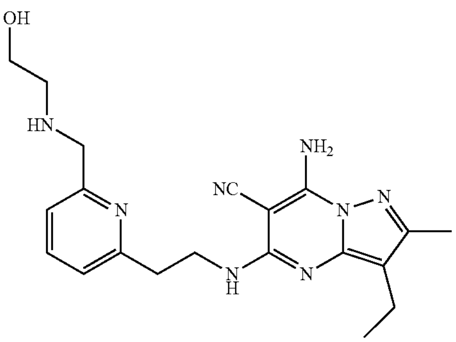

-continued 98. 7-amino-3-chloro-5-((2-(1-(1-(((2-hydroxyethyl) amino) methyl) cyclopropyl)-1H-pyrazol-3-yl) ethyl) amino)-2-methylpyrazolo [1,5-a] pyrimidine-6-carbonitrile;

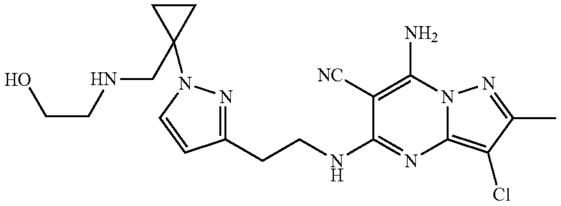

99. N-((1-(3-(2-((7-amino-3-chloro-6-cyano-2-methylpyrazolo [1,5-a] pyrimidin-5-yl) amino) ethyl)-1H-pyrazol-1-yl) cyclopropyl) methyl)-3-hydroxypropanamide;

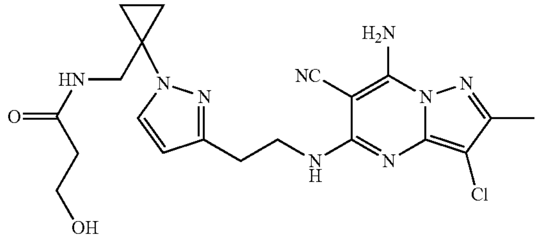

100. 7-amino-3-ethyl-5-((2-(6-(1-hydroxyethyl)49yridine-2-yl) ethyl) amino)-2-methylpyrazolo[1,5-a] pyrimidine-6-carbonitrile;

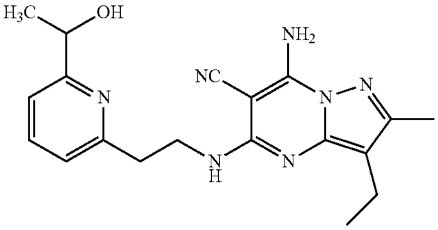

101. 7-amino-3-cyclopropyl-5-((2-(1-(1-(hydroxymethyl) cyclopropyl)-1H-pyrazol-3-yl) ethyl) amino)-2-methylpyrazolo[1,5-a] pyrimidine-6-carbonitrile;

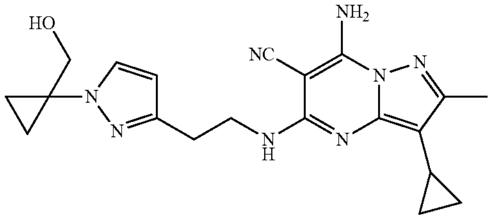

102. 7-amino-2-(difluoro methyl)-3-ethyl-5-((2-(1-(2-(hydroxymethyl) cyclobutyl)-1H-pyrazol-3-yl) ethyl) amino) pyrazolo[1,5-a] pyrimidine-6-carbonitrile;

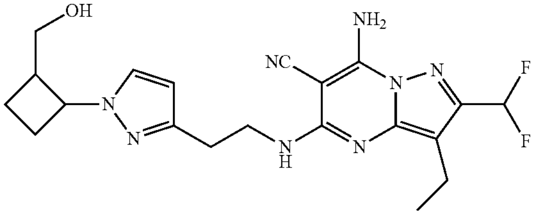

-continued 103. 104a, and 104b. (+-)-7-amino-5-((2-1-(2-(hydroxymethyl) cyclobutyl)-1H-pyrazol-3-yl)ethyl)amino-2,3-dimethylpyrazolo [1,5-a] pyrimidine-6-carbonitrile (103), (+)-7-amino-5-((2-(1-(2-(hydroxymethyl) cyclobutyl)-1H-pyrazol-3-yl)ethyl)amino)-2,3-dimethylpyrazolo[1,5-a]pyrimidine-6-carbonitrile(104a), (-)-7-amino-5-((2-(1-(2-(hydroxymethyl)cyclobutyl)-1H-pyrazol-3-yl) ethyl)amino)-2,3-dimethylpyrazolo[1,5-a]pyrimidine-6-carbonitrile(104b);

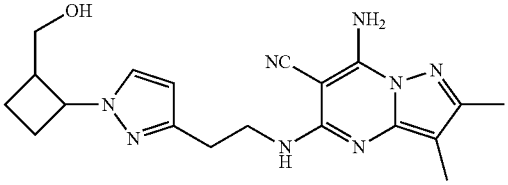

Example 103; racemic(±)
Example 104a; Peak 1; dextro(+) rotatory
Example 104b; Peak 2; leavo(-) rotatory 105. 7-amino-5-((2-(6-(((2-hydroxyethyl) amino) methyl) pyridin-2-yl) ethyl) amino)-2,3-dimethylpyrazolo[1,5-a] pyrimidine-6-carbonitrile;

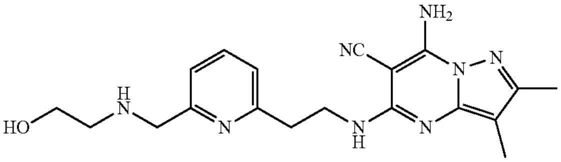

106. 7-amino-3-ethyl-5-((2-(1-(1-(((2-hydroxyethyl) amino) methyl) cyclopropyl)-1H-pyrazol-3-yl) ethyl) amino)-2-methylpyrazolo [1,5-a] pyrimidine-6-carbonitrile;

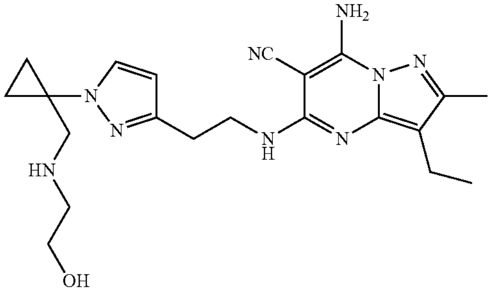

107. 7-amino-3-ethyl-5-((2-(1-(2-methoxyethyl-2-oxo-1,2-dihydropyridin-3-yl) ethyl) amino)-2-methylpyrazolo[1,5-a] pyrimidine-6-carbonitrile;

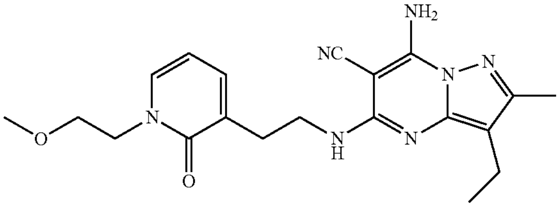

108. 7-amino-3-ethyl-5-((2-(1-(2-hydroxyethyl-2-oxo-1,2-dihydropyridin-3-yl) ethyl) amino)-2-methylpyrazolo[1,5-a] pyrimidine-6-carbonitrile;

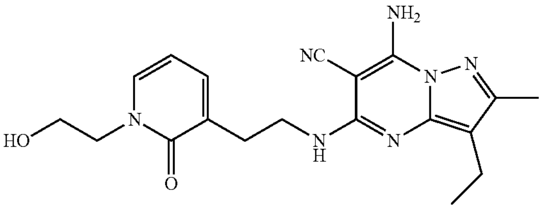

-continued 109. 7-amino-5-((2-(1-(2-(amino methyl) cyclobutyl)-1H-pyrazol-3-yl) ethyl) amino)-3-ethyl-2-methylpyrazolo[1,5-a] pyrimidine-6-carbonitrile;

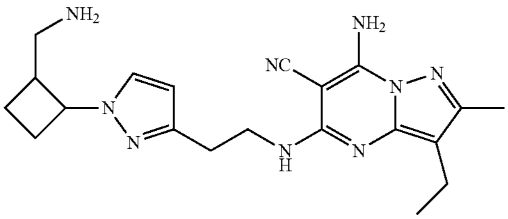

110. 7-amino-3-ethyl-5-((2-(1-(3-hydroxypropyl)-1H-pyrazol-5-yl) ethyl) amino)-2-methylpyrazolo[1,5-a] pyrimidine-6-carbonitrile;

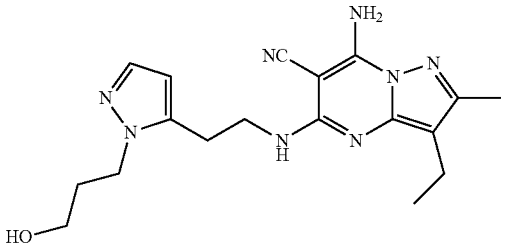

111. 7-amino-3-ethyl-5-((2-(1-(3-hydroxypropyl)-1H-pyrazol-3-yl) ethyl) amino)-2-methylpyrazolo[1,5-a] pyrimidine-6-carbonitirle;

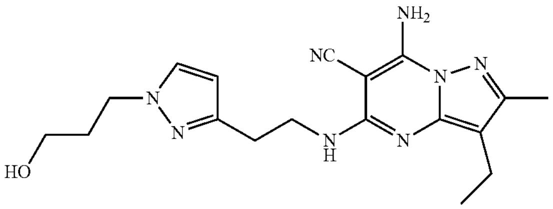

112. 7-amino-3-chloro-5-((2-(1-(1-(2-hydroxyethyl) cyclopropyl)-1H-pyrazol-3-yl) ethyl) amino)-2-methylpyrazolo[1,5-a] pyrimidine-6-carbonitrile;

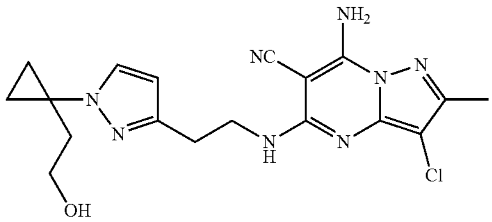

113. 7-amino-3-ethyl-5-((2-(1-(3-hydroxypropyl)-2-oxo-1,2-dihydropyridin-3-yl) ethyl) amino)-2-methylpyrazolo[1,5-a] pyrimidine-6-carbonitrile;

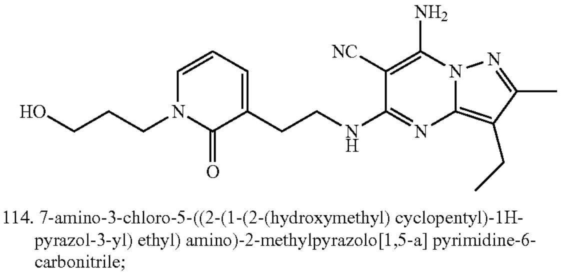

114. 7-amino-3-chloro-5-((2-(1-(2-(hydroxymethyl) cyclopentyl)-1H-pyrazol-3-yl) ethyl) amino)-2-methylpyrazolo[1,5-a] pyrimidine-6-carbonitrile;

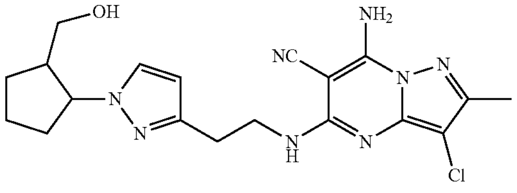

-continued 115. 7-amino-3-ethyl-5-((2-(1-(2-(hydroxymethyl) cyclopentyl)-1H-pyrazol-3-yl) ethyl) amino)-2-methylpyrazolo[1,5-a] pyrimidine-6-carbonitrile;

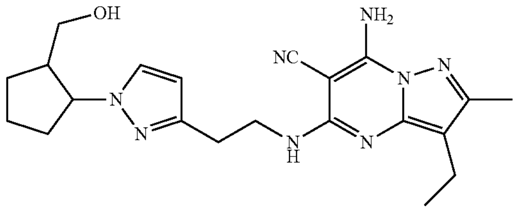

116. 7-amino-3-(cyclopropyl methyl)-5-((2-(1-(2-(hydroxymethyl) cyclobutyl)-1H-pyrazol-3-yl) ethyl) amino)-2-methylpyrazolo [1,5-a] pyrimidine-6-carbonitrile;

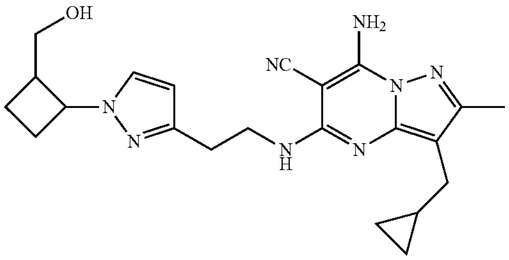

117. 7-amino-3-chloro-5-((2-(1-(2-(((2-hydroxyethyl) amino) methyl) cyclobutyl)-1H-pyrazol-3-yl) ethyl) amino)-2-methylpyrazolo [1,5-a] pyrimidine-6-carbonitrile;

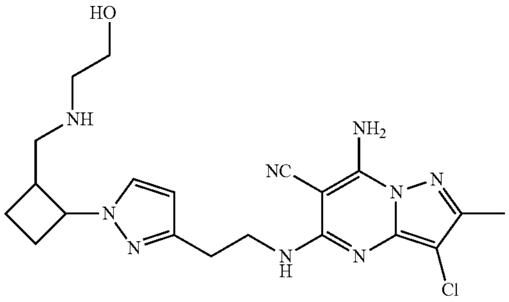

118. 7-amino-5-((2-(1-(2-(amino methyl) cyclopentyl)-1H-pyrazol-3-yl) ethyl) amino)-3-chloro-2-methylpyrazolo[1,5-a] pyrimidine-6-carbonitrile;

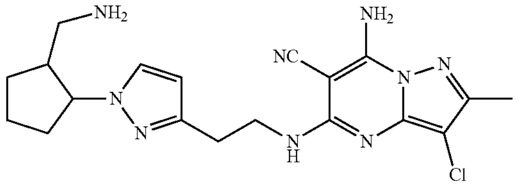

119. 7-amino-3-chloro-2-methyl-5-((2-(6-methylpyridin-2-yl) ethyl) amino) pyrazolo[1,5-a] pyrimidine-6-carbonitrile;

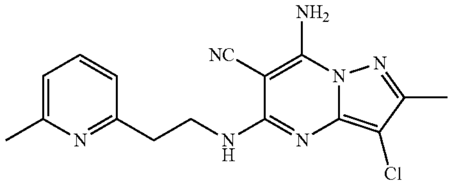

120. 7-amino-3-chloro-5-((2-(6-ethylpyridin-2-yl) ethyl) amino)-2-methylpyrazolo[1,5-a] pyrimidine-6-carbonitrile;

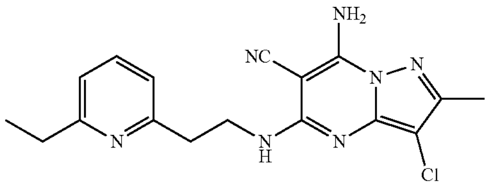

-continued 121. (+-)-7-amino-3-ethyl-5-((2-(1-4-(hydroxymethyl)tetrahydrofuran-3-yl)-1H-pyrazol-3-yl)ethyl)amino)-2-methyl pyrazolo[1,5-a] pyrimidine-6-carbonitrile;

122a. (+)-7-amino-3-ethyl-5-((2-(1-(4-(hydroxy methyl)tetrahydrofuran-3-yl)-1H-pyrazol-3-yl)ethyl)amino)-2-methyl pyrazolo[1,5-a] pyrimidine-6-carbonitrile;

122b. (-)-7-amino-3-ethyl-5-((2-(1-(4-(hydroxy emthyl)tetrahydrofuran-3-yl)1H-pyrazol-3-yl)ethyl)amino)-2-methyl pyrazolo[1,5-a] pyrimidine-6-carbonitrile;

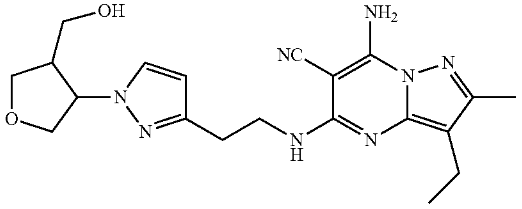

Example 121; racemic(±)
Example 122a; Peak 1;dextro(+) rotatory
Example 122b; Peak 2;leavo(-) rotatory 123. 7-amino-3-ethyl-5-((2-(1-(3-(hydroxymethyl) cyclobutyl)-1H-pyrazol-3-yl) ethyl) amino)-2-methylpyrazolo[1,5-a] pyrimidine-6-carbonitrile;

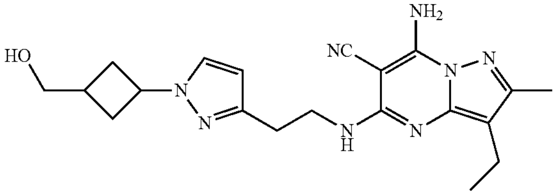

124. 7-amino-3-ethyl-5-((2-(1-(1-(2-hydroxyethyl) cyclopropyl)-1H-pyrazol-3-yl) ethyol) amino)-2-methylpyrazolo[1,5-a] pyrimidine-6-carbonitrile;

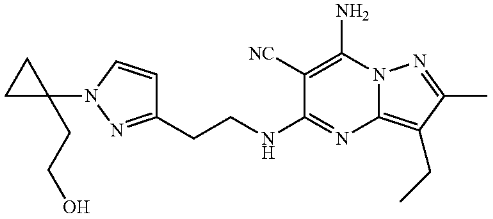

125. 7-amino-5-((2-(1-(2-aminoethyl)-2-oxo-1,2-dihydropyridin-3-yl) ethyl) amino)-3-chloro-2-methylpyrazolo[1,5-a] pyrimidine-6-carbonitrile;

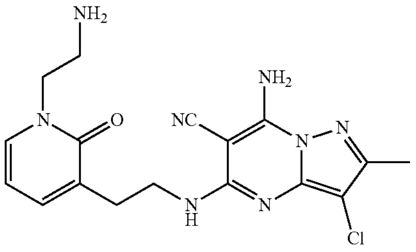

126. 7-amino-5-((2-(1-(2-aminoethyl)-2-oxo-1,2-dihydropyridin-3-yl) ethyl) amino)-3-ethyl-2-methylpyrazolo[1,5-a] pyrimidine-6-carbonitrile;

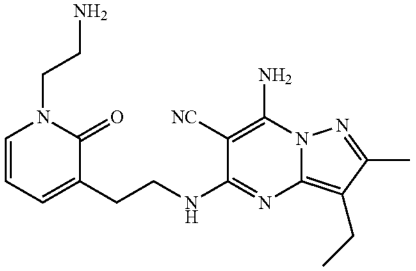

-continued 127. 7-amino-3-chloro-5-((2-(1-(4-(hydroxymethyl) tetrahydrofuran-3-yl)-1H-pyrazol-3-yl) ethyl) amino)-2-methylpyrazolo[1,5-a] pyrimidine-6-carbonitrile;

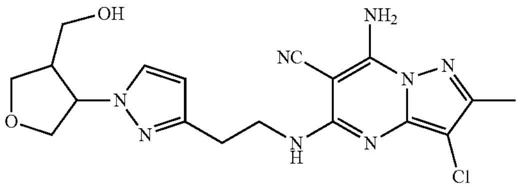

128. 7-amino-3-ethyl-5-((2-(1-((3-hydroxycyclobutyl) methyl)-2-oxo-1,2-dihydropyridin-3-yl) ethyl) amino)-2-methylpyrazolo[1,5-a] pyrimidine-6-carbonitrile;

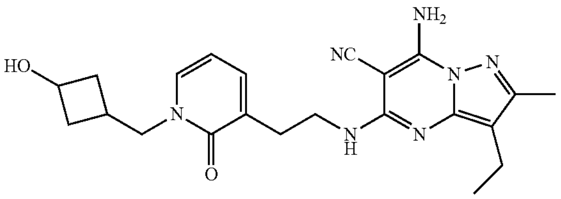

129. 7-amino-5-(92-(1-(3-aminopropyl)-2-oxo-1,2-dihydropyridin-3-yl) ethyl) amino)-3-chloro-2-methylpyrazolo[1,5-a] pyrimidine-6-carbonitrile;

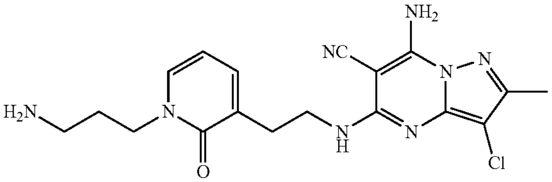

130. 7-amino-3-bromo-5-((2-(1-(2-(hydroxymethyl) cyclobutyl)-1H-pyrazol-3-yl) ethyl) amino)-2-methylpyrazolo[1,5-a] pyrimidine-6-carbonitrile;

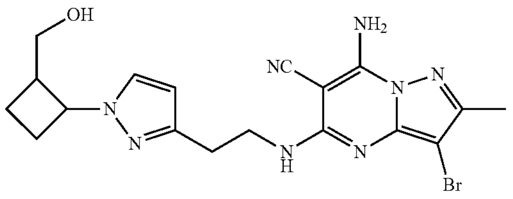

131. 7-amino-2-(difluoromethyl)-3-ethyl-5-((2-(1-(2-hydroxyethyl)-2-oxo-1,2-dihydropyridin-3-yl) ethyl) amino) pyrazolo[1,5-a] pyrimidine-6-carbonitrile;

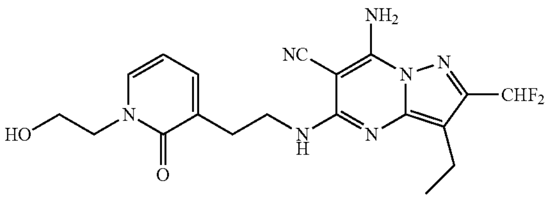

-continued 132. (+-)-7-amino-5-((2-(1-4-(hydroxymethyl) tetrahydrofuran-3-yl)-1H-pyrazol-3-yl) ethyl) amino)-2,3-dimethylpyrazolo[1,5-a] pyrimidine-6-carbonitrile;

133a. (+)-7-amino-5-((2-(1-(4-(hydroxymethyl) tetrahydrofuran-3-yl)-1H-pyrazol-3-yl) ethyl) amino)-2,3-dimethylpyrazolo[1.5-a] pyrimidine-6-carbonitrile;

133b. (-)-7-amino-5-((2-(1-(4-(hydroxymethyl) tetrahydrofuran-3-yl)-1H-pyrazol-3-yl) ethyl) amino)-2,3-dimethylpyrazolo[1,5-a] pyrimidine-6-carbonitrile;

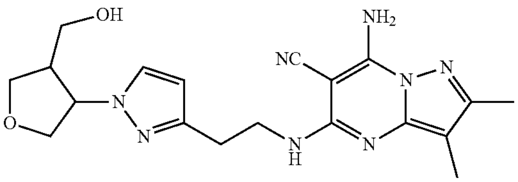

Example 132; racemic(±)
Example 133a; Peak 1;dextro(+) rotatory
Example 133b; Peak 2;leavo(-) rotatory 134. 2-(((2-(3-(2-((7-amino-6-cyano-3-ethyl-2-methylpyrazolo[1,5-a] pyrimidin-5-yl) amino) ethyl)-1H-pyrazol-1-yl) cyclobutyl) methyl) amino) acetamide;

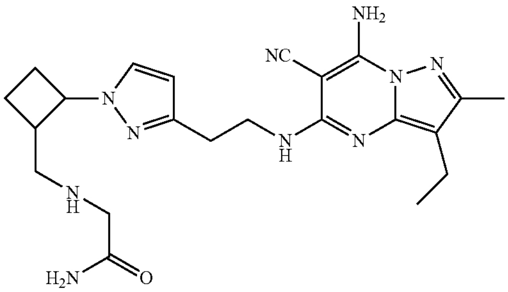

135. 7-amino-3-ethyl-2-methyl-5-((2-(6-(2,2,2-trifluoro-1-hydroxyethyl) pyridine-2-yl) ethyl) amino) pyrazolo[1,5-a] pyrimidine-6 carbonitrile;

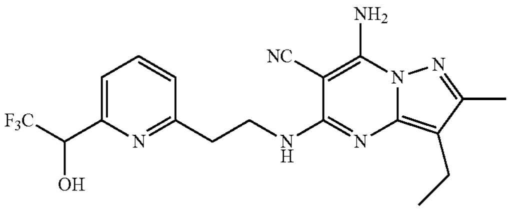

136. 7-amino-5-((2-(1-(3-aminopropyl)-2-oxo-1,2-dihydropyridin-3-yl) ethyl) amino)-3-ethyl-2-methylpyrazolo[1,5-a] pyrimidine-6-carbonitrile;

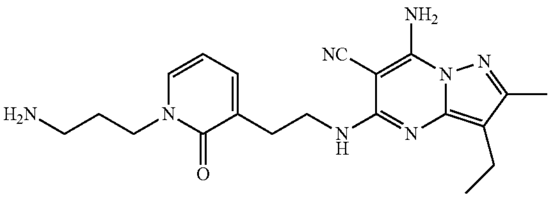

137. 7-amino-3-(cyclo butyl methyl)-5-((2-(1-(1-(hydroxymethyl) cyclopropyl)-1H-pyrazol-3-yl) ethyl) amino)-2-methylpyrazolo [1,5-a] pyrimicine-6-carbonitrile;

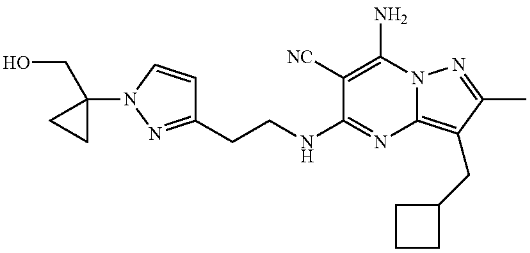

-continued 138. 7-amino-5-((2-(1-(3-hydroxypropyl)-2-oxo-1,2-dihydropyridin-3-yl) ethyl) amino)-2,3-dimethylpyrazolo[1,5-a] pyrimidine-6-carbonitrile;

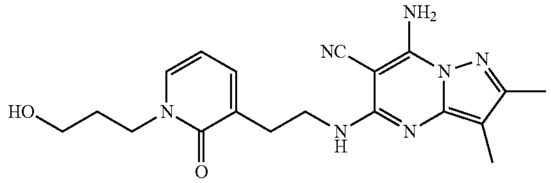

139. 7-amino-3-ethyl-5-((2-(6-(2-hydroxyethyl) pyridine-2-yl) ethyl) amino)-2-methylpyrazolo[1,5-a] pyrimidine-6-carbonitrile;

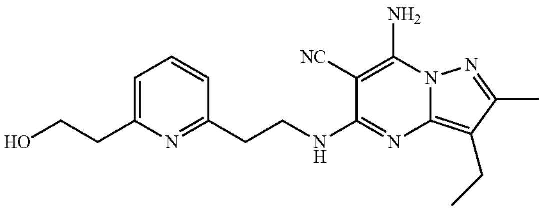

140. 7-amino-2,3-dimethyl-5-((2-(6-methylpyrazin-2-yl) ethyl) amino) pyrazolo[1.5-a] pyrimidine-6-carbonitrile;

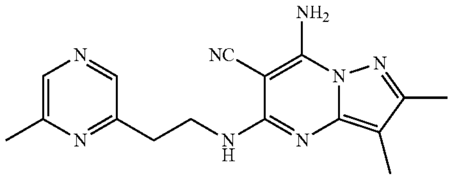

141. 7-amino-5-((2-(1-(3-aminopropyl)-2-oxo-1,2-dihydropyridin-3-yl) ethyl) amino)-2,3-dimethylpyrazolo[1,5-a] pyrimidine-6-carbonitrile;

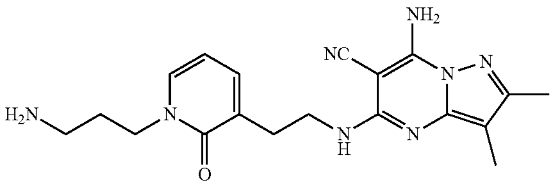

142. 7-amino-3-ethyl-2-methyl-5-((2-(1-(2-(methylthio) ethyl)-2-oxo-1,2-dihydropyridin-3-yl) ethyl) amino) pyrazolo[1,5-a]pyrimidine-6-carbonitrile;

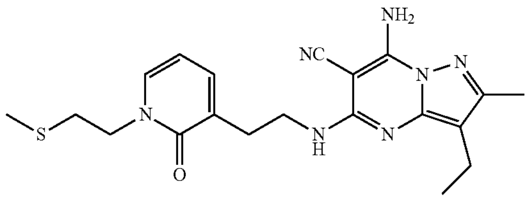

-continued

143. Racemic (+-)7-amino-3-ethyl-2-methyl-5-((2-(1-(2-(methyl sulfinyl) ethyl)-2-oxo-1,2-dihydropyridin-3-yl) ethyl) amino) pyrazolo[1.5-a] pyrimidine-6-carbonitrile;

144a. (+)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a] pyrimidine-6-carbonitrile;

144b. (-)7-amino-3-ethyl-2-methyl-5-((2-(1-(2-(methyl sulfinyl) ethyl)-2-oxo-1,2-dihydropyridin-3-yl) ethyl) amino) pyrazolo[1.5-a] pyrimidine-6-carbonitrile;

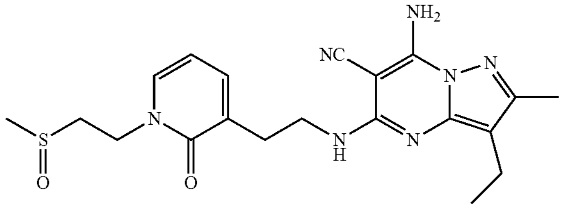

Example 143; racemic(±)
Example 144a; Peak 1;dextro(+) rotatory
Example 144b; Peak 2;leavo(-) rotatory 145. N-(3-(3-(2-((7-amino-6-cyano-3-ethyl-2-methylpyrazolo[1,5-a] pyrimidin-5-yl) amino) ethyl)-2-oxopyridin-1(2H)-yl) propyl) acetamide;

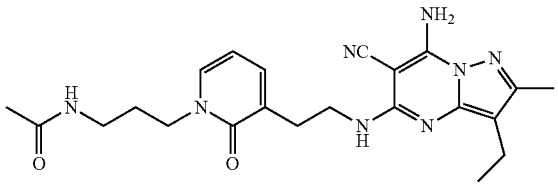

146. 7-amino-5-((2-(1-(1-(amino methyl) cyclopropyl)-1H-pyrazol-3-yl) ethyl) amino)-3-ethyl-2-methylpyrazolo[1,5-a] pyrimidine-6-carbonitrile;

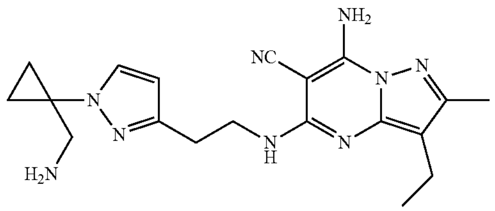

147. N-((1-(3-(2-((7-amino-6-cyano-3-ethyl-2-methylpyrazolo[1,5-a] pyrimidin-5-yl) amino) ethyl)-1H-pyrazol-1-yl) cyclopropyl) methyl) acetamide;

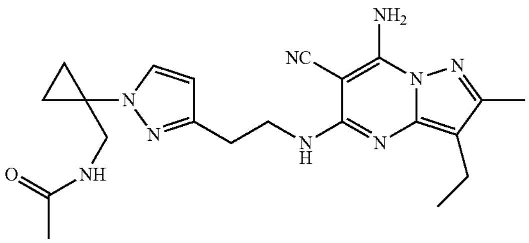

148. 7-amino-5-((2-(1-(1-(2-aminoethyl) cyclopropyl)-1H-pyrazol-3-yl) ethyl) amino)-3-ethyl-2-methylpyrazolo[1,5-a] pyrimidine-6-carbonitrile;

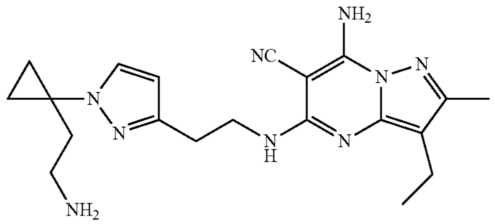

-continued

149. N-(2-(1-(3-(2-((7-amino-6-cyano-3-ethyl-2-methylpyrazolo[1,5-a] pyrimidin-5-yl) amino) ethyl)-1H-pyrazol-1-yl) cyclopropyl) ethyl) acetamide;

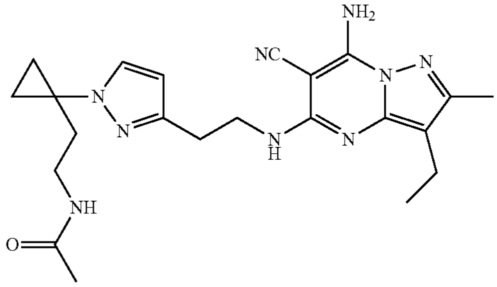

150. 7-amino-3-ethyl-5-(92-(6-(2-hydroxyethoxy)61yridine-2-yl) ethyl) amino)-2-methylpyrazolo[1,5-a] pyrimidine-6-carbonitrile;

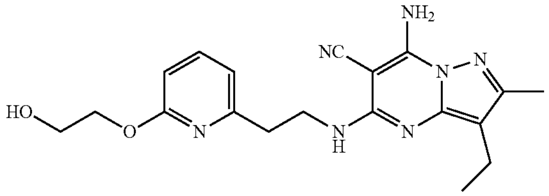

151. 7-amino-5-((2-(1-(1-(2-aminoethyl) cyclopropyl)-1H-pyrazol-3-yl) ethyl) amino)-3-chloro-2-methylpyrazolo[1,5-a] pyrimidine-6-carbonitrile;

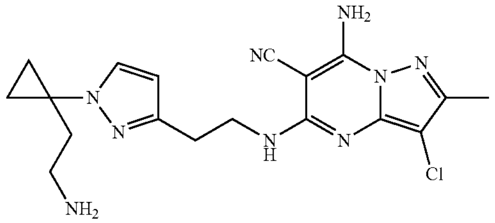

152. 7-amino-5-((2-(6-(2-hydroxyethyl)61yridine-2-yl) ethyl) amino)-2,3-dimethylpyrazolo[1,5-a] pyrimidine-6-carbonitrile;

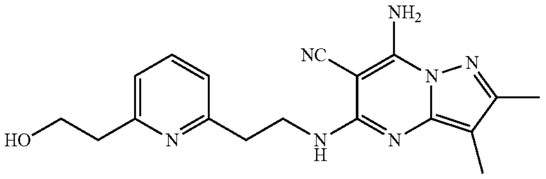

153. 7-amino-3-ethyl-2-methyl-5-((2-(1-(3-(methylthio) propyl)-2-oxo-1,2-dihydropyridin-3-yl) ethyl) amino) pyrazolo[1,5-a] pyrimidine-6-carbonitrile;

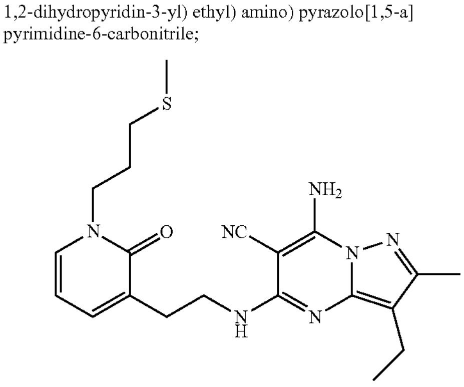

-continued 154a. (-)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a] pyrimidine-6-carbonitrile;

154b. (+)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a] pyrimidine-6-carbonitrile;

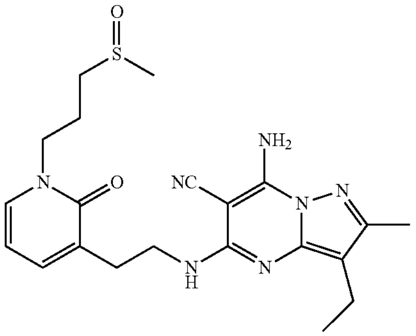

Example 154a; Peak 1; leavo (-) rotatory
Example 154b; Peak 2; dextro (+) rotatory 155. 7-amino-3-ethyl-5-((2-(6-(3-hydroxypropyl) pyridin-2-yl) ethyl) amino)-2-methylpyrazolo[1,5-a] pyrimidine-6-carbonitrile;

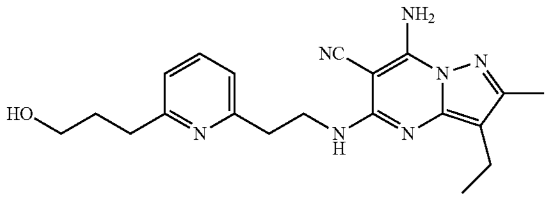

156. 7-amino-5-((2-(1-(3-hydroxypropyl)-2-oxo-1,2-dihydropyridin-3-yl) ethyl) amino)-2-methyl-3-propylpyrazolo[1,5-a] pyrimidine-6-carbonitrile;

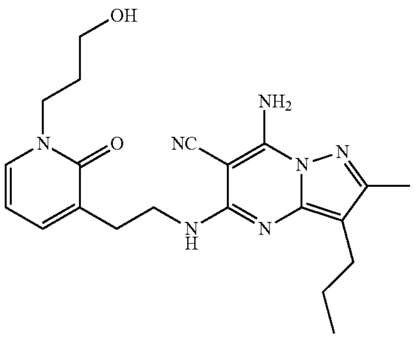

157. 7-amino-5-((2-(6-(hydroxymethyl)63yridine-2-yl) ethyl) amino)-2-methyl-3-propylpyrazolo[1,5-a] pyrimidine-6-carbonitrile;

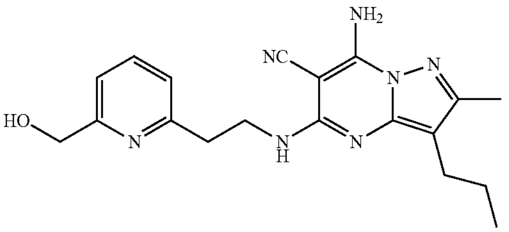

-continued 158. 7-amino-5-((2-(1-(1-(hydroxymethyl) cyclorpopyl)-1H-pyrazol-3-yl) ethyl) amino)-2-methyl-3-propylpyrazolo[1,5-a] pyrimidine-6-carbonitrile;

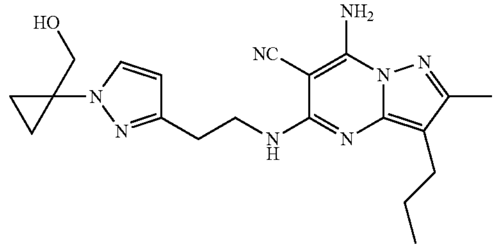

159a. (+)-7-amino-3-ethyl-5-((2-(6-(1-hydroxyethyl_ pyridin-2-yl) ethyl) amino)-2-methylpyrazolo[1,5-a] pyrimidine-6-carbonitrile;

159b. (-)-7-amino-3-ethyl-5-((2-(6-(1-hydroxyethyl) pyridine-2-yl) ethyl) amino)-2-methylpyrazolo[1,5-a] pyrimidine-6-carbonitrile;

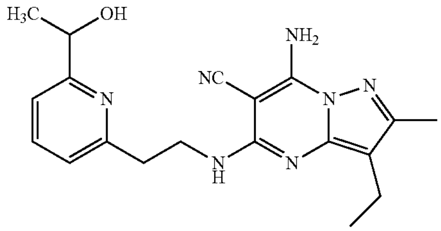

Example 159a Peak1: dextro(+) rotatory
Example 159b Peak1: leavo(-) rotatory 160a. (+) 7-amino-5-((2-(1-(4-(hydroxymethyl) tetrahydrofuran-3-yl)-1H-pyrazol-3-yl) ethyl) amino)-2-methyl-3-propylpyrazolo[1,5-a] pyrimidine-6-carbonitrile;

160b. (-) 7-amino-5-((2-(1-(4-(hydroxymethyl) tetrahydrofuran-3-yl)-1H-pyrazol-3-yl) ethyl) amino)-2-methyl-3-propylpyrazolo [1,5-a] pyrimidine-6-carbonitrile;

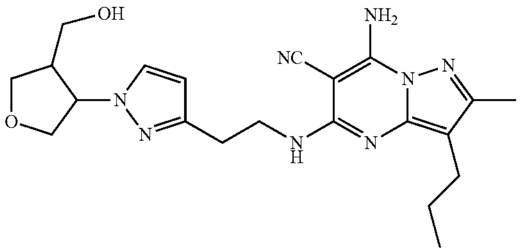

Example 160a; Peak1; Dextro(+) rotatory
Example 160b; Peak2; leavo(-) rotatory 161. 7-amino-3-ethyl-2-methyl-5-((2-(1-(3-(methylthio) propyl)-1H-pyrazol-3-yl) ethyl) amino) pyrazolo[1,5-a] pyrimidine-6-carbonitrile;

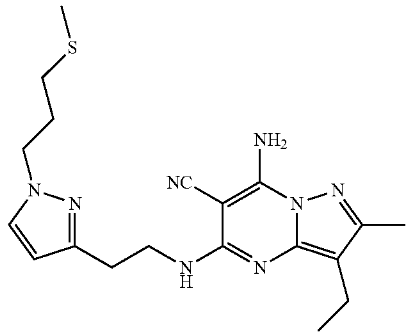

-continued 162a. (-)-7-amino-3-ethyl-2-methyl-5-((2-(1-(3-(methyl sulfinyl) propyl)-1H-pyrazol-3-yl) ethyl) amino) pyrazolo[1,5-a] pyrimidine-6-carbonitrile;

162b. (+)-7-amino-3-ethyl-2-methyl-5-((2-(1-(3-(methylsulfinyl) propyl)-1H-pyrazol-3-yl)ethyl)amino)pyrazolo[1,5-a] pyrimidine-6-carbonitrile;

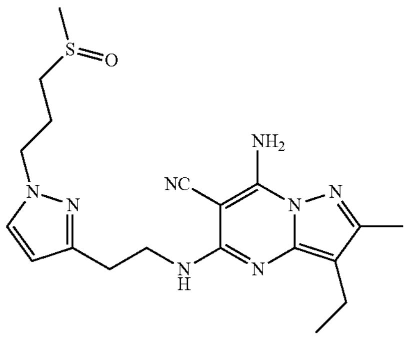

Peak 1; Example 162a; leavo (-) rotatory
Peak 2; Example 162b; dextro (+) rotatory 163a. (-)- 7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a]pyrimidine-6-carbonitrile;

163b. (+)-7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a] pyrimidine-6-carbonitrile;

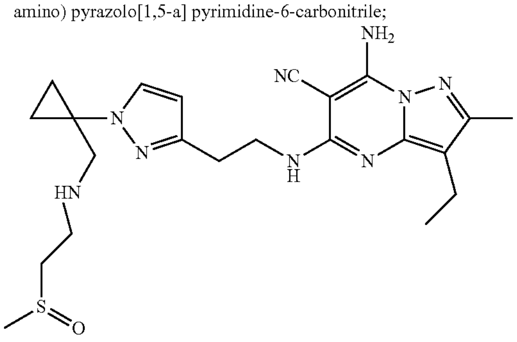

Peak 1; Example 163a; leavo (-) rotatory
Peak 2; Example 163b; dextro (+) rotatory 164. 7-amino-2-methyl-5-((2-(6-methylpyridin-2-yl) ethyl) amino)-3-propylpyrazolo[1,5-a] pyrimidine-6-carbonitrile;

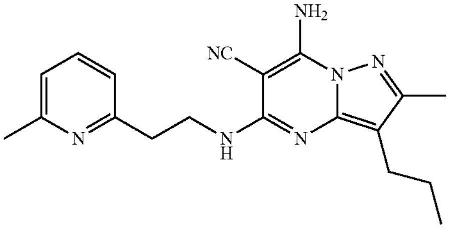

-continued 165a. (+)-7-amino-5-(92-(1-(2-(hydroxymethyl) cyclobutyl)-1H-pyrazol-3-yl) ethyl) amino)-2-methyl-3-propylpyrazolo[1,5-a] pyrimidine-6-carbonitrile;

165b. (-)-7-amino-5-((2-(1-(2-(hydroxymethyl) cyclobutyl)-1H-pyrazol-3-yl) ethyl) amino)-2-methyl-3-propylpyrazolo[1,5-a] pyrimidine-6-carbonitrile;

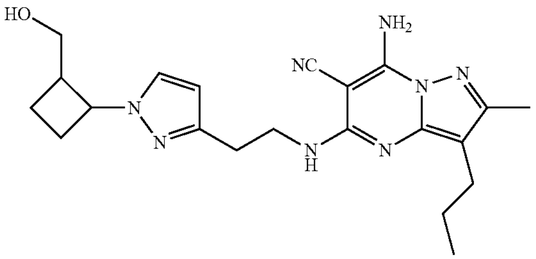

Peak 1; Example 165a; dextro (+) rotatory
Prak 2; Example 165b; leavo (-) rotatory 166. (R)-7-amino-3-ethyl-2-methyl-5-((2-(6-(((tetrahydrofuran-3-yl) oxy) methyl) pyridine-2-yl) ethyl) amino) pyrazolo[1,5-a] pyrimidine-6-carbonitrile;

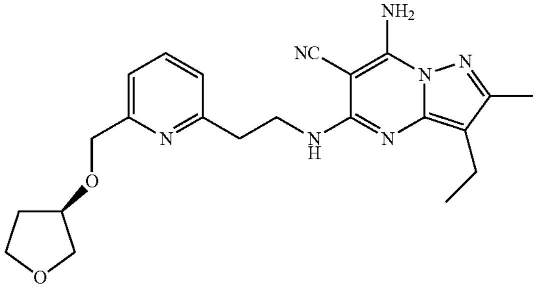

167. (-)-7-amino-3-ethyl-5-(92-(1-(4-(hydroxymethyl) tetrahydrofuran-3-yl)-5-methyl-1H-pyrazol-3-yl) ethyl) amino-2-methylpyrazolo [1,5-a] pyrimidine-6-carbonitrile; and

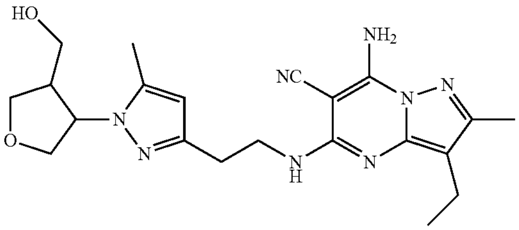

Example 167: Peak 1: Levo (-) rotatory 168. (+) - 7-amino-3-ethyl-5-((2-(1-(4-(hydroxymethyl) tetrahydrofuran-3-yl)-5-methyl-1H-pyrazol-3-yl) ethyl) amino)-2-methylpyrazolo [1,5-a] pyrimidine-6-carbonitrile.

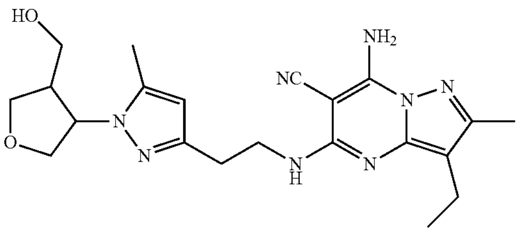

Example 168: Peak 2: Dextro (+) rotatory

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof as disclosed herein, for use as a medicament.

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof, as an antagonist of adenosine 2a receptor ($A_{2a}R$) or adenosine 2b receptor ($A_{2b}R$) or combination of adenosine 2a receptor ($A_{2a}R$) and adenosine 2b receptor ($A_{2b}R$).

In an embodiment of the present disclosure, there is provided a compound of Formula I or its pharmaceutically acceptable salts, complexes, hydrates, solvates, tautomers, polymorphs, stereoisomers, racemates, pharmaceutically active derivatives thereof as disclosed herein for use in treating of a disease, disorder or condition selected from cancer, parkinson's disease, asthma, diabetes, and autoimmune disease mediated at least in part by adenosine 2a receptor ($A_{2a}R$) or adenosine 2b receptor ($A_{2b}R$) or combination of $A_{2a}R$ and $A_{2b}R$.

In an embodiment of the present disclosure, there is provided a process of preparation of compounds of Formula I or its pharmaceutically acceptable salts, complexes, hydrates, solvates, tautomers, polymorphs, stereoisomers, racemates, pharmaceutically active derivatives thereof as disclosed herein, said process comprising: reacting Formula (A), and Formula (B) in the presence of a base to obtain the compounds of Formula I

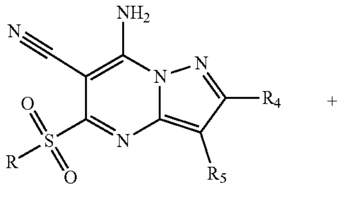

Formula (A)

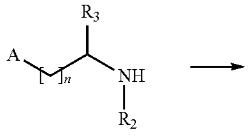

Formula (B)

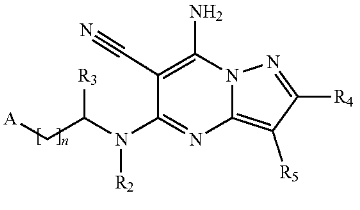

Formula (I)

wherein R is selected from $C_{1-6}$ alkyl, $C_{3-6}$ cycloalkyl, $C_{5-10}$ aryl, $C_{2-10}$ heteroaryl, or $C_{1-10}$ heterocyclyl; and the substituents are as disclosed herein.

In an embodiment of the present disclosure, there is provided a process of preparation of compounds of Formula I or its pharmaceutically acceptable salts, complexes, hydrates, solvates, tautomers, polymorphs, stereoisomers, racemates, pharmaceutically active derivatives thereof as disclosed herein, wherein the base is selected from triethylamine, diisopropylethylamine, pyridine, sodium carbonate, potassium carbonate, sodium hydroxide, potassium tertiarybutoxide potassium tertiarybutoxide, sodium hydride, lithium bis(trimethylsilyl)amide (LiHMDS), N-diisopropylethylamine, or combinations thereof.

In an embodiment of the present disclosure, there is provided a process of preparation of compounds of Formula I or its pharmaceutically acceptable salts, complexes, hydrates, solvates, tautomers, polymorphs, stereoisomers, racemates, pharmaceutically active derivatives thereof as disclosed herein, wherein the process is carried out in the presence of a solvent selected from isopropanol, methanol, n-butanol, dichloromethane, tetrahydrofuran, dimethylformaide, n-methylpyrrolidone, dimethyl sulfoxide, water, dioxane, acetonitrile, or combinations thereof.

In an embodiment of the present disclosure, there is provided a pharmaceutical composition comprising compounds of Formula I as disclosed herein and one or more additional therapeutic agent.

In an embodiment of the present disclosure, there is provided a pharmaceutical composition comprising compounds of Formula I with one or more additional therapeutic agent selected from chemotherapeutic agent, immune checkpoint inhibitors or combinations thereof. In another embodiment of the present disclosure, there is a pharmaceutical composition comprising compounds of Formula I as disclosed herein wherein the one or more additional therapeutic agent is chemotherapeutic agent or immune checkpoint inhibitors.

In an embodiment of the present disclosure, there is provided a pharmaceutical composition as disclosed herein, wherein the one or more additional therapeutic agent is the chemotherapeutic agent selected from phosphoinositide 3-kinase inhibitor (PI3K) inhibitor, tyrosine kinase inhibitor, signal transducer and activator of transcription 3 (Stat-3) inhibitor, topoisomerase inhibitors, Protein kinase B (AKT) inhibitor, c-Jun N-terminal kinase (JNK1/K2) inhibitors, hypoxia-inducible factor 1 alpha (HIF-1a) inhibitor, extracellular signal-regulated kinase (ERK) inhibitor, poly ADP ribose polymerase-1((PARP-1) inhibitor, cisplatin, or oxaplatin.

In an embodiment of the present disclosure, there is provided a pharmaceutical composition as disclosed herein, wherein the one or more additional therapeutic agent is the immune checkpoint inhibitor selected from programmed death-1 (PD-1) inhibitor, programmed death-ligand 1 (PD-L1) inhibitor, anti-PD1 antibody, anti-PD-L1 antibody, cytotoxic T-lymphocyte-associated protein 4 (CTLA-4) inhibitor, anti-CTLA-4 antibody, T cell immunoglobulin and mm domain (TIGIT) inhibitor, ecto-nucleoside triphosphate diphosphohydrolase 1(E-NTPDase, CD39) inhibitor, or ecto-5'-nucleotidase(Ecto5'NTase, CD79) inhibitor.

In an embodiment of the present disclosure, there is provided a pharmaceutical composition comprising the compounds of Formula I or its pharmaceutically acceptable salts, complexes, hydrates, solvates, tautomers, polymorphs, stereoisomers, pharmaceutically active derivatives thereof with one or more additional therapeutic agent selected from chemotherapeutic agent or immune checkpoint inhibitors and wherein the one or more additional therapeutic agent selected from phosphoinositide 3-kinase inhibitor (PI3K) inhibitor, tyrosine kinase inhibitor, signal transducer and activator of transcription 3 (Stat-3) inhibitor, topoisomerase inhibitors, Protein kinase B (AKT) inhibitor, c-Jun N-terminal kinase (JNK1/K2) inhibitors, hypoxia-inducible factor 1 alpha (HIF-1a) inhibitor, extracellular signal-regulated kinase (ERK) inhibitor, poly ADP ribose polymerase-1 ((PARP-1) inhibitor, cisplatin, oxaplatin, programmed death-1 (PD-1) inhibitor, programmed death-ligand 1 (PD-L1) inhibitor, anti-PD1 antibody, anti-PD-L1 antibody, cytotoxic T-lymphocyte-associated protein 4 (CTLA-4)inhibitor, anti-CTLA-4 antibody, T cell immunoglobulin and ITIM domain (TIGIT) inhibitor, ecto-nucleoside triphosphate diphosphohydrolase 1(E-NTPDase, CD39) inhibitor, or ecto-5'-nucleotidase(Ecto5'NTase, CD79) inhibitor.

In an embodiment of the present disclosure, there is provided a method of treatment and/or prevention of a condition mediated by adenosine receptor or a proliferative disorder or a disease or cancer, comprising administering to a subject suffering from a condition mediated by adenosine receptor or a disease or proliferative disorder or a disease or cancer, a therapeutically effective amount of the compounds of Formula I as disclosed herein or the pharmaceutical composition comprising the compounds of Formula I with one or more additional therapeutic agent.

In an embodiment of the present disclosure, there is provided a method of treatment and/or prevention of a condition mediated by adenosine receptor or a proliferative disorder or a disease or cancer, comprising administering to a subject suffering from a condition mediated by adenosine receptor or proliferative disorder or a disease or cancer, a therapeutically effective amount of the compounds of Formula I as disclosed herein or the pharmaceutical composition comprising the compounds of Formula I with one or more additional therapeutic agent, wherein the condition mediated by adenosine receptor or a proliferative disorder or a disease or a cancer at least in part by adenosine 2a receptor ($A_{2a}R$), adenosine 2b receptor ($A_{2b}R$), or combinations thereof.

In an embodiment of the present disclosure, there is provided a method of treatment and/or prevention of a condition mediated by adenosine receptor or a proliferative disorder or cancer, comprising administering to a subject suffering from a condition mediated by adenosine receptor or a disease or proliferative disorder or cancer, a therapeutically effective amount of the compounds of Formula I as disclosed herein or the pharmaceutical composition as disclosed herein, wherein the compounds of Formula (I) administered in an effective amount to reverse or stop the progression of either the adenosine 2a receptor ($A_{2a}R$), or adenosine 2b receptor ($A_{2b}R$), or both mediated immunosuppression.

In an embodiment of the present disclosure, there is provided a method of treatment and/or prevention of a condition mediated by adenosine receptor or a proliferative disorder or a disease or cancer, comprising administering to a subject suffering from a condition mediated by adenosine receptor or proliferative disorder or a disease or cancer, a therapeutically effective amount of the compounds of Formula I as disclosed herein or the pharmaceutical composition as disclosed herein, wherein the proliferative disorder or disease is cancer or an immune response related disorder or disease or condition.

In an embodiment of the present disclosure, there is provided a method of treatment and/or prevention of a condition mediated by adenosine receptor or a proliferative disorder or disease or cancer, comprising administering to a subject suffering from a condition mediated by adenosine receptor or a disease or proliferative disorder or cancer, a therapeutically effective amount of the compounds of Formula I as disclosed herein or the pharmaceutical composition as disclosed herein, wherein the cancer is of adrenal gland, brain, bladder, breast, bone, colon, endometrial, oesophagus, head, gastric, kidney, liver, lung, mouth, muscle, neck, pancreas, prostate, retinal, skin, thyroid or white blood cells and said immune related disease, disorder or condition is selected from the group consisting of allergies, alzheimer, asthma, crohn's disease, colitis, chronic obstructive pulmonary disease, diabetic kidney disorders, glaucoma, lupus, rheumatoid arthritis, multiple sclerosis, pain, panic disorder, pancreatitis, parkinson disease, psoriasis, systemic sclerosis, and ulcerative colitis.

In an embodiment of the present disclosure, there is provided a use of the compounds of Formula I as disclosed herein or the pharmaceutical composition as disclosed herein for treatment of a condition mediated by adenosine receptor $A_{2a}R$; treatment and/or prevention of a proliferative disorder or disease or cancer or immune related disorder or disease or condition; or treatment of cancer together with other clinically relevant cytotoxic agents or non-cytotoxic agents.

In an embodiment of the present disclosure, there is provided a use of the compounds of Formula I as disclosed herein or the pharmaceutical composition as disclosed herein for treatment of a condition mediated by adenosine receptor $A_{2b}R$; treatment and/or prevention of a proliferative disorder or disease or cancer or immune related disorder or disease or condition; or treatment of cancer together with other clinically relevant cytotoxic agents or non-cytotoxic agents.

In an embodiment of the present disclosure, there is provided a use of the compounds of Formula I as disclosed herein or the pharmaceutical composition as disclosed herein for treatment of a condition mediated by adenosine receptors $A_{2a}R$ and $A_{2b}R$; treatment and/or prevention of a proliferative disorder or disease or cancer or immune related disorder or disease or condition; or treatment of cancer together with other clinically relevant cytotoxic agents or non-cytotoxic agents.

EXAMPLES

As used herein the symbols and conventions used in these processes, schemes and examples are consistent with those used in the contemporary scientific literature. Unless otherwise noted, all starting materials were obtained from commercial suppliers and used without further purification. Specifically, the following abbreviations may be used in the examples and throughout the specification:

Abbreviations

The following abbreviations are employed in the examples and elsewhere herein:

TLC—thin layer chromatography;
HPLC—high pressure liquid chromatography;
MPLC—medium pressure liquid chromatography;
NMR—nuclear magnetic resonance spectroscopy;
DMSO—dimethylsulfoxide;
$CDCl_3$—deuterated chloroform;
MeOD—deuterated methanol, i.e. $D_3COD$;
MS—mass spectroscopy; ESP (or ES)—electrospray; EI—electron impact; APCI—atmospheric pressure chemical ionization;
THF—tetrahydrofuran;
DCM—dichloromethane;
MeOH—methanol;
DMF—dimethylformamide;
EtOAc—ethyl acetate;
LC/MS—liquid chromatography/mass spectrometry;
h—hour(s); min is minute(s);
d—day(s);
MTBD—N-methyl-1,5,7-triazabicyclo[4.4.0]dec-5-ene;
TFA—trifluoroacetic acid; v/v—ratio of volume/volume;
Boc—t-butoxycarbonyl;
Cbz—benzyloxycarbonyl;
Bz—benzoyl;

Atm—atmospheric pressure;
rt—room temperature;
mg—milligram; g denotes gram;
μL—microliter;
mL—milliliter;
L—liter;
μM—micromolar;
nM—Nanomolar
mM—millimolar; M denotes molar;
DMAP—dimethyaminopyridine;
TBDMS—tert-butyldimethylsilyl
N—normal; and
nm—nanometer.

The following examples provide the details about the synthesis, activities and applications of the compounds of the present disclosure. It should be understood the following is representative only, and that the invention is not limited by the details set forth in these examples.

Materials and Methods

Evaporations were carried out by rotary evaporation in vacuo and work up procedures were carried out after removal of residual solids by filtration; temperatures are quoted as ° C.; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kieselgel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the invention was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (* scale) and peak multiplicities are shown thus: s, singlet; d, doublet; dd, doublet of doublets; dt, doublet of triplets; dm, doublet of multiplets; t, triplet, m, multiplet; br, broad. Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 Å particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

General Process for the Preparation of the Compounds of Formula (A)

Compounds of formula (A) was prepared from formula (F) via oxidation using appropriate oxidizing agents (e.g., mCPBA) and the compounds of formula (F) was synthesized by reacting compounds of formula (D) with formula (E) in presence of appropriate base (e.g., pyridine). The formula (D) was obtained by treating formula (C) with carbon disulphide and methyl iodide in presence of appropriate base (e.g., sodium hydride) (Scheme 1).

Scheme 1

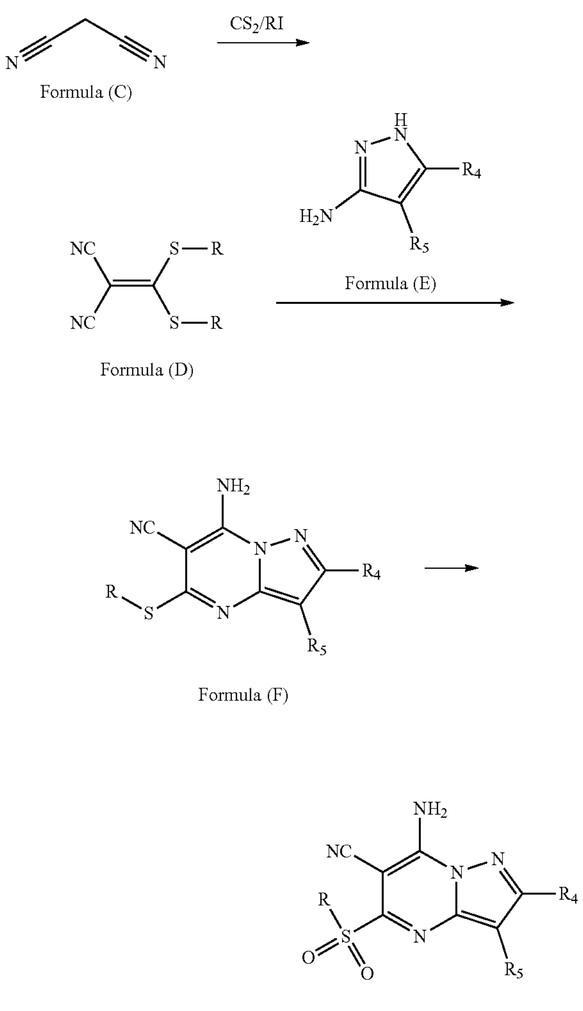

Formula (C)
Formula (E)
Formula (D)
Formula (F)
Formula (A)

General Process for the Preparation of the Compounds of Formula B

The preparation of compounds of Formula (B) may be prepared in a variety of ways and many of them are commercially available. The generic route for Formula (B) is given Scheme 2 wherein, the formula (B) was obtained by treating a carbonyl compound of Formula (B1) with an amine of Formula (B2) with suitable reducing reagent.

Scheme 2
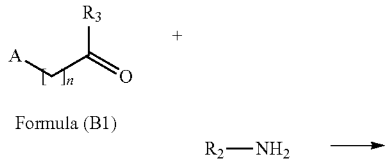
Formula (B1)
Formula (B2)
-continued
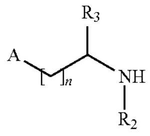
Formula (B)
Further, the processes for one of the representative compounds of formula(B) wherein A is six membered rings shown as formula (N) in scheme 3.
Scheme 3
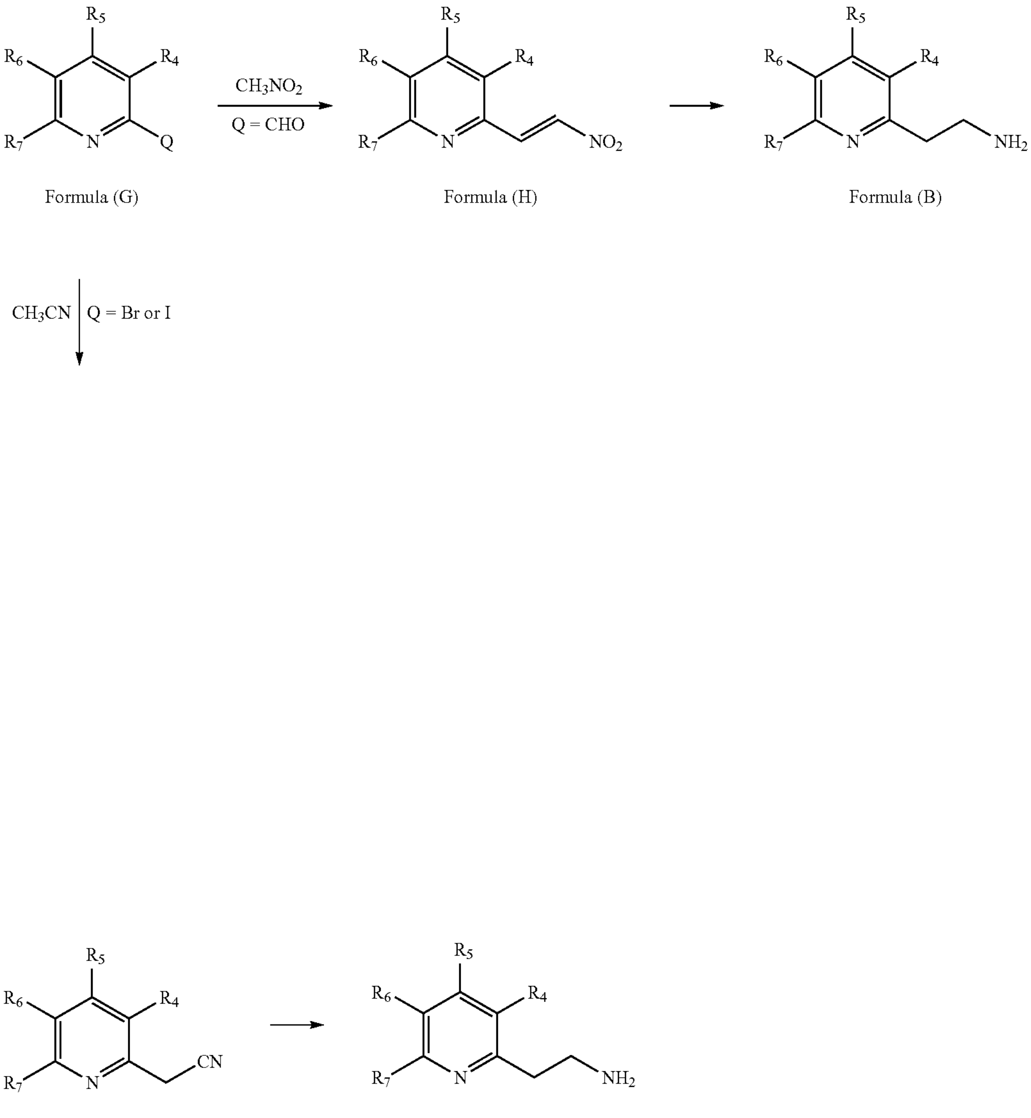
Formula (G)
Formula (H)
Formula (B)
Formula (I)
Formula (B)

The compounds of Formula (B) were obtained by reducing either compounds of Formula (H) or (J) with appropriate reducing agents. The compounds of Formula (H) were obtained by treating compounds Formula (G) with nitromethane wherein Q is an aldehyde. The compounds of Formula (J) were obtained by treating compounds of Formula (G) with acetonitrile in presence appropriate alkali metal base (E.g., nBuLi) where in Q is a halogen (E.g., Br or I).

-continued

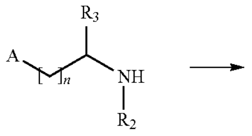

Formula (B)

In similar to the process of making compounds of Formula(I) the

Scheme 4

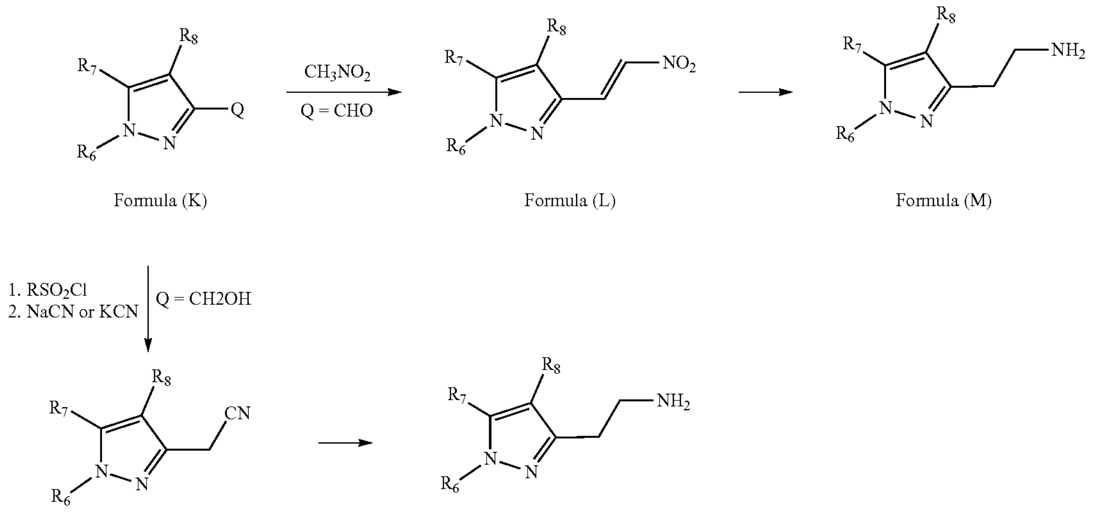

Formula (K) Formula (L) Formula (M)

Formula (N) Formula (M)

processes for one of the representative compounds of Formula(B) with five membered rings shown as Formula (M) in scheme 4.

The examples shown above illustrate some methods useful for the synthesis of compounds of Formula (A) and compound (B) which may be used for the synthesis of compounds of Formula (I). Where a particular solvent or reagent is shown or referred to in the accompanying text, it is to be understood that the chemist of ordinary skill in the art will be able to modify and/or replace that solvent or reagent, as necessary.

In another embodiment, the compounds of Formula I, can be prepared reacting compounds of Formula (B) with compounds of Formula (A), in the presence of appropriate base and solvents as shown scheme 5.

Scheme 5

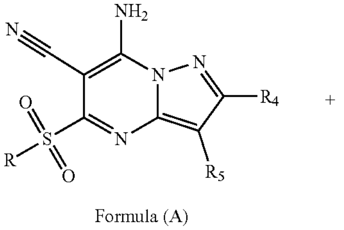

Formula (A)

-continued

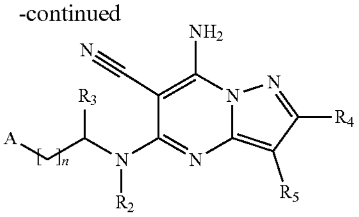

Formula (I)

The present disclosure provides a process for the preparation of compounds of Formula (I) and the compounds of Formula (I) which may be prepared in a variety of ways. The processes and examples shown below illustrate some methods useful for the synthesis of compounds of Formula (I) and intermediates which may be used for the synthesis of compounds of Formula (I). Where a particular solvent or reagent is shown or referred to in the accompanying text, it is to be understood that the chemist of ordinary skill in the art will be able to modify and/or replace that solvent or reagent as necessary Synthesis of Intermediates Synthesis of 7-amino-2,3-dimethyl-5-(methyl sulfonyl) pyrazolo[1,5-a] pyrimidine-6-carbonitrile. (I)

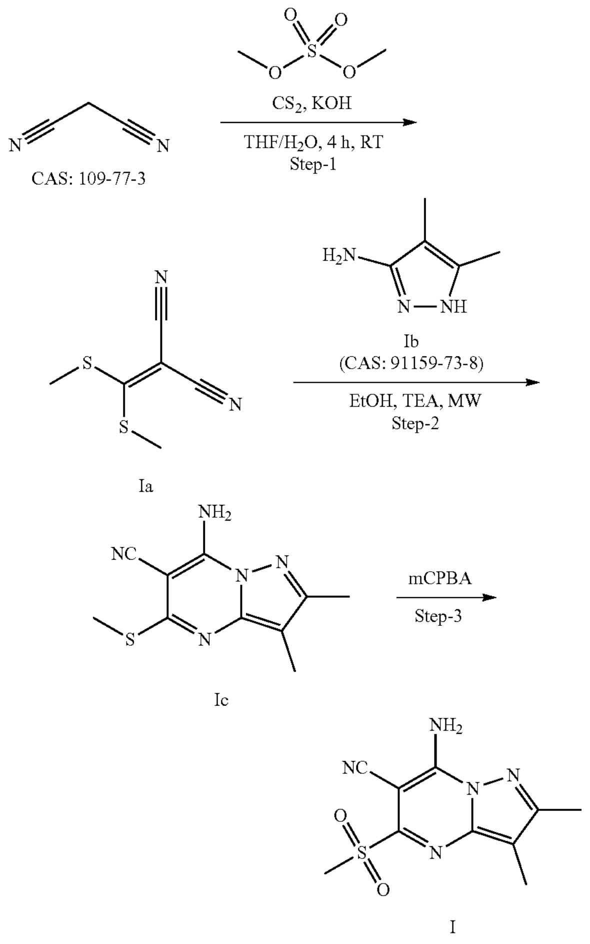

Step-1: Synthesis of 2-(bis(methylthio)methylene) malononitrile (Ia)

A stirred solution of KOH (16.98 g, 302.75 mmol) in water (100 mL) was cooled to 0° C. and was added malononitrile (10 g, 151.37 mmol) in dry THF (20 mL) was added dropwise over a period of 30 min under $N_2$ atmosphere. The reaction was stirred at room temperature for 1 h and was added $CS_2$ (17.2 g, 227.06 mmol) at 0° C. After stirring the reaction mixture at room temperature for about 1 h dimethylsulphate (24.8 g, 196.7 mmol) was added and stirring was continued for another 4 h at room temperature. After completion, the reaction mixture was quenched with ice cold water and the solid precipitated was filtered and dried under vacuo to afford the compound Ia (8 g, 31%) as yellow solid, which was taken forward for further step without purification.

Step-2: Synthesis of 7-amino-2,3-dimethyl-5-(methylthio) pyrazolo[1,5-a] pyrimidine-6-carbonitrile (Ic)

To a stirred solution of Ia (10 g, 58.8 mmol) in ethanol (20 mL) was added Ib (4.57 g, 41.17 mmol) at room temperature under $N_2$ atmosphere. The resulted mixture was heated at 120° C. for 6 h. After that the reaction mixture was cooled to room temperature and the solid precipitated was filtered and washed with ethanol to give off-white solid, it was purified by column chromatography on silica gel (230-400 mesh, 45% ethyl acetate in pet ether) to obtained Ic (3.1 g, 32%); LC-MS Calculated. for $C_{10}H_{11}N_5S$: 233.29; Observed.: 234.0; [$M^+$+H]. $^1$H NMR (400 MHz, DMSO-$D_6$): δ 8.60 (s, 2H), 2.68 (s, 3H), 2.37 (s, 3H), 2.13 (s, 3H).

Step-3: Synthesis of 7-amino-2,3-dimethyl-5-(methyl sulfonyl) pyrazolo[1,5-a] pyrimidine-6-carbonitrile. (I)

A stirred solution of Ic (5 g, 21.45 mmol) in dichloromethane (50 mL) was cooled to 0° C. and was added m-CPBA (11.07 g, 64.37 mmol) under $N_2$ atmosphere. The resulted mixture was stirred at room temperature for 3 h. After that the reaction mixture was quenched with 10% $NaHCO_3$ solution and extracted with DCM (2×300 mL). The combined organic layer was dried over $Na_2SO_4$ and concentrated under vacuo to afford the compound I (3.1 g, 54%) as an off-white solid which was taken forward for further step without purification. LC-MS Calculated. for $C_{10}H_{11}N_5O_2S$: 265.29; Observed.: 266.0; [$M^+$+H]. $^1$H NMR (400 MHz, DMSO-$D_6$): δ 9.1 (br s, 2H), 3.42 (s, 3H), 2.40 (s, 3H), 2.17 (s, 3H).

Synthesis of 7-amino-3-ethyl-2-methyl-5-(methyl sulfonyl) pyrazolo[1,5-a]pyrimidine-6-carbonitrile. (II)

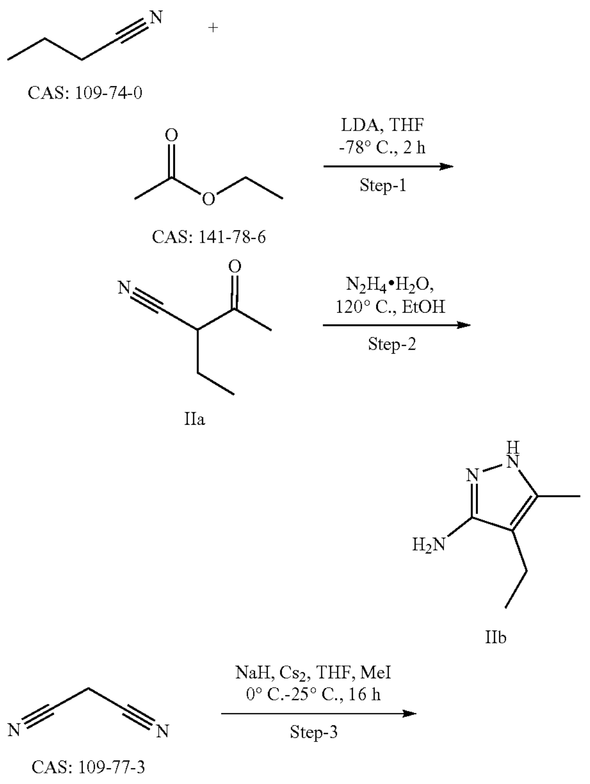

-continued

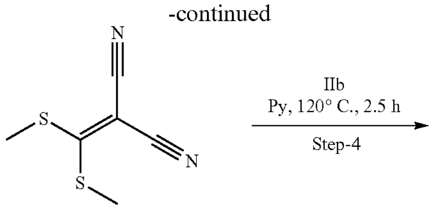

Ia

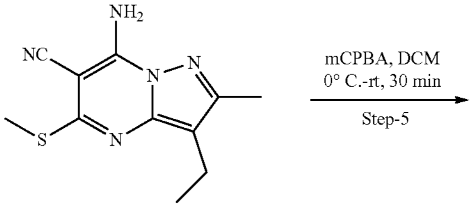

IIc

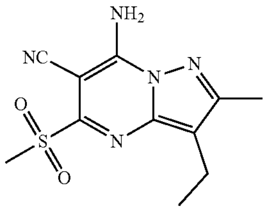

II

Step-1: 2-ethyl-3-oxobutanenitrile (IIa)

To a three neck RB flask, LDA (2M in THF, 36.17 ml, 0.0723 mol) was taken and THF (82.5 ml) was added and cooled to −78° C. To this solution, butyronitrile (5 g, 0.0723 mol) in THF (10 ml) was added dropwise at −78° C. and the reaction mixture was stirred at −78° C. for 1 h. Then, ethyl acetate (6.42 ml, 0.0657 mol) was added dropwise at −78° C. and the reaction mixture was stirred at −78° C. for 2 h. The progress of the reaction was monitored by TLC. After completion, the reaction mixture was cooled to 0° C. and quenched with saturated solution of $NH_4Cl$ (25 ml) and extracted with ethyl acetate (50 ml×3). The organic layer was dried over anhydrous $Na_2SO_4$, filtered and evaporated under reduced pressure to get the title compound IIa as yellow viscous oil; Yield: (8 g, 100%). $^1$H NMR (400 MHz, $CDCl_3$): δ 3.237-3.205 (q, 1H), 2.499 (s, 3H), 1.153-1.137 (d, J=6.4 Hz, 3H), 0.973-0.937 (t, J=7.2 Hz, 3H).

Step-2: 4-ethyl-5-methyl-1H-pyrazol-3-amine (IIb)

To a stirred solution of 2-ethyl-3-oxobutanenitrile 3 (8 g) in EtOH (80 ml) was added hydrazine hydrate (23.80 ml) and the reaction mixture was heated at 120° C. for 1.5 h. The progress of the reaction was monitored by TLC. After completion, the reaction mixture was cooled to rt and evaporated under reduced pressure. The residue was dissolved in 6N HCl (25 ml) and washed with ethyl acetate (3×50 ml). Aq. layer was basified to pH>7 using aqueous ammonia solution and extracted with ethyl acetate (3×50 ml). The organic layer was dried with $Na_2SO_4$, filtered, and evaporated under reduced pressure to get the title compound IIa as light brown viscous liquid was used in the next step without further purification; Yield: (8.1 g, 90%). $^1$H NMR (400 MHz, CD3OD): δ 2.354 (q, J=7.2 Hz, 2H), 2.110 (s, 3H), 1.087-1.049 (t, J=7.2 Hz, 3H).

Step-3: 2-(Bis(methylthio) methylene) malononitrile (Ia)

To a stirred solution of malononitrile (5.0 g, 0.075 mol) in DMSO (50 ml) cooled to 0° C. was added $K_2CO_3$ (11.4 g, 0.0833 mol), $CS_2$ (5.03 g, 0.0833 mol) and stirred at rt for 3 h. Then the reaction mixture cooled to 0° C. and MeI (9.4 ml, 0.1514 mol) was added and the reaction mixture was stirred at rt for 16 h. The progress of the reaction was monitored by TLC. After completion, the reaction mixture was poured into ice cold water (50 ml) and the precipitate formed was filtered, washed with cold water and dried to get the compound Ia as brick red solid which was used in the next step without further purification; Yield: (6.2 g, 51%).

Step-4: 7-amino-3-ethyl-2-methyl-5-(methylthio) pyrazolo[1,5-a] pyrimidine-6-carbonitrile (IIc)

To a stirred solution of 2-(bis(methylthio)methylene) malononitrile Ia (11.0 g, 0.0647 mol) in pyridine (80 ml) was added 4-ethyl-5-methyl-1H-pyrazol-3-amine (8.1 g, 0.0647 mol) and the reaction mixture was heated at 120° C. for 2.5 h. The progress of the reaction was monitored by TLC. After completion, the reaction mixture was evaporated, and the residue was diluted with water (150 ml) and resulting solid was stirred for 2 h at 10-15° C. Filtered the solid and azeotroped with toluene (2×50 ml) to get dried title compound IIc. Yield: (12.3 g, 78%). $^1$H NMR (400 MHz, $CD_3OD$): δ 2.691-2.634 (q, J=7.6 Hz, 2H), 2.583 (s, 3H), 2.371 (s, 3H), 1.257-1.205 (t, J=8 Hz, 3H).

Step-5: 7-amino-3-ethyl-2-methyl-5-(methyl sulfonyl) pyrazolo[1,5-a] pyrimidine-6-carbonitrile. (II)

To a stirred solution of 7-amino-3-ethyl-2-methyl-5-(methylthio) pyrazolo[1,5-a] pyrimidine-6-carbonitrile IIc (11.2 g, 0.0481 mol) in DCM (120 ml) cooled to 0° C., was added m-CPBA (33.20 g, 0.19 mol) slowly and the reaction mixture was stirred at rt for 30 min. The progress of the reaction was monitored by TLC (polar spot). After completion, the reaction mixture was quenched with $NaHCO_3$ (150 ml) and extracted with DCM (150 ml×3). The organic layer was dried with $Na_2SO_4$, filtered, and evaporated under reduced pressure. The crude material was purified using 50% ethyl acetate in hexane to get pure title compound. Yield: (9.5 g, 70%). LC_MS Calculated for $C_{11}H_{13}N_5O_2S$: 279.10; Observed: 280.10 [$M^+$+H]. $^1$H NMR (400 MHz, $CD_3OD$): δ 3.385 (s, 3H), 2.777-2.721 (q, J=7.2 Hz, 2H), 2.463 (s, 3H), 1.260-1.230 (t, J=7.2 Hz, 3H).

Synthesis of 7-amino-3-isopropyl-2-methyl-5-(methyl sulfonyl) pyrazolo[1,5-a] pyrimidine-6-carbonitrile. (III)

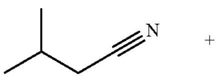

CAS: 625-28-5

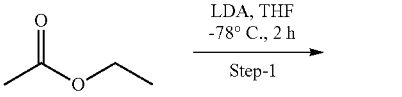

CAS: 141-78-6

-continued

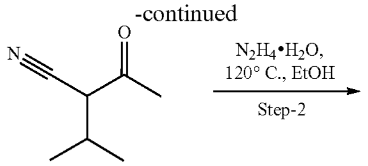

IIIa

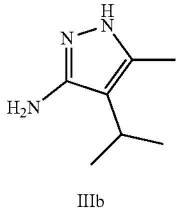

IIIb

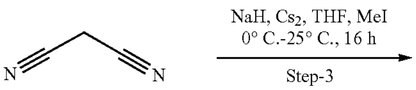

CAS: 109-77-3

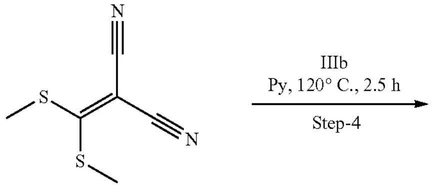

Ia

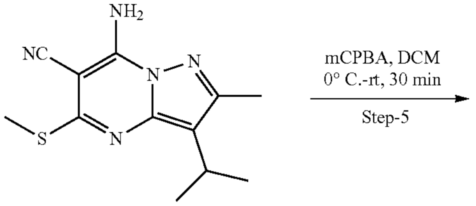

IIIc

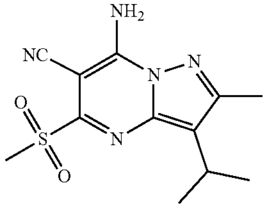

III

Step-1: 2-acetyl-3-methylbutanenitrile. (Ma)

To a three neck RB flask, LDA (2M in THF, 29.8 mL, 0.0595 mol) was taken and THF (100 mL) was added and cooled to −78° C. To this solution, 3-methylbutanenitrile (CAS:625-28-5, 25 g, 0.0595 mol) in THF (40 mL) was added dropwise at −78° C. and the reaction mixture was stirred at −78° C. for 1 h. Then, ethyl acetate (CAS:141-78-6, 5.2 mL, 0.0536 mol) was added dropwise at −78° C. and the reaction mixture was stirred at −78° C. for 1 h. The progress of the reaction was monitored by TLC. After completion, the reaction mixture was cooled to 0° C. and quenched with saturated solution of $NH_4Cl$ (50 mL) and extracted with ethyl acetate (80 mL×3). The organic layer was dried over anhydrous $Na_2SO_4$, filtered and evaporated under reduced pressure to get the title compound Ma as yellow viscous oil; Yield: (6.5 g, 87%). LC_MS Calculated for $C_7H_{11}NO$: 125.08; Observed:124.10 [M−H].

Step-2: 4-isopropyl-5-methyl-1H-pyrazol-3-amine. (IIIb)

To a stirred solution of 2-acetyl-3-methylbutanenitrile Ma (6.5 g, 0.0520 mol) in EtOH (65 mL) was added hydrazine hydrate (19.5 mL, 0.00438 mol) and the reaction mixture was heated at 120° C. for 1.5 h. The progress of the reaction was monitored by TLC. After completion, the reaction mixture was cooled to rt and evaporated under reduced pressure. The residue obtained was diluted with water (100 mL) and extracted with ethyl acetate (80 mL×3). The organic layer was dried over anhydrous $Na_2SO_4$, filtered and evaporated under reduced pressure to get tittle compound IIIb as light brown viscous liquid. This crude product was used as such for the next step without further purification; Yield: (4.5 g, 52%). $^1H$ NMR (400 MHz, $CDCl_3$): δ 5.18 (bs, 2H), 3.18 (d, J=7.6 Hz, 1H), 2.29-2.04 (m, 1H), 1.83 (s, 3H), 1.22 (d, J=10.0 Hz, 1H), 1.11 (d, J=6.8 Hz, 3H), 1.01 (d, J=6.8 Hz, 3H).

Step-3: 2-(Bis(methylthio) methylene) malononitrile. (Ia)

To a stirred solution of malononitrile (5.0 g, 0.075 mol) in DMSO (50 ml) cooled to 0° C. was added $K_2CO_3$ (11.4 g, 0.0833 mol), $CS_2$ (5.03 g, 0.0833 mol) and stirred at rt for 3 h. Then the reaction mixture cooled to 0° C. and MeI (9.4 ml, 0.1514 mol) was added and the reaction mixture was stirred at rt for 16 h. The progress of the reaction was monitored by TLC. After completion, the reaction mixture was poured into ice cold water (50 ml) and the precipitate formed was filtered, washed with cold water and dried to get the compound Ia as brick red solid which was used in the next step without further purification; Yield: (6.2 g, 51%).

Step-4: 7-amino-3-isopropyl-2-methyl-5-(methylthio) pyrazolo[1,5-a]pyrimidine-6-carbonitrile. (Mc)

To a stirred solution of 2-(bis(methylthio)methylene) malononitrile Ia (6.1 g, 0.0360 mol) in pyridine (50 mL) and 4-isopropyl-5-methyl-1H-pyrazol-3-amine IIIb (4.5 g, 0.0360 mol) and the reaction mixture was heated at 120° C. in for 1.5 h. The progress of the reaction was monitored by TLC. After completion, to the reaction 200 mL water was added and the pale-yellow residue formed was collected by filtration. The solid was washed with fresh water (200 mL) and dried under vacuo to afford the desired compound as a pale-yellow solid. The crude material was used in the next step without further purification; Yield: (6.0 g, 71%). LC_MS Calculated for $C_{12}H_{15}N_5S$: 261.10; Observed: 262.10 $[M+H]^+$. $^1H$ NMR (400 MHz, $CDCl_3$): δ 6.20 (bs, 2H), 3.09-3.06 (m, 1H), 2.62 (s, 3H), 2.40 (s, 3H), 1.38 (d, J=6.8 Hz, 6H).

Step-5: 7-amino-3-isopropyl-2-methyl-5-(methyl sulfonyl) pyrazolo[1,5-a] pyrimidine-6-carbonitrile. (III)

To a stirred solution of 7-amino-3-isopropyl-2-methyl-5-(methylthio) pyrazolo[1,5-a] pyrimidine-6-carbonitrile Mc (6.0 g, 0.023 mol) in DCM (60 mL), cooled to 0° C., was portion wise added m-CPBA (16.0 g, 0.092 mol) and the reaction mixture was stirred at rt for 2 h. The progress of the reaction was monitored by TLC (polar spot). After completion, the reaction mixture was quenched with $NaHCO_3$ (100 mL) and extracted with DCM (80 mL×3). The organic layer was dried over anhydrous $Na_2SO_4$, filtered and evaporated under reduced pressure. The crude material was subjected to silica gel (100-200) column chromatography using ethyl acetate (0-30%) in n-hexane to afford the desired compound III as an off-white solid; Yield: (1.5 g, 22%). LC_MS Calculated for $C_{12}H_{15}N_5O_2S$: 293.09; Observed: 294.05 $[M+H]^+$. $^1H$ NMR (400 MHz, DMSO-$D_6$): δ 9.18 (bs, 2H), 3.42 (s, 3H), 3.15-3.12 (m, 1H), 2.45 (s, 3H), 1.34 (d, J=6.8 Hz, 6H).

Synthesis of 7-amino-3-isobutyl-2-methyl-5-(methyl sulfonyl) pyrazolo[1,5-a]pyrimidine-6-carbonitrile. (1V)

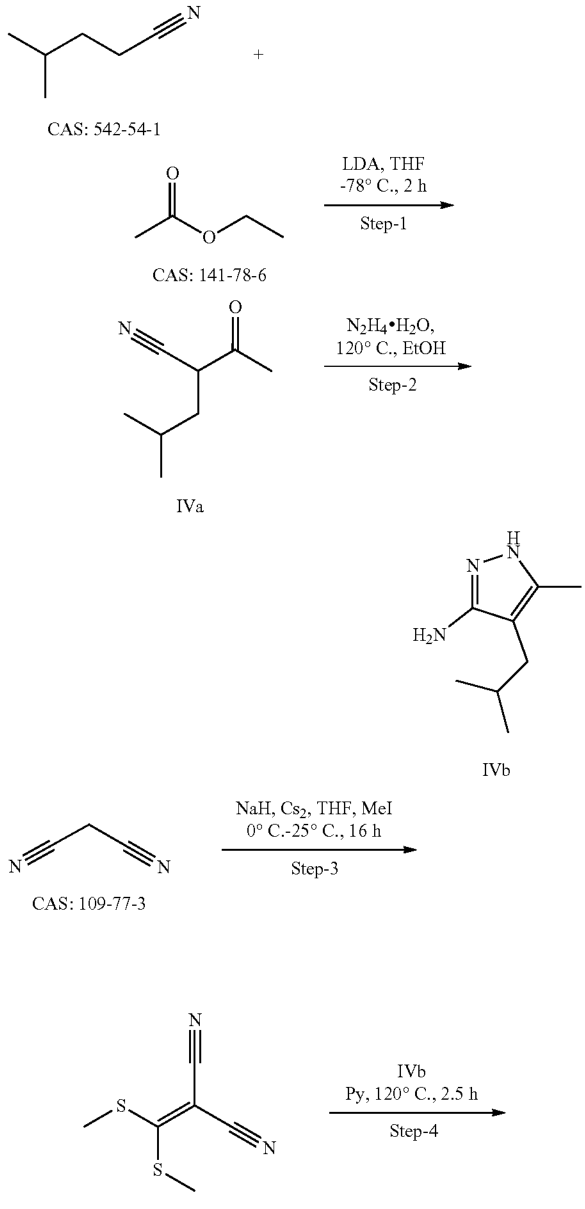

CAS: 542-54-1

CAS: 141-78-6

IVa

IVb

CAS: 109-77-3

Ia

-continued

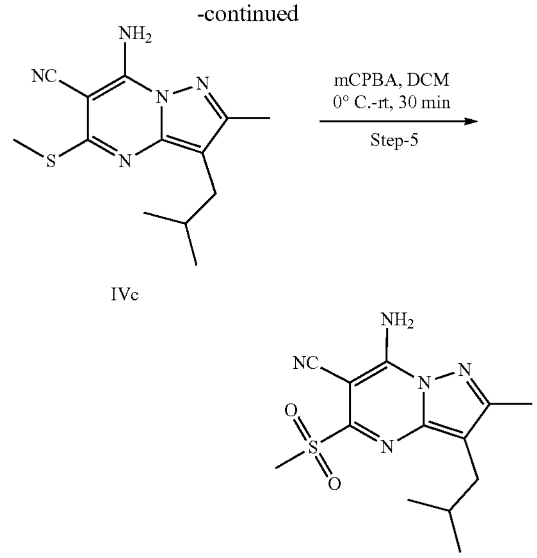

IVc

IV

Step-1: 2-Acetyl-4-methylpentanenitrile. (IVa)

To a three neck RB flask, LDA (2M in THF, 2.5 ml, 0.00514 mol) was taken and THF (10 ml) was added and cooled to −78° C. To this solution, 4-methylpentanenitrile (CAS:542-54-1, 0.5 g, 0.00514 mol) in THF (4 ml) was added dropwise at −78° C. and the reaction mixture was stirred at −78° C. for 1 h. Then, ethyl acetate (CAS:141-78-6, 0.45 ml, 0.00468 mol) was added dropwise at −78° C. and the reaction mixture was stirred at −78° C. for 2 h. The progress of the reaction was monitored by TLC. After completion, the reaction mixture was cooled to 0° C. and quenched with saturated solution of $NH_4Cl$ (5 ml) and extracted with ethyl acetate (20 ml×3). The organic layer was dried over anhydrous $Na_2SO_4$, filtered and evaporated under reduced pressure to get the title compound IVa as yellow viscous oil; Yield: (0.478 g, 66%). $^1H$ NMR (400 MHz, $CDCl_3$): δ 3.46-3.42 (m, 1H), 2.40 (s, 3H), 1.89-1.76 (m, 2H), 1.70-1.65 (m, 1H), 1.0 (d, J=6.4 Hz, 3H), 0.96 (d, J=6.4 Hz, 3H).

Step-2: 4-Isobutyl-5-methyl-1H-pyrazol-3-amine. (IVb)

To a stirred solution of 2-acetyl-4-methylpentanenitrile IVa (0.470 g, 0.00337 mol) in EtOH (20 ml) was added hydrazine hydrate (0.219 g, 0.00438 mol) and the reaction mixture was heated at 90° C. for 15 h. The progress of the reaction was monitored by TLC. After completion, the reaction mixture was cooled to rt and evaporated under reduced pressure. The residue obtained was diluted with water (10 ml) and extracted with ethyl acetate (20 ml×3). The organic layer was dried with $Na_2SO_4$, filtered, and evaporated under reduced pressure to get crude material IVb as light brown viscous liquid. The crude product obtained was taken as such for next step without further purification; Yield: (0.478 g, 92%). $^1H$ NMR (400 MHz, DMSO-$D_6$): δ 10.85 (bs, 1H), 4.13 (bs, 2H), 2.04 (d, J=7.2 Hz, 2H), 1.98 (s, 3H), 1.69-1.62 (m, 1H), 0.83 (d, J=6.8 Hz, 6H).

Step-3: 2-(Bis(methylthio) methylene) malononitrile. (Ia)

To a stirred solution of malononitrile (CAS:109-77-3, 5.0 g, 0.075 mol) in DMSO (50 ml) cooled to 0° C. was added $K_2CO_3$ (11.4 g, 0.0833 mol), $CS_2$ (5.03 g, 0.0833 mol) and stirred at rt for 3 h. Then the reaction mixture cooled to 0° C. and methyl Iodide (9.4 ml, 0.1514 mol) was added and the reaction mixture was stirred at rt for 16 h. The progress of the reaction was monitored by TLC. After completion, the reaction mixture was poured into ice cold water (50 ml) and the precipitate formed was filtered, washed with cold water and dried to get the compound Ia as brick red solid which was used in the next step without further purification; Yield: (6.2 g, 51%).

Step-4: 7-Amino-3-isobutyl-2-methyl-5-(methylthio) pyrazolo[1,5-a] pyrimidine-6-carbonitrile. (IVc)

To a stirred solution of 2-(bis(methylthio)methylene) malononitrile Ia (1.0 g, 0.0065 mol) in EtOH (10 ml) was added TEA (1.81 ml, 0.013 mol) and 4-isobutyl-5-methyl-1H-pyrazol-3-amine IVb (1.1 g, 0.0065 mol) and the reaction mixture was heated at 100° C. in microwave for 1 h. The progress of the reaction was monitored by TLC. After completion, the reaction mixture was evaporated, and the residue was diluted with water (20 ml) and extracted with ethyl acetate (20 ml×3). The organic layer was dried with $Na_2SO_4$, filtered, and evaporated under reduced pressure to get crude compound IVc. The crude product obtained was taken for next step without further purification; Yield: (1.64 g, 92%). LC_MS Calculated for $C_{13}H_{17}N_5S$: 275.12; Observed: 276.20 [$M^+$+H]. 1H NMR (400 MHz, DMSO-$D_6$): δ 8.51 (bs, 2H), 2.53-2.50 (m, 2H), 2.45 (d, J=7.2 Hz, 2H), 2.37 (t, J=3.6 Hz, 1H), 2.29 (s, 3H), 1.95-1.88 (m, 1H), 0.88-0.85 (m, 6H).

Step-5: 7-Amino-3-isobutyl-2-methyl-5-(methyl sulfonyl) pyrazolo[1,5-a] pyrimidine-6-carbonitrile (IV)

To a stirred solution of 7-amino-3-isobutyl-2-methyl-5-(methylthio) pyrazolo[1,5-a] pyrimidine-6-carbonitrile IVc (0.65 g, 0.00236 mol) in DCM (10 ml) cooled to 0° C., was added m-CPBA (1.0 g, 0.0059 mol) slowly and the reaction mixture was stirred at rt for 16 h. The progress of the reaction was monitored by TLC (polar spot). After completion, the reaction mixture was quenched with $NaHCO_3$ (50 ml) and extracted with DCM (50 ml×3). The organic layer was dried with $Na_2SO_4$, filtered, and evaporated under reduced pressure to get the title compound IV. The crude product was used as such for the next step without further purification; Yield: (0.703 g, 97%). LC_MS Calculated for $C_{13}H_{17}N_5O_2S$: 307.11; Observed:308.15 [$M^+$+H]. $^1H$ NMR (400 MHz, DMSO-$D_6$): δ 9.19 (bs, 2H), 3.40 (s, 3H), 2.53-2.52 (m, 2H), 2.41 (s, 3H), 1.95-1.92 (m, 1H), 0.96-0.87 (m, 6H).

Synthesis of 7-amino-3-(cyclopropyl methyl)-2-methyl-5-(methyl sulfonyl) pyrazolo[1,5-a] pyrimidine-6-carbonitrile. (V)

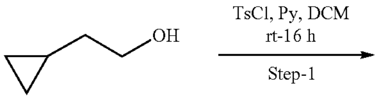

CAS: 2566-44-1

-continued

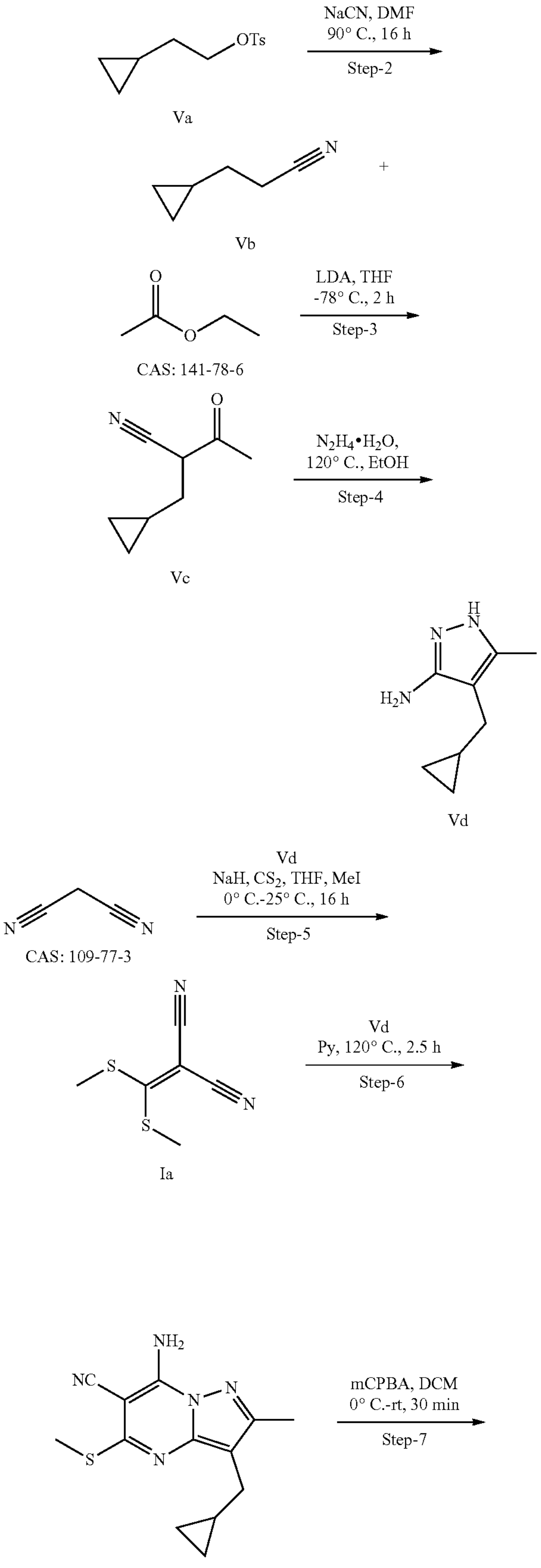

Va

Vb

+

CAS: 141-78-6

Vc

Vd

CAS: 109-77-3

Ia

Ve

-continued

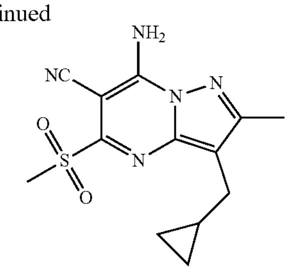

V

Step-1: 2-cyclopropylethyl 4-methylbenzenesulfonate (Va)

To a stirred solution of 2-cyclopropylethan-1-ol 1 (CAS: 2566-44-1, 5.0 g, 0.0581 mol) in DCM (75 mL) cooled to 0° C. was added pyridine (12.6 mL) followed by an addition of p-TsCl (8.9 g, 0.0470 mol) and the reaction mixture was stirred at rt for 16 h. The progress of the reaction was monitored by TLC. After completion, the reaction mixture was diluted with diethyl ether (100 ml) and washed sequentially with water (50 mL), 10% HCl (50 mL), water (10 ml) and dried over anhydrous $Na_2SO_4$, filtered and evaporated under reduced pressure to get compound Va as colorless liquid. The crude product obtained was taken for the next step without further purification; Yield: (8.6 g, 66%). LC_MS Calculated for $C_{12}H_{16}O_3S$: 140.32; Observed. 141.15 [$M^+$+H]. $^1$H NMR (400 MHz, $CDCl_3$): δ 7.81 (d, J=8.4 Hz, 2H), 7.35 (d, J=8.4 Hz, 2H), 4.9 (t, J=6.4 Hz 2H), 2.46 (s, 3H), 1.56-1.51 (m, 2H), 0.67-0.65 (m, 1H), 0.40-0.39 (m, 2H), 0.04-0.01 (m, 2H).

Step-2: 3-Cyclopropylpropanenitrile (Vb)

To a stirred solution of 2-cyclopropylethyl 4-methylbenzenesulfonate Va (8.6 g, 0.0357 mol) in DMF (32 mL) was added TBAI (0.526 g) followed by an addition of sodium cyanide (5.2 g, 0.107 mol) and the reaction mixture was heated at 90° C. for 16 h. The progress of the reaction was monitored by TLC analysis. After completion, the reaction mixture was diluted with diethyl ether (150 mL) and washed with water (100 mL×3), brine (100 mL) and dried over anhydrous $Na_2SO_4$, filtered and evaporated under reduced pressure to get desired product Vb as light brown viscous liquid. This crude product obtained was taken for the next step without further purification; Yield: (3.3 g, 97%). $^1$H NMR (400 MHz, $CDCl_3$): δ 3.74-3.72 (m, 1H), 2.42 (t, J=6.8 Hz 2H), 1.59-1.51 (m, 2H), 0.86-0.81 (m, 1H), 0.56-0.53 (m, 2H), 0.16-0.13 (m, 2H).

Step-3: 2-(cyclopropyl methyl)-3-oxobutanenitrile (Vc)

A three neck RB flask was charged with LDA (2M sol in THF, 15.35 mL, 0.0315 mol) and THF (60 mL) under $N_2$ atmosphere. The resulting mixture was cooled to −78° C. and a solution of 3-cyclopropylpropanenitrile Vb (3.0 g, 0.0315 mol) in THF (24 mL) was dropwise added maintaining temperature to −78° C. The reaction mixture was stirred at −78° C. for 1 h and ethyl acetate (CAS: 141-78-6, 2.52 g, 0.0287 mol) was dropwise added at −78° C. The resulting mixture was stirred at −78° C. for 2 h. The progress of the reaction was monitored by TLC. After completion, the reaction mixture was cooled to 0° C. and quenched with saturated solution of $NH_4Cl$ (50 mL) and extracted with ethyl acetate (50 mL×3). The combined organic layer was dried over anhydrous $Na_2SO_4$, filtered and evaporated under reduced pressure to get the title compound Vc as pale-yellow viscous oil; Yield: (3.25 g, 76%). $^1$H NMR (400 MHz, $CDCl_3$): δ 3.50-3.47 (m, 1H), 2.41 (s, 3H), 1.92-1.82 (m, 1H), 1.80-1.75 (m, 1H), 0.9-0.86 (m, 1H), 0.61-0.55 (m, 2H), 0.25-0.23 (m, 1H), 0.18-0.14 (m, 1H).

Step-4: 4-(cyclopropyl methyl)-5-methyl-1H-pyrazol-3-amine (Vd)

To a stirred solution of 2-(cyclopropyl methyl)-3-oxobutanenitrile Vc (3.2 g, 0.0233 mol) in EtOH (50 mL) was added hydrazine hydrate (2.19 ml, 0.0349) and the reaction mixture was heated at 90° C. for 16 h. The progress of the reaction was monitored by TLC. After completion, the reaction mixture was cooled to rt and evaporated under reduced pressure. The residue obtained was diluted with $NaHCO_3$ solution (50 mL) and extracted with ethyl acetate (50 mL×3). The organic layer was dried over anhydrous $Na_2SO_4$, filtered and evaporated under reduced pressure to get the title compound Vd. The crude product was taken for next step without further purification; Yield: (3.2 g, 91%). LC_MS Calculated for $C_8H_{13}N_3$ is 151.11; Observed. 152.20 [$M^+$+H]. $^1$H NMR (400 MHz, $CDCl_3$): δ 3.80-3.60 (bs, 2H), 2.30 (d, J=5.6 Hz 3H), 1.70-1.50 (bs, 1H), 0.90-0.83 (m, 1H), 0.48-0.44 (m, 2H), 0.14-0.10 (m, 2H).

Step-5: 2-(Bis(methylthio) methylene) malononitrile (Ia)

To a stirred solution of malononitrile (CAS:109-77-3, 5.0 g, 0.075 mol) in DMSO (50 ml) cooled to 0° C. was added $K_2CO_3$ (11.4 g, 0.0833 mol), $CS_2$ (5.03 g, 0.0833 mol) and stirred at rt for 3 h. Then the reaction mixture cooled to 0° C. and methyl Iodide (9.4 ml, 0.1514 mol) was added and the reaction mixture was stirred at rt for 16 h. The progress of the reaction was monitored by TLC. After completion, the reaction mixture was poured into ice cold water (50 ml) and the precipitate formed was filtered, washed with cold water and dried to get the compound Ia as brick red solid which was used in the next step without further purification; Yield: (6.2 g, 51%).

Step-6: 7-amino-3-(cyclopropyl methyl)-2-methyl-5-(methylthio) pyrazolo[1,5-a] pyrimidine-6-carbonitrile (Ve)

To a stirred solution of 2-(bis(methylthio)methylene) malononitrile Ia (3.3 g, 0.0198 mol) in pyridine (40 mL) was added 4-(cyclopropyl methyl)-5-methyl-1H-pyrazol-3-amine Vd (3.0 g, 0.0198 mol) and the reaction mixture was heated at 120° C. for 16 h under $N_2$ atmosphere. The progress of the reaction was monitored by TLC. After completion, the reaction mixture was cooled to rt and poured into ice cold water (50 mL). The precipitate formed was filtered, dried, and washed with cold mixture of ethyl acetate (10%) and n-hexane (90%) and dried under vacuo to afford the desired compound as a pale-yellow solid; Yield: (4.3 g, 80%). LC_MS Calculated for $C_{13}H_{15}N_5S$: 273.10; Observed: 274.10 [$M^+$+H]. $^1$H NMR (400 MHz, $CDCl_3$): δ

6.26 (bs, 2H), 2.61-2.57 (m, 5H), 2.41 (s, 3H), 1.00-0.90 (bs, 1H), 0.45-0.43 (m, 2H), 0.24-0.22 (m, 2H).

Step-7:7-amino-3-(cyclopropyl methyl)-2-methyl-5-(methyl sulfonyl) pyrazolo [1,5-a] pyrimidine-6-carbonitrile. (V)

To a stirred solution of 7-amino-3-(cyclopropyl methyl)-2-methyl-5-(methylthio) pyrazolo[1,5-a] pyrimidine-6-carbonitrile Ve (2.3 g, 0.00842 mol) in DCM (50 mL) cooled to 0° C., was slowly added m-CPBA (5.8 g, 0.0337 mol) and the reaction mixture was stirred at rt for 30 min. The progress of the reaction was monitored by TLC. After completion, the reaction was quenched with $NaHCO_3$ (30 mL) and extracted with DCM (50 mL×3). The combined organic layer was again given the saturated $NaHCO_3$ (30 mL×2) wash followed by with brine. The organic layer was dried over anhydrous $Na_2SO_4$, filtered and concentrated under vacuo to afford the desired compound V as a pale-yellow solid; Yield: (2.1 g, 81%). LC_MS Calculated for $C_{13}H_{15}N_5O_2S$: 305.09; Observed:306.10 [$M^+$+H]. $^1$H NMR (400 MHz, $CDCl_3$): δ 7.00-6.60 (bs, 2H), 3.39 (s, 3H), 2.64 (d, J=6.8, 2H), 2.50 (s, 3H), 0.99-0.97 (bs, 1H), 0.49-0.46 (m, 2H), 0.24-0.22 (m, 2H).

Synthesis of (6-methylpyridin-2-yl) methenamine. (VI)

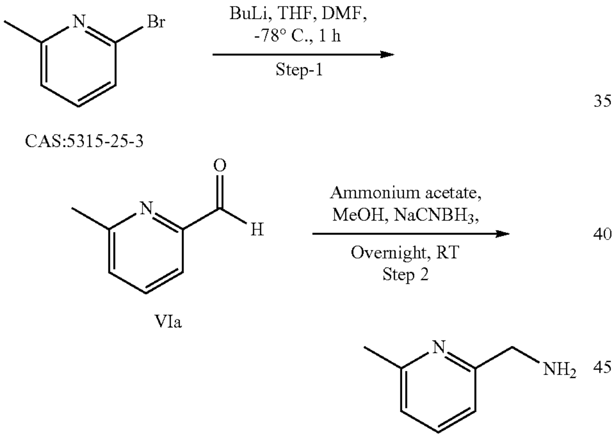

CAS:5315-25-3

VIa

VI

Step-1: 6-methylpicolinaldehyde. (VIa)

To a solution of 2-bromo-6-methylpyridine (CAS: 5315-25-3, 5 g, 0.0290 mol) in Toluene (50 ml) was dropwise added n-BuLi (2.5M sol in THF, 11.62 ml, 0.0290 mol) at −78° C. Reaction mixture was stirred for 1 h at −78° C. To this solution, DMF (2.69 ml, 0.0348 mol) was dropwise added at −78° C. Reaction mixture was stirred for 1 h at −50° C. followed by stirring for 30 min at 5-10° C. and at rt for 40 min. The progress of the reaction was monitored by TLC. After completion, the reaction mixture was cooled to 0° C. and quenched with saturated solution of $NH_4Cl$ (50 ml) and extracted with ethyl acetate (2×75 ml). The organic layer was washed with brine solution (50 ml) and dried with $Na_2SO_4$, filtered, and evaporated under reduced pressure to get crude material which was column purified using 60-120 silica get. Product was eluted with 5% ethyl acetate in hexane to afford compound VIa as pale-yellow liquid. Yield: (1.4 g, 40%). LC-MS Calculated for $C_7H_7NO$: 121.15; Observe. 122.15 [$M^+$+1]. $^1$HNMR (400 MHz, $CDCl_3$): δ 10.054 (s, 1H), 7.745-7.799 (m, 2H), 7.386-7.404 (d, J=6.8 Hz, 1H), 2.672 (s, 3H).

Step-2: (6-methylpyridin-2-yl) methenamine. (VI)

To a stirred solution of 6-methylpicolinaldehyde VIa (1.4 g, 0.0115 mol) in Methanol (25 ml) was added Ammonium acetate (8.9 g, 0.115 mol) and the reaction mixture was stirred for 30 min at rt. Sodium cyanoborohydride (0.58 g, 0.0092 mol) was then portion wise added and continued further stirring at rt for 10 h. Progress of the reaction was monitored by TLC. After completion, solvent from reaction mass was removed under reduced pressure. The residue obtained was taken up with water (50 ml) and basified with aq. KOH. product was extracted with 5% MeOH in DCM (3×100 ml). Combined organic layer was dried over $Na_2SO_4$, filtered, and concentrated at reduced pressure to afford title compound VI as brown liquid. Yield: 1.2 g (85%). LC-MS Calculated for $C_7H_{10}N_2$: 122.08; Observed. 123.08 [$M^+$+1]. $^1$HNMR (400 MHz, $CDCl_3$): δ 7.516-7.554 (t, J=7.6 Hz, 1H), 7.091-7.072 (d, J=7.6 Hz, 1H), 7.025-7.006 (d, J=7.6 Hz, 1H), 3.935 (s, 2H), 2.546 (s, 3H).

Synthesis of (6-ethylpyridin-2-yl) methenamine. (VII)

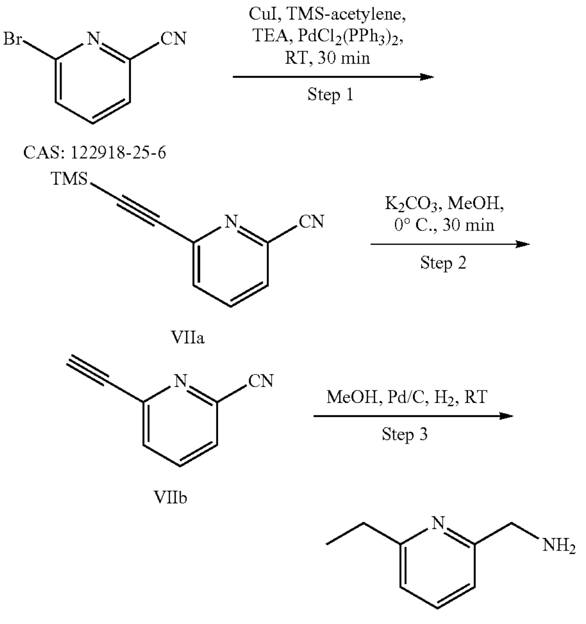

CAS: 122918-25-6

VIIa

VIIb

VII

Step-1: 6-((trimethylsilyl)ethynyl) picolinonitrile. (VIIa)

To a stirred solution of 6-bromopicolinonitrile (CAS: 122918-25-6, 1.5 g, 0.008 mol) in TEA (0.060 mol) was added and it was purged under nitrogen. To this Trimethylsilyl acetylene (1.37 ml, 0.009 mol) followed by copper iodide (0.036 g, 0.0003 mol) was added and purging was continued further for 10 more minutes. After that Pd $(PPh_3)_2Cl_2$ (0.089 g, 0.0001 mol) was added. Then the reaction mixture was stirred at room temperature for 30 minutes. The progress of the reaction was monitored by TLC. After completion, reaction mixture was filtered over celite bed and concentrated to get desired crude product VIIa. Yield: (1.2 g 75%). LC_MS Calculated for $C_{11}H_{12}N_2Si$: 200.08; Observed: 201.15 $[M^{+}+1]$. $^{1}H$ NMR (400 MHz, $CDCl_3$): δ 7.824-7.784 (t, J=8.4 Hz, 1H), 7.652-7.617 (t, J=7.2 Hz, 2H), 0.287 (s, 9H).

Step-2: 6-ethynylpicolinonitrile. (VIIb)

To a stirred solution of 6-((trimethylsilyl)ethynyl) picolinonitrile VIIa (1.5 g, 0.005 mol) in MeOH (15 ml) cooled to 0° C., was added $K_2CO_3$ (0.829 g, 0.005 mol) and the reaction mixture was stirred at 0° C. for 30 min. The progress of the reaction was monitored by TLC. After completion, the reaction mixture was diluted with water (20 ml) and extracted with DCM (3×50 ml). The organic layer was dried with $Na_2SO_4$, filtered, and evaporated under reduced pressure. The crude material was purified by column chromatography by eluting with 20% ethyl acetate in hexane to yield the title compound VIIb as pale-yellow solid; Yield: (0.260 g, 34%). LC_MS Calculated for $C_8H_4N_2$: 128.04; Observed.: Not ionized. $^{1}H$ NMR (400 MHz, $CDCl_3$): δ7.857-7.818 (d, J=7.6 Hz, 1H), 7.684-7.7.664 (d, J=8 Hz, 2H), 3.289 (s, H).

Step-3: (6-ethylpyridin-2-yl) methenamine. (VII)

To a stirred solution of 6-ethynylpicolinonitrile VIIb (0.260 g, 0.00203 mol) in MeOH (3 ml) purged with $N_2$ for 10 min, was added Pd/C (0.100 g) and the reaction mixture was stirred at rt for 24 h under $H_2$ atmosphere. The progress of the reaction was monitored by TLC. After completion, the reaction mixture was filtered through celite and the filtrate was concentrated. The crude material was purified by column chromatography by eluting with 20% ethyl acetate in hexane to yield the title compound VII as pale-yellow liquid; Yield: (0.100 g, 36%). LC_MS Calculated for $C_8H_{12}N_2$: 136.10; Observed.: 137 $[M^{+}+1]$. $^{1}H$ NMR (400 MHz, $CDCl_3$): δ 7.583-7.544 (d, J=7.6 Hz, 1H), 7.094-7.075 (d, J=7.6 Hz, 1H), 7.040-7.021 (d, J=7.6 Hz, 1H), 3.959 (s, 2H), 2.840-2.784 (q, J=7.6 Hz, 2H), 1.322-1.255 (t, J=8 Hz, 3H).

Synthesis of N-methyl-1-(6-methylpyridin-2-yl) methenamine. (VIII)

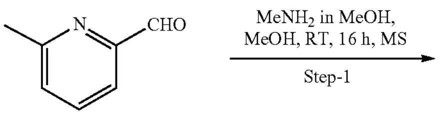

VIa

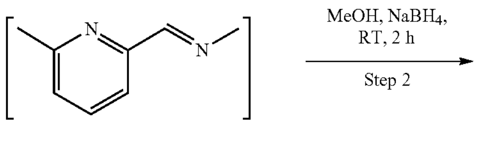

VIIIa

-continued

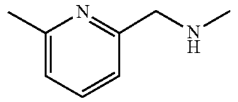

VIII

Step-1: (E)-N-methyl-1-(6-methylpyridin-2-yl) methenamine. (VIIIa)

To a stirred solution of 6-methylpicolinaldehyde VIa (0.1 g, 0.000825 mol) in Methanol (5 ml) in molecular sieve was added methylamine (2 ml, 30% solution in methanol) and the resulting reaction mixture was stirred at rt for 16 h. The progress of the reaction was monitored by TLC. After completion, the reaction mixture was filtered through the celite bed and evaporated under reduced pressure to get crude product VIIIa. The crude compound obtained was taken directly forward to the next step. Yield: (0.12 g, 100%).

Step-2: N-methyl-1-(6-methylpyridin-2-yl) methenamine. (VIII)

To a stirred solution of (E)-N-methyl-1-(6-methylpyridin-2-yl) methenamine VIIIa (0.120 g, 0.00089 mol) in methanol (5 ml), was added sodium borohydride (0.051 g, 0.00134 mol) at 0° C. Then the temp was allowed to reach room temperature and the reaction mixture was stirred at rt for 2 h. The progress of the reaction was monitored by TLC. After completion, the reaction mixture was evaporated under reduced pressure and diluted with 10 ml water and extracted with 10% methanol in DCM (20 ml×3). The organic layer was dried with $Na_2SO_4$, filtered, and evaporated under reduced pressure. The crude purified by manual column by eluted with 10% methanol in DCM product was eluted at 10% methanol in DCM to get the product VIII. Yield: (0.123 g, 101%). LC_MS Calculated. for $C_8H_{12}N_2$: 136.0; Observed:137 $[M^{+}+H]$. $^{1}H$ NMR (400 MHz, $CDCl_3$): δ 7.647-7.608 (t, J=8 Hz, 1H), 7.324-7.305 (d, J=7.6 Hz, 1H), 7.149-7.130 (d, J=7.6 Hz, 1H), 4.229 (s, 2H), 2.730 (s, 3H), 2.559 (s, 3H).

Synthesis of 1-(6-methylpyridin-2-yl) propan-2-amine. (IX)

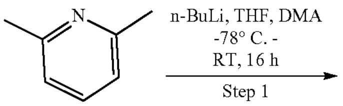

CAS:108-48-5

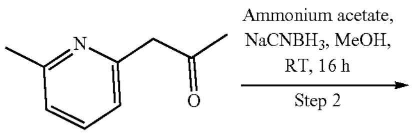

IXa

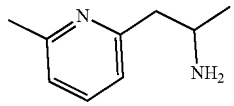

IX

Step-1: 1-(6-Methylpyridin-2-yl) propan-2-one. (IXa)

To a stirred solution of 2,6-dimethylpyridine (CAS: 108-48-5, 5.0 g, 0.046 mol) in THF (65 ml) at −78° C. was added n-BuLi (20.5 ml, 0.0512 mol) dropwise and stirred for 1 h. Then N,N-Dimethylacetamide (4.1 nil. 0.0443 mol) was added slowly at −78° C. and stirred at rt for 16 h. After completion (TLC), the reaction mixture was cooled to rt and quenched with 1.2 M HCl solution (25 ml) and stirred at rt for 30 min. Then, the reaction mixture was extracted with ethyl acetate (200 ml×3). The organic layer was dried with $Na_2SO_4$, filtered, and evaporated under reduced pressure. The crude material was purified by flash column chromatography by eluting with 5% ethyl acetate in hexane to yield the title compound IXa as yellow liquid; Yield: (0.713 g, 10.2%). $^1$H NMR (400 MHz, $CDCl_3$): δ 7.54 (t, J=7.6 Hz, 1H), 7.05 (d, J=7.6 Hz, 1H), 7.00 (d, J=8.0, Hz, 1H), 3.89 (s, 2H), 2.54 (s, 3H), 2.22 (s, 3H).

Step-2: 1-(6-Methylpyridin-2-yl) propan-2-amine. (IX)

To a stirred solution of 1-(6-methylpyridin-2-yl) propan-2-one IXa (0.713 g, 0.00475 mol) in MeOH (20 ml), was added ammonium acetate (3.7 g, 0.04753 mol) and stirred at room temperature for 30 min. Then $NaCNBH_3$ (0.21 g, 0.003327 mol) was added portion-wise and the reaction mixture was stirred at room temperature for 16 h. Then the progress of the reaction was monitored by TLC. After completion, the reaction mixture was concentrated and diluted with saturated $NaHCO_3$ solution (50 ml) and extracted with diethyl ether (50 ml×3). The organic layer was dried with $Na_2SO_4$, filtered, and evaporated under reduced pressure the desired product IX as pale green liquid. This crude product obtained was taken for the next step without further purification; Yield: (0.43 g, 60%). $^1$H NMR (400 MHz, DMSO-$d_6$): δ 7.56 (t, J=7.6 Hz, 1H), 7.04 (d, J=7.6 Hz, 1H), 7.00 (d, J=7.6, Hz, 1H), 3.21-3.18 (m, 1H), 2.64 (dd, J=6.8 Hz, 2.4 Hz, 2H), 2.42 (s, 3H), 0.98 (dd, J=6.4 Hz, 2.4 Hz, 3H).

Synthesis of 2-(6-(aminomethyl)pyridin-2-yl)propan-2-ol. (X)

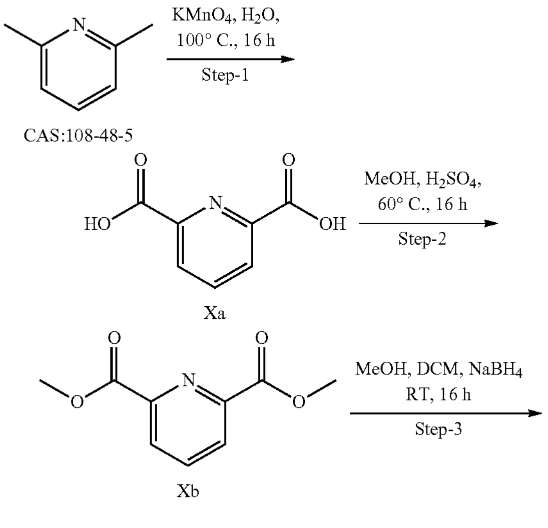

CAS:108-48-5

Xa

Xb

-continued

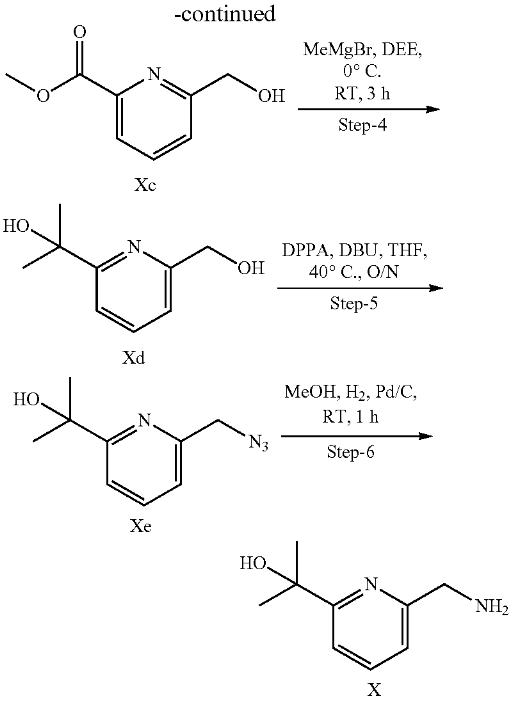

Xc

Xd

Xe

X

Step-1: Pyridine-2,6-dicarboxylic acid. (Xa)

To a solution of 2,6-dimethylpyridine (CAS:108-48-5, 10 g, 0.17 mol) in 250 ml water, was slowly added 29.49 g of potassium permanganate (0.34 mol) with stirring. The mixture was refluxed until the purple color disappeared. Then, the mixture was cooled down to room temperature and another part of potassium permanganate (29.49 g, 0.34 mol) and water (150 ml) was slowly added. The mixture was refluxed at 100° C. over 16 hrs. until the purple color disappeared again. The mixture was cooled down to room temperature. Filtration and removal of solvent until the residual volume down to 100 ml, then sulfuric acid (70%, 17.5 ml) was added slowly. The precipitate was filtered to afford pyridine-2,6-dicarboxylic acid Xa. Yield: (8.5 g, 55%). LC_MS Calculated for $C_7H_5NO_4$: 167.02; Observed.: 168.02 [$M^+$+1].

Step-2: dimethyl pyridine-2,6-dicarboxylate. (Xb)

To a stirred solution of Pyridine-2,6-dicarboxylic acid Xa (8.5 g, 0.00598 mol) in methanol (1 L), added conc. sulphuric acid (4 ml) dropwise. The reaction mixture was refluxed at 60° C. for 16 hrs. After completion of reaction, removed the solvent by evaporation in vacuo, added water, the solid formed was filtered and dried to get the title compound Xb. Yield: (5 g, 51%). LC_MS Calculated for $C_9H_9NO_4$ is 195.05; Observed.: 196.15 [$M^+$+1]. $^1$H NMR (400 MHz, $CDCl_3$): δ 8.338-8.314 (m, 2H), 8.055-8.013 (m, 1H), 4.036 (s, 6H).

Step-3: methyl 6-(hydroxymethyl)picolinate. (Xc)

Into a 500-ml round-bottom flask, was placed a solution of 2,6-dimethyl pyridine-2,6-dicarboxylate Xb (5 g, 0.00487 mol) in a solvent mixture of methanol (174 ml) and dichloromethane (74 ml). $NaBH_4$ (1.45 g, 0.00502 mol) was added to the reaction mixture in portions at 0° C. The resulting solution was stirred overnight at room temperature, and then it was quenched by the addition of Aq. $NH_4Cl$ (250 ml). The resulting solution was extracted with dichloromethane (2×200 ml) and the combined organic layers were dried over $Na_2SO_4$, filtered, and concentrated under vacuum. The residue was applied onto a silica gel column with ethyl acetate/petroleum ether (1:1) as eluent to yield methyl 6-(hydroxymethyl) pyridine-2-carboxylate Xc as white solid. Yield: (3.9 g, 93%). LC_MS Calculated. for $C_8H_9NO_3$ is 167.16; Observed.: 168.20 [$M^{+}$+1]. $^1$H NMR (400 MHz, $CDCl_3$): δ 8.048-8.029 (d, J=7.6 Hz, 1H), 7.875-7.837 (t, J=7.6 Hz, 1H), 7.541-7.522 (d, J=7.6 Hz, 1H), 4.863 (s, 2H), 4.002 (s, 3H).

Step-4: 2-(6-(hydroxymethyl) pyridin-2-yl) propan-2-ol. (Xd)

To a stirred solution of methyl 6-(hydroxymethyl) picolinate Xc (3 g, 0.0179 mol) in diethyl ether (300 ml), added methyl magnesium bromide (3.4 M, 0.0358 mol, 10.5 ml) dropwise at 0° C. Then the reaction mixture was stirred at room temperature for 3 hrs. After completion, the reaction mixture was quenched with $NH_4Cl$ and extracted with ethyl acetate (3×200 ml). The organic layer was dried with $Na_2SO_4$, filtered, and evaporated under reduced pressure. The crude material was purified by column chromatography by eluting with 30% ethyl acetate in hexane to yield the title compound as pale-yellow oil; Yield: (2.2 g, 73%). LC_MS Calc. for $C_8H_9NO_3$ is 167.16; Obs.: 168.20 [$M^{+}$+1]. $^1$H NMR (400 MHz, $CDCl_3$): δ 7.735-7.696 (t, J=8 Hz, 1H), 7.333-7.313 (d, J=8 Hz, 1H), 7.201-7.182 (d, J=7.6 Hz, 1H), 4.783 (s, 2H), 4.412 (s, 1H), 3.190 (s, 1H), 1.566 (s, 6H).

Step-5: 2-(6-(azidomethyl) pyridin-2-yl) propan-2-ol. (Xe)

To a stirred solution of 2-(6-(hydroxymethyl) pyridin-2-yl) propan-2-ol Xd (0.4 g, 0.0832 mol) in THF (5 ml), DPPA (0.0832 mol) at room temperature. The mixture was cooled to 0° C. and DBU (0.0832 mol) was added at rate such that the internal temperature did not exceed 20° C. The reaction mixture was then warmed to 40° C. and stirred for 16 hrs. After completion, the reaction mixture was cooled to room temperature, added water (20 ml) and extracted with ethyl acetate (3×20 ml). The organic layer was dried with $Na_2SO_4$, filtered, and evaporated under reduced pressure. The crude material was purified by column chromatography by eluting with 10% ethyl acetate in hexane to yield the title compound Xe as brown liquid; Yield: (0.26 g, 57%). LC_MS Calculated for $C_9H_2N_4O$ is 192.10; Observed.: 193.10 [$M^{+}$+1]. $^1$H NMR (400 MHz, $CDCl_3$): δ 7.743-7.724 (t, J=7.6 Hz, 1H), 7.337-7.317 (d, J=8 Hz, 1H), 7.245-7.226 (d, J=7.6 Hz, 1H), 4.905 (s, 1H), 4.465 (s, 2H), 1.550 (s, 6H).

Step-6: 2-(6-(aminomethyl) pyridin-2-yl) propan-2-ol. (X)

To a stirred solution of 2-(6-(azidomethyl) pyridin-2-yl) propan-2-ol Xe (0.26 g) in methanol (10 ml), added Pd/C (100 mg) at room temperature. The reaction was stirred at same temperature for 1 hr under hydrogen. After completion, the reaction mixture was filtered through celite bed, and the bed was washed with methanol. The filtrate was concentrated under reduced pressure to get the title compound X as brown liquid; Yield: (0.3 g, crude). The crude product obtained was taken for the next step without further purification.

Synthesis of 2-(5-methylpyridin-2-yl)ethan-1-amine. (XI)

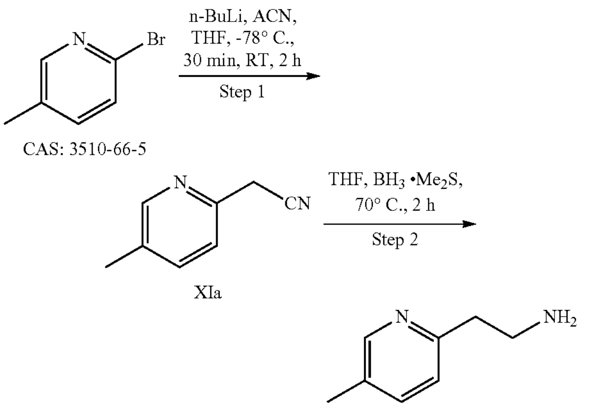

CAS: 3510-66-5
XIa
XI

Step-1: 2-(5-Methylpyridin-2-yl) acetonitrile. (XIa)

To a stirred solution of n-BuLi (14 ml, 0.034 mol) in THF (75 ml) was added ACN (1.75 ml, 0.0388 mol) at −78° C. and stirred for 1 h. Then added 2-bromo-5-methylpyridine (CAS: 3510-66-5, 1.67 g, 0.0097 mol) slowly and stirred at rt for 2 h. After completion (TLC), the reaction mixture was diluted with ice cold water (50 ml) and extracted with ethyl acetate (50 ml×3). The organic layer was dried over $Na_2SO_4$, filtered, and evaporated under reduced pressure to get the desired product Xia Yield: (0.6 g, crude). The crude product was taken for the next step without further purification.

Step-2: 2-(5-Methylpyridin-2-yl) ethan-1-amine. (XI)

To a stirred solution of 2-(5-methylpyridin-2-yl) acetonitrile XIa (0.6 g, 0.0045 mol) in THF (100 ml) was added $BH_3$-$Me_2S$, (10 ml, 0.0020 mol) at room temperature and stirred for 2 h at 70° C. After completion (TLC), the reaction mixture cooled to room temperature, then added MeOH (5 ml) and 10 ml 1N HCl and the aqueous layer washed with ethyl acetate separated the layer and the aqueous layer basified with 1N NaOH and extracted with DCM (100 ml×3). The organic layer was dried with $Na_2SO_4$, filtered and evaporated under reduced pressure to give title compound XI, the crude product was taken for the next step without purification; Yield: (0.2 g, 32%). LC_MS Calculated for $C_8H_{12}N_2$ is 136.10; Observed. 137.2 [$M^{+}$+H]. $^1$H NMR (400 MHz, $CDCl_3$): δ 8.35 (s, 1H), 7.42 (d, J=7.6 Hz 1H), 7.06 (d, J=8.0 Hz 1H), 3.12 (t, J=6.4 Hz, 2H), 2.91 (d, J=6.4 Hz, 2H), 2.3 (s, 3H).

Synthesis of 2-(5-fluoropyridin-2-yl)ethan-1-amine. (XII)

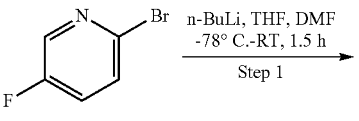

CAS: 41404-58-4

-continued

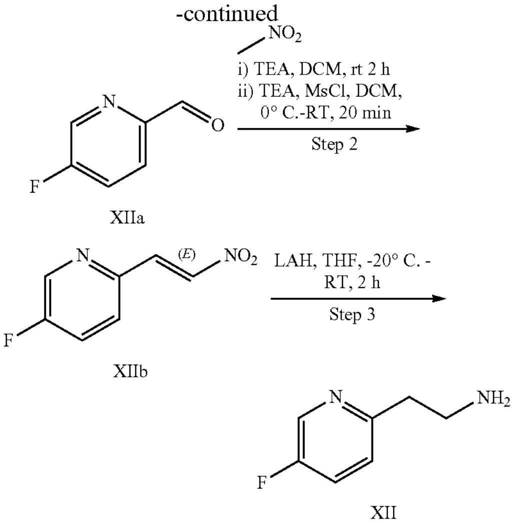

XIIa

XIIb

XII

Step-1: 5-Fluoropicolinaldehyde. (XIIa)

To a stirred solution of 2-bromo-5-fluoropyridine (CAS: 41404-58-4, 2.69 g, 0.0147 mol) in toluene (30 ml) at −78° C. was added n-BuLi (5.9 ml, 0.0147 mol) dropwise and stirred for 1 h. Then DMF (1.36 ml) and added slowly at −50° C. and stirred for 30 min. After completion (TLC), the reaction mixture was quenched with MeOH (30 ml) and stirred at 5-10° C. for 30 min. Then, $NH_4Cl$ solution (75 ml) was added and stirred at rt for 40 min and then extracted with ethyl acetate (100 ml×3). The organic layer was dried with $Na_2SO_4$, filtered, and evaporated under reduced pressure. The crude material was purified by flash column chromatography by eluting with 5% ethyl acetate in hexane to yield the title compound XIIa as yellow liquid; Yield: (1.01 g, 54.89%). LC_MS Calculated for $C_6H_4FNO$ is 125.03; Observed. 126.00 $[M^{+}+H]$. $^1H$ NMR (400 MHz, $CDCl_3$): δ 10.04 (s, 1H), 8.63 (d, J=2.0 Hz, 1H), 8.05-8.02 (m, 1H), 7.58 (dt, J=8.4 Hz, 2.8 Hz, 1H).

Step-2: (E)-5-Fluoro-2-(2-nitrovinyl) pyridine. (XIIb)

To a stirred solution of 5-fluoropicolinaldehyde XIIa (1.01 g, 0.00807 mol) in DCM (20 ml), was added TEA (2.24 ml, 0.0161 mol) and nitromethane (0.52 ml, 0.00968 mol) and the reaction mixture was stirred at rt for 2 h. The progress of the reaction was monitored by TLC. After completion, the reaction mixture was evaporated under reduced pressure. The crude material was dissolved in DCM (20 ml) and treated with TEA (1.77 ml, 0.0242 mol) and MsCl (2.75 ml, 0.0242 mol) at 0° C. and the reaction mixture was stirred at rt for 20 min. The progress of the reaction was monitored by TLC. After completion, the reaction mixture was evaporated under reduced pressure. And the crude was purified by column chromatography by eluting with 10% ethyl acetate in hexane to yield the title compound XIIb as green solid; Yield: (1.2 g, 88.8%). LC_MS Calculated for $C_7H_5FN_2O_2$ is 168.03; Observed. 169.00 $[M^{+}+H]$. $^1H$ NMR (400 MHz, $CDCl_3$): δ 8.54 (s, 1H), 7.93 (q, J=12.8 Hz, 2H), 7.50-7.49 (m, 2H).

Step-3: 2-(5-Fluoropyridin-2-yl) ethan-1-amine. (XII)

To a stirred solution of (E)-5-fluoro-2-(2-nitrovinyl) pyridine XIIb (1.2 g, 0.0071 mol) in THF (50 ml), was added LAH (1M sol in THF, 21.4 ml, 0.024 mol) at −20° C. dropwise. Then the temp was allowed to reach to rt, and the reaction mixture was stirred at rt for 2 h. The progress of the reaction was monitored by TLC. After completion, the reaction mixture was cooled to 0° C. and quenched with saturated $Na_2SO_4$ solution (50 ml) and extracted with ethyl acetate (50 ml×3). The organic layer was dried with $Na_2SO_4$, filtered, and evaporated under reduced pressure. The crude was purified by column chromatography by eluting with 10% methanolic $NH_3$ in DCM to yield the title compound as pale green liquid; Yield: (0.35 g, 35%). LC_MS Calculated for $C_7H_9FN_2$ is 140.07; Observed. 141.2 $[M^{+}+H]$. $^1H$ NMR (400 MHz, DMSO-$d_6$): δ 8.45 (d, J=3.2 Hz, 1H), 7.62 (dd, J=8.4 Hz, 2.8 Hz, 1H), 7.34-7.31 (m, 1H), 2.88 (t, J=6.4 Hz, 2H), 2.81 (d, J=6.4 Hz, 2H), 2.5 (bs, 2H).

Synthesis of 2-(6-methoxypyridin-2-yl) ethan-1-amine. (XIII)

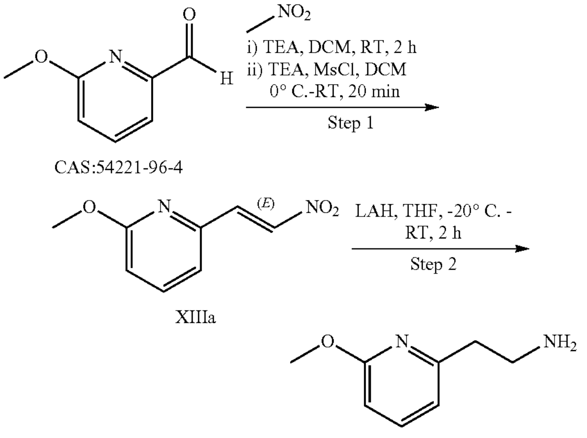

CAS:54221-96-4

XIIIa

XIII

Step-1: (E)-6-Methoxy-2-(2-nitrovinyl) pyridine. (XIIIa)

To a stirred solution of 6-methoxypicolinaldehyde (CAS: 54221-96-4, 1.0 g, 0.00724 mol) in DCM (20 ml), was added TEA (2.19 g, 0.0217 mol) and nitromethane (1.32 g, 0.0216 mol) and the reaction mixture was stirred at rt for 2 h. The progress of the reaction was monitored by TLC. After completion, the reaction mixture was evaporated under reduced pressure. The crude material was dissolved in DCM (20 ml) and treated with TEA (2.19 g, 0.0217 mol) and mesyl chloride (2.47 g, 0.0217 mol) at 0° C. and the reaction mixture was stirred at rt for 30 min. The progress of the reaction was monitored by TLC. After completion, the reaction mixture was evaporated under reduced pressure. And the crude was purified by column chromatography by eluting with 7% ethyl acetate in hexane to yield the title compound XIIa as yellow solid; Yield: (0.8 g, 80%). $^1H$ NMR (400 MHz, $CDCl_3$): δ8.016-7.983 (d, J=13.2 Hz, 1H), 7.845-7.812 (d, J=13.2 Hz, 1H), 7.652-7.614 (t, J=8 Hz, 1H), 7.069-7.052 (d, J=6.8 Hz, 1H), 6.863-6.843 (d, J=8 Hz, 1H), 3.969 (s, 3H).

Step-2: 2-(6-Methoxypyridin-2-yl) ethan-1-amine. (XIII)

To a stirred solution of (E)-6-methoxy-2-(2-nitrovinyl) pyridine 2 (0.8 g, 0.0044 mol) in DEE (16 ml), was added LAH (1M sol in THF, 13.3 ml, 0.0133 mol) at −10° C. dropwise. Then the temp was allowed to reach to rt and the reaction mixture was stirred at rt for 2 h. The progress of the reaction was monitored by TLC. After completion, the reaction mixture was cooled to 0° C. and quenched with chilled water (10 ml), 15N aq. NaOH (1 ml), and extracted with 10% methanol in DCM (20 ml×3). The organic layer was dried with $Na_2SO_4$, filtered, and evaporated under reduced pressure to give crude product XIII as brown liquid. The crude product was carried forward to next step without purification; Yield: (0.43 g, 63%). LC_MS Calculated for $C_8H_{12}N_2O$: 152; Observe. 153 [$M^+$+H]. $^1$H NMR (400 MHz, $CDCl_3$): δ 7.477 (d, 1H), 6.733-6.726 (d, J=2.8 Hz, 1H), 6.570-6.560 (m, 2H), 3.918 (s, 3H), 3.108 (t, 2H), 2.820 (t, 2H).

Synthesis of 2-(6-methylpyridin-2-yl) ethan-1-amine. (XIV)

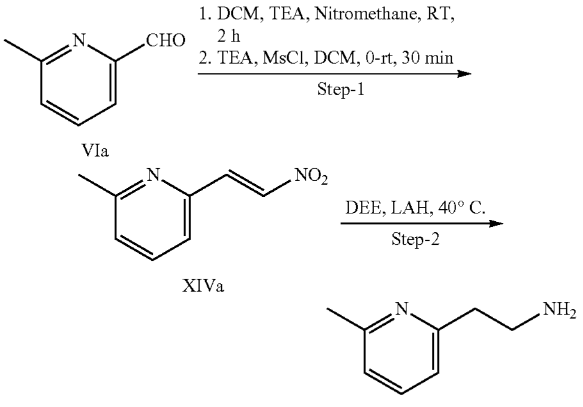

VIa

XIVa

XIV

Step-1. (E)-6-Methoxy-2-(2-nitrovinyl) pyridine. (XVa)

To a stirred solution of 6-methylpicolinaldehyde Via (8.0 g, 0.0660 mol) in DCM (80 ml), was added TEA (13.36 g, 0.132 mol) and nitromethane (5.15 g, 0.079 mol) and the reaction mixture was stirred at rt for 2 h. The progress of the reaction was monitored by TLC. After completion, the reaction mixture was evaporated under reduced pressure. The crude material was dissolved in DCM (80 ml) and treated with TEA (20.03 g, 0.198 mol) and mesyl chloride (22.58 g, 0.198 mol) at 0° C. and the reaction mixture was stirred at rt for 30 min. The progress of the reaction was monitored by TLC. After completion, the reaction mixture was evaporated under reduced pressure. And the crude was purified by column chromatography by eluting with 7-10% ethyl acetate in hexane to yield the title compound XVa as brown liquid; Yield: (9 g, 83.33%). $^1$H NMR (400 MHz, $CDCl_3$): δ 8.076-8.042 (d, J=13.6 Hz, 1H), 7.942-7.910 (d, J=12.8 Hz, 1H), 7.722-7.605 (t, J=7.2 Hz, 1H), 7.331-7.314 (d, J=6.8 Hz, 1H), 7.278-7.7.266 (d, J=4.8 Hz, 1H), 2.263 (s, 3H).

Step-3: 2-(6-methylpyridin-2-yl) ethan-1-amine (XIV)

To a stirred solution of (E)-6-methoxy-2-(2-nitrovinyl) pyridine 2 (9.18 g, 0.0559 mol) in DEE (700 ml), was added LAH (1M sol in THF, 224 ml, 0.22 mol) at 0° C. dropwise. Then the temp was raised to 40° C. and continued for 2 h. The progress of the reaction was monitored by TLC. After completion, the reaction mixture was cooled to 0° C. and quenched with chilled water (50 ml), 15N aq. NaOH (5 ml), and filtered through celite bed. Celite bed was washed with DEE (250 ml). DEE from filtrate was distilled off at reduced pressure to get title compound XIV brown liquid which was used for next step without further purification. Yield: (5.09 g, 67%). LC_MS Calculated. for $C_{18}H_{12}N_2$: 136; Observed. 137 [$M^+$+H]. $^1$H NMR (400 MHz, $CDCl_3$): δ 7.577-7.539 (t, J=8 Hz, 1H), 7.050-7.012 (m, 2H), 2.867-2.807 (t, J=6.8 Hz, 2H), 2.771-2.750 (t, J=8.4 Hz, 2H), 2.420 (s, 3H).

Synthesis of 2-(6-(2-aminoethyl) pyridin-2-yl)propan-2-ol. (XV)

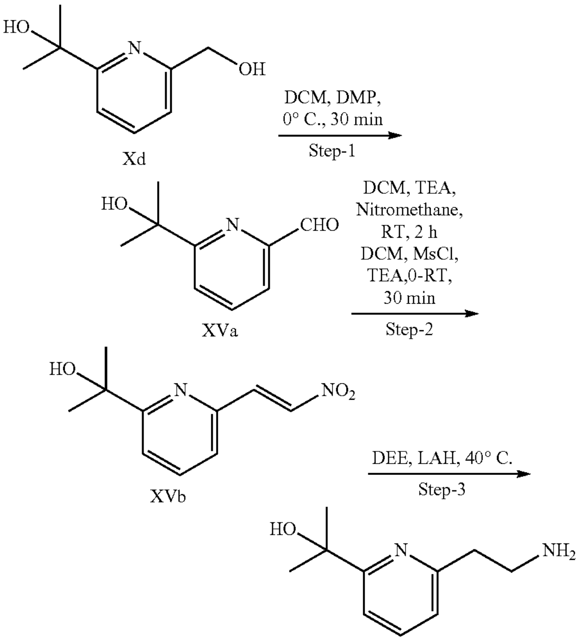

Xd

XVa

XVb

XV

Step-1: 6-(2-hydroxypropan-2-yl) picolinaldehyde (XVa)

To a stirred solution of 2-(6-(hydroxymethyl) pyridin-2-yl) propan-2-ol Xd (1.8 g, 0.0107 mol) in DCM (50 ml), added DMP (6.85 g, 0.0161 mol) portion wise at 0° C. And the reaction mixture was stirred at same temperature for 30 min. The reaction was monitored by TLC. After completion, the reaction mixture was quenched with aq. Sodium bicarbonate (50 ml) and extracted by DCM (100 ml×3 times). The organic layer was dried over sodium sulfate, filtered, and concentrated under reduced pressure. Crude compound was purified by column chromatography, the product was eluted at 10% ethyl acetate/Hexane to afford title compound XVa as pale-yellow oil. Yield: (1.1 g, 62%). $^1$H NMR (400 MHz, $CDCl_3$): δ 10.094 (s, 1H), 7.929-7.870 (m, 2H), 7.659-7.641 (d, J=7.2 Hz, 1H), 4.606 (bs, 1H), 1.607 (s, 6H).

Step-2: (E)-2-(6-(2-nitrovinyl) pyridin-2-yl) propan-2-ol (XVb)

To a stirred solution of 6-(2-hydroxypropan-2-yl) picolinaldehyde XVa (0.5 g, 0.00303 mol) in DCM (5 ml), was added TEA (0.613 g, 0.00606 mol) and nitromethane (0.1 g, 0.0016 mol) and the reaction mixture was stirred at rt for 2 h. The progress of the reaction was monitored by TLC. After completion, the reaction mixture was evaporated under reduced pressure. The crude material was dissolved in DCM (20 ml) and treated with TEA (0.67 g, 0.00663 mol) and mesyl chloride (0.756 g, 0.00663 mol) at 0° C. and the reaction mixture was stirred at rt for 30 min. The progress of the reaction was monitored by TLC. After completion, the reaction mixture was evaporated under reduced pressure. And the crude was purified by column chromatography by eluting with 7% ethyl acetate in hexane to yield the title compound XVb as yellow solid; Yield: (0.35 g, 76%). LC_MS Calculated for $C_{10}H_{12}N_2O_3$: 208.08; Observed: 209.20 [$M^+$+H]. $^1$H NMR (400 MHz, $CDCl_3$): δ 8.036-8.003 (d, J=13.2 Hz, 1H), 7.951-7.918 (d, J=13.2 Hz, 1H), 7.841-7.801 (t, J=8 Hz, 1H), 7.531-7.510 (d, J=8.4 Hz, 1H), 7.406-7.388 (d, J=7.2 Hz, 1H), 1.577 (s, 6H).

Step-3: 2-(6-(2-aminoethyl) pyridin-2-yl) propan-2-ol (XV)

To a stirred solution of (E)-1-Methyl-3-(2-nitrovinyl)-1H-pyrazole 3 (0.55 g, 0.00264 mol) in diethyl ether (26 ml), was added LAH (1M solution in THF, 0.401 g, 0.0106 mol) at 0° C. dropwise. Then the temp was allowed to reach to rt and the reaction mixture was stirred at 40° C. for 3 h. The progress of the reaction was monitored by TLC. After completion, the reaction mixture was cooled to 0° C. and quenched with chilled water (3 ml), 15N aq. NaOH (2 ml). Inorganic salts were filtered and washed with DEE (25 ml). Solvent from filtrate were concentrated under reduced pressure to afford crude compound XV which was used for next step without further purification. Yield: (0.3 g, 63%). 1H NMR (400 MHz, DMSO-$d_6$): δ 7.666-7.628 (t, J=7.2 Hz, 1H), 7.450-7.432 (d, J=7.2 Hz, 1H), 7.069-7.050 (d, J=7.6 Hz, 1H), 2.886-2.870 (t, J=6.4 Hz, 2H), 2.784-2.766 (t, J=7.2 Hz, 2H), 1.414 (s, 6H).

Synthesis of 2-(1-ethyl-1H-pyrazol-3-yl) ethan-1-amine. (XVI)

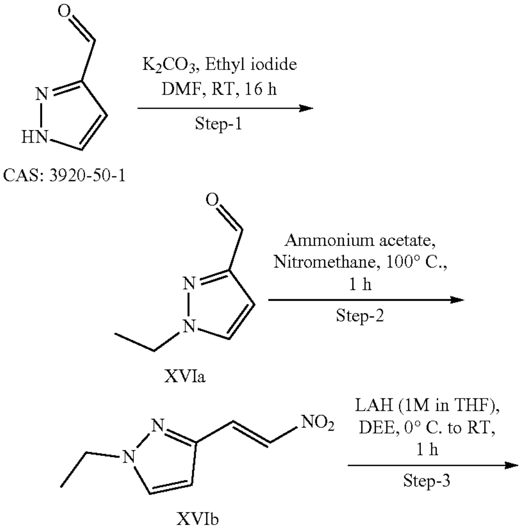

CAS: 3920-50-1

XVIa

XVIb

-continued

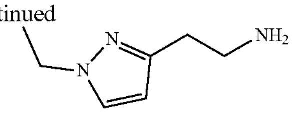

XVI

Step-1: 1-ethyl-1H-pyrazole-3-carbaldehyde (XVIa)

To a stirred solution of 1H-pyrazole-3-carbaldehyde (CAS: 3920-50-1, 3 g, 0.031 mol) in DMF (20 ml) was added Potassium carbonate (10 g, 0.0723 mol) and Ethyl iodide (5.8 g, 0.0374 mol) and the reaction mixture was stirred at rt for 16 h. The progress of the reaction was monitored by TLC. After completion, water (30 ml) was added and extracted with ethyl acetate (3×30 ml). Combined ethyl acetate layer was washed with 10% brine solution (50 ml). Organic layer was dried over sodium sulphate, filtered, and concentrated to afford crudel-ethyl-1H-pyrazole-3-carbaldehyde which was further purified by column chromatography using 30% ethyl acetate in hexane to afford title compound XVI as yellow colored liquid. Yield: (2.4 g, 63%). $^1$H NMR (400 MHz, $CDCl_3$): δ 9.982 (s, 1H), 7.467-7.462 (d, J=2 Hz, 1H), 6.808-6.802 (d, J=2.4 Hz, 1H), 4.307-4.252 (q, J=7.2 Hz, 2H), 1.572-1.536 (t, J=7.2 Hz, 3H).

Step-2: (E)-1-ethyl-3-(2-nitroyinyl)-1H-pyrazole (XVIb)

To a stirred solution of 1-ethyl-1H-pyrazole-3-carbaldehyde 2 (2.4 g, 0.0193 mol) in nitromethane (22 ml) was added Ammonium acetate (2.3 g, 0.029 mol) and the reaction mixture was stirred for 1 h at 100° C. Progress of reaction was monitored by TLC. After completion, solvent from reaction mass was removed under reduced pressure. Residue was taken up with water (50 ml) and extracted with ethyl acetate (3×35 ml). Combined ethyl acetate layer was washed with 10% brine solution (35 ml). Organic layer was dried over $Na_2SO_4$, filtered, and concentrated under reduced pressure to get the desired product XVIb. The crude product was carried forward to next step without further purification. Yield: (1.6 g, 49%). $^1$H NMR (400 MHz, $CDCl_3$): δ 7.990-7.956 (d, J=13.6 Hz, 1H), 7.637-7.604 (d, J=13.2 Hz, 1H), 7.450-7.446 (d, J=1.6 Hz, 1H), 6.542-6.538 (d, J=1.6 Hz, 1H), 4.253-4.190 (q, J=7.2 Hz, 2H), 1.543-1.506 (t, J=7.2 Hz, 3H).

Step-3: 2-(1-ethyl-1H-pyrazol-3-yl) ethan-1-amine (XVI)

To a stirred solution of (E)-1-ethyl-3-(2-nitrovinyl)-1H-pyrazole 3 (1.5 g, 0.0089 mol) in DEE (60 ml), was added LAH (1M sol in THF, 36 ml, 0.036 mol) at 0° C. dropwise. Then the temp was allowed to reach to rt and the reaction mixture was stirred at 40° C. for 3 h. The progress of the reaction was monitored by TLC. After completion, the reaction mixture was cooled to 0° C. and quenched with chilled water (2 ml), 15N aq. NaOH (1 ml). Inorganic salts were filtered and washed with DEE (25 ml). Solvent from filtrate were concentrated under reduced pressure to afford crude compound XVI which was used for next step without further purification. Yield: (1 g, 81%). $^1$H NMR (400 MHz, $CDCl_3$): δ 7.312 (d, 1H), 6.054-6.050 (d, 1H), 4.150-4.096

(q, J=7.2 Hz, 2H), 3.008-2.974 (t, 2H), 2.787-2.754 (t, 2H), 1.483-1.432 (t, J=7.2 Hz, 3H).

Synthesis of 2-(1-ethyl-1H-pyrazol-3-yl)ethan-1-amine. (XVII)

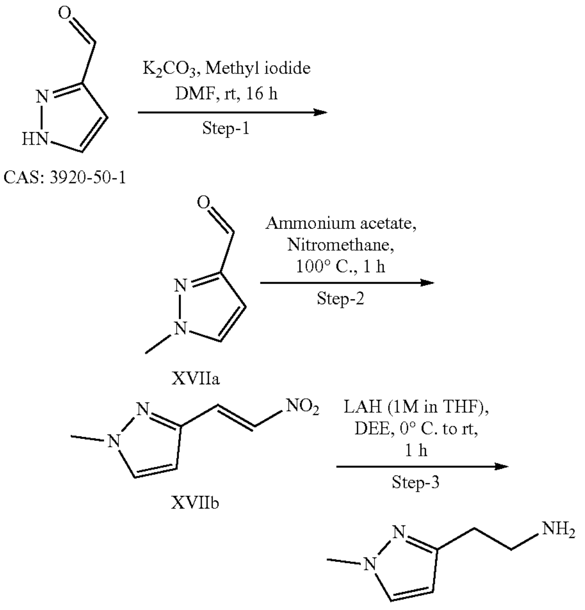

CAS: 3920-50-1

XVIIa

XVIIb

XVII

Step-1: 1-methyl-1H-pyrazole-3-carbaldehyde (XVIIa)

To a stirred solution of 1H-pyrazole-3-carbaldehyde (CAS: 3920-50-1.5 g, 0.052 mol) in DMF (25 ml) was added Potassium carbonate (17.97 g, 0.13 mol) and Methyl iodide (8.86 g, 0.0624 mol) and the reaction mixture was stirred at room temperature for 16 h. The progress of the reaction was monitored by TLC. After completion, water (50 ml) was added and extracted with ethyl acetate (3×50 ml). Combined ethyl acetate layer was washed with 10% brine solution (50 ml). Organic layer was dried over sodium sulphate, filtered, and concentrated to afford crude 1-Methyl-1H-pyrazole-3-carbaldehyde, which was further purified by column chromatography using 30% ethyl acetate in hexane to afford title compound XVIIa as yellow colored liquid. Yield: (2.6 g, 45%). $^1$H NMR (400 MHz, $CDCl_3$): δ 9.960 (s, 1H), 7.431-7.427 (d, J=1.6 Hz, 1H), 6.812-6.805 (d, J=2.8 Hz, 1H), 4.020 (s, 1H).

Step-2: (E)-1-methyl-3-(2-nitrovinyl)-1H-pyrazole (XVIIb)

To a stirred solution of 1-Methyl-1H-pyrazole-3-carbaldehyde XVIIa (2.4 g, 0.020 mol) in nitromethane (43 ml) was added ammonium acetate (2.5 g, 0.031 mol) and the reaction mixture was stirred for 1 h at 100° C. Then the progress of reaction was monitored by TLC. After completion, solvent from reaction mass was removed under reduced pressure. Residue was taken up with water (50 ml) and extracted with ethyl acetate (3×50 ml). Combined ethyl acetate layer was washed with 10% brine solution (50 ml). Organic layer was dried over $Na_2SO_4$, filtered, and concentrated under reduced pressure. Crude product was purified by column chromatography using 20% ethyl acetate in hexane to afford pure title compound XVIIb. Yield: (1.4 g, 49%). $^1$H NMR (400 MHz, $CDCl_3$): δ7.970-7.936 (d, J=13.6 Hz, 1H), 7.631-7.598 (d, J=13.2 Hz, 1H), 7.428-7.422 (d, J=2.4 Hz, 1H), 6.549-6.543 (d, J=2.4 Hz, 1H), 3.971 (s, 3H).

Step-3: 2-(1-Methyl-1H-pyrazol-3-yl) ethan-1-amine (XVII)

To a stirred solution of (E)-1-Methyl-3-(2-nitrovinyl)-1H-pyrazole 3 (1.4 g, 0.009 mol) in DEE (60 ml), was added LAH (1M solution in THF, 29 ml, 0.029 mol) at 0° C. dropwise. Then the temp was allowed to reach to rt and the reaction mixture was stirred at 40° C. for 3 h. The progress of the reaction was monitored by TLC. After completion, the reaction mixture was cooled to 0° C. and quenched with chilled water (2 ml), 15N aq. NaOH (1 ml). Inorganic salts were filtered and washed with DEE (25 ml). Solvent from filtrate were concentrated under reduced pressure to afford crude compound XVII which was used for next step without further purification. Yield: (1 g, 87%). $^1$H NMR (400 MHz, $CDCl_3$): δ 7.278-7.268 (d, J=4 Hz, 1H), 6.053-6.050 (d, J=1.2 Hz, H), 3.853 (s, 3H), 3.008-2.969 (t, J=6.8 Hz, 2H), 2.778-2.745 (t, J=6.8 Hz, 2H).

Synthesis of 2-(3-(2-aminoethyl)-1H-pyrazol-1-yl)-2-methylpropan-1-ol. XVIII

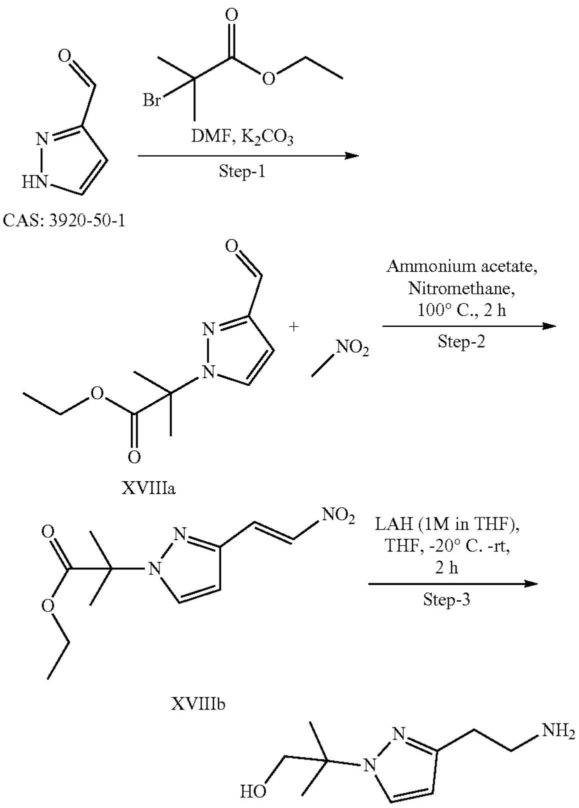

CAS: 3920-50-1

XVIIIa

XVIIIb

XVIII

Step-1: Ethyl 2-(3-formyl-1H-pyrazol-1-yl)-2-methylpropanoate (XVIIIa)

To a stirred solution of 1H-pyrazole-3-carbaldehyde (CAS: 3920-50-1, 1 g, 0.01 mol) in DMF (5 ml) was added Potassium carbonate (3 g, 0.02 mol) and ethyl 2-bromo-2-methylpropanoate (2 g, 0.01 mol) and the reaction mixture was stirred at room temperature for 16 h. Then the progress of the reaction was monitored by TLC. After completion, water (25 ml) was added and extracted with ethyl acetate (3×25 ml). Combined ethyl acetate layer was washed with 10% brine solution (25 ml). Organic layer was dried over sodium sulphate, filtered, and concentrated to afford crud compound which was further purified by column chromatography using 30% ethyl acetate in hexane to afford title compound XVIIIa. Yield: (1.8 g, 82%). LC_MS Calculated for $C_{10}H_{14}N_2O_3$ is 210.06; Observed.: 211.20 [$M^{+}$+1]. $^1H$ NMR (400 MHz, $CDCl_3$): δ 9.980 (s, 1H), 7.623 (s, 1H), 6.836 (s, 1H), 4.217-4.164 (q, J=7.2 Hz, 2H), 1.999 (s, 6H), 1.235-1.200 (t, J=6.8 Hz, 3H).

Step-2: ethyl (E)-2-methyl-2-(3-(2-nitrovinyl)-1H-pyrazol-1-yl) propanoate (XVIIIb)

To a stirred solution of ethyl 2-(3-formyl-1H-pyrazol-1-yl)-2-methylpropanoate XVIIIa (1.8 g, 0.008 mol) in nitromethane (17 ml) was added Ammonium acetate (0.99 g, 0.0121 mol) and the reaction mixture was stirred for 1 h at 100° C. Progress of reaction was monitored by TLC. After completion, solvent from reaction mass was removed under reduced pressure. Crude product was purified by column chromatography using 20% ethyl acetate in hexane to afford pure title compound XVIIIb. Yield: (0.55 g, 25%). LC_MS Calculated for $C_{11}H_{15}N_3O_4$ is 253.11; Observed: 254.20 [$M^{+}$+1]. In NMR (400 MHz, $CDCl_3$): δ 8.007-7.973 (d, J=13.6 Hz, 1H),7.629-7.611 (m, 2H), 7.509-7.504 (d, J=2 Hz, 1H), 6.580-6.574 (d, J=2.4 Hz, 1H), 4.210-4.120 (q, J=7.6 Hz, 2H), 1.187 (s, 6H), 1.237-1.163 (t, J=7.6 Hz, 3H).

Step-3: 2-(3-(2-aminoethyl)-1H-pyrazol-1-yl)-2-methylpropan-1-ol (XVIII)

To a stirred solution of ethyl (E)-2-methyl-2-(3-(2-nitrovinyl)-1H-pyrazol-1-yl) propanoate 4 (0.55 g, 0.0021 mol) in DEE (15 ml), was added LAH (1M solution in THF, 8.7 ml, 0.0086 mol) at 0° C. dropwise. Then the temp was allowed to reach to rt and the reaction mixture was stirred at 40° C. for 3 h. The progress of the reaction was monitored by TLC. After completion, the reaction mixture was cooled to 0° C. and quenched with chilled water (2 ml), 15N aq. NaOH (1 ml). Inorganic salts were filtered and washed with DEE (25 ml). Solvent from filtrate were concentrated under reduced pressure to afford crude compound XVIII which was used for next step without further purification. Yield: (0.35 g, 88%). LC_MS Calculate for $C_9H_{17}N_3O$ is 183.14; Observe: 184.30 [$M^{+}$+1]. In NMR (400 MHz, $CDCl_3$): δ 7.449 (s, 2H), 6.071 (s, 1H), 3.76 (s, 2H), 2.999-2.968 (t, J=7.6 Hz, 2H), 2.811-2.740 (t, J=7.6 Hz, 2H), 1.596 (s, 6H).

Synthesis of 2-(5-methoxypyridin-2-yl)ethan-1-amine. XIX

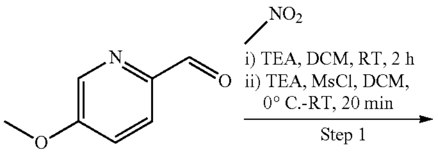

CAS: 22187-96-8

-continued

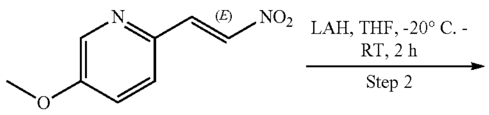

XIXa

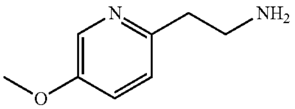

XIX

Step-1: (E)-5-Methoxy-2-(2-nitrovinyl) pyridine (XIXa)

To a stirred solution of 5-methoxypicolinaldehyde 1 (2.0 g, 0.0145 mol) in DCM (20 ml), was added TEA (4.04 ml, 0.029 mol) and nitromethane 2 (1.06 g, 0.0174 mol) and the reaction mixture was stirred at rt for 2 h. The progress of the reaction was monitored by TLC. After completion, the reaction mixture was evaporated under reduced pressure. The crude material was dissolved in DCM (20 ml) and treated with TEA (6.06 ml, 0.0435 mol) and mesyl chloride (3.37 ml, 0.0435 mol) at 0° C. and the reaction mixture was stirred at rt for 30 min. The progress of the reaction was monitored by TLC. After completion, the reaction mixture was evaporated under reduced pressure. The crude was purified by column chromatography by eluting with 10% ethyl acetate in hexane to yield the title compound XIXa as yellow solid; Yield: (2.47 g, 94%). LC_MS Calculated for $C_8H_8N_2O_3$: 180.05; Observe: 181.00 [$M^{+}$+H]. $^1H$ NMR (400 MHz, $CDCl_3$): δ 8.38 (d, J=3.2 Hz, 1H), 7.43 (d, J=8.4 Hz, 1H), 7.26 (s, 1H), 7.22 (dd, J=8.4, 2.8 Hz, 1H), 3.92 (s, 3H).

Step-2: 2-(5-Methoxypyridin-2-yl) ethan-1-amine (XIX)

To a stirred solution of (E)-5-methoxy-2-(2-nitrovinyl) pyridine 3 (2.74 g, 0.0152 mol) in THF (90 ml), was added LAH (1M sol in THF, 45.6 ml, 0.0456 mol) at −10° C. dropwise. Then the temp was allowed to reach to rt and the reaction mixture was stirred at rt for 2 h. The progress of the reaction was monitored by TLC. After completion, the reaction mixture was cooled to 0° C. and quenched with saturated $Na_2SO_4$ solution (50 ml) and extracted with ethyl acetate (50 ml×3). The organic layer was dried with $Na_2SO_4$, filtered, and evaporated under reduced pressure. The crude was purified by column chromatography by eluting with 10% methanolic $NH_3$ in DCM to yield the title compound XIX as brown liquid; Yield: (0.8 g, 34.78%). $^1H$ NMR (400 MHz, DMSO): δ 8.19 (d, J=2.8 Hz, 1H), 7.3 (dd, J=8.4, 3.2 Hz, 1H), 7.19 (d, J=8.8 Hz, 1H), 3.79 (s, 3H), 2.88 (t, J=6.0 Hz, 2H), 2.74 (t, J=6.8 Hz, 2H).

Synthesis of a mixture of 7-amino-3-chloro-2-methyl-5-(methyl sulfonyl)pyrazolo[1,5-a] pyrimidine-6-carbonitrile (XX) and 7-amino-3-chloro-2-methyl-5-(methyl sulfinyl) pyrazolo[1,5-a] pyrimidine-6-carbonitrile. (XXa)

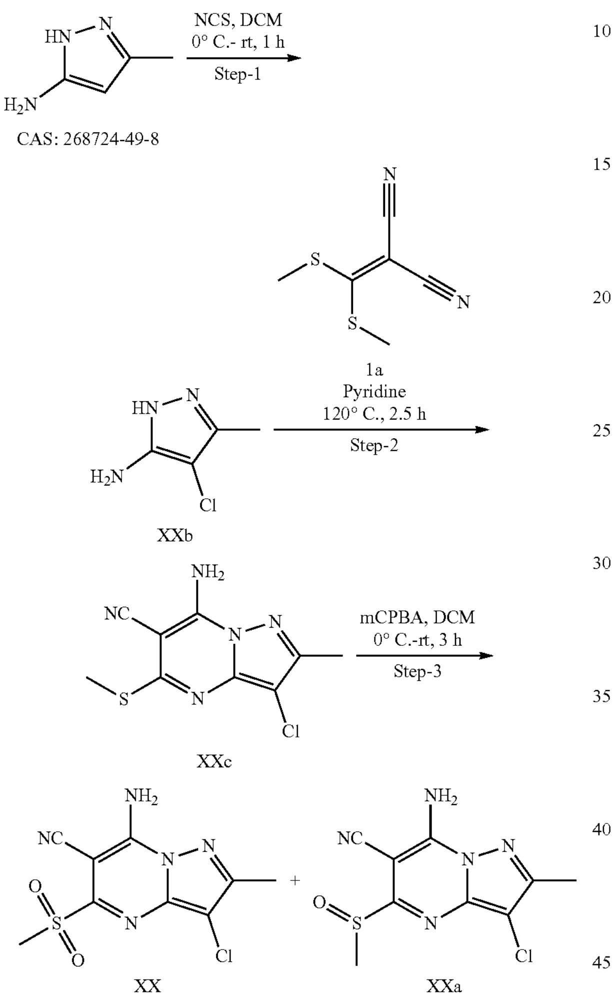

CAS: 268724-49-8

1a

XXb

XXc

XX

XXa

Step-1: Synthesis of 4-chloro-3-methyl-1H-pyrazol-5-amine (XXb)

N-Chlorosuccinimide (3.3 g, 0.025 mol) was added portion wise to the stirred solution of 3-methyl-1H-pyrazol-5-amine (CAS: 268724-49-8, 2.0 g, 0.021 mol) in DCM (50 mL) at 0° C., Then the reaction mixture was stirred at rt for 1 h. The progress of the reaction was monitored by TLC. Then the reaction mixture was diluted with water (20 mL) and extracted with ethyl acetate (3×50 mL). The combined organic layer was dried over anhydrous $Na_2SO_4$ and evaporated under reduced pressure to get the crude product. Crude compound obtained was purified by Biotage column chromatography using silica gel (230-400) and 1-5% methanol in DCM as eluent to afford desired product XXb as an off white solid. Yield: 2.0 g, 74%. LCMS Calculated. for $C_4H_6ClN_3$ is 131.56; Observed. 132.0 $[M+H]^+$ Step-2: Synthesis of 7-amino-3-chloro-2-methyl-5-(methylthio) pyrazolo[1,5-a] pyrimidine-6-carbonitrile (XXc)

To a stirred solution of 4-chloro-5-methyl-1H-pyrazol-3-amine XXb (1.8 g, 0.0136 mol) in pyridine (5 mL) was added 2-(bis (methylthio) methylene) malononitrile Ia (2.8 g, 0.016 mol). The resulting reaction mixture was heated at 120° C. for 2.5 h. Then the progress of the reaction was monitored by TLC. Reaction mixture was cooled to room temperature and poured into ice cold water (20 mL). Precipitated compound was filtered and washed with cold water. Then the obtained solid was dried under vacuum and purified by biotage column chromatography using silica gel (230-400) and 5-20% ethyl acetate in hexane as eluent to afford desired product XXc as pale brown colour solid. Yield: 3.5 g, 99%. LCMS Calculated. for $C_9H_8ClN_5S$ is 253.71; Observed. 254.0 $[M+H]^+$. $^1H$ NMR (400 MHz, DMSO-$D_6$): δ 8.90 (bs, 2H), 2.57 (S, 3H), 2.37 (S, 3H).

Step-3: Synthesis of 7-amino-3-chloro-2-methyl-5-(methyl sulfonyl) pyrazolo[1,5-a]pyrimidine-6-carbonitrile. (XX) and 7-amino-3-chloro-2-methyl-5-(methyl sulfinyl) pyrazolo[1,5-a]pyrimidine-6-carbonitrile (XXa)

meta-Chloroperoxybenzoic acid (9.5 g, 0.055 mol) was added portion wise to a stirred solution of 7-amino-3-chloro-2-methyl-5-(methylthio) pyrazolo[1,5-a] pyrimidine-6-carbonitrile XXc (3.5 g, 0.013 mol) in DCM (50 mL) at 0° C. The reaction mixture was stirred at rt for 3 h. Then the progress of the reaction was monitored by TLC. The reaction mixture was quenched with aqueous $NaHCO_3$ solution (50 mL) and extracted with DCM (3×50 mL). The combined organic layer was dried over anhydrous $Na_2SO_4$ and evaporated under reduced pressure and dried under vacuum to get a mixture of 7-amino-3-chloro-2-methyl-5-(methyl sulfonyl) pyrazolo[1,5-a] pyrimidine-6-carbonitrile XX and 7-amino-3-chloro-2-methyl-5-(methyl sulfinyl) pyrazolo[1,5-a] pyrimidine-6-carbonitrile XXa as an off white solid. Yield (2.2 g, 56%). This crude material was taken as such for next step without further purification. LCMS Calculated. for $C_9H_8ClN_5O_2S$ is 285.71; Observed. 286.1 [M+H] $^1H$ NMR (400 MHz, DMSO-D6): δ 9.48 (bs, 2H), 3.42 (S, 3H), 2.45 (S, 3H).

Synthesis of 2-(6-(methoxymethyl) pyridin-2-yl) ethan-1-amine (XXI)

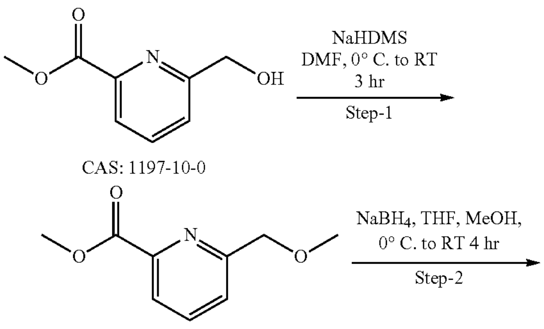

CAS: 1197-10-0

XXIa

-continued

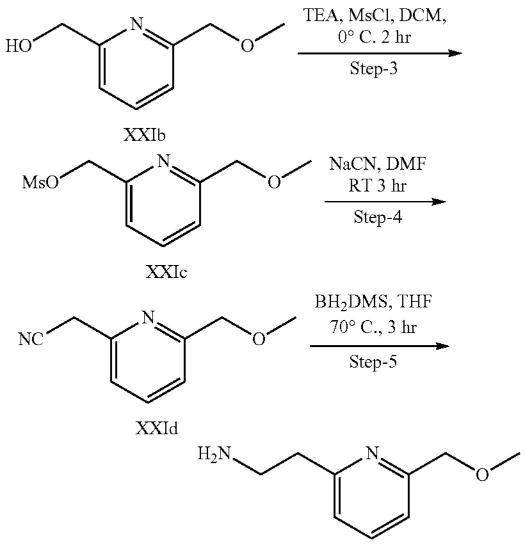

XXIb

XXIc

XXId

XXI

Step-1: Synthesis of methyl 6-methoxy methyl) picolinate. (XXIa)

A solution of methyl 6-(hydroxymethyl) picolinate (CAS: 1197-10-0, 25 g, 0.15 mol) in DMF (250 mL) was cooled to 0° C., added NaH (7.2 g, 60% wt, 0.18 mol) portion wise and dimethyl sulphate (19 mL, 0.19 mol) dropwise to it and the reaction mixture was stirred at rt for 3 hours. Then the progress of the reaction was monitored by TLC. After completion, the reaction mixture was quenched with ice cold water (200 mL) and extracted with ethyl acetate (3×200 mL) and concentrated. Crude product obtained was purified by gravity column used 230-400 silica mesh and the desired product was eluted at 15-20% ethyl acetate in hexane to afford XXIa as yellow viscous oil. Yield: 21 g, 78%. LCMS Calculated. for $C_9H_{11}NO_3$ is 181.07; Observed 182.20 [M+H]. $^1H$ NMR (400 MHz, $CDCl_3$): δ 8.04 (d, J=7.6 Hz, 1H), 7.86 (t, J=7.6 Hz 1H), 7.66 (d, J=7.6 Hz, 1H), 4.69 (s, 2H), 4.00 (s, 3H), 3.49 (s, 3H).

Step-2: Synthesis of (6-(methoxy methyl) pyridin-2-yl) methanol (XXIb)

A solution of methyl 6-(methoxymethyl) picolinate XXIa (21 g, 0.12 mol) in THF (200 mL) was cooled to 0° C., added $NaBH_4$ (13 g, 0.35 mol) portion wise and then reaction mixture was stirred at 25° C. for 3 hours. The progress of the reaction was monitored by TLC. Reaction mixture concentrated at low vacuum and added $NaHCO_3$ solution (100 mL) and extracted with DCM (3×300 mL). The combined organic layer was dried over anhydrous $Na_2SO_4$, filtered, and evaporated under reduced pressure. Crude compound obtained was purified by gravity column used 230-400 silica mesh and the desired product was eluted at 25-30% ethyl acetate in hexane to afford XXIb as yellow viscous oil. Yield: 16.8 g, 93%. LCMS Calculated. for $C_8H_{11}NO_2$ is 153.08; Observed 154.25 $[M+H]^+$. $^1H$ NMR (400 MHz, $CDCl_3$): δ 7.69 (t, J=7.6 Hz, 1H), 7.33 (d, J=7.6 Hz, 1H), 7.14 (d, J=7.6 Hz, 1H), 4.74 (d, J=4.8 Hz, 2H), 4.59 (s, 2H), 3.77 (t, J=4.8, 5.2 Hz, 1H) 3.48 (s, 3H).

Step-3: Synthesis of (6-(methoxy methyl) pyridin-2-yl) methyl methane sulfonate (XXIc)

A solution of (6-(methoxymethyl) pyridin-2-yl) methanol XXIb (7 g, 0.05 mol) in DCM (140 mL) was cooled to 0° C., added TEA (7 g, 0.01 L, 0.07 mol) and MsCl (4 mL, 0.05 mol) dropwise and the reaction mixture was stirred at 0° C. for 2 hours. The progress of the reaction was monitored by TLC. Reaction mixture was quenched with $NaHCO_3$ solution (100 mL) and extracted with DCM (3×200 mL) and the combined organic layer was dried over anhydrous $Na_2SO_4$, filtered, and evaporated under reduced pressure to get brown liquid XXIc which was used as such for the next step without further purification. Yield: 10 g, 92%. $^1H$ NMR (400 MHz, $CDCl_3$): δ 7.79-7.75 (m, 1H), 7.42 (d, 1H, J=8.0 Hz), 7.38 (d, J=7.6 Hz, 1H), 5.32 (s, 2H), 4.57 (s, 2H), 3.48 (s, 3H), 3.09 (s, 3H).

Step-4: Synthesis of 2-(6-(methoxy methyl) pyridin-2-yl) acetonitrile (XXId)

To a stirred solution of (6-(methoxymethyl) pyridin-2-yl) methyl methane sulfonate XXIc (10 g, 0.043 mol) in DMF (100 mL) was added NaCN (2.3 g, 0.048 mol) portion wise and the reaction mixture was stirred at 24° C. for 3 hours. The progress of the reaction was monitored by TLC. Reaction Mixture quenched with ice cold water (100 mL) and extracted with EtOAc (3×100 mL). The combined organic layer was dried over anhydrous $Na_2SO_4$, filtered, and evaporated under reduced pressure. The crude material obtained was purified by flash Chromatography using silica gel 230-400 mesh, the desired product was eluted with 20-25% EtOAc in hexane to afford XXId as yellow viscous oil. Yield: 5.1 g, 73%. LCMS Calculated. for $C_9H_{10}N_2O$ is 162.08; Observed 163.25 $[M+H]^+$. $^1H$ NMR (400 MHz, $CDCl_3$) δ 7.7-7.7 (m, 1H), 7.40-7.26 (m, 2H), 4.56 (s, 2H), 3.92 (s, 2H), 3.48 (s, 3H).

Step-5: Synthesis of 2-(6-(methoxy methyl) pyridin-2-yl) ethan-1-amine (XXI)

A solution of 2-(6-(methoxymethyl) pyridin-2-yl) acetonitrile XXId (5.1 g, 0.031 mol) in THF (80 mL) was cooled to 0° C. and added $BH_3$·DMS (15 mL, 0.16 mol) dropwise and the reaction mixture was stirred at 70° C. for 3 hours. The progress of the reaction was monitored by TLC. After completion, the reaction was cooled to room temperature and quenched by MeOH (15 mL). The resulting mixture was stirred at room temperature for 30 min. The mixture was acidified using 1 M HCl solution (15 mL) and concentrated under reduced pressure. The residue obtained was taken in water (20 mL) and EtOAc (50 mL) and DCM (50 mL) were added to remove the impurities. The aqueous layer was separated and basified with 2N NaOH solution. The resulting mixture was extracted with DCM (3×300 mL). The combined organic layer was dried over anhydrous $Na_2SO_4$, filtered, and concentrated under reduced pressure to afford the desired compound XXI as a brown viscous liquid. The crude compound was used in the next step without further purification. Yield: 3.4 g, 65%. LCMS Calculated. for $C_9H_{11}NO_3$ is 166.11; Observed 167.30 $[M+H]^+$. $^1H$ NMR (400 MHz, CDCL3): δ 7.64-7.60 (m, 1H), 7.26 (d, J=8 Hz, 1H), 7.07 (d, J=7.6 Hz, 1H), 4.56 (s, 2H), 3.47 (s, 3H), 3.10-3.07 (m, 2H), 2.93-2.90 (m, 2H).

Synthesis of (1-(6-(2-aminoethyl) pyridin-2-yl) cyclopropyl) methanol (XXII)

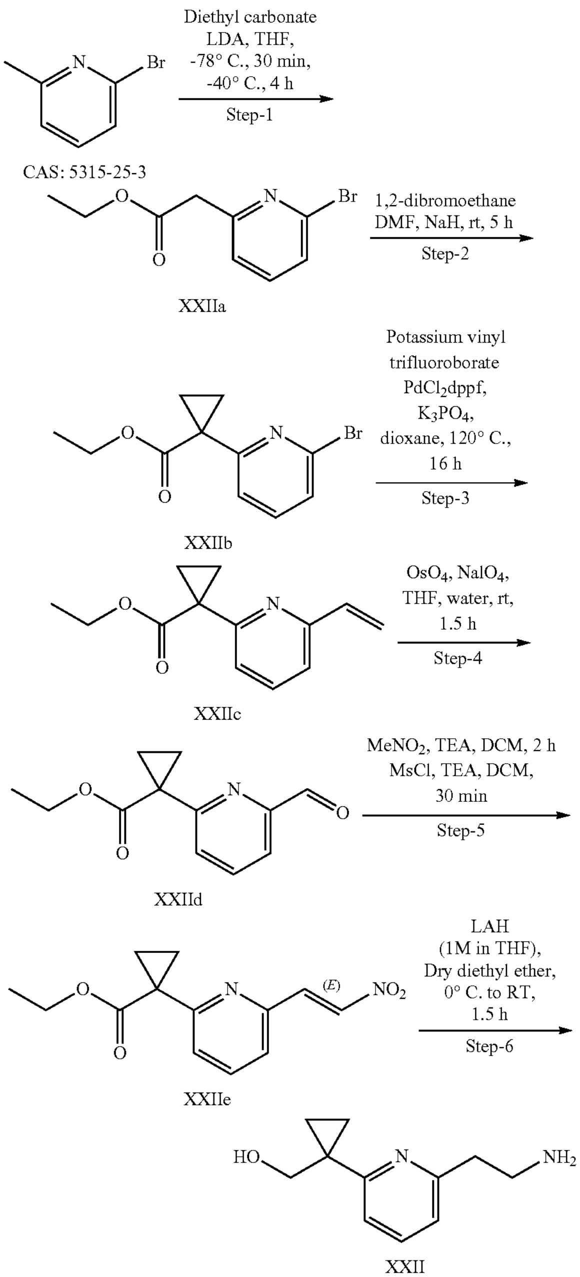

CAS: 5315-25-3

XXIIa

XXIIb

XXIIc

XXIId

XXIIe

XXII

Step-1: Synthesis of Ethyl 2-(6-bromopyridin-2-yl) acetate (XXIIa)

To a solution of lithium diisopropylamide (8 g, 0.04 L, 2M, 2.5 eq, 0.07 mol) in THF (150 mL) at −78° C. under nitrogen atmosphere was added 2-bromo-6-methylpyridine (CAS: 5315-25-3, 5 g, 1 eq, 0.03 mol) dropwise and the resulting mixture was stirred at −78° C. for 30 min. This was followed by an addition of diethyl carbonate (9 g, 2.5 eq, 0.07 mol). The resulting mixture was stirred at −40° C. for 6 hours. The progress of the reaction was monitored by TLC for the absence of starting material. The reaction was quenched with saturated solution of $NH_4Cl$ (60 mL) and the resulting mixture was extracted with ethyl acetate (70 mL×2). The combined organic layer was dried over anhydrous sodium sulfate and concentrated under reduced pressure to afford light brown viscous liquid. The crude compound was purified by column chromatography using silica gel (100-200; 250 g) and EtOAc (0-10%) in hexane as eluent. The peak eluted with 7% of EtOAc in hexane was concentrated to afford the desired product XXIIa as a colorless viscous liquid. Yield: 5.3 g, 70%. LCMS Calculated. for $C_9H_{10}BrNO_2$ is 242.99; Observed. 244.10 $[M+H]^+$. $^1H$ NMR (400 MHz, $CDCl_3$): δ 7.53 (t, J=7.6 Hz, 1H), 7.40 (d, J=8.0 Hz, 1H), 7.28 (t, J=7.2 Hz, 1H), 4.19 (q, J=7.2 Hz, 2H), 3.83 (s, 2H), 1.27 (t, J=6.8 Hz, 3H).

Step-2: Synthesis of Ethyl 1-(6-bromopyridin-2-yl) cyclopropane-1-carboxylate (XXIIb)

A stirred solution of ethyl 2-(6-bromopyridin-2-yl) acetate XXIIa (4.2 g, 1 eq, 17 mmol) in DMF (25 mL) was cooled to 0° C. sodium hydride (1.5 g, 60% Wt. 2.2 eq, 38 mmol) was added. To the resulting mixture 1,2-dibromoethane (7.1 g, 2.2 eq, 38 mmol) was added drop wise and stirred at rt for 4 hr. The reaction was monitored by TLC for the absence of starting material. To the reaction mixture (25 mL) ice cold water was added and the resulting mixture was extracted with ethyl acetate (25 mL×2). The combined organic layer was given brine wash, dried over anhydrous sodium sulphate, filtered, and concentrated under reduced pressure to afford a pale brown viscous liquid. The crude compound was purified by silica gel (100-200; 24 g) column chromatography using EtOAc (0-20%) in hexane. The peak eluted with 7% EtOAc in hexane was concentrated to afford the desired product XXIIb as a pale brown viscous liquid. Yield: 4.1 g, 88%. LCMS Calculated. for $C_{11}H_{12}BrNO_2$ is 271.00; Observed. 272.05 $[M+H]^+$. $^1H$ NMR (400 MHz, $CDCl_3$): δ 7.54 (d, J=7.6 Hz, 1H), 7.50 (t, J=7.6 Hz, 1H), 7.34 (d, J=7.6 Hz, 1H), 4.15 (q, J=7.2 Hz, 2H), 1.67 (t, J=4.4 Hz, 2H), 1.50 (t, J=4.4 Hz, 2H), 1.23 (t, J=7.2 Hz, 3H).

Step-3: Synthesis of Ethyl 1-(6-vinylpyridin-2-yl) cyclopropane-1-carboxylate (XXIIc)

A solution of ethyl 1-(6-bromopyridin-2-yl) cyclopropane-1-carboxylate XXIIb (2.8 g, 1 eq, 10 mmol), potassium trifluoro(vinyl)borate (1.7 g, 1.2 eq, 12 mmol) and potassium phosphate, tribasic (3.3 g, 1.3 mL, 1.5 eq, 16 mmol) in 1,4-dioxane (20 mL) was purged with $N_2$ gas for 15 min with vigorous stirring. To the reaction was added $PdCl_2(dppf)$ (0.38 g, 0.05 eq, 0.52 mmol) and heated to 120° C. for 16 hours. The progress of the reaction was monitored by TLC analysis. The reaction was cooled to room temperature and reaction mixture was concentrated under reduced pressure. The residue was added water (70 mL) and the resulting mixture was extracted with ethyl acetate (50 mL×2). The organic layer was dried over anhydrous sodium sulphate and concentrated under reduced pressure to afford a light brown viscous liquid. The crude compound was purified by combi-flash (230-400, 120 g packed) column chromatography using ethyl acetate in hexane and peak eluted with 5% EtOAc in hexane was concentrated to afford XXIIc as a light brown viscous liquid; Yield: 1 g, 40%. LCMS Calculated. for $C_{13}H_{15}NO_2$ is 217.11; Observed. 218.25 $[M+H]^+$ $^1H$ NMR (400 MHz, $CDCl_3$): δ 7.58 (t, J=7.6 Hz, 1H), 7.41 (d, J=7.6 Hz, 1H), 7.19 (d, J=7.6 Hz, 1H), 6.78 (q, J=6.4 Hz, 1H), 6.17 (dd, J=17.4 & 1.6 Hz, 1H), 5.43 (dd, J=11.0 & 1.2

Hz, 1H), 4.15 (q, J=7.2 Hz, 2H), 1.65-1.63 (m, 2H), 1.56-1.53 (m, 2H), 1.21 (t, J=7.2 Hz, 3H).

Step-4: Synthesis of Ethyl 1-(6-formylpyridin-2-yl) cyclopropane-1-carboxylate (XXIId)

To a solution of ethyl 1-(3-vinylphenyl) cyclopropane-1-carboxylate XXIIc (1 g, 1 eq, 5 mmol) in THF (18 mL) and water (40 mL) osmium tetra-oxide (4.68 mL, 2.5% Wt. in isobutanol, 0.1 eq, 0.5 mmol) was added and the reaction was stirred at rt for 30 min. Then sodium metaperiodate (1 g, 0.4 mL, 1.5 eq, 7 mmol) was added and the reaction was stirred at rt for 2 h. The progress of the reaction was monitored by TLC analysis. The mixture was diluted with water (50 mL) and extracted with EtOAc (50 mL×2). The combined organic layer was dried over anhydrous $Na_2SO_4$, filtered and evaporated under vacuum to afford XXIId as brown viscous liquid. The crude was used in the next step without further purification. Yield: 0.95 g, 90%). %. LCMS Calculated. for $C_{13}H_{14}O_3$ is 219.09; Observed. 220.20 $[M+H]^+$. $^1H$ NMR (400 MHz, $CDCl_3$): δ 10.02 (s, 1H), 7.3 (s, 3H), 4.18 (q, J=7.2 Hz, 2H), 1.73-1.61 (m, 4H), 1.22 (t, J=7.2 Hz, 3H).

Step-5: Synthesis of Ethyl (E)-1-(6-(2-nitrovinyl) pyridin-2-yl) cyclopropane-1-carboxylate (XXIIe)

A stirred solution of ethyl 1-(6-formylpyridin-2-yl) cyclopropane-1-carboxylate XXIId (950 mg, 1 eq, 4.33 mmol) in DCM (20 mL) was cooled to 0° C. To the resulting mixture nitromethane (317 mg, 280 μL, 1.2 eq, 5.20 mmol), triethylamine (2.19 g, 3.02 mL, 5 eq, 21.7 mmol) were added under $N_2$ gas. The resulting mixture was stirred at rt for 2 h. The reaction mixture was concentrated under reduced pressure to afford a brown viscous liquid. The mixture was dissolved in fresh DCM (20 mL) and was cooled to 0° C. Then triethylamine (2.19 g, 3.02 mL, 5 eq, 21.7 mmol) was added to the reaction and this was followed by a drop-wise addition of mesylchloride (1.49 g, 1.01 mL, 3 eq, 13.0 mmol) under $N_2$ gas. The reaction mixture was stirred at rt for 30 min. The progress of the reaction was monitored by TLC analysis which indicated completion of the reaction. The reaction mixture was concentrated under reduced pressure and water (15 mL) was added and extracted with ethyl acetate (15 mL×2). The combined organic layer was given brine wash, dried over anhydrous sodium sulphate, and concentrated under reduced pressure to afford XXIIe as brown viscous liquid. The crude product was taken for next step without further purification. Yield: 1.0 g, 86%. LCMS Calculated. for $C_{13}H_{14}N_2O_4$ is 262.10; Observed. 263.20 $[M^++H]$

Step-6: Synthesis of (1-(6-(2-Aminoethyl) pyridin-2-yl) cyclopropyl) methanol (XXII)

To an ice-cold solution of $LiAlH_4$ (20 mL, 1M, 4 eq,) in dry diethyl ether (80 mL) solution was dropwise added a solution of ethyl (E)-1-(6-(2-nitrovinyl) pyridin-2-yl) cyclopropane-1-carboxylate XXIIe (1 g, 1 eq, 4 mmol) in dry diethyl ether (7 mL). The resulting mixture was stirred at rt for 1 hr. The reaction was monitored by TLC analysis which indicated the completion of reaction. The reaction mixture was cooled to 0° C. and quenched water (2 mL) followed by with 15% KOH solution (3 mL). To the mixture was added ethyl acetate (100 mL) and stirred at rt for 20 min. The reaction mixture was filtered, and the residue was washed with 100 mL of ethyl acetate. The combined filtrate was concentrated under reduced pressure to afford a desired compound as pale brown viscous liquid XXII. The crude was used in the next step without further purification. Yield: 0.6 g, 80%. LCMS Calculated. for $C_{11}H_{16}N_2O$ is 192.13; Observed. 193.25 $[M+H]^+$. $^1H$ NMR (400 MHz, DMSO-$D_6$): δ 7.52-7.50 (m, 1H), 6.98 (d, J=8.0 Hz, 1H), 6.70 (d, J=8.0 Hz, 1H), 3.83 (d, J=3.6 Hz, 4H), 3.13 (t, J=6.8 Hz, 2H), 2.90 (t, J=6.4 Hz, 2H); 1.05-1.01 (m, 2H) 0.90-0.85 (m, 2H).

Synthesis of 2-(1-(2-methoxyethyl)-1H-pyrazol-3-yl) ethan-1-amine (XXIII)

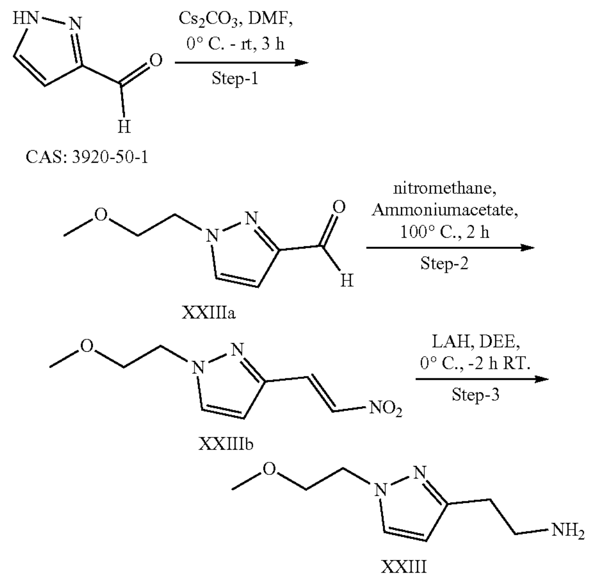

CAS: 3920-50-1
XXIIIa
XXIIIb
XXIII

Step-1: Synthesis of 1-(2-methoxyethyl)-1H-pyrazole-3-carbaldehyde) XXIIIa 1-bromo-2-methoxyethane (5.2 g, 0.037 mol) was added dropwise to a stirred solution of 1H-pyrazole-3-carbaldehyde (CAS: 3920-50-1: 3.0 g, 0.031 mol) and $CS_2CO_3$ (20.0 g, 0.0624 mol) in DMF (50 mL) at 0° C. Then reaction mixture was stirred at rt for 3 h. The progress of the reaction was monitored by TLC. Then the reaction mixture was diluted with water (500 mL) and extracted with ethyl acetate (3×50 mL). The combined organic layer was washed with water (50 mL). the combined organic layer was dried over anhydrous $Na_2SO_4$ and evaporated under reduced pressure to get crude product. Crude product obtained was purified by biotage column chromatography using silica gel (230-400 mesh) and the desired product was eluted at 5-20% ethyl acetate in hexane to afford XXIIIa as colourless liquid Yield: 3.2 g, 66%. LCMS Calculated. for $C_7H_{10}N_2O$ is 154.17; Observed. 155.2 $[M+H]^+$. $^1H$ NMR (400 MHz, DMSO-$D_6$): δ 9.97 (S, 1H), 7.54 (d, J=1.6 Hz, 1H), 6.80 (d, J=2.0 Hz, 1H), 4.38 (t, J=4.8 Hz, 2H), 3.78 (t, J=5.6 Hz, 2H), 3.34 (S, 3H).

Step-2: Synthesis of (E)-1-(2-methoxyethyl)-3-(2-nitrovinyl)-1H-pyrazole XXIIIb A mixture of 1-(2-methoxyethyl)-1H-pyrazole-3-carbaldehyde XXIIIa (3.2 g, 0.019 mol), nitromethane (35 g, 31 mL, 0.57 mol) and ammonium acetate (2.2 g, 0.029 mol) were taken in a round bottom flask and the reaction mixture was stirred at 100° C. for 2 h. Then the progress of the reaction was monitored by TLC for the absence of staring material. The reaction mixture was evaporated under vacuum to get crude residue which was purified by biotage column chromatography using silica (230-400 mesh). The desired product was eluted at 5-20% ethyl acetate in hexane as eluent to afford desired product as colourless liquid XXIIIb. Yield: 2.4 g, 60%. LCMS Calculated. for $C_8H_{11}N_3O_3$ is 197.19; Observed. 198.2 $[M+H]^+$.

Step-3: Synthesis of 2-(1-(2-methoxyethyl)-1H-pyrazol-3-yl) ethan-1-amine XXIII

To a stirred solution of LAH 1.0M in THF (50 mL, 0.048 mol) in diethyl ether (125 mL), was added (E)-1-(2-methoxyethyl)-3-(2-nitrovinyl)-1H-pyrazole XXIIIb (2.4 g, 0.012 mol) in THF (5 ml) at 0° C., under argon atmosphere. The reaction mixture was stirred at rt for 2 h. Then the progress of the reaction was monitored by TLC. The reaction mixture was quenched with water (2.4 ml) at 0° C. followed by addition of 15% KOH solution (2.4 mL) and water (8 mL). Then the reaction mixture was filtered and washed the solid with ethyl acetate (3×100 mL). The combined organic layer was dried over anhydrous $Na_2SO_4$ and evaporated under reduced pressure to get crude XXIII as pale-yellow liquid. Yield: 1.5 g, 83% crude.

Synthesis of (1-(3-(2-aminoethyl)-1H-pyrazol-1-yl) cyclopropyl) methanol. (XXIV)

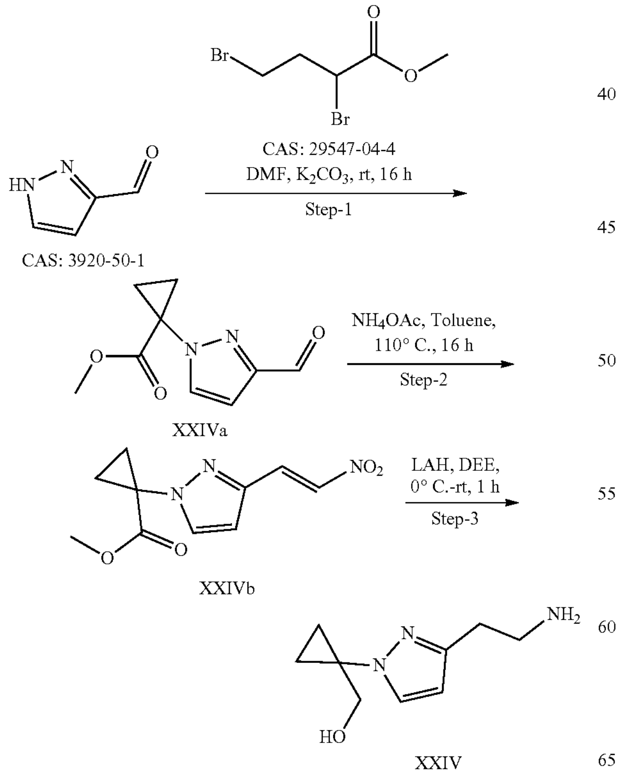

Step-1: Synthesis of methyl 1-(3-formyl-1H-pyrazol-1-yl) cyclopropane-1-carboxylate (XXIVa)

Methyl 2,4-dibromobutanoate (CAS: 29547-04-4, 35 g, 0.14 mol) was added to the stirred solution of 1H-pyrazole-3-carbaldehyde (CAS: 3920-50-1, 10 g, 0.1 mol), $K_2CO_3$ (58 g, 0.42 mol) in DMF (100 mL) at 0° C. Then the reaction mixture was stirred at room temperature for 16 hours. Progress of the reaction was monitored by TLC analysis. Reaction mixture was quenched with cold water and extracted with ethyl acetate (2×200 mL). The combined organic layer was washed with water (3×100 mL) and followed by brine solution, dried over anhydrous sodium sulphate, and concentrated. The crude material was purified by combi-flash using 80 g column, eluted with 0-25% ethyl acetate:hexane, to afford XXIVa as white solid. Yield: 13.5 g, 67%. LCMS Calculated. for $C_9H_{10}N_2O_3$ is 194.07; Observed. 195.15 $[M+H]^+$. $^1H$ NMR (400 MHz, $CDCl_3$): δ 9.97 (s, 1H), 7.58 (s, 1H), 6.82 (s, 1H), 3.70 (d, J=6.8 Hz, 3H), 1.93-1.90 (m, 2H), 1.73-1.70 (m, 2H).

Step-2: Synthesis of methyl (E)-1(3-(2-nitrovinyl)-1H-pyrazol-1-yl) cyclopropane-1-carboxylate (XXIVb)

To a stirred solution of ethyl 1-(3-formyl-1H-pyrazol-1-yl) cyclopropane-1-carboxylate XXIVa (1 g, 0.0051 mol) in toluene (25 mL) was added ammonium acetate (0.6 g, 0.0077 mol) and nitromethane (3.1 g, 0.051 mol), and the resulting mixture was stirred at 100° C. for 16 hrs. The progress of the reaction was monitored by TLC. After completion of the reaction, reaction mixture was quenched with 1N HCl solution (20 mL), extracted with ethyl acetate (2×20 mL). The combined organic layer was washed with brine solution (15 mL), dried over anhydrous sodium sulphate. Solvent was removed under vacuum. The crude compound was passed through flash column and eluted with 10-20% ethyl acetate in hexane to afford XXIVb as white solid. Yield: 1.2 g, 35%. LCMS Calculated. for $C_{10}H_{11}N_3O_4$ is 237.07; Observed. 238.15 $[M+H]^+$. $^1H$ NMR (400 MHz, $CDCl_3$): δ 7.95 (d, J=13.6 Hz, 1H), 7.61 (d, J=13.6 Hz, 1H), 7.57 (d, J=2.4 Hz, 1H), 6.56 (d, J=2.4 Hz, 1H), 3.7 (s, 3H), 1.91-1.87 (m, 2H), 1.7-1.66 (m, 2H).

Step-3: Synthesis of (1-(3-(2-aminoethyl)-1H-pyrazol-1-yl) cyclopropyl) methanol (XXIV)

Methyl (E)-1 (3-(2-nitrovinyl)-1H-pyrazol-1-yl) cyclopropane-1-carboxylate XXIVb (0.430 g, 0.0018 mol) in THF (5 mL) was added dropwise to a stirred solution of LAH (1M in THF, 7.25 ml, 0.0072 mol) in $Et_2O$ (10 mL) at 0° C. and stirred the reaction mixture for 1 hr at room temperature. The progress of the reaction was monitored by TLC. After completion of the reaction, the reaction mixture was cooled to 0° C. and quenched with water (0.4 mL) followed by 15% KOH solution (0.4 mL), water (1.2 mL) and the reaction mixture was stirred for 15-20 min. Reaction mixture was filtered and washed with EtOAc (3×20). The combined organic layer was dried over anhydrous sodium sulphate. Concentrated the solvent under reduced pressure to get pale yellow oil XXIV. Yield: 0.329 g, 93.8%. LCMS Calculated. for $C_9H_{15}N_3O$ is 181.24; Observed. 182.25 $[M+H]^+$. $^1H$ NMR (400 MHz, DMSO-$d_6$): δ 7.40 (d, J=2.4 Hz, 1H), 6.05 (d, J=2.0 Hz, 1H), 3.74 (s, 3H), 2.98 (t, J=6.8 Hz, 2H), 2.76 (t, J=7.2 Hz, 2H), 1.26-1.23 (m, 2H), 1.09-1.08 (m, 2H).

Synthesis of (2-(6-(2-aminoethyl) pyridin-2-yl) cyclopropyl) methanol (XXV)

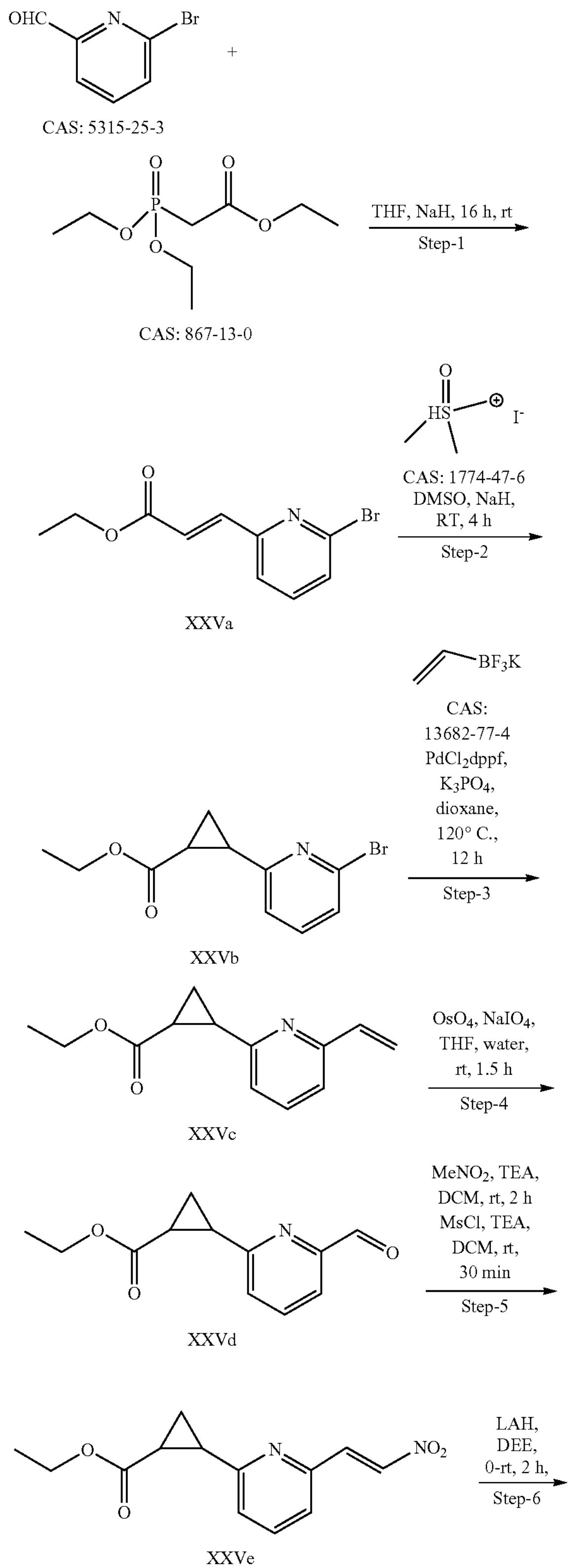

CAS: 5315-25-3

CAS: 867-13-0

XXVa

XXVb

XXVc

XXVd

XXVe

-continued

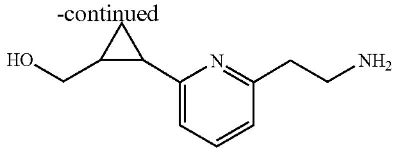

XXV

Step-1: Synthesis of ethyl (E)-3-(6-bromopyridin-2-yl) acrylate (XXVa)

To a suspension of sodium hydride (3.2 g, 55% wt, 1.35 eq, 73 mmol) in THF (300 mL) was dropwise added ethyl 2-(diethoxy phosphoryl) acetate (CAS:867-13-0, 15 g, 1.25 eq, 67 mmol) at 0° C. After 30 min, solution of 6-bromopicolinaldehyde (10 g, 1 eq, 54 mmol) in 30 mL THF was added and the reaction mixture was stirred at rt for 4 h. the progress of reaction was monitored by TLC analysis. After completion of the reaction, the reaction was cooled to 0° C. and water (75 mL) was dropwise added. The resulting mixture was extracted with ethyl acetate (75 mL×2). The combined organic layer was dried over anhydrous sodium sulphate and concentrated under reduced pressure to afford the light brown viscous liquid. The crude compound was purified by silica gel (100-200; 150 g) column chromatography using EtOAc (0-20%) in hexane. The peak eluted with 10% of EtOAc in hexane was concentrated to afford XXVa as an off white solid. Yield: 10 g, 73%. LCMS Calculated. for $C_{10}H_{10}BrNO_2$ is 254.99; Observed. 256.05 $[M+H]^+$. $^1H$ NMR (400 MHz, $CDCl_3$): δ 7.60-7.54 (m, 2H), 7.45 (d, J=8.0 Hz, 1H), 7.35 (d, J=7.6 Hz, 1H), 6.96 (d, J=15.2 Hz, 1H), 4.27 (q, J=7.2 Hz, 2H), 1.33 (t, J=7.2 Hz, 3H.

Step-2: Synthesis of ethyl 2-(6-bromopyridin-2-yl) cyclopropane-1-carboxylate (XXVb)

To a solution of Trimethylsulfoxonium Iodide (CAS: 1774-47-6, 19 g, 2.2 eq, 86 mmol) in DMSO (140 mL) was added sodium hydride portion wise (2.2 g, 55% Wt. 1.3 eq, 51 mmol) and the resulting mixture was stirred for one hour at room temperature. A solution of ethyl (E)-3-(6-bromopyridin-2-yl) acrylate (10 g, 1 eq, 39 mmol) in mixture of DMSO (60 mL) and THF (60 mL) was slowly added to the reaction. The resulting mixture was stirred for four hours at room temperature. The progress of the reaction was monitored by TLC analysis. After completion of the reaction, 1N HCl (10 mL) was added, and the reaction mixture extracted with diethyl ether (30 mL×2). The combined organic layer was dried over anhydrous sodium sulphate, the solvent was removed under vacuo. The crude compound was passed through a plug of silica gel (100-200; 120 g) in ethyl acetate in hexane (7%) to afford the desired compound XXVb as a colourless viscous liquid. Yield: 6.0 g, 60%. $^1H$ NMR (400 MHz, $CDCl_3$): δ 7.57-7.39 (m, 1H), 7.27-7.26 (m, 1H), 7.18 (d, J=7.6 Hz, 1H), 4.25-4.12 (m, 2H), 2.58-2.51 (m, 2H), 2.29-2.25 (m, 2H), 1.34-1.23 (m, 3H)

Step-3: Synthesis of Ethyl 2-(6-vinylpyridin-2-yl) cyclopropane-1-carboxylate (XXVc)

A solution of ethyl 2-(6-bromopyridin-2-yl) cyclopropane-1-carboxylate (3.9 g, 1 eq, 14 mmol), Potassium Vinyl trifluoroborate (CAS: 13082-77-4, 2.1 g, 1.1 eq, 16 mmol) and potassium phosphate, tribasic (4.6 g, 1.8 mL, 1.5 eq, 22 mmol) in 1,4 dioxane (60 mL) was purged with $N_2$ gas for 15 min with vigorous stirring. To the reaction was added $PdCl_2$ (dppf) (0.53 g, 0.05 eq, 0.72 mmol) and the seal tube was closed and heated to 120° C. for 16 hours. The progress of the reaction was monitored by TLC analysis. After completion of the reaction, it was cooled to room temperature and reaction mixture was concentrated under reduced pressure. To the residue obtained was added water (80 mL) and the resulting mixture was extracted with ethyl acetate (50 mL×2). The organic layer was dried over anhydrous sodium sulphate and concentrated under reduced pressure to afford a light brown viscous liquid. The crude compound was purified by combi-flash (230-400, 120 g packed) column chromatography using ethyl acetate in hexane and peak eluted with 5% EtOAc in hexane was concentrated to afford XXVc as a pale-yellow viscous liquid. Yield: 1.8 g, 57%. LCMS Calculated. for $C_{13}H_{15}NO_2$ is 217.11; Observed. 218.20 $[M+H]^+$. $^1H$ NMR (400 MHz, $CDCl_3$): δ 7.51 (t, J=7.2 Hz, 1H), 7.10-7.07 (m, 2H), 6.78-6.68 (m, 1H), 6.78-6.68 (m, 1H), 5.42-5.39 (m, 1H), 4.19-4.14 (m, 1H), 2.63-2.57 (m, 2H), 2.31-2.29 (m, 1H), 1.66-1.56 (m, 2H), 1.34-1.26 (m, 3H).

Step-4: Synthesis of ethyl 2-(6-formylpyridin-2-yl) cyclopropane-1-carboxylate (XXVd)

To a solution of ethyl 2-(6-vinylpyridin-2-yl) cyclopropane-1-carboxylate XXVc (1.6 g, 1 eq, 7.4 mmol) in THF (4.4 mL) and water (10 mL) a solution of osmium tetroxide (7.4 mL g, 2.5% wt % in isobutanol, 0.1 eq, 0.74 mmol) was added and the reaction was stirred at rt for 30 min. Then, sodium metaperiodate (2.4 g, 0.59 mL, 1.5 eq, 11 mmol) was added and the reaction was stirred at rt for 2 h. Then the progress of the reaction was monitored by TLC analysis which indicated completion of the reaction. The mixture was diluted with water (35 mL) and extracted with EtOAc (30 mL×2). The combined organic layer was dried over anhydrous $Na_2SO_4$, filtered and evaporated under vacuum to afford XXVd as brown viscous liquid. The crude product obtained was used as such in the next step without further purification. Yield: (1.56 g, 97%). LCMS Calculated. for $C_{12}H_{13}NO_3$ is 219.09; Observed. 220.20 $[M+H]^+$. $^1H$ NMR (400 MHz, $CDCl_3$): δ 9.95 (s, 1H), 7.76-7.72 (m, 2H), 7.47-7.45 (m, 1H), 4.27-4.16 (m, 2H), 2.70-2.65 (m, 2H), 2.39-2.37 (m, 2H), 1.30-1.27 (m, 3H).

Step-5: Synthesis of ethyl (E)-2-(6-(2-nitrovinyl) pyridin-2-yl) cyclopropane-1-carboxylate (XXVe)

A stirred solution of ethyl 2-(6-formylpyridin-2-yl) cyclopropane-1-carboxylate XXVd (1.72 g, 1 eq, 7.85 mmol) in DCM (15 mL) was cooled to 0° C. To the resulting mixture nitromethane (575 mg, 1.2 eq, 9.41 mmol) and triethylamine (2.19 mL, 2.0 eq, 15.7 mmol) were added under $N_2$ gas. The resulting mixture was stirred at rt for 2 h. The reaction mixture was concentrated under reduced pressure to afford a brown viscous liquid. The mixture was dissolved in fresh DCM (10 mL) and was cooled to 0° C. Then triethylamine (3.02 mL, 5 eq, 21.7 mmol) was added to the reaction and this was followed by a drop-wise addition of mesyl chloride (1.49 g, 1.01 mL, 3 eq, 13.0 mmol) under $N_2$ gas. The reaction mixture was stirred at rt for 30 min. The progress of the reaction was monitored by TLC analysis which indicated completion of reaction. The reaction mixture was concentrated under reduced pressure and water (15 mL) was added and extracted with ethyl acetate (15 mL×2). The combined organic layer was given brine wash, dried over anhydrous sodium sulphate, and concentrated under reduced pressure to afford XXVe as a brown viscous liquid. The crude was used in the next step without further purification. Yield: 1.87 g, 100%.

Step-6: Synthesis of (2-(6-(2-Aminoethyl) pyridin-2-yl) cyclopropyl) methanol (XXV)

To a cooled $LiAlH_4$ (30 mL, 1M, 4 eq,) in dry diethyl ether (160 mL) using ice bath, was added dropwise a solution of ethyl (E)-2-(6-(2-nitrovinyl) pyridin-2-yl) cyclopropane-1-carboxylate (2 g, 1 eq, 8 mmol) in dry diethyl ether (7 mL). The resulting mixture was stirred at rt for 2 h. The reaction was monitored by TLC analysis which indicated the completion of reaction. The reaction mixture was cooled to 0° C. and quenched water (3 mL) followed by with 15% KOH solution (15 mL). To the mixture was added ethyl acetate (75 mL) and stirred at rt for 20 min. The reaction mixture was filtered, and the residue was washed with 100 mL of ethyl acetate. The combined filtrate was concentrated under reduced pressure to afford XXV as pale brown viscous liquid. The crude was used as such in the next step without further purification. Yield: 1.03 g, 100%. LCMS Calculated. for $C_{11}H_{16}N_2O$ is 192.13; Observed. 193.25 $[M+H]^+$.

Synthesis of 2-(6-ethylpyridin-2-yl) ethan-1-amine (XXVI)

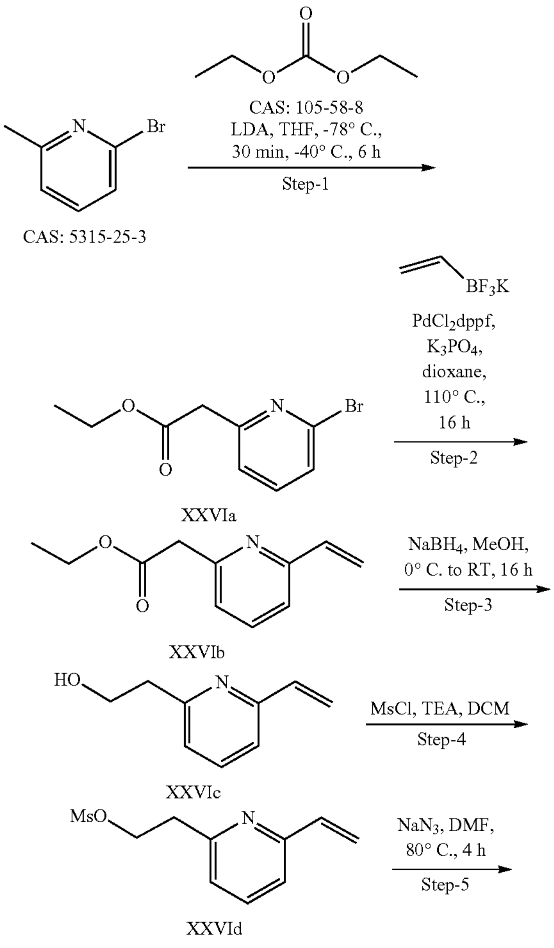

XXVIa

XXVIb

XXVIc

XXVId

-continued

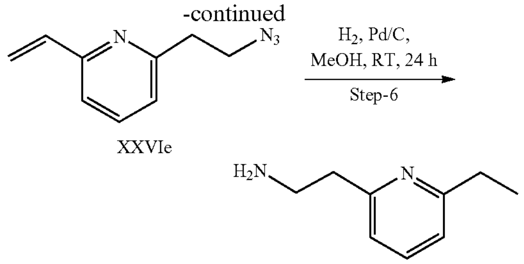

XXVIe

XXVI

Step-1: Ethyl 2-(6-bromopyridin-2-yl) acetate (XXVIa)

To a stirred solution of lithium diisopropylamide (110 mL, 2 molar, 220 mmol) in dry THF (500 mL) at −78° C. under inert atmosphere was dropwise added 2-bromo-6-methylpyridine (CAS:5315-25-3, 15 g, 87 mmol) and the resulting mixture was stirred at −78° C. for 30 min. This was followed by an addition of diethyl carbonate (CAS: 105-58-8, 26 g, 220 mmol) mixture was stirred at −40° C. for 4 hours. The progress of the reaction was monitored by TLC analysis. After completion, the reaction was quenched with saturated solution of $NH_4Cl$ (150 mL), and the resulting mixture was extracted with ethyl acetate (170 mL×2). The combined organic layer was dried over anhydrous sodium sulphate and concentrated under reduced pressure to afford light brown viscous liquid. The crude compound was purified by silica gel (100-200) column chromatography using ethyl acetate (0-10%) in n-hexane. The peak eluted with 7% of ethyl acetate in n-hexane was concentrated to afford the desired product XXVIa as a colorless viscous liquid. Yield: 12.2 g (57%); LCMS Calculated. for $C_9H_{11}BrNO_2$ is 246.00, Observed, 246.15; $[M+H]^+$; $^1H$ NMR (400 MHz, $CDCl_3$): δ 7.53 (t, J=7.6 Hz, 1H), 7.40 (d, J=8.0 Hz, 1H), 7.28 (t, J=7.6 Hz, 1H), 4.19 (q, J=7.2 Hz, 2H), 3.83 (s, 2H), 1.27 (t, J=7.2 Hz, 3H).

Step-2: Ethyl 2-(6-vinylpyridin-2-yl) acetate (XXVIb)

A solution of ethyl 2-(6-bromopyridin-2-yl) acetate XXVIa (3 g, 10.0 mmol), potassium trifluoro(vinyl)borate (2 g, 11.0 mol) and potassium phosphate, tribasic (4 g, 20 mmol) in 1,4 dioxane (40 mL) was purged with $N_2$ gas for 15 min with vigorous stirring. To the reaction was added $PdCl_2$(dppf) (0.4 g, 0.6 mmol) and the seal tube was closed and heated to 120° C. for 16 hours. The progress of the reaction was monitored by TLC analysis. The reaction was cooled to room temperature and reaction mixture was concentrated under reduced pressure. The residue was added water (70 mL) and the resulting mixture was extracted with ethyl acetate (75 mL×2). The organic layer was dried over anhydrous sodium sulphate and concentrated under reduced pressure to afford a light brown viscous liquid. The crude compound was purified by combi-flash (230-400) column chromatography using ethyl acetate in n-hexane and peak eluted with 3% ethyl acetate in hexane was concentrated to afford the desired compound XXVIb as a colorless viscous liquid. Yield: 2.0 g (90%); LCMS Calculated. for $C_{11}H_{14}NO_2$ is 192.10, Observed, 192.25; $[M+H]^+$; $^1H$ NMR (400 MHz, $CDCl_3$): δ 7.62 (t, J=7.6 Hz, 1H), 7.25 (d, J=7.6 Hz, 1H), 7.17 (d, J=7.6 Hz, 1H), 6.80 (q, J=6.4 Hz, 1H), 6.19 (d, J=17.6 Hz, 1H), 5.47 (d, J=10.8 Hz, 1H), 4.19 (q, J=7.2 Hz, 2H), 1.27 (t, J=7.2 Hz, 3H).

Step-3: 2-(6-Vinylpyridin-2-yl) ethan-1-ol. (XXVIc)

To a stirred solution of ethyl 2-(6-vinylpyridin-2-yl) acetate XXVIb (2 g, 10.0 mmol) in methanol (30 mL) under nitrogen atmosphere was portion wise added at 0° C. sodium borohydride (2 g, 50 mmol). The resulting mixture was stirred at 0° C. for 30 min and at room temperature for 6 h. The progress of the reaction was monitored by TLC analysis which indicates completion of reaction. To the reaction mixture saturated $NaHCO_3$ solution (50 mL) was added and extracted with ethyl acetate (75 mL×2). The organic layer was given brine (35 mL) wash, dried over anhydrous sodium sulphate, and concentrated under reduced pressure to afford XXVIc as colorless viscous liquid. The crude was taken for next step without further purification. Yield: 1.2 g (80%); LCMS Calculated. for $C_9H_{12}NO$ is 150.09, Observed, 150.00; $[M+H]^+$; $^1H$ NMR (400 MHz, $CDCl_3$): δ 7.59 (t, J=7.6 Hz, 1H), 7.19 (d, J=7.6 Hz, 1H), 7.02 (d, J=8.0 Hz, 1H), 6.81-6.74 (m, 1H), 6.16 (d, J=17.6 Hz, 1H), 5.47 (d, J=10.8 Hz, 1H), 4.03 (t, J=5.6 Hz, 2H), 3.01 (t, J=5.6 Hz, 2H).

Step-4: 2-(6-Vinylpyridin-2-yl) ethyl methane sulfonate (XXVId)

To a stirred solution of 2-(6-vinylpyridin-2-yl) ethan-1-ol XXVIc (1.2 g, 8.0 mmol) in DCM (30 mL) triethylamine (4.5 mL, 32 mmol) was added under nitrogen atmosphere. The resulting mixture was cooled to 0° C. and mesyl-Cl (0.81 mL, 10.0 mmol) was drop wise added. The reaction mixture was stirred at 0° C. for 30 min. The progress of the reaction was monitored by TLC analysis which indicates completion of reaction. To the reaction mixture water (30 mL) was added and extracted with DCM (30 mL×3). The organic layer was washed with brine (25 mL), dried over anhydrous sodium sulphate, and concentrated under reduced pressure to afford XXVId as brown viscous liquid. The crude was taken for next step without further purification. Yield: 1.7 g (93%); LCMS Calculated. for $C_{10}H_{14}NO_3S$ is 228.08, Observed, 228.20; $[M+H]^+$; $^1H$ NMR (400 MHz, $CDCl_3$): δ 7.60 (t, J=7.6 Hz, 1H), 7.22 (d, J=8.0 Hz, 1H), 7.08 (d, J=8.0 Hz, 1H), 6.82-6.75 (m, 1H), 6.22 (d, J=17.6 Hz, 1H), 5.48 (d, J=10.8 Hz, 1H), 4.73-4.66 (m, 2H), 3.21 (t, J=6.4 Hz, 2H), 2.88 (s, 3H).

Step-5: 2-(2-Azidoethyl)-6-vinylpyridine (XXVIe)

To a stirred solution of 2-(6-vinylpyridin-2-yl) ethyl methane sulfonate XXVId (1.7 g, 7.5 mmol) in DMF (20 mL) sodium azide (1.5 g, 22 mmol) was added under nitrogen atmosphere. The resulting mixture was stirred at 100° C. for 4 h. The progress of the reaction was monitored by TLC analysis. After completion of the reaction water (30 mL) was added and extracted with ethyl acetate (30 mL×3). The organic layer was washed with brine (25 mL), dried over anhydrous sodium sulphate, and concentrated under reduced pressure to afford brown viscous liquid. The crude product was purified by combi-flash (silica gel 230-400) column chromatography using ethyl acetate (0-40%) in n-hexane. The peak eluted with 5% ethyl acetate was concentrated to afford the desired compound XXVIe as a colorless viscous liquid. Yield: 0.87 g (67%); LCMS Calculated. for $C_9H_{11}N_4$ is 175.10, Observed, 175.25; $[M+H]^+$; $^1H$ NMR (400 MHz, $CDCl_3$): δ 7.58 (t, J=7.6 Hz, 1H), 7.21

(d, J=7.6 Hz, 1H), 7.06 (d, J=7.6 Hz, 1H), 6.84-6.77 (m, 1H), 6.22 (d, J=17.6 Hz, 1H), 5.47 (d, J=10.8 Hz, 1H), 3.74 (t, J=6.8 Hz, 2H), 3.06 (t, J=6.8 Hz, 2H).

Step-6: 2-(6-Ethylpyridin-2-yl) ethan-1-amine (XXVI)

In RB flask 2-(2-azidoethyl)-6-vinylpyridine XXVIe (0.87 g, 5.0 mmol) was dissolved in methanol (30 mL) and purged with nitrogen for 10 minutes. To this solution palladium on carbon (450 mg, 10%) was added. The reaction was evacuated and refilled with $H_2$ gas, this procedure was repeated for 3-4 times and the reaction was stirred at room temperature for 16 h maintaining $H_2$ atmosphere. The progress of reaction was monitored by TLC. After completion, the reaction mixture was filtered through a celite bed and washed with fresh methanol. The combined filtrate was concentrated under vacuo to afford the desired compound XXVI as a pale-yellow viscous liquid which was taken for the next step without further purification. Yield: 0.67 g (89%); LCMS Calculated for $C_9H_{15}N_2$ is 151.13, Observed, 151.25; $[M+H]^+$; $^1H$ NMR (400 MHz, $CDCl_3$): δ 7.54-7.46 (m, 1H), 7.01-6.94 (m, 2H), 3.09-2.73 (m, 6H), 1.28 (m, 3H).

Synthesis of 2-(3-fluoro-6-methylpyridin-2-yl) ethan-1-amine (XXVII)

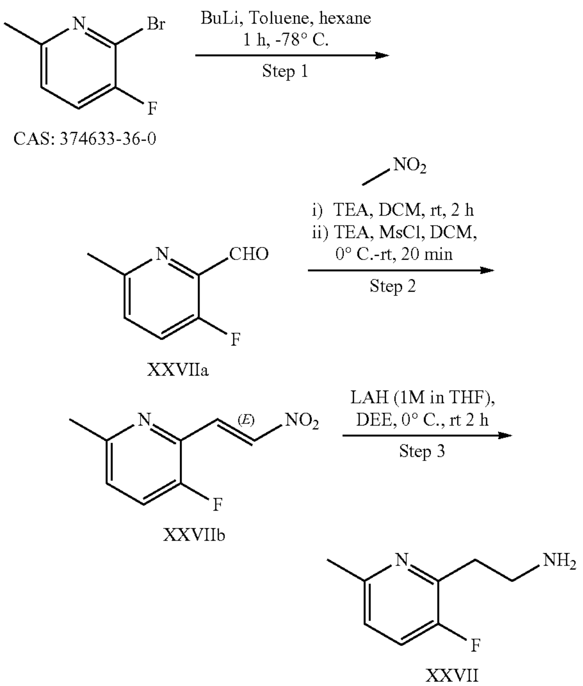

CAS: 374633-36-0

XXVIIa

XXVIIb

XXVII

Step-1: 3-Fluoro-6-methylpicolinaldehyde (XXVIIa)

A two neck RB flask equipped with two way stop-cock, septum and magnetic bar was charged with 2-bromo-3-fluoro-6-methylpyridine (CAS: 374633-36-0; 1.66 g, 8.74 mmol) and dry toluene (10 mL) under $N_2$ at RT. The resulting mixture was cooled to −78° C. and n-butyllithium (3.5 mL, 2M in THF, 8.74 mmol) was added dropwise and stirred the reaction mixture maintaining temperature −78° C. under proper $N_2$ atmosphere. This was followed by slow addition of dry DMF (1.92 g, 26.2 mmol) at −78° C. under $N_2$ atmosphere. The reaction was stirred at −78° C. under $N_2$ atmosphere for additional one hour and at −50° C. for 2 h. The progress of the reaction was monitored by TLC analysis. The reaction was quenched by slow addition sat. ammonium chloride solution at −78° C. The resulting mixture was extracted with ethyl acetate (10 mL×3). The combined organic layer was dried over anhydrous sodium sulphate, filtered, and concentrated under reduced pressure to get the crude brown semi-solid. The crude was subjected to silica gel (230-400 mesh) column chromatography purification using 0-10% ethyl acetate in n-hexane to afford the desired compound XXVIIa as off-white solid. Yield: 0.175 g (14.4%); LCMS Calculated. for $C_7H_7FNO$ is 140.05, Observed, 140.25; $[M+H]^+$; $^1H$ NMR (400 MHz, $CDCl_3$): δ 10.19 (s, 1H), 7.49-7.38 (m, 2H), 2.64 (s, 3H).

Step-2: (E)-3-fluoro-6-methyl-2-(2-nitrovinyl) pyridine (XXVIIb)

To a solution of 3-fluoro-6-methylpicolinaldehyde XXVIIa (0.4 g, 3 mmol) in DCM (4 mL) under $N_2$ at room temperature were added triethylamine (0.6 g, 6 mmol) and nitromethane (0.2 mL, 3 mmol) under $N_2$. The reaction was stirred at RT for 30 min and the progress of the reaction was monitored by TLC analysis. After completion, the reaction mixture was concentrated to dryness under vacuo and the residue was dissolved in fresh dry DCM (4 mL). The mixture was cooled to 0° C. under $N_2$ atmosphere and TEA (1 mL, 9 mmol) was added. This was followed by slow addition of mesyl chloride (0.7 mL, 9 mmol) at 0° C. under $N_2$. The reaction was stirred at room temperature for 1 h under $N_2$ at RT. The progress of the reaction was monitored by TLC analysis. After completion, water (10 mL) was added, and the resulting mixture was extracted with DCM (5 mL×3). The combined organic layer was given brine wash, dried over anhydrous sodium sulphate, and concentrated under reduced pressure to get the brown semisolid. The crude was subjected to silica gel column (230-400) chromatography using 0-10% ethyl acetate in n-hexane to afford the desired compound XXVIIb as a colorless viscous liquid. Yield: 93 mg (20%); $^1H$ NMR (400 MHz, $CDCl_3$): δ 8.15 (d, J=13.2 Hz, 1H), 8.04 (d, J=13.6 Hz, 1H), 7.39 (t, J=9.2 Hz, 1H), 7.25 (t, J=3.6 Hz, 1H), 2.57 (s, 3H).

Step-3: 2-(3-fluoro-6-methylpyridin-2-yl) ethan-1-amine (XXVII)

To a two neck 100 mL round bottom flask was charged with dry diethyl ether under $N_2$ and the solvent was cooled to 0° C. To this was added LAH (1 mL, 2M in THF, 2.0 mmol) followed by an addition of solution of 1(E)-3-fluoro-6-methyl-2-(2-nitrovinyl) pyridine XXVIIb (93 mg, 0.51 mmol) in dry diethyl ether:THF (1:1, 2 mL). The resulting mixture was stirred 1 h at RT under $N_2$. The progress of the reaction was monitored using TLC analysis. After completion, the reaction was cooled to 0° C. and quenched with water (0.2 mL) and ethyl acetate (5 mL). The solution was filtered through celite bed. Bed was given wash with ethyl acetate followed by 10% MeOH in DCM. The combined filtrate was dried over anhydrous sodium sulphate and concentrated under vacuo to get XXVII as brown semisolid crude material. The crude product obtained was taken for the next step without further purification. Yield: 47 mg (60%).

Synthesis of 7-amino-2-ethyl-3-methyl-5-(methyl sulfonyl) pyrazolo[1,5-a] pyrimidine-6-carbonitrile (XXVIII)

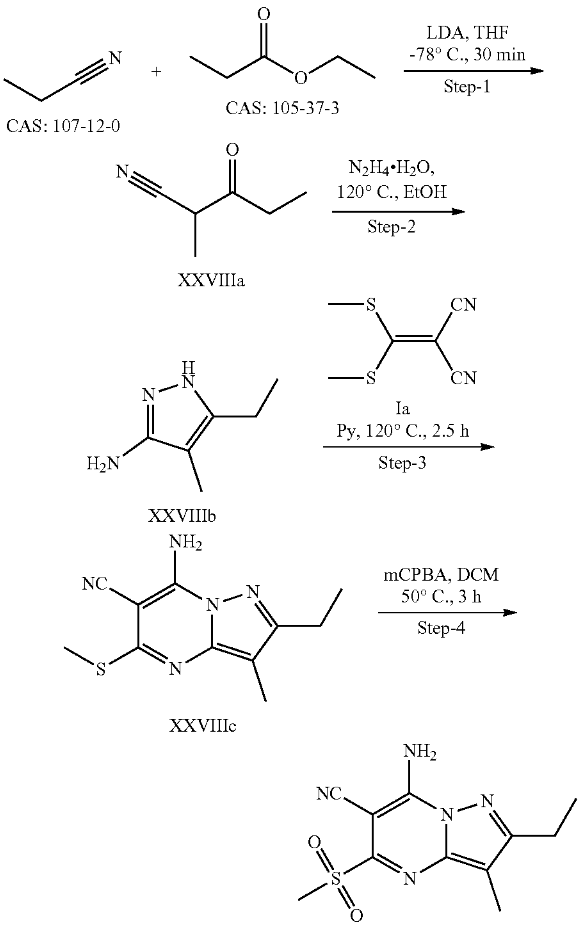

XXVIIIa

XXVIIIb

XXVIIIc

XXVIII

Step-1: 2-methyl-3-oxopentanenitrile (XXVIIIa)

To a stirred solution of lithium diisopropylamide (110 mL, 2 M, 60 mmol) in dry THF (56 mL) at −78° C. under inert atmosphere was dropwise added propionitrile (CAS: 107-12-0; 4 mL, 60 mmol) and the resulting mixture was stirred at −78° C. for 1 h. This was followed by an addition of ethyl propionate (CAS: 105-37-3; 6 mL, 50 mmol) and the reaction was stirred at −78° C. for additional 1 hour. The progress of the reaction was monitored by TLC analysis. After completion, the reaction was quenched with saturated solution of $NH_4Cl$ (20 mL), and the resulting mixture was extracted with ethyl acetate (50 mL×2). The combined organic layer was dried over anhydrous sodium sulphate and concentrated under reduced pressure to afford as light brown viscous liquid. The crude compound was purified by silica gel (100-200) column chromatography using ethyl acetate (0-10%) in n-hexane. The peak eluted with 7% of ethyl acetate in n-hexane was concentrated to afford the desired product XXVIIIa as a colorless viscous liquid. The crude was taken for next step without further purification. Yield: 4.3 g (71%).

Step-2: 5-ethyl-4-methyl-1H-pyrazol-3-amine (XXVIIIb)

To a stirred solution of 2-methyl-3-oxopentanenitrile XXVIIIa (4.3 g, 39 mmol) in ethanol (4 mL) was added hydrazine hydrate (1:1) (2.9 g, 58 mmol) at room temperature and the reaction mixture was stirred at 120° C. for 2 h. The progress of the reaction was monitored by TLC analysis. After completion, reaction mixture was cooled to room temperature and concentrated to remove solvent. Obtained residue was dissolved in water (50 mL) and extracted with 10% methanol in DCM (100 mL×3). The combined organic layer was dried over anhydrous sodium sulphate and concentrated to afford the desired product XXVIIIb as a yellowish viscous liquid. The crude was taken for next step without further purification. Yield: 5.4 g (69%).

Step-3: 7-amino-2-ethyl-3-methyl-5-(methylthio) pyrazolo[1,5-a] pyrimidine-6-carbonitrile (XXVIIIc)

To a stirred solution of 5-ethyl-4-methyl-1H-pyrazol-3-amine XXVIIIb (5.4 g, 32 mmol) in pyridine (30 mL) was added 2-(bis (methylthio) methylene) malononitrile Ia (4.0 g 32 mmol). Then reaction mixture was stirred at 120° C. for 3 hours. The progress of the reaction was monitored by TLC. After completion, reaction mixture was cooled to room temperature then poured into ice cold water (100 mL). The formed solid was filtered and washed with ice cold water. solid was dried under vacuum to afford the desired product XXVIIIc as an off-white solid. The crude was taken for next step without further purification. Yield: 5.3 g (68%); LCMS Calculated. for $C_{11}H_{14}N_5S$ is 248.32, Observe, 248.20; $[M+H]^+$; $^1H$ NMR (400 MHz, $CDCl_3$): δ 6.19 (bs, 2H), 2.75 (q, J=7.6 Hz, 2H), 2.62 (s, 3H), 2.19 (s, 3H), 1.3 (t, J=7.6 Hz, 3H).

Step-4: 7-amino-2-ethyl-3-methyl-5-(methylsulfonyl)-1,2-dihydropyrazolo[1,5-a] pyrimidine-6-carbonitrile (XXVIII)

To a stirred solution of 7-amino-2-ethyl-3-methyl-5-(methylthio)-1,2-dihydropyrazolo[1,5-a] pyrimidine-6-carbonitrile XXVIIIc (5.4 g, 22 mmol) in DCM (60 mL) was portion wise added mCPBA (15 g, 87 mmol) at 0° C. under inert atmosphere. The resulting mixture was stirred at room temperature for 4 hours. The progress of reaction was monitored by TLC analysis. After completion, the reaction mixture was quenched with $NaHCO_3$ (50 mL) and extracted with DCM (50 mL×3). The organic layer was dried over anhydrous $Na_2SO_4$, filtered, and concentrated under reduced pressure to afford the desired product XXVIII as an off-white solid. The obtained solid was washed with n-hexane (10 mL×2). The crude solid was taken for next step without further purification. Yield: 1.0 g (18%); LCMS Calculated. for $C_{11}H_{16}N_5O_2S$ is 282.33, $[M+H]^+$, Observed, 280.25; $[M+H]^{-2}$ Synthesis of 7-amino-2-cyclopropyl-3-methyl-5-(methyl sulfonyl) pyrazolo[1,5-a] pyrimidine-6-carbonitrile. (XXIX)

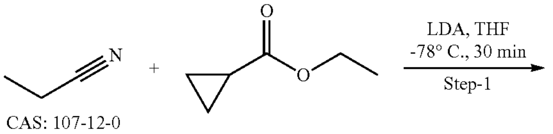

-continued

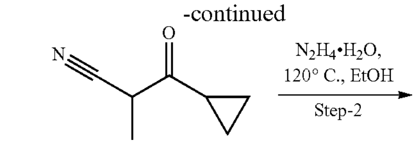

XXIXa

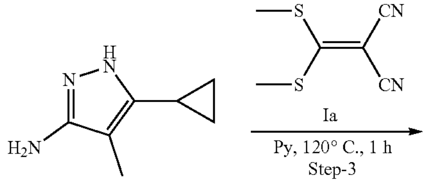

XXIXb

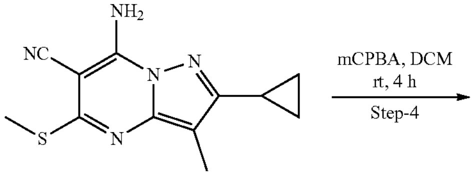

XXIXc

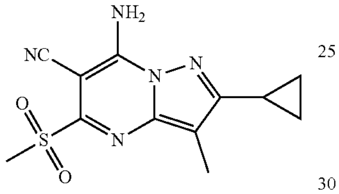

XXIX

Step-1: 3-cyclopropyl-2-methyl-3-oxopropanenitrile (XXIXa)

To a stirred solution of LDA (30 mL, 2 M, 50 mmol) in dry THF (70 mL) at −78° C. under inert atmosphere was added a solution of propenonitrile (CAS:107-12-0; 3 g, 50 mmol) in THF (20 mL) and the resulting mixture was stirred at −78° C. for 1 h. This was followed by an addition of ethyl cyclopropane carboxylate (6 g, 50 mmol) and the mixture was stirred at −70° C. for 1 h. The progress of the reaction was monitored by TLC analysis. After completion, the reaction was quenched with saturated solution of $NH_4Cl$ (50 mL) and the resulting mixture was extracted with ethyl acetate (50 mL×3) The combined organic layer was dried over anhydrous sodium sulphate and concentrated under reduced pressure to afford XXIXa as light brown viscous liquid. The crude compound was used as such in the next step without further purification. Yield: 4.5 g (70%).

Step-2: 5-cyclopropyl-4-methyl-1H-pyrazol-3-amine (XXIXb)

To a stirred solution of 3-cyclopropyl-2-methyl-3-oxopropanenitrile XXIXa (4.2 g, 34 mmol) in ethanol (50 mL) was added hydrazine hydrate (3.3 mL, 50% Wt., 34 mmol) and the reaction mixture was heated at 90° C. for 16 h. The progress of the reaction was monitored by TLC. After completion, the reaction mixture was cooled to rt and evaporated under reduced pressure. The residue obtained was diluted with water (50 mL) and extracted with ethyl acetate (50 mL×3). The combined organic layer was dried over anhydrous $Na_2SO_4$, filtered, and evaporated under reduced pressure. The crude material XXIXb obtained was used as such in the next step without further purification. Yield: 4.2 g (90%); LCMS Calculated. for $C_7H_{12}N_3$ is 138.20, Observed, 138.25; $[M+H]^+$ Step-3: 7-amino-2-cyclopropyl-3-methyl-5-(methylthio) pyrazolo[1,5-a] pyrimidine-6-carbonitile (XXIXc)

To a stirred solution of 2-(bis(methylthio)methylene) malononitrile Ia (5.2 g, 31 mmol) in pyridine (35 mL) was added 5-cyclopropyl-4-methyl-1H-pyrazol-3-amine XXIXb (4.2 g, 31 mmol) and the reaction mixture was heated at 120° C. for 1 h under $N_2$ atmosphere. The progress of the reaction was monitored by TLC analysis. After completion, the reaction mixture was cooled to rt and poured into ice cold water (50 mL). The precipitate formed was filtered, dried, and washed with cold mixture of ethyl acetate (10%) and n-hexane (90%), dried under vacuo to afford the desired compound as a pale-yellow solid. The crude compound XXIXc obtained was taken for the next step without further purification. Yield: 4.1 g (52%); LC_MS Calculated. for $C_{12}H_{14}N_5S$ is 260.34, Observed, 260.20; $[M+H]^+$ Step-4: 7-amino-2-cyclopropyl-3-methyl-5-(methyl sulfonyl) pyrazolo[1,5-a] pyrimidine-6-carbonitrile (XXIX)

To a solution of 7-amino-2-cyclopropyl-3-methyl-5-(methylthio) pyrazolo[1,5-a] pyrimidine-6-carbonitrile XXIXc (1 g, 4 mmol) in DCM (20 mL) at 0° C. under $N_2$ atmosphere was added mCPBA (4 g, 60% Wt., 20 mmol) and the resulting mixture was stirred at rt for 4 h. The progress of the reaction was monitored by TLC analysis. After completion of the reaction, added sat. $NaHCO_3$ solution (50 ml) and the mixture was stirred vigorously for 15 min. The organic layer was separated and given fresh wash of sat. $NaHCO_3$ solution (50 mL×3). The organic layers were separated, washed with brine, dried over anhydrous $Na_2SO_4$ and concentrated under vacuo to afford the desired compound as a pale-yellow solid. The compound XXIX was used in the next step without further purification. Yield: 0.35 g (30%), LC_MS Calculated. for is 292.34, Observed, 292.20; $[M+H]^+$ Synthesis of 7-amino-2-(difluoro methyl)-3-ethyl-5-(methyl sulfonyl) pyrazolo[1,5-a] pyrimidine-6-carbonitrile (XXX)

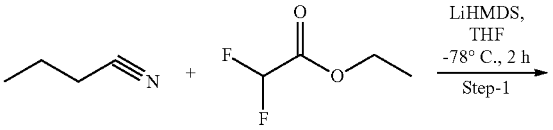

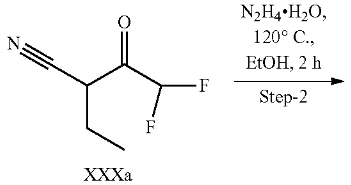

XXXa

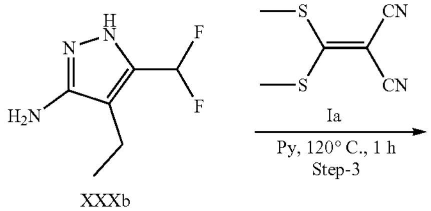

XXXb

-continued

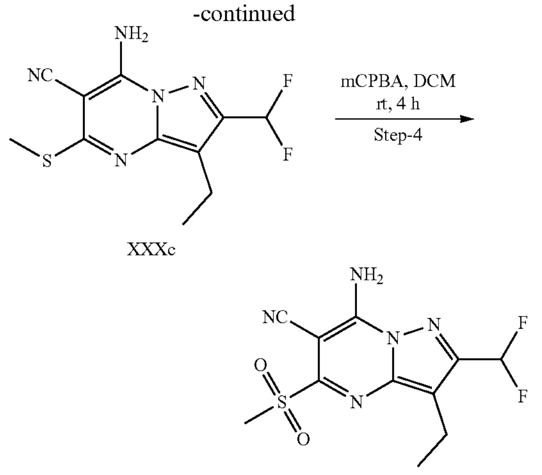

XXXc

XXX

Step-1: 2-ethyl-4,4-difluoro-3-oxobutanenitrile (XXXa)

To a solution of LiHMDS (2.4 g, 14 mmol) in THF (200 mL) at −78° C. under inert atmosphere was drop wise added butyronitrile (1.0 g, 14 mmol) in THF (4 mL) and the reaction mixture was stirred at −78° C. for 1 h. This was followed by a dropwise addition of ethyl 2,2-difluoroacetate (1.6 g, 13 mmol) at −78° C. and the reaction mixture was stirred for 2 h. The progress of the reaction was monitored by TLC analysis. After the completion of the reaction, the reaction mixture was cooled to 0° C. and quenched with saturated solution of ammonium chloride (5 mL) and extracted with ethyl acetate (20 mL×3). The combined organic layer was dried over anhydrous $Na_2SO_4$, filtered, and evaporated under reduced pressure. The crude was purified by silica gel (230-400 mesh) column chromatography using 0-10% ethyl acetate in n-hexane to afford the desired compound XXXa as a light brown viscous liquid. Yield: 1.2 g (57%); LC_MS Calculated. for $C_6H_6F_2NO$ is 147.11, Observed, 146.12; $[M-H]^-$.

Step-2: 5-(difluoro methyl)-4-ethyl-1H-pyrazol-3-amine (XXXb)

To a stirred solution of 2-ethyl-4,4-difluoro-3-oxobutanenitrile XXXa (1.2 g, 8.2 mmol) in ethanol (40 mL) was added hydrazine hydrate (1:1) (0.49 g, 9.8 mmol) at room temperature and the reaction mixture was stirred at 120° C. for 2 h. The progress of the reaction was monitored by TLC analysis. After the completion of the reaction, reaction mixture was cooled to room temperature and concentrated to remove the solvent. The obtained residue was dissolved in water (30 mL) and extracted with 10% methanol in DCM (50 mL×2). The combine organic layer was dried over anhydrous sodium sulphate and concentrated to get crude material XXXb. The crude was taken for next step without further purification. LCMS Calculated. for $C_6H_9F_2N_3$ is 161.15 Observed. 160.10; $[M-H]^-$.

Step-3: 7-amino-2-(difluoro methyl)-3-ethyl-5-(methylthio) pyrazolo[1,5-a] pyrimidine-6-carbonitrile (XXXc)

To a stirred solution of 5-(difluoro methyl)-4-ethyl-1H-pyrazol-3-amine XXXb (0.6 g, 4 mmol) in pyridine (2 mL) was added 2-(bis(methylthio)methylene) malononitrile Ia (0.8 g, 4 mmol) and the reaction mixture was heated at 120° C. for 2.5 h (using the guard tube). The progress of the reaction was monitored by TLC analysis. After completion, the reaction mixture was cooled to rt and poured into ice cold water (100 mL). The precipitate formed was filtered and washed with cold water. The solid obtained was dried and azeotrope with toluene to yield the title compound as a pale-yellow solid. The crude was purified by silica gel (230-400) column chromatography by using 0-30% ethyl acetate in n-hexane afford the desired compound XXXc as a pale-yellow solid. Yield: 0.5 g (50%); LCMS Calculated. for $C_{11}H_{11}F_2N_5S$ is 283.29, Observed, 284.20; $[M+H]^+$. $^1H$ NMR (400 MHz, $CDCl_3$): δ 6.77 (s, 1H), 6.30 (s, 2H), 2.87-2.81 (m, 2H), 2.64 (s, 3H), 1.29 (t, J=8.0 Hz 3H).

Step-4: 7-amino-2-(difluoro methyl)-3-ethyl-5-(methyl sulfonyl) pyrazolo[1,5-a] pyrimidine-6-carbonitrile (XXX)

To a stirred solution of 7-amino-2-(difluoro methyl)-3-ethyl-5-(methylthio) pyrazolo[1,5-a] pyrimidine-6-carbonitrile XXXc (0.5 g, 2 mmol) in DCM (50 ml) at 0° C. was added mCPBA (1 g, 7 mmol) slowly and the reaction mixture was stirred at rt for 2 h. The progress of the reaction was monitored by TLC. After completion of the reaction, the reaction mixture was quenched with aq. $NaHCO_3$ (50 ml) and extracted with DCM (50 ml×3). The organic layer was dried with $Na_2SO_4$, filtered, and evaporated under reduced pressure. Crude product XXX was taken for next step without further purification. Yield: 0.3 g (50%); LC_MS Calculated. for $C_{11}H_{11}F_2N_5O_2S$ is 315.28, Observed, 316.20; [M+H]+. 1H NMR (400 MHz, $CDCl_3$): δ 9.53 (s, 2H), 7.31 (s, 1H), 3.33 (s, 3H), 2.84-2.78 (m, 2H), 1.23 (t, J=8 Hz 3H).

Synthesis of 2-(6-(1-(methoxymethyl) cyclopropyl) pyridin-2-yl) ethan-1-amine (XXXI)

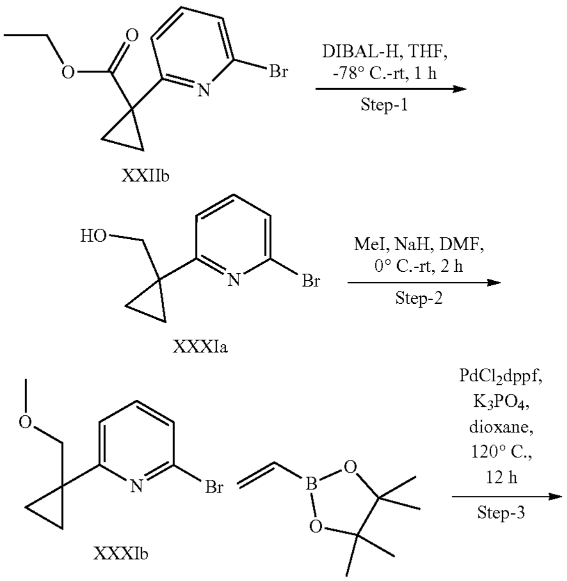

XXIIb

XXXIa

XXXIb

7

-continued

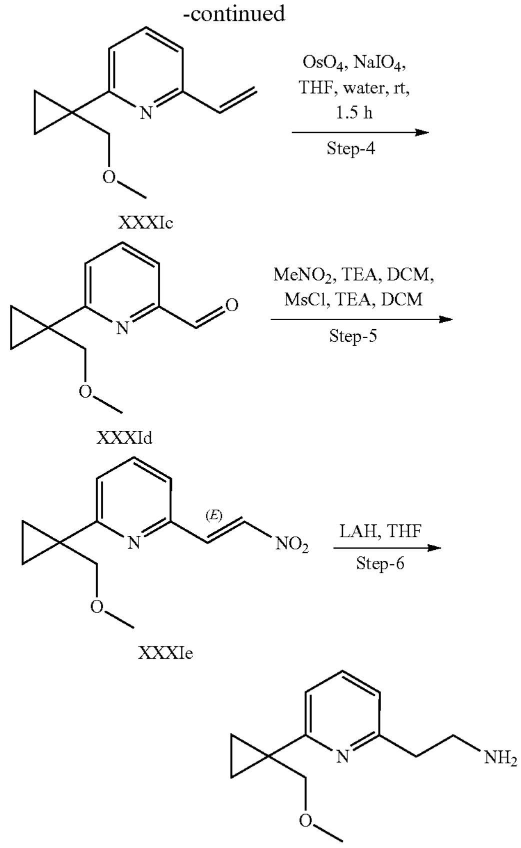

XXXIc

XXXId

XXXIe

XXXI

Step-1: (1-(6-bromopyridin-2-yl) cyclopropyl) methanol (XXIIa)

To a solution of ethyl 1-(6-bromopyridin-2-yl) cyclopropane-1-carboxylate XXIIb (2.2 g, 8.1 mmol) in THF (88 mL) at 0° C. was added DIBAL-H (18 mL, 1 M, 18 mmol) under $N_2$ atmosphere and the resulting mixture was stirred at 0° C. for 30 min. The progress of the reaction was monitored by TLC analysis. After the completion of the reaction, the reaction mixture was quenched with saturated solution of $NH_4Cl$ (25 mL) and added ethyl acetate (50 ml). The resulting solid was filtered through a celite bed and washed with ethyl acetate (30 mL). The filtrate was concentrated under reduced pressure to afford the desired compound XXXIa as a pale-yellow viscous liquid. Yield: 1.68 g (90%); LCMS Calculated. for $C_9H_{10}BrNO$ is 228.08, Observed, 230.10; $[M+H]^+$; $^1H$ NMR (400 MHz, dmso-d6): δ 7.64 (t, J=8 Hz, 1H), 7.53 (d, J=8.0 Hz, 1H), 7.38 (d, J=8 Hz, 1H), 4.82 (t, J=8 Hz, 1H), 3.71 (d, J=8 Hz 2H), 1.07-1.04 (m, 2H), 0.94-0.91 (m, 2H).

Step-2: 2-bromo-6-(1-(methoxymethyl)cyclopropyl) pyridine (XXXIb)

To a stirred solution of (1-(6-bromopyridin-2-yl) cyclopropyl) methanol XXXIa (1.68 g, 7.37 mmol) in DMF (10 mL) at 0° C. under inert atmosphere was added sodium hydride (482 mg, 55% Wt., 11.0 mmol) and the resulting mixture was stirred at 0° C. for 5 min. This was followed by an addition of methyl iodide (0.55 mL, 8.84 mmol) and mixture was stirred at rt for 30 min. The progress of the reaction was monitored by TLC analysis. After completion, the reaction was quenched with ice cold water (20 mL) and the resulting mixture was extracted with ethyl acetate (20 mL×2). The combined organic layer was dried over anhydrous sodium sulphate and concentrated under reduced pressure to afford XXXIb as light brown viscous liquid. The crude was taken for next step without further purification. Yield: 1.79 g (99%); LCMS Calculated. for $C_{10}H_{12}BrNO$ is 242.12, Observed, 242.15; $[M+H]^+$; $^1H$ NMR (400 MHz, $CDCl_3$): δ 7.42 (t, J=8 Hz, 1H), 7.35 (d, J=4 Hz, 1H), 7.23 (t, J=8.0 Hz, 1H), 3.65 (S, 2H), 3.4 (S, 3H), 1.63-1.31 (m, 2H),1.26-0.96 (m, 2H)

Step-3: 2-(1-(methoxymethyl) cyclopropyl)-6-vinylpyridine (XXXIc)

To a solution of 2-bromo-6-(1-(methoxymethyl) cyclopropyl) pyridine XXXIb (0.8 g, 3 mmol) in 1,4-Dioxane (15 mL) was added vinyl boronic acid pinacol ester (0.6 mL, 4 mmol) and tri potassium phosphate (1 g, 7 mmol), purged with N2 gas for 15 min with vigorous stirring. This was followed by an addition of PdCl2(dppf) (0.1 g, 0.2 mmol) and heated to 120° C. for 16 h. The progress of the reaction was monitored by TLC analysis. The reaction was cooled to room temperature and reaction mixture was concentrated under reduced pressure. Then added water (70 mL) and the resulting mixture was extracted with ethyl acetate (50 mL×2). The organic layer was dried over anhydrous sodium sulphate and concentrated under reduced pressure to afford a light brown viscous liquid. The crude compound was purified by combi-flash (230-400, 120 g packed) column chromatography using ethyl acetate in hexane and peak eluted with 5% ethyl acetate in hexane was concentrated to afford the desired compound XXXIc as an off-white solid. Yield: 0.42 g (70%); LCMS Calculated. for $C_{12}H_{15}NO$ is 189.26, Observed, 190.25; $[M+H]^+$; $^1H$ NMR (400 MHz, $CDCl_3$): δ 7.55-7.51 (m, 2H), 7.06 (d, J=4 Hz, 1H), 6.74 (t, J=8 Hz, 1H), 6.18 (d, J=16 Hz 1H), 5.38 (d, J=8 Hz 1H), 3.72 (S, 2H),3.40 (S, 3H),1.35 (d, J=4 Hz, 2H), 0.93 (t, J=4 Hz, 2H), Step-4: 6-(1-(methoxymethyl) cyclopropyl) picolinaldehyde (XXXId)

To a solution of 2-(1-(methoxymethyl) cyclopropyl)-6-vinylpyridine XXXIc (0.425 g, 2.25 mmol) in THF (9 mL) and water (20 mL), a solution of osmium tetroxide (0.06 mL, 1.12 mmol) was added, and the reaction was stirred at rt for 30 min. This was followed by an addition of sodium periodate (720 mg, 3.37 mmol) and the reaction was stirred at rt for 1 h. The mixture was diluted with water (20 mL) and extracted with ethyl acetate (20 mL×2). The combined organic layer was dried over anhydrous $Na_2SO_4$, filtered, and evaporated under reduced pressure to afford XXXId as brown viscous liquid. The crude was taken for next step without further purification. Yield: 290 mg (67.5%); LCMS Calculated. for $C_{11}H_{14}NO_2$ is 191.23, Observed, 192.25; $[M+H]^+$; $^1H$ NMR (400 MHz, $CDCl_3$): δ 9.97 (S, 1H), 7.76-7.71 (m, 2H), 7.63 (d, J=8.0 Hz, 1H), 3.74 (S, 2H), 3.43 (S, 3H), 1.43 (t, J=4 Hz, 2H), 1.02 (t, J=4 Hz, 2H).

Step-5: (E)-2-(1-(methoxymethyl) cyclopropyl)-6-(2-nitrovinyl) pyridine (XXXIe)

To a solution of 6-(1-(methoxymethyl) cyclopropyl) picolinaldehyde XXXId (0.6 g, 3 mmol) in DCM (12 mL) at 0° C. under inert atmosphere was added nitromethane (0.2 mL, 4 mmol), triethylamine (2 mL, 20 mmol) and the resulting mixture was stirred at rt for 2 h. The progress of the reaction was monitored by TLC analysis. After the completion of (CHO—OH), DCM was evaporated under reduced pressure to afford a brown viscous liquid. To this added mesyl-Cl (0.7 mL, 9 mmol) and triethylamine (2 mL, 20 mmol) drop wise in DCM (10 mL) under $N_2$ gas at 0° C. The reaction mixture was stirred at rt for 30 min. The progress of the reaction was monitored by TLC analysis which indicated completion of the reaction. The reaction mixture was concentrated under reduced pressure. Added water (10 mL) and extracted with ethyl acetate (10 mL*2). The combined organic layer was given brine wash and concentrated under reduced pressure to afford XXXIe a brown viscous liquid. The crude was taken for next step without further purification. Yield: 0.7 g (99%); LCMS Calculated. for $C_{12}H_{15}N_2O_3$ is 234.26, Observed, 235.25; $[M+H]^+$.

Step-6: 2-(6-(1-(methoxymethyl) cyclopropyl) pyridin-2-yl) ethan-1-amine (XXXI)

To a solution of $LiAlH_4$ (0.06 g, 2 mmol) in dry diethyl ether (20 mL) at 0° C. under inert atmosphere was added (E)-2-(1-(methoxymethyl) cyclopropyl)-6-(2-nitrovinyl) pyridine XXXIe (0.4 g, 2 mmol) in dry diethyl ether (7 mL) and the resulting mixture was stirred at rt for 1 h. The progress of the reaction was monitored by TLC analysis. After completion of the reaction, the reaction mixture was cooled to 0° c. and quenched with water (1 mL). To the resulting mixture 15% KOH solution was added and stirred for 10 min. Added ethyl acetate (25 ml) and stirred at rt for 20 min. The resulting mixture was filtered through a celite bed and the residue was washed with ethyl acetate (50 ml×4). The combined filtrate was concentrated under reduced pressure to afford a desired compound XXXI as a pale brown viscous liquid. The crude was taken for next step without further purification. Yield: 0.34 g (99%).

Synthesis of 2-(6-(2-aminoethyl) pyridin-2-yl)-2-methylpropan-1-ol. (XXXII)

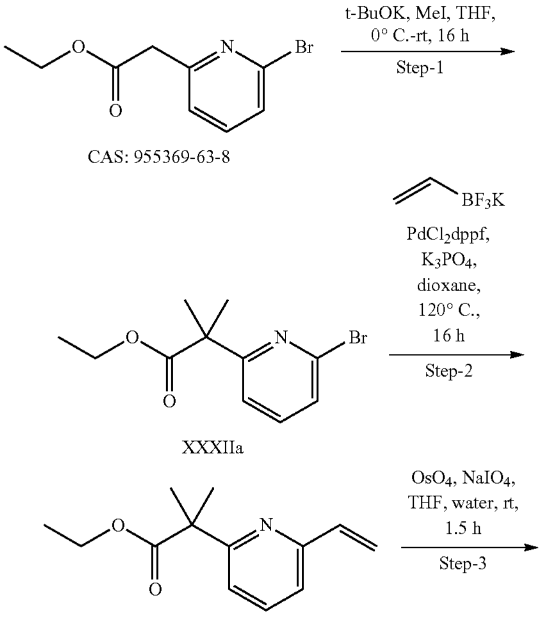

CAS: 955369-63-8

XXXIIa

XXXIIb

-continued

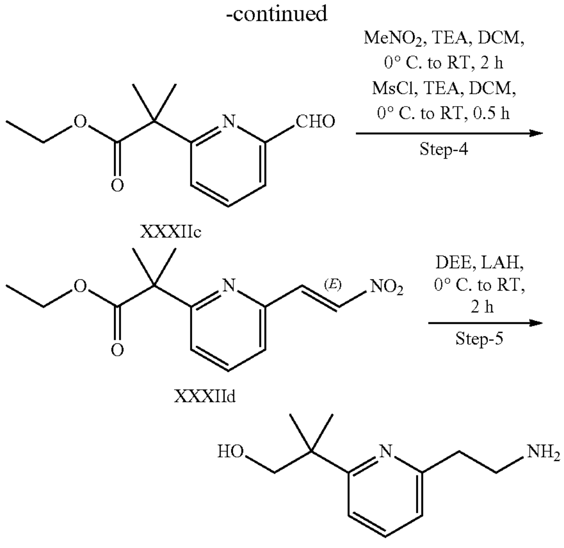

XXXIIc

XXXIId

XXXII

Step-1: Ethyl 2-(6-bromopyridin-2-yl)-2-methylpropanoate (XXXIIa)

A solution of ethyl 2-(6-bromopyridin-2-yl) acetate (CAS: 955369-63-8; 1 g, 4 mmol) in THF (15 mL) was cooled to 0° C. and potassium tert-butoxide (1 g, 10 mmol) was added and the resulting mixture was stirred for 30 min under $N_2$ atmosphere. Then methyl iodide (1 mL, 20 mmol) was drop wise added and reaction mixture was stirred at RT for 16 h. The progress of the reaction was monitored by TLC analysis. After completion, the reaction mixture was concentrated under reduced pressure and water (25 mL) was added. The solution was extracted with ethyl acetate (25 mL×2). The combined organic layer was dried over anhydrous sodium sulphate and concentrated reduced pressure to afford a light brown viscous liquid. The crude compound was subjected to silica gel (200-300) column chromatography using 0-10% ethyl acetate in n-hexane to afford the desired compound XXXIIa as colorless viscous liquid. Yield: 1.18 g (100%); LCMS Calculated. for $C_{11}H_{15}BrNO_2$ is 274.03, Observed, 274.15; $[M+H]^+$.

Step-2: Ethyl 2-methyl-2-(6-vinylpyridin-2-yl) propanoate (XXXIIb)

A solution of ethyl 2-(6-bromopyridin-2-yl)-2-methylpropanoate XXXIIa (1 g, 4 mmol), potassium trifluoro(vinyl) borate (0.5 g, 4 mmol) and potassium phosphate tribasic (1 g, 6 mmol) in 1,4 dioxane (20 mL) was purged with $N_2$ gas for 15 min with vigorous stirring. To the reaction was added $PdCl_2$(dppf) (0.1 g, 0.2 mmol) and the seal tube was closed and heated to 120° C. for 16 h. The progress of the reaction was monitored by TLC analysis. The reaction was cooled to room temperature and reaction mixture was concentrated under reduced pressure. To the residue was added water (70 mL) and the resulting mixture was extracted with ethyl acetate (50 mL×2). The organic layer was dried over anhydrous sodium sulphate and concentrated under reduced pressure to afford a light brown viscous liquid. The crude compound was purified by combi-flash silica gel (230-400) column chromatography using ethyl acetate in n-hexane and the peak eluted with 5% ethyl acetate in n-hexane was concentrated to afford the desired compound XXXIIb as an off-white solid. Yield: 0.73 g (90%); LCMS Calculated. for $C_{13}H_{17}NO_2$ is 220.17, Observed, 220.20; $[M+H]^+$; $^1H$ NMR (400 MHz, $CDCl_3$): δ 7.59 (t, J=7.6 Hz, 1H), 7.15-7.13 (m, 2H), 6.25 (d, J=17.6 Hz, 1H), 5.42 (d, J=10.8 Hz, 1H), 4.16 (q, J=7.2 Hz, 2H), 1.57 (s, 6H), 1.18 (t, J=7.2 Hz, 3H).

Step-3: ethyl 2-(6-formylpyridin-2-yl)-2-methylpropanoate (XXXIIc)

To a solution of ethyl 2-methyl-2-(6-vinylpyridin-2-yl) propanoate XXXIIb (0.73 g, 3.3 mmol) in THF (14 mL) and water (25 mL) and a solution of osmium tetroxide (680 μL, 0.33 mmol) 2.5% wt in isopropanol was added and the reaction was stirred at room temperature for 30 min. Then, Sodium metaperiodate (1.1 g, 5.0 mmol) was added and the reaction was stirred for additional 1 h. The mixture was diluted with water (15 mL) and extracted with ethyl acetate (15 mL×2). The combined organic layer was dried over anhydrous $Na_2SO_4$, filtered and evaporated under vacuum to afford XXXIIc the brown viscous liquid. The crude was taken for the next step without further purification. Yield: 0.503 g (68%); LCMS Calculated. for $C_{12}H_{16}NO_3$ is 222.12, Observed, 222.20; $[M+H]^+$; $^1H$ NMR (400 MHz, $CDCl_3$): δ 10.03 (s, 1H), 7.83 (d, J=3.6 Hz, 2H), 7.53 (t, J=4.4 Hz, 1H), 4.17 (q, J=7.2 Hz, 2H), 1.57 (s, 6H), 1.20 (t, J=7.2 Hz, 3H).

Step-4: Ethyl (E)-2-methyl-2-(6-(2-nitrovinyl) pyridin-2-yl) propanoate (XXXIId)

A stirred solution of ethyl 2-(6-formylpyridin-2-yl)-2-methylpropanoate XXXIIc (506 mg, 2.29 mmol) in DCM (15 mL) was cooled to 0° C. and nitromethane (168 mg, 2.74 mmol), triethylamine (1.16 g, 1.59 mL, 11.4 mmol) were added under $N_2$ atmosphere. The resulting mixture was stirred at rt for 2 h. The progress of the reaction was monitored by TLC analysis. After completion of reaction solvent was evaporated under reduced pressure to afford a brown viscous liquid. To the reaction mixture fresh DCM (10 mL) was added and was cooled to 0° C. This was followed a dropwise addition of methane sulfonyl chloride (786 mg, 6.86 mmol) under $N_2$ atmosphere. The reaction mixture was stirred at rt for 30 min and the progress of the reaction was monitored by TLC analysis. The reaction mixture was concentrated under reduced pressure and water (20 mL) was added. The mixture was extracted with ethyl acetate (20 mL×2). The combined organic layer was given brine wash and concentrated under reduced pressure to afford XXXIId as brown viscous liquid. The crude was taken for the next step without further purification. Yield: 0.6 g (99.3%); LCMS Calculated. for $C_{13}H_{17}N_2O_4$ is 265.12, Observed, 265.20; $[M+H]^+$; $^1H$ NMR (400 MHz, $CDCl_3$): δ 8.03-7.89 (m, 2H), 7.75 (t, J=7.6 Hz, 1H), 7.40-7.34 (m, 2H), 4.17 (q, J=6.8 Hz, 2H), 1.58 (s, 6H), 1.20 (t, J=7.2 Hz, 3H).

Step-5: 2-(6-(2-aminoethyl) pyridin-2-yl)-2-methylpropan-1-ol (XXXII)

A solution of aluminum lithium hydride (9 mL, 1 molar, 9 mmol) in dry diethyl ether (50 mL) was cooled to 0° C. To the resulting mixture a solution of ethyl (E)-2-methyl-2-(6-(2-nitrovinyl) pyridin-2-yl) propanoate XXXIId (0.6 g, 2 mmol) in dry diethyl ether (10 mL) was added drop wise. The resulting mixture was stirred at rt for 1 h. The progress of the reaction was monitored by TLC analysis which indicated the completion of reaction. The reaction mixture was cooled to 0° C. and dropwise added ice cold water (1 mL). To the resulting mixture 15% KOH solution (5 mL) was dropwise added followed by dropwise addition of ethyl acetate (50 mL). The resulting mixture was vigorously stirred at room temperature for 15-20 min. The reaction mixture was filtered through a celite bed, and the residue was washed with fresh ethyl acetate (50 mL×3). The combined filtrate was concentrated under reduced pressure to afford a desired compound XXXII as a light brown viscous liquid. The crude was taken for the next step without further purification. Yield: 0.4 g (100%).

Synthesis of 2-(3-(amino methyl)-1H-pyrazol-1-yl)-2-methylpropan-1-ol (XXXIII)

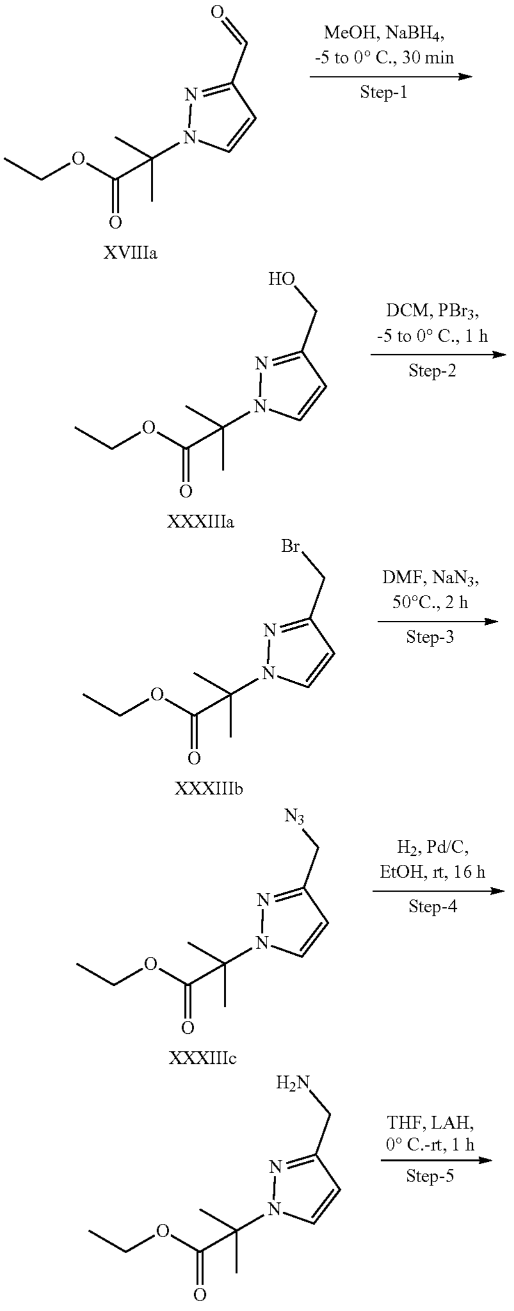

XVIIIa
XXXIIIa
XXXIIIb
XXXIIIc
XXXIIId

-continued

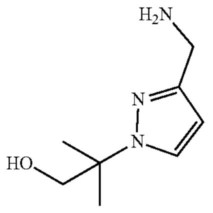

XXXIII

Step-1: Ethyl 2-(3-(hydroxymethyl)-1H-pyrazol-1-yl)-2-methylpropanoate (XXXIIIa)

A stirred solution of ethyl 2-(3-formyl-1H-pyrazol-1-yl)-2-methylpropanoate XVIIIa (1.0 g, 4.8 mmol) in ethanol (10 mL) was cooled to 0° C., and added sodium borohydride (90 mg, 2.4 mmol) in portions. The reaction mixture was stirred at 0° C. for 30 min and the progress of the reaction was monitored by TLC analysis (polar spot). The reaction mixture was diluted with water 1 mL and removed the solvent under vacuo. To the residue was added water (10 mL) and extracted with DCM (10 mL×3). The combined organic layer was dried anhydrous $Na_2SO_4$, filtered and concentrated under reduced pressure. The crude product XXXIIIa was taken for the next step without further purification. Yield: 0.9 g (90%); LCMS Calculated. for $C_{10}H_{17}N_2O_3$ is 213.13, Observed, 213.25; $[M+H]^+$; $^1H$ NMR (400 MHz, $CDCl_3$): δ 7.52 (d, J=2.0 Hz, 1H), 6.28 (d, J=2.0 Hz, 1H), 4.69 (d, J=4.4 Hz, 2H), 4.16 (q, J=6.8 Hz, 2H), 2.09 (s, 1H), 1.84 (s, 6H), 1.21 (t, J=7.2 Hz, 3H).

Step-2: Ethyl 2-(3-(bromomethyl)-1H-pyrazol-1-yl)-2-methyl propanoate (XXXIIIb)

A stirred solution of ethyl 2-(3-(hydroxymethyl)-1H-pyrazol-1-yl)-2-methylpropanoate XXXIIIa (0.2 g, 0.9 mmol) in DCM (5 mL) cooled to 0° C. under inert atmosphere and dropwise added $PBr_3$ (0.1 mL, 1 mmol). The reaction mixture was stirred at room temperature for 12 h. The progress of the reaction was monitored by TLC analysis (less polar spot). The reaction mixture was diluted with water (10 mL) and extracted with DCM (10 mL×3). The organic layer was dried over anhydrous $Na_2SO_4$, filtered and concentrated under reduced pressure. The crude compound was subjected to silica gel (230-400 mesh) combi-flash column chromatography using ethyl acetate (0-10%) in n-hexane to afford the desired compound XXXIIIb as a pale-yellow viscous liquid. Yield: 0.16 g (53%); LCMS Calculated. for $C_{10}H_{16}BrN_2O_2$ is 275.04, Observed, 275.15; $[M+H]^+$; $^1H$ NMR (400 MHz, $CDCl_3$): δ 7.52 (d, J=2.0 Hz, 1H), 6.28 (d, J=2.0 Hz, 1H), 4.69 (d, J=4.4 Hz, 2H), 4.16 (q, J=6.8 Hz, 2H), 2.09 (s, 1H), 1.84 (s, 6H), 1.21 (t, J=7.2 Hz, 3H).

Step-3: Ethyl 2-(3-(azidomethyl)-1H-pyrazol-1-yl)-2-methyl propanoate (XXXIIIc)

To a stirred solution of ethyl 2-(3-(bromomethyl)-1H-pyrazol-1-yl)-2-methylpropanoate XXXIIIb (400 mg, 1.45 mmol) in DMF (4 mL) was added sodium azide (123 mg, 1.89 mmol) and the reaction mixture was heated at 50° C. for 2 h. The progress of the reaction was monitored by TLC analysis. After completion, the reaction mixture was diluted with ice cold water (50 mL) and extracted with ethyl acetate (50 mL×3). The combined organic layer was dried over anhydrous $Na_2SO_4$, filtered and concentrated under reduced pressure. The crude was purified by combi flash (230-400 mesh) using 0-2% ethyl acetate in n-hexane to afford the desired compound XXXIIIc as a pale-yellow viscous liquid. Yield: 0.17 g (49.3%); $^1H$ NMR (400 MHz, $CDCl_3$): δ 7.55 (d, J=2.4 Hz, 1H), 6.30 (d, J=2.0 Hz, 1H), 4.33 (s, 2H), 4.16 (q, J=6.8 Hz, 2H), 1.85 (s, 6H), 1.20 (t, J=6.8 Hz, 3H).

Step-4: Ethyl 2-(3-(amino methyl)-1H-pyrazol-1-yl)-2-methylpropanoate (XXXIIId)

To a stirred solution of ethyl 2-(3-(azidomethyl)-1H-pyrazol-1-yl)-2-methylpropanoate XXXIIIc (170 mg, 0.717 mmol) in ethanol (5 mL), added Pd/C (76.3 mg, 10%, 0.717 mmol) under $N_2$ atmosphere. hydrogen. The reaction was evacuated and refilled with $H_2$ gas. The procedure was repeated for 3-4 times and stirred at room temperature under $H_2$ balloon pressure for 16 h. The progress of the reaction was monitored by TLC analysis (polar spot). After completion, the reaction mixture was filtered through celite bed, and the bed was washed with methanol. The combined filtrate was concentrated under reduced pressure. The crude was purified by silica gel flash (230-400 mesh) column chromatography using 0-5% methanol in DCM to afford the desired compound XXXIIId as a pale-yellow liquid. Yield: 0.15 g (99.3%); LCMS Calculated. for $C_{10}H_{18}N_3O_2$ is 212.14, Observed, 212.30; $[M+H]^+$; $^1H$ NMR (400 MHz, $CDCl_3$): δ 7.81 (d, J=2.4 Hz, 1H), 6.27 (d, J=2.4 Hz, 1H), 4.07 (q, J=7.2 Hz, 2H), 3.72 (s, 2H), 1.72 (s, 6H), 1.12 (t, J=6.8 Hz, 3H).

Step-5: 2-(3-(Amino methyl)-1H-pyrazol-1-yl)-2-methylpropan-1-ol (XXXIII)

To a stirred solution of LAH (2.84 mL, 1 M, 2.84 mmol) in dry diethyl ether (20 mL) solution of ethyl 2-(3-(amino methyl)-1H-pyrazol-1-yl)-2-methylpropanoate XXXIIId (150 mg, 0.710 mmol) in diethyl ether (5 ML) was added dropwise at 0° C. The reaction mixture was stirred at RT for 1 h. The reaction mixture was cooled to 0° C. and quenched with water (0.15 mL), 15% NaOH (0.15 mL) and then with ethyl acetate (10 mL). The residue was filtered through a celite bed and washed with ethyl acetate (50 mL×3 times). The filtrate was concentrated under reduced pressure to get the compound XXXIII as a pale-yellow liquid. The crude was taken for the next step without further purification. Yield: 0.12 g (100%).

Synthesis of (1-(2-(2-aminoethyl) thiazol-4-yl) cyclopropyl) methanol (XXXIV)

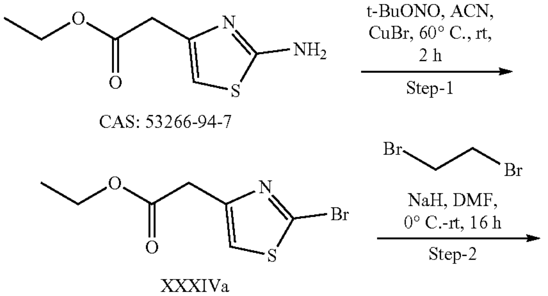

CAS: 53266-94-7

XXXIVa

-continued

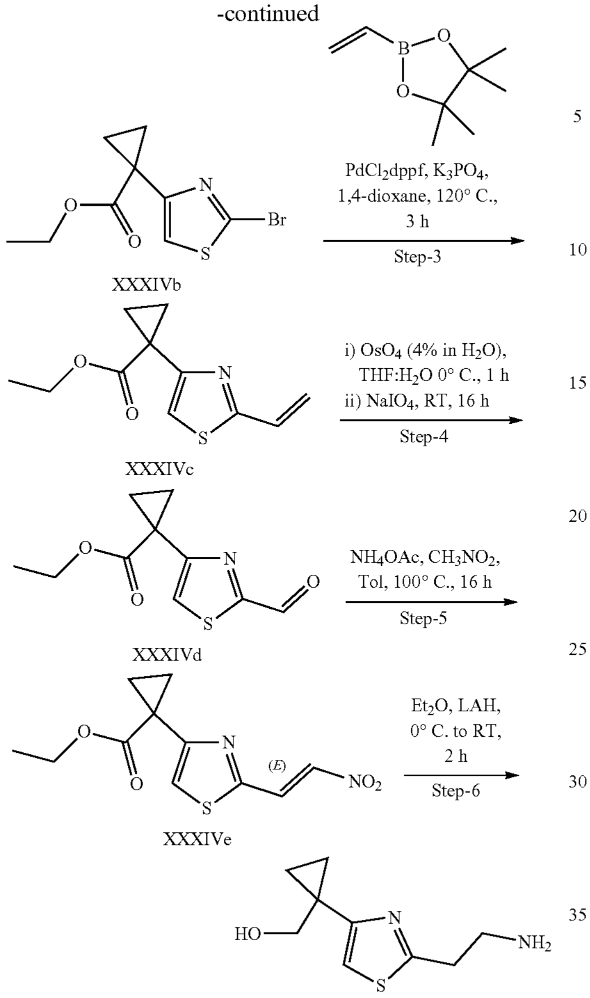

XXXIVb

XXXIVc

XXXIVd

XXXIVe

XXXIV

Step-1: Ethyl 2-(2-bromothiazol-4-yl) acetate (XXXIVa)

To a stirred solution of ethyl 2-(2-aminothiazol-4-yl) acetate (CAS: 53266-94-7, 1.0 g, 5.4 mmol) in ACN (10 mL) was added tert-butyl nitrite (0.84 g, 0.97 mL, 8.2 mmol) and the reaction mixture was stirred at 60° C. for 30 min. Then copper(I) bromide (0.77 g, 5.4 mmol) was added, and the reaction was heated at 75° C. for 2 h. The progress of the reaction was monitored by TLC analysis. After completion, the reaction mixture was concentrated, and the residue was subjected silica gel (230-400) column chromatography using 0-10% ethyl acetate in n-hexane to afford the desired compound as a pale-yellow viscous liquid. Yield: 0.45 g (34.0%); LCMS Calculated. for $C_7H_9BrNO_2S$ is 249.96; Observed. 250.00 $[M+H]^+$; $^1H$ NMR (400 MHz, $CDCl_3$): δ 7.18 (s, 1H), 4.20 (q, J=7.2 Hz, 2H), 3.81 (s, 2H), 1.28 (t, J=7.2 Hz, 3H).

Step-2: Ethyl 1-(2-bromothiazol-4-yl) cyclopropane-1-carboxylate (XXXIVb)

A stirred solution of ethyl 2-(2-bromothiazol-4-yl) acetate XXXIVa (200 mg, 0.80 mmol) in DMF (2 mL) was cooled to 0° C. and NaH (42.2 mg, 1.76 mmol) was portion wise added under inert atmosphere. This was followed by drop-wise addition of 1,2-dibromoethane (330 mg, 1.76 mmol) over 10 min and the resulting mixture was stirred at room temperature for 16 h. The progress of the reaction was monitored by TLC analysis. The reaction mixture quenched with ice cold water and extracted by ethyl acetate (20 mL×3) and the combined organic layer was dried over anhydrous sodium sulphate. The solvent was concentrated under reduced pressure to afford the desired compound XXXIVb as a light brown viscous liquid. Yield: 160 mg (72%); LCMS Calculated. for $C_9H_{11}BrNO_2S$ is 277.97; Observed. 278.10 $[M+H]^+$; $^1H$ NMR (400 MHz, $CDCl_3$): δ 7.47 (s, 1H), 4.17 (q, J=7.2 Hz, 2H), 1.70-1.68 (m, 2H), 1.50-1.49 (m, 2H), 1.26 (t, J=7.2 Hz, 3H).

Step-3: Ethyl 1-(2-vinylthiazol-4-yl) cyclopropane-1-carboxylate (XXXIVc)

To a stirred solution of ethyl 1-(2-bromothiazol-4-yl) cyclopropane-1-carboxylate XXXIVb (2.2 g, 8.0 mmol) in 1, 4-dioxane (40 mL) was added trifluoro(vinyl)-14-borane, potassium salt (1.2 g, 8.8 mmol) and the resulting mixture was purged argon for 10 min. This was followed by an addition of potassium phosphate (2.5 g, 12 mmol) and the mixture was further purged for 5 min before $PdCl_2$(dppf) (0.29 g, 0.40 mmol) was added. The seal tube was closed and heated at 120° C. for 3 h. The progress of the reaction was monitored by TLC analysis. After completion, the reaction mass was concentrated under vacuo the residue was subjected silica gel (230-400 mesh) column chromatography using 0-10% ethyl acetate in n-hexane to afford the desired compound XXXIVc as a light brown liquid. Yield: 1.1 g (61%); LCMS Calculated. for $C_{11}H_{14}NO_2S$ is 224.08; Observed. 224.15 $[M+H]^+$; $^1H$ NMR (400 MHz, $CDCl_3$): δ 7.36 (s, 1H), 6.77 (q, J=6.8 Hz, 1H), 5.98 (d, J=17.6 Hz, 1H), 5.50 (d, J=11.2 Hz, 1H), 4.16 (t, J=7.2 Hz, 2H), 1.69-1.66 (m, 2H), 1.50-1.47 (m, 2H), 1.28-1.22 (m, 3H).

Step-4: Ethyl 1-(2-formylthiazol-4-yl) cyclopropane-1-carboxylate (XXXIVd)

A stirred solution of ethyl 1-(2-vinylthiazol-4-yl) cyclopropane-1-carboxylate XXXIVc (1.1 g, 4.9 mmol) in THF: water (2:1; 16.5 mL) was cooled to 0° C. and added osmium tetroxide (15.75 mL 4% in water, 2.5 mmol) and the reaction mixture was stirred at 0° C. for 1 h. Then sodium periodate (1.6 g, 7.4 mmol) was added, and reaction stirred was stirred at room temperature for 16 h. The progress of the reaction was monitored by TLC analysis. The reaction was quenched with water (20 mL) and extracted with ethyl acetate (100 mL×3). The combined organic layer was concentrated under reduced pressure. The crude residue was subjected to silica gel (230-400) column chromatography using 0-10% ethyl acetate/n-hexane to afford the desired compound XXXIVd as a pale-yellow viscous liquid. Yield: 1.0 g (90%); $^1H$ NMR (400 MHz, $CDCl_3$): δ 9.92 (s, 1H), 8.04 (s, 1H), 4.20 (q, J=7.2 Hz, 2H), 1.79 (t, J=4.0 Hz, 2H), 1.67-1.62 (m, 2H), 1.28-1.22 (m, 3H).

Step-5: Ethyl (E)-1-(2-(2-nitrovinyl) thiazol-4-yl) cyclopropane-1-carboxylate (XXXIVe)

To a stirred solution of ethyl 1-(2-formylthiazol-4-yl) cyclopropane-1-carboxylate XXXIVd (1.1 g, 4.9 mmol) in DCM (14 mL) were added TEA (2.0 mL, 15 mmol) and nitromethane (0.53 mL, 9.8 mmol) and the reaction mixture was stirred at room temperature for 2 h. The progress of the reaction was monitored by TLC analysis. After completion, reaction mixture was concentrated under vacuo. The residue was immediately dissolved in fresh DCM (14 mL) and the resulting mixture was cooled to 0° C. TEA (2.0 mL, 15 mmol) and mesyl-Cl (0.76 mL, 9.8 mmol) were added, and the reaction mixture was stirred at 0° C. for 1 h. The reaction was quenched with saturated solution of $NaHCO_3$ and extracted with DCM (10 mL×3). The combined organic layer was dried over sodium sulphate and concentrated under reduced pressure. The crude compound XXXIVe was taken for the next step without further purification. Yield: 1.2 g (92.3%); LCMS Calculated. for $C_{11}H_{13}N_2O_4S$ is 269.06; Observed. 269.15 $[M+H]^+$; $^1H$ NMR (400 MHz, $CDCl_3$): δ 7.97 (m, 1H), 7.81 (s, J=13.2 Hz, 1H), 4.20 (q, J=7.2 Hz, 2H), 1.72 (q, J=3.6 Hz, 2H), 1.61-1.55 (m, 4H), 1.29-1.24 (m, 3H).

Step-6: (1-(2-(2-aminoethyl) thiazol-4-yl) cyclopropyl) methanol (XXXIV)

A stirred solution of ethyl (E)-1-(2-(2-nitrovinyl) thiazol-4-yl) cyclopropane-1-carboxylate XXXIVe (1.2 g, 4.5 mmol) in dry diethyl ether (25 mL) was cooled to 0° C. and $LiAlH_4$ solution (18 mL, 1 M, 18 mmol) was dropwise added. The reaction mixture was stirred at room temperature for 2 h. The progress of the reaction was monitored by TLC analysis. The reaction was quenched with ice cold water (1 mL), 15% NaOH solution (1 mL). The resulting mixture was stirred at 0° C. for 10 min and ethyl acetate (20 mL) was slowly added. The mixture was stirred for 10 min before it was passed through a celite bed. The bed was washed thoroughly with ethyl acetate (100 mL×3), and the combined filtrate was dried over anhydrous sodium sulphate and concentrated under reduced pressure to afford the desired compound XXXIV as a pale-yellow viscous liquid. Yield: 0.79 g (78.6%).

Synthesis of 2-(3-(2-aminoethyl)-4-fluoro-1H-pyrazol-1-yl)-2-methylpropan-1-ol (XXXV)

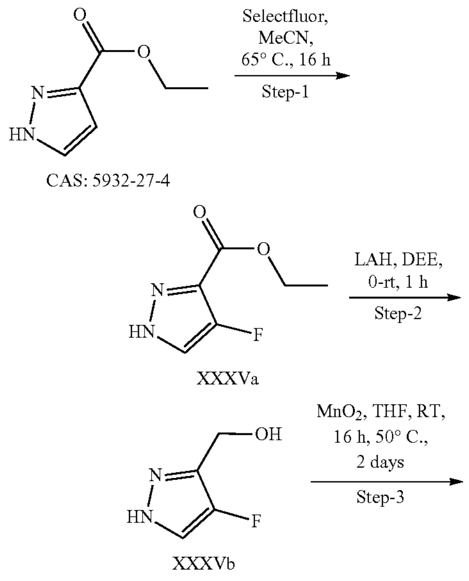

-continued

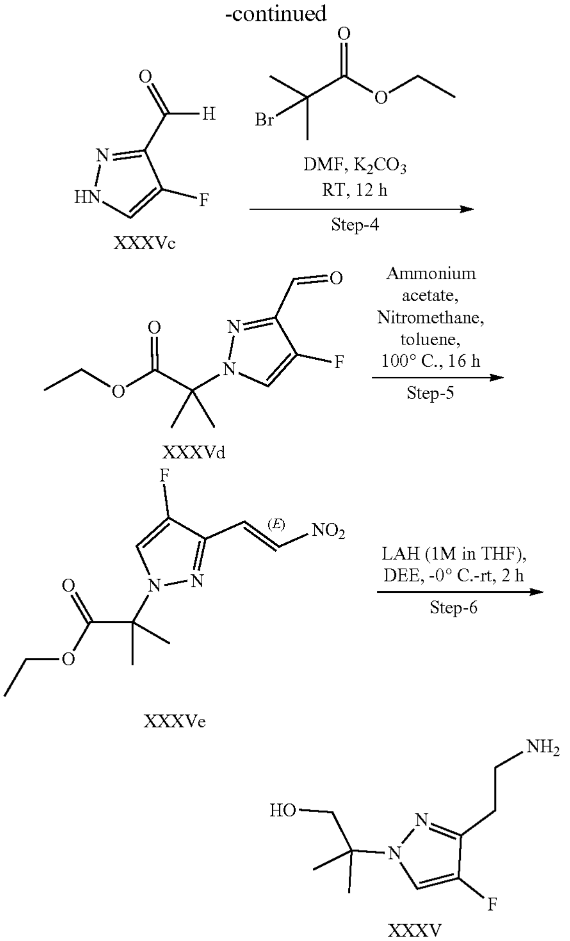

Step-1: Ethyl 4-fluoro-1H-pyrazole-3-carboxylate (XXXVa)

To a stirred solution of ethyl 1H-pyrazole-3-carboxylate (CAS: 5932-27-4, 1 g, 7.0 mmol) in acetonitrile (15 mL) was added select fluor (4 g, 11.3 mmol) and the reaction mixture was stirred at 65° C. for 16 h under nitrogen atmosphere. The progress of the reaction was monitored by TLC analysis. After completion, the reaction was cooled room temperature, diluted with water (100 mL) and extracted with ethyl acetate (100 mL×3). The combined organic layer was dried over anhydrous $Na_2SO_4$, filtered, and concentrated under reduced pressure. The crude was purified by combi flash silica gel column chromatography using 0-10% ethyl acetate in n-hexane to afford the desired compound XXXVa as off-white solid. Yield: 0.5 g (50%); NMR (400 MHz, $CDCl_3$): δ 10.95 (bs, 1H), 7.59 (s, 1H), 4.46-4.41 (m, 2H) 1.41 (t, J=7.2 Hz, 3H).

Step-2: (4-Fluoro-1H-pyrazol-3-yl) methanol (XXXVb)

A solution of $LiAlH_4$ (15.2 mL, 1 M in THF, 15.2 mmol) in diethyl ether (20 mL) was cooled to 0° C. and drop wise added a solution of ethyl 4-fluoro-1H-pyrazole-3-carboxylate XXXVa (600 mg, 3.79 mmol) in diethyl ether (5 mL) under inert atmosphere. The reaction was stirred at rt for 1 h under and the progress of the reaction was monitored by TLC analysis. After completion, the reaction mixture cooled with ice bath, quenched with drop wise addition of water (3.6 mL) and 15% NaOH (0.6 mL). To the resulting mixture was added ethyl acetate (50 mL) and stirred at rt for 30 min. The mixture was filtered, and the residue was thoroughly washed with fresh ethyl acetate (50 mL×2). The combined filtrate was concentrated under reduced pressure to afford the desired compound XXXVb as a pale-yellow liquid. The crude was taken for next step without further purification Yield: 0.40 g (90%). LCMS Calculated. for $C_4H_5FN_2O$ is 116.10, Observed. 115.00; $[M-H]^+$.

Step-3: 4-Fluoro-1H-pyrazole-3-carbaldehyde (XXXVc)

To a stirred solution of (4-fluoro-1H-pyrazol-3-yl) methanol XXXVb (400 mg, 3.45 mmol) in THF (20 mL) was added $MnO_2$ (15.0 g, 172 mmol) at 0° C. The resulting reaction mixture was stirred at 50° C. for 48 h under nitrogen atmosphere. The reaction was cooled to room temperature and filtered through a celite bed. The bed was washed with fresh ethyl acetate (10 mL×3). The combined filtrate was concentrated under reduced pressure to afford desired product XXXVc as a pale-yellow liquid. The crude was taken for next step without further purification. Yield: 0.39 g (99%). LC_MS Calculated. for $N_2O$ is 114.02, Observed. 113.10; $[M-H]^+$.

Step-4: Ethyl 2-(4-fluoro-3-formyl-1H-pyrazol-1-yl)-2-methylpropanoate (XXXVd)

To a stirred solution of 4-fluoro-1H-pyrazole-3-carbaldehyde XXXVc (400 mg, 3.51 mmol) in DMF (10 mL) was added cesium carbonate (2.28 g, 7.01 mmol) followed by an addition of ethyl-2-bromo-2-methylpropanoate (821 mg, 4.21 mmol). The resulting reaction mixture was stirred at rt for 12 h under nitrogen atmosphere. The progress of the reaction was monitored by TLC analysis. After completion, the reaction mixture was diluted with ice cold water (200 mL) and extracted with ethyl acetate (100 mL×3). The organic layer was dried over anhydrous $Na_2SO_4$, filtered, and concentrated under reduced pressure. The crude material was purified by silica gel (230-400) column chromatography using 0-5% ethyl acetate in n-hexane to afford the desired compound XXXVd as a colorless liquid. Yield: 0.9 g (100%); NMR (400 MHz, $CDCl_3$): δ 9.93 (s, 1H), 7.51-7.49 (m, 1H), 4.22-4.17 (m, 2H) 1.86 (s, 6H), 1.23 (t, J=7.2 Hz, 3H).

Step-5: Ethyl (E)-2-(4-fluoro-3-(2-nitrovinyl)-1H-pyrazol-1-yl)-2-methylpropanoate (XXXVe)

To a stirred solution of ethyl 2-(4-fluoro-3-formyl-1H-pyrazol-1-yl)-2-methylpropanoate XXXVd (800 mg, 3.51 mmol) in toluene (20 mL) were added nitromethane (2.84 mL, 52.6 mmol) and ammonium acetate (405 mg, 5.26 mmol) under nitrogen atmosphere. The resulting mixture was stirred at 100° C. for 16 h. The progress of the reaction was monitored by TLC analysis. After completion, the reaction mixture was cooled to room temperature, diluted with 1N HCl (20 mL) and extracted with ethyl acetate (50 mL×3). The combined organic layer was dried with anhydrous $Na_2SO_4$, filtered, and concentrated under reduced pressure. The crude was purified by combi flash column chromatography using 0-2% ethyl acetate in n-hexane to afford the desired compound XXXVe as an yellow solid. Yield: 0.5 g (52%); NMR (400 MHz, $CDCl_3$): δ 7.94-7.93 (m, 1H), 7.69-7.64 (m, 1H), 7.51 (d, J=5.2 Hz, 1H), 4.21-4.16 (m, 2H) 1.83 (s, 6H), 1.23 (t, J=7.2 Hz, 3H).

Step-6: 2-(3-(2-Aminoethyl)-4-fluoro-1H-pyrazol-1-yl)-2-methylpropan-1-ol (XXXV)

A stirred solution of $LiAlH_4$ (7.37 mL, 1 M in THF, 7.37 mmol) in diethyl ether (80 mL) cooled to 0° C. and dropwise added solution of ethyl (E)-2-(4-fluoro-3-(2-nitrovinyl)-1H-pyrazol-1-yl)-2-methylpropanoate XXXVe (500 mg, 1.84 mmol) in diethyl ether (10 mL) under nitrogen atmosphere. The reaction was stirred at rt for 2 h. The progress of the reaction was monitored by TLC analysis. After completion, the reaction mixture was cooled to 0° C. and quenched with water (0.5 mL), 15% NaOH (0.5 mL) and again water (1.5 mL) was added. To the resulting mixture was added ethyl acetate (30 mL) and stirred for 30 min. The mixture was filtered, and the residue was washed with fresh ethyl acetate (100 mL×3). The combined filtrate was concentrated under reduced pressure to afford the desired compound XXXV as pale-yellow liquid. The crude was taken for next step without further purification. Yield: 0.35 g (94%).

Synthesis of 7-amino-3-bromo-2-methyl-5-(methyl sulfonyl) pyrazolo[1,5-a] pyrimidine-6-carbonitrile (XXXVI)

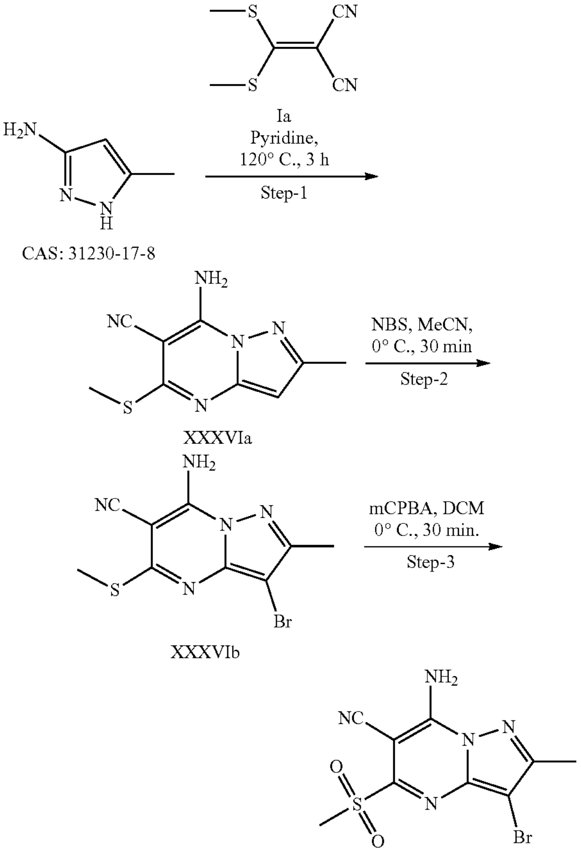

CAS: 31230-17-8
XXXVIa
XXXVIb
XXXVI

Step-1: 7-amino-2-methyl-5-(methylthio) pyrazolo [1,5-a] pyrimidine-6-carbonitrile (XXXVIa)

To a solution of 5-methyl-1H-pyrazol-3-amine (CAS: 31230-17-8, 2 g, 20 mmol) in pyridine (50 mL) was added 2-(bis(methylthio)methylene) malononitrile Ia (4 g, 20 mmol) and stirred at 120° C. for 3 h. The progress of the reaction was monitored by TLC analysis. After the completion of the reaction, added water (500 mL) and filtered the solid to afford the crude compound XXXVIa as a pink solid. The crude compound was taken for the next step without further purification. Yield: 3.9 g, (90.0%); LCMS Calculated. for $C_9H_9N_5S$ is 219.06; Observed: 220.25 $[M+H]^+$. $^1H$ NMR (400 MHz, DMSO-$D_6$): δ 8.68 (s, 2H), 6.25 (s, 1H), 2.52 (d, J=5.6 Hz, 3H), 2.37 (s, 3H).

Step-2: 7-amino-3-bromo-2-methyl-5-(methylthio) pyrazolo[1,5-a] pyrimidine-6-carbonitrile (XXXVIb)

To a solution of 7-amino-2-methyl-5-(methylthio) pyrazolo[1,5-a] pyrimidine-6-carbonitrile XXXVIa (1.89 g, 8.62 mmol) in acetonitrile (25 mL) at 0° C. was added N-Bromo succinimide (1.89 g, 10.6 mmol) and stirred at 0° C. for 30 min. The progress of the reaction was monitored by TLC analysis. After the completion of the reaction, added water (50 mL) and extracted with ethyl acetate (2×50 mL). The combined organic layer was dried over anhydrous sodium sulphate, filtered, and concentrated under reduced pressure to afford the desired compound XXXVIb as a brown solid. The crude compound was taken for the next step without any further purification. Yield: 1.9 g, (74.0%); LCMS Calculated. for $C_9H_8BrN_5S$ is 296.97; Observed.: 298.15 $[M+H]^+$. $^1H$NMR (400 MHz, $CDCl_3$): δ 6.27 (s, 2H), 2.67 (s, 3H), 2.43 (s, 3H).

Step-3: 7-amino-3-bromo-2-methyl-5-(methyl sulfonyl) pyrazolo[1,5-a] pyrimidine-6-carbonitrile (XXXVI)

To a solution of 7-amino-3-bromo-2-methyl-5-(methylthio) pyrazolo[1,5-a] pyrimidine-6-carbonitrile XXXVIb (0.8 g, 2.68 mmol) in acetonitrile (15 mL) at 0° C. was added mCPBA (2.31 g, 13.4 mmol) and stirred at 0° C. for 30 min. The progress of the reaction was monitored by TLC analysis. After the completion of the reaction, the reaction mixture was quenched with sodium bicarbonate (100 mL) and extracted with ethyl acetate (2×15 mL). The combined organic layer was dried over anhydrous sodium sulphate, filtered, and concentrated under reduced pressure to afford the crude compound XXXVI as a brown solid. The crude compound was taken for the next step without further purification. Yield: 600 mg, (67.7%); LCMS Calculated. for $C_9H_8BrN_5O_2S$ is 328.96; Observed.: 332 $[M+H]^+$.

Synthesis of 2-(1-41-(((tert-butyldimethylsilyl) oxy) methyl) cyclopropyl) methyl)-1H-pyrazol-3-yl) ethan-1-amine (XXXVII)

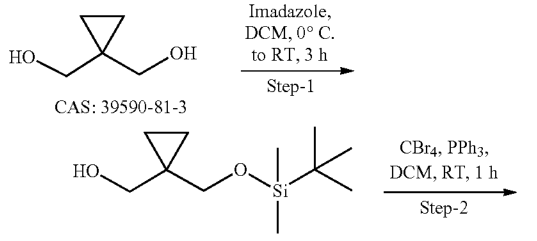

CAS: 39590-81-3

XXXVIIa

-continued

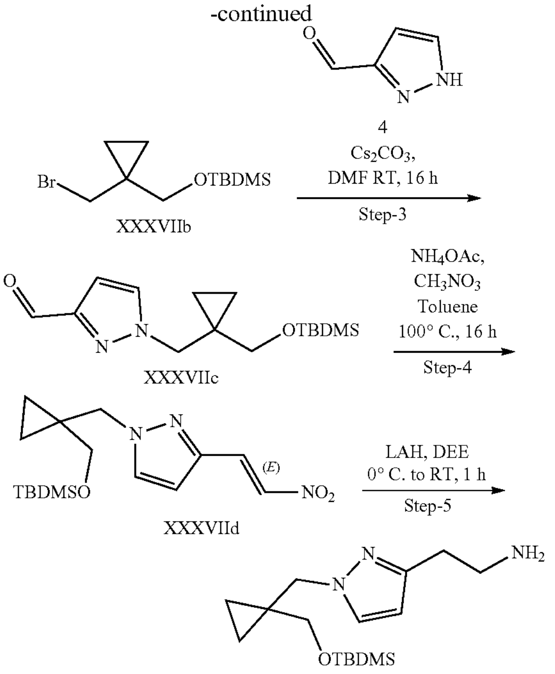

4

XXXVIIb

XXXVIIc

XXXVIId

XXXVII

Step-1: (1-(((tert-Butyldimethylsilyl) oxy) methyl) cyclopropyl) methanol (XXXVIIa)

To a stirred solution of cyclopropane-1,1-diyldimethanol (CAS: 39590-81-3, 5 g, 0.05 mol) in DCM (100 mL) was added imidazole (5 g, 0.07 mol) and stirred at room temperature for 10 min, then reaction mixture was cooled to 0° C. followed by drop wise addition of TBDMS-Cl (7 g, 0.05 mol) under nitrogen atmosphere. The reaction mixture was stirred at room temperature for 3 h and the reaction was monitored by TLC analysis. After completion, the reaction was quenched with water (50 mL) and extracted with DCM (30 mL×2). The combined organic layer was dried over anhydrous sodium sulphate. The residue obtained upon removal of the solvent was subjected to silica gel (230-400 mesh) column chromatography using (0-30%) ethyl acetate in n-hexane to afford the desired compound XXXVIIa as a colorless liquid. Yield: 5.0 g (50%). $^1H$ NMR (400 MHz, $CDCl_3$): δ 3.61 (s, 2H), 3.57 (d, J=5.6 Hz, 2H), 2.74 (t, J=5.6 Hz, 1H), 0.91 (s, 9H), 0.53-0.50 (m, 2H), 0.47-0.43 (m, 2H). 0.07 (s, 6H).

Step-2: ((1-(Bromomethyl) cyclopropyl) methoxy) (tert-butyl) dimethyl silane (XXXVIIb)

To a stirred solution of (1-(((tert-butyldimethylsilyl) oxy) methyl) cyclopropyl) methanol XXXVIIa (4 g, 20 mmol) in DCM (100 mL) was added triphenylphosphine (7 g, 30 mmol) and stirred at room temperature for 20 min, then reaction mixture was cooled to 0° C. followed by drop wise addition of carbon tetrabromide (9 g, 30 mmol) under nitrogen atmosphere. Then reaction was stirred at room temperature for 1 h and the reaction was monitored by TLC analysis. After completion, the reaction mixture was diluted with water (50 mL) and extracted with DCM (25 mL×3). The combined organic layer was dried over anhydrous sodium sulphate. The residue obtained upon removal of the solvent was subjected to silica gel (230-400 mesh) column chromatography using (0-20%) ethyl acetate in n-hexane to afford the desired compound XXXVIIb as a colorless liquid. Yield: 4.0 g (80%). $^1$H NMR (400 MHz, $CDCl_3$): δ 3.56 (s, 2H), 3.49 (s, 2H), 0.93-0.89 (m, 9H), 0.74-0.71 (m, 2H), 0.61-0.57 (m, 2H). 0.07 (s, 6H).

Step-3: 1-((1-(((tert-Butyldimethylsilyl) oxy) methyl) cyclopropyl) methyl)-1H-pyrazole-3-carbaldehyde (XXXVIIc)

To a stirred solution of 1H-pyrazole-3-carbaldehyde (1 g, 10 mmol) in DMF (10 mL) was added cesium carbonate (7 g, 20 mmol) and stirred at room temperature for 20 min, then reaction mixture was cooled to 0° C. followed by drop wise addition of ((1-(bromomethyl) cyclopropyl) methoxy) (tert-butyl) dimethyl silane XXXVIIb (3 g, 10 mmol) under nitrogen atmosphere. Then reaction mixture was stirred at room temperature for 16 h and the reaction was monitored by TLC analysis. After completion, the reaction mixture was diluted with water (50 mL) and extracted with ethyl acetate (25 mL×3). The combined organic layer was dried over anhydrous sodium sulphate. The residue obtained upon removal of the solvent was subjected to silica gel (230-400 mesh) column chromatography using (0-20%) ethyl acetate in n-hexane to afford the desired compound XXXVIIc as a colorless liquid. Yield: 1.5 g (50%). LCMS Calculated. for $C_{15}H_{26}N_2O_2Si$ is 294.17; Observed. 295.25 $[M+H]^+$; $^1$H NMR (400 MHz, $CDCl_3$): δ 9.97 (s, 1H), 7.52 (d, J=1.6 Hz, 1H), 6.80 (d, J=2.4 Hz, 1H), 4.21 (s, 2H), 3.32 (s, 2H), 0.90 (s, 9H), 0.70-0.68 (m, 2H), 0.58-0.56 (m, 2H). 0.02 (s, 6H).

Step-4: (E)-1-((1-(((tert-Butyldimethylsilyl) oxy) methyl) cyclopropyl) methyl)-3-(2-nitrovinyl)-1H-pyrazole (XXXVIId)

To a stirred solution of 1-((1-(((tert-Butyldimethylsilyl) oxy) methyl) cyclopropyl) methyl)-1H-pyrazole-3-carbaldehyde XXXVIIc (1.5 g, 5.1 mmol) in toluene (50 mL) was added nitromethane (4.7 g, 4.1 mL, 76 mmol) and stirred at room temperature for 10 min followed by addition of ammonium acetate (0.59 g, 7.6 mmol) then reaction mixture was stirred at 100° C. for 16 h. The progress of the reaction was monitored by TLC analysis. After completion, reaction mixture was cooled to room temperature, diluted with 1N HCl (50 mL) and extracted with ethyl acetate (25 mL×3). The combined organic layer was dried over anhydrous sodium sulphate. The residue obtained upon removal of the solvent was subjected to silica gel (230-400 mesh) column chromatography using (0-30%) ethyl acetate in n-hexane to afford the desired compound XXXVIId as a light-yellow solid. Yield: 1.15 g (65%). LCMS Calculated. for $C_{16}H_{27}N_3O_3Si$ is 337.18; Observed. 338.20 $[M+H]^+$; $^1$H NMR (400 MHz, $CDCl_3$): δ 7.96 (d, J=13.2 Hz, 1H), 7.61 (d, J=13.2 Hz, 1H), 7.26 (s, 1H), 6.53 (s, 1H), 4.16 (s, 2H), 3.31 (s, 2H), 0.90 (s, 9H), 0.67 (m, 2H), 0.55 (m, 2H). 0.02 (s, 6H).

Step-5: 2-(1-41-(((tert-Butyldimethylsilyl) oxy) methyl) cyclopropyl) methyl)-1H-pyrazol-3-yl) ethan-1-amine (XXXVII)

To a stirred solution of lithium aluminum hydride (0.01 L, 1.0 molar in THF, 10 mmol) in diethyl ether (70 mL) was added (E)-1-((1-(((tert-Butyldimethylsilyl) oxy) methyl) cyclopropyl) methyl)-3-(2-nitrovinyl)-1H-pyrazole XXXVIId (1.15 g, 3.41 mmol) dropwise at 0° C. under nitrogen atmosphere. The reaction mixture was stirred at room temperature for 1 h and the progress of the reaction was monitored by TLC analysis. After completion, the reaction mixture was cooled to 0° C. was added 1.2 mL of ice-cold water and 1.2 mL of 15% KOH solution then stirred at room temperature for another 30 min. The resulting reaction mixture was diluted with 100 mL of ethyl acetate filtered through Buchner funnel and the solid was thoroughly washed with 250 mL of ethyl acetate. The filtrate was dried over anhydrous sodium sulphate and concentrated under reduced pressure to afford a desired compound XXXVII as light-yellow liquid. The crude product was taken for the next step without further purification. Yield: 0.81 g (100%). LCMS Calculated for $C_{16}H_{31}N_3OSi$ is 309.22; Observed: 310.30 $[M+H]^+$.

Synthesis of 2-(6-(2-aminoethyl) pyridin-2-yl)-2,2-difluoroethan-1-ol (XXXVIII)

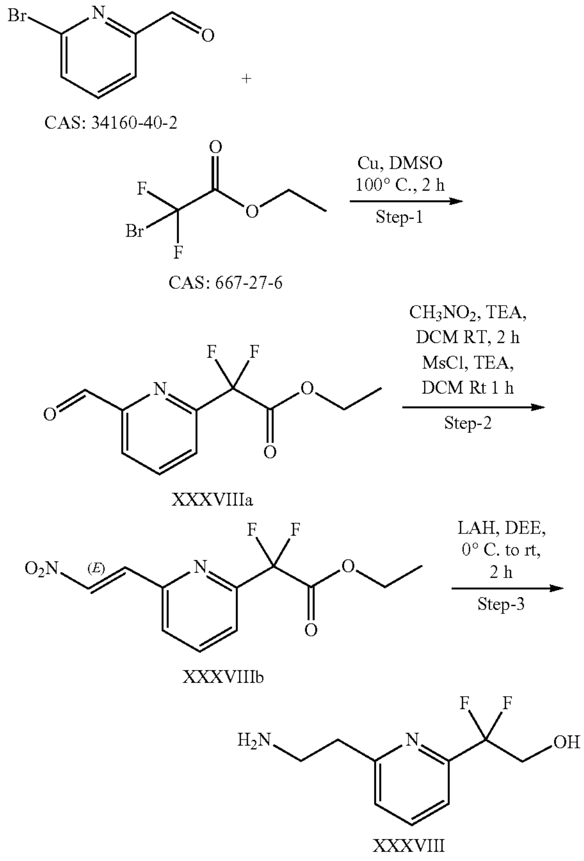

Step-1: Ethyl 2,2-difluoro-2-(6-formylpyridin-2-yl) acetate (XXXVIIIa)

To a solution of 6-bromopicolinaldehyde (CAS: 34160-40-2, 1 g, 5 mmol) in DMSO (5 mL) were added copper (0.8 g, 0.01 mol) and ethyl 2-bromo-2,2-difluoroacetate (CAS: 667-27-6, 1 g, 7 mmol) under $N_2$ at room temperature in a seal tube with Teflon screw-stopper. Seal tube was closed, and reaction mixture was stirred at 100° C. for 2 h. The reaction was monitored by TLC analysis. After completion, the reaction mixture was cooled to room temperature was added 50 mL of ethyl acetate and 50 mL 1.3 molar potassium dihydrogen phosphate solution. The resulting mixture was stirred at room temperature for 30 min. The solid was filtered off and thoroughly washed with the ethyl acetate (30 mL×2). The filtrate was dried over anhydrous sodium sulphate and concentrated under reduced pressure. The residue obtained upon removal of the solvent was subjected to silica gel (230-400 mesh) column chromatography using 0-6% EtOAc in n-hexane to afford the desired compound XXXVIIIa as an off-white solid. Yield: 0.93 g (80%). LCMS Calculated. for $C_{10}H_9F_2NO_3$ is 229.05; Observed. 230.15 $[M+H]^+$; $^1H$ NMR (400 MHz, DMSO-$D_6$): δ 9.95 (bs, 1H), 8.35-8.13 (m, 3H), 4.38 (q, J=7.2 Hz, 2H), 1.25 (t, J=7.2 Hz, 3H).

Step-2: Synthesis of ethyl (E)-2,2-difluoro-2-(6-(2-nitrovinyl) pyridin-2-yl) acetate (XXXVIIIb)

To the stirred solution of ethyl 2,2-difluoro-2-(6-formylpyridin-2-yl) acetate XXXVIIIa (930 mg, 4.06 mmol) in DCM (20 mL) was added triethylamine (1.13 mL, 8.12 mmol) and nitromethane (263 μL, 4.87 mmol) at room temperature under $N_2$. The resulting reaction mixture was stirred at room temperature for 2 h and the reaction was monitored by TLC analysis. After completion, DCM was concentrated to dryness and the residue was immediately taken for next in situ step. To a solution of crude ethyl 2,2-difluoro-2-(6-(1-hydroxy-2-nitroethyl) pyridin-2-yl) acetate (1.177 g, 4.06 mmol) in DCM (25 mL) was added triethylamine (1.70 mL, 12.17 mmol) and cooled to 0° C. followed by a dropwise addition of methane sulfonyl chloride (1.394 g, 1.226 mL, 12.17 mmol). The reaction was stirred at room temperature for 1 h. The progress of reaction was monitored by TLC analysis. After completion, the reaction mixture was quenched with water (25 mL) and extracted with DCM (20×2). The combined organic layer was washed with 25 mL of brine, passed through anhydrous sodium sulphate, and concentrated under reduced pressure. The residue obtained upon removal of the solvent was subjected to silica gel (230-400 mesh) column chromatography using 0-6% ethyl acetate in n-hexane to afford the desired compound XXXVIIIb as a viscous brown liquid. Yield: 0.77 g (70%). LCMS Calculated. for $C_{11}H_{10}F_2N_2O_4$ is 272.06; Observed. 273.15 $[M+H]^+$; $^1H$ NMR (400 MHz, DMSO-$D_6$): δ 8.26-7.97 (m, 5H), 4.38 (q, J=7.2 Hz, 2H), 1.25 (t, J=4.0 Hz, 3H).

Step-3: Synthesis of 2-(6-(2-Aminoethyl) pyridin-2-yl)-2,2-difluoroethan-1-ol (XXXVIII)

To a stirred solution of lithium aluminum hydride (11.3 mL, 1.0 molar in THF, 11.3 mmol) in diethyl ether (10 mL) followed by dropwise addition of solution of (E)-2,2-difluoro-2-(6-(2-nitrovinyl) pyridin-2-yl) acetate XXXVIIIb (0.770 g, 2.83 mmol) in diethyl ether (5 mL) at 0° C. under nitrogen atmosphere. The resulting mixture was stirred at room temperature for 2 h and the reaction was monitored by TLC analysis. After completion, the reaction mixture was cooled to 0° C. was added 0.7 mL of ice-cold water and 0.7 mL of 15% KOH solution then stirred at room temperature for another 30 min. The resulting reaction mixture was diluted with 100 mL of ethyl acetate filtered and the solid was thoroughly washed with 100 mL of ethyl acetate. The filtrate was dried over anhydrous sodium sulphate and concentrated under reduced pressure to afford a desired compound XXXVIII as light brown viscous liquid. The crude was taken for the next step without further purification. Yield: 0.56 g (98%). LCMS Calculated. for $C_9H_{12}F_2N_2O$ is 202.09; Observed. 203.25 $[M+H]^+$.

Synthesis of (2-(3-(2-aminoethyl)-1H-pyrazol-1-yl) cyclobutyl) methanol (XXXIX)

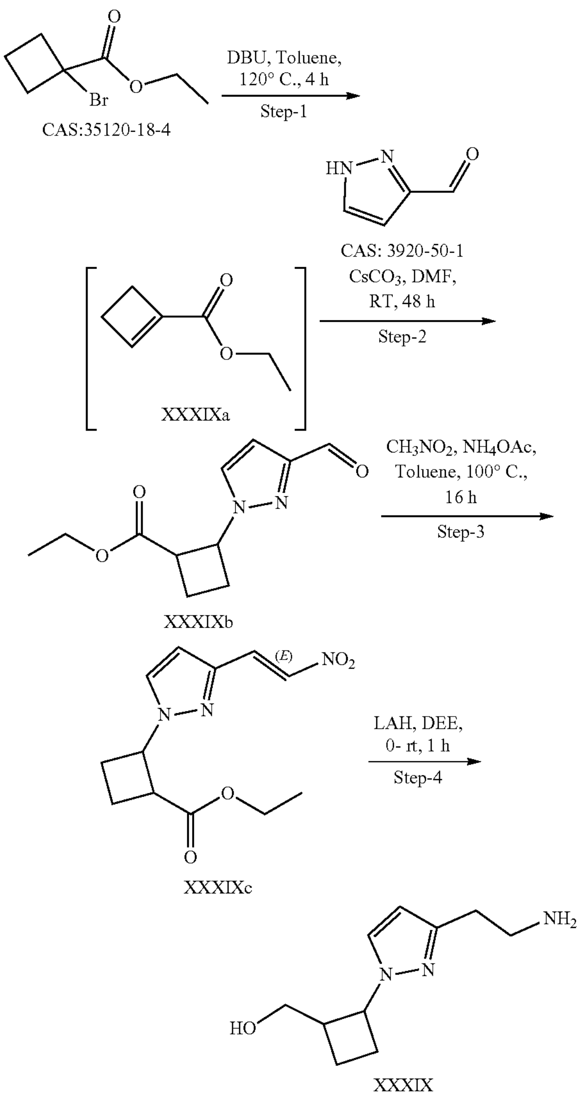

CAS:35120-18-4

XXXIXa

XXXIXb

XXXIXc

XXXIX

Step-1: Ethyl cyclobut-1-ene-1-carboxylate (XXXIXa)

A stirred solution of DBU (54 mL, 312.3 mmol) in toluene (50 mL) was heated at 150° C. for 20 min and ethyl 1-bromocyclobutane-1-carboxylate (CAS: 35120-18-4, 5.0 g, 52.050 mmol) was added dropwise through septum under inert atmosphere. The reaction mixture was stirred at 110° C. for 3.5 h. The progress of the reaction was monitored by TLC analysis. After completion, the reaction mixture was cooled to room temperature and diluted with ice cold water (200 mL). The mixture was extracted with n-hexane (100 mL×3). The combined organic layer was washed with saturated aq. $NaHSO_4$ (100 mL) solution, followed by with water (100 mL). The organic layer was separated and dried over anhydrous $Na_2SO_4$, filtered, and concentrated at ambient temperature (20° C., 100 mbar vacuum). (Note: The desired product appeared to be volatile and was passing to the receiver while concentration on rotavapor; the compound). The crude compound XXXIXa (compound+some quantity of toluene) was taken for next step by assuming quantitative yield.

Step-2: Ethyl 2-(3-formyl-1H-pyrazol-1-yl) cyclobutane-1-carboxylate (XXXIXb)

A stirred solution of 1H-pyrazole-3-carbaldehyde (CAS: 3920-50-1, 5.0 g, 52 mmol) in DMF (20 mL), was added $K_2CO_3$ (14 g, 100 mmol) and the reaction mixture was cooled to 0° C. under inert atmosphere. This was followed by dropwise addition of above mixture of ethyl cyclobut-1-ene-1-carboxylate XXXIXa (16 g, 78 mmol) and toluene. The resulting mixture was stirred at rt for 48 h and progress of the reaction was monitored by TLC analysis. After completion, the reaction mixture was diluted with ice cold water (500 mL) and extracted with ethyl acetate (200 mL×3). The combined organic layer was dried over anhydrous $Na_2SO_4$, filtered, and concentrated under reduced pressure. The crude was purified by combi flash (230-400 silica) column chromatography using 0-5% ethyl acetate in n-hexane to afford the desired compound XXXIXb as a colorless viscous liquid. Yield: 1.4 g (10%); LCMS Calculated. for $C_{11}H_{14}N_2O_3$ is 222.10; Observed. 223.05 $[M+1]^+$. $^1H$ NMR (400 MHz, $CDCl_3$) δ 9.99 (s, 1H), 7.50 (d, J=1.6 Hz, 1H), 6.79 (d, J=2.0 Hz, 1H), 5.00 (t, J=8.8 Hz, 1H), 4.16 (q, J=7.2 Hz, 2H), 3.68-3.66 (m, 1H), 2.75-2.70 (m, 1H), 2.46-2.44 (m, 1H), 2.31-2.26 (m, 1H), 2.10-2.04 (m, 1H), 1.25 (t, J=7.2 Hz, 3H).

Step-3: Ethyl (E)-2-(3-(2-nitrovinyl)-1H-pyrazol-1-yl) cyclobutane-1-carboxylate (XXXIXc)

To a stirred solution of ethyl 2-(3-formyl-1H-pyrazol-1-yl) cyclobutane-1-carboxylate XXXIXb (1.4 g, 6.3 mmol) in toluene (20 mL) were added nitromethane (5.1 mL, 94 mmol) and ammonium acetate (0.73 g, 9.4 mmol) under nitrogen atmosphere. The resulting reaction mixture was stirred at 100° C. for 16 h. The reaction was monitored by TLC analysis. After completion, the reaction mixture was cooled to rt and diluted with 1 N HCl (100 mL). The mixture was extracted with ethyl acetate (300 mL×3) and combined organic layer was dried with $Na_2SO_4$. The solution was concentrated under reduced pressure. The crude was purified by combi flash (230-400) column chromatography using 0-5% ethyl acetate in n-hexane to afford the desired compound XXXIXc as a pale-yellow viscous liquid. Yield: 1.2 g (71%); LCMS Calculated. for $C_{12}H_{15}N_3O_4$ is 265.10; Observed. 267.30 $[M+1]^+$. $^1H$ NMR (400 MHz, $CDCl_3$): δ 7.98 (d, J=13.6 Hz, 1H), 7.63 (d, J=13.6 Hz, 1H), 7.48 (s, 1H), 6.52 (d, J=2.0 Hz, 1H), 4.95 (d, J=8.4 Hz, 1H), 4.19-4.13 (m, 2H), 3.67-3.60 (m, 1H), 2.45-2.38 (m, 1H), 2.33-2.25 (m, 1H), 2.10-2.00 (m, 1H), 2.09-1.99 (m, 1H), 1.27 (t, J=7.2 Hz, 3H).

Step-4: (2-(3-(2-aminoethyl)-1H-pyrazol-1-yl) cyclobutyl) methanol (XXXIX)

To a stirred solution of $LiAlH_4$ (18 mL, 1 molar in THF, 18 mmol) in diethyl ether (100 mL), was dropwise added a solution of ethyl (E)-2-(3-(2-nitrovinyl)-1H-pyrazol-1-yl) cyclobutane-1-carboxylate XXXIXc (1.2 g, 4.5 mmol) in diethyl ether (50 mL) at 0° C. under inert atmosphere. The resulting mixture was allowed to warm to rt and stirred for 1 h. The reaction was monitored by TLC analysis. After completion, the reaction mixture was cooled to 0° C. and quenched with water (1.2 mL) and 15% KOH (1.2 mL). The mixture was stirred for 5 min and again added water (2.4 mL). The residue was filtered and washed with ethyl acetate (200 mL×3). The filtrate was concentrated under reduced pressure to afford the desired compound XXXIX as pale-yellow liquid. The crude product was taken for the next step without further purification. Yield: 1.1 g (88%).

Synthesis of 3-(2-aminoethyl)-1-methylpyridin-2(1H)-one (XL)

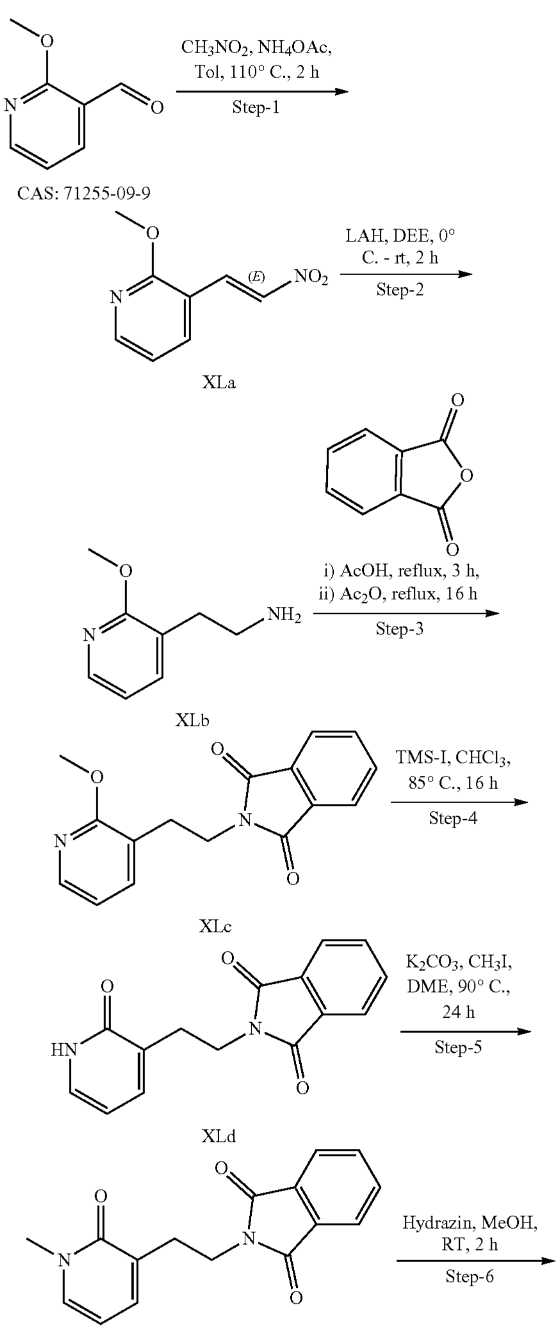

CAS: 71255-09-9

XLa

XLb

XLc

XLd

XLe

-continued

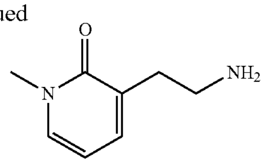

XL

Step-1: (E)-2-methoxy-3-(2-nitrovinyl) pyridine (XLa)

To a stirred solution of 2-methoxynicotinaldehyde (CAS: 71255-09-9, 5.50 g, 40.1 mmol) in toluene (60 mL) were added ammonium acetate (4.64 g, 60.2 mmol) and nitromethane (32.4 mL, 602 mmol). The reaction was stirred at 110° C. for 2 h and progress of the reaction was monitored by TLC analysis. After completion, the reaction mixture was cooled to room temperature and diluted with water (100 mL) and the resulting mixture was extracted with ethyl acetate (200 mL×3). The combined organic layer was dried over anhydrous sodium sulphate and concentrated under reduced pressure. The crude was purified by flash silica gel column chromatography using 0-10% ethyl acetate in n-hexane to afford the compound as a yellow solid. Yield: 4.5 g (62%). LCMS Calculated. for $C_8H_8N_2O_3$ is 180.05, Observed. 181.25 $[M+H]^+$. $^1$H NMR (400 MHz, $CDCl_3$): δ 8.28-8.26 (m, 1H), 8.02-7.92 (m, 2H), 7.76-7.73 (m, 1H), 7.02-6.99 (m, 1H). 4.10 (s, 3H).

Step-2: 2-(2-Methoxypyridin-3-yl) ethan-1-amine (XLb)

To a stirred solution of (E)-2-methoxy-3-(2-nitrovinyl) pyridine XLa (8.5 g, 47 mmol) in diethyl ether (170 mL) at 0° C. was dropwise added $LiAlH_4$ (141 mL, 1 M in THF, 140 mmol) under inert atmosphere over 20 min. The reaction was stirred at rt for 2 h and progress of the reaction was monitored by TLC analysis. After completion, the reaction was quenched with water (17 mL) followed by with 15% NaOH solution (8.5 mL) and ethyl acetate (200 mL). The mixture was diluted with ethyl acetate (300 mL) and stirred for 20 min. The white precipitate formed was filtered and washed thoroughly with fresh ethyl acetate (300 mL×3). The combined organic layer was dried over in sodium sulphate and concentrated under vacuum to afford the compound XLb as brown liquid. Yield: 6.5 g (92%). $^1$HNMR (400 MHz, $CDCl_3$): δ 8.04-8.03 (m, 1H), 7.41-7.39 (m, 1H), 6.83-6.80 (m, 1H), 3.97-3.94 (m, 5H), 2.95-2.92 (m, 2H), 2.73-2.69 (m, 2H).

Step-3: 2-(2-(2-methoxypyridin-3-yl) ethyl) isoindoline-1,3-dione (XLc)

To a stirred solution of 2-(2-(2-methoxypyridin-3-yl) ethan-1-amine XLb (5.2 g, 34 mmol) in acetic acid (60 mL) was added isobenzofuran-1,3-dione (5.1 g, 34 mmol) at room temperature. The resulting reaction mixture was refluxed with vigorous stirring for 3 h. The progress of the reaction was monitored by TLC analysis. After completion, reaction mixture was concentrated under vacuum. The residue was dissolved in acetic anhydride (19 mL, 20 mmol) refluxed with vigorous stirring for 16 h. The progress of the reaction was monitored by TLC analysis. After completion, the reaction was cooled to room temperature and quenched with saturated $NaHCO_3$ solution (200 mL). The mixture was extracted with DCM (300 mL×3) and combined organic layer was dried over anhydrous $Na_2SO_4$. The solvent was removed under reduced pressure to afford the crude compound which was subjected to combi flash column chromatography using 0-20% ethyl acetate in n-hexane to afford the desired product XLc as a yellow solid. Yield: 5.0 g (52%). LCMS Calculated. for $C_{16}H_{14}N_2O_3$ is 282.10; Observed. 283.25 $[M+H]^+$.

Step-4: 2-(2-(2-oxo-1,2-dihydropyridin-3-yl) ethyl) isoindoline-1,3-dione (XLd)

To a stirred solution of 2-(2-(2-methoxypyridin-3-yl) ethyl) isoindoline-1,3-dione XLc (2.5 g, 8.9 mmol) in chloroform (50 mL) was added TMS-I (6.0 mL, 44 mmol) at room temperature under inert atmosphere. The reaction mixture was stirred at 85° C. for 16 h and progress of the reaction was monitored by TLC analysis. After completion, the reaction mixture was quenched by adding methanol (5 mL) and concentrated the reaction mixture. The crude was triturated with ethanol/MTBE (1:3). The solid formed was collected by filtration and dried under vacuum to afford the desired compound XLd as a yellow solid. Yield: 1.9 g (79%). LCMS Calculated. for $C_{15}H_{12}N_2O_3$ is 268.08; Observed. 269.05 $[M+H]^+$. $^1$H NMR (400 MHz, $CDCl_3$): δ 7.95 (d, J=6.4 Hz, 1H), 7.80 (t, J=3.2 Hz, 2H) 7.71-7.69 (m, 3H), 6.67 (bs, 1H), 4.04 (bs, 2H), 3.06 (bs, 2H).

Step-5: 2-(2-(1-methyl-2-oxo-1,2-dihydropyridin-3-yl) ethyl) isoindoline-1,3-dione (XLe)

To a stirred solution of 2-(2-(2-oxo-1,2-dihydropyridin-3-yl) ethyl) isoindoline-1,3-dione XLd (700 mg, 5.69 mmol) in dimethoxymethane (14 mL) was added $K_2CO_3$ (1.57 g, 11.4 mmol) followed by an addition of iodomethane (0.7 ml, 11.4 mmol). The resulting reaction mixture was stirred at 90° C. for 24 h under nitrogen atmosphere. The progress of the reaction was monitored by TLC analysis. After completion, the reaction was cooled to room temperature and solid was filtered off. The filtrate was concentrated under vacuum and the residue was purified by combi flash silica gel (230-400) column chromatography using 0-20% ethyl acetate in n-hexane to afford the desired product XLe as a yellow solid. Yield: 0.58 g (74%). LCMS Calculated. for $C_{16}H_{14}N_2O_3$ is 282.10; Observed. 283.25 $[M^++1]$. $^1$HNMR (400 MHz, $CDCl_3$): δ 7.82-7.80 (m, 2H), 7.71-7.68 (m, 2H), 7.19-7.17 (m, 1H), 7.11-7.10 (m, 1H), 5.99 (t, J=6.8 Hz, 1H), 4.01 (t, J=6.8 Hz, 2H), 3.55 (s, 3H), 2.92 (t, J=6.4 Hz, 2H).

Step-6: 3-(2-aminoethyl)-1-methylpyridin-2(1H)-one (XL)

To a stirred solution of 2-(2-(1-methyl-2-oxo-1,2-dihydropyridin-3-yl) ethyl) isoindoline-1,3-dione XLe (580 mg, 2.05 mmol) in methanol (5 mL) was added hydrazine hydrate (0.015 mL, 3.08 mmol). The reaction was stirred at rt for 2 h under nitrogen atmosphere. The progress of the reaction was monitored by TLC analysis. After completion, reaction mixture was concentrated under vacuum. Then crude was diluted with water (2 mL) and acidified with conc. HCl (pH=2). The solid formed was filtered and washed with water (2 mL). The aqueous layer was basified with 1N NaOH solution and extracted with 10% methanol in DCM (100 mL×3). The combined organic layer was dried over sodium sulphate and concentrated under vacuum to afford the desired title compound XL as a pale-yellow viscous liquid. The crude was taken for next step without further purification. Yield: 0.3 g (95%). LC_MS Calculated. for $C_8H_{12}N_2O$ is 152.09; Observed. 153.00 $[M+H]^+$.

Synthesis of 3-(2-aminoethyl)-1-ethylpyridin-2(1H)-one XLI

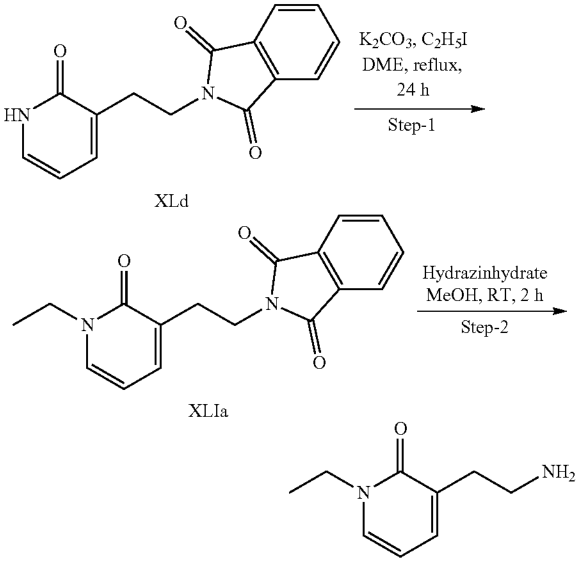

XLd

XLIa

XLI

Step-1: Synthesis of 2-(2-(1-ethyl-2-oxo-1,2-dihydropyridin-3-yl) ethyl) isoindoline-1,3-dione (XLIa)

To a solution of (2-(2-oxo-1,2-dihydropyridin-3-yl) ethyl) isoindoline-1,3-dione XLd (0.6 g, 2.24 mmol) in dimethoxy ethane (3 mL) was added $K_2CO_3$ (0.62 g, 4.47 mmol) and iodoethane (0.7 g, 4.47 mmol). The reaction mixture was stirred at 90° C. for 24 h. The progress of the reaction was monitored by TLC analysis. After the completion of the reaction, reaction mixture was filtered and concentrated under reduced pressure. The crude compound was purified by silica gel (230-400 mesh) column chromatography with ethyl acetate in hexane (0-50%) to get the desired compound XLIa as a yellow solid. Yield: 0.6 g, (90.0%); LC_MS calculated for $C_{17}H_{16}N_2O_3$ is 296.12; Observed: 297.20 $[M+H]^+$.

Step-2: 3-(2-aminoethyl)-1-ethylpyridin-2(1H)-one (XLI)

To a solution of 2-(2-(1-ethyl-2-oxo-1,2-dihydropyridin-3-yl) ethyl) isoindoline-1,3-dione XLIa (0.6 g, 2.02 mmol) in methanol (6 mL) was added hydrazine hydrate (0.15 mL, 3.04 mmol) and the reaction mixture was stirred at rt for 2 h. The progress of the reaction was monitored by TLC analysis. After the completion of the reaction, the reaction mixture was concentrated and added water (2 mL), acidified with Conc. HCl to pH~2. Solids were filtered, basified by sodium hydroxide (5 mL) and extracted with ethyl acetate (50 mlx3). The combined organic layer was dried over anhydrous sodium sulphate and concentrated under reduced pressure to afford the crude compound XLI. The crude compound was taken for the next step without further purification. Yield: 0.3 g, (89.02%); LCMS Calculated. for $C_9H_{14}N_2O$ is 166.11; Observed. 167.30 $[M+H]^+$.

Synthesis of 7-amino-3-ethyl-5-(methyl sulfonyl) pyrazolo[1,5-a] pyrimidine-6-carbonitrile (XLII)

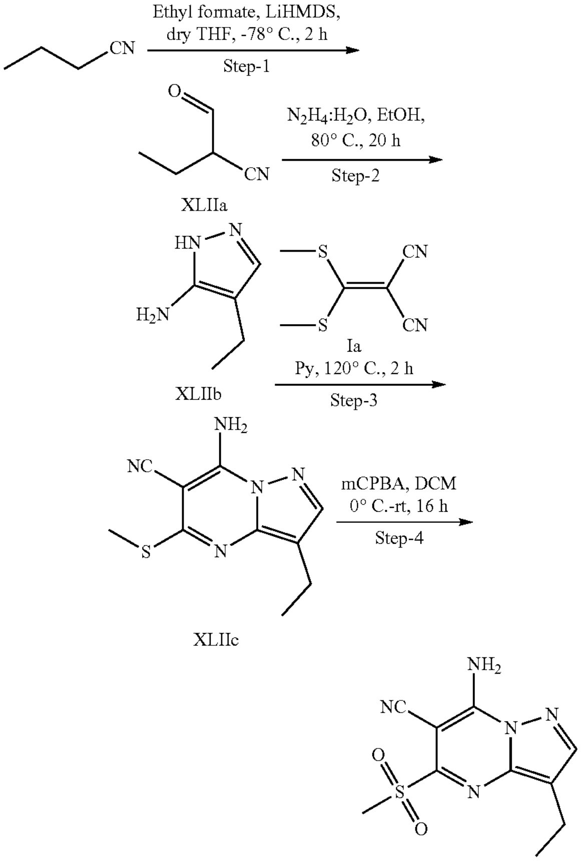

XLIIa

XLIIb

Ia

XLIIc

XLII

Step-1: 2-formylbutanenitrile (XLIIa)

To a solution of LiHMDS (20 g, 100 mmol) in THF (200 mL) at −78° C. was added butyronitrile (5 g, 70 mmol) and stirred at the same temperature for 1 h. This was followed by an addition of ethyl formate (6 mL, 70 mmol) and stirred for 1 h. The progress of the reaction was monitored by TLC analysis. After the completion of the reaction, the reaction mixture was quenched with saturated ammonium chloride (50 mL) and extracted with diethyl ether (200 mL*3). The combined organic layer was dried over anhydrous sodium sulphate, filtered and concentrated under reduced pressure to afford the crude compound XLIIa as a pale-yellow viscous liquid. The crude compound was directly taken for next step without any further purification. Yield:7.1 g, (89.0%); LCMS Calculated. for $C_5H_7NO$ is 97.05; Observed. 96.00 $[M+H]^+$.

Step-2: 4-Ethyl-1H-pyrazol-5-amine (XLIIb)

To a solution of 2-formylbutanenitrile XLIIa (7.9 g, 81 mmol) and hydrazine hydrate (1:1, 4.8 mL, 98 mmol) in ethanol (80 mL) was added acetic acid (1.6 mL, 28 mmol)

and stirred at 80° C. for 20 h. The progress of the reaction was monitored by TLC analysis. After the completion of the reaction, the reaction mixture was concentrated, added water (100 mL) and extracted with 0.5% methanol in dichloromethane (300 mL*3). The combined organic layer was dried over anhydrous sodium sulphate and concentrated under reduced pressure to get the crude compound. The crude compound was purified by silica gel (100-200 mesh) column chromatography with methanol in dichloromethane (0-2%) to afford the desired compound XLIIb as a pale-yellow viscous liquid. Yield: 5.0 g, (60.0%).

Step-3: 7-amino-3-ethyl-5-(methylthio) pyrazolo[1,5-a] pyrimidine-6-carbonitrile (XLIIc)

To a solution of 4-ethyl-1H-pyrazol-3-amine XLIIb (1 g, 9 mmol) in pyridine (10 mL) was added 2-(bis(methylthio) methylene) malononitrile Ia (2 g, 10 mmol) and stirred the reaction mixture at 120° C. for 2 h. The progress of the reaction was monitored by TLC analysis. After the completion of the reaction, the reaction mixture was poured into ice-cooled water and filtered the solid. The crude compound was purified by silica gel (100-200 mesh) column chromatography with ethyl acetate in n-hexane (0-10%) to afford the desired compound XLIIc as a brownish solid. Yield: 1.5 g, (70.0%); LCMS Calculated. for $C_{10}H_{11}N_5S$ is 233.07; Observed. 232.5 $[M+H]^+$ Step-4: 7-amino-3-ethyl-5-(methyl sulfonyl) pyrazolo[1,5-a] pyrimidine-6-carbonitrile (XLII)

To a solution of 7-amino-3-ethyl-5-(methylthio) pyrazolo [1,5-a] pyrimidine-6-carbonitrile (0.7 g, 3.00 mmol) in dichloromethane (20 mL) at 0° C. was added mCPBA (2.59 g, 15.0 mmol) and stirred at rt for 16 h. The progress of the reaction was monitored by TLC analysis. After the completion of the reaction, the reaction mixture was cooled to 0° C. and quenched with saturated sodium bicarbonate (5 mL) and extracted with ethyl acetate (30 mL×3). The combined organic layer was dried over anhydrous sodium sulphate and concentrated to get crude material. The crude compound was washed with pentane and stirred with methanol (2 mL) for 10 min. Solid was filtered and organic layer was concentrated to afford the desired compound XLII as an off-white solid. Yield:125 mg, (15.7%); LCMS Calculated. for $C_{10}H_{11}N_5O_2S$ is 265.06; Observed. 266.20 $[M+H]^+$.

Synthesis of (6-(2-aminoethyl)$_{164}$yridine-2-yl) methanol (XLIII)

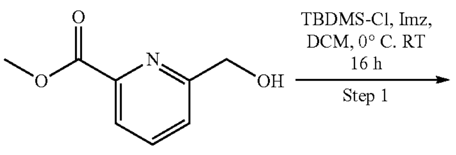

CAS: 39977-44-1

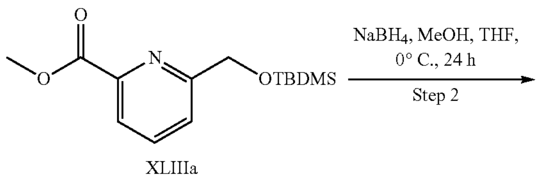

XLIIIa

-continued

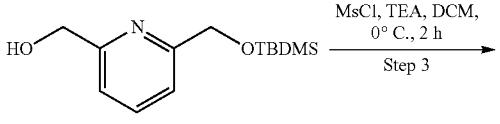

XLIIIb

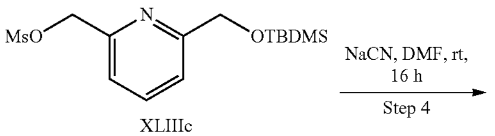

XLIIIc

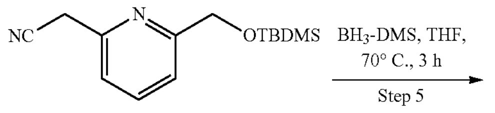

XLIIId

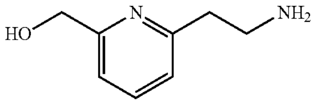

XLIII

Step-1: Methyl 6-(((tert-butyldimethylsilyl) oxy) methyl) picolinate (XLIIIa)

A stirred solution of methyl 6-(hydroxymethyl) picolinate (CAS: 39977-44-1, 25 g, 0.15 mol) in DCM (500 mL) at 0° C. under inert atmosphere was added imidazole (20 g, 0.30 mol) and the resulting mixture was stirred for 10 min. This was followed by a portion wise addition of TBDMS-Cl (45 g, 0.30 mol) and the was stirred at rt for 16 h. The progress of the reaction was monitored by TLC analysis. After completion, the reaction was quenched with water (500 mL) and the resulting mixture was extracted with ethyl acetate (500 mL×3). The combined organic layer was dried over anhydrous sodium sulphate and concentrated under reduced pressure to get crude compound. The crude compound was purified by silica gel (100-200) column chromatography using 0-10% ethyl acetate in n-hexane to afford the desired compound XLIIIa as an off-white solid. Yield: 33 g (78.0%); LCMS Calculated. $C_{14}H_{23}NO_3Si$ for is 281.14; Observed. 282.35 $[M+H]^+$. $^1H$ NMR (400 MHz, $CDCl_3$): 8.01 (d, J=7.6 Hz, 1H), 7.86 (t, J=8.0 Hz, 1H), 7.74 (d, J=8.0 Hz, 1H), 4.93 (s, 2H), 3.99 (s, 3H), 0.96 (s, 9H), 0.12 (s, 6H).

Step-2: (6-(((tert-butyldimethylsilyl) oxy) methyl) pyridin-2-yl) methanol (XLIIIb)

A stirred solution of methyl 6-(((tert-butyldimethylsilyl) oxy) methyl) picolinate XLIIIa (33 g, 0.12 mol) in THF: MeOH (525 mL; 2:1) was cooled to 0° C. and added $NaBH_4$ (13 g, 0.35 mol) in portions under inert atmosphere over 20 min maintaining reaction temperature below 5° C. The reaction mixture was stirred at rt for 16 h and the progress of the reaction was monitored by TLC analysis. After completion, the reaction mixture was concentrated under reduced pressure and to the residue was added sat. $NaHCO_3$ solution (300 mL). The mixture was extracted with DCM (300 mL×3) and combined organic layer was dried over anhydrous sodium sulphate. The solution was filtered and concentrated under reduced pressure. The crude compound was purified by silica gel (100-200) column chromatography using 10-20% ethyl acetate in n-hexane to afford the desired compound XLIIIb as a colorless viscous liquid. Yield: 29 g (99.0%); LCMS Calculated. $C_{13}H_{23}NO_2Si$ for is 253.15; Observed. 254.30 $[M+H]^+$. $^1H$ NMR (400 MHz, $CDCl_3$): 7.70 (t, J=7.6 Hz, 1H), 7.40 (d, J=8.0 Hz, 1H), 7.08 (d, J=8.0 Hz, 1H), 4.33 (s, 2H), 4.73 (d, J=4.8 Hz, 2H), 3.78 (t, J=4.8 Hz, 1H), 0.96 (s, 9H), 0.13 (s, 6H).

Step-3: (6-(((tert-butyldimethylsilyl) oxy) methyl) pyridin-2-yl) methyl methane sulfonate (XLIIIc)

A stirred solution of (6-(((tert-butyldimethylsilyl) oxy) methyl) pyridin-2-yl) methanol XLIIIb (29 g, 0.11 mol) and TEA (24 mL, 0.17 mol) in DCM (300 mL) was cooled to 0° C. under inert atmosphere. To the resulting mixture was dropwise added mesyl-Cl (11 mL, 1.2 Eq, 0.14 mol) over 30 min and the reaction mixture was stirred at 0° C. for 2 h. The progress of the reaction was monitored by TLC analysis. After completion, reaction mixture was quenched with sat. $NaHCO_3$ solution (300 mL) and extracted with DCM (300 mL×3). The combined organic layer was dried over anhydrous sodium sulphate and concentrated over reduced pressure to afford the desired compound XLIIIc as a pale-yellow solid. Yield: 40 g (100%); LCMS Calculated. $C_{14}H_{25}NO_4SSi$ for is 331.13; Observed. 332.30 $[M+H]^+$.

Step-4: 2-(6-(((tert-butyldimethylsilyl) oxy) methyl) pyridin-2-yl) acetonitrile (XLIIId)

To a stirred solution of (6-(((tert-butyldimethylsilyl) oxy) methyl) pyridin-2-yl) methyl methane sulfonate XLIIIc (40 g, 120 mmol) in DMF (300 mL) was added NaCN (6.49 g, 132 mmol) and the reaction mixture was stirred at rt for 16 h. The progress of the reaction was monitored by TLC analysis. After completion, the reaction was quenched with water (500 mL) and the resulting mixture was extracted with ethyl acetate (500 mL×3). The combined organic layer was dried over anhydrous sodium sulphate and concentrated under reduced pressure. The crude was purified by silica gel column chromatography using 0-15% ethyl acetate in n-hexane to afford the desired compound XLIIId as a yellow viscous liquid. Yield: 21 g (66.7%); $^1H$ NMR (400 MHz, $CDCl_3$): 7.75 (t, J=8.0 Hz, 1H), 7.48 (d, J=7.6 Hz, 1H), 7.29 (d, J=7.6 Hz, 1H), 4.80 (s, 2H), 3.89 (s, 2H), 0.96 (s, 9H), 0.12 (s, 6H).

Step-5: Synthesis of (6-(2-aminoethyl) pyridin-2-yl) methanol (XLIII)

To a stirred solution of 2-(6-(((tert-butyldimethylsilyl) oxy) methyl) pyridin-2-yl) acetonitrile (21 g, 80 mmol) in dry THF (250 mL) at 0° C. was added $BH_3$. DMS (28.8 mL, 320 mmol) and the reaction mixture was stirred at 70° C. for 3 h. The progress of the reaction was monitored by TLC analysis. After completion, the reaction mixture was cooled to 0° C. and the reaction was quenched with MeOH (15 mL), and stirred for 30 min. Then added water (20 mL) and 1 M HCl solution (15 mL) and the resulting mixture was extracted with ethyl acetate (50 mL) followed by with DCM (50 mL) to get rid of the impurities. The aqueous layer was basified with 2N NaOH solution and extracted with DCM (500 mL×3). The combined organic layer was dried over anhydrous sodium sulphate and concentrated to afford the desired compound XLIII as a brown viscous liquid. Yield: 9.8 g (81%); LCMS Calculated. $C_8H_{12}N_2O$ for is 152.09; Observed. 153.00 $[M+H]^+$. $^1H$ NMR (400 MHz, $CDCl_3$): 7.61 (t, J=7.6 Hz, 1H), 7.51 (d, J=7.6 Hz, 2H), 4.73 (s, 2H), 3.11 (q, J=6.4 Hz, 2H), 2.92 (q, J=6.4 Hz, 2H).

Synthesis of (1-(4-(2-aminoethyl)-1H-pyrazol-1-yl) cyclopropyl) methanol. (XLIV)

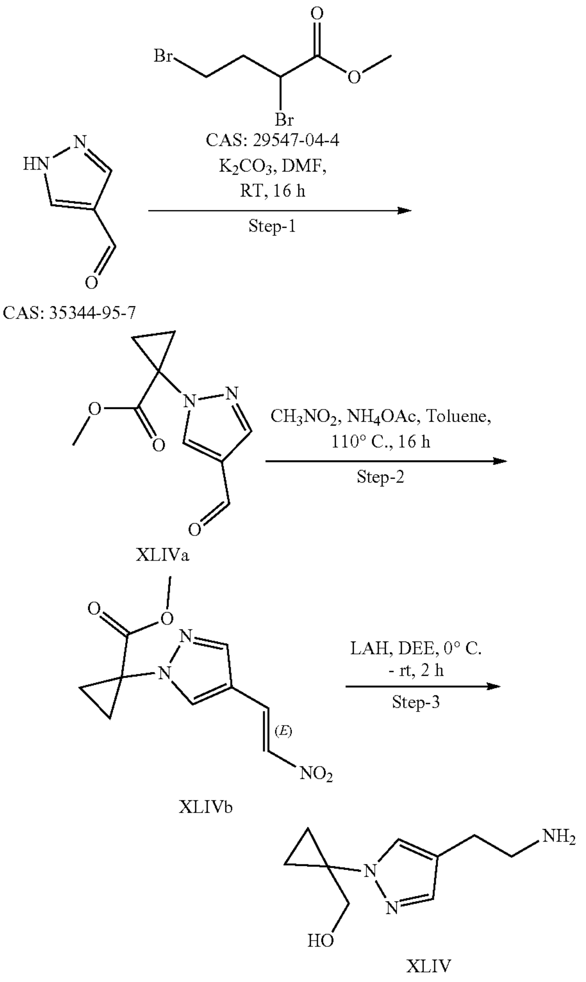

Step-1: Methyl 1-(4-formyl-1H-pyrazol-1-yl) cyclopropane-1-carboxylate (XLIVa)

To a stirred solution of 1H-pyrazole-4-carbaldehyde (CAS: 35344-95-7; 600 mg, 6.24 mmol) in DMF (3 mL) was added $K_2CO_3$ (3.45 g, 25.0 mmol) at room temperature under inert atmosphere. The reaction mixture was cooled to 0° C. and added methyl 2,4-dibromobutanoate (CAS: 29547-04-4, 2.11 g, 8.12 mmol). The reaction was stirred at rt for 16 h. Progress of the reaction was monitored by TLC analysis. After completion, the reaction mixture was diluted with water (100 mL) and extracted with ethyl acetate (100 mL×3). The combined organic layer was dried over anhydrous $Na_2SO_4$, filtered, and concentrated under reduced pressure. The crude was purified by combi flash silica (230-400) column chromatography by using 0-20% ethyl acetate in n-hexane to afford the desired product XLIVa as a yellow liquid. Yield: 0.9 g (75%). LCMS Calculated. for: $C_9H_{10}N_2O_3$ is 194.06; Observed. 195.20 $[M+H]^+$. $^1H$ NMR (400 MHz, $CDCl_3$): δ 9.88 (s, 1H), 8.06-8.01 (m, 1H), 7.98 (s, 1H), 3.71 (s, 3H) 1.92-1.89 (m, 2H), 1.70-1.67 (m, 2H).

Step-2: Methyl (E)-1-(4-(2-nitrovinyl)-1H-pyrazol-1-yl) cyclopropane-1-carboxylate (XLIVb)

To a stirred solution of methyl 1-(4-formyl-1H-pyrazol-1-yl) cyclopropane-1-carboxylate XLIVa (800 mg, 4.12 mmol) in toluene (16 mL) were added ammonium acetate (476 mg, 6.18 mmol) and nitromethane (3.77 g, 61.8 mmol) at room temperature. The reaction mixture was stirred at 110° C. for 16 h. The progress of the reaction was monitored by TLC analysis. After completion, the reaction mixture was diluted with 1N HCl (20 mL) and extracted with ethyl acetate (100 mL×3). The combined organic layer was dried over anhydrous sodium sulphate and concentrated under reduced pressure. The crude was purified by flash chromatography (silica gel 230-400 mess) using 0-25% ethyl acetate in n-hexane to afford the compound XLIVb as yellow solid. Yield: 0.6 g (62%). LCMS Calculated. for $C_{10}H_{11}N_3O_4$ is 237.07; Observed. 238.20 $[M+H]^+$; $^1H$ NMR (400 MHz, $CDCl_3$): δ 7.92 (d, J=13.6 Hz, 1H), 7.83 (s, 1H), 7.77 (s, 1H), 7.44 (d, 13.2 Hz, 1H), 3.71 (s, 3H) 1.92-1.88 (m, 2H), 1.68-1.58 (m, 2H).

Step-3: (1-(4-(2-aminoethyl)-1H-pyrazol-1-yl) cyclopropyl) methanol (XLIV)

A solution $LiAlH_4$ (15 mL, 1M in THF, 0.02 mol) in DEE (20 mL) was cooled to 0° C. and dropwise added a solution of methyl(E)-1-(4-(2-nitrovinyl)-1H-pyrazol-1-yl) cyclopropane-1-carboxylate XLIVb (0.9 g, 4 mmol) in THF (5 mL). The reaction mixture was stirred at rt for 2 h. The progress of the reaction was monitored by TLC analysis. After completion, the reaction mixture was cooled to 0° C., quenched with water (3 mL), 15% NaOH solution (1 mL) and ethyl acetate (30 mL). The mixture was stirred at RT for 30 min and filtered and the residue was washed with fresh ethyl acetate (50 mL×3). The combined organic layer was dried over anhydrous sodium sulphate and concentrated under reduced pressure to afford the desired compound XLIV as a brown liquid. The crude was taken for next step without further purification. Yield: 0.6 g (75%).

Synthesis of (1-(3-(2-aminoethyl)-5-methyl-1H-pyrazol-1-yl) cyclopropyl) methanol. XLV

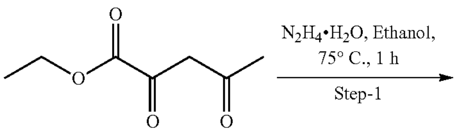

CAS:615-79-2

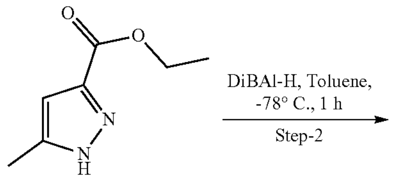

XLVa

-continued

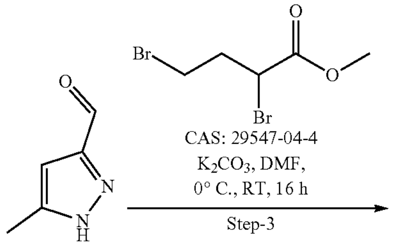

XLVb

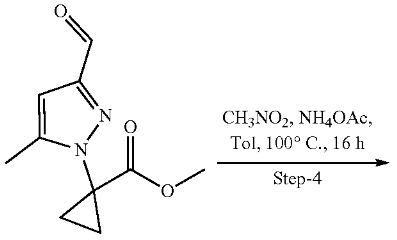

XLVc

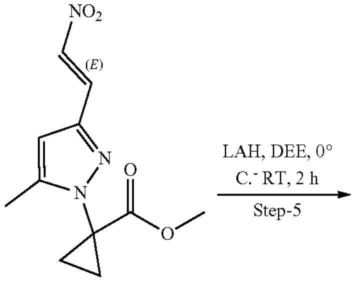

XLVd

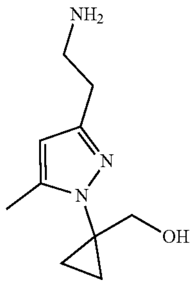

XLV

Step-1: Ethyl 5-methyl-1H-pyrazole-3-carboxylate (XLVa)

A solution of ethyl 2,4-dioxopentanoate (CAS: 615-79-2, 5 g, 0.03 mol) in ethanol (4 mL) was cooled to 0° C. and hydrazine hydrate (2 mL, 0.03 mol, 1:1) was added dropwise at 0° C. under inert atmosphere. The reaction mixture was refluxed for 1 h. The progress of the reaction was monitored by TLC analysis. After completion, the reaction mixture was concentrated under reduced pressure and the residue was dissolved in water (50 mL). The mixture was extracted with ethyl acetate (50 mL×3) and the combined organic layer was given brine wash, dried over anhydrous sodium sulphate. The solution was concentrated under reduced pressure to obtain the desired product as a pale-yellow solid. The crude was taken for the next step without further purification. Yield: 3.7 g (72%). LCMS Calculated. for $C_7H_{10}N_2O_2$ is 154.07; Observed. 155.05 [M+H]+; $^1$H NMR (400 MHz, $CDCl_3$): δ 6.60 (s, 1H), 4.38 (q, J=6.8 Hz, 2H), 2.36 (s, 3H), 1.38 (t, J=6.8 Hz, 3H).

Step-2: 5-methyl-1H-pyrazole-3-carbaldehyde (XLVb)

A solution of ethyl 5-methyl-1H-pyrazole-3-carboxylate XLVa (3.6 g, 23 mmol) in dry toluene (54 mL) was cooled to −78° C. under inert atmosphere and DIBAL-H (31 mL, 1.5 molar, 47 mmol) was added dropwise at −78° C. The reaction mixture was stirred at −78° C. for 1 h and the progress of the reaction was monitored by TLC analysis. After completion, the reaction was quenched with water (10 mL) and methanol (2 mL) at −78° C. The mixture was stirred at rt for 10-15 min and ethyl acetate (30 mL) was added. The mixture was filtered through celite bed and washed with ethyl acetate thoroughly. The combined organic layer was separated, washed brine solution, and dried over anhydrous sodium sulphate. The solution was concentrated under reduced pressure to afford the desired compound XLVb as a pale-yellow solid. The crude product was taken for the next step without further purification. Yield: 1.3 g (50%

Step-3: Methyl 1-(3-formyl-5-methyl-1H-pyrazol-1-yl) cyclopropane-1-carboxylate (XLVc)

A solution of 5-methyl-1H-pyrazole-3-carbaldehyde XLVb (1.3 g, 12 mmol) in DMF (11 mL) was cooled to 0° C. and portion wise added $K_2CO_3$ (6.5 g, 47 mmol). This was followed by a dropwise addition of methyl 2,4-dibromobutanoate (2.2 mL, 15 mmol) and the reaction mixture was stirred at room temperature for 16 h. The progress of reaction was monitored by TLC analysis. After completion, cold water (50 mL) was added and extracted with ethyl acetate (50 mL×3). The combined organic layer was given brine wash, dried over anhydrous sodium sulphate, and concentrated to get crude material. The crude material was purified by Combi-flash chromatography (mesh 230-400 silica gel) column chromatography using 0-10% ethyl acetate in n-hexane to afford the desired compound XLVc as an off-white solid. Yield: 0.47 g, (18.7%). LCMS Calculated. for $C_{10}H_{12}N_2O_3$ is 208.08; Observed. 209.10 [M+H]+; $^1$H NMR (400 MHz, $CDCl_3$): δ 6.90 (s, 1H), 6.56 (s, 1H), 3.72 (s, 3H), 2.32 (s, 3H), 1.96 (s, 2H), 1.72 (s, 2H).

Step-4: Methyl (E)-1-(5-methyl-3-(2-nitrovinyl)-1H-pyrazol-1-yl) cyclopropane-1-carboxylate (XLVd)

To a solution of methyl 1-(3-formyl-5-methyl-1H-pyrazol-1-yl) cyclopropane-1-carboxylate XLVc (480 mg, 2.31 mmol) in toluene (20 mL) were added ammonium acetate (267 mg, 3.46 mmol) and nitromethane (1.24 mL, 23.1 mmol) under inert atmosphere. The reaction mixture was stirred at 100° C. for 16 h and the progress of the was monitored by TLC analysis. After completion, the reaction was quenched by dropwise addition of 1N HCl solution (20 mL) and the resulting mixture was extracted with ethyl acetate (20 mL×3). The combined organic phase was washed with 1N HCl solution (20 mL), followed by with brine. The organic layer was dried over anhydrous sodium sulphate and concentrated under reduced pressure. The crude material was purified by Combi-flash chromatography silica gel (mesh 230-400) column chromatography using 0-10% ethyl acetate in n-hexane to afford the desired product XLVd as an off-white solid. Yield: (0.383 g, 66.14%); LCMS Calculated. for $C_{11}H_{13}N_3O_4$ is 251.09; Observed. 252.20 [M+H]+; $^1$H NMR (400 MHz, $CDCl_3$): δ 7.90 (d, J=13.2 Hz, 1H), 7.55 (d, J=14.0 Hz, 1H), 6.32 (s, 1H), 3.71 (s, 3H), 2.31 (s, 3H), 1.94 (s, 2H), 1.69 (s, 2H).

Step-5: (1-(3-(2-Aminoethyl)-5-methyl-1H-pyrazol-1-yl) cyclopropyl) methanol (XLV)

A solution of $LiAlH_4$ (6.05 mL, 1 M in THF, 6.05 mmol) in dry diethyl ether (20 mL) was cooled to 0° C. and solution of methyl (E)-1-(5-methyl-3-(2-nitrovinyl)-1H-pyrazol-1-yl) cyclopropane-1-carboxylate XLVd (380 mg, 1.51 mmol) in THF (5 mL) was added dropwise. The reaction mixture was stirred at room temperature for 2 h and the progress of the reaction was monitored by TLC analysis. After completion, the reaction was cooled to 0° C. and water (0.4 mL) was added slowly. This was followed by slow addition of 15% KOH solution (0.4 mL) and water (1.2 mL). The mixture was stirred at rt for 10 minutes, ethyl acetate (50 mL) was added and stirring at rt was continued for additional 15 minutes. The mixture was passed through a celite bed and washed thoroughly with fresh ethyl acetate. The combined organic layer was dried over anhydrous sodium sulphate and concentrated to get desired product XLV as pale-yellow oil. The compound was used as such for the next step without further purification. Yield: 0.370 g (crude).

Synthesis of 3-((3-(2-aminoethyl)-1H-pyrazol-1-yl) methyl) cyclobutan-1-one. (XLVI)

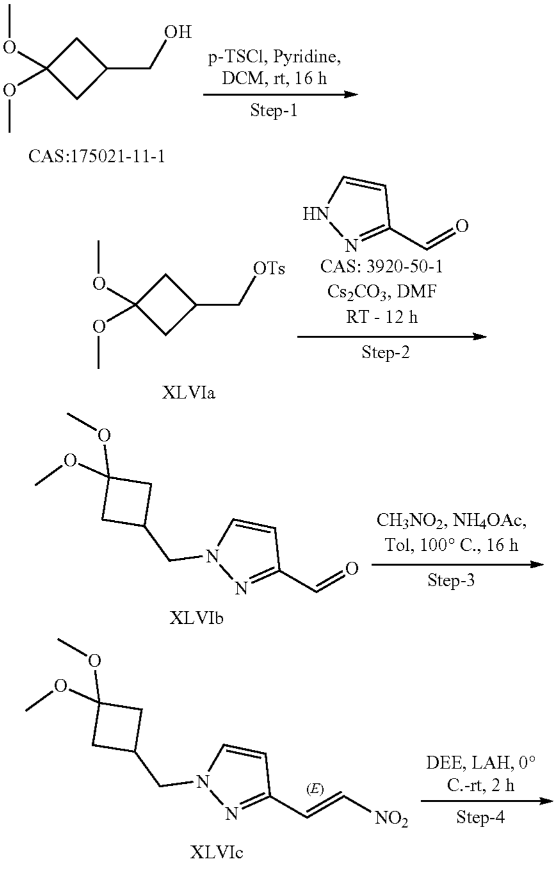

CAS:175021-11-1

XLVIa

XLVIb

XLVIc

-continued

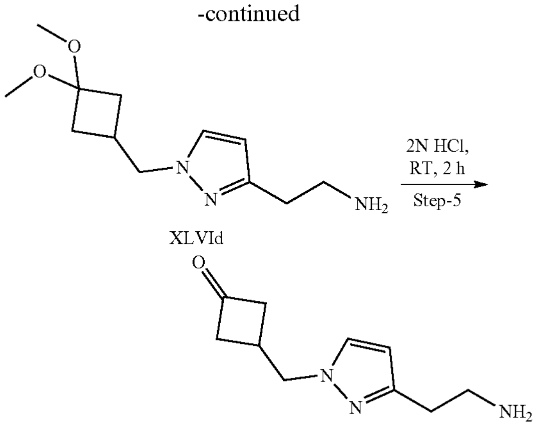

XLVId

XLVI

Step-1: (3,3-dimethoxycyclobutyl) methyl 4-methylbenzenesulfonate (XLVIa)

To a stirred solution of (3,3-dimethoxycyclobutyl) methanol (CAS:175021-11-1, 5.0 g, 34 mmol) in DCM (100 mL) was added pyridine (8.3 mL, 1.00 mmol) and the reaction mixture was cooled to 0° C. pTSCl (7.2 g, 38 mmol) was added in portions under nitrogen atmosphere. The resulting mixture was stirred at rt for 16 h. The progress of the reaction was monitored by TLC analysis. After completion, reaction mixture was diluted with saturated $NaHCO_3$ solution (100 mL) and extracted with DCM (100 mL×3). Combined organic layer was dried over anhydrous $Na_2SO_4$, filtered and concentrated under reduced pressure. The crude compound was purified by combi-flash column chromatography (230-400 silica) using 0-15% ethyl acetate in n-hexane to afford the desired compound XLVIa as a colorless liquid. Yield: 8.2 g, (82%); $^1H$ NMR (400 MHz, $CDCl_3$): δ 7.79 (d, J=8.4 Hz, 2H), 7.34 (d, J=8.4 Hz, 2H) 4.03 (d, J=7.2 Hz, 2H), 3.11 (s, 3H), 3.06 (s, 3H), 2.45 (s, 3H), 2.39-2.36 (m, 1H), 2.27-2.23 (m, 2H), 1.83-1.78 (m, 2H).

Step-2: 1-((3,3-dimethoxycyclobutyl) methyl)-1H-pyrazole-3-carbaldehyde (XLVIb)

To a stirred solution of 1H-pyrazole-3-carbaldehyde (CAS: CAS: 3920-50-1, 2.4 g, 25 mmol) in DMF (20 mL) was added cesium carbonate (16 g, 50 mmol) and the reaction mixture was cooled to 0° C. (3,3-dimethoxycyclobutyl) methyl 4-methylbenzenesulfonate XLVIa (8.3 g, 27 mmol) was added slowly under nitrogen atmosphere. The resulting reaction mixture was stirred at rt for 12 h. Progress of the reaction was monitored by TLC analysis. After completion, the reaction mixture was diluted with water (100 mL) and extracted with ethyl acetate (200 mL×3). The combined organic layer was dried over anhydrous $Na_2SO_4$, filtered and concentrated under reduced pressure. The crude compound was purified by combi-flash column chromatography using 0-15% ethyl acetate in n-hexane to afford the desired compound XLVIb as a pale-yellow viscous liquid. Yield: 4.4 g, (78%); Chemical Formula: $C_{11}H_{16}N_2O_3$, $^1H$ NMR (400 MHz, $CDCl_3$): δ 9.96 (s, 1H), 7.42 (d, J=2.0 Hz, 1H), 6.80 (d, J=2.0 Hz, 1H) 4.29 (d, J=7.6 Hz, 2H), 3.13 (s, 6H), 2.70-2.45 (m, 1H), 2.34-2.32 (m, 2H), 1.96-1.91 (m, 2H).

Step-3: (E)-1-((3,3-dimethoxycyclobutyl) methyl)-3-(2-nitrovinyl)-1H-pyrazole (XLVIc)

To a stirred solution of 1-((3,3-dimethoxycyclobutyl) methyl)-1H-pyrazole-3-carbaldehyde XLVIb (4.4 g, 20 mmol) in toluene (50 mL) was added nitromethane (16 mL, 290 mmol) followed by an addition of ammonium acetate (2.3 g, 29 mmol). The resulting mixture was stirred at 100° C. for 16 h. The progress of the reaction was monitored by TLC analysis. After completion, reaction mixture was cooled rt, diluted with 1N HCl (50 mL) and extracted with ethyl acetate (100 mL×3). The combined organic layer was dried over anhydrous $Na_2SO_4$, filtered and concentrated under reduced pressure. The crude compound was purified by combi-flash column chromatography using 0-10% ethyl acetate in n-hexane to afford the desired compound XLVIc as a pale-yellow solid. Yield: 3.3 g, (63%).

Step-4: 2-(1-((3,3-dimethoxycyclobutyl) methyl)-1H-pyrazol-3-yl) ethan-1-amine (XLVId)

A stirred solution of $LiAlH_4$ (49 mL, 1 molar in THF, 49 mmol) in diethyl ether (100 mL) was cooled to 0° C. and drop wise added a solution of (E)-1-((3,3-dimethoxycyclobutyl) methyl)-3-(2-nitrovinyl)-1H-pyrazole XLVIc (3.3 g, 12 mmol) under inert atmosphere. The resulting mixture was stirred at rt for 2 h. The progress of the reaction was monitored by TLC analysis. After completion, the reaction mixture was cooled to 0° C. and quenched with slowly addition of water (3.3 mL), 15% KOH solution (3.3 mL) and again added (10 mL) of water. The resulting reaction mixture was stirred at rt for 20 min and ethyl acetate (100 mL) was added. The mixture was filtered, and the residue was washed fresh ethyl acetate (100 mL×3). The combined organic layer was dried over anhydrous $Na_2SO_4$, filtered, and concentrated under reduced pressure. The crude product XLVId was directly taken for next step without purification. Yield: 2.4 g, (crude); LCMS Calculated. for $C_{12}H_{21}N_3O_2$ is 239.32; Observed. 240.35 $[M+H]^+$.

Step-5: 3-((3-(2-aminoethyl)-1H-pyrazol-1-yl) methyl) cyclobutan-1-one (XLVI)

To a stirred solution of 2-(1-((3,3-dimethoxycyclobutyl) methyl)-1H-pyrazol-3-yl) ethan-1-amine XLVId (2.6 g, 11 mmol) in ethanol (50 mL) was a slowly added 2N HCl (3 mL) at 0° C. under nitrogen atmosphere. The reaction was stirred at rt for 2 h and progress of the reaction was monitored by TLC analysis. After completion, the reaction mixture was concentrated under vacuum. The crude product XLVI was taken directly forward to next step without further purification. Yield:2.4 g crude Synthesis of 2-(3-(2-aminoethyl)-1H-pyrazol-1-yl) propan-1-ol. (XLVII)

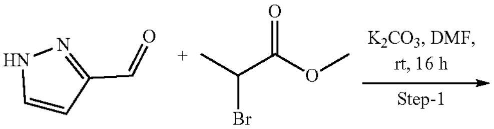

CAS: 3920-50-1

CAS: 5445-17-0

-continued

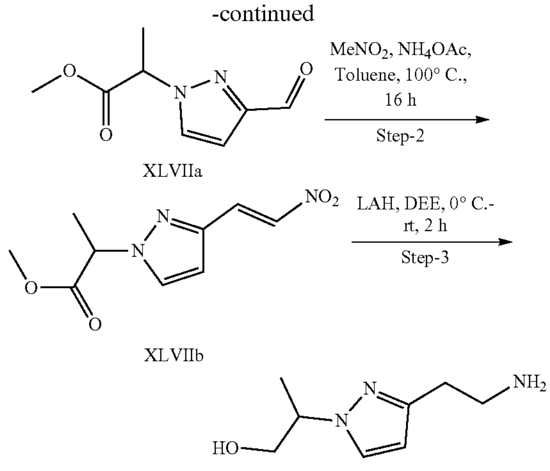

XLVIIa

XLVIIb

XLVII

Step-1: Methyl 2-(3-formyl-1H-pyrazol-1-yl) propanoate (XLVIIa)

To a solution of 1H-pyrazole-3-carbaldehyde (CAS: 3920-50-1, 3.0 g, 31 mmol) in DMF (30 mL) was added $K_2CO_3$ (17 g, 0.12 mol) and the solution was cooled to 0° C. under inert atmosphere. Then methyl 2-bromopropanoate (CAS: 5445-17-0, 5.2 mL, 47 mmol) was added dropwise and the reaction mixture was stirred at room temperature for 16 h. The progress of the reaction was monitored by TLC analysis. After completion, the reaction was quenched with cold water (50 mL) and extracted with ethyl acetate (100 mL×3). The combined organic phase was washed with brine and dried over anhydrous sodium sulphate. The solution was concentrated under reduced pressure and the crude material was purified by combi-flash silica gel (230-400) column chromatography using 0-10% ethyl acetate in n-hexane to afford the desired compound XLVIIa as a colorless oil. Yield: 0.70 g, (13.0%); LCMS Calculated. for $C_8H_{10}N_2O_3$ is 182.06; Observed. 183.25 $[M+H]^+$. $^1H$ NMR (400 MHz, $CDCl_3$): δ 9.98 (s, 1H), 7.59 (s, 1H), 6.86 (s, 1H), 5.19 (q, J=7.2 Hz, 1H), 3.78 (s, 3H), 1.86 (d, J=6.8 Hz, 3H).

Step-2: methyl (E)-2-(3-(2-nitrovinyl)-1H-pyrazol-1-yl) propanoate (XLVIIb)

To a solution of methyl 2-(3-formyl-1H-pyrazol-1-yl) propanoate XLVIIa (700 mg, 3.84 mmol) was dissolved in toluene (20 mL) under inert atmosphere were added ammonium acetate (444 mg, 5.76 mmol) and nitromethane (2.07 mL, 38.4 mmol), and the resulting mixture was mixture was stirred at 100° C. for 16 h. The progress of the reaction was monitored by TLC analysis. After completion, the reaction mixture was cooled to rt and quenched with 1N HCl solution (25 mL). The organic phase was separated, and the aqueous phase was extracted with ethyl acetate (100 mL×3). The combined organic layer was washed with brine, dried over anhydrous sodium sulphate, filtered, and concentrated under reduced pressure. The crude material was purified by combi-flash silica gel (230-4000 column chromatography using 0-20% ethyl acetate in n-hexane to afford the desired compound XLVIIb as pale-yellow oil. Yield: 560 mg, (65.7%); LCMS Calculated. for $C_9H_{11}N_3O_4$ is 225.07; Observed. 226.15 $[M+H]^+$. $^1H$ NMR (400 MHz, $CDCl_3$): δ 7.97 (d, J=13.6 Hz, 1H), δ 7.61, (d, J=14.0 Hz, 2H), 6.61 (s, 1H), 5.14 (q, J=7.2 Hz, 1H), 3.77 (s, 3H), 1.83 (d, J=7.2 Hz, 3H).

Step-3: 2-(3-(2-aminoethyl)-1H-pyrazol-1-yl) propan-1-ol (XLVII)

A solution of $LiAlH_4$ (9.95 mL, 1 M in THF, 9.95 mmol) in diethyl ether (20 mL) was cooled to 0° C. under inert atmosphere and dropwise added a solution of methyl (E)-2-(3-(2-nitrovinyl)-1H-pyrazol-1-yl) propanoate XLVIIb (560 mg, 2.49 mmol) in diethyl ether (8 mL). The reaction mixture was stirred at room temperature for 2 h and the progress of reaction was monitored by TLC analysis. After completion, the reaction mixture was cooled to 0° C. and quenched with sequential dropwise addition of water (0.6 mL), 15% KOH solution (0.6 mL) and again water (1.8 mL). The reaction mixture was stirred at rt for 10 min and ethyl acetate (50 mL) was added and stirred for additional 15 min. The mixture was filtered and thoroughly washed with ethyl acetate (50 mL×3). The combined organic layer was concentrated under reduced pressure to afford the desired product XLVII as pale-yellow oil. Yield: 0.47 g, (100%); LCMS Calculated. for is 169.12; Observed. 170.35 $[M+H]^+$.

Synthesis of (6-(2-aminoethyl)-3-fluoropyridin-2-yl) methanol (XLVIII)

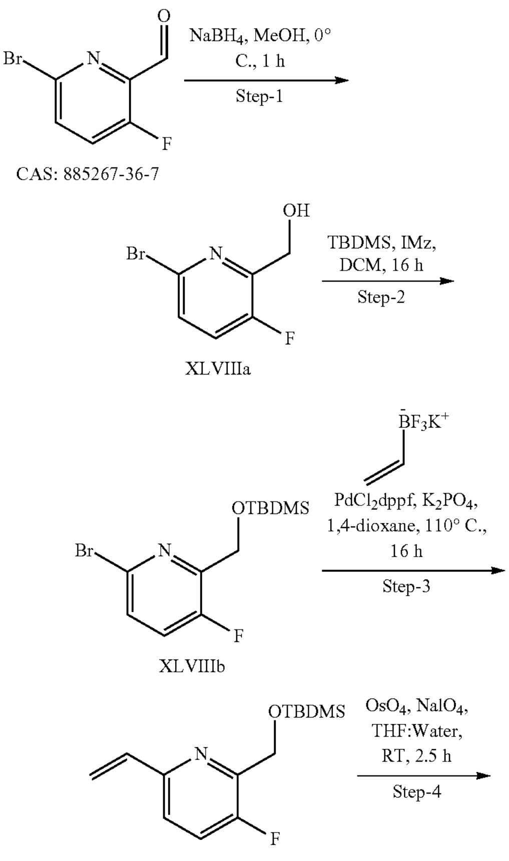

CAS: 885267-36-7

XLVIIIa

XLVIIIb

XLVIIIc

-continued

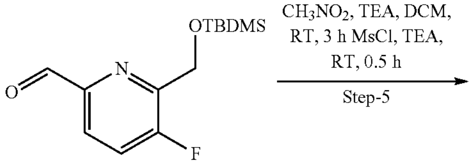

XLVIIId

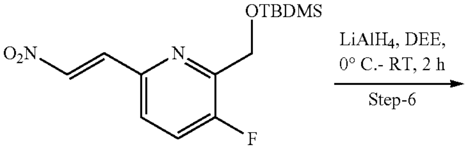

XLVIIIe

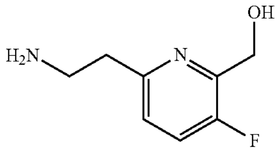

XLVIII

Step-1: (6-bromo-3-fluoropyridin-2-yl) methanol (XLVIIIa)

To a solution of 6-bromo-3-fluoropicolinaldehyde (CAS: 885267-36-7, 2 g, 10 mmol) in Methanol (20 mL) at 0° C. was added $NaBH_4$ (0.4 g, 10 mmol) and stirred at the same temperature for 30 min. The progress of the reaction was monitored by TLC analysis. After the completion of the reaction, added $NaHCO_3$ (50 mL) and extracted with ethyl acetate (50 mL×2). The combined organic layer was washed with brine (25 mL), dried over anhydrous sodium sulphate, and concentrated under reduced pressure to afford the desired product XLVIIIa as off-white solid. The crude was taken for the next step without any further purification. Yield: 1.96 g, (100.0%); LCMS calculated for $C_6H_5BrFNO$ is 204.95; Observed: 206.20 $[M+H]^+$. $^1$HNMR (400 MHz, $CDCl_3$): δ 7.74-7.63 (m, 2H), 5.47 (t, J=6.4 Hz, 1H), 4.55-4.54 (m, 2H).

Step-2: 6-bromo-2-(((tert-butyldimethylsilyl) oxy) methyl)-3-fluoropyridine (XLVIIIb)

To a solution of (6-bromo-3-fluoropyridin-2-yl) methanol XLVIIIa (1.96 g, 9.51 mmol) in DCM (50 mL) was added imidazole (0.972 g, 14.3 mmol). The reaction mixture was stirred at rt for 30 min This was followed by an addition of TBDMS-Cl (1.72 g, 11.4 mmol) at 0° C. and stirred at rt for 16 h. The progress of the reaction was monitored by TLC analysis. After the completion of the reaction, water (50 mL) was added and extracted with dichloromethane (50 mL×2). The combined organic layer was washed with brine (25 mL) dried over anhydrous sodium sulphate and concentrated under reduced pressure. The crude compound was purified by silica gel (230-400 mesh) column chromatography using ethyl acetate in n-hexane (0-15%) to afford the desired compound XLVIIIb as a colorless viscous liquid. Yield: 2.8 g, (98.0%); LCMS calculated for $C_{12}H_{19}BrFNOSi$ is 319.04; Observed. 321.95 $[M+H]^+$. $^1$H NMR (400 MHz, cdcl$_3$): δ 7.41-7.38 (m, 1H), 7.28-7.24 (m, 1H), 4.82 (d, J=6.0 Hz, 2H), 0.91 (s, 9H), 0.12 (s, 6H).

Step-3: 2-(((tert-butyldimethylsilyl) oxy) methyl)-3-fluoro-6-vinylpyridine (XLVIIIc)

To a solution of 6-bromo-2-(((tert-butyldimethylsilyl) oxy) methyl)-3-fluoropyridine XLVIIIb (1.8 g, 5.6 mmol) and potassium trifluoro(vinyl)borate (1-) (0.90 g, 6.7 mmol) in 1,4-dioxane (20 mL) was added potassium phosphate, tribasic (1.8 g, 8.4 mmol) and purged with $N_2$ for 10 min. This was followed by an addition of $PdCl_2$(dppf) (0.21 g, 0.28 mmol) and stirred at 110° C. for 16 h. The progress of the reaction was monitored by TLC analysis. After the completion, the reaction mixture was cooled to room temperature and added water (50 mL), extracted with ethyl acetate (50 mL×2). The combined organic layer was washed with brine (30 mL), dried over anhydrous sodium sulphate, and concentrated under reduced pressure. The crude compound was purified by silica gel (230-400 mesh) column chromatography using ethyl acetate in n-hexane (0-10%) to afford the desired product XLVIIIc as a colorless viscous liquid. Yield: 2.67 g, (93.0%); LCMS calculated for $C_{14}H_{22}FNOSi$ is 267.15; Observed. 268.35 $[M+H]^+$. $^1$HNMR (400 MHz, $CDCl_3$): δ 7.34-7.24 (m, 2H), 6.82-6.75 (m, 1H), 6.13 (d, J=17.6 Hz, 1H), 5.43 (d, J=10.8 Hz, 1H), 4.87 (s, 2H), 0.92 (s, 9H), 0.12 (s, 6H).

Step-4: 6-(((tert-butyldimethylsilyl) oxy) methyl)-5-fluoropicolinaldehyde (XLVIIId)

To a solution of 2-((tert-butyldimethylsilyl) oxy)-3-fluoro-6-vinylpyridine XLVIIIc (2.67 g, 10.5 mmol) in THF (25 mL) at 0° C. was added osmium (VIII) oxide (6.67 mL, 4% in water, 1.05 mmol) and the stirred at rt for 30 min. This was followed by an addition of sodium periodate (2.25 g, 10.5 mmol) and stirred at rt for 2 h. The reaction was monitored by TLC analysis. After the completion of the reaction, added water (35 mL) and extracted with ethyl acetate (35 mL×2). The combined organic layer was dried over anhydrous $Na_2SO_4$, filtered and evaporated under reduced pressure to afford the crude as a brown viscous liquid. The crude compound was purified by silica gel (230-400 mesh) column chromatography using ethyl acetate in n-hexane (0-5%) to afford the desired compound XLVIIId as a colorless viscous liquid. Yield: 1.3 g, (48.0%); LCMS calculated for $C_{12}H_{20}FNO_2Si$ is 269.12; Obs. 270.30 $[M+H]^+$. $^1$H NMR (400 MHz, $CDCl_3$): δ 10.04 (s, 1H), 7.96 (q, J=4.8 Hz, 1H), 7.53 (t, J=8.4 Hz, 1H), 4.96 (s, 2H), 0.93 (s, 9H), 0.14 (s, 6H).

Step-5: (E)-2-(((tert-butyldimethylsilyl) oxy) methyl)-3-fluoro-6-(2-nitrovinyl) pyridine (XLVIIIe)

To a solution of 6-(((tert-butyldimethylsilyl) oxy) methyl)-5-fluoropicolinaldehyde XLVIIId (1.3 g, 4.8 mmol) in dichloromethane (15 mL) at 0° C. were added nitromethane (0.31 mL, 5.8 mmol) and triethylamine (3.4 mL, 24 mmol). The resulting mixture was stirred at rt for 3 h. The progress of the reaction was monitored by TLC analysis. After the complete consumption of the starting material, the reaction mixture was concentrated, and the residue was dissolved in fresh DCM (10 mL). The resulting mixture was cooled to 0° C. and triethyl amine (3.4 mL, 34 mmol) was added followed by a dropwise addition of solution of mesyl-Cl (1.1 mL, 14 mmol) under inert atmosphere. The reaction mixture was stirred at rt for 30 min. The progress of the reaction was monitored by TLC analysis. After the completion of the reaction, the reaction mixture was concentrated, added water (25 mL) and extracted with ethyl acetate (25 mL×2). The combined organic layer was washed with brine (50 mL) and concentrated under reduced pressure. The crude compound was purified by silica gel (230-400 mesh) column chromatography using ethyl acetate in n-hexane (0-5%) to afford the desired product XLVIIIe as a colorless viscous liquid. Yield: 0.78 g, (52.0%); LCMS calculated for $C_{14}H_2FN_2O_3Si$ is 312.13; Observed. 313.30 $[M+H]^+$ $^1$HNMR (400 MHz, cdcl$_3$): δ 7.97-7.90 (m, 2H), 7.44 (t, J=5.2 Hz, 2H), 4.89 (s, 2H), 0.93 (s, 9H), 0.13 (s, 6H).

Step-6: (6-(2-aminoethyl)-3-fluoropyridin-2-yl) methanol (XLVIII)

To a solution of lithium aluminum (III) hydride (10 mL, 1 M, 10 mmol) in dry diethyl ether (60 mL) at 0° C. was added a solution of (E)-2-((tert-butyldimethylsilyl) oxy)-3-fluoro-6-(2-nitrovinyl) pyridine XLVIIIe (0.78 g, 2.6 mmol) in dry diethyl ether (10 mL). The resulting mixture was stirred at rt for 2 h. The progress of the reaction was monitored by TLC analysis. After the completion of the reaction, the reaction mixture was cooled to 0° C. and added ice cold water (0.7 mL). This was followed by an addition of 15% KOH (0.7 mL) and stirred for 20 min. Added ethyl acetate (75 mL) and stirred at rt for 30 min. The reaction mixture was filtered, and the residue was washed with ethyl acetate (100 mL). Filtrate was concentrated under reduced pressure to afford the desired compound XLVIII as a pale-yellow viscous liquid. The crude was taken for the next step without any further purification. Yield: 0.4 g, (90.0%); LCMS calculated for $C_8H_{11}FN_2O$ is 170.09; Observed: 171.30 $[M+H]^+$.

Synthesis of 3-(2-aminoethyl)-1-(2-methoxyethyl) pyridine-2(1H)-one (XLIX)

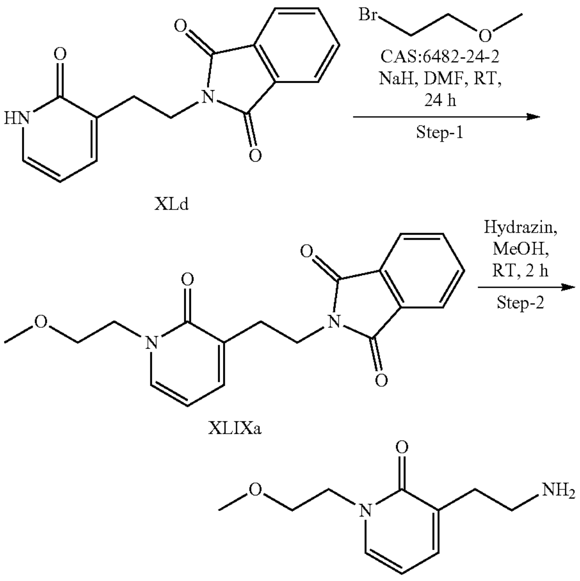

XLd

XLIXa

XLIX

Step-1 2-(2-(1-(2-methoxyethyl)-2-oxo-1,2-dihydropyridin-3-yl) ethyl) isoindoline-1,3-dione (XLIXa)

To a stirred solution of 2-(2-(2-oxo-1,2-dihydropyridin-3-yl) ethyl) isoindoline-1,3-dione XLd (1.2 g, 4.5 mmol) in DMF (10 mL) was cooled 0° C. and added NaH (0.13 g, 5.4 mmol). This was followed by dropwise addition of 1-bromo-2-methoxyethane (CAS:6482-24-2, 0.93 g, 6.7 mmol) and the resulting reaction mixture was stirred at room temperature for 24 hours. The progress of the reaction was monitored by TLC. The reaction was quenched with water (100 mL) and the resulting mixture was extracted with ethyl acetate (200 ml×3) and the combined organic layer was dried over anhydrous sodium sulphate and concentrated under reduced pressure. The crude residue was subjected silica gel (230-400 mesh) column chromatography using 10-70% ethyl acetate in n-hexane to afford the desired compound XLIXa as a yellow liquid. Yield: 400 mg (27%); LCMS Calculated. for $C_{18}H_{18}$ $N_2O_4$ is 326.13; Observed. 327.00 $[M+H]^+$; $^1$H NMR (400 MHz, CDCl$_3$): δ 7.811-7.791 (m, 2H), 7.696-7.674 (m, 2H), 7.244-7.222 (m, 1H), 7.121-7.104 (m, 1H), 5.973 (t, J=6.8 Hz, 1H), 4.099 (t, J=5.2 Hz, 2H), 4.016 (t, J=6.4 Hz, 2H), 3.663 (t, J=5.2 Hz, 2H), 3.329 (s, 3H), 2.959-2.931 (m, 2H).

Step-2: 3-(2-aminoethyl)-1-(2-methoxyethyl) pyridin-2(1H)-one (XLIX)

To a stirred solution of 2-(2-(1-(2-methoxyethyl)-2-oxo-1,2-dihydropyridin-3-yl) ethyl) isoindoline-1,3-dione XLIXa (400 mg, 1.23 mmol) in MeOH (4 mL) was added hydrazine hydrate (61.4 mg, 1.23 mmol) and the reaction mixture was stirred at room temperature for 2 h. The progress of the reaction was monitored by TLC. After completion, the reaction mixture was concentrated and was added 2 mL of water then acidified with conc. HCl (pH=2). Filtered the precipitated solids and washed with water. The filtrate was basified with 4M. NaOH solution and extracted with ethyl acetate (50 ml×3), the combined organic layer was dried over anhydrous sodium sulphate and concentrated under reduced pressure to afford the desired compound a XLIX s a yellow liquid. Yield: 200 mg (91%); LCMS Calculated. for $C_{10}H_{16}$ $N_2O_4$ is 196.12; Observed. 197.30 $[M+H]^+$; $^1$H NMR (400 MHz, CDCl$_3$): δ 7.257-7.212 (m, 2H), 6.110 (t, J=6.8 Hz, 1H), 4.980 (bs, 2H), 4.124 (t, J=4.8 Hz, 2H), 3.678 (t, J=4.8 Hz, 2H), 3.326 (s, 3H), 2.959 (t, J=6.8 Hz, 2H), 2.689 (t, J=6.8 Hz, 2H).

Synthesis of 7-amino-2-methyl-5-(methyl sulfonyl)-3-(trifluoromethyl) pyrazolo[1,5-a] pyrimidine-6-carbonitrile (L)

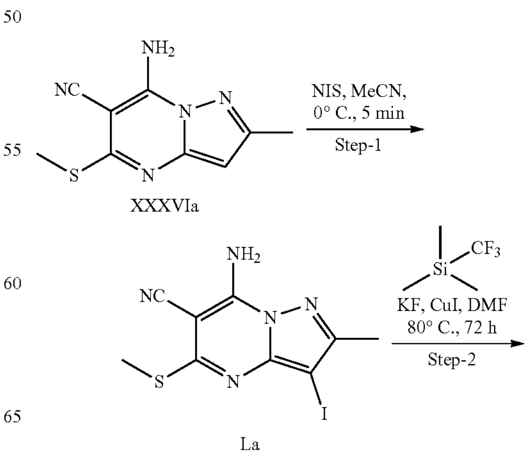

XXXVIa

La

-continued

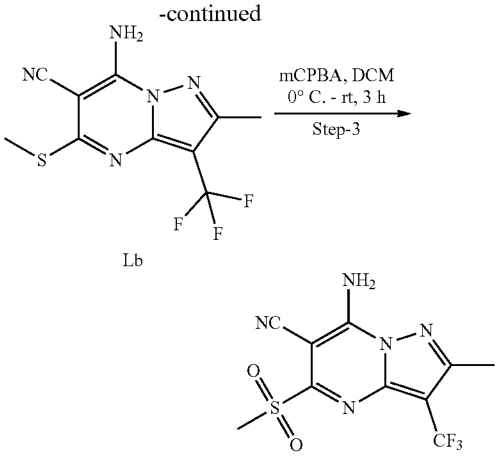

Lb

L

Step-1: 7-amino-3-iodo-2-methyl-5-(methylthio) pyrazolo[1,5-a] pyrimidine-6-carbonitrile (La)

To a stirred solution of 7-amino-2-methyl-5-(methylthio) pyrazolo[1,5-a] pyrimidine-6-carbonitrile XXXVIa (2.0 g, 9.00 mmol) in acetonitrile (20 mL) was added N-iodosuccinimide (2.0 g, 9.00 mmol) at 0° C. The resulting mixture was stirred at 0° C. for 5 min. The progress of the reaction was monitored by TLC analysis. After completion, precipitated solid was filtered and collected solid was washed with excess of acetonitrile (50 mL) dried under high vacuo to afford desired pure product La as a brown solid. Yield: 2.8 g (90%); LCMS Calculated. for $C_9H_8IN_5S$ is 344.95; Observed. 346.10 $[M+H]^+$; $^1$HNMR (400 MHz, DMSO-$D_6$): δ 8.84 (bs, 2H), 2.59 (s, 3H), 2.37 (s, 3H).

Step-2: 7-amino-2-methyl-5-(methylthio)-3-(trifluoromethyl) pyrazolo[1,5-a] pyrimidine-6-carbonitrile (Lb)

To a stirred solution of 7-amino-3-iodo-2-methyl-5-(methylthio) pyrazolo[1,5-a] pyrimidine-6-carbonitrile La (1.0 g, 2.897 mmol) in DMF (10 mL) were added CuI (2.43 g, 12.75 mmol), trifluoro methyl trimethyl silane (1.483 g, 10.43 mmol) and potassium fluoride (0.606 g, 10.43 mmol) at room temperature under $N_2$ atmosphere. The resulting mixture was stirred at 80° C. for 72 h. The progress of the reaction was monitored by TLC analysis. After completion, the reaction mixture was diluted with 35 mL of DCM and filtered. The filtrate was concentrated under reduced pressure to afford black crude semi-solid. The crude compound Lb was taken for the next step without further purification. Yield: 0.32 g (40.4%); LC-MS Calculated. for $C_{10}H_8F_3N_5S$ is 287.05; Observed. 286.15 $[M-H]^+$; $^1$HNMR (400 MHz, $CDCl_3$): δ 6.34 (bs, 2H), 2.96 (s, 3H), 2.89 (s, 3H).

Step-3: 7-amino-2-methyl-5-(methyl sulfonyl)-3-(trifluoromethyl) pyrazolo[1,5-a] pyrimidine-6-carbonitrile (L)

To a stirred solution of 7-amino-2-methyl-5-(methylthio)-3-(trifluoromethyl) pyrazolo[1,5-a] pyrimidine-6-carbonitrile Lb (0.23 g, 0.801 mmol) in acetonitrile (10 mL) was added mCPBA (0.691 g, 4.00 mmol) at 0° C. under $N_2$ atmosphere. The resulting mixture was stirred at room temperature for 3 h. The progress of the reaction was monitored by TLC analysis. After completion, to the reaction mixture was added sat. sodium bicarbonate solution (10 mL) and filtered the precipitated solid and dried under vacuo to afford desired product L as an off-white solid. The crude compound was taken for the next step without further purification. Yield: 0.17 g (66.5%); LCMS Calculated. for $C_{10}H_8F_3N_5O_2S$ is 319.04; Observed. 318.10 $[M-H]^+$; $^1$HNMR (400 MHz, $CDCl_3$): δ 2.77 (s, 3H), 2.23 (s, 3H).

Synthesis of 7-amino-3-cyclopropyl-2-methyl-5-(methyl sulfonyl) pyrazolo[1,5-a] pyrimidine-6-carbonitrile (LI)

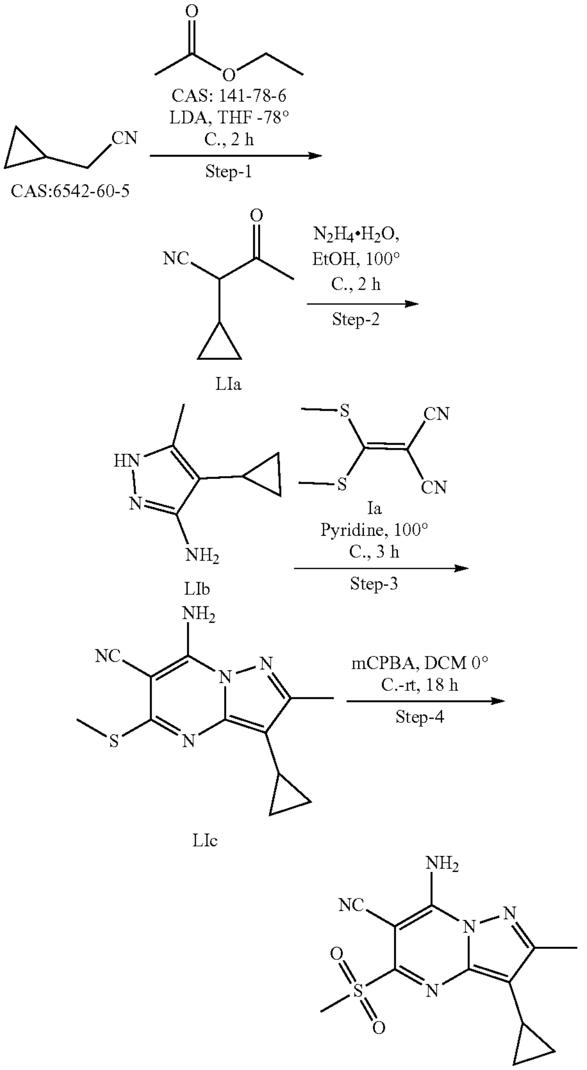

LIa

LIb

LIc

LI

Step-1: 2-cyclopropyl-3-oxobutanenitrile (LIa)

To a stirred solution of LDA (9.2 mL, 2 molar, 8 mmol) in THF (30 mL) at −78° C. was drop wise added solution of 2-cyclopropylacetonitrile (CAS: 6542-60-5, 1.5 g, 18 mmol) in THF (10 mL) over 10-15 min. The resulting mixture was stirred for 1 h at the same temperature. This was followed by a dropwise addition of dry ethyl acetate (CAS: 141-78-6, 1.6 mL, 17 mmol) at −78° C. The resulting mixture was stirred at same temperature for additional 1 h. The progress of the reaction was monitored by TLC analysis. After completion, the reaction mixture was quenched with sat. $NH_4Cl$ solution (50 mL) and extracted with ethyl acetate (100 mL×3). The combined organic layer was dried over anhydrous sodium sulphate, filtered, and concentrated under reduced pressure to afford the desired compound LIa as brown liquid. Yield: 2.0 g (86%). LCMS Calculated. for $C_7H_9NO$ is 123.06; Observed: 122.25 $[M-1]^+$.

Step-2: 4-cyclopropyl-5-methyl-1H-pyrazol-3-amine (LIb)

To a stirred solution of 2-cyclopropyl-3-oxobutanenitrile LIa (2.4 g, 19 mmol) in ethanol (20 mL) was added hydrazine hydrate (1:1, 1.4 mL, 29 mmol) under inert atmosphere and the reaction mixture was heated at 100° C. for 2 h. The progress of the reaction was monitored by TLC analysis. After completion, the reaction mixture was cooled to rt and concentrated under reduced pressure. The obtained residue was dissolved in water (50 mL) and extracted with 10% MeOH in DCM (50 mL×3). The combined organic layer was dried over anhydrous $Na_2SO_4$, filtered and concentrated under reduced pressure to afford the desired compound LIb as a pale-yellow viscous liquid. Yield: 1.65 g (61%). LCMS Calculated. for $C_7H_{11}N_3$ is 137.09; Observed. 138.30 $[M+H]^+$.

Step-3: 7-amino-3-cyclopropyl-2-methyl-5-(methylthio) pyrazolo[1,5-a] pyrimidine-6-carbonitrile (LIc)

To a stirred solution of 4-cyclopropyl-5-methyl-4H-pyrazol-3-amine LIb (2.0 g, 15 mmol) in pyridine (10 mL) was added 2-(bis(methylthio)methylene) malononitrile Ia (2.5 g, 15 mmol). The resulting mixture was stirred at 100° C. for 3 h. The progress of the reaction was monitored by TLC analysis. After completion, the reaction mixture was cooled to rt and poured into ice cold water (500 mL). The precipitate formed was filtered and washed with cold water (100 mL). The obtained solid was dried and under vacuum to get the title compound LIc as pale-yellow solid. Yield: 2.2 g (52%). LCMS Calculated. for $C_{12}H_{13}N_5S$ is 259.09; Observed. 260.25 $[M+1]^+$.

Step-4:7-amino-3-cyclopropyl-2-methyl-5-(methyl sulfonyl) pyrazolo[1,5-a] pyrimidine-6-carbonitrile (LI)

A stirred solution of 7-amino-3-cyclopropyl-2-methyl-5-(methylthio) pyrazolo[1,5-a] pyrimidine-6-carbonitrile LIc (2.2 g, 8.5 mmol) in DCM (50 mL) at 0° C. was portion-wise added mCPBA (7.3 g, 42 mmol). The resulting reaction mixture was stirred at RT for 18 h. The progress of the reaction was monitored by TLC analysis. After completion, the reaction mixture was concentrated under vacuum. The crude was diluted with saturated sodium bicarbonate solution (100 mL) and stirred for 30 min. The solid formed was filtered and washed with water (100 mL×3) followed by with n-pentane (100 mL×3). The solid was dried under vacuum to afford the compound LI as an off-white solid. Yield: 2.2 g (52%). $^1$HNMR (400 MHz, DMSO-$D_6$): δ 9.06 (bs, 2H), 3.38 (s, 3H), 2.46 (s, 3H), 1.81-1.77 (m, 1H), 1.06-1.01 (m, 2H), 0.19-0.89 (m, 2H).

Synthesis of 2-(1-(3-methoxypropyl)-1H-pyrazol-5-yl) ethan-1-amine. (LII)

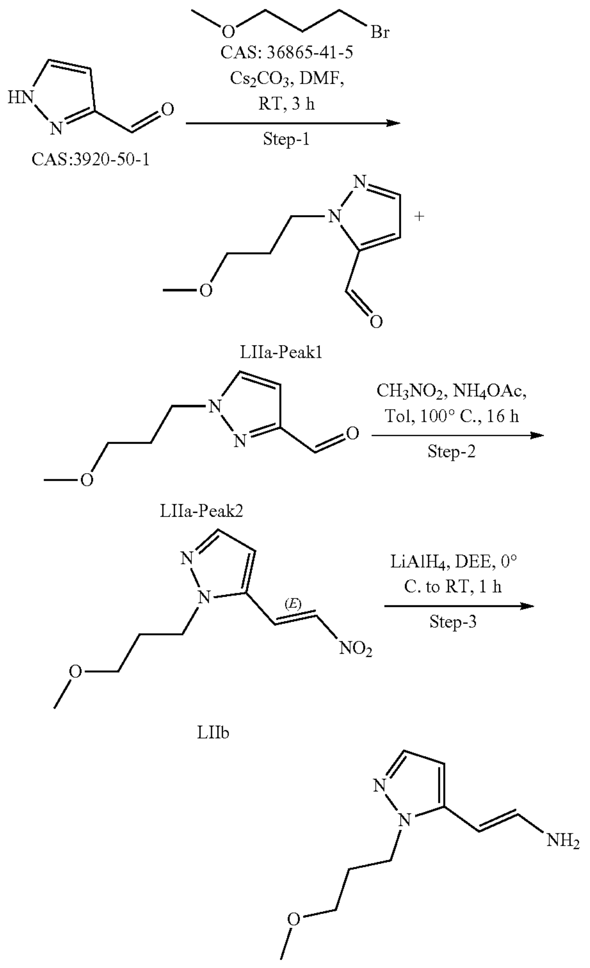

LIIa-Peak1

LIIa-Peak2

LIIb

LII

Step-1: 1-(3-methoxypropyl)-1H-pyrazole-5-carbaldehyde (LIIa-Peak1) and 1-(3-methoxypropyl)-1H-pyrazole-3-carbaldehyde (LIIa-Peak2)

To a solution of 1H-pyrazole-3-carbaldehyde (CAS:3920-50-1, 3 g, 30 mmol) in DMF (15 mL) was added cesium carbonate (30 g, 90 mmol) and stirred at rt for 10 min. This was followed by an addition of 1-bromo-3-methoxypropane (CAS: 36865-41-5, 6 g, 40 mmol) and stirred at rt for 3 h. The progress of the reaction was monitored by TLC analysis. The TLC and LC-MS analyses indicated formation of less polar close two spots with same molecular ion peaks (m/z=169.15) indicated formation of the regio-isomers. After the completion of the reaction, water (25 mL) was added and extracted with ethyl acetate (3×25 mL). The combined organic layer was washed with brine (20 mL), dried over anhydrous sodium sulphate, and concentrated under reduced pressure to afford the crude compound as a pale-yellow solid. The crude compound was purified by silica gel (230-400 mesh) column chromatography using ethyl acetate in n-hexane (0-20%) to afford the desired products as off-white solids. The structures of the desired products (LIIa-Peak 1 and LIIa-Peak II) were confirmed by $^{1}H$ NOESY study, the fraction-1 was corresponding to LIIa-Peak 1 whereas the fraction 2 was corresponds to LIIa-Peak II.

LIIa-Peak I: Yield: 0.6 g (11.4%); LCMS Calculated. for $C_8H_{12}N_2O_2$ is 168.08; Observed. 169.30 $[M+H]^+$; $^{1}H$ NMR (400 MHz, $CDCl_3$): δ 9.88 (s, 1H), 7.56 (s, 1H), 6.91 (d, J=4.0 Hz 1H), 4.64 (t, J=7.2 Hz, 2H), 3.36 (t, J=6.0 Hz, 2H), 3.31 (s, 3H), 2.10 (t, J=6.8 Hz, 2H).

LIIa-Peak II: Yield: 3.0 g, (57.0%); LCMS Calculated. for $C_8H_{12}N_2O_2$ is 168.08; Observed. 169.15 $[M+H]^+$ $^{1}H$ NMR (400 MHz, $CDCl_3$): δ 9.96 (s, 2H), 7.45 (d, J=2.0 Hz 1H), 6.79 (d, J=2.8 Hz 1H), 4.33 (t, J=6.8 Hz, 2H), 3.33 (t, J=5.2 Hz, 5H), 2.16 (t, J=6.0 Hz, 2H).

Step-2: (E)-1-(3-methoxypropyl)-5-(2-nitrovinyl)-1H-pyrazole (LIIb)

To a solution of 1-(3-methoxypropyl)-1H-pyrazole-5-carbaldehyde (LIIa-Peak 1) (0.79 g, 4.67 mmol) in toluene (25 mL) were added ammonium acetate (0.54 g, 7.00 mmol) and nitromethane (2.52 mL, 46.7 mmol). The reaction mixture was stirred at 100° C. for 16 h. The progress of the reaction was monitored by TLC analysis. After the completion of the reaction, the reaction mixture was quenched with 1N HCl (25 mL) and extracted with ethyl acetate (3×25 mL). The combined organic layer was washed with brine (10 mL), dried over anhydrous sodium sulphate, and concentrated under reduced pressure to get the crude material. The crude compound was purified by silica gel (230-400 mesh) column chromatography with ethyl acetate in n-hexane (0-20%) to afford the desired product LIIb as a pale-yellow solid. Yield: 0.51 g, (51.6%); LCMS Calculated. for $C_9H_{13}N_3O_3$ is 211.09; Observed. 212.30 $[M+H]^+$.

Step-3: 2-(1-(3-methoxypropyl)-1H-pyrazol-5-yl) ethan-1-amine (LII)

To a solution of lithium aluminum hydride (9 mL, 1 M in THF, 9 mmol) in diethyl ether (20 mL) at 0° C. was added a solution of (E)-1-(3-methoxypropyl)-5-(2-nitrovinyl)-1H-pyrazole LIIb (0.5 g, 2 mmol) in diethyl ether (20 mL) and stirred at rt for 1 h. The progress of the reaction was monitored by TLC analysis. After the completion, the reaction mixture was cooled to 0° C., added water (0.5 mL), 15% KOH (0.5 mL), water (1.5 mL) and stirred for 10 min. Added ethyl acetate (50 mL) and stirred for 15 min. The solids were filtered and washed with ethyl acetate (20 mL*3). The combined organic layer was concentrated and washed with hexane to afford the desired product LII as a colorless oil. Yield:0.29 g, (70%); LCMS Calculated. for $C_9H_{17}N_3O$ is 183.14; Observed. 183.00 $[M+H]^+$.

Synthesis of 2-(1-(3-methoxypropyl)-1H-pyrazol-3-yl) ethan-1-amine. (LIII)

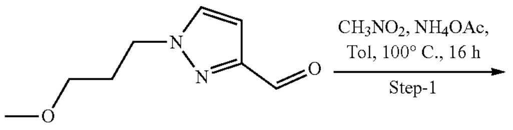

LIIa-Peak2

-continued

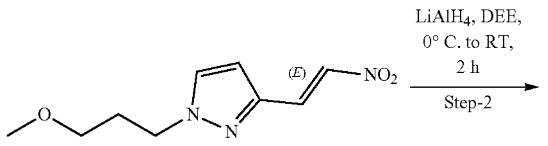

LIIIa

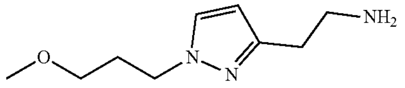

LIII

Step-1: (E)-1-(3-methoxypropyl)-3-(2-nitrovinyl)-1H-pyrazole (LIIIa)

To a solution of 1-(3-methoxypropyl)-1H-pyrazole-3-carbaldehyde. LIIa-Peak 2 (3.5 g, 21 mmol) in toluene (100 mL) were added ammonium acetate (2.4 g, 31 mmol) and nitromethane (11.0 mL, 210 mmol) and the reaction mixture was stirred at 100° C. for 16 h. The progress of the reaction was monitored by TLC analysis. After the completion of the reaction, the reaction mixture was quenched with 1N HCl (100 mL) and extracted with ethyl acetate (100 mL*3). The combined organic layer was washed with brine (50 mL), dried over anhydrous sodium sulphate, and concentrated under reduced pressure to get the crude material. The crude compound was purified by silica gel (230-400 mesh) column chromatography with ethyl acetate in n-hexane (0-20%) to afford desired product LIIIa as a pale-yellow solid. Yield: 2.72 g, (62.0%); LCMS Calc. for $C_9H_{13}N_3O_3$ is 211.09; Obs. 212.30 $[M+H]^+$. $^{1}H$ NMR (400 MHz, $CDCl_3$): δ 7.97 (d, J=13.6 Hz, 1H), 7.61 (d, J=13.6 Hz, 1H), 7.43 (d, J=2 Hz, 1H), 7.26-7.23 (m, 1H), 4.28 (q, J=15.6 Hz, 2H), 3.33-3.31 (m, 5H), 2.17 (q, J=4 Hz, 2H)

Step-2: 2-(1-(3-methoxypropyl)-1H-pyrazol-3-yl) ethan-1-amine (LIII)

To a solution of lithium aluminum hydride (51 mL, 1 M in THF, 51 mmol) in diethyl ether (100 mL) at 0° C. was added a solution of (E)-1-(3-methoxypropyl)-3-(2-nitrovinyl)-1H-pyrazole LIIIa (2.7 g, 13 mmol) in diethyl ether (100 mL). The reaction mixture was stirred at rt for 1 h. The progress of the reaction was monitored by TLC analysis. After the completion of the reaction, the reaction mixture was cooled to 0° C., added of water (2.7 mL) followed by of 15% KOH (2.7 mL) and water (8.1 mL). The reaction mixture was stirred for 10 min. Then added ethyl acetate (150 mL) and stirred for 15 min. The solid was filtered and washed with ethyl acetate (3×50 mL). The combined organic layer was concentrated and washed with n-hexane to afford the desired product LIII as a yellow solid. Yield: 2.15 g, (92%); LCMS Calculated. for $C_9H_{17}N_3O$ is 183.13. Observed. 183.65 $[M+H]^+$. $^{1}H$ NMR (400 MHz, $CDCl_3$): δ 7.32-7.25 (m, 2H), 6.04 (d, J=2.0 Hz, 1H), 4.16 (t, J=4.0 Hz, 2H), 3.32-3.29 (m, 5H), 2.99-2.96 (m, 2H), 2.76 (t, J=8.0 Hz, 1H), 2.12-2.05 (m, 2H)

Synthesis of 2-(1-(3-(2-aminoethyl)-1H-pyrazol-1-yl) cyclopropyl) ethan-1-ol. (LIV)

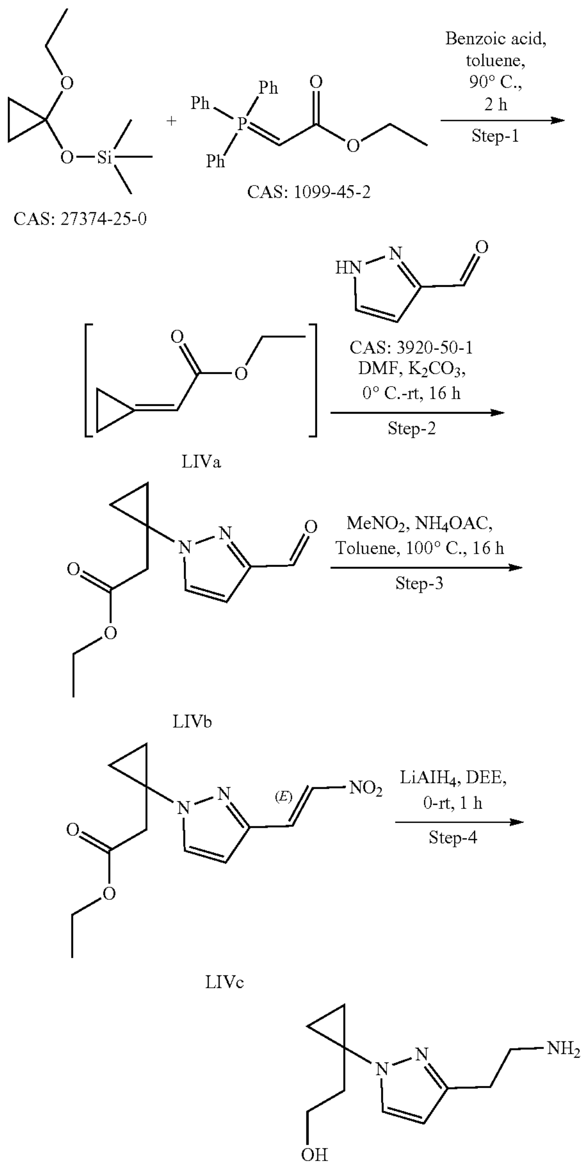

CAS: 27374-25-0

CAS: 1099-45-2

LIVa

LIVb

LIVc

LIV

Step-1: ethyl 2-cyclopropylideneacetate (LIVa)

To a solution of (1-ethoxycyclopropoxy) trimethyl silane (CAS: 27374-25-0, 10.0 g, 11.5 mL, 57.37 mmol) in toluene (100 mL) were added ethyl 2-(triphenyl-15-phosphaneylidene) acetate (CAS: 1099-45-2, 21.98 g, 63.10 mmol) and benzoic acid (7.36 g, 60.23 mmol). The reaction mixture was stirred at 90° C. for 2 h. The progress of the reaction was monitored by TLC analysis. After the completion, the reaction mixture was cooled to rt, diluted with n-pentane, and poured onto the silica gel (100-200) bed and eluted with 0-1% $Et_2O$ in n-pentane to afford the desired compound as a colorless liquid. Yield: 5.3 g (73.6%).

Step-2: Ethyl 2-(1-(3-formyl-1H-pyrazol-1-yl) cyclopropyl) acetate (LIVb)

To a solution of 1H-pyrazole-3-carbaldehyde (CAS: 3920-50-1, 2.0 g, 21 mmol) in N, N-dimethyl formamide (20 mL) was added potassium carbonate (4.3 g, 31 mmol) and the reaction mixture was stirred at rt for 20 min. This was followed by an addition of ethyl 2-cyclopropylideneacetate LIVa (5.3 g, 42 mmol) at 0° C. and the reaction mixture was stirred at rt for 16 h. The progress of the reaction was monitored by TLC analysis. After the completion of the reaction, the reaction mixture was diluted with water (100 mL) and extracted with ethyl acetate (100 mL×3). The combined organic layer was dried over anhydrous $Na_2SO_4$, filtered and concentrated under reduced pressure. The crude compound was purified by silica gel (230-400 mesh) column chromatography using ethyl acetate in n-hexane (0-30%) to afford the desired product LIVb as a light-yellow color liquid. Yield: 1.46 g, (32.0%); LCMS Calculated. for $C_{11}H_{14}N_2O_3$ is 222.1; Observed: 223.2 $[M+H]^+$. $^1H$ NMR (400 MHz, $CDCl_3$): δ 9.95 (s, 1H), 7.65 (d, J=2 Hz, 1H), 6.72 (d, J=2.4 Hz, 1H), 4.10 (q, J=7.2 Hz, 2H), 2.87 (s, 2H), 1.422-1.35 (m, 2H), 1.26-1.18 (m, 5H).

Step-3: Ethyl (E)-2-(1-(3-(2-nitrovinyl)-1H-pyrazol-1-yl) cyclopropyl) acetate (LIVc)

To a solution of ethyl 2-(1-(3-formyl-1H-pyrazol-1-yl) cyclopropyl) acetate LIVb (1.46 g, 6.57 mmol) in toluene (50 mL) was added nitromethane (6.02 g, 98.5 mmol) and the reaction mixture was stirred at rt for 10 min. This was followed by an addition of ammonium acetate (0.76 g, 9.85 mmol) and the reaction mixture was stirred at 100° C. for 16 h. The progress of the reaction was monitored by TLC analysis. After the completion, the reaction mixture was cooled rt, diluted with 1N HCl (50 mL) and extracted with ethyl acetate (100 mL×3). The combined organic layer was dried over anhydrous $Na_2SO_4$ and concentrated under reduced pressure. The crude compound was purified by silica gel (230-400 mesh) column chromatography using 0-10% ethyl acetate in n-hexane to afford the desired product LIVc as a light-yellow color liquid. Yield:1.2 g, (69%). $^1H$ NMR (400 MHz, $CDCl_3$): δ 7.95 (d, J=13.2 Hz, 2H), 7.64-7.27 (m, 2H), 6.45 (d, J=2.4 Hz, 1H), 4.12-4.07 (m, 2H), 2.84 (s, 2H), 1.42-1.31 (m, 2H), 1.29-1.15 (m, 4H).

Step-4: 7-amino-3-ethyl-5-((2-(1-(3-hydroxypropyl)-1H-pyrazol-3-yl) ethyl) amino)-2-methylpyrazolo[1, 5-a] pyrimidine-6-carbonitrile (LIV)

To a solution of $LiAlH_4$ (0.69 g, 18 mmol) in diethyl ether (100 mL) at 0° C. was added a solution of ethyl (E)-2-(1-(3-(2-nitrovinyl)-1H-pyrazol-1-yl) cyclopropyl) acetate (1.2 g, 4.5 mmol) in diethyl ether (50 mL) and the reaction mixture was stirred at rt for 1 h. The progress of the reaction was monitored by TLC analysis. After the completion of the reaction, the reaction mixture was cooled to 0° C. and quenched with water (1.2 mL), 15% KOH (1.2 mL) followed by water (3.6 mL). The mixture was filtered, and the white residue was thoroughly washed with ethyl acetate (150 mL×3). The combined filtrate was concentrated under reduced pressure to afford the desired product LIV as a pale-yellow viscous liquid. Yield: 0.6 g, (67.7%); LCMS Calculated. for $C_{10}H_{17}N_{30}$ is 195.14; Observed. 196.50 $[M+H]^+$.

Synthesis of 3-(2-aminoethyl)-1-(3-methoxypropyl) pyridin-2(1H)-one. (LV)

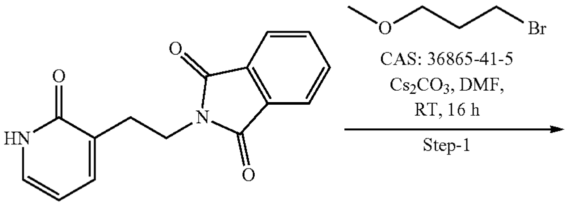

XLd

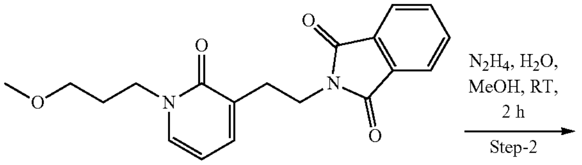

LVa

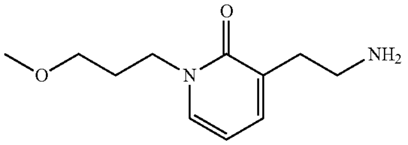

LV

Step-1: 2-(2-(1-(3-methoxypropyl)-2-oxo-1,2-dihydropyridin-3-yl) ethyl) isoindoline-1,3-dione (LVa)

To a stirred solution of 2-(2-(2-oxo-1,2-dihydropyridin-3-yl) ethyl) isoindoline-1,3-dione XLd (1.2 g, 4.5 mmol) in DMF (10 mL) was added $Cs_2CO_3$ (2.2 g, 6.7 mmol) at room temperature under $N_2$ atmosphere. The reaction mixture was cooled to 0° C., drop wise added 1-bromo-3-methoxypropane (CAS: 36865-41-5, 0.60 mL, 5.4 mmol. The resulting reaction mixture was stirred at 25° C. for 16 h. The progress of the reaction was monitored by TLC analysis. After completion, the reaction mixture was diluted with water (20 mL) and extracted with ethyl acetate (2×50 mL). Combined organic layer was washed with brine, dried over anhydrous sodium sulphate, and concentrated under vacuum. The crude compound was purified by combi flash column chromatography using ethyl acetate in n-hexane (0-30%) to afford the desired compound LVa as colorless viscous liquid. Yield: 0.6 g, (40%); LCMS Calculated. for $C_{19}H_{20}N_2O_4$ is 340.14; Observed.: 341.30 $[M+H]^+$.

Step-2: 3-(2-aminoethyl)-1-(3-methoxypropyl) pyridin-2(1H)-one (LV)

To a stirred solution of 2-(2-(1-(3-methoxypropyl)-2-oxo-1,2-dihydropyridin-3-yl) ethyl) isoindoline-1,3-dione LVa (600 mg, 1.76 mmol) in MeOH (6 mL) was added hydrazine hydrate (1:1, 107 µL, 2.12 mmol). The reaction mixture was stirred at rt for 2 h. The progress of the reaction was monitored by TLC analysis. After completion, the reaction mixture was concentrated, and crude was diluted with water (2 mL). The mixture was acidified with conc. HCl (pH=2). Solid formed was filtered and washed by water. The aqueous layer was basified (pH=9). with 1N NaOH solution and extracted with ethyl acetate (3×50 mL). Combined organic layer was dried over anhydrous sodium sulphate and concentrated under vacuum to afford the desired compound LV as a colorless viscous liquid. The crude was as such taken for next step without further purification. Yield: 350 mg, (94.4%); LCMS Calculated. for $C_{11}H_{18}N_2O_2$ is 210.14; Observed.: 211.30 $[M+H]^+$.

Synthesis of (2-(3-(2-aminoethyl)-1H-pyrazol-1-yl) cyclopentyl) methanol. (LVI)

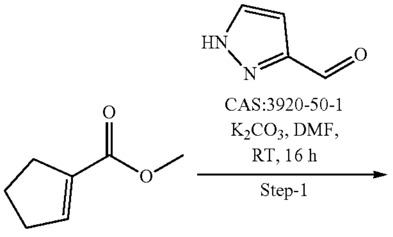

CAS: 25662-28-6

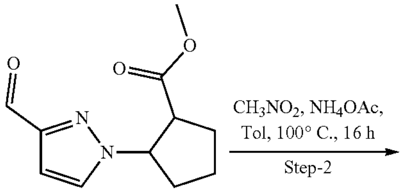

LVIa

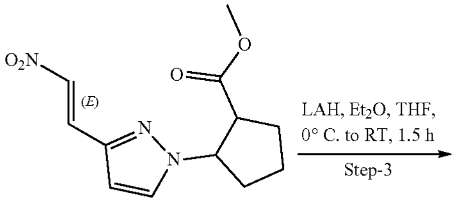

LVIb

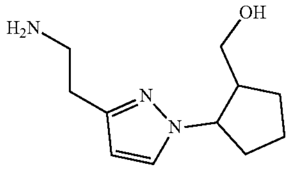

LVI

Step-1: methyl 2-(3-formyl-1H-pyrazol-1-yl) cyclopentane-1-carboxylate (LVIa)

To stirred solution of 1H-pyrazole-3-carbaldehyde (CAS: 3920-50-1, 2 g, 20 mmol) in DMF (15 mL) was added potassium carbonate (6 g, 40 mmol) under $N_2$ and stirred at rt for 10 min under inert atmosphere. To the resulting mixture was added methyl cyclopent-1-ene-1-carboxylate (CAS: 25662-28-6, 3 g, 20 mmol) and stirred at rt for 16 h. The progress of the reaction was monitored by TLC analysis. After completion, the reaction mixture was diluted with water (30 mL) and extracted with ethyl acetate (30 mL×3). The combine organic layer was washed with brine (50 mL), dried over anhydrous sodium sulphate, and concentrated under vacuum to afford pale-yellow solid. The crude was purified by combi flash silica gel (230-400) column chromatography using 0-15% ethyl acetate in n-hexane to afford the desired compound LVIa as a colorless viscous oil. Yield:

2.32 g (50%); LCMS Calculated. for $C_{11}H_{14}N_2O$ is 222.10; Observed. 223.25 $[M+H]^+$. $^1H$ NMR (400 MHz, $CDCl_3$): δ 9.95 (s, 1H), 7.51 (d, J=2 Hz, 1H), 6.77-6.76 (m, 1H), 5.00 (q, J=8.0 Hz, 1H), 3.68 (s, 3H), 3.42-3.32 (m, 1H), 2.35-2.08 (m, 3H), 2.06-1.26 (m, 3H).

Step-2: Methyl (E)-2-(3-(2-nitrovinyl)-1H-pyrazol-1-yl) cyclopentane-1-carboxylate (LVIb)

To a stirred solution of methyl 2-(3-formyl-1H-pyrazol-1-yl) cyclopentane-1-carboxylate LVIa (2.32 g, 10.4 mmol) in toluene (75 mL) were added ammonium acetate (1.21 g, 15.7 mmol) and nitromethane (5.63 mL, 104 mmol) under inert atmosphere. The resulting mixture was stirred at 100° C. for 16 h. The progress of reaction was monitored by TLC analysis. After completion, the reaction mixture was diluted with 1N HCl solution (75 mL) and extracted with ethyl acetate (50 mL×3). The combine organic layer was washed with brine (100 mL), dried over anhydrous sodium sulphate, and concentrated under reduced pressure to get crude material. The crude was purified by Combi-flash chromatography (230-400 silica gel) column chromatography using 0-15% ethyl acetate in n-hexane to afford the desired compound LVIb as a pale-yellow solid. Yield: 1.6 g (58%); LCMS Calculated. for $C_{12}H_{15}N_3O_4$ is 265.10; Observed.: 266.25 $[M+H]^+$. $^1H$ NMR (400 MHz, $CDCl_3$): δ 7.96 (d, J=13.2, Hz 1H), 7.60 (d, J=13.6 Hz, 1H), 7.50 (d, J=1.6 Hz, 1H), 6.50 (d, J=2.0 Hz, 1H), 4.95-4.93 (m, 1H), 3.69 (s, 3H), 3.30-3.28 (m, 1H), 2.30-2.21 (m, 3H), 2.03-1.85 (m, 3H).

Step-3: (2-(3-(2-aminoethyl)-1H-pyrazol-1-yl) cyclopentyl) methanol (LVI)

A stirred solution of $LiAlH_4$ (30 mL, 1 M in THF, 30 mmol) in diethyl ether (80 mL) was cooled to 0° C. and drop wise added a solution of methyl (E)-2-(3-(2-nitrovinyl)-1H-pyrazol-1-yl) cyclopentane-1-carboxylate LVIb (1.6 g, 6.0 mmol) in THF (10 mL) under inert atmosphere. The resulting mixture was stirred at room temperature for 1.5 h. The progress of reaction was monitored by TLC analysis. After completion, reaction mixture was cooled to 0° C., quenched by dropwise addition of water (1.6 mL). This was followed by addition of 15% KOH solution (1.6 mL) and again water (4.8 mL). Then ethyl acetate (50 mL) was added to the resulting mixture and stirred for 20 minutes at rt. The mixture was filtered and solid was washed with fresh ethyl acetate (100 mL×3). The combined organic layer was dried over anhydrous sodium sulphate and concentrated to afford the desired compound LVI as a pale-yellow thick oil. The crude material was washed with n-hexane, dried under vacuo, and used for next step without purification. Yield: 1.25 g (99%); LCMS Calculated. for $C_{11}H_{19}N_3O$ is 209.15; Observed.: 210.30 $[M+H]^+$.

Synthesis of (4-(3-(2-aminoethyl)-1H-pyrazol-1-yl) tetrahydrofuran-3-yl)methanol. LVII

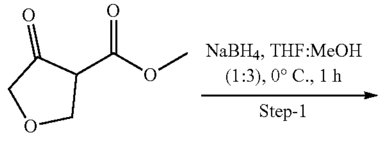

CAS: 57595-23-0

-continued

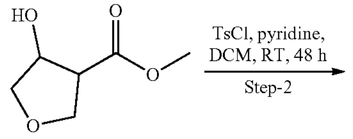

LVIIa

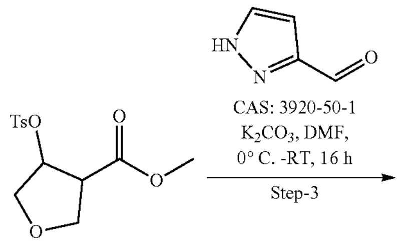

LVIIb

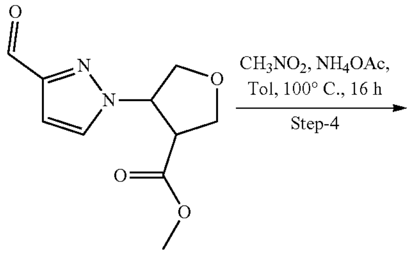

LVIIc

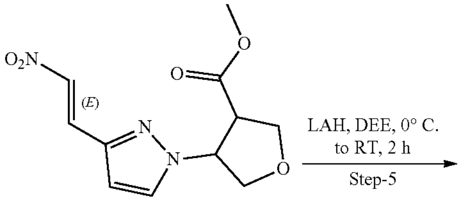

LVIId

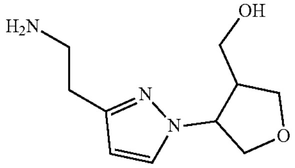

LVII

Step-1: methyl 4-hydroxytetrahydrofuran-3-carboxylate (LVIIa)

To a solution of methyl 4-oxotetrahydrofuran-3-carboxylate (CAS: 57595-23-0, 25 g, 0.173 mol) in THF: MeOH (2.5 L; 1:3) and the solution was cooled to 0° C. under inert atmosphere. To this solution, sodium borohydride (3.25 g, 0.087 mol) was added portion wise. The reaction mixture was stirred at 0° C. for 1 h and the progress of reaction was monitored by TLC analysis. After completion, the reaction was quenched by slow addition of water (400 mL). The resulting mixture was extracted with chloroform (700 mL×3). The combined organic layer dried over anhydrous sodium sulphate, filtered, and concentrated under vacuo to afford the desired compound LVIIa as a colorless oil. The crude was taken for the next step without purification (product is active for $KMnO_4$ stain). Yield: 21 g (83.3%).

Step-2: methyl 4-(tosyloxy) tetrahydrofuran-3-carboxylate (LVIIb)

To a stirred solution of methyl 4-hydroxytetrahydrofuran-3-carboxylate LVIIa (43 g, 0.294 mmol) in DCM (800 mL) were added pyridine (71 mL, 0.882 mol) and 4-methylbenzenesulfonyl chloride (168.15 g, 0.882 mol) under $N_2$ atmosphere. The reaction mixture was stirred at rt for 48 h and the progress of the reaction was monitored by TLC analysis. After completion, water (250 mL) was added, and the resulting mixture was extracted with DCM (300 mL×3). The combined organic layer was dried over anhydrous sodium sulphate and concentrated under vacuum to get the light brown oil. The crude was subjected to silica gel (60-120) column chromatography using 0-15% ethyl acetate in n-hexane to afford the desired compound LVIIb as a pale-yellow oil. Yield: 80 g (90.6%); Note: Tosyl elimination product also forms along with the expected product. The mixture was taken as such for the next step as both leads to the formation of desired product. LCMS Calculated for $C_{13}H_{16}O_6S$ is 300.06; Observe: 301.25 $[M+H]^+$.

Step-3: Methyl 4-(3-formyl-1H-pyrazol-1-yl) tetrahydrofuran-3-carboxylate (LVIIc)

To a solution of 1H-pyrazole-3-carbaldehyde (26 g, 0.270 mol) in DMF (1.2 L) under $N_2$ was added potassium carbonate (74 g, 0.535 mmol) and the resulting mixture was stirred at rt for 10 min. Methyl 4-(tosyloxy) tetrahydrofuran-3-carboxylate LVIIb (83 g, 0.276 mol) was added drop wise, and the reaction was stirred at rt for 16 hours under $N_2$ atmosphere. The progress of the reaction was monitored by TLC analysis. After completion, water (1.5 L) was added, and the mixture was extracted with ethyl acetate (700 mL×3). The combined organic layer washed with brine, dried over anhydrous sodium sulphate, and concentrated under vacuo to afford the crude as brown viscous liquid. The crude was subjected to silica gel column chromatography (60-120 mesh) using 0-15% ethyl acetate in n-hexane to afford the desired compound LVIIc as a pale-yellow viscous liquid. Yield: 35 g (50.7%). LCMS Calculated. for $C_{10}H_{12}N_2O_4$ is 224.07; Observed.: 225.25 $[M+H]^+$; $^1H$ NMR (400 MHz, $CDCl_3$): δ 9.97 (s, 1H), 7.57 (d, J=2.0 Hz, 1H), 6.82 (d, J=2.4 Hz, 1H), 5.37-5.33 (m, 1H), 4.44 (t, J=8.4 Hz, 1H), 4.28-4.17 (m, 2H), 4.12-4.08 (m, 1H), 3.86-3.77 (m, 3H), 3.65-3.60 (m, 1H).

Step-4: Methyl (E)-4-(3-(2-nitrovinyl)-1H-pyrazol-1-yl) tetrahydrofuran-3-carboxylate (LVIId)

To a solution of methyl 4-(3-formyl-1H-pyrazol-1-yl) tetrahydrofuran-3-carboxylate LVIIc (28 g, 0.127 mol) toluene (750 mL) were added ammonium acetate (14.7 g, 0.191 mol) and nitromethane (68.4 mL, 1.27 mol). The reaction mixture was stirred at 100° C. for 16 h under inert atmosphere. The progress of the reaction was monitored by TLC analysis and complete consumption of the starting material was confirmed by using 2,4 DNP stain. After completion, the reaction mixture was cooled to rt and quenched with 1N HCl (750 mL) and the organic layer was separated. The aqueous layer was extracted with ethyl acetate (500 mL×3). The combined organic layer was given brine wash, dried over anhydrous sodium sulphate, and concentrated under reduced pressure. The crude material was purified by silica gel (mesh 60-120) column chromatography using 0-15% ethyl acetate in n-hexane to afford the desired compound LVIId as a pale-yellow oil. Yield: 19.6 g (57.8%). LCMS Calculated. for $C_{11}H_{13}N_3O_5$ is 267.08; Observed. 268.25 $[M+H]^+$; $^1H$ NMR (400 MHz, $CDCl_3$): δ 9.96 (t, J=6.4 Hz, 1H), 7.63-7.55 (m, 2H), 6.55 (d, J=2.4 Hz, 1H), 5.31-5.27 (m, 1H), 4.48-4.39 (m, 1H), 4.27-4.22 (m, 1H), 4.16-4.06 (m, 2H), 3.75 (s, 3H), 3.61-3.56 (m, 1H).

Step-5: (4-(3-(2-aminoethyl)-1H-pyrazol-1-yl) tetrahydrofuran-3-yl) methanol (LVII)

A solution of $LiAlH_4$ (365 mL, 1 M in THF, 0.365 mol) in diethyl ether (1000 mL) was cooled to 0° C. under inert atmosphere. To resulting mixture was drop wise added a solution methyl (E)-4-(3-(2-nitrovinyl)-1H-pyrazol-1-yl) tetrahydrofuran-3-carboxylate LVIId (19.5 g, 0.073 mol) in diethyl ether (200 mL) over period of 15 min. The reaction mixture was stirred at room temperature for 1.5 h. The progress of the reaction was monitored by TLC analysis (ninhydrin stain). After completion, the reaction mixture was cooled to 0° C. and water (19.5 mL) was added slowly. This was followed a slow addition of (19.5 mL) of 15% KOH solution. Again water (58.5 mL) was added slowly the mixture was stirred at rt for 10 min. To this was added ethyl acetate (500 mL) and stirred for additional 30 min. The mixture was filtered, and the residue was washed thoroughly with ethyl acetate (500 mL). The residue was transferred back to reaction flask and stirred with fresh ethyl acetate (500 mL) for 10 min and filtered. The procedure was repeated for 3-4 times and the combined filtrate was dried over anhydrous sodium sulphate. The solvent was removed under reduced pressure to afford the desired product LVII a light brown viscous liquid. Yield: 13.9 g (90.2% crude). LCMS Calculated for $C_{10}H_{17}N_3O_2$ is 211.13; Observe 212.30 $[M+H]^+$.

Synthesis of (3-(3-(2-aminoethyl)-1H-pyrazol-1-yl) cyclobutyl) methanol. (LVIII)

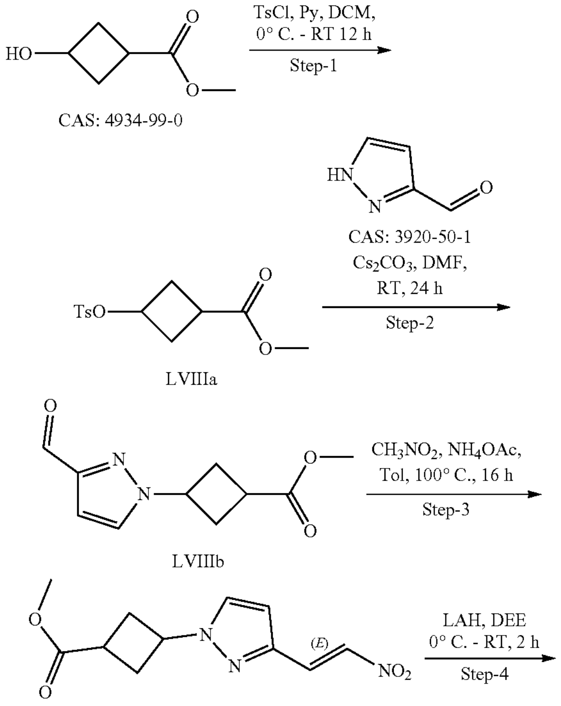

LVIIIc

-continued

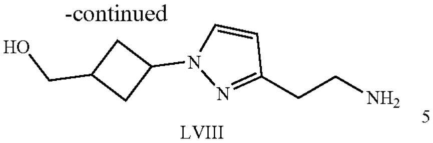

LVIII

Step-1: Methyl 3-(tosyloxy) cyclobutane-1-carboxylate (LVIIIa)

To a stirred solution of methyl 3-hydroxycyclobutane-1-carboxylate (CAS: 4934-99-0, 5 g, 40 mmol) in DCM (30 mL) was added pyridine (9 mL, 100 mmol) under inert atmosphere. The reaction mixture was cooled to 0° C. and portion wise added 4-methylbenzenesulfonyl chloride (10 g, 60 mol). The resulting mixture was stirred at rt for 12 h. The progress of the reaction was monitored by TLC analysis. After completion, the reaction mixture was diluted with water (30 mL) and extracted with DCM (35 mL×2). The combined organic layer was washed with brine (20 mL), dried over anhydrous sodium sulphated and concentrated under reduced pressure. The crude product was purified by combi-flash column chromatography by eluting with ethyl acetate in n-hexane (0-15%). The peak was eluted at 10% ethyl acetate in n-hexane was concentrated to afford the desired compound LVIIIa as colorless viscous liquid. Yield: 8 g (70%). LCMS Calculated. for $C_{13}H_{16}O_5S$ is 284.07; Observed: 285 $[M+H]^+$. δ 7.78 (d, J=8.0 2H), 7.34 (d, J=8.0 2H), 4.75-4.71 (m, 1H), 3.66 (s, 3H), 2.62-2.60 (m, 1H), 2.51-2.39 (m, 7H).

Step-2: Methyl 3-(3-formyl-1H-pyrazol-1-yl) cyclobutane-1-carboxylate (LVIIIb)

To a stirred solution of 1H-pyrazole-3-carbaldehyde (CAS: 3920-50-1, 1.5 g, 16 mmol) in DMF (30 mL) were added cesium carbonate (10 g, 31 mmol) and methyl 3-(tosyloxy) cyclobutane-1-carboxylate LVIIIa (5.8 g, 20 mmol) under nitrogen. The resulting reaction mixture was stirred at rt for 24 h. The progress of the reaction was monitored by TLC analysis. After completion, reaction mixture was diluted with water (50 mL) and extracted with ethyl acetate (75 mL×2). The combined organic layer was washed with brine (35 mL), dried over anhydrous sodium sulphate, and concentrated under reduced pressure. The crude product was purified by combi-flash silica gel (100-200) column chromatography using 0-20% ethyl acetate in n-hexane to afford the desired compound LVIIIb as a colorless viscous liquid. Yield: 1.7 g (52%). LCMS Calculated. for $C_{10}H_2N_2O_3$ is 208.08; Observed. 209.25 $[M+H]^+$.

Step-3: Methyl (E)-3-(3-(2-nitrovinyl)-1H-pyrazol-1-yl) cyclobutane-1-carboxylate (LVIIIc)

To a stirred solution of methyl 3-(3-formyl-1H-pyrazol-1-yl) cyclobutane-1-carboxylate LVIIIb (1.4 g, 6.7 mmol) in toluene (15 mL) were added ammonium acetate (0.78 g, 10 mmol) and nitromethane (5.4 mL, 10 mmol) under nitrogen. The resulting mixture was stirred at 100° C. for 16 h. The progress of the reaction was monitored by TLC analysis. After completion, reaction mixture was cooled to room temperature diluted with water (15 mL). The resultant mixture was extracted with ethyl acetate (20 mL×2) and combined organic layer was washed with brine. The organic layer was dried over anhydrous sodium sulphate, concentrated under reduced pressure. The crude compound was purified by silica gel (100-200; 250 g) combi flash column chromatography using methanol in DCM (0-0.5%) to afford the desired compound LVIIIc as a colorless viscous liquid. Yield: 0.35 g (21%). LCMS Calculated. for $C_{11}H_{13}N_3O_4$ is 251.09; Observed.: 252.25 $[M+H]^+$.

Step-4: (3-(3-(2-aminoethyl)-1H-pyrazol-1-yl) cyclobutyl) methanol (LVIII)

A stirred solution of $LiAlH_4$ (5.6 mL, 1 M in THF, 5.6 mmol) in diethyl ether (100 mL), was cooled to 0° C. and dropwise added a solution of methyl (E)-3-(3-(2-nitrovinyl)-1H-pyrazol-1-yl) cyclobutane-1-carboxylate (0.35 g, 1.4 mmol) under nitrogen atmosphere. The reaction mixture was stirred at rt for 2 h. The progress of the reaction was monitored by TLC analysis. After completion, the reaction mixture was cooled to 0° C., quenched with water (0.35 mL), 15% KOH (0.35 mL) and again with water (1.2 mL). The resulting reaction mixture was filtered and washed with ethyl acetate (50 mL×3). The combined filtrate was concentrated under reduced pressure to afford the compound LVIII as colorless viscous liquid. The crude was directly taken for next step without purification. Yield: 0.2 g (70%). LCMS Calculated. for $C_{10}H_{17}N_3O$ is 195.13; Observed. 196.45 $[M+H]^+$.

Synthesis of tert-butyl (2-(3-(2-aminoethyl)-2-oxopyridin-1(2H)-yl) ethyl) carbamate (LIX)

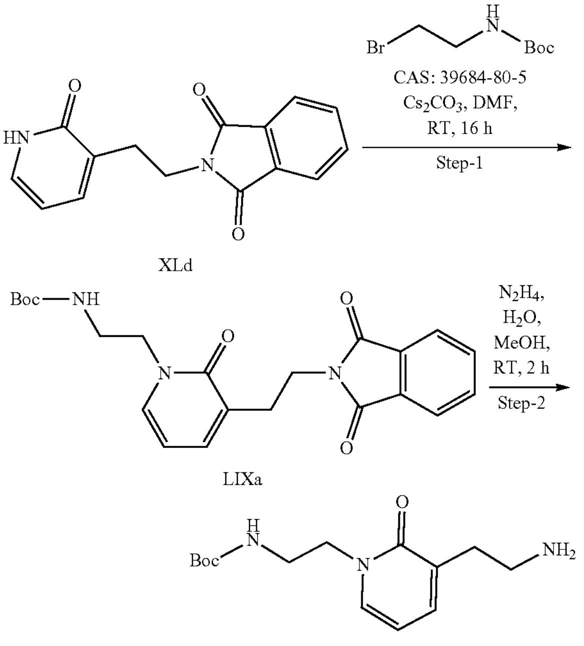

XLd

LIXa

LIX

Step-1: tert-butyl (2-(3-(2-(1,3-dioxoisoindolin-2-yl) ethyl)-2-oxopyridin-1(2H)-yl) ethyl) carbamate (LIXa)

To a stirred solution of 2-(2-(2-oxo-1,2-dihydropyridin-3-yl) ethyl) isoindoline-1,3-dione XLd (0.8 g, 3 mmol) in DMF (7 mL) was added cesium carbonate (1.0 g, 4.00 mmol) and tert-butyl (2-bromoethyl) carbamate (CAS:

39684-80-5, 0.8 g, 4.00 mmol) and the reaction mixture was stirred at room temperature for 16 h. The progress of the reaction was monitored by TLC analysis. After completion, the reaction was quenched with water (10 mL) and the resulting mixture was extracted with ethyl acetate (50 mL×3). The combined organic layer was dried over sodium sulphate and concentrated under reduced pressure. The residue obtained upon removal of the solvent was subjected to silica gel (230-400 mesh) column chromatography using (10-50%) ethyl acetate in n-hexane to afford the desired compound LIXa as a yellow liquid. Yield: 0.520 g (50%). LCMS Calculated. for $C_{22}H_{25}N_3O_5$ is 411.17; Obs. 412.30 $[M+H]^+$; $^1H$ NMR (400 MHz, $CDCl_3$): δ 8.01-8.00 (m, 1H), 7.84-7.82 (m, 2H), 7.72-7.70 (m, 2H), 7.40 (d, J=6.4 Hz, 1H), 6.79-6.76 (m, 1H), 4.38 (s, 2H), 3.96 (t, J=7.6 Hz, 2H), 3.57 (s, 2H), 2.95 (t, J=9.2 Hz, 2H), 1.54-1.39 (m, 9H).

Step-2: tert-butyl (2-(3-(2-aminoethyl)-2-oxopyridin-1(2H)-yl) ethyl) carbamate (LIX)

To a stirred solution of tert-butyl (2-(3-(2-(1,3-dioxoisoindolin-2-yl) ethyl)-2-oxopyridin-1(2H)-yl) ethyl) carbamate LIXa (0.52 g, 1.3 mmol) in MeOH (4 mL) was added hydrazine hydrate (1:1; 0.15 mL, 1.5 mmol) and the reaction mixture was stirred at room temperature for 2 h. The progress of the reaction was monitored by TLC analysis. After completion of the reaction, MeOH was concentrated and was added 2 mL of water then acidified with conc. HCl (pH=2). Filtered the precipitated solid and washed with water. The filtrate was basified with 4M. NaOH solution and extracted with 10% MeOH/DCM (100 mL×3). The combined organic layer was dried over anhydrous sodium sulphate and concentrated under reduced pressure to afford the desired compound LIX as a yellow liquid. Yield: 0.260 g (72.22%). LCMS Calculated. for $C_{14}H_{23}N_3O_3$ is 281.17; Observed. 282.30 $[M+H]^+$; $^1H$ NMR (400 MHz, $CDCl_3$): δ 7.24 (d, J=6.4 Hz, 1H), 7.16 (d, J=6.4 Hz, 1H), 6.85 (bs, 1H), 6.13 (t, J=6.4 Hz, 1H), 5.14 (bs, 1H), 4.02 (t, J=5.2 Hz, 2H), 3.48-3.45 (m, 2H), 2.97 (t, J=6.8 Hz, 2H), 2.69 (t, J=6.8 Hz, 2H), 1.42 (s, 9H).

Synthesis of 3-(2-aminoethyl)-1-((3-hydroxycyclobutyl) methyl) pyridine-2(1H)-one. (LX)

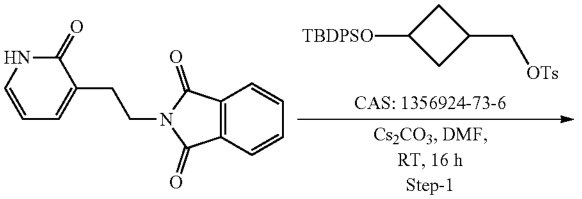

XLd

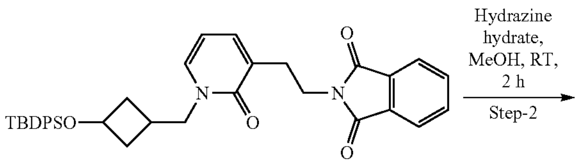

LXa

-continued

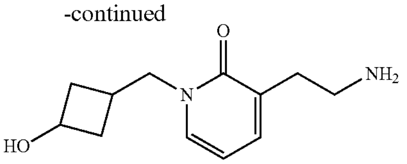

LX

Step-1: 2-(2-(1-((3-((tert-butyl diphenyl silyl) oxy) cyclobutyl) methyl)-2-oxo-1,2-dihydropyridin-3-yl) ethyl) isoindoline-1,3-dione (LXa)

A stirred solution of 2-(2-(2-oxo-1,2-dihydropyridin-3-yl) ethyl) isoindoline-1,3-dione XLd (1.2 g, 4.5 mmol) in DMF (15 mL) was cooled to 0° C. and added $Cs_2CO_3$ (1.7 g, 5.4 mmol) followed by an addition of (3-((tert-butyldiphenylsilyl) oxy) cyclobutyl) methyl 4-methylbenzenesulfonate (CAS: 1356924-73-6, 3.1 g, 6.3 mmol). The reaction mixture was stirred at rt for 16 h. The progress of the reaction was monitored by TLC analysis. After completion, the reaction mixture was quenched with water (25 mL) and extracted with ethyl acetate (50 mL×3). The combined organic layer was dried over anhydrous sodium sulphate and concentrated under reduced pressure. The crude was purified by combi flash column chromatography (silica gel 230-400) eluted with 0-50% ethyl acetate in n-hexane to afford the desired compound LXa as a brown liquid. Yield: 1.1 g (42%). LCMS Calculated. for $C_{36}H_{38}N_2O_4Si$ is 590.26; Observed.: 591.40 $[M+H]^+$.

Step-2: 3-(2-aminoethyl)-1-((3-hydroxycyclobutyl) methyl) pyridin-2(1H)-one (LX)

To a stirred solution of 2-(2-(1-((3-((tert-butyldiphenylsilyl) oxy) cyclobutyl) methyl)-2-oxo-1,2-dihydropyridin-3-yl) ethyl) isoindoline-1,3-dione LXa (1.1 g, 1.9 mmol) in MeOH (25 mL) was added hydrazine hydrate (1:1, 0.2 mL, 2.8 mmol) drop wise under $N_2$ atmosphere. The resulting reaction mixture was stirred at rt for 2 h. The progress of the reaction was monitored by TLC analysis. After completion, reaction mixture was concentrated under vacuum. The crude was diluted with water (2 mL), acidified with conc. HCl (pH=2). The solid formed was filtered and washed with water. The combined filtrate was basified with 10% NaOH solution, extracted with 10% methanol in DCM (200 mL×3). The combined organic layer was dried over anhydrous sodium sulphate, filtered, and concentrated under reduced pressure to afford the desired compound LX as light brown viscous liquid. Yield: 0.380 g (92%). LCMS Calculated. for $C_{12}H_{18}N_2O_2$ is 222.29; Observed. 223.30 $[M+H]^+$.

Synthesis of tert-butyl (3-(3-(2-aminoethyl)-2-oxopyridin-1(2H)-yl) propyl) carbamate. (LXI)

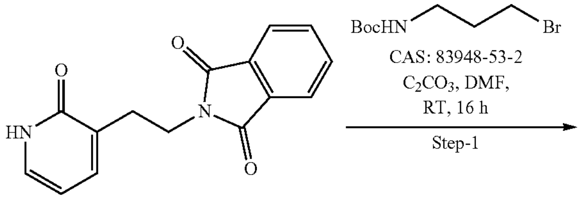

XLd

-continued

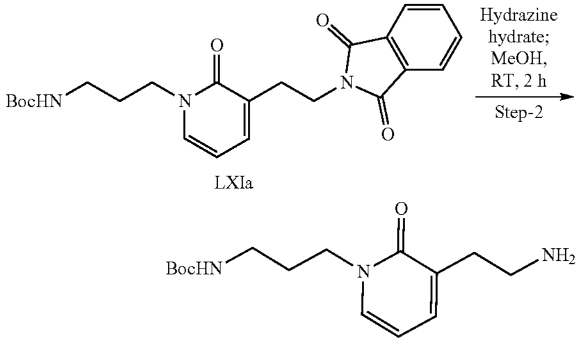

LXIa

LXI

Step-1: tert-butyl (3-(3-(2-(1,3-dioxoisoindolin-2-yl) ethyl)-2-oxopyridin-1(2H)-yl) propyl) carbamate (LXIa)

To a solution of 2-(2-(2-oxo-1,2-dihydropyridin-3-yl) ethyl) isoindoline-1,3-dione XLd (0.6 g, 2.24 mmol) in DMF (6 mL) at rt was added $Cs_2CO_3$ (0.874 g, 2.68 mmol) followed by tert-butyl (3-bromopropyl) carbamate (CAS: 83948-53-2, 0.639 g, 2.68 mmol) and the reaction mixture was stirred at rt for 16 h. The progress of the reaction was monitored by TLC analysis. After the completion, added water (20 mL) and extracted with ethyl acetate (25 mL×2). The combined organic layer was washed with brine (10 mL×2), dried over anhydrous sodium sulphate, and concentrated under reduced pressure. The crude compound was purified by silica gel (100-200 mesh) with ethyl acetate in n-hexane (0-50%) to afford the desired product LXIa as a colorless liquid. Yield: 0.7 g, (74.0%); LCMS Calculated. for $C_{23}H_{27}N_3O_5$ is 425.19; Observed: 426.35 $[M+H]^+$.

Step-2: tert-butyl (3-(3-(2-aminoethyl)-2-oxopyridin-1(2H)-yl) propyl) carbamate (LXI)

To a solution of tert-butyl (3-(3-(2-(1,3-dioxoisoindolin-2-yl) ethyl)-2-oxopyridin-1(2H)-yl) propyl) carbamate LXIa (0.7 g, 2 mmol) in methanol (10 mL) at rt was added hydrazine hydrate (0.2 mL, 3 mmol) and the reaction mixture was stirred at rt for 2 h. The progress of the reaction was monitored by TLC analysis. After the completion, the reaction mixture was concentrated, added water (2 mL) and acidified with conc. HCl to pH-2. The solids were filtered, basified by 2N sodium hydroxide, and extracted with dichloromethane (200 mL×3). The combined organic layer was dried over anhydrous sodium sulphate and concentrated under reduced pressure to afford the desired product as a colorless viscous liquid. The crude compound LXI was taken for the next step without any further purification. Yield: 0.38 g, (80%); LCMS Calculated. for $C_{15}H_{25}N_3O_3$ is 295.18; Observed: 296.35 $[M+H]^+$.

Synthesis of 3-(2-aminoethyl)-1-(2-((tert-butyl diphenyl silyl) oxy) ethyl) pyridine-2(1H)-one. (LXII)

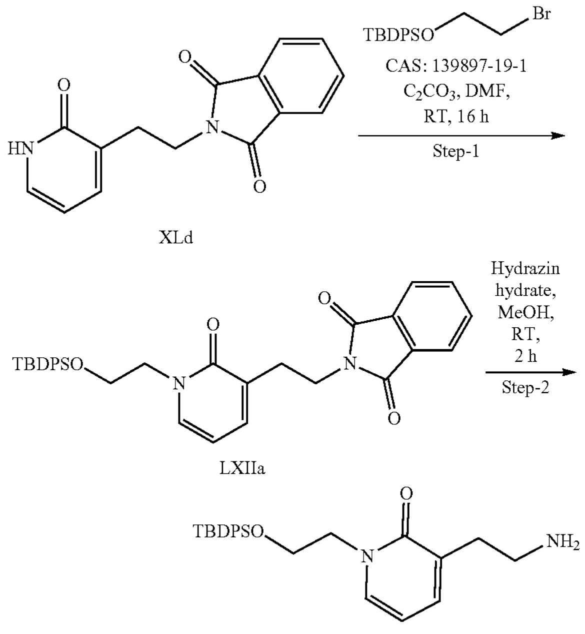

XLd

LXIIa

LXII

Step-1: tert-butyl (3-(3-(2-(1,3-dioxoisoindolin-2-yl) ethyl)-2-oxopyridin-1(2H)-yl) propyl) carbamate (LXIIa)

To a solution of 2-(2-(2-oxo-1,2-dihydropyridin-3-yl) ethyl) isoindoline-1,3-dione XLd (1.2 g, 4.5 mmol) in DMF (10 mL) were added (2-bromoethoxy) (tert-butyl) diphenyl silane (CAS: 139897-19-1, 2.0 g, 5.4 mmol) and cesium carbonate (2.2 g, 6.7 mmol). The reaction mixture was stirred at rt for 16 h. The progress of the reaction was monitored by TLC analysis. After the completion of the reaction, added water (50 mL) and extracted with ethyl acetate (200 mL×3). The combined organic layer was dried over anhydrous sodium sulphate and concentrated under reduced pressure. The crude compound was purified by silica gel (60-120 mesh) column chromatography with ethyl acetate in hexane (0-50%) to afford the desired product LXIIa as a pale-yellow solid. Yield:1.2 g, (48%); LCMS Calculated. for $C_{33}H_{34}N_2O_4Si$ is 550.22; Observed: 551.40 $[M+H]^+$. $^1H$ NMR (400 MHz, $CDCl_3$): δ 7.79 (q, J=2.8 Hz, 2H), 7.68-7.67 (m, 2H), 7.53 (d, J=7.2 Hz, 4H), 7.42-7.26 (m, 7H), 7.14 (d, J=6.4 Hz, 1H), 5.97 (t, J=7.2 Hz, 1H), 4.08-3.93 (m, 6H), 2.90 (t, J=8.0 Hz, 2H), 1.01 (s, 9H).

Step-2: tert-butyl (3-(3-(2-aminoethyl)-2-oxopyridin-1(2H)-yl) propyl) carbamate (LXII)

To a solution of 2-(2-(1-(2-((tert-butyl diphenyl silyl) oxy) ethyl)-2-oxo-1,2-dihydropyridin-3-yl) ethyl) isoindoline-1,3-dione LXIIa (1.2 g, 2.2 mmol) in methanol (4 mL) was added hydrazine hydrate (0.13 g, 2.6 mmol) and the reaction mixture was stirred at rt for 2 h. The progress of the reaction was monitored by TLC analysis. After the completion, the reaction mixture was concentrated, added water (2 mL) and acidified with conc. HCl to pH~2. The solids were filtered, basified by 2N NaOH and extracted with 10% methanol in dichloromethane (200 mL×3). The combined organic layer was dried over anhydrous sodium sulphate and concentrated to afford the desired product LXII as a pale-yellow viscous liquid. The crude compound was taken for the next step without any further purification. Yield: 7 g; LCMS Calculated. for $C_2H_{32}N_2O_2Si$ is 420.22; Observed: 421.35 $[M+H]^+$.

Synthesis of 2-(6-(1-((tert-butyl diphenyl silyl) oxy)-2,2,2-trifluoroethyl) pyridin-2-yl) ethan-1-amine. (LXIII)

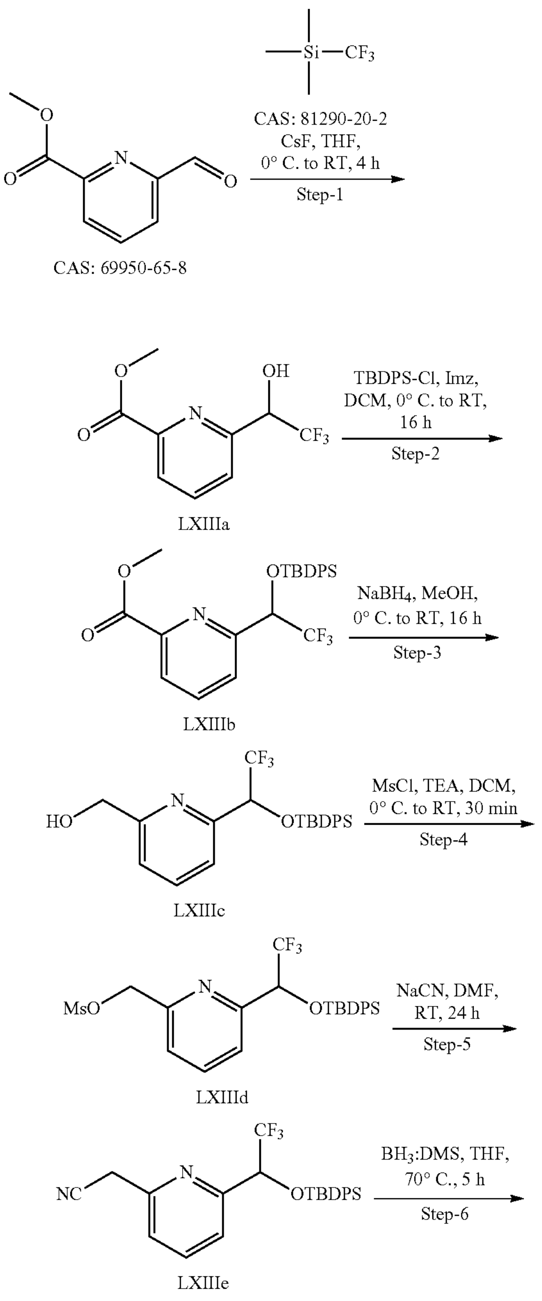

-continued

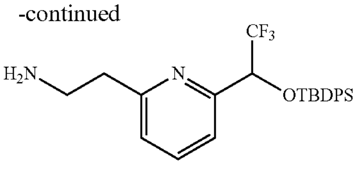

LXIII

Step-1: Synthesis of methyl 6-(2,2,2-trifluoro-1-hydroxyethyl) picolinate (LXIIIa)

A stirred solution of methyl 6-formylpicolinate (CAS: 69950-65-8, 2.5 g, 15 mmol) in THF (10 mL) was cooled to 0° C. under inert atmosphere and were added CsF (4.6 g, 30 mmol) and trimethyl(trifluoromethyl)silane (CAS: 81290-20-2, 3.2 g, 23 mmol). The reaction mixture was stirred at rt for 4 h and the progress of the reaction was monitored by TLC analysis. After completion, the reaction was quenched with water (30 mL) and extracted with ethyl acetate (100 mL×3). The combined organic layer was concentrated under reduced pressure. The crude was triturated with n-pentane (20 mL×3) and dried to afford the desired compound LXIIIa as a pale-yellow solid. Yield: 3.0 g (83.0%); LCMS Calculated. for $C_9H_8F_3NO_3$ is 235.05; Observed: 236.20 $[M+H]^+$. $^1$H NMR (400 MHz, $CDCl_3$): δ 8.18 (d, J=7.6 Hz, 1H), 7.96 (t, J=7.6 Hz, 1H), 7.65 (d, J=8.0 Hz, 1H), 5.17-5.14 (q, J=6.4 Hz, 1H), 4.01 (s, 3H)

Step-2: methyl 6-(1-((tert-butyl diphenyl silyl) oxy)-2,2,2-trifluoroethyl) picolinate (LXIIIb)

A stirred solution of methyl 6-(2,2,2-trifluoro-1-hydroxyethyl) picolinate LXIIIa (3 g, 0.01 mol) in DCM (500 mL) was cooled to 0° C. and added imidazole (2 g, 0.03 mol). This was followed by drop wise addition of tert-butyl choro diphenyl silane (7 g, 0.03 mol). The reaction mixture was stirred at rt for 16 h. The progress of the reaction was monitored by TLC analysis. After completion, the reaction was quenched with water (50 mL) and the resulting mixture was extracted with ethyl acetate (200 mL×3). The combined organic layer was dried over anhydrous sodium sulphate and concentrated under reduced pressure. The crude was purified by silica gel (230-400) column chromatography using 10-20% ethyl acetate/n-hexane to afford the desired compound LXIIIb as a pale-yellow liquid. Yield: 6.0 g, (100%); LCMS Calculated. for $C_{25}H_{26}F_3NO_3Si$ is 473.16; Observed: 474.25 $[M+H]^+$.

Step-3: (6-(1-((tert-butyl diphenyl silyl) oxy)-2,2,2-trifluoroethyl)pyridin-2-yl)methanol (LXIIIc)

A stirred solution of methyl 6-(1-((tert-butyl diphenyl silyl) oxy)-2,2,2-trifluoroethyl) picolinate LXIIIb (6 g, 0.01 mol) in MeOH (60 mL) was cooled to 0° C. and $NaBH_4$ (2 g, 0.05 mol) was added in portions. The reaction mixture was stirred at rt for 16 h and the progress of the reaction was monitored by TLC analysis. After completion, the reaction mixture was concentrated and added sat. $NaHCO_3$ solution (500 mL). The resulting mixture was extracted with DCM (600 mL×3) and concentrated under reduced pressure. The crude was purified by silica gel (230-400 mesh) column chromatography using 10-50% ethyl acetate in n-hexane to afford the desired compound LXIIIc as a pale-yellow viscous liquid. Yield: 4.5 g (75%); LCMS Calculated. for $C_{24}H_{26}F_3NO_2Si$ is 445.17; Observed. 446.30 $[M+H]^+$. $^1H$ NMR (400 MHz, $CDCl_3$): δ 7.64 (q, J=7.6 Hz, 3H), 7.51 (d, J=7.6 Hz, 1H), 7.44 (d, J=6.8 Hz, 3H), 7.38-7.32 (m, 3H), 7.26-7.20 (m, 2H), 7.11 (t, J=7.6 Hz, 1H), 5.07 (q, J=6.4 Hz, 1H), 4.61 (d, J=4.8 Hz, 2H), 3.41 (t, J=4.8 Hz, 1H), 1.55 (s, 1H), 1.08 (s, 9H).

Step-4: (6-(1-((tert-butyl diphenyl silyl) oxy)-2,2,2-trifluoroethyl) pyridin-2-yl) methyl methane sulfonate (LXIIId)

A stirred solution of (6-(1-((tert-butyl diphenyl silyl) oxy)-2,2,2-trifluoroethyl) pyridin-2-yl) methanol LXIIIc (4.5 g, 10 mmol) in DCM (100 mL) was cooled to 0° C. and added TEA (6.1 g, 8.4 mL, 61 mmol). The resulting mixture was stirred for 5 min and mesyl-Cl (1.2 mL, 15 mmol) was added dropwise. The reaction mixture was stirred at 0° C. for 30 min and the progress of the reaction was monitored by TLC analysis. After completion, the reaction was quenched with sat. $NaHCO_3$ solution (100 mL) and extracted with DCM (300 mL×3). The combined organic layer was dried over anhydrous sodium sulphate and concentrated under reduced pressure to afford desired compound LXIIId as a brown liquid. The crude compound was taken for next step without further purification. Yield: 5 g (96%).

Step-5: 2-(6-(1-((tert-butyl diphenyl silyl) oxy)-2,2,2-trifluoroethyl) pyridin-2-yl) acetonitrile (LXIIIe)

To a stirred solution of (6-(1-((tert-butyl diphenyl silyl) oxy)-2,2,2-trifluoroethyl) pyridin-2-yl) methyl methane sulfonate LXIIId (6 g, 11.4 mmol) in DMF (60 mL) was added NaCN (1.34 g, 22.9 mmol) and the reaction mixture was stirred at rt for 24 h. The progress of the reaction was monitored by TLC analysis. After completion, the reaction was quenched with water (50 mL) and the resulting mixture was extracted with ethyl acetate (100 mL×3). The combined organic layer was dried over anhydrous sodium sulphate and concentrated under reduced pressure. The crude was purified by silica gel (230-400 mesh) column chromatography using 10-30% ethyl acetate in n-hexane to afford the desired compound LXIIIe a pale-yellow viscous liquid. Yield: 2.5 g (83.0%); LCMS Calculated. for $C_{25}H_{25}F_3N_2OSi$ is 454.17; Observed.: 455.30 $[M+H]^+$. $^1H$ NMR (400 MHz, $CDCl_3$): δ 7.72-7.67 (m, 2H), 7.59 (t, J=8.0 Hz, 2H), 7.46-7.32 (m, 6H), 7.25-7.21 (m, 2H), 5.06 (q, J=6.4 Hz, 1H), 3.73 (d, J=8.0 Hz, 2H) 1.07 (bs, 9H)

Step-6: 2-(6-(1-((tert-butyl diphenyl silyl) oxy)-2,2,2-trifluoroethyl) pyridin-2-yl) ethan-1-amine (LXIII)

To a stirred solution of 2-(6-(1-((tert-butyl diphenyl silyl) oxy)-2,2,2-trifluoroethyl) pyridin-2-yl) acetonitrile LXIIIe (2.5 g, 5.5 mmol) in THF (40 mL) at 0° C. was dropwise added $BH_3$·DMS (11 mL, 2 M in THF, 22.0 mmol). The reaction mixture was stirred at 70° C. for 5 h. The progress of the reaction was monitored by TLC analysis. After completion, the reaction mixture was cooled to 0° C. before it was quenched with MeOH (7 mL). The mixture was stirred for 30 min and added 1 M HCl solution (10 mL). The mixture was concentrated to half under reduced pressure and extracted with ethyl acetate (50 mL) followed by with DCM (50 mL) to get rid of impurities. The aqueous layer was basified (pH 8-9) with 2N NaOH and extracted with DCM (500 mL×3), dried over sodium sulphate, and concentrated under reduced pressure to afford the desire compound LXIII as a brown liquid. The crude compound taken for next step without further purification. Yield: 1.6 g (64%); LCMS Calculated. for $C_{25}H_{29}F_3N_2OSi$ is 458.20; Observed.: 459.35 [M+H]

Synthesis of 7-amino-3-(cyclo butyl methyl)-2-methyl-5-(methyl sulfonyl) pyrazolo[1,5-a] pyrimidine-6-carbonitrile. (LXIV)

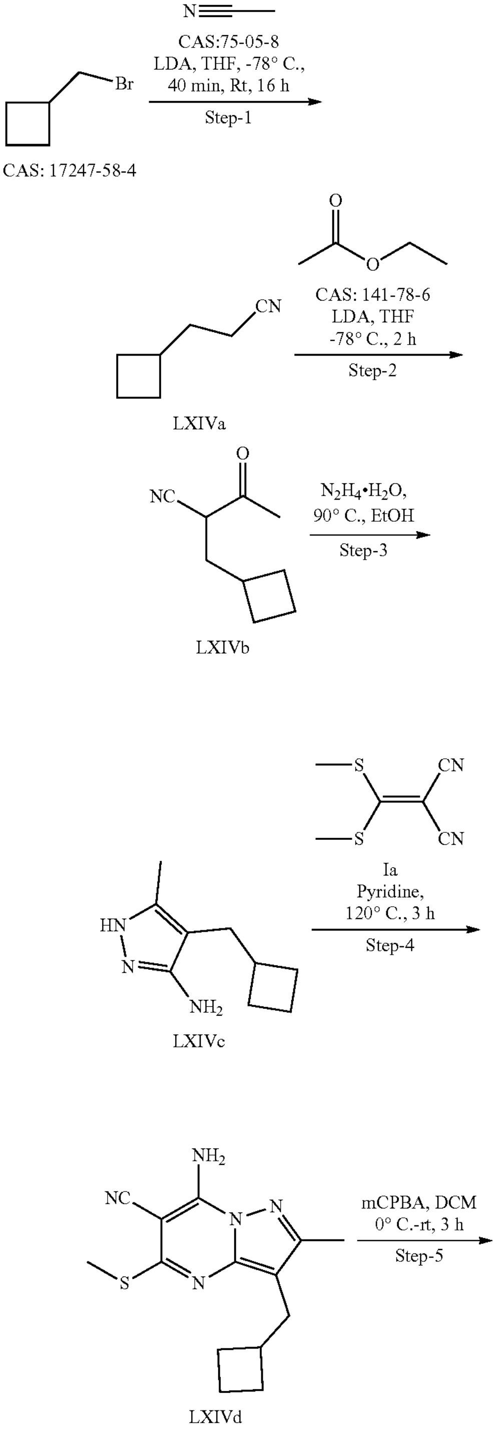

LXIVa
LXIVb
LXIVc
LXIVd

-continued

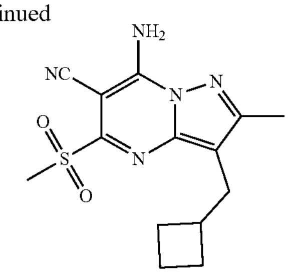

LXIV

Step-1: 3-cyclobutylpropanenitrile (LXIVa)

In a 3 neck RB flask, acetonitrile (CAS:75-05-8, 1.4 g, 1.8 mL, 34 mmol) was taken in dry THF (74.2 mL) and the solution was cooled to −78° C. To this was dropwise added LDA (17 mL, 2.0 M in THF/heptane/ethylbenzene, 34 mmol) under inert atmosphere. The reaction mixture was stirred at −78° C. for 40 min and a solution of (bromomethyl)cyclo butane (CAS: 17247-58-4, 3.8 mL, 34 mmol) in dry THF (15 mL) was added drop wise at −78° C. The reaction mixture was stirred at room temperature for 16 h. The reaction mixture was cooled to 0° C. and quenched with saturated ammonium chloride solution (65 mL). The resulting mixture was extracted with DCM (50 mL×3). The combined organic layer was dried over anhydrous sodium sulphate and concentrated under reduced pressure. The crude was purified by flash column chromatography using 0-10% ethyl acetate in n-hexane to afford the desired compound LXIVa as a pale-yellow liquid. Yield: 1.65 g, (37.2%).

Step-2: 2-(cyclo butyl methyl)-3-oxobutanenitrile (LXIVb)

In a 3 neck RB flask, LDA (5.0 mL, 2.0 M in THF/heptane/ethylbenzene, 10 mmol) was diluted with dry THF (11.5 mL) under inert atmosphere and cooled to −78° C. To this was dropwise added a solution 3-cyclobutylpropanenitrile LXIVa (1.1 g, 10 mmol) in dry THF (6.0 mL) at −78° C. The reaction mixture was stirred at −78° C. for 1 h. Then dry ethyl acetate (CAS: 141-78-6, 0.81 g, 0.90 mL, 9.2 mmol) was drop wise added at −78° C. and stirring was continued for additional 1 h maintaining reaction temperature at −78° C. The reaction mixture was quenched with saturated ammonium chloride solution (6.0 mL) and extracted with diethyl ether (20 mL×3). The combined organic layer was dried over anhydrous sodium sulphate and concentrated under reduced pressure to afford the desired product LXIVb as a brown liquid. The crude product was taken for the next step without further purification. Yield: (1.65 g, 37.24%).

Step-3: 4-(cyclobutylmethyl)-5-methyl-1H-pyrazol-3-amine (LXIVc)

To a solution of 2-(cyclobutylmethyl)-3-oxobutanenitrile LXIVb (1.5 g, 9.9 mmol) in ethanol (16 mL) was added hydrazine hydrate (4.5 mL, 92 mmol) and the reaction mixture was stirred at 120° C. for 1.5 h. The progress of reaction was monitored by TLC analysis. After completion, the reaction mixture was cooled to room temperature and concentrated under reduced pressure. The residue was washed with n-hexane (20 mL×2) and dried under vacuo. To the residue was added water (10 mL) and extracted with 40% isopropanol in chloroform (15 mL×3). The combined organic layer was dried over anhydrous sodium sulphate and concentrated under reduced pressure to afford the desired product LXIVc as a brown oil. The crude was taken for the next step without further purification. Yield: (0.711 g, 44.43%); LCMS Calculated for $C_9H_{15}N_3$ is 165.13; Observed:166.30 $[M+H]^+$.

Step-4: 7-amino-3-(cyclobutylmethyl)-2-methyl-5-(methylthio) pyrazolo[1,5-a] pyrimidine-6-carbonitrile (LXIVd)

To a solution of 4-(cyclobutylmethyl)-5-methyl-1H-pyrazol-3-amine (707 mg, 4.28 mmol) in pyridine (7 mL) was added 2-(bis (methylthio) methylene) malononitrile LXIVc (728 mg, 4.28 mmol) under inert atmosphere. The reaction mixture was stirred at 120° C. for 3 h and progress of the reaction was monitored by TLC analysis. After completion, the reaction was cooled to room temperature and quenched with ice cold water. The mixture was extracted with ethyl acetate (10 mL×3). The combined organic layer was washed with brine, dried over anhydrous sodium sulphate, and concentrated under reduced pressure to get crude material. The crude material was purified by silica gel (100-200) column chromatography using 0-20% ethyl acetate in n-hexane to afford the desired LXIVd as an off-white solid. Yield: 0.40 g (32.5%); LCMS Calculated. for $C_{14}H_{17}N_5S$ is 287.12; Observed: 288.25 $[M+H]^+$.

Step-5: 7-amino-3-(cyclobutylmethyl)-2-methyl-5-(methyl sulfonyl) pyrazolo[1,5-a] pyridine-6carbonotrile (LXIV)

A solution of 7-amino-3-(cyclobutylmethyl)-2-methyl-5-(methylthio) pyrazolo[1,5-a] pyrimidine-6-carbonitrile LXIVd (400 mg, 1.39 mmol) in DCM (10 mL) was cooled to 0° C. and m-CPBA (961 mg, 5.57 mmol) was added in portions. The reaction mixture was stirred at room temperature for 3 h. Progress of reaction was monitored by TLC analysis. After completion, the reaction mixture was quenched by slow addition of saturated sodium bicarbonate solution (50 mL). The resulting mixture was extracted with DCM (20 mL×3). The combined organic layer was dried over anhydrous sodium sulphate and concentrated under reduced pressure to get crude material. The crude material was purified by flash column chromatography (combi-flash) using 0-30% ethyl acetate in n-hexane to afford the desired product LXIV as an off white-solid. Yield: (203 mg (45.61%); LCMS Calculated. for $C_{14}H_{17}N_5O_2S$ is 319.11, Observed. 320.25 $[M+H]^+$; $^1H$ NMR (400 MHz, DMSO-$D_6$): δ 9.19 (bs, 2H), 3.42 (s, 3H), 2.73 (d, J=7.6 Hz, 2H), 2.61-2.58 (m, 1H), 2.41 (s, 3H), 1.93 (d, J=4.4 Hz, 1H), 1.80-1.67 (m, 4H).

Synthesis of 2-(6-(2-((tert-butyl dimethyl silyl) oxy) ethyl) pyridin-2-yl) ethan-1-amine. (LXV)

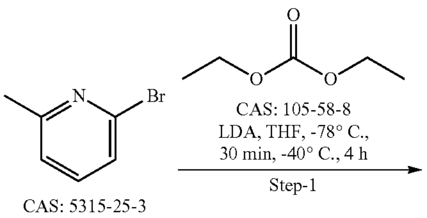

-continued

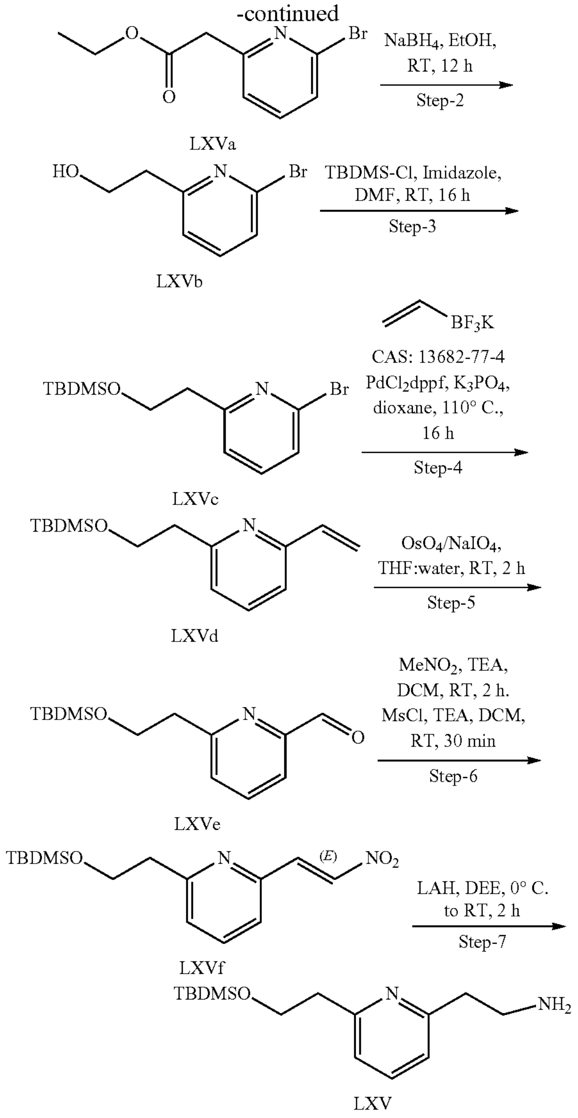

LXVa

LXVb

LXVc

LXVd

LXVe

LXVf

LXV

Step-1: ethyl 2-(6-bromopyridin-2-yl) acetate (LXVa)

A stirred solution of lithium diisopropylamide (110 mL, 2.0 M in THF/heptane/ethylbenzene, 0.22 mol) in THF (500 mL) was cooled to −78° C. and added 2-bromo-6-methylpyridine (CAS: 5315-25-3, 15 g, 87 mmol) under $N_2$ atmosphere. The mixture was stirred at −78° C. for 30 min followed by a dropwise addition of diethyl carbonate (CAS: 105-58-8, 26 g, 0.22 mol) and the reaction mixture was stirred at −40° C. for 4 h. The progress of the reaction was monitored by TLC analysis. After completion, the reaction was quenched with saturated ammonium chloride solution (150 mL) and extracted with ethyl acetate (100 mL×3). The combined organic layer was dried over anhydrous sodium sulfate and concentrated under reduced pressure. The crude residue was subjected to silica gel (230-400) column chromatography using 0-10% ethyl acetate in n-hexane to afford the desired compound LXVa as a colorless liquid. Yield: (12.2 g, 57%); LCMS Calculated. for $C_9H_{10}BrNO_2$ is 242.98; Observed. 244.15 $[M+H]^+$; $^1H$ NMR (400 MHz, $CDCl_3$): δ 7.53 (t, J=7.6 Hz, 1H), 7.39 (d, J=7.6 Hz, 1H), 7.30-7.27 (m, 1H), 4.18 (q, J=7.2 Hz, 2H), 3.83 (s, 2H), 1.27 (t, J=7.2 Hz, 3H).

Step-2: 2-(6-bromopyridin-2-yl) ethan-1-ol. (LXVb)

To a stirred solution of ethyl 2-(6-methylpyrazin-2-yl) acetate LXVa (3 g, 10 mmol) in ethanol (30 mL) was added sodium borohydride (2.32 g, 61.47 mmol) at 0° C. in portions under $N_2$ atmosphere and the reaction mixture was stirred at room temperature for 12 h. The progress of the reaction was monitored by TLC analysis. After completion, the reaction was quenched with water (50 mL) and the resulting mixture was extracted with ethyl acetate (30 mL×3). The combined organic layer was dried over sodium sulphate and concentrated under reduced pressure to afford the pure compound LXVb as colorless viscous liquid. Yield: (1.7 g, 70%); LCMS Calculated. for $C_7H_8BrNO$ is 200.97; Observed. 202.00 $[M+H]^+$; $^1H$ NMR (400 MHz, $CDCl_3$): δ 7.48 (t, J=8.0 Hz, 1H), 7.35 (d, J=8.0 Hz, 1H), 7.14 (d, J=8.0 Hz, 1H), 4.02 (q, J=5.2 Hz, 2H), 3.03-3.00 (m, 3H).

Step-3: 2-bromo-6-(2-((tert-butyldimethylsilyl) oxy) ethyl) pyridine (LXVc)

To a stirred solution of 2-(6-bromopyridin-2-yl) ethan-1-ol LXVb (1.7 g, 8.4 mmol) in DCM (25 mL) was added 1H-imidazole (1.1 g, 17 mmol) and the reaction mixture stirred at room temperature for 30 min under nitrogen followed by drop wise addition of tert-butyl choro dimethyl silane (2.5 g, 17 mmol) at 0° C. The resulting mixture was stirred at room temperature for 16 h and the progress of the reaction was monitored by TLC analysis. After completion, the reaction mixture was quenched with water (50 mL) and extracted with DCM (20 mL×2). The combined organic layer was dried over anhydrous sodium sulphate. The residue obtained upon removal of the solvent was subjected to silica gel (230-400 mesh) column chromatography using (0-6%) ethyl acetate in n-hexane to afford the desired compound LXVc as a colorless viscous liquid. Yield: 2.3 g (86%); LCMS Calculated. for $C_3H_{22}BrNOSi$ is 315.06; Observed. 316.25 $[M+H]^+$; $^1H$NMR (400 MHz, $CDCl_3$): δ 7.44 (t, J=7.6 Hz, 1H), 7.31 (d, J=7.6 Hz, 1H), 7.16 (d, J=7.6 Hz, 1H), 3.96 (t, J=6.0 Hz, 2H), 2.95 (t, J=6.0 Hz, 2H), 0.82 (s, 9H), 0.06 (s, 6H).

Step-4: 2-(2-((tert-butyldimethylsilyl) oxy) ethyl)-6-vinylpyridine (LXVd)

To a stirred solution of 2-bromo-6-(2-((tert-butyldimethylsilyl) oxy) ethyl) pyridine LXVc (2.3 g, 7.3 mmol) was added potassium trifluoro(vinyl)borate (1.1 g, 8.0 mmol) and potassium phosphate tribasic (2.3 g, 11 mmol) in 1,4 dioxane (30 mL) and purged with $N_2$ gas for 15 min with vigorous stirring. To the reaction was added $PdCl_2(dppf)$ (0.27 g, 0.36 mmol) and the seal tube with Teflon screw-stopper was closed and heated to 110° C. for 16 h. The progress of the reaction was monitored by TLC analysis. After completion, the reaction mixture was cooled to room temperature and concentrated under reduced pressure. To the residue was added 70 mL of water and extracted with ethyl acetate (50 mL×2). The combined organic layer was dried over anhydrous sodium sulphate and concentrated to obtain crude product. The crude product was subjected to silica gel (230-400 mesh) column chromatography using 0-6% ethyl acetate in n-hexane to afford the desired compound LXVd as a colorless viscous liquid. Yield: 1.6 g (84%); LCMS Calculated. for $C_{15}H_{25}NOSi$ is 263.17; Observed. 264.30 $[M+H]^+$; $^1H$ NMR (400 MHz, $CDCl_3$): δ 7.54 (t, J=7.6 Hz, 1H), 7.18 (d, J=7.6 Hz, 1H), 7.07 (d, J=7.6 Hz, 1H), 6.81 (dd, J=17.6, 10.8 Hz, 1H), 6.17 (d, J=17.6 Hz, 1H), 5.44 (d, J=10.8 Hz, 1H), 4.00 (t, J=6.4 Hz, 2H), 2.99 (t, J=6.4 Hz, 2H), 0.83 (s, 9H), 0.05 (s, 6H).

Step-5: 6-(2-((tert-butyldimethylsilyl) oxy) ethyl) picolinaldehyde (LXVe)

To a stirred solution of 2-(2-((tert-butyldimethylsilyl) oxy) ethyl)-6-vinylpyridine LXVd (1.6 g, 6.1 mmol) in THF (1.1 mL) and water (2.5 mL) was added osmium (VIII) oxide (3.8 mL, 4% in $H_2O$, 0.61 mmol) at 0° C. and the reaction mixture was stirred at room temperature for 30 min. This was followed by portion wise addition of sodium metaperiodate (1.9 g, 9.1 mmol) and the reaction was stirred at room temperature for 2 h. The progress of the reaction was monitored by TLC analysis. After completion, the reaction mixture was diluted with water (15 mL) and the resulting mixture was extracted with ethyl acetate (20 mL×2). The combined organic layer was dried over anhydrous sodium sulphate. The residue obtained upon removal of the solvent was subjected to silica gel (230-400 mesh) column chromatography using 0-6% ethyl acetate in n-hexane to afford the desired compound LXVe as a colorless viscous liquid. Yield: 0.7 g (40%); LCMS Calculated. for $C_{14}H_{23}NO_2Si$ is 265.14; Observed. 266.30 $[M+H]^+$; $^1H$ NMR (400 MHz, $CDCl_3$): δ 10.06 (s, 1H), 7.82-7.75 (m, 2H), 7.44 (d, J=7.2 Hz, 1H), 4.03 (t, J=6.4 Hz, 2H), 3.09 (t, J=6.4 Hz, 2H), 0.82 (s, 9H), 0.06 (s, 6H).

Step-6: (E)-2-(2-((tert-butyldimethylsilyl) oxy) ethyl)-6-(2-nitrovinyl) pyridine (LXVf)

To a stirred solution of 6-(2-((tert-butyldimethylsilyl) oxy) ethyl) picolinaldehyde LXVe (0.7 g, 3 mmol) in DCM (20 mL) was added triethylamine (2.78 mL, 20 mmol) and nitromethane (0.3 mL, 8 mmol) under nitrogen atmosphere. The resulting mixture was stirred at room temperature for 2 h and the progress of the reaction was monitored by TLC analysis. After completion of reaction, DCM was concentrated under reduced pressure. The resulting residue was taken in DCM (20 mL) was added triethylamine (2.78 mL, 20 mmol) and cooled to 0° C. followed by drop wise addition of methane sulfonyl chloride (0.6 mL, 8 mmol). The resulting mixture was stirred at 0° C. for 30 min and the progress of the reaction was monitored by TLC analysis. After completion, the reaction mixture was diluted with water (40 mL) and extracted with DCM (20 mL×2). The combined organic layer was dried over anhydrous sodium sulphate. The residue obtained upon removal of the solvent was subjected to silica gel (230-400 mesh) column chromatography using 0-6% ethyl acetate in n-hexane to afford the desired compound LXVf as a yellow viscous liquid. Yield: 0.7 g, (90%); LCMS Calculated. for $C_{15}H_{24}N_2O_3Si$ is 308.15; Observed. 309.30 $[M+H]^+$; $^1H$ NMR (400 MHz, $CDCl_3$): δ 8.02 (d, J=13.2 Hz, 1H), 7.89 (d, J=13.2 Hz, 1H), 7.66 (t, J=7.6 Hz, 1H), 7.31-7.29 (m, 2H), 4.00 (t, J=6.4 Hz, 2H), 3.07-2.99 (m, 2H), 0.80 (s, 9H), 0.06 (s, 6H).

Step-7: 2-(6-(2-((tert-butyldimethylsilyl) oxy) ethyl) pyridin-2-yl) ethan-1-amine (LXV)

To a stirred solution of aluminum (III) lithium hydride (10 mL, 1.0 M in THF, 10 mmol) in diethyl ether (70 mL) was dropwise added (E)-2-(2-((tert-butyldimethylsilyl) oxy) ethyl)-6-(2-nitrovinyl) pyridine LXVf (0.7 g, 3 mmol) at 0° C. under nitrogen atmosphere. The reaction mixture was stirred at room temperature for 2 h and the reaction was monitored by TLC analysis. After completion, the reaction mixture was cooled to 0° C. was added 1 mL of ice-cold water and 1 mL of 15% KOH solution then stirred at room temperature for another 30 min. The resulting reaction mixture was diluted with 250 mL of ethyl acetate filtered through Buchner funnel and the solid was thoroughly washed with 250 mL of ethyl acetate. The filtrate was dried over anhydrous sodium sulphate and concentrated under reduced pressure to afford a desired compound LXV as light brown viscous liquid. Yield: 0.54 g (85%); LCMS Calculated. for $C_{15}H_{28}N_2OSi$ is 280.20; Observed. 281.35 $[M+H]^+$; $^1H$ NMR (400 MHz, $CDCl_3$): δ 7.50 (t, J=7.6 Hz, 1H), 7.31-7.29 (m, 1H), 7.05-6.98 (m, 2H), 6.89 (d, J=8.4 Hz, 1H), 3.96 (t, J=6.4 Hz, 2H), 3.10-2.88 (m, 6H), 0.80 (s, 9H), 0.06 (s, 6H).

Synthesis of 2-(6-methylpyrazin-2-yl) ethan-1-amine (LXVI)

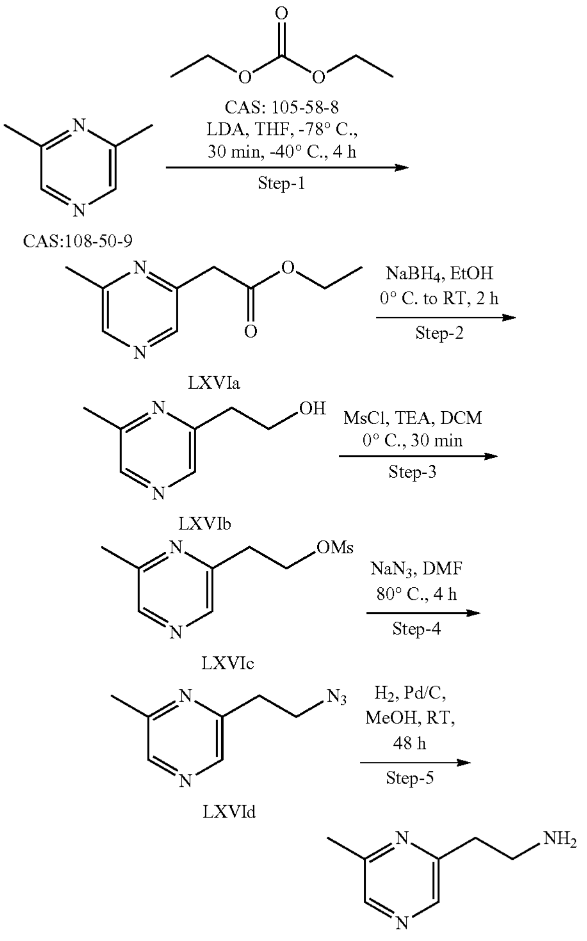

CAS:108-50-9

LXVIa

LXVIb

LXVIc

LXVId

LXVI

Step-1: Synthesis of ethyl 2-(6-methylpyrazin-2-yl) acetate (LXVIa)

To a stirred solution of 1.0 M lithium diisopropylamide (7 g, 0.07 L, 70 mmol) in THF (80 mL) was cooled to −78° C.

was added 2,6-dimethylpyrazine (CAS:108-50-9, 3 g, 30 mol) under $N_2$ atmosphere and stirred at −78° C. for 30 min followed by dropwise addition of diethyl carbonate (CAS: 105-58-8, 4 g, 4 mL, 30 mol) and then the reaction mixture was stirred at −40° C. for 4 h. The progress of the reaction was monitored by TLC analysis. After completion, the reaction was quenched with saturated ammonium chloride solution (50 mL) and extracted with ethyl acetate (30 mL×3). The combined organic layer was dried over anhydrous sodium sulfate and concentrated under reduced pressure. The crude residue was subjected to silica gel (230-400) column chromatography using 0-30% ethyl acetate in n-hexane to afford the desired compound LXVIa as a colorless liquid. Yield: 4.5 g (90%); LCMS Calculated. for $C_9H_{12}N_2O_2$ is 180.08; Observed. 181.30 $[M+H]^+$; $^1$HNMR (400 MHz, $CDCl_3$): δ 8.39-8.36 (m, 2H), 4.20 (q, J=7.2 Hz, 2H), 3.83 (s, 2H), 2.55 (s, 3H), 1.27 (t, J=7.2 Hz, 3H).

Step-2: 2-(6-methylpyrazin-2-yl) ethan-1-ol (LXVIb)

To a stirred solution of ethyl 2-(6-methylpyrazin-2-yl) acetate LXVIa (4.5 g, 25 mmol) in ethanol (100 mL) was added sodium borohydride (3.8 g, 100 mmol) at 0° C. in portions under $N_2$ atmosphere and the reaction mixture was stirred at room temperature for 2 h. The progress of the reaction was monitored by TLC analysis. After completion, the reaction was quenched with water (50 mL) and the resulting mixture was extracted with ethyl acetate (30 mL×3). The combined organic layer was dried over sodium sulphate and concentrated under reduced pressure to afford the pure compound LXVIb as colorless viscous liquid. Yield: (3.5 g, 100%); LCMS Calculated. for $C_7H_{10}N_2O$ is 138.07; Observed. 139.30 $[M+H]^+$; $^1$HNMR (400 MHz, $CDCl_3$): δ 8.33-8.29 (m, 2H), 5.31 (t, 1H), 4.03 (t, J=5.6 Hz, 2H), 3.02 (t, J=5.6 Hz, 2H) 2.55 (s, 3H).

Step-3: 2-(6-methylpyrazin-2-yl) ethyl methane sulfonate (LXVIc)

To a stirred solution of 2-(6-methylpyrazin-2-yl) ethan-1-ol LXVIb (3.5 g, 25 mmol) in DCM (100 mL) was added triethylamine (6.4 g, 8.8 mL, 63 mmol) followed by dropwise addition of mesyl chloride (3.8 g, 2.6 mL, 33 mmol) at 0° C. and stirred the reaction mixture at 0° C. for 30 min. The progress of the reaction was monitored by TLC analysis. After completion, the reaction was quenched with water (20 mL) and the resulting mixture was extracted with DCM (20 mL×3). The combined organic layer was dried over sodium sulphate and concentrated under reduced pressure to afford the pure compound LXVIc as a brown liquid. Yield: 5.0 g (90%); LCMS Calculated. for $C_8H_{12}N_2O_3S$ is 216.05; Observed. 217.25 $[M+H]^+$; $^1$HNMR (400 MHz, $CDCl_3$): δ 8.35-8.31 (m, 2H), 4.65 (t, J=6.0 Hz, 2H), 3.21 (t, J=6.4 Hz, 2H), 3.01 (s, 3H) 2.55 (s, 3H).

Step-4: 2-(2-azidoethyl)-6-methylpyrazine (LXVId)

To a solution of 2-(6-methylpyrazin-2-yl) ethyl methane sulfonate LXVIc (5 g, 20 mmol) in DMF (50 mL) was added sodium azide (6 g, 90 mmol) and the resulting mixture was stirred at 80° C. for 4 h under $N_2$ atmosphere. The progress of the reaction was monitored by TLC analysis. After completion, the reaction was quenched with ice cold water (20 mL) and the resulting mixture was extracted with ethyl acetate (20 mL×3). The combined organic layer was dried over sodium sulphate and concentrated under reduced pressure to afford the pure compound LXVId as a brown viscous liquid. Yield: 3.9 g (97.5%); LCMS Calculated. for $C_7H_9N_5$ is 163.08; Observed. 164.05 $[M+H]^+$; $^1$HNMR (400 MHz, $CDCl_3$): δ 8.38-8.31 (m, 2H), 3.73 (t, J=6.4 Hz, 2H), 3.04 (t, J=6.8 Hz, 2H), 2.56 (s, 3H).

Step-5: 2-(6-methylpyrazin-2-yl) ethan-1-amine (LXVI)

To a stirred solution of 2-(2-azidoethyl)-6-methylpyrazine LXVId (3.9 g, 24 mmol) in methanol (80 mL) was added Pd/C (10%, 1.3 g, 12 mmol) under $N_2$ atmosphere and stirred at room temperature for 48 h under $H_2$ bladder. The progress of the reaction was monitored by TLC analysis. After completion, the reaction mixture was filtered through celite bed, washed with methanol (25 ml×2) and concentrated under reduced pressure to afford the desired compound LXVI as a colorless viscous liquid. Yield: 2.2 g (67%); LCMS Calculated. for $C_7H_{11}N_3$ is 137.09; Observed. 138.30 $[M+H]^+$; $^1$HNMR (400 MHz, $CDCl_3$): δ 8.29 (d, J=8.8 Hz, 2H), 3.10 (t, J=6.8 Hz, 2H), 2.96-2.89 (m, 4H), 2.55 (s, 3H).

Synthesis of 3-(2-aminoethyl)-1-(2-(methylthio) ethyl) pyridine-2(1H)-one (LXVII)

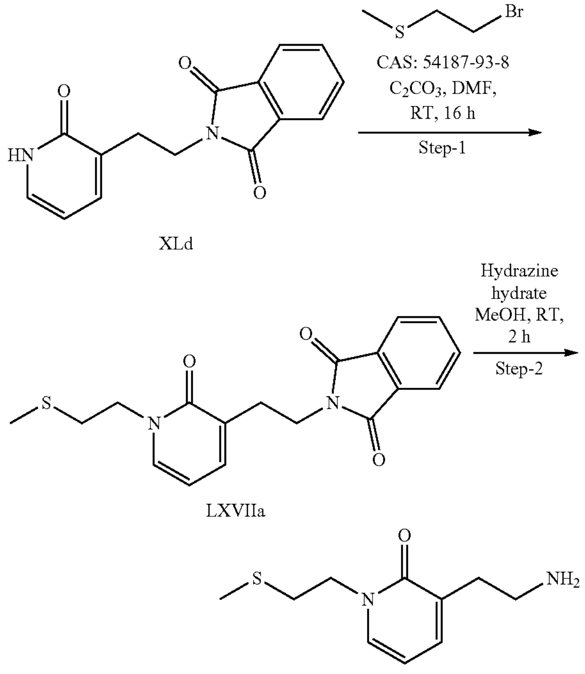

XLd
LXVIIa
LXVII

Step-1: 2-(2-(1-(2-(methylthio) ethyl)-2-oxo-1,2-dihydropyridin-3-yl) ethyl) isoindoline-1,3-dione (LXVIIa)

To a stirred solution of 2-(2-(2-oxo-1,2-dihydropyridin-3-yl) ethyl) isoindoline-1,3-dione XLd (8 g, 0.03 mol) in DMF (80 mL) was added $Cs_2CO_3$ (10 g, 0.04 mol) at rt under $N_2$ atmosphere. This was followed by a drop wise addition of (2-chloroethyl) (methyl) sulfane (CAS: 54187-93-8, 4 g, 0.04 mol) and the reaction mixture was stirred at rt for 16 h. The progress of the reaction was monitored by TLC analysis which indicated the formation of less polar spot corresponds to O-alkylated product and polar spot corresponds to N-alkylated product. After completion of the reaction, water (100 ml) was added, and the mixture was extracted with ethyl acetate (150 mL×2). The combined organic layer was washed with brine, dried over anhydrous sodium sulfate, and concentrated over reduced pressure. The crude compound was purified by flash column chromatography (silica gel, 230-400) using ethyl acetate in n-hexane (0-40%) to afford the desired compound LXVIIa as a colorless viscous liquid. Yield: 6.0 g (60%); LCMS Calculated. for $C_{18}H_{18}N_2O_3S$ is 342.10; Observed. 343.25. $[M+H]^+$. $^1H$ NMR (400 MHz, $CDCl_3$) δ 7.80 (q, J=2.8 Hz, 2H), 7.69 (q, J=3.2 Hz, 2H), 7.22 (t, J=6.4 Hz, 1H), 7.12 (d, J=6.0 Hz, 1H), 6.02 (t, J=6.4 Hz, 1H), 4.10-4.00 (m, 4H), 3.31-2.70 (m, 4H), 2.07 (s, 3H).

Step-2: 3-(2-aminoethyl)-1-(2-(methylthio) ethyl) pyridin-2(1H)-one (LXVII)

To a stirred solution of 2-(2-(1-(2-(methylthio) ethyl)-2-oxo-1,2-dihydropyridin-3-yl) ethyl) isoindoline-1,3-dione LXVIIa (6.0 g, 17.52 mmol) in MeOH (60 mL) was added hydrazine hydrate (1.316 g, 26.28 mmol) and the reaction mixture was stirred at rt for 2 h. The progress of the reaction was monitored by TLC analysis. After completion, the reaction mixture was concentrated, and the residue was dissolved in water (10 mL). The resulting mixture was acidified (pH=2) with conc. HCl and the solid formed was removed by filtration. The filtrate was basified with 4N NaOH solution (pH=8-9) and extracted with methanol: DCM (0.5:9.5 v/v) (300 mL×3). The combined organic layer was dried over anhydrous sodium sulphate and concentrated under reduced pressure to afford the desired compound LXVII as a sticky solid. The crude compound was taken for next step without further purification. Yield: 4.0 g (100%); LCMS Calculated. for $C_{10}H_{16}N_2OS$ is 212.10; Observed. 213.25 $[M+H]^+$. $^1H$ NMR (400 MHz, $CDCl_3$): δ 8.02 (s, 4H), 7.24 (t, J=13.6 Hz, 2H), 6.14 (t, J=6.8 Hz, 1H), 4.11 (d, J=6.8 Hz, 2H), 3.47 (s, 2H), 2.94 (m, 2H), 2.68 (t, J=6.8 Hz, 2H), 2.11 (s, 3H).

Synthesis of N-(3-(3-(2-aminoethyl)-2-oxopyridin-1 (2H)-yl) propyl) acetamide (LXVIII)

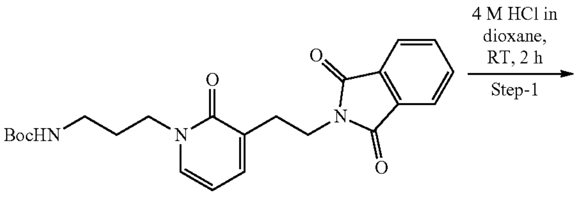

LXIa

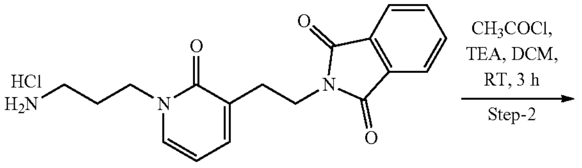

LXVIIIa

-continued

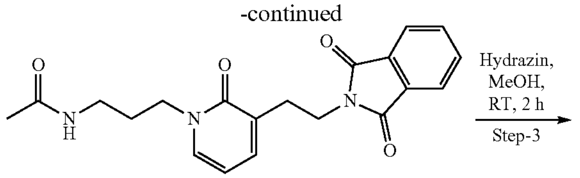

LXVIIIb

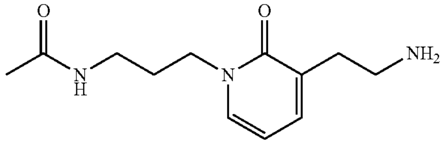

LXVIII

Step-1: 2-(2-(1-(3-aminopropyl)-2-oxo-1,2-dihydropyridin-3-yl)ethyl)isoindoline-1,3-dione (LXVIIIa)

To a stirred solution of tert-butyl (3-(3-(2-(1,3-dioxoisoindolin-2-yl)ethyl)-2-oxopyridin-1(2H)-yl)propyl)carbamate LXIa (700 mg, 1.65 mmol) in 1,4-dioxane (4 mL) was added HCl in dioxane (0.412 mL, 4 molar, 1.65 mmol) at 0° C. under $N_2$ atmosphere. The reaction mixture was stirred at rt for 2 h and progress of the reaction was monitored by TLC analysis. After completion, the reaction mixture was concentrated under reduced pressure, the residue was triturated with diethyl ether and dried under vacuo to afford the desired compound LXVIIIa as an off-white solid. Yield: 430 mg (80%); LCMS Calculated. for $C_{18}H_{19}N_3O_3$ is 325.14; Observed.: 326.25 $[M+H]^+$; $^1H$ NMR (400 MHz, DMSO-$D_6$): 8.06 (s, 3H), 7.83 (d, J=1.6 Hz, 4H), 7.63 (d, J=5.2 Hz, 1H), 7.19 (d, J=5.6 Hz, 1H), 6.10 (t, J=6.4 Hz, 1H), 3.98 (t, J=6.4 Hz, 2H), 3.85 (t, J=6.0 Hz, 2H), 2.79-2.72 (m, 3H), 1.99-1.92 (m, 2H).

Step-2: N-(3-(3-(2-(1,3-dioxoisoindolin-2-yl) ethyl)-2-oxopyridin-1(2H)-yl) propyl) acetamide (LXVIIIb)

To a stirred solution of 2-(2-(1-(3-aminopropyl)-2-oxo-1,2-dihydropyridin-3-yl) ethyl) isoindoline-1,3-dione LXVIIIa (400 mg, 1.23 mmol) in THF (10 mL) were added TEA (171 μL, 1.23 mmol) and DMAP (15.0 mg, 123 μmol) at rt under $N_2$ atmosphere. This was followed by a drop wise addition of acetic anhydride (139 μL, 1.48 mmol) and the resulting reaction mixture was stirred at rt for 3 h. The progress of the reaction was monitored by TLC analysis. After completion, sat. $NaHCO_3$ solution (10 mL) was added, and the resulting mixture was extracted with DCM (50 ml×2). The combined organic layer was dried over anhydrous sodium sulfate and concentrated under reduced pressure to afford the desired compound LXVIIIb as an off-white solid. Yield: 350 mg (78%); LCMS Calculated. for $C_{20}H_{21}N_3O_4$ is 367.15; Observed.: 368.30 $[M+H]^+$.

Step-3: N-(3-(3-(2-aminoethyl)-2-oxopyridin-1(2H)-yl) propyl) acetamide (LXVIII)

To a stirred solution of N-(3-(3-(2-(1,3-dioxoisoindolin-2-yl) ethyl)-2-oxopyridin-1(2H)-yl) propyl) acetamide LXVIIIb (350 mg, 953 μmol) in MeOH (5 mL) was added hydrazine hydrate (71.5 mg, 1.43 mmol) and the reaction mixture was stirred at rt for 2 h. The progress of the reaction was monitored by TLC analysis. After completion, the reaction mixture was concentrated, and the residue was dissolve in water (2 mL). The mixture was acidified (pH=2) using conc. HCl, the solid formed was filtered and washed with water. The filtrate was basified with 4N NaOH solution (pH=8-9) and extracted with DCM (50 ml×3). The combined organic layer was dried over anhydrous sodium sulfate and concentrated over reduced pressure. The crude compound LXVIII was taken for next step without further purification. Yield: 210 mg (93%); LCMS Calculated. for $C_{12}H_{19}N_3O_2$ is 237.14; Observed. 238.30 [M+H]$^+$.

Synthesis of 2-(6-(2-methoxyethoxy) pyridin-2-yl) ethan-1-amine (LXIX)

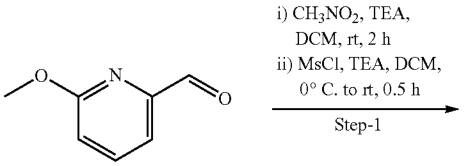

CAS: 54221-96-4

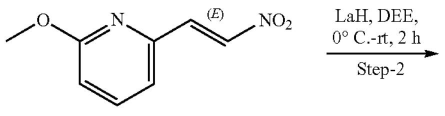

LXIXa

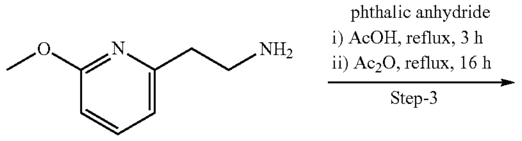

LXIXb

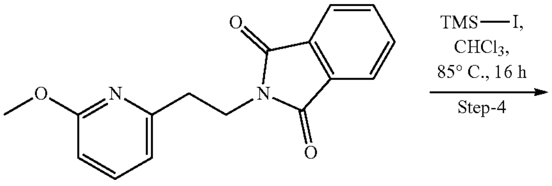

LXIXc

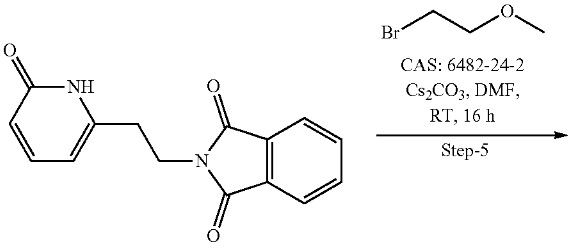

LXIXd

-continued

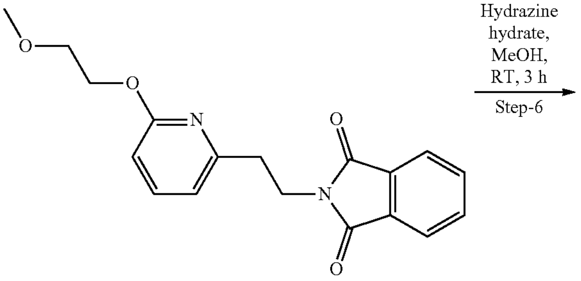

LXIXe

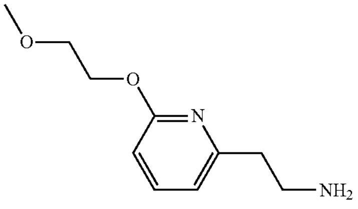

LXIX

Step-1: (E)-2-methoxy-6-(2-nitrovinyl) pyridine (LXIXa)

To a stirred solution of 6-methoxypicolinaldehyde (CAS: 54221-96-4, 3 g, 0.02 mol) in DCM (30 mL) under inert atmosphere were added TEA (6 mL, 0.04 mol) and nitromethane (2 g, 0.03 mol) at room temperature. The reaction mixture was stirred at rt for 2 h and the progress of the reaction was monitored by TLC analysis. The reaction mixture was concentrated to dryness under reduced pressure and the residue was dissolved in fresh DCM (40 mL). The solution was cooled to 0° C. under inert atmosphere and was added TEA (9 mL, 0.07 mol). This was followed by a dropwise addition of mesyl-Cl (3 mL, 0.03 mol) over 10 min. The resultant mixture was stirred at 0° C. for 30 min and quenched with saturated solution of $NaHCO_3$. The mixture was extracted with DCM (100 mL×3). The combined organic layer was dried over anhydrous sodium sulphate and concentrated over reduced pressure. The crude was purified by silica-gel (230-400) column chromatography using 10-30% ethyl acetate in n-hexane to afford the desired compound LXIXa as a pale-yellow solid. Yield: 1.8 g (45%). LCMS Calculated. for $C_8H_8N_2O_3$ is 180.05; Observed. 181.25; [M+H]$^+$: $^1$H NMR (400 MHz, $CDCl_3$): δ 8.00 (d, J=12.8 Hz, 1H), 7.83 (d, J=12.8 Hz, 1H), 7.64 (t, J=7.2 Hz, 1H), 7.06 (d, J=7.2 Hz, 1H), 6.85 (d, J=8.4 Hz, 1H), 3.97 (s, 3H).

Step-2: 2-(6-methoxypyridin-2-yl) ethan-1-amine (LXIXb)

A stirred solution of $LiAlH_4$ (120 mL, 1 M in THF, 0.12 mol) in diethyl ether (300 mL) was cooled to 0° C. under inert atmosphere and dropwise added a solution of (E)-2-methoxy-6-(2-nitrovinyl) pyridine LXIXa (7.3 g, 41 mmol) in THF (30 mL) over 15 min. The resulting mixture was stirred at room temperature for 2 h. The progress of the reaction was monitored by TLC analysis. After completion, the reaction was cooled to 0° C. and quenched with ice cold water (24 mL). Then added 15% NaOH solution (8 ml) and ethyl acetate (200 mL). The mixture was stirred at rt for 15 min and filtered. The residue was washed thoroughly with ethyl acetate (500 mL×3). The combined filtrate was dried over anhydrous sodium sulphate and concentrated under reduced pressure to afford the desired compound LXIXb as a pale-yellow viscous liquid. Yield: 5.0 g (80.6%). LCMS Calculated. for $C_8H_2N_2O$ is 152.09; Observed. 153.30; $[M+H]^+$.

Step-3: 2-(2-(6-methoxypyridin-2-yl) ethyl) isoindoline-1,3-dione (LXIXc)

To a stirred solution of 2-(6-methoxypyridin-2-yl) ethan-1-amine LXIXb (5 g, 0.03 mol) in acetic acid (50 mL) was added in isobenzofuran-1,3-dione (6 g, 0.04 mol) under inert atmosphere. The resulting mixture was stirred at 140° C. for 3 h. Then reaction mixture was concentrated under reduced pressure to dryness. To the residue was added acetic anhydride (20 mL, 0.2 mol) and stirring at 140° C. was continued for additional 16 h. The progress of the reaction was monitored by TLC analysis. After completion, the reaction was cooled to rt and quenched with sat. $NaHCO_3$ solution (200 mL). The resulting mixture was extracted with DCM (300 mL×3) and the combined organic layer was dried over anhydrous sodium sulphate. The organic layer was filtered and concentrated under reduced pressure. The crude was purified by silica-gel (230-400) column chromatography using 0-10% ethyl acetate in n-hexane to afford the desired compound LXIXc as off-white solid. Yield: 5.0 g (55%). LCMS Calculated. for $C_{16}H_{14}N_2O_3$ is 282.10; Obs. 283.20; $[M+H]^+$.

Step-4: 2-(2-(6-oxo-1,6-dihydropyridin-2-yl) ethyl) isoindoline-1,3-dione (LXIXd)

To a stirred solution of 2-(2-(6-methoxypyridin-2-yl) ethyl) isoindoline-1,3-dione LXIXc (5.0 g, 18 mmol) in $CHCl_3$ (80 mL) was added TMS-I (4.8 mL, 35 mmol) and the reaction mixture was stirred at 85° C. for 16 h. The progress of the reaction was monitored by TLC analysis. After completion, reaction was cooled to rt and quenched with MeOH (20 mL). The resulting mixture was concentrated under reduced pressure and the residue was triturated in MTBE/EtOH (5:1). The solid formed was collected by filtration and dried to afford the desired compound LXIXd as an off-white solid. Yield: 2.8 g (58%). LCMS Calculated. for $C_{15}H_{12}N_2O_3$ is 268.09; Observed. 269.25; $[M+H]^+$; $^1H$ NMR (400 MHz, CD3OD): δ 7.84 (bs, 4H), 7.54 (t, J=7.2 Hz, 1H), 6.44 (d, J=8.8 Hz, 1H), 6.33 (d, J=6.8 Hz, 1H), 3.90 (bs, 2H), 2.88 (bs, 2H).

Step-5: 2-(2-(6-(2-methoxyethoxy) pyridin-2-yl) ethyl) isoindoline-1,3-dione (LXIXe)

To a stirred solution of 2-(2-(6-oxo-1,6-dihydropyridin-2-yl) ethyl) isoindoline-1,3-dione LXIXd (0.70 g, 2.61 mmol) in DMF (10 mL) was added $Cs_2CO_3$ (1.70 g, 5.22 mmol) and stirred for 20 min at rt. The mixture was cooled to 0° C. and added 1-chloro-2-methoxyethane (370 mg, 3.91 mmol) slowly under nitrogen atmosphere. The reaction was stirred at rt for 16 h and the reaction was monitored by TLC analysis. After completion, the reaction mixture was diluted with water (100 mL) and extracted with ethyl acetate (50 mL×3). The combined organic layer was dried over anhydrous $Na_2SO_4$, filtered and concentrated under reduced pressure. The crude was purified by combi flash column silica gel (230-400) column chromatography using 0-20% ethyl acetate in n-hexane to afford the desired compound LXIXe as a pale-yellow viscous liquid. The crude compound was taken for the next step without further purification; Yield: 0.35 g (39%).

Step-6: 2-(6-(2-methoxyethoxy) pyridin-2-yl) ethan-1-amine (LXIX)

To a stirred solution of 2-(2-(6-(2-methoxyethoxy)-1,6-dihydropyridin-2-yl) ethyl) isoindoline-1,3-dione LXIXe (0.65 g, 2.0 mmol) in methanol (10 mL) was added hydrazine hydrate (0.14 mL, 3.0 mmol) and the reaction was stirred for at rt for 3 h. The progress of the reaction was monitored by TLC analysis. After completion, the reaction mixture was concentrated, and the crude was diluted with 10% NaOH solution (50 mL). The mixture was extracted with ethyl acetate (20 mL×3). The combined organic layer was dried over anhydrous $Na_2SO_4$, filtered and concentrated under reduced pressure to afford the desired compound LXIX as a pale-yellow viscous liquid. The crude taken for the next step without further purification. Yield: 0.5 g (80%)

Synthesis of 3-(2-aminoethyl)-1-(3-(methylthio) propyl) pyridin-2(1H)-one. (LXX)

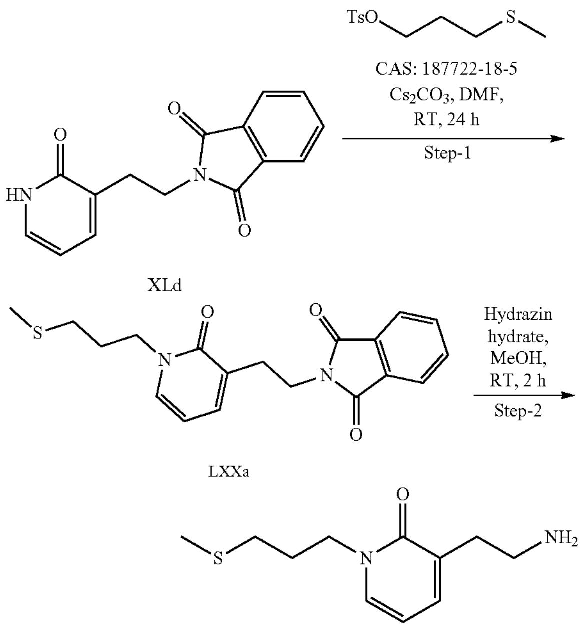

XLd

LXXa

LXX

Step-1: 2-(2-(1-(3-(methylthio) propyl)-2-oxo-1,2-dihydropyridin-3-yl) ethyl) isoindoline-1,3-dione (LXXa)

To a solution of 2-(2-(2-oxo-1,2-dihydropyridin-3-yl) ethyl) isoindoline-1,3-dione XLd (5.0 g, 18.64 mmol) in N, N-dimethyl formamide (15 mL) were added cesium carbonate (12.15 g, 37.28 mmol) and 3-(methylthio) propyl 4-methylbenzenesulfonate (CAS:187722-18-5, 5.82 g, 22.37 mmol). The reaction mixture was stirred at rt for 24 h. The progress of the reaction was monitored by TLC analysis. After the completion of the reaction, added water (300 mL) and extracted with ethyl acetate (500 mL×3). The combined organic layer was dried over anhydrous sodium sulphate and concentrated under reduced pressure. The crude compound was purified by silica gel (230-400 mesh) column chromatography with ethyl acetate in n-hexane (0-50%) to afford the desired product LXXa as a pale-yellow viscous liquid. Yield: 3.9 g, (59.0%); LCMS Calculated. for $C_{19}H_{20}N_2O_3S$ is 356.12; Observed 357 $[M+H]^+$. $^1H$ NMR (400 MHz, $CDCl_3$): δ 8.02 (s, 3H), 7.80 (q, J=2.4 Hz, 2H), 7.68 (q, J=2.4 Hz, 2H), 4.02 (q, J=8 Hz, 4H), 2.91 (d, J=4 Hz, 4H), 2.52 (t, J=8 Hz, 2H), 2.11 (s, 1H), 2.04 (t, J=8 Hz, 2H).

Step-2: 3-(2-aminoethyl)-1-(3-(methylthio) propyl) pyridin-2(1H)-one (LXX)

To a solution of 2-(2-(1-(3-(methylthio) propyl)-2-oxo-1,2-dihydropyridin-3-yl) ethyl) isoindoline-1,3-dione LXXa (1.90 g, 5.330 mmol) in methanol (4 mL) was added hydrazine hydrate (0.32 g, 6.397 mmol) and the reaction mixture was stirred at rt for 2 h. The progress of the reaction was monitored by TLC analysis. After the completion of the reaction, the reaction mixture was concentrated, added water (5 mL) and acidified with conc. HCl to pH-1. The solids were filtered, basified by sodium hydroxide (1 N) and extracted with 10% methanol in dichloromethane (500 mL×3). The combined organic layer was dried over anhydrous sodium sulphate to afford the desired compound LXX as a pale-yellow viscous liquid. The crude compound was taken for the next step without any further purification. Yield: 0.9 g, (75.0%); LCMS Calculated. for $C_{11}H_{18}N_2OS$ is 226.11; Observed: 227.25 [M+H]+. $^1H$ NMR (400 MHz, $CDCl_3$): δ 7.22 (d, J=6.4 Hz, 2H), 6.13 (d, J=6.8 Hz, 1H), 4.05 (t, J=6.8 Hz, 2H), 2.95 (t, J=6.4 Hz, 3H), 2.68 (t, J=6.8 Hz, 2H), 2.53 (t, J=7.2 Hz, 2H), 2.11-2.01 (m, 6H).

Synthesis of 3-(6-(2-aminoethyl)$_{222}$yridine-2-yl) propan-1-ol (LXXI)

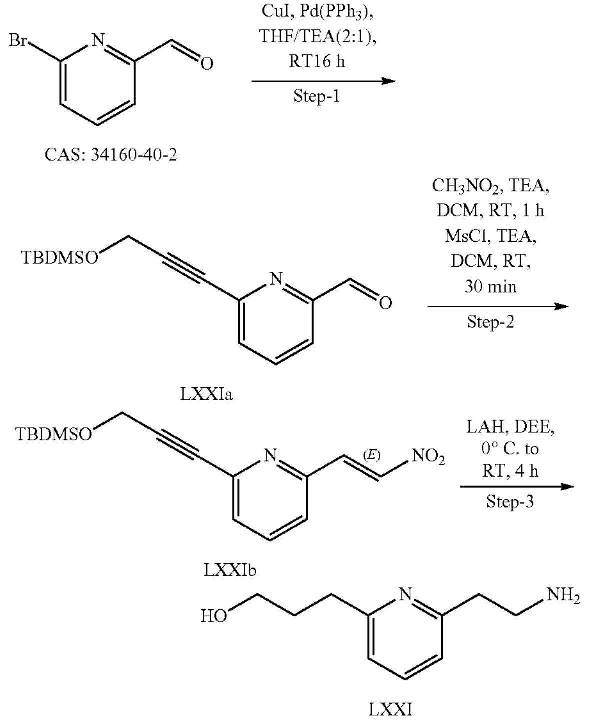

CAS: 34160-40-2

LXXIa

LXXIb

LXXI

Step-1: 6-(3-((tert-butyldimethylsilyl) oxy) prop-1-yn-1-yl) picolinaldehyde (LXXIa)

To a stirred solution of 6-bromopicolinaldehyde (CAS: 34160-40-2, 1.0 g, 5.38 mmol) was added CuI (0.372 g, 1.61 mmol) and tetrakis(triphenyiphospiline)pailadium (0) (0.932 g, 0.81 mmol) in 2:1 THF/triethylamine (10 mL) and purged with $N_2$ gas for 15 min with vigorous stirring. To the reaction was added tert-butyl dimethyl(prop-2-yn-1-yloxy) silane (1.10 g, 6.45 mmol) and the seal tube with Teflon screw-stopper was closed and stirred at room temperature for 16 h. The progress of the reaction was monitored by TLC analysis. After completion, the reaction mixture was diluted with 100 mL of water and extracted with ethyl acetate (50 mL×2). The combined organic layer was dried over anhydrous sodium sulphate and concentrated to obtain crude product. The crude product was subjected to silica gel (230-400 mesh) column chromatography using 0-6% ethyl acetate in n-hexane to afford the desired compound LXXIa as a colorless viscous liquid. Yield: (1.4 g, 95%); LCMS Calculate. for $C_{15}H_{21}NO_2Si$ is 275.13; Observed. 276.00 $[M+H]^+$; $^1$HNMR (400 MHz, $CDCl_3$): δ 10.05 (s, 1H), 7.91 (dd, J=7.6, 1.2 Hz, 1H), 7.85 (t, J=7.6 Hz, 1H), 7.64 (dd, J=7.6, 1.2 Hz, 1H), 4.60 (s, 2H), 0.85 (s, 9H), 0.18 (s, 6H).

Step-2: (E)-2-(3-((tert-butyldimethylsilyl) oxy) prop-1-yn-1-yl)-6-(2-nitrovinyl) pyridine (LXXIb)

To a stirred solution of 6-(3-((tert-butyldimethylsilyl) oxy) prop-1-yn-1-yl) picolinaldehyde LXXIa (1.4 g, 5.1 mmol) in DCM (20 mL) was added triethylamine (1.5 g, 2.1 mL, 15 mmol) and nitromethane (4.7 g, 4.1 mL, 76 mmol) under nitrogen atmosphere. The resulting mixture was stirred at room temperature for 1 h and the progress of the reaction was monitored by TLC analysis. After completion of reaction, DCM was concentrated under reduced pressure. The resulting residue was taken in DCM (20 mL) was added triethylamine (1.5 g, 2.1 mL, 15 mmol) and cooled to 0° C. followed by drop wise addition of methane sulfonyl chloride (1.7 g, 1.2 mL, 7.6 mmol). The mixture was stirred at 0° C. for 30 min and the progress of the reaction was monitored by TLC analysis. After completion, the reaction mixture was diluted with water (40 mL) and extracted with DCM (20 mL×2). The combined organic layer was dried over anhydrous sodium sulphate. The residue obtained upon removal of the solvent was subjected to silica gel (230-400 mesh) column chromatography using 0-6% ethyl acetate in n-hexane to afford the desired compound LXXIb as a yellow viscous liquid. Yield: 1.1 g (68%); LCMS Calculate. for $C_{16}H_{22}N_2O_3Si$ is 318.14; Observed. 319.30 $[M+H]^+$; $^1H$ NMR (400 MHz, $CDCl_3$): δ 8.03 (d, J=13.2 Hz, 1H), 7.87 (d, J=13.2 Hz, 1H), 7.75 (t, J=8.0 Hz, 1H), 7.48 (d, J=8.0 Hz, 1H), 7.40 (d, J=8.0 Hz, 1H), 4.49 (s, 2H), 0.94 (s, 9H), 0.18 (s, 6H).

Step-3: 3-(6-(2-aminoethyl) pyridin-2-yl) propan-1-ol. (LXXI)

To a stirred solution of lithium aluminum hydride (13.8 mL, 1.0 M in THF, 14 mmol) in diethyl ether (70 mL) was added (E)-2-(2-((tert-butyldimethylsilyl) oxy) ethyl)-6-(2-nitrovinyl) pyridine LXXIb (1.1 g, 3.5 mmol) dropwise at 0° C. under nitrogen atmosphere. The reaction mixture was stirred at room temperature for 4 h and the reaction was monitored by TLC analysis. After completion, the reaction mixture was cooled to 0° C. was added 1 mL of ice-cold water and 1 mL of 15% KOH solution then stirred at room temperature for another 30 min. The resulting reaction mixture was diluted with 100 mL of ethyl acetate filtered through Buchner funnel and the solid was thoroughly washed with 100 mL of ethyl acetate. The filtrate was dried over anhydrous sodium sulphate and concentrated under reduced pressure to afford a desired compound LXXI as light brown viscous liquid. Yield: (0.7 g, 85%).

Synthesis of 7-amino-2-methyl-5-(methyl sulfonyl)-3-propylpyrazolo[1,5-a] pyrimidine-6-carbonitrile. (LXXII)

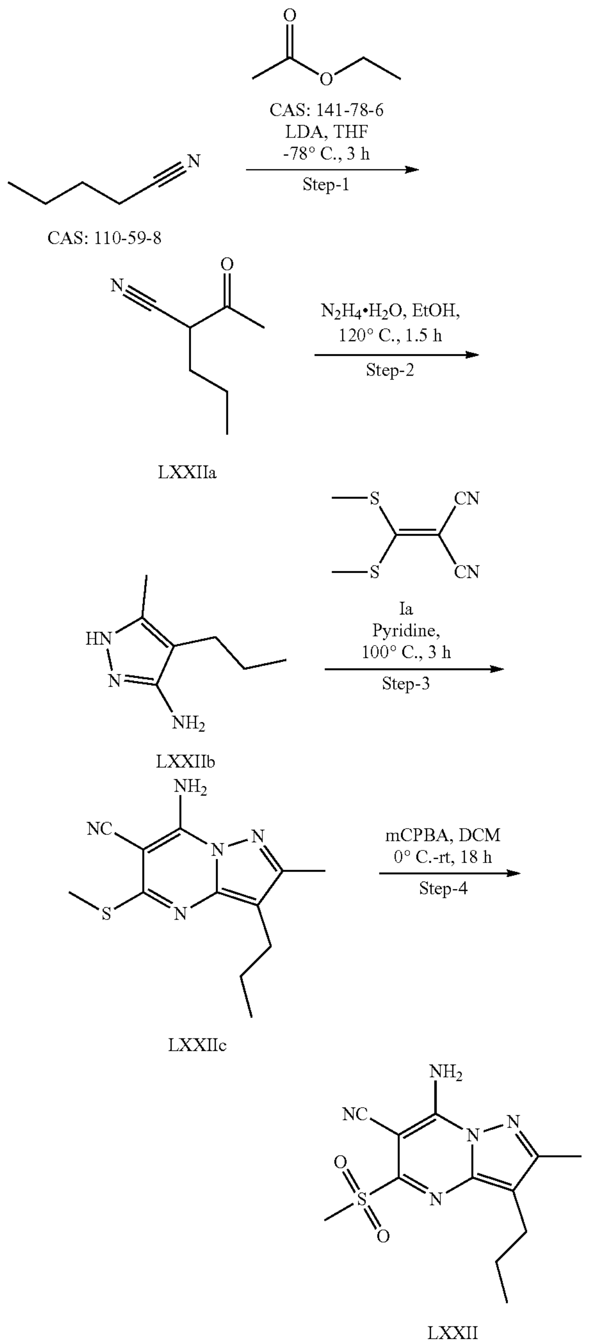

CAS: 110-59-8

LXXIIa

LXXIIb

LXXIIc

LXXII

Step-1: 2-acetylpentanenitrile (LXXIIa)

A stirred solution of lithium diisopropylamide (30 mL, 2.0 M in THF/heptane/ethylbenzene, 0.06 mol) in dry THF (300 mL) was cooled to −78° C. under inert atmosphere and dropwise added a solution of pentane nitrile (CAS:110-59-8, 5 g, 6.48 mL, 1 Eq, 0.06 mol) in THF (20 mL). The resulting mixture was stirred −78° C. for 1 h. To the reaction was dropwise added dry ethyl acetate (6 mL, 0.06 mol) over 10 min and the mixture was stirred at −78° C. for additional 2 h. The progress of the reaction was monitored by TLC analysis. After completion, the reaction mixture was quenched with saturated solution of $NH_4Cl$ (100 mL) and extracted with ethyl acetate (200 mL×3). The combined organic layer was dried over anhydrous $Na_2SO_4$, filtered and concentrated under reduced pressure to afford the desired compound LXXIIa as a pale-yellow viscous liquid. Yield: 10.0 g.

Step-2: 5-methyl-4-propyl-1H-pyrazol-3-amine (LXXIIb)

To a stirred solution of 2-acetylpentanenitrile LXXIIa (10 g, 80 mmol) in ethanol (100 mL) was added hydrazine hydrate (5.8 mL, 0.12 mol) and the reaction mixture was stirred under inert atmosphere at 120° C. for 1.5 h. The progress of the reaction was monitored by TLC analysis. After completion, the reaction mixture was cooled to rt and concentrated under reduced pressure. The residue obtained was diluted with water (100 mL) and extracted with 10% MeOH in DCM (200 mL×5). The combined organic layer was dried over anhydrous $Na_2SO_4$, filtered and concentrated under reduced pressure to afford the desired compound LXXIIb as a pale-yellow viscous liquid. The crude material was used in the next step without further purification. Yield: 9.3 g. (83.6%); LCMS Calculated. for $C_7H_{13}N_3$ is 139.11; Observed. 140.30 $[M+H]^+$.

Step-3: 7-amino-2-methyl-5-(methylthio)-3-propylpyrazolo[1,5-a] pyrimidine-6-carbonitrile (LXXIIc)

A mixture of 5-methyl-4-propyl-1H-pyrazol-3-amine (9.3 g, 67 mmol), 2-(bis(methylthio)methyl) malononitrile LXXIIb (13 g, 73 mmol) and pyridine (50 mL) was stirred at 100° C. under inert atmosphere for 3 h. The progress of the reaction was monitored by TLC analysis. After completion, the reaction mixture was cooled to rt and poured into ice cold water (1000 mL). The precipitate formed was filtered and washed with cold water. The solid obtained was dried under vacuum to afford the title compound LXXIIc as a pale-yellow solid. Yield: 15 g (88%). LCMS Calculated. for $C_{12}H_{15}N_5S$ is 261.10; Observed. 262.20 $[M+H]^+$.

Step-4: 7-amino-2-methyl-5-(methylsulfonyl)-3-propylpyrazolo[1,5-a] pyrimidine-6-carbonitrile (LXXII)

To a stirred solution of 7-amino-2-methyl-5-(methylthio)-3-propylpyrazolo [1,5-a] pyrimidine-6-carbonitrile LXXIIc (15 g, 57 mmol) in solvent DCM (1000 mL) at 0° C. was added mCPBA (50 g, 0.29 mol) in portions under inert atmosphere. The resulting mixture was stirred at room temperature for 18 h and progress of the reaction was monitored by TLC analysis. After completion, the solvent was removed under vacuum and to the yellow precipitate was added saturated sodium bicarbonate solution (250 mL). The resulting mixture was stirred at rt for 30 min, the solid was collected by filtration and dried under reduced pressure to afford the desired compound LXXII as a pale-yellow solid. Yield: 7.5 g (44%); LCMS: Calculated. for $C_{12}H_{15}N_5O_2S$ is 293.09; Observed. 294.20 [M+H]

Synthesis of 2-(1-(3-(methylthio) propyl)-1H-pyrazol-3-yl) ethan-1-amine (LXXIII)

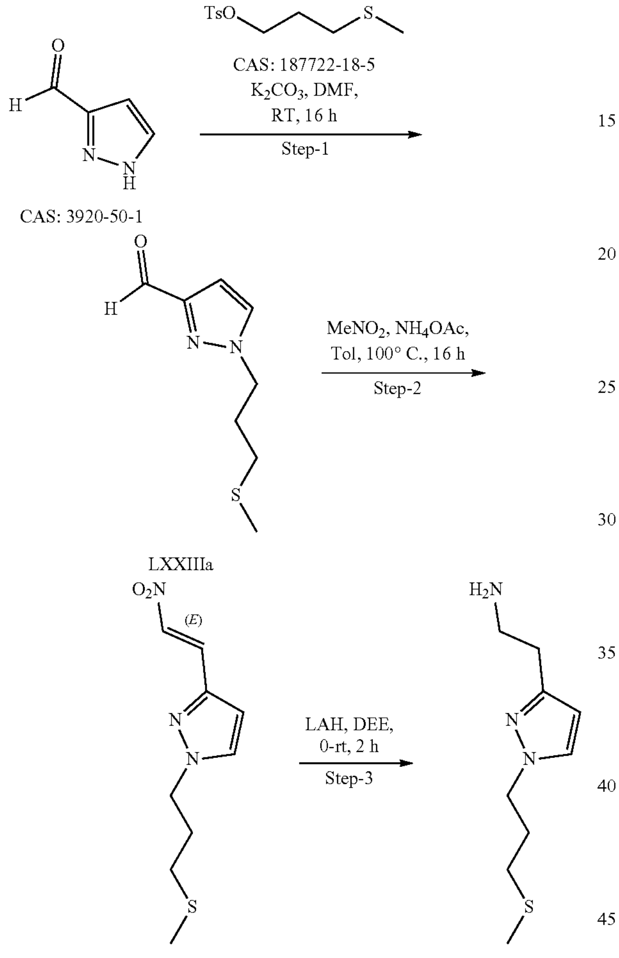

CAS: 3920-50-1

LXXIIIa

LXXIIIb

LXXIII

Step-1: 1-(3-(methylthio) propyl)-1H-pyrazole-3-carbaldehyde (LXXIIIa)

To a stirred solution of 1H-pyrazole-3-carbaldehyde (CAS:3920-50-1, 3 g, 0.0312 mol) in DMF (50 mL) was added $Cs_2CO_3$ (15.27 g, 0.0469 mol) and the resulting reaction mixture was cooled to 0° C. To this was dropwise added of 3-(methylthio) propyl 4-methylbenzenesulfonate (CAS:187722-18-5, 9.75 g, 0.037 mol) under nitrogen. The resulting mixture was stirred at rt for 16 h. The progress of the reaction was monitored by TLC analysis. After completion, the reaction mixture was diluted with water (100 mL) and extracted with ethyl acetate (2×200 mL). The combined organic layer was dried over anhydrous sodium sulphate, filtered, and concentrated under reduced pressure to afford the crude yellow liquid. The crude material was purified by column chromatography (silica 230-400) eluted with 0-10% ethyl acetate in n-hexane to afford the compound LXXIIIa as a pale-yellow liquid. Yield: 2.5 g (40%). $^1H$ NMR (400 MHz, DMSO-$D_6$): δ 9.87 (s, 1H), 7.96 (s, 1H), 6.78 (d, J=1.6 Hz, 1H), 4.33 (t, J=6.8 Hz, 2H), 2.44 (t, J=7.2 Hz, 2H), 2.11-2.08 (m, 2H), 2.05 (s, 3H).

Step-2: (E)-1-(3-(methylthio) propyl)-3-(2-nitrovinyl)-1H-pyrazole (LXXIIIb)

To a stirred solution of 1-(3-(methylthio) propyl)-1H-pyrazole-3-carbaldehyde LXXIIIa (1.1 g, 6.0 mmol) in toluene (20 mL) were added nitromethane (5.5 g, 90 mmol) and ammonium acetate (0.69 g, 9.0 mmol) under nitrogen atmosphere. The resulting mixture was stirred at 100° C. for 16 h and progress of the reaction was monitored by TLC analysis. After completion, reaction mixture was cooled to room temperature, diluted with cold 1N HCl solution (15 mL) and extracted with ethyl acetate (100 mL×3). The combined organic layer was washed with water (100 mL). The organic layer was dried over anhydrous sodium sulphate, filtered, and concentrated under reduced pressure to afford the crude brown semi-solid. The crude material was purified by silica gel (100-200) column chromatography using 0-10% ethyl acetate in n-hexane to afford the desired compound LXXIIIb as a pale-yellow liquid. Yield: 0.9 g (66%); δ 7.96 (d, J=13.6 Hz, 1H), 7.61 (d, J=13.6 Hz, 1H), 7.47 (d, J=1.6 Hz, 1H), 6.53 (d, J=1.6 Hz, 1H), 4.30 (t, J=6.4 Hz, 2H), 2.46 (t, J=6.8 Hz, 2H), 2.22-2.15 (m, 2H), 2.10 (s, 3H).

Step-3: 2-(1-(3-(methylthio) propyl)-1H-pyrazol-3-yl) ethan-1-amine (LXXIII)

A stirred solution of $LiAlH_4$ (15.8 mL, 1 M in THF, 15.8 mmol) in diethyl ether (50 mL) was cooled to 0° C. and dropwise added solution of (E)-1-(3-(methylthio) propyl)-3-(2-nitrovinyl)-1H-pyrazole LXXIIIb (900 mg, 3.96 mmol) in diethyl ether (5 mL). The reaction mixture was stirred at rt for 2 h and progress of the reaction was monitored by TLC analysis. After completion, reaction mixture was cooled to 0° C. and quenched with water (0.9 mL), followed by with 15% KOH ((0.9 mL). Then water (1.8 mL) and ethyl acetate (50 mL) were added. The resulting reaction mixture was stirred at rt for 30 min. The mixture was filtered, and solid residue was washed with fresh ethyl acetate (250 mL×3). The combined filtrate was concentrated under reduced pressure to afford the desired compound LXXIII as a light brown viscous liquid. Yield: 700 mg (88.7%); LCMS Calculated. for $C_9H_{17}N_3S$ is 199.11; Observed. 200.25 $[M+H]^+$.

Synthesis of (4-(3-(2-aminoethyl)-5-methyl-1H-pyrazol-1-yl) tetrahydrofuran-3-yl) methanol (LXXIV)

LXXIV

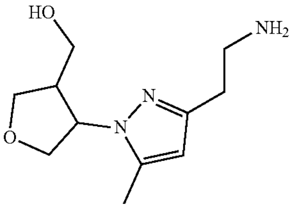

The title compound LXXIV was prepared in analogus to LVII by using 5-methyl-1H-pyrazole-3-carbaldehyde (CAS: 3273-44-7) instead of 1H-pyrazole-3-carbaldehyde (CAS: 3920-50-1). LXXIV was obtained as an off white solid. The crude product obtained is taken for the next step without further purification. LCMS Calculated. for $C_{11}H_{19}N_3O_2$ is 225.29; Observed. 226.40 $[M+H]^+$.

Example 1: 7-amino-2,3-dimethyl-5-{[1-(6-methylpyridin-2-yl) ethyl]amino}pyrazolo[1,5-a]pyrimidine-6-carbonitrile

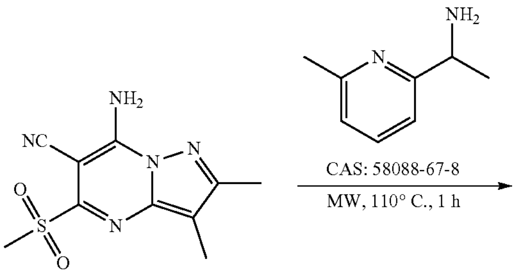

I

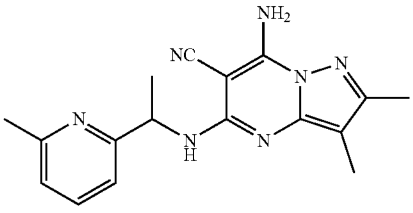

Example 1

To a mixture of 1 (80 mg, 0.30 mmol) and racemic 1-(6-methylpyridin-2-yl) ethan-1-amine (CAS: 58088-67-8) (65 mg, 0.45 mmol) in DMF (3 mL) was added $Et_3N$ (0.1 mL). The resulted mixture was irradiated under constant microwave for about 1 h at 120° C. After completion, the reaction mixture was concentrated in vacuo to get the crude. The crude was purified by reverse phase preparative HPLC to afford the title compound (Example 1) as white solid. Yield: 15 mg, 15.62%; LC-MS Calculated for $C_{17}H_{19}N_7$: 321.39; Observed.: 322.1; $[M^++H]$. $^1H$ NMR (400 MHz, DMSO-$D_6$): δ 8.21 (s, 2H), 7.69-7.64 (m, 1H), 7.27 (d, J=8.00 Hz, 1H), 7.14 (dd, J=1.60, 7.60 Hz, 1H), 6.97 (d, J=4.40 Hz, 1H), 5.28-5.25 (m, 1H), 2.50 (s, 3H) 2.22 (s, 3H), 1.95 (s, 3H), 1.51-1.48 (m, 3H). HPLC: 2.39 min; 98.85%; HPLC Column: Atlantis dC18 (250*4.6) mm Mobile Phase A: 0.1% TFA in water, Mobile Phase B: Acetonitrile.

Example 2: 7-amino-2,3-dimethyl-5-{[(1S)-1-(6-methylpyridin-2-yl)ethyl]amino}pyrazolo [1,5-a] pyrimidine-6-carbonitrile

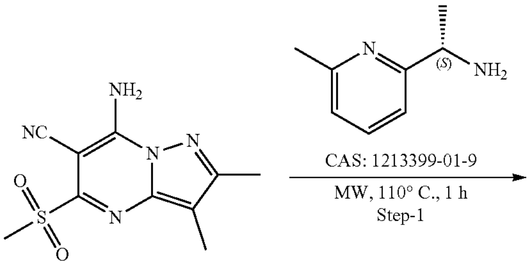

I

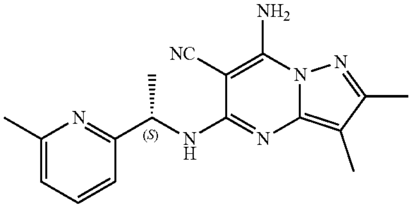

Example 2

Example 2 was synthesized similar to example 1 using intermediate I and charily pure (S)-1-(6-methylpyridin-2-yl) ethan-1-amine (CAS:1213399-01-9)

LC-MS Calculated for $C_{17}H_{19}N_7$: 321.39; Observe.: 322.0; [M+H]. $^1H$ NMR (400 MHz, DMSO-$D_6$): δ 8.19 (br s, 1H), 7.66 (t, J=7.60 Hz, 1H), 7.27 (d, J=7.60 Hz, 1H), 7.14 (d, J=7.60 Hz, 1H), 6.97 (d, J=7.20 Hz, 1H), 5.27 (t, J=7.20 Hz, 1H), 2.23 (s, 3H), 1.94 (s, 3H), 1.50 (d, J=6.80 Hz, 3H). HPLC: 2.39 min; 95.99%; Column: X-Bridge C8(50×4.6) mm, 3.5 μm, Mobile Phase A: 0.1% TFA in water, Mobile Phase B: Acetonitrile. Chiral HPLC: 4.23 min; 100% ee; Column: Lux C4, Mobile Phase A: 0.5% Isopropyl amine in methanol, Mobile phase B: Methanol (30%), Flowrate: 3 mL/min, Injected Volume: 15 μl.

Example 3: (R)-7-Amino-3-ethyl-2-methyl-5-((1-(pyridin-2-yl) ethyl) amino) pyrazolo[1,5-a] pyrimidine-6-carbonitrile

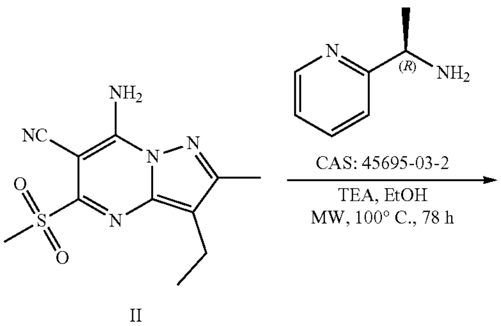

II

-continued

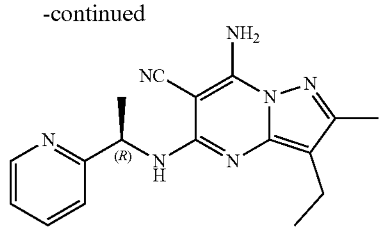

Example 3

To a stirred solution of 7-amino-3-ethyl-2-methyl-5-(methylthio) pyrazolo[1,5-a] pyrimidine-6-carbonitrile II (0.15 g, 0.0005376 mol) and (R)-1-(pyridin-2-yl) ethan-1-amine (CAS: 45695-03-2, 0.2627 g, 0.00215 mol) in EtOH (15 ml) in a sealed tube, was added TEA (0.6 ml, 0.0043 mol) and the reaction mixture was stirred at 100° C. for 78 h. The progress of the reaction was monitored by TLC. After completion, the reaction mixture was evaporated under reduced pressure and the crude material was purified by column chromatography by eluting with 20% EtOAc in hexane to yield the title compound (Example 3) as off-white solid; Yield: (0.038 g, 22%). LC-MS Calculated for $C_{17}H_{19}N_7$ is 321.17; Observe: 322.15 [$M^{+}$+1]. $^1$H NMR (400 MHz, DMSO-$d_6$): δ 8.530-8.541 (d, J=4.4 Hz, 1H), 8.165 (bs, 2H), 7.730-7.773 (m, 1H), 7.449-7.469 (d, J=8 Hz, 1H), 7.241-7.272 (m, 1H), 6.869-6.852 (d, J=6.8 Hz, 1H), 5.229-5.298 (m, 1H), 2.387-2.406 (q, J=7.6 Hz, 2H), 2.229 (s, 3H), 1.496-1.513 (d, J=6.8 Hz, 3H), 1.002-1.040 (t, J=7.2 Hz, 3H). HPLC: 10.35 min; 97.80%, XBridge C18 (4.6*150) mm, 5μ, Mobile Phase A: 10 mM ammonium bicarbonate in water, Mobile Phase B: Acetonitrile: Chiral HPLC: 4.56 min; >97% ee; Column: Chiral Pak IC (250*4.6) mm, 5μ; Mobile Phase A: 0.1% diethylamine in hexane, Mobile phase B: Ethanol (90:10), Flowrate: 1 mL/min, Injected Volume: 5 μl Example 4: (S)-7-Amino-3-ethyl-2-methyl-5-((1-(pyridin-2-yl) ethyl) amino) pyrazolo[1,5-a] pyrimidine-6-carbonitrile

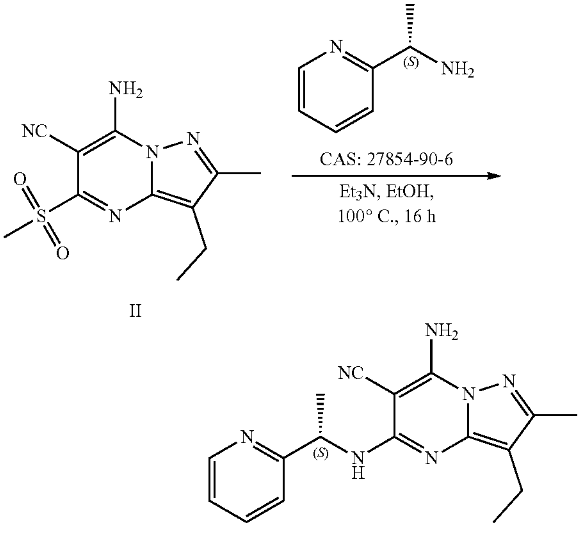

II

Example 4

To a stirred solution of 7-amino-3-ethyl-2-methyl-5-(methylthio) pyrazolo[1,5-a] pyrimidine-6-carbonitrile II (0.15 g, 0.0005376 mol) and (S)-1-(pyridin-2-yl) ethan-1-amine (CAS:27854-90-6; 0.262 g, 0.00215 mol) in EtOH (12 ml) in a sealed tube, was added TEA (0.21 ml, 0.0016 mol) and the reaction mixture was stirred at 100° C. for 16 h. The progress of the reaction was monitored by TLC. After completion, the reaction mixture was diluted with water (20 ml) and extracted with EtOAc (20 ml×3). The organic layer was dried with $Na_2SO_4$, filtered, and evaporated under reduced pressure. The crude material was purified by column chromatography by eluting with 30% EtOAc in hexane to yield the title compound (Example 4) as off-white solid; Yield: (0.040 g, 23%). LC-MS: Calculated for $C_{17}H_{19}N_7$ is 321.17; Observe: 322.15 [$M^{+}$+1]. $^1$HNMR (400 MHz, DMSO-$d_6$): δ 8.533-8.5444 (d, J=4.4 Hz, 1H), 8.190 (bs, 2H), 7.734-7.772 (t, J=7.2 Hz, 1H), 7.452-7.471 (d, J=7.6 Hz, 1H), 7.242-7.273 (m, 1H), 6.872-6.855 (d, J=6.8 Hz, 1H), 5.249-5.283 (m, 1H), 2.370-2.426 (q, J=8 Hz, 2H), 2.231 (s, 3H), 1.514-1.497 (d, J=6.8 Hz, 3H), 1.004-1.041 (t, J=6.8 Hz, 3H). HPLC: 10.34 min; 96.02%, Column: X Bridge C18 (4.6*150) mm, 5μ, Mobile Phase A: 10 mM Ammonium bicarbonate in water, Mobile Phase B: Acetonitrile. Chiral HPLC: 4.72 min; >97% ee; Column: Chiral Pak IC (250*4.6) mm, 5μ Mobile Phase A: 0.1% Diethylamine in hexane, Mobile phase B: EtOH (90:10). Flowrate: 1 mL/min, Injected Volume: 5 μl Example 5: (S)-7-Amino-3-ethyl-2-methyl-5-((1-(6-methylpyridin-2-yl) ethyl) amino) pyrazolo [1,5-a] pyrimidine-6-carbonitrile

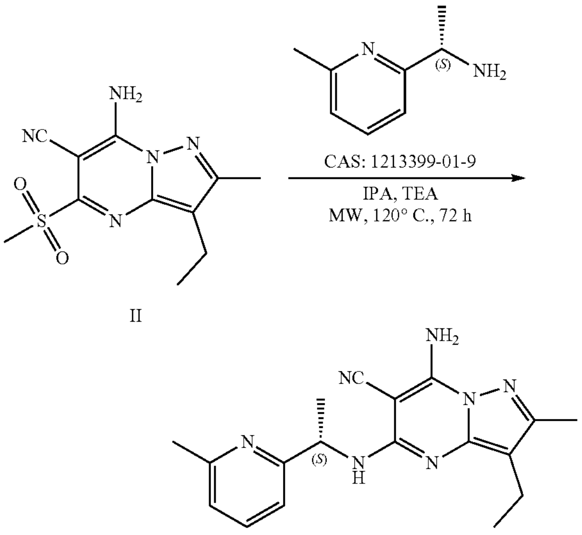

II

Example 5

To a stirred solution of 7-amino-3-ethyl-2-methyl-5-(methylthio) pyrazolo[1,5-a] pyrimidine-6-carbonitrile II (0.205 g, 0.000735 mol) and (S)-1-(6-methylpyridin-2-yl) ethan-1-amine (CAS: 1213399-01-9, 0.2 g, 0.00147 mol) in IPA (4 ml) in a sealed tube was added TEA (0.32 ml, 0.00172 mol) and the reaction mixture was stirred at 120° C. for 72 h. The progress of the reaction was monitored by TLC. After completion, the reaction mixture was diluted with water (20 ml) and extracted with EtOAc (20 ml×3). The organic layer was dried with $Na_2SO_4$, filtered, and evaporated under reduced pressure. The crude material was purified by column chromatography by eluting with 20% EtOAc in hexane to yield the title compound as off-white solid; Yield: (0.0358 g, 17.4%). LC_MS Calc. for $C_{18}H_{21}N_7$ is 335.17; Obs.336.20 [$M^{+}$+H]. $^{1}H$ NMR (400 MHz, DMSO-$d_6$): δ 8.18 (bs, 2H), 7.64 (t, J=7.6 Hz, 1H), 7.6 (d, J=7.6 Hz, 1H), 6.98 (d, J=7.2 Hz, 1H), 5.19 (t, J=6.8 Hz, 1H), 2.42 (q, J=7.2, Hz, 2H), 2.23 (s, 3H), 1.49 (d, J=6.8 Hz, 3H), 1.04 (t, J=7.6 Hz, 3H). HPLC: 11.02 min; 95.75%, Column: X-Bridge C18 (50×4.6) mm, mm, 5 μm, Mobile Phase A: 10 mM ammonium bicarbonate in water, B: Acetonitrile Example 6: 7-amino-2,3-dimethyl-5-{[(6-methylpyridin-2-yl) methyl]amino}pyrazolo[1,5-a] pyrimidine-6-carbonitrile

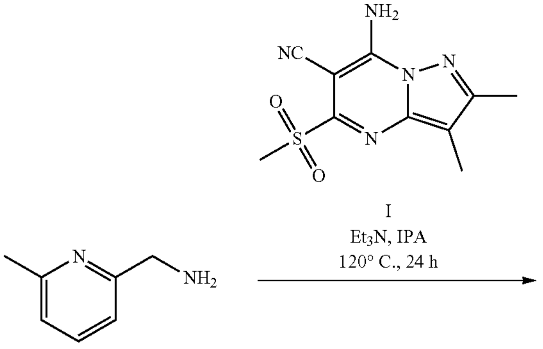

I

VI

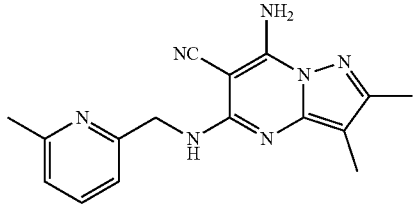

Example 6

To a stirred solution of 7-amino-2,3-dimethyl-5-(methyl sulfonyl) pyrazolo[1,5-a] pyrimidine-6-carbonitrile I (0.25 g, 0.00094 mol) and (6-methylpyridin-2-yl)methanamine VI (0.46 g, 0.00377 mol) in IPA (10 ml) in a sealed tube, was added TEA (1.3 ml g, 0.00377 mol) and the reaction mixture was stirred at 120° C. for 16 h. The progress of the reaction was monitored by TLC. After completion, the reaction mixture was evaporated under reduced pressure and the crude material was purified by column chromatography by eluting with 20% ethyl acetate in hexane to yield the title compound (Example 6) as off-white solid; Yield: (0.1 g, 38%). LC-MS Calculated for $C_{16}H_{17}N_7$ is 307.15; Observe. 308.20 [$M^{+}$+1]. $^{1}H$ NMR (400 MHz, DMSO-$d_6$): δ 8.177 (bs, 2H), 7.633-7.594 (t, J=8 Hz, 1H), 7.232-7.206 (t, J=4.8 Hz, 1H), 7.141-7.096 (m, 2H), 4.616-4.604 (d, J=4.8 Hz, 2H), 2.465 (s, 3H), 2.215 (s, 3H), 1.896 (s, 3H). HPLC: 9.34 min, 97.80%, Column: X Bridge C18 (4.6×150) mm, 5μ, Mobile Phase A: 10 mM Ammonium bicarbonate in water, Mobile Phase B: Acetonitrile.

Example 7: 7-amino-5-{[(6-ethylpyridin-2-yl) methyl]amino}-2,3-dimethylpyrazolo[1,5-a] pyrimidine-6-carbonitrile

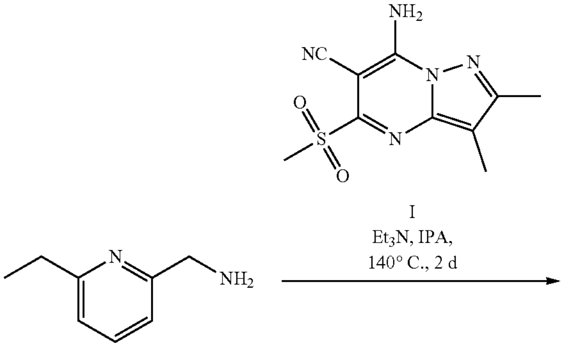

I

VII

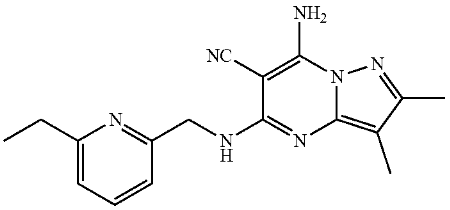

Example 7

To a stirred solution of 7-amino-2,3-dimethyl-5-(methyl sulfonyl) pyrazolo[1,5-a] pyrimidine-6-carbonitrile I (0.100 g, 0.000377 mol) and (6-ethylpyridin-2-yl) methenamine VII (0.102 g, 0.000754 mol) in IPA (10 ml), was added TEA (0.2 ml, 0.00150 mol) and the reaction mixture was heated at 140° C. for 2 days. The progress of the reaction was monitored by TLC. After completion, the reaction mixture was diluted with water (20 ml) and extracted with ethyl acetate (3×20 ml). The organic layer was dried with $Na_2SO_4$, filtered, and evaporated under reduced pressure. The crude material was purified by column chromatography by eluting with 20% ethyl acetate in hexane to yield the title compound (Example 7) as off-white solid; Yield: (0.1 g, 12%). LC-MS Calculated for $C_{17}H_{19}N_7$ is 324.18; Observe: 321.17 [$M^{+}$+1]. $^{1}H$NMR (400 MHz, DMSO-$d_6$): δ8.213 (bs, 2H), 7.665-7.628 (t, J=7.6 Hz, 1H), 7.247 (bs, 1H), 7.169-7.150 (d, J=7.6 Hz, 1H), 7.136-7.117 (d, J=7.6 Hz, 1H), 4.630-4.619 (d, J=4.4 Hz, 2H), 2.777-2.721 (q, J=7.6 Hz, 2H), 2.217 (s, 3H), 1.905 (s, 3H), 1.268-1.233 (t, J=7.6 Hz, 3H). HPLC: 10.18 min, 99.44%, Column: X Bridge C18 (4.6×150) mm, 5μ, Mobile Phase A: Ammonium bicarbonate in water, Mobile Phase B: Acetonitrile.

Example 8: 7-amino-2,3-dimethyl-5-{methyl[(6-methylpyridin-2-yl) methyl]amino}pyrazolo [1,5-a] pyrimidine-6-carbonitrile

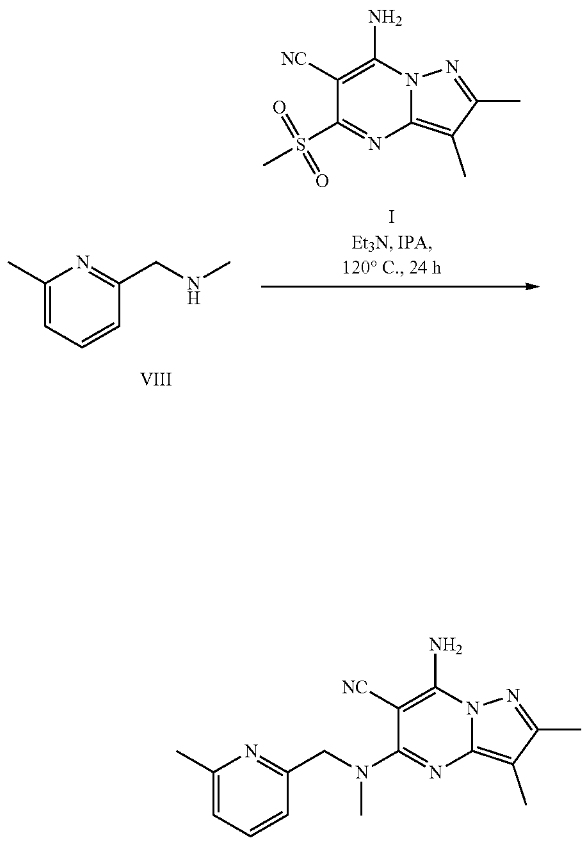

VIII

Example 8

To a stirred solution of 7-amino-2,3-dimethyl-5-(methyl sulfonyl) pyrazolo[1,5-a] pyrimidine-6-carbonitrile I (0.2 g, 0.000754 mol) and N-methyl-1-(6-methylpyridin-2-yl) methanamine VIII (0.123 g, 0.9056 mmol) in IPA (4 ml), was added TEA (0.2 nil, 0.0015 mol) and the reaction mixture was heated at 150° C. for 16 h. The progress of the reaction was monitored by TLC. After completion, the reaction mixture was diluted with water (20 ml) and extracted with DCM (20 ml×3). The organic layer was dried with $Na_2SO_4$, filtered, and evaporated under reduced pressure to give the desired product (Example 8). The crude material was purified by Prep HPLC. Yield: 25 mg. LC_MS Calculated for $C_{17}H_{19}N_7$: 321.17; Observe: 322.17 [$M^+$+H]. $^1$H NMR (400 MHz, DMSO-$d_6$): δ 8.187 (bs, 2H), 7.656-7.617 (d, J=8 Hz, 1H), 7.128-7.086 (d, J=8.4 Hz, 2H), 4.831 (s, 2H), 3.153 (s, 3H), 2.447 (s, 3H), 2.250 (s, 3H), 1.0 (s, 3H). HPLC: 9.73 min, 98.52%, Column: X-Bridge C18 (50×4.6) mm, mm, 5 μm, Mobile Phase A: 10 mM Ammonium bicarbonate in water, B: ACN.

Example 9: 7-amino-5-({[6-(2-hydroxypropan-2-yl) pyridin-2-yl]methyl}amino)-2,3-dimethylpyrazolo[1,5-a] pyrimidine-6-carbonitrile

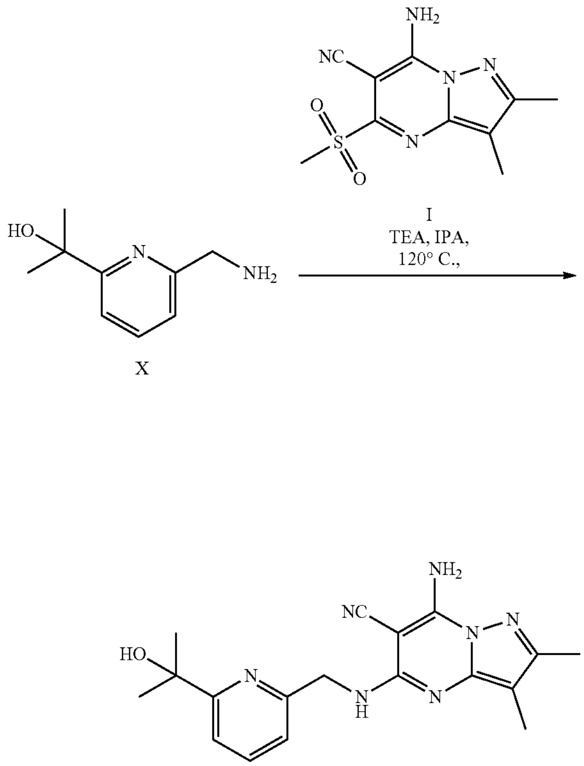

X

Example 9

To a stirred solution 7-amino-2,3-dimethyl-5-(methyl sulfonyl) pyrazolo[1,5-a]pyrimidine-6-carbonitrile I (0.15 g, 0.00039 mol) and 2-(6-(aminomethyl) pyridin-2-yl) propan-2-ol X (0.3 g, 0.00180 mol) in IPA (5 ml), was added TEA (0.6 ml, 0.0043 mol) and the reaction mixture was heated at 120° C. for 16 hrs. The progress of the reaction was monitored by TLC. After completion, the reaction mixture was diluted with water (20 ml) and extracted with ethyl acetate (3×20 ml). The organic layer was dried with $Na_2SO_4$, filtered, and evaporated under reduced pressure. The crude material was purified by prep HPLC to yield the title compound as off-white solid; Yield: (0.03 g, 15%). LC-MS Calculated for $C_{18}H_{21}N_7O$: 351.18; Observe: 352.25 [$M^+$+1]. $^1$HNMR (400 MHz, DMSO-$d_6$): δ 8.202 (bs, 2H), 7.744-7.706 (t, J=7.6 Hz, 1H), 7.529-7.511 (d, J=7.2 Hz, 1H), 7.218-7.199 (d, J=7.6 Hz, 2H), 5.215 (bs, 1H), 4.649-4.637 (d, J=4.8 Hz, 2H), 2.221 (s, 3H), 1.920 (s, 3H), 1.461 (s, 6H). HPLC: 9.42 min, 97.56%, X Bridge C18 (4.6×150) mm, 5μ, Mobile Phase A: 10 mM Ammonium bicarbonate in water, Mobile Phase B: Acetonitrile.

Example 10: 7-Amino-2,3-dimethyl-5-((2-(5-methylpyridin-2-yl) ethyl) amino) pyrazolo[1,5-a] pyrimidine-6-carbonitrile

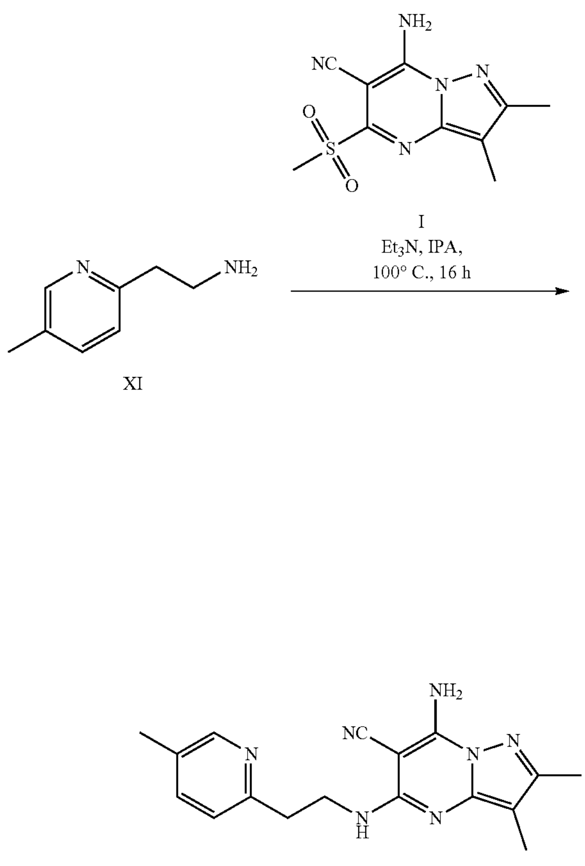

XI

Example 10

To a stirred solution of 7-amino-2,3-dimethyl-5-(methylthio) pyrazolo[1,5-a] pyrimidine-6-carbonitrile I (0.25 g, 0.000943 mol) and 2-(5-methylpyridin-2-yl) ethan-1-amine XI (0.192 g, 0.00141 mol) in IPA (5 ml), was added TEA (0.5 ml, 0.00377 mol) and the reaction mixture was heated at 100° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 40% ethyl acetate in hexane to yield the title compound (Example 10) as off-white solid; Yield: (0.050 g, 20%). LC_MS Calculated for $C_{17}H_{19}N_7$: 321.39; Observe: 322.20 [$M^+$+H]. $^1H$ NMR (400 MHz, DMSO-$d_6$): δ 8.32 (bs, 1H), 8.09 (bs, 2H),7.52 (d, J=6.8 Hz, 1H), 7.18 (d, J=8.0 Hz, 1H), 6.80-6.78 (m, 1H), 3.67-3.64 (m, 2H), 2.99 (d, J=6.8, Hz, 2H), 2.23 (d, J=12, Hz, 3H),1.96 (s, 1H). HPLC: 9.55 min, 96.36%, Column: X-Bridge $C^{18}$ (50×4.6) mm, mm, 5 μm, Mobile Phase A: 10 mM ammonium bicarbonate in water, B: Acetonitrile.

Example 11: 7-amino-5-((2-(5-fluoropyridin-2-yl) ethyl) amino)-2,3-dimethylpyrazolo[1,5-a]pyrimidine-6-carbonitrile

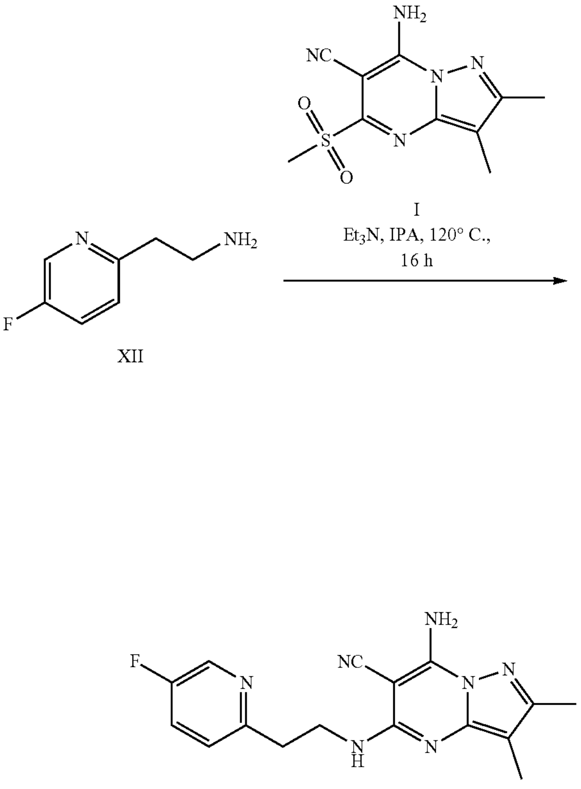

XII

Example 11

To a stirred solution of 7-amino-3-ethyl-2-methyl-5-(methylthio) pyrazolo[1,5-a] pyrimidine-6-carbonitrile I (0.2 g, 0.000754 mol) and 2-(5-fluoropyridin-2-yl) ethan-1-amine XII (0.35 g, 0.0025 mol) in IPA (10 ml), was added TEA (0.63 ml, 0.0045 mol) and the reaction mixture was heated at 120° C. for 3 days. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 50% ethyl acetate in hexane to yield the title compound (Example 11) as off-white solid; Yield: (0.070 g, 28%). LC_MS Calculated for $C_{16}H_{16}FN_7$: 325.155; Observe: 326.15 [$M^+$+H]. $^1H$ NMR (400 MHz, DMSO-$d_6$): δ 8.45 (d, J=2.40 Hz, 1H), 8.09 (bs, 2H), 7.64 (dt, J=8.8 Hz, 3.2 Hz, 1H), 7.36-7.33 (m, 1H), 6.78-6.67 (m, 1H), 3.67 (q, J=6.8, Hz, 2H), 3.05 (t, J=7.2, Hz, 2H), 2.24 (s, 3H), 1.95 (s, 3H). HPLC: 97.34%, Column: X-Bridge C18 (50×4.6) mm, 5 μm, Mobile Phase A: 10 mM ammonium bicarbonate in water, B: Acetonitrile Example 12: 7-amino-5-((2-(6-methoxypyridin-2-yl) ethyl)amino)-2,3-dimethylpyrazolo[1,5-a]pyrimidine-6-carbonitrile

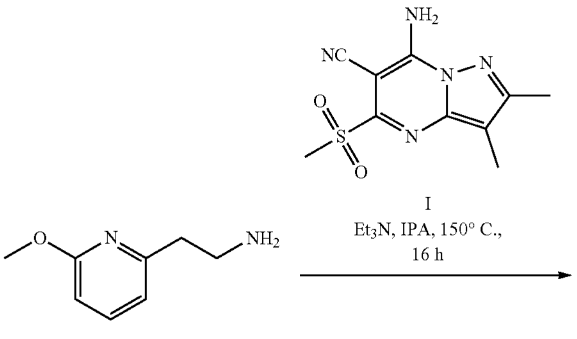

I

XIII

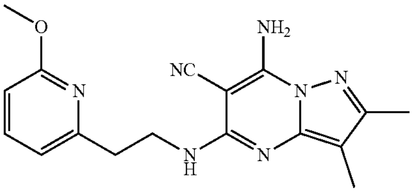

Example 12

To a stirred solution of 7-amino-2,3-dimethyl-5-(methyl sulfonyl) pyrazolo[1,5-a] pyrimidine-6-carbonitrile I (0.2 g, 0.000754 mol) and 2-(6-methoxypyridin-2-yl) ethan-1-amine XIII (0.353 g, 0.00226 mol) in IPA (4 ml), was added TEA (0.229 g, 0.00226 mol) and the reaction mixture was heated at 150° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 20% ethyl acetate in hexane to yield the title compound (Example 12) as off-white solid; Yield: (0.10 g, 40%). LC_MS Calculated for $C_{17}H_{19}N_7O$: 337.17; Observe: 338.15 [$M^+$+H]. $^1$H NMR (400 MHz, DMSO-$d_6$): δ 8.1 (bs, 2H), 7.624-7.585 (t, J=7.6 Hz, 1H), 6.862-6.844 (d, J=7.2 Hz, 1H), 6.640-6.598 (m, 2H), 3.870 (s, 3H), 3.718-3.703 (m, 2H), 2.982-2.965 (t, J=6.8 Hz, 2H), 2.227 (s, 3H), 1.965 (s, 3H). HPLC: 10.83 min, 98.823%, Column: X-Bridge $C^{18}$ (50×4.6) mm, 5 μm, Mobile Phase A: 10 mM Ammonium bicarbonate in water, B: Acetonitrile.

Example 13: 7-amino-5-((2-(6-methylpyridin-2-yl) ethyl)amino)-2,3-dimethylpyrazolo[1,5-a]pyrimidine-6-carbonitrile

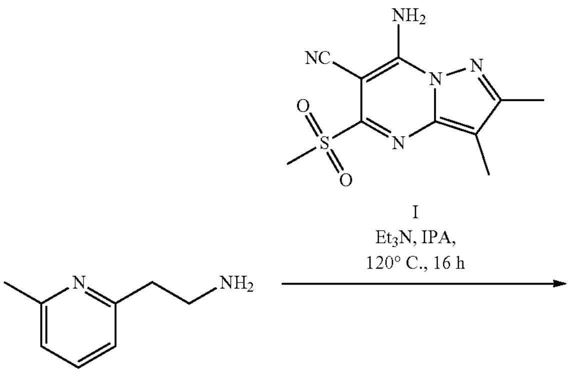

I

XIV

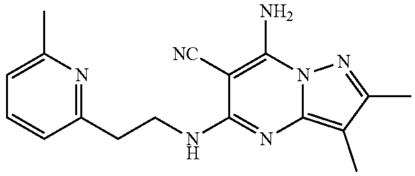

Example 13

To a stirred solution of 7-amino-2,3-methyl-5-(methylthio) pyrazolo[1,5-a] pyrimidine-6-carbonitrile I (0.2 g, 0.0007547 mol) and 2-(6-methylpyridin-2-yl) ethan-1-amine XIV (0.411 g, 0.00301 mol) in IPA (10 ml) in a sealed tube, was added TEA (0.6 ml, 0.0045 mol) and the reaction mixture was stirred at 120° C. for 16 h. The progress of the reaction was monitored by TLC. After completion, the reaction mixture was evaporated under reduced pressure and the crude material was purified by combi flash by eluting with 15% ethyl acetate in hexane to yield the title compound (Example 13) as off-white solid; Yield: (0.105 g, 43%). LC_MS Calculated for $C_{17}H_{19}N_7$ is 321.17; Observe: 322.25 [$M^+$+H]. $^1$H NMR (400 MHz, DMSO-$d_6$): δ 8.11 (bs, 2H), 7.60 (t, J=7.2 Hz, 1H), 7.08 (d, J=8.0 Hz, 2H), 6.93-6.90 (m, 1H), 3.67 (q, J=6.4, Hz, 2H), 2.99 (d, J=6.8, Hz, 2H), 2.22 (s, 3H), 2.48 (s, 3H), 1.96 (s, 3H). HPLC: 98.96%, Column: X-Bridge C18 (50×4.6) mm, mm, 5 μm, Mobile Phase A: 10 mM ammonium bicarbonate in water, B: Acetonitrile.

Example 14 and 15 (Racemic): 7-Amino-3-ethyl-2-methyl-5-((1-(pyridin-2-yl) propan-2-yl) amino) pyrazolo[1,5-a]pyrimidine-6-carbonitrile

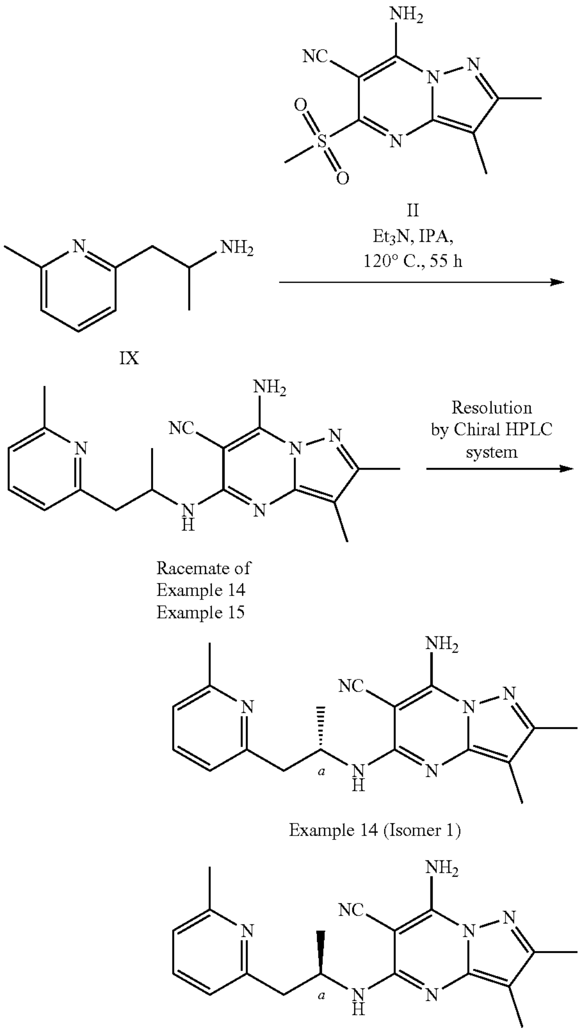

II

IX

Racemate of
Example 14
Example 15

Example 14 (Isomer 1)

Example 15 (Isomer 2)
a = Absolute configuration unknown

To a stirred solution of 7-amino-3-ethyl-2-methyl-5-(methylthio) pyrazolo[1,5-a]pyrimidine-6-carbonitrile II (0.150 g, 0.000537 mol) and 1-(pyridin-2-yl) propan-2-amine IX (0.220 g, 0.00484 mol) in IPA (3 ml), was added TEA (0.6 ml, 0.0032 mol) and the reaction mixture was heated in a sealed tube at 120° C. for 60 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 50% ethyl acetate in hexane to yield the title compound (Example 14 and 15 Racemate) as off-white solid; Yield: (0.071 g, 39%). The crude racemic compound obtained (220 mg) was resolved into its two enantiomers by chiral preparative HPLC system.

Example 14: Chiral 7-amino-2,3-dimethyl-5-{[1-(6-methylpyridin-2-yl)propan-2-yl]amino}pyrazolo[1,5-a]pyrimidine-6-carbonitrile. (Isomer 1)

Yield: 64.1 gm: LC-MS Calculated for $C_{18}H_{21}N_7$: 335.19; Observe: 336.20 $[M+1]^+$. $^1$HNMR (400 MHz, DMSO-$d_6$): δ 8.10 (bs, 2H), 7.60 (t, J=7.2 Hz, 1H), 7.09 (t, J=8.0 Hz, 2H), 6.91 (d, J=6.8 Hz, 1H), 4.51-4.48 (m, 1H), 3.00-2.96 (m, 2H), 2.50 (s, 3H), 2.22 (s, 3H), 1.96 (s, 3H), 1.14 (d, J=5.6 Hz, 3H); HPLC: 10.31 min, 99.38%, 10.307 min; X Bridge C18 (4.6×150) mm, 5μ, Mobile Phase A: 10 mM Ammonium bicarbonate in water, Mobile Phase B: Acetonitrile. Chiral HPLC: Purity=98.91%, Rt=17.205 min, Chiral Pak IC (250*4.6) mm, 5μ, Mobile Phase A: 0.1% diethyl amine in n-hexane, Mobile Phase B: Isopropanol: dichloromethane (90:5:5); Flow rate: 0.8 mL/min

Example 15: Chiral 7-amino-2,3-dimethyl-5-{[1-(6-methylpyridin-2-yl)propan-2-yl]amino}pyrazolo[1,5-a]pyrimidine-6-carbonitrile. (Isomer 2)

Yield: 55.6 gm; LC-MS Calculated for $C_{18}H_{21}N_7$: 335.19; Observe: 336.20 $[M+1]^+$. $^1$HNMR (400 MHz, DMSO-$d_6$): δ 8.10 (bs, 2H), 7.60 (t, J=7.2 Hz, 1H), 7.09 (t, J=8.0 Hz, 2H), 6.91 (d, J=6.8 Hz, 1H), 4.51-4.48 (m, 1H), 3.00-2.96 (m, 2H), 2.50 (s, 3H), 2.22 (s, 3H), 1.96 (s, 3H), 1.14 (d, J=5.6 Hz, 3H); HPLC Purity=99.52%, Rt=10.312 min; X Bridge C18 (4.6×150) mm, 5μ, Mobile Phase A: 10 mM Ammonium bicarbonate in water, Mobile Phase B: Acetonitrile. Chiral HPLC: Purity=100%, Rt=20.769 min, Chiral Pak IC (250*4.6) mm, 5μ, Mobile Phase A: 0.1% diethyl amine in n-hexane, Mobile Phase B: Isopropanol: dichloromethane (90:5:5); Flow rate: 0.8 mL/min

Example 16: 7-amino-5-({2-[6-(2-hydroxypropan-2-yl) pyridin-2-yl]ethyl}amino)-2,3-dimethylpyrazolo[1,5-a]pyrimidine-6-carbonitrile

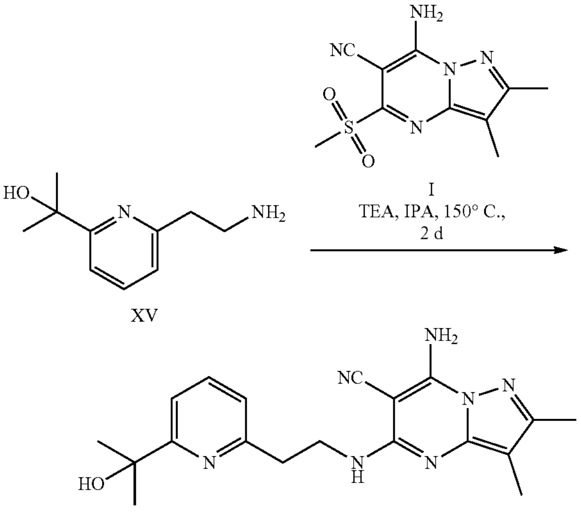

I

XV

Example 16

To a stirred solution of 7-amino-2,3-dimethyl-5-(methyl sulfonyl) pyrazolo[1,5-a] pyrimidine-6-carbonitrile I (0.15 g, 0.00056 mol) and 2-(6-(2-aminoethyl) pyridin-2-yl) propan-2-ol XV (0.153 g, 0.00084 mol) in IPA (10 ml), was added TEA (0.343 g, 0.00339 mol) and the reaction mixture was heated at 150° C. for 2 days. The progress of the reaction was monitored by TLC. After completion, the reaction mixture was diluted with water (20 ml) and extracted with DCM (20 ml×3). The organic layer was dried with $Na_2SO_4$, filtered, and evaporated under reduced pressure. The crude material was purified by Prep HPLC to get off white title compound (Example 16). Yield: (0.025 g, 12%). LC_MS Calculated for $C_{19}H_{23}N_7O$: 365.20; Observe: 388.1 $[M+Na]^+$. $^1H$ NMR (400 MHz, DMSO-$d_6$): δ 8.086 (bs, 2H), 7.677 (t, 1H), 7.477-7.458 (d, J=7.6 Hz, 1H), 7.124-7.105 (d, J=7.6 Hz, 1H), 6.609 (t, 1H), 5.163 (s, 1H), 3.726-3.711 (t, J=6 Hz, 2H), 3.046-3.012 (t, J=6.8 Hz, 2H), 2.227 (s, 3H), 1.964 (s, 3H), 1.435 (s, 6H). HPLC: 9.69 min, 98.95%, X-Bridge C18 (50×4.6) mm, mm, 5 μm, Mobile Phase A: 10 mM Ammonium bicarbonate in water, B: Acetonitrile.

Example 17: 7-Amino-3-ethyl-2-methyl-5-((2-(6-methylpyridin-2-yl) ethyl) amino) pyrazolo[1,5-a] pyrimidine-6-carbonitrile

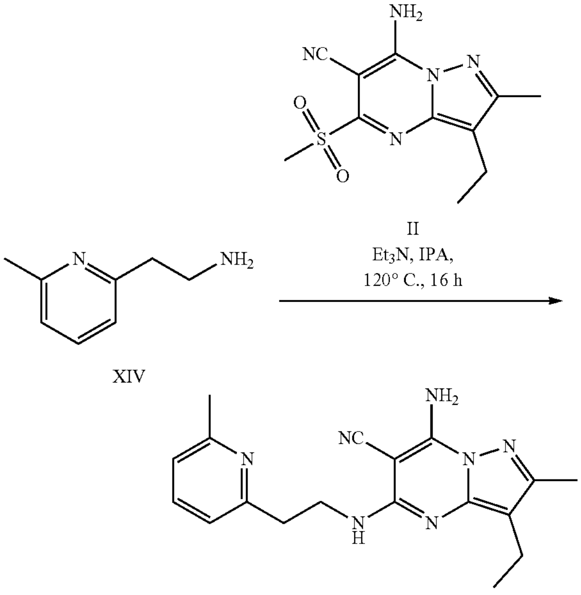

XIV

Example 17

To a stirred solution of 7-amino-3-ethyl-2-methyl-5-(methylation) pyrazolo[1,5-a] pyrimidine-6-carbonitrile II (0.15 g, 0.0005376 mol) and 2-(6-methylpyridin-2-yl) ethan-1-amine XIV (0.292 g, 0.00215 mol) in IPA (5 ml) in a sealed tube, was added TEA (0.23 ml, 0.0016 mol) and the reaction mixture was stirred at 120° C. for 16 h. The progress of the reaction was monitored by TLC (non-polar spot). After completion, the reaction mixture was evaporated under reduced pressure and the crude material was purified by column chromatography by eluting with 40% ethyl acetate in hexane to yield the title compound (Example 17) as off-white solid; Yield: (0.056 g, 31%). LC_MS Calculated for $C_{18}H_{21}N_7$: 335.17; Obs.336.15 $[M^{+}+H]$. $^1H$ NMR (400 MHz, DMSO-$d_6$): δ 8.10 (bs, 1H), 7.60 (t, J=7.6 Hz, 1H), 7.08 (dd, J=8.0, 3.6 Hz, 2H), 6.92 (t, J=4.8 Hz, 1H), 3.66 (q, J=6.0, Hz, 2H), 2.99 (t, J=6.8, Hz, 2H), 2.50-2.43 (m, 5H), 2.24 (s, 3H), 1.24 (t, J=7.6 Hz, 3H). _HPLC: 99.57%, X-Bridge C18 (50×4.6) mm, mm, 5 μm, Mobile Phase A: 10 mM ammonium bicarbonate in water, B: Acetonitrile.

Example 18: 7-Amino-3-ethyl-2-methyl-5-((2-(5-methylpyridin-2-yl) ethyl) amino) pyrazolo[1,5-a] pyrimidine-6-carbonitrile

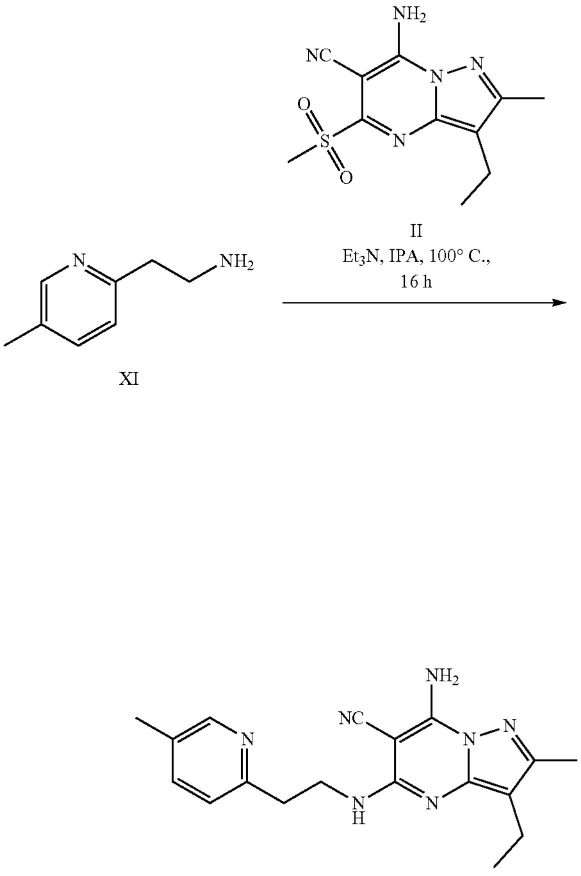

XI

Example 18

To a stirred solution of 7-amino-3-ethyl-2-methyl-5-(methylthio) pyrazolo[1,5-a] pyrimidine-6-carbonitrile II (0.15 g, 0.00049 mol) and 2-(5-methylpyridin-2-yl) ethan-1-amine XI (0.166 g, 0.00122 mol) in IPA (10 ml), was added TEA (0.342 ml, 0.000725 mol) and the reaction mixture was heated at 100° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 40% ethyl acetate in hexane to yield the title compound (Example 18) as off-white solid; Yield: (0.050 g, 31%). LC_MS Calculated. for $C_{18}H_{21}N_7$. 335.17; Obs.336.15 $[M^{+}+H]$. $^1H$ NMR (400 MHz, DMSO-$d_6$): δ 8.32 (s, 1H), 8.09 (bs, 2H), 7.52 (d, J=6.4 Hz, 1H), 7.17 (d, J=8.0 Hz, 1H), 6.80 (t, J=5.2 Hz, 1H), 3.67-3.62 (m, 2H), 2.99 (t, J=7.2, Hz, 2H), 2.43 (d, J=7.6, Hz, 2H), 2.25 (d, J=4.0 Hz, 6H), 1.11 (t, J=7.6 Hz, 3H). HPLC: 98.81%, Zorbax SB-C8 (4.6*75) mm, 3.5μ, Mobile Phase A: 10 mM ammonium bicarbonate in water, B: Acetonitrile.

Example 19: 7-Amino-3-ethyl-5-((2-(5-methoxy-pyridin-2-yl) ethyl) amino)-2-methylpyrazolo [1,5-a]pyrimidine-6-carbonitrile

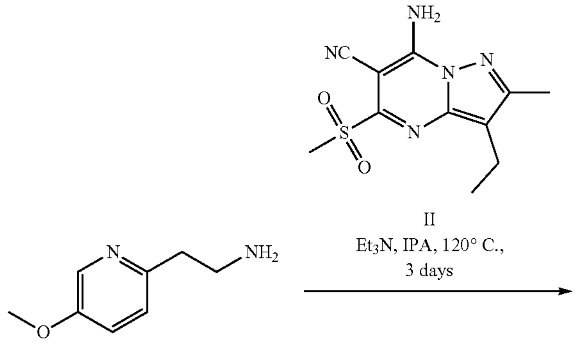

XIX

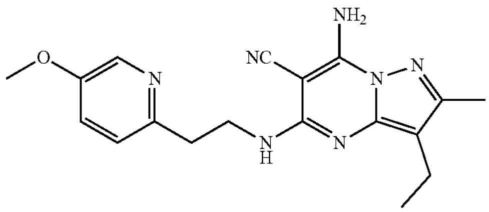

Example 19

To a stirred solution of 7-amino-3-ethyl-2-methyl-5-(methylthio) pyrazolo[1,5-a] pyrimidine-6-carbonitrile II (0.2 g, 0.000716 mol) and 2-(5-methoxypyridin-2-yl) ethan-1-amine XIX (0.435 g, 0.00286 mol) in IPA (5 ml), was added TEA (0.6 ml, 0.0043 mol) and the reaction mixture was heated at 120° C. for 3 days. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 50% ethyl acetate in hexane to yield the title compound (Example 19) as off-white solid; Yield: (0.080 g, 31.8%). LC_MS Calculated for $C_{18}H_{21}N_7O$: 351.18; Observe: 352.20 [$M^+$+H]. $^1H$ NMR (400 MHz, DMSO-$d_6$): δ 8.20 (d, J=2.8 Hz, 1H), 8.08 (bs, 2H), 7.33 (dd, J=8.4, 2.8 Hz, 1H), 7.21 (d, J=8.4 Hz, 1H), 6.75 (t, J=5.6 Hz, 1H), 3.79 (s, 3H), 3.64 (q, J=6.8, Hz, 2H), 2.98 (t, J=7.2, Hz, 2H), 2.5-2.40 (m, 2H), 2.24 (s, 3H), 1.12 (t, J=7.6 Hz, 3H). HPLC: 99.23%, X-Bridge C18 (50×4.6) mm, mm, 5 μm, Mobile Phase A: 10 mM ammonium bicarbonate in water, B: Acetonitrile Example 20: 7-Amino-3-ethyl-5-((2-(6-methoxy-pyridin-2-yl) ethyl) amino)-2-methylpyrazolo [1,5-a]pyrimidine-6-carbonitrile

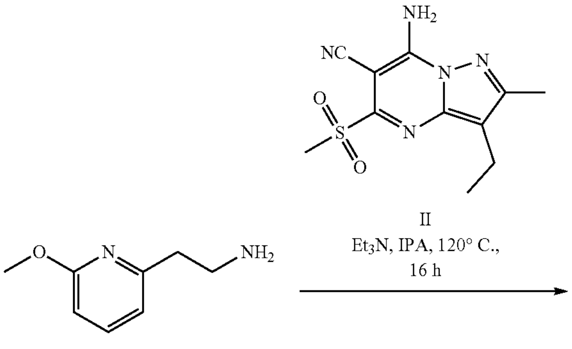

XIII

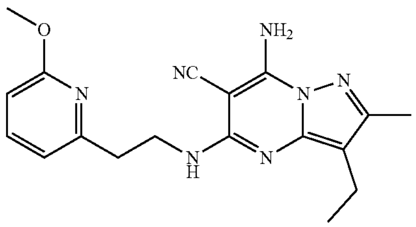

Example 20

To a stirred solution of 7-amino-3-ethyl-2-methyl-5-(methylthio) pyrazolo[1,5-a] pyrimidine-6-carbonitrile II (0.2 g, 0.000716 mol) and 2-(6-methoxypyridin-2-yl) ethan-1-amine XIII (0.230 g, 0.00151 mol) in IPA (5 ml), was added TEA (0.6 ml, 0.0043 mol) and the reaction mixture was heated at 120° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by flash column chromatography by eluting with 50% ethyl acetate in hexane to yield the title compound (Example 20) as off-white solid; Yield: (0.097 g, 38.6%). LC_MS Calculated. for $C_{18}H_{21}N_7O$ is 351.18; Observe: 352.25 [$M^+$+H]. $^1H$ NMR (400 MHz, DMSO-$d_6$): δ 8.09 (bs, 2H), 7.60 (t, J=8.0 Hz, 1H), 6.84 (d, J=7.20 Hz, 1H), 6.64-6.61 (m, 2H), 3.86 (s, 3H), 3.69 (q, J=6.0, Hz, 2H), 2.96 (t, J=7.2, Hz, 2H), 2.46 (q, J=7.2 Hz, 2H), 2.24 (s, 3H), 1.12 (t, J=7.6 Hz, 3H). HPLC: 98.52%, X-Bridge C18 (50×4.6) mm, mm, 5 μm, Mobile Phase A: 10 mM ammonium bicarbonate in water, B: Acetonitrile.

Example 21: 7-Amino-3-ethyl-5-((2-(5-fluoropyridin-2-yl) ethyl) amino)-2-methylpyrazolo[1,5-a] pyrimidine-6-carbonitrile

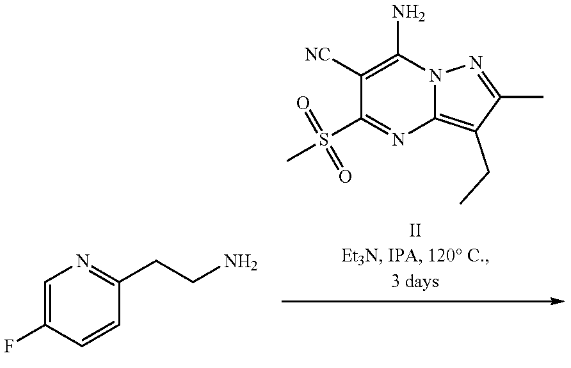

XII

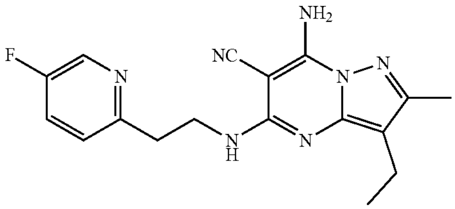

Example 21

To a stirred solution of 7-amino-3-ethyl-2-methyl-5-(methylthio) pyrazolo[1,5-a] pyrimidine-6-carbonitrile II (0.2 g, 0.000716 mol) and 2-(5-fluoropyridin-2-yl) ethan-1-amine XII (0.4 g, 0.00286 mol) in IPA (5 ml), was added TEA (0.6 ml, 0.0043 mol) and the reaction mixture was heated at 120° C. for 3 days. The progress of the reaction was monitored by TLC (non-polar spot). After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 50% ethyl acetate in hexane to yield the title compound (Example 21) as off-white solid; Yield: (0.050 g, 20.5%). LC_MS Calculated for $C_{17}H_{18}FN_7$: 339.16; Observe. 340.20 [$M^+$+H]. $^1$H NMR (400 MHz, DMSO-$d_6$): δ 8.45 (d, J=2.40 Hz, 1H), 8.10 (bs, 2H), 7.64 (dt, J=8.4, 2.8 Hz, 1H), 7.35-7.31 (m, 1H), 6.75 (d, J=5.2 Hz, 1H), 3.67 (q, J=6.8, Hz, 2H), 3.05 (t, J=7.2, Hz, 2H), 2.44 (q, J=7.2 Hz, 2H), 2.24 (s, 3H), 1.11 (t, J=7.6 Hz, 3H), HPLC: 98.34%, X-Bridge C18 (50×4.6) mm, mm, 5 μm, Mobile Phase A: 10 mM ammonium bicarbonate in water, B: Acetonitrile.

Example 22 and 23 (Racemate): 7-Amino-3-ethyl-2-methyl-5-((1-(pyridin-2-yl) propan-2-yl) amino) pyrazolo[1,5-a] pyrimidine-6-carbonitrile (Racemic)

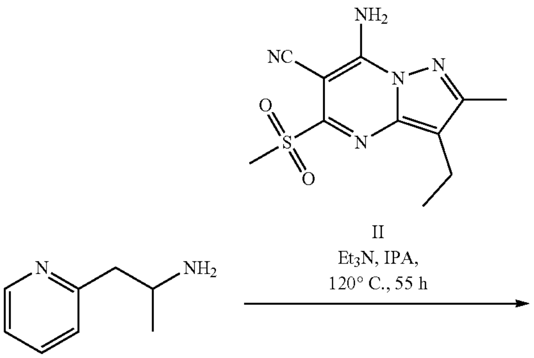

CAS: 51038-40-5

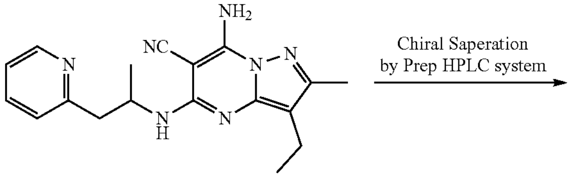

Racemate of
Example 22
Example 23

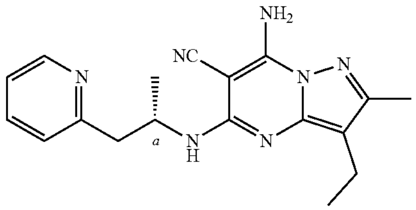

Example 22 (Isomer 1)

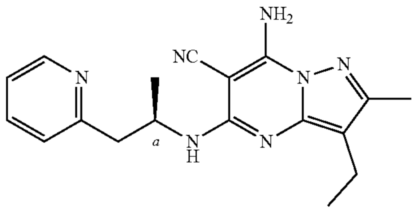

Example 23 (Isomer 2)
a = Absolute configuration unknown

To a stirred solution of 7-amino-3-ethyl-2-methyl-5-(methylthio) pyrazolo[1,5-a] pyrimidine-6-carbonitrile II (0.150 g, 0.000537 mol) and 1-(pyridin-2-yl) propan-2-amine (CAS: 51038-40-5, 0.220 g, 0.00484 mol) in IPA (3 ml), was added TEA (0.6 ml, 0.0032 mol) and the reaction mixture was heated in a sealed tube at 120° C. for 60 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 50% ethyl acetate in hexane to yield the title compound as off-white solid; Yield: (0.071 g, 39%). Then the racemic compound of (Example 22 and 23) (71 mg) was resolved into its two enantiomers by chiral preparative HPLC system Example 22: Chiral 7-Amino-3-ethyl-2-methyl-5-((1-(pyridin-2-yl) propan-2-yl) amino) pyrazolo[1,5-a]pyrimidine-6-carbonitrile. (Isomer 1)

Yield: 0.0154 g: LC_MS Calculated for $C_{18}H_{21}N_7$: 335.19; Observe: 336.20 $[M^{+}+H]$. $^1H$ NMR (400 MHz, DMSO-$d_6$): δ 8.48 (d, J=4.4 Hz, 1H), 8.07 (bs, 2H), 7.70 (dt, J=7.6 Hz, 1.6 Hz, 1H), 7.30 (d, J=7.6 Hz, 1H), 7.20 (t, J=7.2 Hz, 1H), 6.71 (d, J=7.6 Hz, 1H), 4.51-4.48 (m, 1H), 3.11-3.06 (m, 1H), 2.96-2.91 (m, 1H), 2.45 (q, J=7.6 Hz, 2H), 2.23 (s, 3H) 1.16 (d, J=6.4, Hz, 3H), 1.10 (t, J=7.6 Hz, 3H). HPLC: 97.85%, Column: X-Bridge C8 (50×4.6) mm, mm, 5 μm, Mobile Phase A: 0.1% TFA in water, Mobile Phase B: Acetonitrile.

Example 23: Chiral 7-Amino-3-ethyl-2-methyl-5-((1-(pyridin-2-yl) propan-2-yl) amino) pyrazolo[1,5-a]pyrimidine-6-carbonitrile. (Isomer 2)

Yield: 0.0164 g: LC_MS Calculated for $C_8H_{21}N_7$: 335.19; Observe: 336.20 $[M^{+}+H]$. $^1H$ NMR (400 MHz, DMSO-$d_6$): δ 8.48 (d, J=4.0 Hz, 1H), 8.07 (bs, 2H), 7.69 (t, J=7.6 Hz, 1H), 7.31 (d, J=7.6 Hz, 1H), 7.20 (t, J=6.8 Hz, 1H), 6.71 (d, J=7.6 Hz, 1H), 4.51-4.48 (m, 1H), 3.11-3.06 (m, 1H), 2.96-2.91 (m, 1H), 2.45 (q, J=7.6 Hz, 2H), 2.23 (s, 3H) 1.16 (d, J=6.4, Hz, 3H), 1.10 (t, J=7.2 Hz, 3H). HPLC: 98.38%, X-Bridge C8 (50×4.6) mm, mm, 5 μm, Mobile Phase A: 0.1% TFA in water, Mobile Phase B: Acetonitrile.

Example 24: 7-Amino-3-ethyl-2-methyl-5-((1-(6-methylpyridin-2-yl) propan-2-yl) amino) pyrazolo [1,5-a]pyrimidine-6-carbonitrile

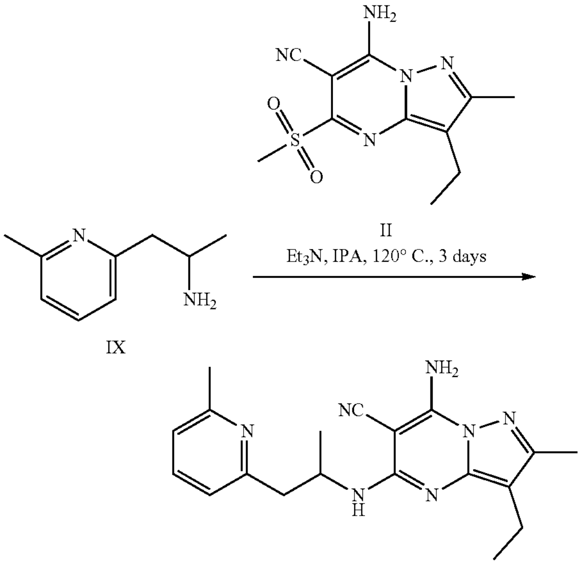

Example 24

To a stirred solution of 7-amino-3-ethyl-2-methyl-5-(methylthio) pyrazolo[1,5-a] pyrimidine-6-carbonitrile II (0.5 g, 0.00179 mol) and 1-(6-methylpyridin-2-yl) propan-2-amine IX (0.430 g, 0.00284 mol) in IPA (10 ml), was added TEA (1.49 ml, 0.01075 mol) and the reaction mixture was heated at 120° C. for 3 days. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by flash column chromatography by eluting with 10% ethyl acetate in hexane to yield the title compound (Example 24) as racemic off-white solid; Yield: (0.350 g, 56%).). LC_MS Calculated for $C_{19}H_{23}N_7$ is 349.2; Observe: 350.20 $[M^{+}+H]$. $^1H$ NMR (400 MHz, DMSO-$d_6$): δ 8.11 (brs, 2H), 7.59 (t, J=7.6 Hz, 1H), 7.09 (t, J=8.80 Hz, 2H), 6.93 (d, J=7.2, Hz, 1H), 4.5-4.4 (m, 1H), 2.9-2.93 (m, 2H), 2.49 (s, 3H), 2.43 (q, J=7.60 Hz, 2H), 2.23 (s, 3H), 1.15 (d, J=6.8, Hz, 3H), 1.10 (t, J=7.6, Hz, 3H HPLC: 95.52%, X-Bridge C18 (50×4.6) mm, mm, 5 μm, Mobile Phase A: 10 mM ammonium bicarbonate in water B: Acetonitrile.

Example 25: 7-amino-3-ethyl-5-({2-[6-(2-hydroxy-propan-2-yl) pyridin-2-yl]ethyl}amino)-2-methylpyrazolo[1,5-a]pyrimidine-6-carbonitrile

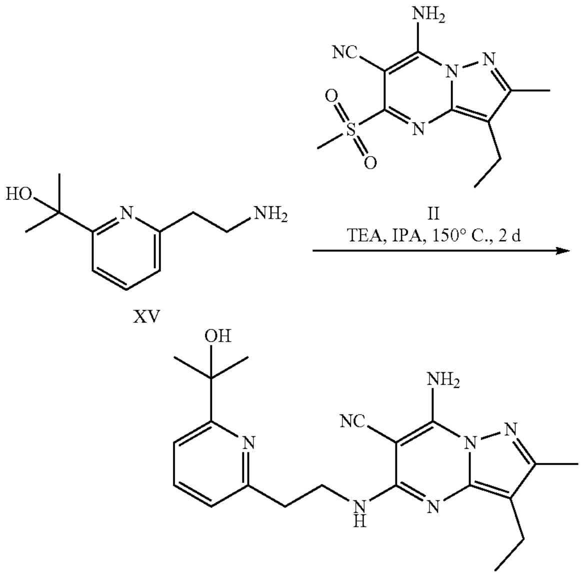

Example 25

To a stirred solution of 7-amino-3-ethyl-2-methyl-5-(methyl sulfonyl) pyrazolo[1,5-a] pyrimidine-6-carbonitrile II (0.15 g, 0.000537 mol) and 2-(6-(2-aminoethyl) pyridin-2-yl) propan-2-ol XV (0.145 g, 0.000804 mol) in IPA (10 ml), was added TEA (0.326 g, 0.00322 mol) and the reaction mixture was heated at 150° C. for 2 days. The progress of the reaction was monitored by TLC. After completion, reaction mixture was concentrated to dryness under reduced pressure. the reaction mixture was diluted with water (20 ml) and extracted with Ethyl acetate (20 ml×3). The organic layer was dried with $Na_2SO_4$, filtered, and evaporated under reduced pressure to get the desired product (Example 25). The crude material was purified by Prep HPLC. Yield: (0.03 g, 14.7%). LC_MS Calculated for $C_{20}H_{25}N_7O$ is 379.21; Observe: 380.25 $[M^{+}+H]$. $^1H$ NMR (400 MHz, DMSO-$d_6$): δ 8.104 (bs, 2H), 7.695-7.657 (t, J=7.2 Hz, 1H), 7.478-7.459 (d, J=7.6 Hz, 1H), 7.113-7.094 (d, J=7.6 Hz, 1H), 6.659 (t, 1H), 5.170 (s, 1H), 3.709-3.694 (t, J=6 Hz, 2H), 3.044-3.011

(t, J=6.8 Hz, 2H), 2.455 (t, 2H), 2.247 (s, 3H), 1.434 (s, 6H), 1.145-1.108 (t, J=7.2 Hz, 3H). HPLC: 98.77%, X-Bridge C18 (50×4.6) mm, mm, 5 μm, Mobile Phase A: 10 mM Ammonium bicarbonate in water, B: Acetonitrile.

Example 26: 7-amino-3-(cyclopropylmethyl)-2-methyl-5-((2-(6-methylpyridin-2-yl) ethyl) amino) pyrazolo[1,5-a]pyrimidine-6-carbonitrile

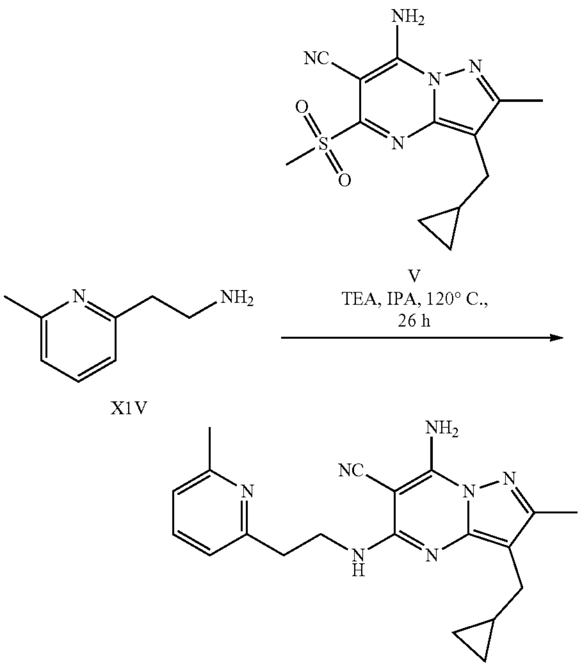

Example 26

A solution of 7-amino-3-(cyclopropyl methyl)-2-methyl-5-(methyl sulfonyl) pyrazolo[1,5-a] pyrimidine-6-carbonitrile V (0.212 g, 0.000697 mol) and 2-(6-methylpyridin-2-yl) ethan-1-amine XIV (0.190 g, 0.00139 mol) in IPA (5 mL) was purged with $N_2$ gas for 10 min and TEA (0.58 ml, 0.00418 mol) was added. The reaction mixture was heated at 120° C. for 16 h. The progress of the reaction was monitored by TLC. After completion, the reaction mixture was concentrated under reduced pressure and the residue was dissolved in ethyl acetate (50 mL). The resulting was extracted with water (20 mL×3). The organic layer was washed with brine and dried over anhydrous $Na_2SO_4$, filtered and evaporated under reduced pressure. The crude material was purified by silica gel (combi flash) column chromatography by eluting with 40% ethyl acetate in n-hexane to yield the title compound (Example 26) as an off-white solid; Yield: (0.140 g, 56%). LC_MS Calculated for $C_{20}H_{23}N_7$ is 361.20; Observe: 362.20 [$M^+$+H]. $^1$H NMR (400 MHz, DMSO-$d_6$): δ 8.12 (bs, 2H), 7.6 (t, J=7.6 Hz, 1H), 7.07 (t, J=7.2 Hz, 2H), 6.98-6.92 (m, 1H), 3.65 (q, J=6.0, Hz, 2H), 2.98 (t, J=6.8, Hz, 2H), 2.4 (d, J=6.8 Hz, 2H), 2.2 (s, 3H), 1.0-0.95 (m, 1H), 0.35 (d, J=7.6 Hz, 2H), 0.18 (d, J=4.4 Hz, 2H). HPLC: 11.10 min, 95.83%, X-Bridge C18 (50×4.6) mm, mm, 5 μm, Mobile Phase A: 10 mM ammonium bicarbonate in water, B: Acetonitrile.

Example 27: 7-amino-3-(isopropylmethyl)-2-methyl-5-((2-(6-methylpyridin-2-yl)ethyl) amino) pyrazolo[1,5-a]pyrimidine-6-carbonitrile

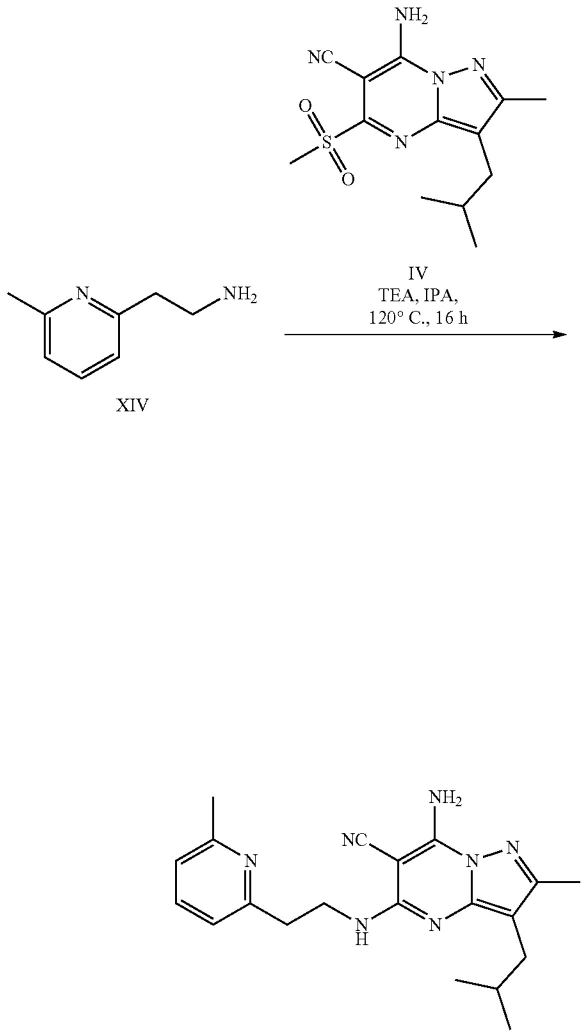

Example 27

To a stirred solution of 7-amino-3-isobutyl-2-methyl-5-(methyl sulfonyl) pyrazolo[1,5-a] pyrimidine-6-carbonitrile IV (0.150 g, 0.00049 mol) and 2-(6-methylpyridin-2-yl) ethan-1-amine XIV (0.2 g, 0.00146 mol) in isopropanol (15 ml) in a sealed tube, was added TEA (0.41 ml, 0.0029 mol) and the reaction mixture was stirred at 120° C. for 16 h. The progress of the reaction was monitored by TLC (less-polar spot). After completion, the reaction mixture was evaporated under reduced pressure and the crude material was purified by column chromatography by eluting with 0-25% ethyl acetate in n-hexane to yield the title compound (Example 27) as an off-white solid; Yield: (0.125 g, 71%). LC_MS Calculated for $C_{20}H_{25}N_7$ is 363.22; Observe. 364.20 [$M^+$+H]. $^1$H NMR (400 MHz, DMSO-$D_6$): δ 8.11 (bs, 2H), 7.60 (t, J=8.0 Hz, 1H), 7.01 (t, J=7.6 Hz, 2H), 6.92 (s, 1H), 3.64-3.61 (m, 2H), 3.00 (t, J=7.2 Hz, 2H), 2.47 (s, 3H), 2.32 (d, J=7.2 Hz, 2H), 2.23 (s, 3H), 1.81-1.95 (m, 1H) 0.87 (d, J=6.8 Hz, 6H); HPLC: 11.66 min, 97.26%, X-Bridge C18 (50×4.6) mm, mm, 5 μm, Mobile Phase A: 10 mM Ammonium bicarbonate in water, B: Acetonitrile.

Example 28: 7-amino-3-(isopropyl)-2-methyl-5-((2-(6-methylpyridin-2-yl)ethyl) amino) pyrazolo[1,5-a] pyrimidine-6-carbonitrile

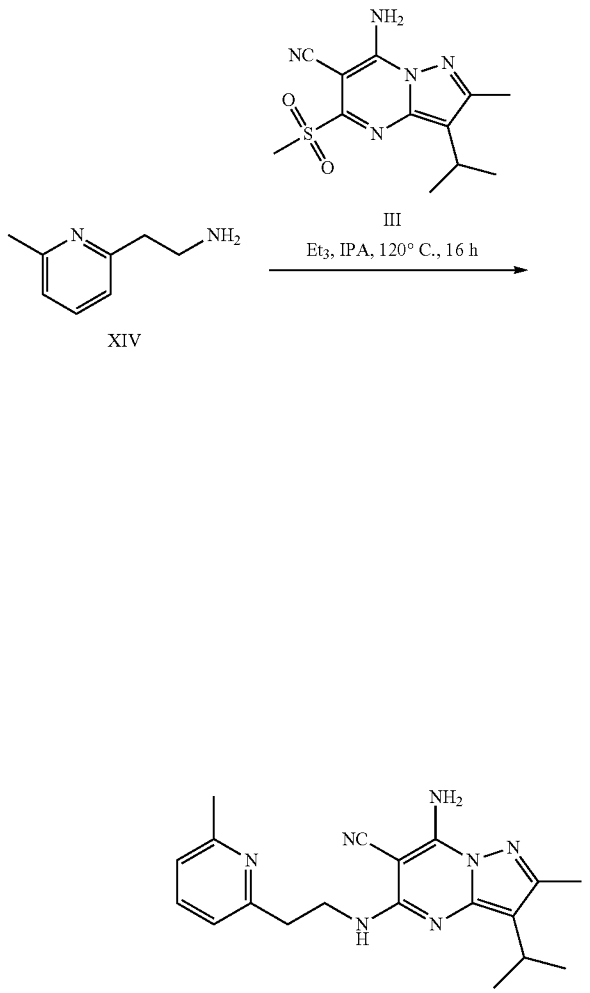

III

XIV

Example 28

To a stirred solution of 7-amino-3-isopropyl-2-methyl-5-(methyl sulfonyl) pyrazolo[1,5-a] pyrimidine-6-carbonitrile III (0.2 g, 0.00068 mol) and 2-(6-methylpyridin-2-yl)ethan-1-amine XIV (0.278 g, 0.00204 mol) in IPA (2 ml) in a sealed tube, was added TEA (0.278 g, 0.00274 mol) and the reaction mixture was stirred at 120° C. for 16 h. The progress of the reaction was monitored by TLC. After completion, the reaction mixture was evaporated under reduced pressure and the crude material was purified by column chromatography by eluting with 20% ethyl acetate in hexane to yield the title compound (Example 28) as off-white solid; Yield: (0.068 g, 29%). LC-MS Calculated for $C_{19}H_{23}N_7$349.20; Observe: 350.20 [$M^+$+1]. $^1$HNMR (400 MHz, DMSO-$d_6$): δ 8.063 (bs, 2H), 7.612-7.574 (t, J=7.6 Hz, 1H),7.088-7.047 (t, J=8.4 Hz, 2H), 6.893 (bs, 1H), 3.657-3.644 (m 2H), 2.995-2.979 (t, J=6.4 Hz, 2H), 2.942-2.908 (m, 1H), 2.460 (s, 3H), 2.257 (s, 3H), 1.303-1.286 (d, J=6.8 Hz, 6H). HPLC: 11.28 min, 98.85%, Column: X Bridge C18 (4.6×150) mm, 5μ, Mobile Phase A: 10 mM Ammonium bicarbonate in water, Mobile Phase B: Acetonitrile.

Example 29: 7-amino-5-{[2-(1-ethyl-1H-pyrazol-3-yl) ethyl]amino}-2,3-dimethylpyrazolo[1,5-a]pyrimidine-6-carbonitrile

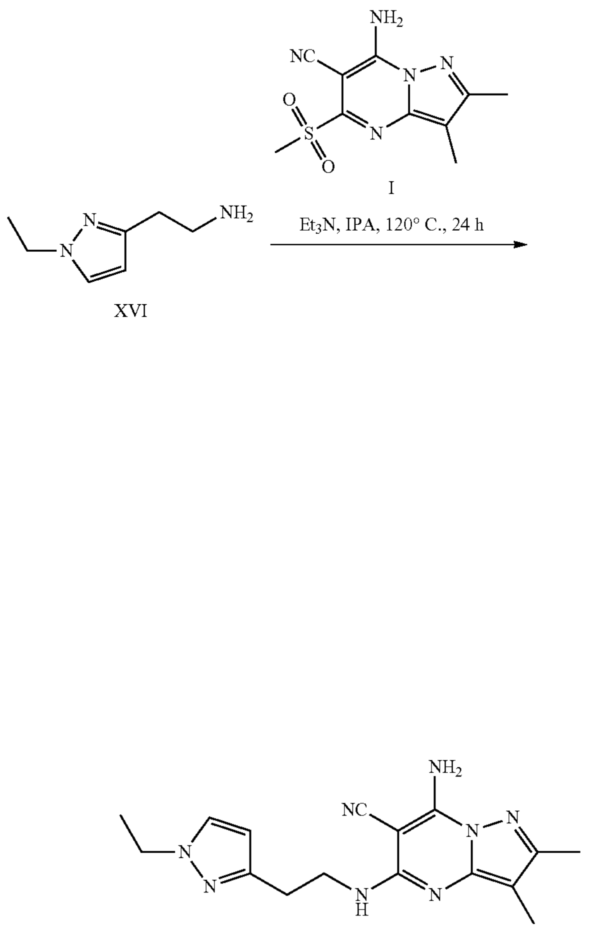

I

XVI

Example 29

To a stirred solution of 7-amino-2,3-dimethyl-5-(methyl sulfonyl) pyrazolo[1,5-a] pyrimidine-6-carbonitrile I (0.2 g, 0.000943 mol) and 2-(1-ethyl-1H-pyrazol-3-yl) ethan-1-amine XVI (0.387 g, 0.00282 mol) in IPA (3 ml), was added TEA (0.381 g, 0.00377 mol) and the reaction mixture was heated at 120° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 20% ethyl acetate in hexane to yield the title compound (Example 29) as off-white solid; Yield: (0.057 g, 18%). LC-MS Calculated for $C_{17}H_{19}N_7$: 324.39; Observe: 3325.2 [$M^+$+1]. $^1$HNMR (400 MHz, DMSO-$d_6$): δ 8.11 (bs, 2H), 7.611-7.608 (d, J=1.2 Hz, 1H), 6.642 (m, 1H), 6.071-6.067 (d, J=1.6 Hz, 1H), 4.092-4.037 (q, J=7.6 Hz, 2H), 3.590-3.575 (t, J=6 Hz, 2H), 2.840-2.804 (t, J=7.2 Hz, 2H), 2.229 (s, 3H), 1.966 (s, 3H), 1.369-1.332 (t, J=7.6 Hz, 3H). HPLC: 9.28 min, 99.42%, X Bridge C18 (4.6×150) mm, 5μ, Mobile Phase A: 10 mM Ammonium bicarbonate in water, Mobile Phase B: Acetonitrile.

Example 30: 7-amino-3-ethyl-5-{[2-(1-ethyl-1H-pyrazol-3-yl)ethyl]amino}-2-methylpyrazolo [1,5-a] pyrimidine-6-carbonitrile

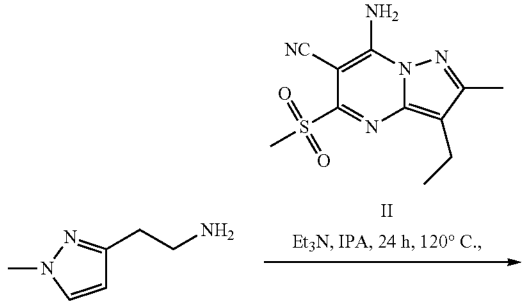

II

XVII

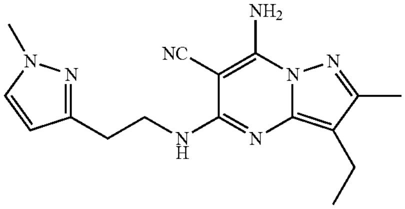

Example 30

To a stirred solution of 7-amino-3-ethyl-2-methyl-5-(methyl sulfonyl) pyrazolo[1,5-a] pyrimidine-6-carbonitrile II (0.25 g, 0.000925 mol) and 2-(1-Methyl-1H-pyrazol-3-yl) ethan-1-amine XVII (0.343 g, 0.00278 mol) in IPA (5 ml), was added TEA (0.374 g, 0.00370 mol) and the reaction mixture was heated at 120° C. for 24 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 20% ethyl acetate in hexane to yield the title compound (Example 30) as off-white solid; Yield: (0.037 g, 12%). LC-MS Calculated for $C_{16}H_{20}N_8$: 324.18; Observe: 325.18 [M++1]. $^1$HNMR (400 MHz, DMSO-$d_6$): δ 8.094 (bs, 2H), 7.560-7.556 (d, J=1.6 Hz, 1H), 6.685-6.658 (t, J=5.2 Hz, 1H), 6.054-6.049 (d, J=2 Hz, 1H), 3.772 (s, 3H), 3.582-3.533 (t, J=6.8 Hz, 2H), 2.830-2.794 (t, J=7.2 Hz, 2H), 2.446-2.428 (q, 2H), 2.247 (s, 3H), 1.136-1.099 (t, J=7.2 Hz, 3H). HPLC: 9.49 min, 97.43%, X Bridge C18 (4.6×150) mm, 5μ, Mobile Phase A: 10 mM Ammonium bicarbonate in water, Mobile Phase B: Acetonitrile.

Example 31: 7-amino-5-({2-[1-(1-hydroxy-2-methylpropan-2-yl)-1H-pyrazol-3-yl]ethyl}amino)-2,3-dimethylpyrazolo[1,5-a]pyrimidine-6-carbonitrile

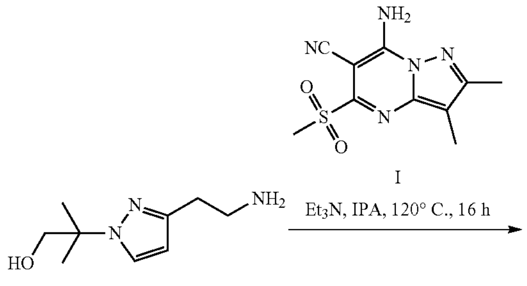

I

XVIII

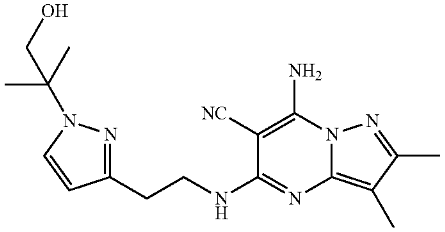

Example 31

To a stirred solution of 7-amino-2,3-dimethyl-5-(methyl sulfonyl) pyrazolo[1,5-a] pyrimidine-6-carbonitrile I (0.2 g, 0.00075 mol) and 2-(3-(2-aminoethyl)-1H-pyrazol-1-yl)-2-methylpropan-1-ol XVIII (0.345 g, 0.00188 mol) in IPA (5 ml), was added TEA (0.229 g, 0.00226 mol) and the reaction mixture was heated at 120° C. for 16 h. The progress of the reaction was monitored by TLC. After completion, the reaction mixture was diluted with water (20 ml) and extracted with ethyl acetate (20 ml×3). The organic layer was dried with $Na_2SO_4$, filtered, and evaporated under reduced pressure. The crude material was purified by column chromatography by eluting with 20-50% ethyl acetate in hexane to yield the title compound (Example 31) as off-white solid; Yield: (0.1 g, 36%). LC-MS Calculated for $C_{18}H_{24}N_8O$ 368.21; Observe: 369.21 [$M^+$+1]. $^1$HNMR (400 MHz, DMSO-$d_6$): δ 8.105 (bs, 1H), 7.650 (s, 1H), 6.593-6.581 (t, 1H), 6.062 (s, 1H), 4.901-4.874 (t, J=5.6 Hz, 1H), 3.616-3.548 (m, 4H), 2.840-2.805 (t, J=6.8 Hz, 2H), 2.229 (s, 3H), 1.968 (s, 3H), 1.439 (s, 6H). HPLC: 8.93 min, 97.57%, Column: X Bridge C18 (4.6×150) mm, 5μ, Mobile Phase A: 10 mM Ammonium bicarbonate in water, Mobile Phase B: Acetonitrile.

Example 32: 7-amino-3-ethyl-5-((2-(1-(1-hydroxy-2-methylpropan-2-yl)-1H-pyrazol-3-yl) ethyl) amino)-2-methylpyrazolo[1,5-a]pyrimidine-6-carbonitrile

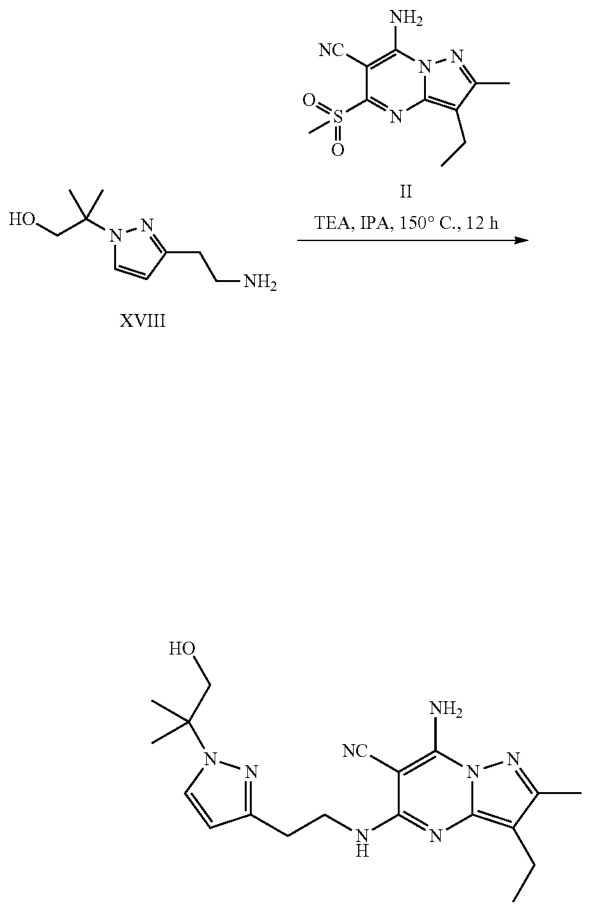

II
XVIII
Example 32

7-amino-3-ethyl-2-methyl-5-(methyl sulfonyl) pyrazolo [1,5-a] pyrimidine-6-carbonitrile II (2.0 g, 0.0071 mol), 2-(3-(2-aminoethyl)-1H-pyrazol-1-yl)-2-methylpropan-1-ol XXIV (3.2 g, 0.017 mol), IPA (5 mL) and triethylamine (6.0 mL, 0.043 mol) were taken in a seal tube and the reaction mixture was stirred at 150° C. for 12 h. The reaction was monitored by TLC. The reaction mixture was diluted with water (20 mL) and extract with ethyl acetate (3×20 mL). The combined organic layer was dried over $Na_2SO_4$ and evaporated under reduced pressure to get crude product. Crude product was purified by biotage column chromatography using silica gel (230-400) and 10-30% ethyl acetate in hexane as eluent to afford the title compound Example 32 as an off white solid. Yield: 1.048 g, 38.8%. LCMS Calculated. for $C_{19}H_{26}N_8O$ is 382.47; Observed. 383.1 $[M+H]^+$. $^1H$ NMR (400 MHz, DMSO-$d_6$): δ 8.09 (bs, 2H), 7.64 (d, J=2.0 Hz, 1H), 6.59 (t, J=5.2 Hz, 1H), 6.05 (d, J=2.4 Hz, 2H), 4.88 (m, 1H), 3.59-3.54 (m, 4H),2.82 (t, J=6.8 Hz, 2H), 2.5-2.4 (m, 2H), 2.47 (s, 3H), 1.437 (s, 6H), 1.12 (t, J=7.2 Hz, 3H). HPLC: 99.11%, X-Bridge C18 (50×4.6) mm, 5 μm, Mobile Phase A: 10 mM ammonium bicarbonate in water, B: Acetonitrile

Example 33: 7-amino-3-chloro-5-((2-(6-(hydroxymethyl) pyridin-2-yl) ethyl) amino)-2-methylpyrazolo [1,5-a]pyrimidine-6-carbonitrile

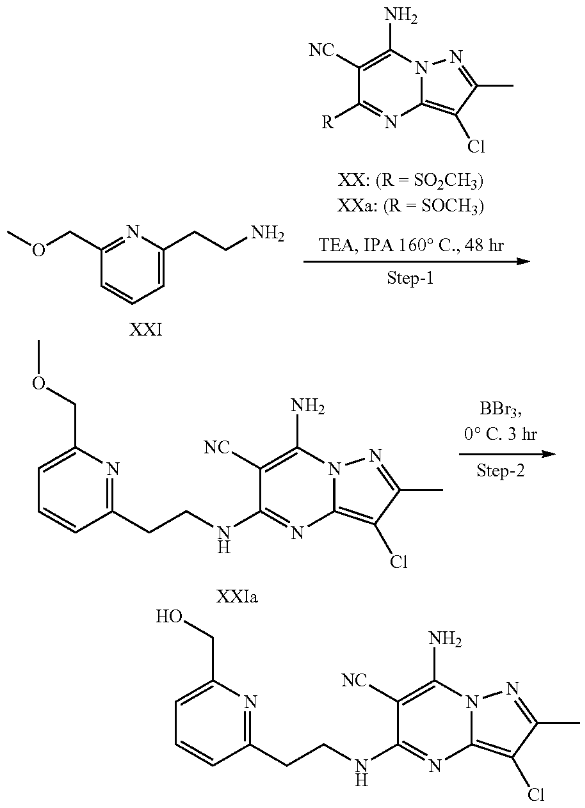

XX: (R = $SO_2CH_3$)
XXa: (R = $SOCH_3$)
XXI
XXIa
Example 33

Synthesis of 7-amino-3-ethyl-5-((2-(6-(methoxymethyl) pyridin-2-yl) ethyl) amino)-2-methylpyrazolo [1,5-a] pyrimidine-6-carbonitrile. XXIa A stirred solution of 7-amino-3-chloro-2-methyl-5-(methyl sulfonyl)pyrazolo[1,5-a] pyrimidine-6-carbonitrile XX and 7-amino-3-chloro-2-methyl-5-(methyl sulfinyl) pyrazolo[1,5-a] pyrimidine-6-carbonitrile XXa (1.6 g, 0.056 mol) in IPA (60 mL) was added 2-(6-(methoxy methyl) pyridin-2-yl) ethan-1-amine XXI (3.7 g, 0.022 mol) and TEA (4.7 mL, 0.034 mol) in a sealed tube under argon atmosphere and the reaction mixture was stirred at 160° C. for 48 hours. The progress of the reaction was monitored by TLC. After completion of the reaction mixture was evaporated under reduced pressure and the crude material was purified by gravity column and compound eluted in 25-30% Ethyl acetate in DCM. To yield the desired compound XXIa as off-white solid; Yield: 1.2 g, 57%. LCMS Calculated for $C_7H_{18}ClN_7O$ is 371.13; Observed. 372.15 $[M+H]^+$. $^1H$ NMR (400 MHz, DMSO-$D_6$): δ 8.42 (bs, 2H), 7.74 (t, J=8.0 Hz, 1H), 7.26-7.19 (m, 3H), 4.51 (s, 2H), 3.69 (t, J=5.6 Hz, 2H), 3.36 (s, 3H), 3.03 (t, J=5.6 Hz, 2H), 2.27 (s, 3H).

Synthesis of 7-amino-3-ethyl-5-((2-(6-(hydroxymethyl) pyridin-2-yl) ethyl) amino)-2-methylpyrazolo [1,5-a] pyrimidine-6-carbonitrile A stirred solution of 7-amino-3-ethyl-5-((2-(6-(methoxymethyl) pyridin-2-yl) ethyl) amino)-2-methylpyrazolo[1,5-a] pyrimidine-6-carbonitrile XXIa (1.2 g, 0.0032 mol) in DCM (3 ml) was cool to 0° C. added $BBr_3$ (0.46 mL, 0.0048 mol) dropwise and the reaction mixture was stirred at 0° C. for 3 hours. The progress of the reaction was monitored by TLC. The reaction mixture quenched with $NaHCO_3$ solution (100 mL) and extracted with DCM (3×200 mL). The combined organic layer was dried over anhydrous sodium sulphate, filtered, and concentrated to afford crude product. Crude compound obtained was purified by gravity column using 230-400 mesh silica gel. The desired product eluted at 35-40% ethyl acetate in hexane to afford title compound (Example 33) as off-white solid. Yield: 0.631 g, 53%. LCMS Calculated for $C_{16}H_{16}ClN_7O$ is 357.11; Observed. 358.15 $[M+H]^+$. $^1H$ NMR (400 MHz, DMSO-$D_6$): δ 8.40 (bs, 2H), 7.72 (t, J=7.6 Hz, 1H), 7.32 (d, J=7.6 Hz, 1H), 7.20-7.15 (m, 2H), 5.36 (t, J=5.6 Hz, 1H), 4.58 (d, J=5.6 Hz, 2H), 3.70-3.68 (m, 2H), 3.02 (t, J=7.2 Hz, 2H), 2.27 (s, 3H). HPLC: 97.91%, INT ODS 3V-C18 (4.6×250) mm, 5 μm, Mobile phase A: 0.1% Formic acid in water, B: Acetonitrile Example 34: 7-amino-3-chloro-5-((2-(6-(1-(hydroxymethyl) cyclopropyl) pyridin-2-yl) ethyl) amino)-2-methylpyrazolo[1,5-a]pyrimidine-6-carbonitrile

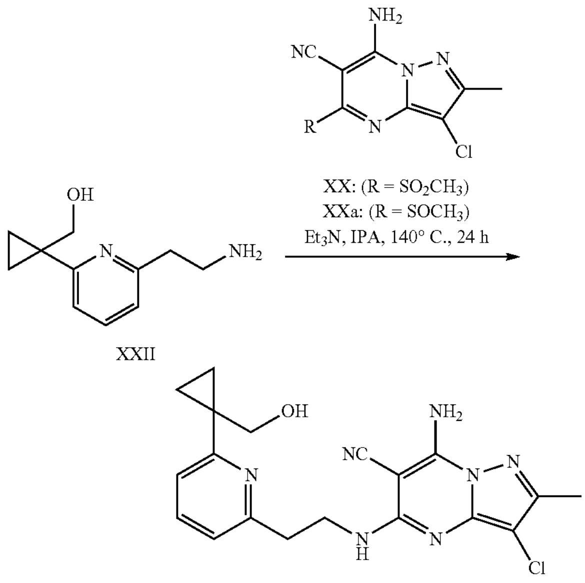

XXII

Example 34

To a mixture of 7-amino-3-chloro-2-methyl-5-(methylsulfonyl)pyrazolo[1,5-a]pyrimidine-6-carbonitrile XX and 7-amino-3-chloro-2-methyl-5-(methyl sulfinyl) pyrazolo [1,5-a] pyrimidine-6-carbonitrile XXa (0.25 g, 1 eq, 0.88 mmol) in isopropanol (10 mL) was added (1-(6-(2-aminoethyl) pyridin-2-yl)cyclopropyl)methanol XXII (0.34 g, 2 eq, 1.8 mmol) followed by triethylamine (0.27 g, 0.37 mL, 3 eq, 2.6 mmol) in a sealed tube and the resulting mixture was purged with $N_2$ for 10 min and caped. Then the reaction mixture was heated at 140° C. for 24 hours. Then the progress of the reaction was monitored by TLC for the absence of starting material. The reaction was cooled to RT and concentrated under vacuo. The residue obtained was added ethyl acetate (20 mL) and water (20 mL). The organic layer was separated, washed with brine, dried over anhydrous sodium sulphate, concentrated under vacuo to afford light brown viscous liquid. The crude compound was subjected to silica gel (230-400) column chromatography using ethyl acetate (0-80%) in n-hexane. The peak eluted with 45% Ethyl acetate in hexane was concentrated to afford the title compound (Example 34) as an off white solid. Yield: 0.04 g, 11%. LCMS Calculated. for $C_{19}H_{20}ClN_7O$ is 397.14; Observed. 398.20 $[M+H]^+$. $^1H$ NMR (400 MHz, DMSO-$D_6$): δ 8.38 (bs, 2H), 7.60 (t, J=7.6 Hz, 1H), 7.30 (d, J=8.0 Hz, 1H), 7.03 (d, J=7.6 Hz, 1H), 6.94 (t, J=6.0 Hz, 1H), 4.71 (t, J=6.0 Hz, 1H), 3.75-3.67 (m, 4H), 2.97 (t, J=7.2 Hz, 2H), 2.28 (s, 3H), 1.13-1.10 (m, 2H), 0.87-0.85 (m, 2H), HPLC: 99.63%, X-Bridge C18 (50×4.6) mm, 5 μm, Mobile Phase A: 10 mM Ammonium bicarbonate in water, B: Acetonitrile.

Example 35: 7-amino-3-chloro-5-((2-(1-(2-hydroxyethyl)-4,5-dihydro-1H-pyrazol-3-yl) ethyl) amino)-2-methylpyrazolo[1,5-a] pyrimidine-6-carbonitrile

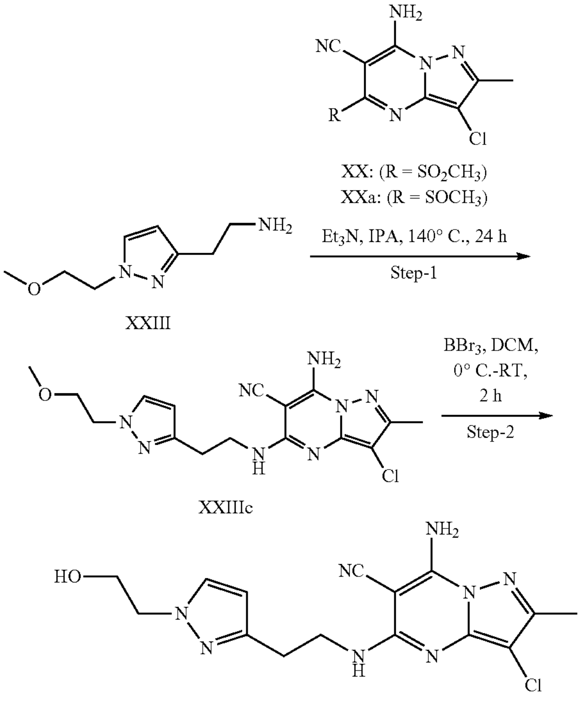

XXIII

XXIIIc

Example 35

Synthesis of 7-amino-3-chloro-5-((2-(1-(2-methoxyethyl)-4,5-dihydro-1H-pyrazol-3-yl) ethyl) amino)-2-methylpyrazolo[1,5-a] pyrimidine-6-carbonitrile (XXIIIc)

To a mixture of 7-amino-3-chloro-2-methyl-5-(methylsulfonyl)pyrazolo[1,5-a]pyrimidine-6-carbonitrile XX and 7-amino-3-chloro-2-methyl-5-(methyl sulfinyl) pyrazolo [1,5-a] pyrimidine-6-carbonitrile XXa (0.25 g, 1 eq, 0.88 mmol) in isopropanol (5 mL) was added 2-(1-(2-methoxyethyl)-1H-pyrazol-3-yl) ethan-1-amine XXIII (0.296 g, 0.0014 mol) and triethylamine (0.3 mL, 0.0021 mol) was taken in the seal tube and the resulting reaction mixture was stirred at 150° C. for 12 h. The reaction was monitored by TLC. The reaction mixture was diluted with water (20 mL)

and extracted with ethyl acetate (3×20 mL). The combined organic layer was dried over anhydrous $Na_2SO_4$ and evaporated under reduced pressure to get crude product. Crude product obtained was purified by biotage column chromatography using silica gel (230-400) and 1% methanol in DCM as eluent to afford XXIIIc as an off white solid. Yield: 0.160 g, 61%, LCMS Calculated. for $C_{16}H_{21}ClN_8O$ is 374.85; Observed. 375.25 $[M+H]^+$.

7-amino-3-chloro-5-((2-(1-(2-hydroxyethyl)-1H-pyrazol-3-yl) ethyl) amino)-2-methyl pyrazolo [1,5-a] pyrimidine-6-carbonitrile To a stirred solution of 7-amino-3-chloro-5-((2-(1-(2-methoxyethyl)-1H-pyrazol-3-yl) ethyl) amino)-2-methylpyrazolo[1,5-a] pyrimidine-6-carbonitrile XXIIIc (0.160 g, 4.268 mol) in DCM (15 mL), slowly added $BBr_3$ (0.06 mL, 6.4 mol) at 0° C., and then reaction mixture was stirred at RT for 1 h. The reaction mixture was diluted with water (20 mL) and extracted with EtOAc (3×20 mL). the combined organic layer was dried over anhydrous $Na_2SO_4$ and evaporated under reduced pressure to get crude product. The crude product obtained was purified by biotage column chromatography (12 g silica gel column) and by eluting with methanol in DCM (0-2%). to afford title compound (Example 35) as an off white solid. Yield: 0.066 g, 43%. LCMS Calculated. for $C_{15}H_{19}ClN_8O$ is 360.81; Observed. 361.25 $[M+H]^+$. $^1H$ NMR (400 MHz, DMSO-$D_6$): δ 8.39 (bs, 2H), 7.58 (S, 1H), 7.02 (m, 1H), 6.07 (s, 1H), 4.83 (t, J=10.8 Hz, 1H), 4.07 (t, J=11.2 Hz, 2H), 3.73-3.70 (m, 2H) 3.62-3.57 (M, 2H), 2.82 (t, J=7.2 Hz, 2H), 2.27 (s, 3H). HPLC: 98.51%, YMC-Pack ODS-AQ (4.6×250) mm, 5 μm, Mobile Phase A: 10 mM ammonium acetate in water, B: Acetonitrile Example 36: 7-amino-3-chloro-5-((2-(1-(1-hydroxy-2-methylpropan-2-yl)-1H-pyrazol-3-yl) ethyl) amino)-2-methylpyrazolo[1,5-a]pyrimidine-6-carbonitrile

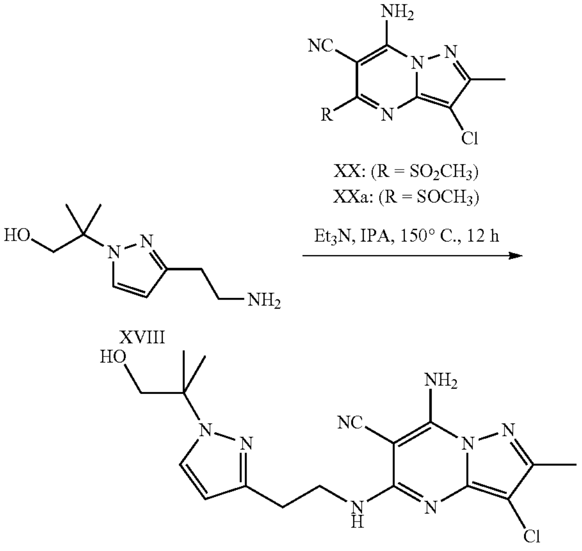

XVIII

Example 36

To a mixture of 7-amino-3-chloro-2-methyl-5-(methylsulfonyl)pyrazolo[1,5-a]pyrimidine-6-carbonitrile XX and 7-amino-3-chloro-2-methyl-5-(methyl sulfinyl) pyrazolo [1,5-a] pyrimidine-6-carbonitrile XXa (0.25 g, 1 eq, 0.88 mmol) in isopropanol (10 mL) was added 2-(3-(2-aminoethyl)-1H-pyrazol-1-yl)-2-methylpropan-1-ol XVIII (0.096 g, 5.25 mol), triethylamine (0.1 mL, 0.0011 mol) were taken in a seal tube and the resulting reaction mixture was stirred at 150° C. for 12 h. Then the progress of the reaction was monitored by TLC. The reaction mixture was diluted with water (20 mL) and extracted with ethyl acetate (3×20 mL). The combined organic layer was dried over anhydrous $Na_2SO_4$ and evaporated under reduced pressure to get crude product. Then the obtained crude product was purified by biotage column chromatography using silica gel (230-400) and 1% methanol in DCM as eluent to afford title compound (Example 36) as an off white solid. Yield: 0.055 g, 40%. LCMS Calculated. for $C_{16}H_{21}ClN_8O$ is 388.86; Observed. 389.2 $[M+H]^+$. $^1H$ NMR (400 MHz, $CDCl_3$): δ 7.46 (d, J=2.4 Hz, 1H), 6.11 (d, J=2.0 Hz, 1H), 6.04 (bs, 2H), 5.78 (bs, 1H), 3.88-3.83 (m, 4H), 3.49-3.47 (m, 1H), 2.95 (d, J=6.4 Hz, 2H) 2.3 (s, 3H), 1.55 (s, 6H). HPLC: 97.5%, INT ODS 3V-C18 (4.6×250) mm, 5 μm, Mobile Phase A: 0.1% Formic acid in water B: Acetonitrile Example 37: 7-amino-3-chloro-5-((2-(1-(1-(hydroxymethyl) cyclopropyl)-1H-pyrazol-3-yl) ethyl) amino)-2-methylpyrazolo[1,5-a]pyrimidine-6-carbonitrile

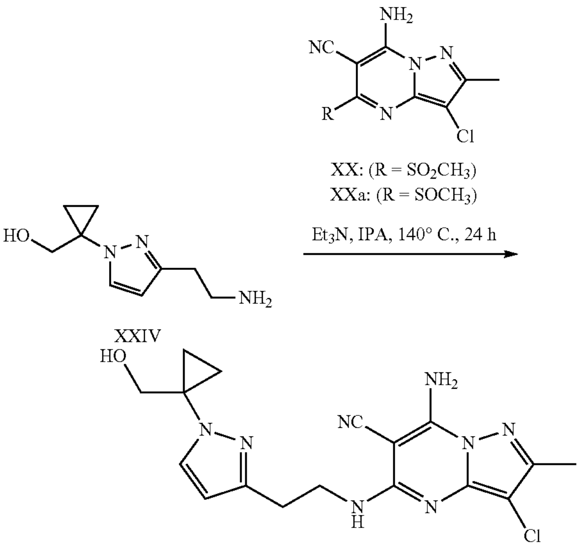

XXIV

Example 37

To a mixture of 7-amino-3-chloro-2-methyl-5-(methylsulfonyl)pyrazolo[1,5-a]pyrimidine-6-carbonitrile XX and 7-amino-3-chloro-2-methyl-5-(methyl sulfinyl) pyrazolo [1,5-a] pyrimidine-6-carbonitrile XXa (0.25 g, 1 eq, 0.88 mmol) in isopropanol (10 mL) was added a mixture of (1-(3-(2-aminoethyl)-1H-pyrazol-1-yl) cyclopropyl)methanol (0.30 g, 0.0017 mol), XXIV (0.3 g, 0.0007 mol), triethylamine (0.425 g, 0.0042 mol) were taken in a seal tube and purged with $N_2$ for 10 min. Then the resulting reaction mixture was heated at 140° C. for 24 hours. The progress of the reaction was monitored by TLC. The reaction was cooled to rt and concentrated under vacuo. To the residue add ethyl acetate (20 mL) and water (20 mL). The organic layer was separated, washed with brine, dried over anhydrous sodium sulphate. The organic layer was concentrated under vacuo and the crude compound was purified by combi-flash (230-400; 40 g column) using 80% ethyl acetate and hexane to afford the title compound (Example 37) as an off white solid. Yield: 0.1 g, 36.9%. LCMS Calculated. for $C_{17}H_{19}ClN_8O$ is 386.14; Observed. 387.15 $[M+H]^+$; $^1H$ NMR (400 MHz, DMSO-$D_6$): δ 8.40 (bs, 2H), 7.62 (d, J=2.0 Hz, 1H), 6.94 (t, J=5.6 Hz, 1H), 6.06 (d, J=2.0 Hz, 1H), 4.88 (t, J=5.6 Hz, 1H), 3.63-3.58 (m, 4H), 2.82 (t, J=7.6 Hz, 2H), 2.28 (s, 3H), 1.09-1.07 (m, 2H), 0.97-0.95 (m, 2H). HPLC: 99.14%, X-Bridge C18 (50×4.6) mm, 5 μm, Mobile Phase A: 10 mM Ammonium bicarbonate in water, B: Acetonitrile.

Example 38: 7-amino-3-chloro-5-((2-(6-(2-(hydroxymethyl) cyclopropyl) pyridin-2-yl) ethyl) amino)-2-methylpyrazolo[1,5-a]pyrimidine-6-carbonitrile

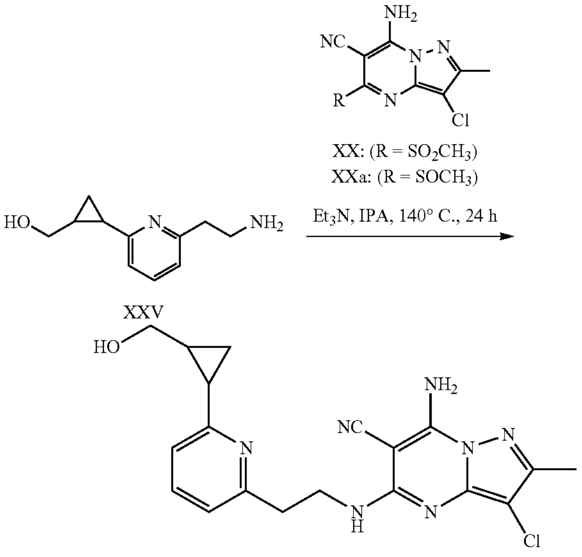

Example 38

To a mixture of 7-amino-3-chloro-2-methyl-5-(methyl sulfonyl) pyrazolo[1,5-a]pyrimidine-6-carbonitrile XX and 7-amino-3-chloro-2-methyl-5-(methyl sulfinyl) pyrazolo [1,5-a] pyrimidine-6-carbonitrile XXa (0.25 g, 0.88 mmol) in isopropanol (10 mL) was added triethylamine (0.27 g, 2.6 mmol) and (2-(6-(2-aminoethyl) pyridin-2-yl)cyclopropyl) methanol XXV (0.3 g, 2 mmol) in a seal tube. The resulting reaction mixture was purged with $N_2$ for 10 min and heated at 140° C. for 24 hours. Then the progress of the reaction was monitored by TLC analysis. The reaction was cooled to room temperature and concentrated under vacuo. To the residue was added ethyl acetate (20 mL) and water (20 mL). The organic layer was separated, washed with brine, dried over anhydrous sodium sulphate, and concentrated under vacuo to afford light brown viscous liquid. The crude compound was purified by prep-HPLC to get the title compound (Example 38) as white solid using X-bridge Prep C18 (250×19) mm, 5.0 μm, mobile phase A: 10 mm ammonium bi-carbonate in water; B: acetonitrile. Yield: 0.04 g, 11%. LCMS Calculated. for $C_{19}H_{20}ClN_7O$ is 397.14; Observed. 398.15 $[M+H]^+$. $^1H$ NMR (400 MHz, DMSO-$D_6$): δ 8.39 (bs, 2H), 7.54 (t, J=7.2 Hz, 1H), 7.06-7.00 (m, 3H), 4.56 (t, J=5.2 Hz, 1H), 3.70-3.65 (m, 2H), 3.50-3.44 (m, 1H), 3.40-3.33 (m, 1H), 2.96 (t, J=6.8 Hz, 2H), 2.28 (s, 3H), 1.99-1.95 (m, 1H), 1.58-1.55 (m, 1H), 1.10-1.06 (m, 1H), 0.89-0.84 (m, 1H). HPLC: 97.87%, INT ODS 3V-C18 (4.6×250) mm, 5 μm. Mobile Phase A: 0.1% formic acid in water, B: Acetonitrile.

Example 39: 7-amino-3-ethyl-5-((2-(1-(1-(hydroxymethyl) cyclopropyl)-1H-pyrazol-3-yl) ethyl) amino)-2-methylpyrazolo[1,5-a] pyrimidine-6-carbonitrile

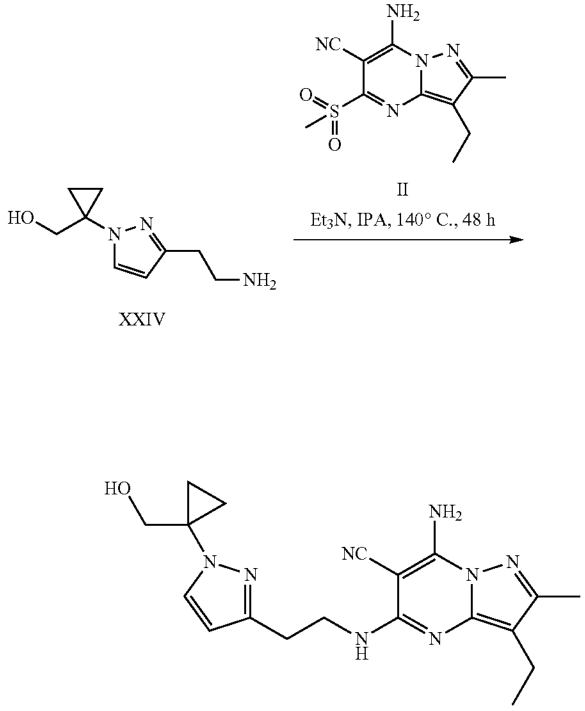

Example 39

In a seal tube, a solution of (1-(3-(2-aminoethyl)-1H-pyrazol-1-yl) cyclopropyl) methanol XXIV (260 mg, 0.0009 mol) and 7-amino-3-ethyl-2-methyl-5-(methyl sulfonyl) pyrazolo[1,5-a] pyrimidine-6-carbonitrile II (420 mg, 0.0023 mol) in isopropanol (15 mL) was taken and added triethylamine (0.7 mL, 0.0055 mol). The resulting reaction mixture was purged with $N_2$ for 10 min. The seal tube was heated at 140° C. for 48 hours. The progress of the reaction was monitored by TLC. The reaction was cooled to room temperature and concentrated under vacuo. To the residue was added ethyl acetate and water. The organic layer was separated, washed with brine, dried over anhydrous sodium sulphate, and concentrated under vacuum. The crude compound was purified by preparative HPLC to obtain the title compound (Example 39) as yellow solid. Yield: (0.025 g, 7.1%). LCMS Calculated. for $C_{19}H_{24}N_8O$ is 380.21; Observed. 381.25 $[M+H]^+$. $^1H$ NMR (400 MHz, DMSO-$D_6$): δ 8.10 (bs, 1H), 7.61 (d, J=1.6 Hz, 1H), 6.59 (s, 1H), 6.04 (d, J=1.6 Hz, 1H), 4.87 (t, J=5.6 Hz, 1H), 3.59-3.54 (m, 3H), 2.80 (t, J=6.8 Hz, 2H), 2.5 (m, 2H), 2.47 (s, 3H), 1.13-1.07 (m, 5H), 0.97-0.94 (m, 2H). HPLC: 97.16%, X-Bridge C18 (50×4.6) mm, 5 μm, Mobile Phase A: 10 mM Ammonium bicarbonate in water, B: Acetonitrile.

Example 40: 7-amino-5-((2-(6-ethylpyridin-2-yl) ethyl) amino)-2,3-dimethyl pyrazolo [1,5-a] pyrimidine-6-carbonitrile

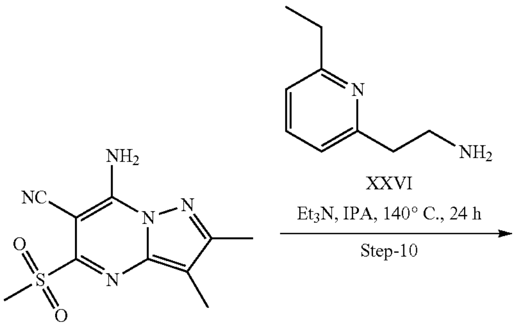

I

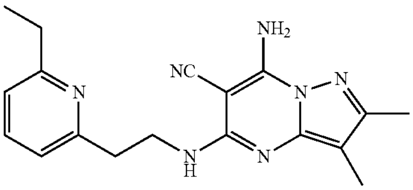

Example 40

To a solution of 2-(6-ethylpyridin-2-yl) ethan-1-amine XXVI (0.74 g, 4.9 mmol) and 7-amino-2,3-dimethyl-5-(methyl sulfonyl) pyrazolo[1,5-a] pyrimidine-6-carbonitrile I (0.65 g, 2.5 mmol) in isopropanol (10 mL) was added triethylamine (2.0 mL, 15 mmol). The resulting mixture was purged with $N_2$ for 10 min. The seal tube was closed tightly and heated at 140° C. for 48 h. The progress of the reaction was monitored by TLC analysis. The reaction was cooled to room temperature and the reaction mixture was concentrated under vacuo. To the residue were added ethyl acetate (50 mL) and water (50 mL) and mixed well. The organic layer was separated, washed with brine, dried over anhydrous sodium sulphate, and concentrated under vacuo to afford light brown viscous liquid. The crude compound was purified by combi-flash (230-400) silica gel column chromatography using ethyl acetate in n-hexane and peak eluted with 15% ethyl acetate in n-hexane was concentrated to afford the desired title compound (Example 40) as an off-white solid. Yield: 0.3 g (34%); LC_MS Calculated. for $C_{18}H_{22}N_7$ is 336.20, Observed, 336.30; $[M+H]^+$; $^1H$ NMR (400 MHz, DMSO-$D_6$): δ 8.11 (s, 2H), 7.63 (t, J=7.6 Hz, 1H), 7.11 (d, J=7.6 Hz, 2H), 6.86 (t, J=5.2 Hz, 1H), 3.71-3.67 (m, 2H), 3.01 (t, J=6.8 Hz, 2H), 5.47 (d, J=10.8 Hz, 1H), 3.74 (t, J=6.8 Hz, 2H), 2.75 (q, J=7.6 Hz, 2H), 2.23 (s, 1H), 1.97 (s, 3H), 1.23 (t, J=7.6 Hz, 2H); HPLC Purity=98.00%, INT ODS 3V-C18 (4.6×250) mm, 5μ; Mobile Phase A: 0.1% Formic acid in water: Mobile Phase B: Acetonitrile; Retention time=7.721 min.

Example 41: 7-amino-5-((2-(3-fluoro-6-methylpyridin-2-yl) ethyl)amino)-2,3-dimethylpyrazolo[1,5-a] pyrimidine-6-carbonitrile

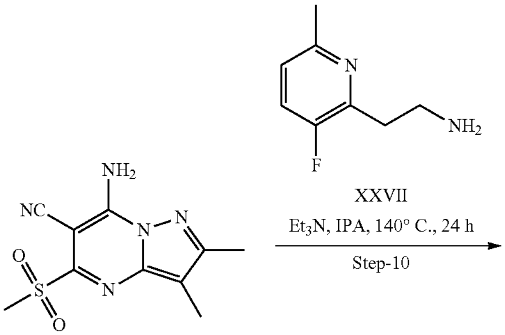

I

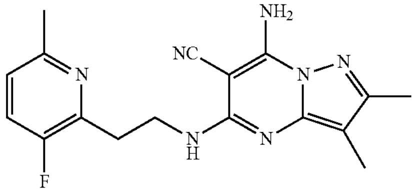

Example 41

To a solution of 2-(3-fluoro-6-methylpyridin-2-yl) ethan-1-amine XXVII (203 mg, 1.32 mmol) and 7-amino-2,3-dimethyl-5-(methyl sulfonyl) pyrazolo[1,5-a] pyrimidine-6-carbonitrile I (175 mg, 0.66 mmol) in isopropanol (10 mL) was added TEA (0.55 mL, 3.96 mmol). The resulting mixture was purged with $N_2$, sealed the tube, and heated at 150° C. for 48 h. The progress of the reaction was monitored by TLC analysis. After completion, the reaction mixture was concentrated under reduced pressure. To the residue water (15 mL) was added and the resulting mixture was extracted with ethyl acetate (15 mL×2). The combined organic layer was given brine wash, dried over anhydrous sodium sulphate, and concentrated under reduced pressure. The crude obtained subjected to silica gel (230-400) column chromatography using 5-35% ethyl acetate in n-hexane to afford the desired compound as an off-white solid. Yield: 10.2 g (5%); LC_MS Calculated. for $C_{17}H_{19}FN_7$ is 340.17, Observed: 340.25; $[M+H]^+$; $^1H$ NMR (400 MHz, DMSO-$D_6$): δ 8.10 (s, 2H), 7.51 (t, J=84 Hz, 1H), 7.15 (q, J=4.4 Hz, 1H), 6.85 (t, J=5.2 Hz, 1H), 3.70 (q, J=6.0 Hz, 1H), 3.05 (t, J=4.8 Hz, 2H), 2.45 (s, 3H), 2.22 (s, 3H), 1.95 (s, 3H); HPLC Purity=95.27%)(Bridge C18 (4.6×150) mm, 5μ; Mobile Phase A: 10 mM ammonium bicarbonate in $H_2O$: Mobile Phase B: Acetonitrile; Retention time=10.10 min.

Example 42: 7-amino-2-ethyl-3-methyl-5-((2-(6-methylpyridin-2-yl) ethyl) amino) pyrazolo[1,5-a] pyrimidine-6-carbonitrile

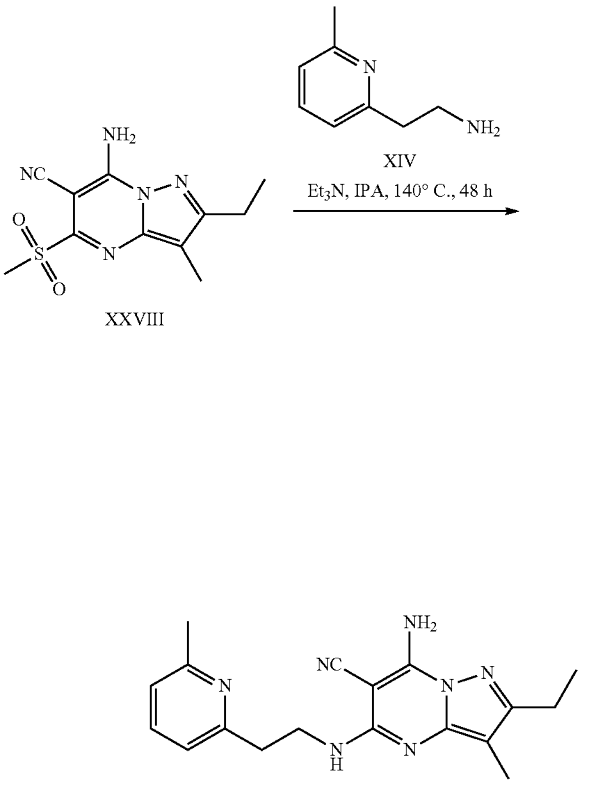

XIV
XXVIII

Example 42

To a mixture of 7-amino-2-ethyl-3-methyl-5-(methyl sulfonyl) pyrazolo[1,5-a] pyrimidine-6-carbonitrile (0.200 g, 0.716 mmol) XXVIII and 2-(6-methylpyridin-2-yl) ethan-1-amine XIV (0.300 g, 2.20 mmol) in isopropanol (5 mL) was added triethylamine (0.6 mL, 4.0 mmol). The resulting mixture was purged with $N_2$ for 10 min. The seal tube was closed tightly and heated at 140° C. for 48 h. The progress of the reaction was monitored by TLC analysis. The reaction mixture was cooled to room temperature and the reaction mixture was concentrated under vacuo. To the residue were added ethyl acetate (50 mL) and water (50 mL) and mixed well. The organic layer was separated, washed with brine, dried over anhydrous sodium sulphate, and concentrated under vacuo to afford light brown viscous liquid. The crude compound was purified by combi-flash (230-400) silica gel column chromatography using ethyl acetate in n-hexane and peak eluted with 70% ethyl acetate in n-hexane fraction solvent was concentrated to afford the desired compound as an off-white solid. Yield: 0.088 g (44%), LC_MS Calculated. for is 336.42, Observed: 336.30; $[M+H]^+$; $^1H$ NMR (400 MHz, DMSO-$D_6$): δ 8.07 (bs, 2H), 7.60 (t, J=8.0 Hz, 1H), 7.08 (d, J=8.0 Hz, 2H), 6.91 (t, J=5.2 Hz, 1H), 3.69-3.64 (m, 2H), 2.99 (t, J=6.8 Hz, 2H), 2.67-2.58 (m, 2H), 2.47 (s, 3H), 1.98 (s, 3H), 1.19 (t, J=7.2 Hz, 3H); HPLC Purity=97.67%) (Bridge C18 (4.6×150) mm, 5μ, Mobile phase A: 10 mM ammonium bicarbonate in $H_2O$: Mobile Phase B: Acetonitrile; Retention time=10.406 min.

Example 43: 7-amino-2-ethyl-5-((2-(6-(2-hydroxy-propan-2-yl) pyridin-2-yl) ethyl) amino)-3-methylpyrazolo[1,5-a]pyrimidine-6-carbonitrile

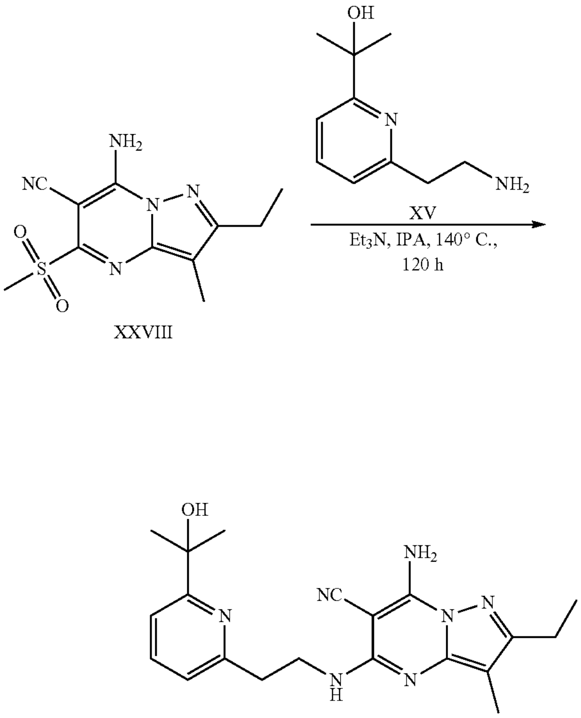

XV
XXVIII

Example 43

To a stirred solution of 7-amino-2-ethyl-3-methyl-5-(methyl sulfonyl) pyrazolo[1,5-a] pyrimidine-6-carbonitrile XXVIII (150 mg, 0.537 mmol) in isopropanol (5 mL) were added triethylamine (0.3 mL, 2.68 mmol) followed by 2-(6-(2-aminoethyl) pyridin-2-yl) propan-2-ol XV (0.145 g, 0.80 mmol). The resulting mixture was purged with $N_2$ for 10 min. The seal tube was closed tightly and heated at 140° C. for 120 h. The progress of the reaction was monitored by TLC analysis. Then reaction was cooled to room temperature and added water (50 mL). The aqueous layer was extracted with ethyl acetate (50 mL). The organic layer was separated, washed with brine, dried over anhydrous sodium sulphate, and concentrated under vacuum to afford light brown viscous liquid. The crude material was purified by prep HPLC method using YMC AQUA ODS (250×20) mm, 5.0 microns column; Mobile phase A: 10 mM Ammonium bicarbonate in water. Mobile phase B: ACN:MeOH (1:1) to afford the desired title compound Example 43 as an off-white solid. Yield: 0.014 g (7%); LC_MS Calculated. for $C_{20}H_{25}N_7O$ is 379.21, Observed, 380.30; $[M+H]^+$; $^1H$ NMR (400 MHz, DMSO-$D_6$): δ 8.06 (bs, 2H), 7.67 (t, J=7.6 Hz, 1H), 7.46 (d, J=7.6 Hz, 1H), 7.11 (d, J=7.6 Hz, 1H), 6.61 (bs, 1H), 5.16 (s, 1H), 3.72-3.71 (m, 2H), 3.03 (t, J=6.4 Hz, 2H), 2.67-2.59 (m, 2H), 1.98 (s, 3H), 1.43 (s, 6H), 1.19-1.17 (m, 3H); HPLC Purity=97.65%)(Bridge C18 (4.6×150) mm, 5μ; Mobile Phase A: 10 mM ammonium bicarbonate in $H_2O$: Mobile Phase B: Acetonitrile; Retention time=10.42 min.

Example 44: 7-amino-5-((2-(6-(hydroxymethyl) pyridin-2-yl) ethyl) amino)-2,3-dimethylpyrazolo[1,5-a]pyrimidine-6-carbonitrile

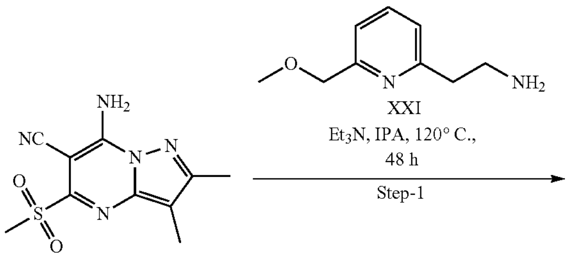

I

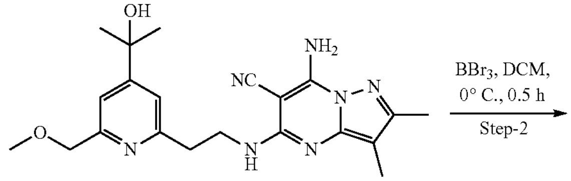

Example 44a

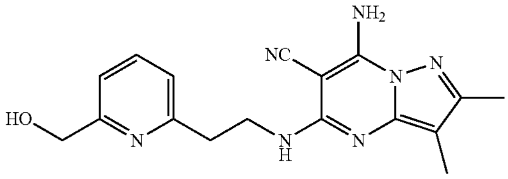

Example 44

Step-1: 2-amino-5-((2-(6-(methoxymethyl) pyridin-2-yl) ethyl) amino)-2,3-dimethylpyrazolo[1,5-a] pyrimidine-6-carbonitrile (44a)

A stirred solution of 2-(6-(methoxymethyl) pyridin-2-yl) ethan-1-amine XXI (0.414 g, 2.49 mmol) and 7-amino-2,3-dimethyl-5-(methyl sulfonyl) pyrazolo[1,5-a] pyrimidine-6-carbonitrile I (0.300 g, 1.13 mmol) in isopropanol (7 mL) was added triethylamine (0.8 mL, 5.65 mmol) and the resulting mixture was purged with $N_2$ for 10 min. The seal tube was closed tightly and heated at 120° C. for 48 h. The progress of the reaction was monitored by TLC analysis. The reaction was cooled to room temperature and the reaction mixture was concentrated under vacuo. To the residue were added ethyl acetate (50 mL) and water (50 mL) and mixed well. The organic layer was separated, washed with brine, dried over anhydrous sodium sulphate, and concentrated under vacuo to afford light brown viscous liquid. The crude compound was purified by combi-flash (230-400) silica gel column chromatography using ethyl acetate in n-hexane and peak eluted with 20% ethyl acetate in n-hexane. Product fractions solvent was concentrated to afford the desired title compound Example 44a as off-white solid. Yield: 0.230 g (58%); LC_MS Calculated. for $C_{18}H_{21}N_7O$ is 351.18, Observed, 352.25; $[M+H]^+$; $^1H$ NMR (400 MHz, DMSO-$D_6$): δ 8.11 (bs, 2H), 7.73 (d, J=7.6 Hz, 1H) 7.22 (m, 2H), 6.84 (m, 1H) 4.51 (S, 2H), 3.68-3.67 (m, 2H), 3.36 (s, 3H), 3.02 (t, J=6.8 Hz, 2H), 2.27 (s, 3H), 1.96 (s, 3H), HPLC Purity=98.27%, INT ODS 3V-C18 (4.6×250) mm, 5μ; Mobile Phase A: 0.1% Formic acid in water: Mobile Phase B: Acetonitrile; Retention time=8.70 min.

Step-2: 7-amino-5-((2-(6-(hydroxymethyl) pyridin-2-yl) ethyl) amino)-2,3-dimethylpyrazolo[1,5-a] pyrimidine-6-carbonitrile (44)

A stirred solution of 7-amino-5-((2-(6-(methoxymethyl) pyridin-2-yl) ethyl) amino)-2,3-dimethylpyrazolo[1,5-a] pyrimidine-6-carbonitrile Example 44a (120 mg, 0.341 mmol) in DCM (5 mL) was cool to 0° C. then added $BBr_3$ (0.03 mL, 0.341 mmol) and the reaction mixture was stirred at 0° C. for 30 min. The progress of the reaction was monitored by TLC. After completion of the reaction, the reaction mixture was quenched with $NaHCO_3$ solution 2 ml and extracted with DCM (10 ml×3) and dried over anhydrous sodium sulphate and concentrated at low vacuum. Crude solid was washed with 2 ml acetonitrile to get the pure title compound Example 44 as off-white solid. Yield: 0.230 g (58%); LC_MS Calculated for $C_{17}H_{19}N_7O$ is 338.4, $[M+H]^+$; Observed 337.17; $[M+H]^+$; $^1H$ NMR (400 MHz, DMSO-$D_6$): δ 8.05 (bs, 2H), 7.72 (d, J=7.6 Hz, 1H) 7.31 (d, J=7.2 Hz, 1H), 7.15 (d, J=7.6 Hz, 1H) 6.78 (bs, 1H) 5.36 (bs, 1H), 4.58 (S, 2H), 3.68-3.67 (m, 2H), 3.01 (t, J=6.4 Hz, 2H), 2.22 (s, 3H), 1.96 (s, 3H), HPLC Purity=98.19%, XBridge C18 (4.6×150) mm, 5μ, Mobile Phase A: 10 mM ammonium bicarbonate in water: Mobile Phase B: Acetonitrile; Retention time=8.30 min.

Example 45: 7-amino-3-ethyl-5-((2-(6-(hydroxymethyl) pyridin-2-yl) ethyl) amino)-2-methylpyrazolo [1,5-a]pyrimidine-6-carbonitrile

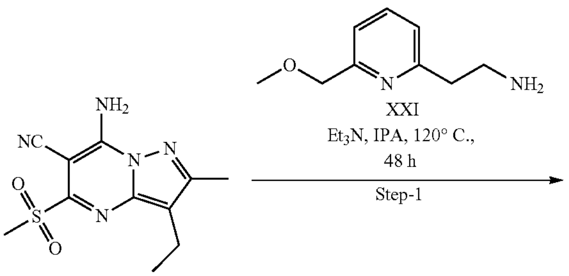

II

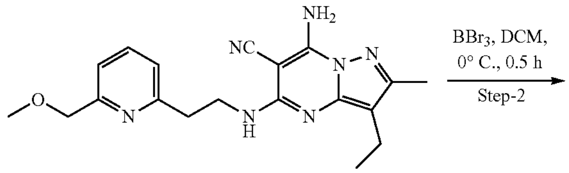

Example 45a

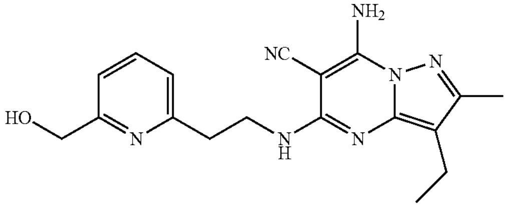

Example 45

Step-1: Synthesis of 7-amino-3-ethyl-5-((2-(6-(methoxymethyl) pyridin-2-yl) ethyl) amino)-2-methylpyrazolo[1,5-a] pyrimidine-6-carbonitrilev (Example 45a)

To a stirred solution of 7-amino-3-ethyl-2-methyl-5-(methyl sulfonyl) pyrazolo[1,5-a] pyrimidine-6-carbonitrile II (2.0 g, 7.2 mmol) in isopropanol (40 mL) were added TEA (5.9 mL, 43 mmol) and 2-(6-(methoxymethyl) pyridin-2-yl) ethan-1-amine XXI (3.0 g, 18 mmol). The resulting mixture was purged with $N_2$ for 10 min. The seal tube was closed tightly and heated at 140° C. for 48 h. The progress of the reaction was monitored by TLC analysis. The reaction was cooled to room temperature and the reaction mixture was concentrated under vacuo. To the residue were added ethyl acetate (50 mL) and water (50 mL) and mixed well. The organic layer was separated, washed with brine, dried over anhydrous sodium sulphate, and concentrated under vacuo to afford light brown viscous liquid. The crude compound was purified by combi-flash silica gel (230-400) column chromatography using 10-70% ethyl acetate in n-hexane to afford the desired compound Example 45a as off-white solid. Yield: 1.3 g (50%); LC_MS Calculated for $C_{19}H_{23}N_7O$ is 365.20; Observed. 366.25 $[M+H]^+$; $^1H$ NMR (400 MHz, DMSO-$D_6$): δ 8.112 (bs, 2H), 7.751-7.713 (t, J=7.2 Hz, 1H), 7.256-7.185 (m, 2H), 6.854 (bs, 1H), 4.507 (s, 2H), 3.693-3.647 (m, 2H), 3.361 (s, 3H), 3.044-3.010 (t, J=6.8 Hz, 2H), 2.469-2.431 (m, 2H), 2.247 (s, 3H), 1.139-1.101 (t, J=7.6 Hz, 3H).

Step-2:7-amino-3-ethyl-5-((2-(6-(hydroxymethyl) pyridin-2-yl) ethyl)amino)-2-methylpyrazolo[1,5-a] pyrimidine-6-carbonitrile A stirred solution of 7-amino-3-ethyl-5-((2-(6-(methoxymethyl) pyridin-2-yl)ethyl)amino)-2-methylpyrazolo[1,5-a] pyrimidine-6-carbonitrile (75 mg, 0.205 mmol) in DCM (5 mL) was cooled to 0° C. and added $BBr_3$ (0.0 19 mL, 0.205 mmol). The resulting mixture was stirred at 0° C. for 1 h. The progress of the reaction was monitored by TLC analysis. After completion of the reaction, reaction mixture was quenched with sat. $NaHCO_3$ solution (2 mL) and extracted with DCM (10 mL×3). Combined organic layer was dried over anhydrous sodium sulphate, filtered, and concentrated under vacuo. The crude solid was washed with n-pentane (2 mL) to get the pure compound as an off-white solid. Yield: 30 mg (42%); LCMS Calculated. for $C_{18}H_{21}N_7O$ is 351.18, $[M+H]^+$; Observed, 352.30; $[M+H]^+$; 1H NMR (400 MHz, DMSO-$D_6$): δ 8.085 (bs, 2H), 7.739-7.700 (t, J=8.0 Hz, 1H) 7.326-7.306 (d, J=8.0 Hz, 1H), 7.149-7.130 (d, J=7.6 Hz, 1H), 6.873-6.846 (t, J=5.2 Hz, 1H), 5.371-5.342 (d, J=5.6 Hz, 1H), 4.588-4.574 (d, J=5.6 Hz, 2H), 3.687-3.639 (m, 2H), 3.030-2.996 (d, J=6.8 Hz, 2H), 2.449-2.434 (m, 2H), 2.248 (s, 3H), 1.175-1.105 (t, J=7.2 Hz, 3H), HPLC Purity=99.09%, Retention time=8.228 min. INT ODS 3V-C18 (4.6×250) mm, 5μ; 0.1% Formic acid in water: Mobile Phase B: Acetonitrile; Flow rate: 1.0 mL/min.

Example 46: 7-amino-3-(cyclopropyl methyl)-5-((2-(6-(hydroxymethyl) pyridin-2-yl) ethyl) amino)-2-methylpyrazolo[1,5-a]pyrimidine-6-carbonitrile

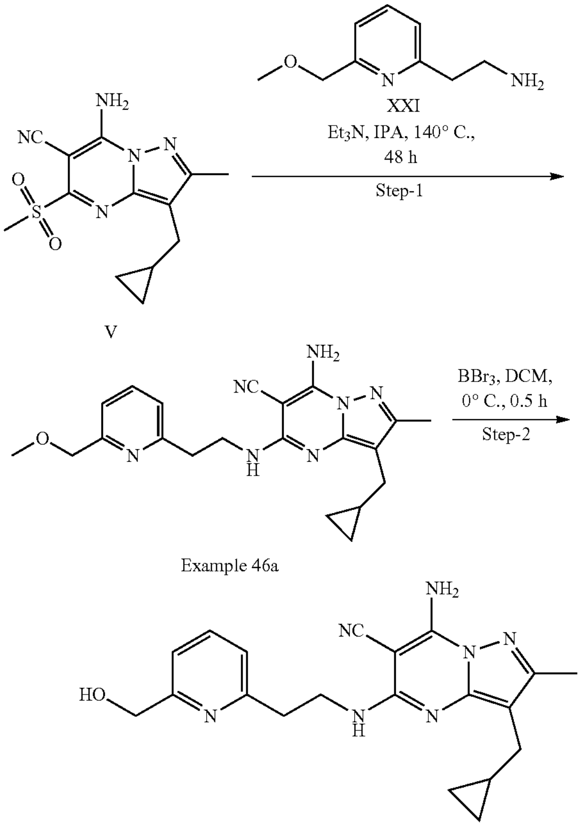

XXI

V

Example 46a

Example 46

Step-1: Synthesis of 7-amino-3-(cyclopropyl methyl)-5-((2-(6-(methoxymethyl) pyridin-2-yl) ethyl) amino)-2-methylpyrazolo[1,5-a]pyrimidine-6-carbonitrile (46a)

A stirred solution of 7-amino-3-(cyclopropyl methyl)-2-methyl-5-(methyl sulfonyl) pyrazolo[1,5-a] pyrimidine-6-carbonitrile V (220 mg, 0.720 mmol) in isopropanol (10 mL) were added 2-(6-(methoxymethyl) pyridin-2-yl) ethan-1-amine XXI (299 mg, 1.80 mmol) and TEA (0.703 mL, 5.04 mmol). The resulting mixture was purged with nitrogen for 10 min. The seal tube was closed tightly and heated at 140° C. for 48 h. The progress of the reaction was monitored by TLC analysis. The reaction was cooled to room temperature and the reaction mixture was concentrated under vacuo. To the residue were added ethyl acetate (50 mL) and water (50 mL) and mixed well. The organic layer was separated, washed with brine, dried over anhydrous sodium sulphate, and concentrated under vacuum to afford light brown viscous liquid. The crude compound was purified by combi-flash (230-400) silica gel column chromatography using ethyl acetate in DCM and peak eluted with 25% ethyl acetate in DCM, fraction solvent was concentrated to afford the desired compound Example 46a as off-white solid. Yield: 0.160 g (57%); LC_MS Calculated. for $C_{21}H_{25}N_7O$ is 391.47 Observed. 392.30 $[M+H]^+$; $^1H$ NMR (400 MHz, DMSO-$D_6$): δ 8.12 (bs, 2H), 7.73 (t, J=7.2 Hz, 1H), 7.25-7.17 (m, 2H), 6.86 (bs, 1H), 4.50 (s, 2H), 3.68-3.65 (m, 2H), 3.36 (s, 3H), 3.04-3.00 (t, J=6.4 Hz, 2H), 2.38-2.33 (m, 2H), 2.26 (s, 3H), 0.95-0.94 (m, 1H), 0.36-0.34 (m, 2H), 0.17-0.16 (m, 2H). HPLC Purity=96.56%, INT ODS 3V-C18 (4.6×250) mm, 5μ; Mobile Phase A: 0.1% Formic acid in water: Mobile Phase B: Acetonitrile; Retention time=9.49 min.

Step-2: 7-amino-3-(cyclopropyl methyl)-5-((2-(6-(hydroxymethyl) pyridin-2-yl) ethyl) amino)-2-methylpyrazolo[1,5-a] pyrimidine-6-carbonitrile A stirred solution of 7-amino-3-(cyclopropyl methyl)-5-((2-(6-(methoxymethyl) pyridin-2-yl) ethyl) amino)-2-methylpyrazolo[1,5-a] pyrimidine-6-carbonitrile (70 mg, 0.18 mmol) in DCM (5 mL) was added $BBr_3$ (0.017 mL, 0.18 mmol) at 0° C. The resulting mixture was stirred for 30 min at 0° C. The progress of the reaction was monitored by TLC analysis. After completion of the reaction mixture was quenched with $NaHCO_3$ solution (2 ml) and extracted with dichloromethane (10 ml×3) and dried over sodium sulphate and concentrated at low vacuum. Crude was purified by prep-HPLC. Method: Xbridge C18, 19×250 mm, 5 mic. 10 mm ammonium bicarbonate in water and acetonitrile. Prep fractions was evaporated to get pure title compound Example 46 as off-white solid. Yield: 6.8 mg (10%). LCMS Calculated. for $C_{20}H_{23}N_7O$ is 377.20 $[M+H]^+$; Observed. 378.3 $[M+H]^+$; $^1H$ NMR (400 MHz, DMSO-$D_6$): δ 8.11 (bs, 2H), 7.73-7.96 (m, 1H), 7.31 (d, J=7.6 Hz, 1H), 7.13 (d, J=7.6 Hz, 1H), 6.87 (bs, 1H), 5.35 (t, J=5.6 Hz, 1H), 4.58-4.57 (m, 2H), 3.66-3.64 (m, 2H), 3.00 (t, J=6.8 Hz, 3H), 2.39-2.32 (m, 2H), 2.26 (s, 3H), 0.85-0.83 (m, 1H), 0.36-0.34 (m, 2H), 0.17-0.16 (m, 2H). HPLC Purity=92.88%, INT ODS 3V-C18 (4.6×250) mm, 5μ; Mobile Phase A: 0.1% Formic acid in water: Mobile Phase B: Acetonitrile; Retention time=9.58 min.

Example 47: 7-amino-2-cyclopropyl-5-((2-(6-(2-hydroxypropan-2-yl) pyridin-2-yl) ethyl)amino)-3-methylpyrazolo[1,5-a]pyrimidine-6-carbonitrile

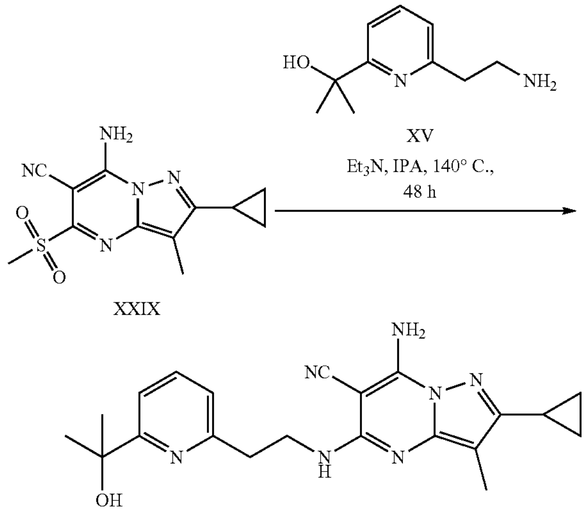

XXIX

Example 47

To a solution of 7-amino-2-cyclopropyl-3-methyl-5-(methyl sulfonyl) pyrazolo[1,5-a] pyrimidine-6-carbonitrile XX1X (0.13 g, 0.45 mmol) in IPA (4 mL) at rt under $N_2$ atmosphere were added 2-(6-(2-aminoethyl) pyridin-2-yl) propan-2-ol XV (0.24 g, 1.3 mmol) and triethylamine (0.31 mL, 2.2 mmol) and the seal tube was heated at 140° C. for 48 h. The progress of the reaction was monitored by TLC analysis. After completion of the reaction, the reaction mixture was cooled to rt, and 20 mL water was added. The resulting mixture was extracted with ethyl acetate (20 mL×2). The combined organic layers were washed with brine, dried over anhydrous $Na_2SO_4$ and concentrated under vacuo to afford light brown semi solid. The compound was purified by reverse phase HPLC using Mobile phase A: 10 mM ammonium bicarbonate in water: Mobile phase B: acetonitrile (column: YMC pack ODS-Aq; 250×20 mm; 50 um) and the peak eluted at retention time 17 min with 50% acetonitrile and flow rate 17 mL/min was concentrated to afford the desired compound Example 47 as off-white solid. Yield: 3.4 mg (2%), LC_MS Calculated. for $C_{21}H_{26}N_7O$ is 392.49, Observed, 392.30; [M+H] HPLC Purity=97.04%, Column: INT ODS 3V-C18 (4.6×250) mm, Mobile phase A: 0.1% TFA in water Mobile phase B: Acetonitrile Example 48: 7-amino-2-(difluoromethyl)-3-ethyl-5-((2-(1-(1-hydroxy-2-methylpropan-2-yl)-1H-pyrazol-3-yl) ethyl) amino) pyrazolo[1,5-a]pyrimidine-6-carbonitrile

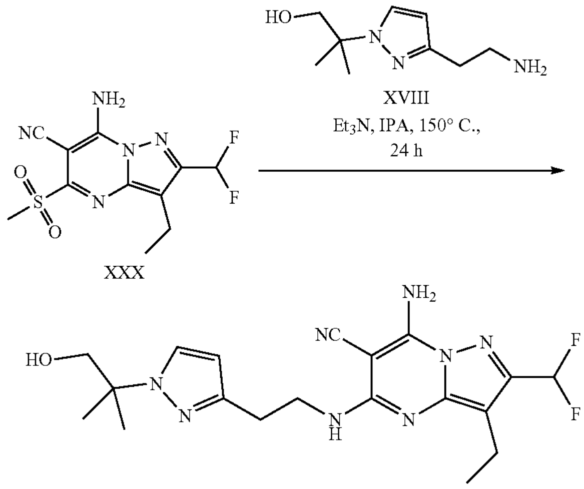

XXX

Example 48

To a stirred solution of 7-amino-2-(difluoro methyl)-3-ethyl-5-(methyl sulfonyl) pyrazolo[1,5-a]pyrimidine-6-carbonitrile XXX (0.3 g, 0.951 mmol) and 2-(3-(2-aminoethyl)-1H-pyrazol-1-yl)-2-methylpropan-1-ol XVIII (0.523 g, 2.85 mmol) in IPA (5 mL) was added TEA (0.8 mL, 5.71 mmol) and the reaction mixture was heated at 150° C. for 24 h. The progress of the reaction was monitored by TLC. After completion, after completion, the reaction mixture was diluted with water (20 mL) and extracted with ethyl acetate (20 mL×3). The organic layer was dried over anhydrous $Na_2SO_4$, filtered, and evaporated under reduced pressure. The crude material was purified by column chromatography by eluting with 50% ethyl acetate in hexane to yield the title compound as off-white solid. Yield: 0.098 g (25%); LC_MS Calculated. for $C_{19}H_{24}F_2N_8O$ is 418.20, Observed. 419.30;

[M+1-1]+. 1H NMR (400 MHz, dmso-d6): δ 8.42 (s, 2H), 7.64 (d, J=4 Hz, 1H), 7.04-6.90 (m, 2H), 6.05 (d, J=2 Hz, 1H), 4.88 (s, 1H), 3.61-3.32 (m, 4H), 2.83 (t, J=4 Hz, 2H), 2.62-2.50 (m, 2H), 1.43 (s, 6H), 1.16 (t, J=4 Hz, 3H). HPLC Purity=99.09%, Column: XBridge C18 (4.6×150) mm, 5μ Mobile phase A: 10 mM ammonium bicarbonate in $H_2O$ Mobile phase B: acetonitrile; Retention time=10.250 min.

Example 49: 7-amino-5-((2-(6-(1-(hydroxymethyl) cyclopropyl) pyridin-2-yl) ethyl) amino)-2,3-dimethylpyrazolo[1,5-a]pyrimidine-6-carbonitrile

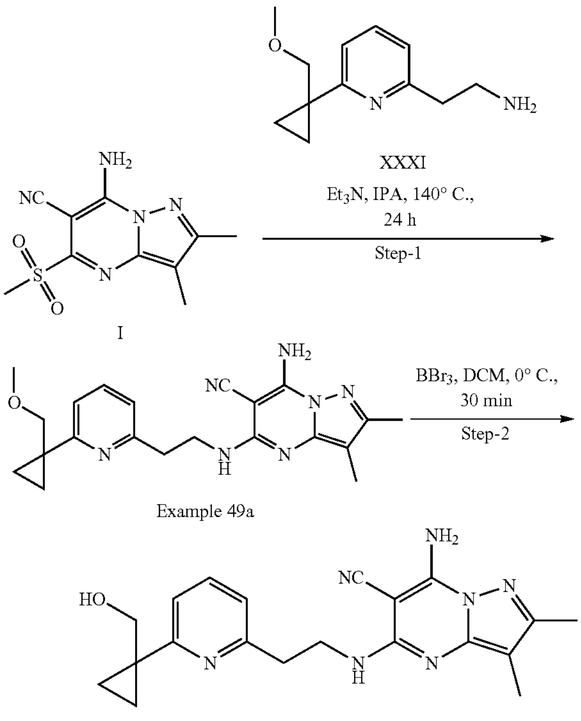

XXXI

I

Example 49a

Example 49

Step-1: 7-amino-5-((2-(6-(1-(methoxymethyl) cyclopropyl) pyridin-2-yl) ethyl) amino)-2,3-dimethylpyrazolo[1,5-a] pyrimidine-6-carbonitrile (49a)

To a solution of 2-(6-(1-(methoxymethyl) cyclopropyl) pyridin-2-yl) ethan-1-amine (0.53 g, 2.6 mmol) XXXI and 7-amino-2,3-dimethyl-5-(methyl sulfonyl) pyrazolo[1,5-a] pyrimidine-6-carbonitrile I (0.34 g, 1.3 mmol) in isopropanol (10 mL) was added triethylamine (0.54 mL, 3.8 mmol) and the resulting mixture was purged with $N_2$ for 10 min. The seal tube was closed tightly and heated at 140° C. for 48 h. The progress of the reaction was monitored by TLC analysis. After the completion of the reaction, the reaction mixture was cooled to room temperature and concentrated under vacuo. To this, added ethyl acetate (20 mL) and water (20 mL). The organic layer was separated, washed with brine, dried over anhydrous sodium sulphate, and concentrated under vacuo to afford light brown viscous liquid. The crude compound was subjected to silica gel (230-400; packed 40 g) column chromatography using ethyl acetate (0-25%) in n-hexane. The peak eluted with 22% ethyl acetate in hexane was concentrated to afford the desired compound Example 49a as off-white solid. Yield: 100 mg (20%); LC_MS Calculated. for $C_{21}H_{25}N_7O$ is 391.48, Observed 392.25; $[M+H]^+$; HPLC Purity=95.12%, INT_9010_AA_22.1 cm; $^1H$ NMR (400 MHz, DMSO-$D_6$): δ 8.08 (S, 2H), 7.58 (d, J=8 Hz 1H), 7.24 (d, J=8.0 Hz, 1H), 7.02 (d, J=8 Hz, 1H), 6.57 (S, 1H), 3.68 (t, J=8 Hz, 4H), 3.30 (d, J=20 Hz, 3H), 2.96 (t, J=8 Hz, 2H), 2.23 (S, 3H), 1.97 (S, 3H), 1.19 (S, 2H), 0.87 (d, J=4 Hz, 2H).

Step-2: 7-amino-5-((2-(6-(1-(hydroxymethyl) cyclopropyl) pyridin-2-yl) ethyl) amino)-2,3-dimethylpyrazolo[1,5-a]pyrimidine-6-carbonitrile To a solution of 7-amino-5-((2-(6-(1-(methoxymethyl) cyclopropyl)pyridin-2-yl)ethyl)amino)-2,3-dimethylpyrazolo[1,5-a]pyrimidine-6-carbonitrile Example 49a (70 mg, 0.18 mmol) in DCM (7 mL) at 0° C. was added $BBr_3$ (0.02 mL, 0.18 mmol) drop wise and stirred for 30 min. The reaction mixture was monitored by TLC analysis in which both bromo analogue and desired product was observed. Then to the resulting mixture, sodium formate (0.007 mL, 0.18 mmol) and catalytic amount of TBAB was added and stirred for 48 h. The reaction was monitored by TLC analysis. After the completion of the reaction, the reaction mixture was quenched with saturated $NH_4Cl$ solution. To this, water (2 mL) was added and extracted with DCM (2 mL×2). The combined organic layer was washed with brine and concentrated under reduced pressure to afford a light brown viscous liquid. The crude compound was purified by reverse phase HPLC; YMC AQUA ODS (250×20) mm. 5.0 microns. Mobile phase A: 10 mm Ammonium bicarbonate in $H_2O$; Mobile phase B: ACN:MeOH (1:1) to afford the desired title compound Example 49 as a light brown solid. Yield: 67 mg (43%); LCMS Calculated. for $C_{20}H_{23}N_7O$ is 377.47, Observed, 378.25; $[M+H]^+$; HPLC Purity=98.27%, Column: Symmetry-C18 (4.6*75) mm, 3.5μ Mobile phase A: 10 mM ammonium bicarbonate in water. Mobile phase B: ACN. $^1H$ NMR (400 MHz, dmso-d6): δ 8.08 (S, 2H), 7.59 (t, j=8 Hz 1H), 7.29 (t, J=8.0 Hz, 1H), 7.02 (d, j=8 Hz, 1H), 6.57 (t, j=8 Hz 1H), 4.72 (t, J=4 Hz, 1H), 3.75-3.66 (m, 4H), 2.96 (t, J=8 Hz, 2H), 2.23 (S, 3H), 1.97 (S, 3H), 1.19 (S, 2H), 0.87 (d, J=4 Hz, 2H).

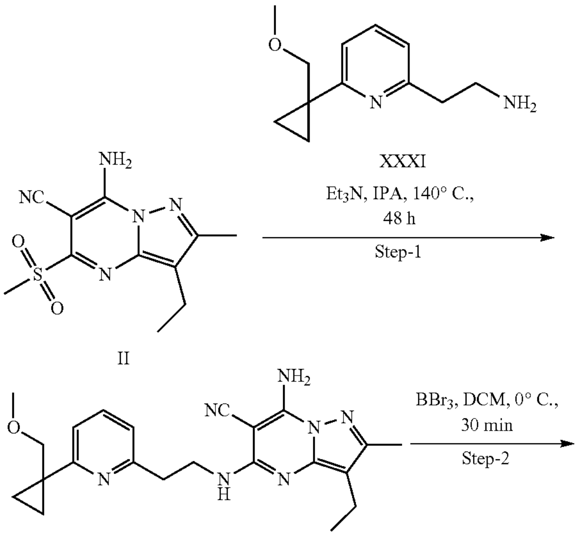

XXXI

II

Example 50a

-continued

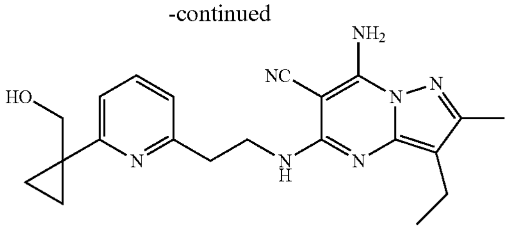

Example 50

Step-1: 7-amino-3-ethyl-5-((2-(6-(1-(methoxymethyl) cyclopropyl) pyridin-2-yl) ethyl) amino)-2-methylpyrazolo[1,5-a] pyrimidine-6-carbonitrile (50a)

To a solution of 2-(6-(1-(methoxymethyl) cyclopropyl) pyridin-2-yl) ethan-1-amine XXXI (0.24 g, 1.1 mmol) and 7-amino-3-ethyl-2-methyl-5-(methyl sulfonyl) pyrazolo[1,5-a] pyrimidine-6-carbonitrile II (0.16 g, 0.57 mmol) in isopropanol (10 mL) was added triethylamine (0.24 mL, 1.7 mmol) and the resulting mixture was purged with $N_2$ for 10 min. The seal tube was closed tightly and heated at 140° C. for 48 h. the progress of the reaction was monitored by TLC analysis. After the completion of the reaction, the reaction mixture was cooled to room temperature and concentrated under vacuo. Added ethyl acetate (20 mL) and water (20 mL). The organic layer was separated, washed with brine, dried over anhydrous sodium sulphate, and concentrated under vacuo to afford light brown viscous liquid. The crude compound was subjected to silica gel (230-400; packed 40 g) column chromatography using ethyl acetate (0-25%) in n-hexane. The peak eluted with 22% ethyl acetate in n-hexane was concentrated to afford the desired compound Example 50a as an off-white solid. Yield: 0.095 g (41%). LCMS Calculated. for $C_{22}H_{27}N_7O$ is 405.51; Observed. 406.35 $[M+H]^+$; $^1H$ NMR (400 MHz, DMSO-$D_6$): δ 8.08 (s, 2H), 7.59 (t, J=8 Hz, 1H), 7.24 (d, J=8.0 Hz, 1H), 7.01 (d, J=8 Hz, 1H), 6.60 (t, J=4 Hz 1H), 3.65 (t, J=12 Hz 4H), 3.30 (d, J=16 Hz, 3H), 2.96 (t, J=8 Hz, 2H), 2.50-2.43 (m, 2H), 2.25 (s, 3H), 1.23-1.19 (m, 2H), 1.15 (t, J=8 Hz 3H), 0.89-0.86 (m, 2H); HPLC Purity=98.45%, Column: XBridge C18 (4.6×150) mm, 5 μMobile phase A: 10 mM ammonium bicarbonate in $H_2O$. Mobile phase B: acetonitrile Step-2: 7-amino-3-ethyl-5-((2-(6-(1-(hydroxymethyl) cyclopropyl) pyridin-2-yl) ethyl) amino)-2-methylpyrazolo[1,5-a] pyrimidine-6-carbonitrile To a solution of 7-amino-3-ethyl-5-((2-(6-(1-(methoxymethyl) cyclopropyl) pyridin-2-yl) ethyl) amino)-2-methylpyrazolo[1,5-a] pyrimidine-6-carbonitrile Example 50a (70 mg, 0.17 mmol) in DCM (7 mL) at 0° C. was added $BBr_3$ (0.02 mL, 0.17 mmol) in dropwise and stirred for 30 min. The reaction mixture was monitored by TLC analysis in which both bromo analogue and desired product was observed. Then added sodium formate (0.007 mL, 0.17 mmol) and catalytic amount of TBAB, stirred for 48 h. The reaction was monitored by TLC analysis. After the completion of the reaction, the reaction mixture was quenched with saturated $NH_4Cl$ solution. Added water (2 mL) and extracted with DCM (2 mL×2). The combined organic layer was washed with brine and concentrated under reduced pressure to afford a light brown viscous liquid. The crude compound was purified by Reverse phase HPLC: YMC AQUA ODS (250×20) mm, 5.0 microns; Mobile phase A: 10 mm Ammonium bicarbonate in $H_2O$; Mobile phase B: ACN:MeOH (1:1) to afford the desired title compound Example 50 as an off-white solid. Yield: 0.015 g (22%). LCMS Calculated. for $C_{21}H_{25}N_7O$ is 391.47; Observed. 392.25 $[M+H]^+$; $^1H$ NMR (400 MHz, DMSO-$D_6$): δ 8.08 (s, 2H), 7.59 (t, J=8.0 Hz, 1H), 7.24 (d, J=8.0 Hz, 1H), 7.01 (d, J=8.0 Hz, 1H), 6.60 (t, J=4.0 Hz 1H), 4.71 (d, J=4.0 Hz, 1H) 3.74-3.65 (m, 4H), 2.96 (t, J=8.0 Hz, 2H), 2.50-2.43 (m, 2H), 2.25 (s, 3H), 1.23-1.19 (m, 2H), 1.15 (t, J=8.0 Hz 3H), 0.89-0.86 (m, 2H); HPLC Purity=98.78%, Column: Symmetry-C18 (4.6×75) mm, 3.5μ; Mobile phase A: 10 mM ammonium acetate in $H_2O$ Mobile phase B: Acetonitrile.

Example 51: 7-amino-5-((2-(6-(2-(hydroxymethyl) cyclopropyl) pyridin-2-yl) ethyl) amino)-2,3-dimethylpyrazolo[1,5-a]pyrimidine-6-carbonitrile

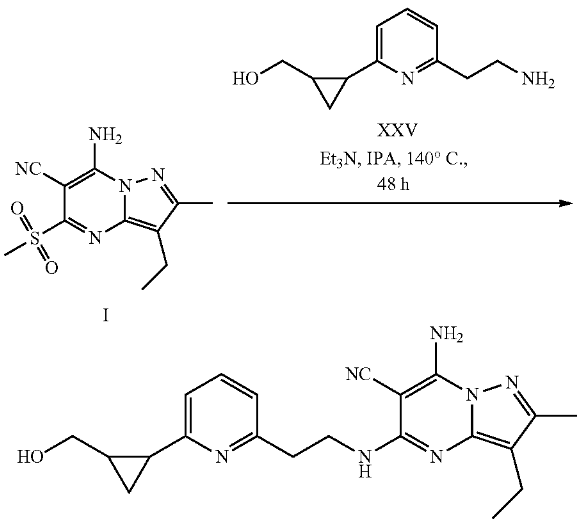

Example 51

To a solution of (2-(6-(2-aminoethyl) pyridin-2-yl) cyclopropyl) methanol XXV (0.36 g, 1.9 mmol) and 7-amino-2,3-dimethyl-5-(methylsulfonyl)pyrazolo[1,5-a]pyrimidine-6-carbonitrile I (0.25 g, 0.94 mmol) in IPA (10 mL) was added triethylamine (0.39 mL, 2.8 mmol) and purged with $N_2$ for 10 min. The seal tube was closed tightly and heated at 140° C. for 48 h. The progress of the reaction was monitored by TLC analysis. After the completion of the reaction, the reaction mixture was cooled to rt and concentrated under vacuo. Added water (20 mL) and extracted with ethyl acetate (20 mL×2). The organic layer was separated, washed with brine, dried over anhydrous sodium sulphate, and concentrated under vacuo to afford light brown viscous liquid. The crude compound was purified by silica gel (230-400 mesh) column chromatography using ethyl acetate in n-hexane (0-80%) to afford the desired title compound Example 51 as an off-white solid. Yield: (30 mg, 8.4%); LC_MS Calculated. for $C_{20}H_{23}N_7O$ is 377.45; Observed. 378.25 $[M+H]^+$. HPLC Purity=99.36%, Column: YMC-Pack ODS-AQ (4.6×150) mm, 5μ Mobile phase A: 10 mM ammonium acetate in $H_2O$; Mobile phase B: ACN; Rt=11.620 min. $^1H$ NMR (400 MHz, DMSO-$D_6$): δ 8.09 (s, 2H), 7.53 (t, J=8 Hz, 1H), 7.06-6.98 (m, 2H), 6.65 (t, J=4 Hz, 1H), 4.56 (t, J=6.8 Hz, 1H), 3.68-3.35 (m, 4H), 2.95 (t, J=8

Hz, 2H), 2.23 (s, 3H), 1.95 (t, J=4 Hz, 4H), 1.59-1.54 (m, 1H), 1.10-1.06 (m, 1H), 1.06-0.85 (m, 1H).

Example 52: 7-amino-3-ethyl-5-((2-(6-(1-hydroxy-2-methylpropan-2-yl) pyridin-2-yl) ethyl) amino)-2-methylpyrazolo[1,5-a] pyrimidine-6-carbonitrile

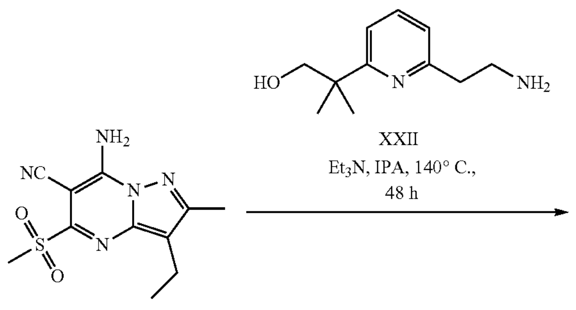

II

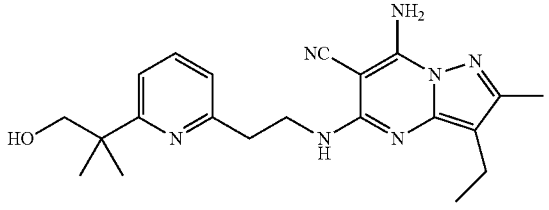

Example 52

To a solution of 2-(6-(2-aminoethyl) pyridin-2-yl)-2-methylpropan-1-ol XXXII (0.2 g, 1 mmol) and 7-amino-3-ethyl-2-methyl-5-(methyl sulfonyl) pyrazolo[1,5-a]pyrimidine-6-carbonitrile II (0.2 g, 0.7 mmol) in isopropanol (10 mL) was added triethylamine (0.4 mL, 3 mmol) and the resulting mixture was purged with $N_2$ for 10 min. The seal tube was closed tightly and heated at 140° C. for 48 h. The progress of the reaction was monitored by TLC analysis. The reaction was cooled to RT and the reaction mixture was concentrated under vacuo. To the residue was added ethyl acetate (20 mL) and water (20 mL). The organic layer was separated, washed with brine, dried over anhydrous sodium sulphate, and concentrated under vacuo to afford light brown viscous liquid. The crude compound was purified by reverse phase HPLC, Column: Xbridge Prep C18 (250×19) mm, 5.0μ; Mobile phase A: 10 mm Ammonium bi carbonate in water; Mobile phase B: Acetonitrile to afford the desired title compound Example 52 as an off-white solid. Yield: 32 mg (10%); LC_MS Calculated. for $C_{21}H_{28}N_7O$ is 394.24; Observed. 394.30 $[M+H]^+$; $^1H$ NMR (400 MHz, DMSO-$D_6$): δ 8.09 (bs, 2H), 7.63 (t, J=7.6 Hz, 1H), 7.22 (d, J=8.0 Hz, 1H), 7.07 (d, J=7.2 Hz, 1H), 6.65 (bs, 1H), 4.64 (t, J=5.6 Hz, 1H), 3.73-3.68 (m, 2H), 3.55 (d, J=5.6 Hz, 2H), 3.02 (t, J=6.8 Hz, 2H), 2.46-2.41 (m, 2H), 2.25 (s, 3H), 1.26 (s, 6H), 1.13 (t, J=7.2 Hz, 3H); HPLC Purity=98.27%, YMC-Pack ODS-AQ(4.6×150) mm, 5μ, Mobile phase A: 10 mM ammonium acetate in water Mobile phase B: Acetonitrile.

Example 53: 7-amino-5-((2-(6-(1-hydroxy-2-methylpropan-2-yl) pyridine-2-yl) ethyl) amino)-2,3-dimethylpyrazolo[1,5-a]pyrimidine-6-carbonitrile

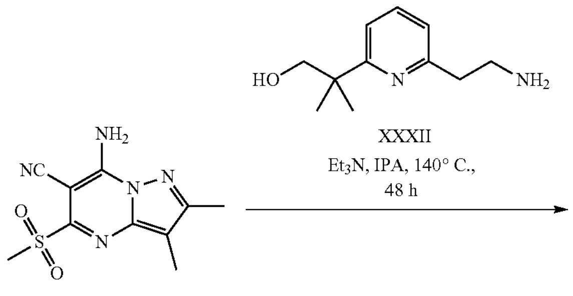

I

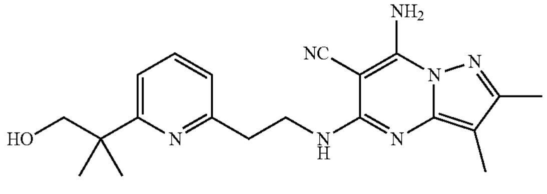

Example 53

To a solution of 2-(6-(2-aminoethyl) pyridin-2-yl)-2-methylpropan-1-ol (0.2 g, 1 mmol) and 7-amino-2,3-dimethyl-5-(methylsulfonyl) pyrazolo[1,5-a]pyrimidine-6-carbonitrile (0.2 g, 0.8 mmol) in isopropanol (10 mL) was added triethylamine (0.4 mL, 3 mmol) and the resulting mixture was purged with $N_2$ for 10 min. The seal tube was closed tightly and heated at 140° C. for 48 h. The progress of the reaction was monitored by TLC analysis. The reaction was cooled to RT and the reaction mass was concentrated under vacuo. To the residue were added ethyl acetate (20 mL) and water (20 mL). The organic layer was separated, washed with brine, dried over anhydrous sodium sulphate, and concentrated under vacuo to afford light brown viscous liquid. The crude compound was purified by reverse phase HPLC, Column: Xbridge Prep C18 (250×19) mm, 5.0μ; Mobile phase A: 10 mm Ammonium bicarbonate in water; Mobile phase B: Acetonitrile to afford the desired compound Example 53 as off-white solid. Yield: 32 mg (10%); LC_MS Calculated. for $C_{20}H_{26}N_7O$ is 380.22; Observed. 380.25 $[M+H]^+$; $^1H$ NMR (400 MHz, DMSO-$D_6$): δ 8.09 (bs, 2H), 7.63 (t, J=7.6 Hz, 1H), 7.22 (d, J=8.0 Hz, 1H), 7.09 (d, J=7.6 Hz, 1H), 6.62 (bs, 1H), 4.65 (t, J=5.6 Hz, 1H), 3.74-3.69 (m, 2H), 3.55 (d, J=5.6 Hz, 2H), 3.02 (t, J=7.2 Hz, 2H), 2.23 (s, 3H), 1.97 (s, 3H), 1.24 (s, 6H); HPLC Purity=98.27%, YMC-Pack ODS-AQ(4.6×150) mm, 5μ, Mobile phase A: 10 mM ammonium acetate in $H_2O$: Acetonitrile.

Example 54: 7-amino-3-ethyl-5-((2-(1-(2-hydroxyethyl)-1H-pyrazol-3-yl) ethyl) amino)-2-methylpyrazolo[1,5-a]pyrimidine-6-carbonitrile

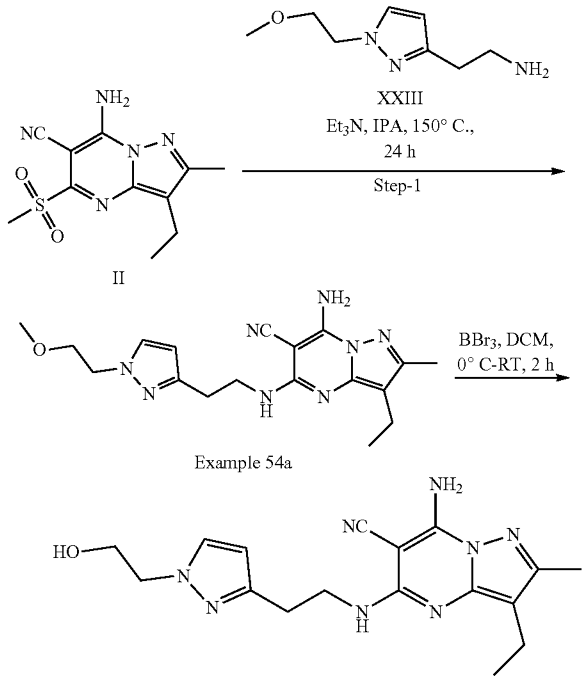

II

Example 54a

Example 54

Step-1: 7-amino-3-ethyl-5-((2-(1-(2-methoxyethyl)-1H-pyrazol-3-yl) ethyl) amino)-2-methylpyrazolo[1,5-a]pyrimidine-6-carbonitrile (Example 54a)

To a stirred solution of 7-amino-3-ethyl-2-methyl-5-(methyl sulfonyl) pyrazolo[1,5-a]pyrimidine-6-carbonitrile II (0.700 g, 2.51 mmol) and 2-(1-(2-methoxyethyl)-1H-pyrazol-3-yl)ethan-1-amine XXIII (0.85 g, 5.02 mmol) in isopropanol (2.5 mL) in a sealed tube was added triethylamine (2.10 mL, 15.0 mmol) and the reaction mixture was stirred at 150° C. for 24 h. The progress of the reaction was monitored by TLC analysis. After completion, the reaction mixture was diluted with water (20 mL) and extracted with ethyl acetate (20 mL×3). The organic layer was dried over anhydrous $Na_2SO_4$, filtered, and concentrated under reduced pressure. The crude material was purified by silica gel (100-200) column chromatography by eluting with 50% ethyl acetate in n-hexane to yield the title compound Example 54a as an off-white solid. Yield: 0.3 g (32.5%); LC_MS Calculate. for $C_{18}H_{25}N_8O$ is 369.22; Observed. 369.25 $[M+H]^+$; $^1H$ NMR (400 MHz, DMSO-$D_6$): δ 8.10 (bs, 2H), 7.58 (d, J=2.0 Hz, 1H), 6.66 (t, J=5.2 Hz, 1H), 6.06 (d, J=2.0 Hz, 1H), 4.18 (q, J=5.2 Hz, 2H), 3.66 (t, J=5.2 Hz, 2H), 3.59-3.55 (m, 2H), 2.21 (s, 3H), 2.82 (t, J=7.2 Hz, 2H), 2.47-2.43 (m, 2H), 2.25 (s, 3H), 1.12 (t, J=7.6 Hz, 3H); HPLC Purity=99.78%, YMC-Pack ODS-AQ (4.6×150) mm, 5μ, Mobile phase A: 10 mM ammonium acetate in water. Mobile phase B: Acetonitrile.

Step-2: 7-amino-3-ethyl-5-((2-(1-(2-hydroxyethyl)-1H-pyrazol-3-yl) ethyl) amino)-2-methylpyrazolo[1,5-a] pyrimidine-6-carbonitrile A stirred solution of 7-amino-3-ethyl-5-((2-(1-(2-methoxyethyl)-1H-pyrazol-3-yl) ethyl) amino)-2-methylpyrazolo[1,5-a] pyrimidine-6-carbonitrile Example 54a (0.3 g, 0.8 mmol) in DCM (50 ml) was cooled to 0° C., and $BBr_3$ (0.09 mL, 1 mmol) was added slowly. After completion, the reaction mixture was quenched with methanol (0.5 mL) and diluted with water (20 mL). The resulting mixture was extracted with DCM (20 mL×3). The organic layer was dried over anhydrous $Na_2SO_4$, filtered, and concentrated under reduced pressure. The crude material was purified by silica gel (100-200) column chromatography by eluting with 1-5% methanol in DCM to afford the desired title compound Example 54 as off-white solid. Yield: 50 mg (33%); LC_MS Calculated for $C_{17}H_{23}N_8O$ is 355.20; Observed. 355.25 $[M+H]^+$; $^1H$ NMR (400 MHz, DMSO-$D_6$): δ 8.29 (bs, 2H), 7.65 (s, 1H), 6.89 (bs, 1H), 6.12 (s, 1H), 4.09 (t, J=5.6 Hz, 2H), 3.71 (t, J=5.6 Hz, 2H), 3.62 (t, J=7.2 Hz, 2H), 2.86 (t, J=7.2 Hz, 2H), 2.55-2.50 (m, 3H), 2.26 (s, 3H), 1.11 (t, J=7.6 Hz, 3H); HPLC Purity=99.78%, YMC-Pack ODS-AQ (4.6×150) mm, 5μ, Mobile phase A: 10 mM ammonium acetate in water. Mobile phase B: Acetonitrile.

Example 55: 7-amino-5-((2-(1-(1-(hydroxymethyl) cyclopropyl)-1H-pyrazol-3-yl) ethyl) amino)-2,3-dimethylpyrazolo[1,5-a]pyrimidine-6-carbonitrile

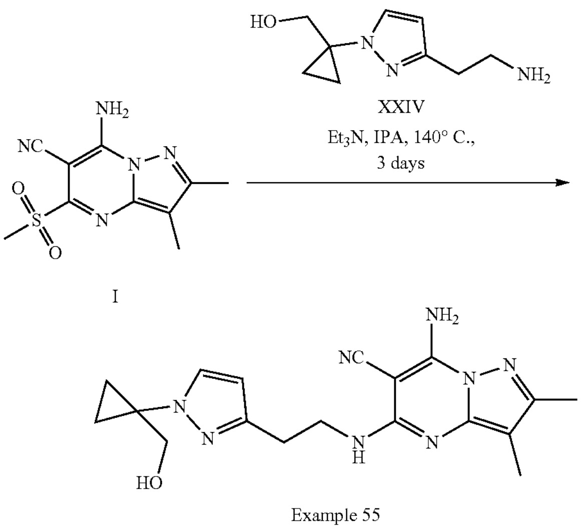

I

Example 55

In a seal tube was charged with 7-amino-2,3-dimethyl-5-(methyl sulfonyl) pyrazolo[1,5-a] pyrimidine-6-carbonitrile I (2.1 g, 7.9 mmol), (1-(3-(2-aminoethyl)-1H-pyrazol-1-yl) cyclopropyl) methanol XXIV (2 g, 11 mmol) and isopropanol (60 mL). The resulting mixture was purged with $N_2$ gas for 5 min and TEA (6.6 mL, 47 mmol) was added. The seal tube was stirred at 140° C. for 3 days. The progress of reaction was monitored by TLC analysis. After completion, the reaction mixture was concentrated to remove the solvent. The residue was dissolved in water (40 mL) and extracted with ethyl acetate (50 mL×3). The combined organic layer was washed with brine and dried over anhydrous sodium sulphate. The crude material obtained upon removal of the solvent was purified by flash chromatography (combi-flash)

using 50-100% ethyl acetate in n-hexane to afford the desired compound as an off-white solid. Yield: 1.0 g (34.4%); LC_MS Calculated. for $C_{18}H_{23}N_8O$ is 367.20; Observed. 367.25 $[M+H]^+$; $^1H$ NMR (400 MHz, DMSO-$D_6$): δ 8.12 (bs, 2H), 7.62 (d, J=2.0 Hz, 1H), 6.58 (t, J=5.6 Hz, 1H), 6.05 (d, J=2.0 Hz, 1H), 4.89 (d, J=5.6 Hz, 1H), 3.61-3.56 (m, 4H), 2.81 (t, J=7.2 Hz, 2H), 2.50 (s, 3H), 1.97 (s, 3H), 1.10-1.07 (m, 2H), 0.98-0.95 (m, 2H); HPLC Purity=99.01%.

Example 56: 7-amino-2-(difluoro methyl)-3-ethyl-5-((2-(6-(hydroxymethyl) pyridine-2-yl) ethyl) amino) pyrazolo[1,5-a] pyrimidine-6-carbonitrile

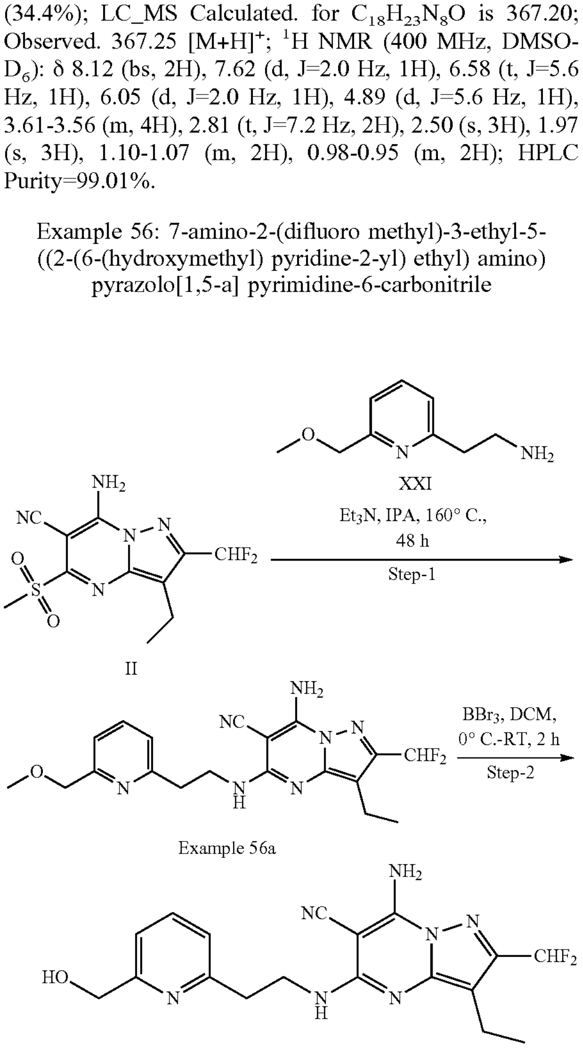

Example 56

Step-1: 7-amino-2-(difluoro methyl)-3-ethyl-5-((2-(6-(methoxymethyl) pyridin-2-yl) ethyl) amino) pyrazolo[1,5-a] pyrimidine-6-carbonitrile (Example 56a)

To a stirred solution of 7-amino-2-(difluoro methyl)-3-ethyl-5-(methyl sulfonyl) pyrazolo[1,5-a] pyrimidine-6-carbonitrile XXX (200 mg, 0.634 mmol) in isopropanol (6 mL) were added TEA (0.53 mL, 3.81 mmol) and 2-(6-(methoxymethyl) pyridin-2-yl) ethan-1-amine XXI (264 mg, 1.59 mmol). The resulting mixture was purged with $N_2$ gas for 5 min and the seal tube was heated at 160° C. with vigorous stirring for 48 h. The progress of the reaction was monitored by TLC analysis. After completion, the reaction mixture was concentrated under reduced pressure. The crude was subjected to silica gel (230-400) combi-flash column chromatography using 0-25% ethyl acetate/n-hexane to afford the desired compound Example 56a as an off-white solid. Yield: 140 mg (55%); LC_MS Calculated. for $C_{19}H_{22}F_2N_7O$ is 402.19; Observed. 402.20 $[M+H]^+$; $^1H$ NMR (400 MHz, DMSO-$D_6$): δ 8.43 (bs, 2H), 7.73 (t, J=7.6 Hz, 1H), 7.26-7.21 (m, 2H), 7.13-6.91 (m, 2H), 4.50 (s, 2H), 3.69 (bs, 1H), 3.36 (s, 3H), 3.04 (t, J=6.4 Hz, 2H), 2.67-2.61 (m, 3H), 1.16 (t, J=7.6 Hz, 3H).

Step-2: 7-amino-2-(difluoro methyl)-3-ethyl-5-((2-(6-(hydroxymethyl) pyridin-2-yl) ethyl) amino) pyrazolo[1,5-a] pyrimidine-6-carbonitrile A stirred solution of 7-amino-2-(difluoro methyl)-3-ethyl-5((2-(6-(methoxymethyl) pyridin-2-yl) ethyl) amino) pyrazolo[1,5-a] pyrimidine-6-carbonitrile Example 56a (140 mg, 0.349 mmol) in dry DCM (5 mL) was cooled to 0° C. under $N_2$ atmosphere and $BBr_3$ (49.5 μL, 0.523 mmol) in dry DCM (0.5 mL) was slowly added. The reaction mixture was stirred at 0° C. for 2 h and the progress of the reaction was monitored by TLC analysis. After completion, the reaction cooled to 0° C. and was quenched with MeOH (0.5 mL). The reaction mixture was concentrated under reduced pressure and the crude was stirred in sat. $NaHCO_3$ solution for 30 min. The solid was collected by filtration and was purified by silica gel (230-400 mesh) column chromatography using 30-80% ethyl acetate in n-hexane to afford the desired title compound Example 56 as off-white solid. Yield: 72.2 mg (53%); LC_MS Calculated. for $C_{17}H_{22}N_8O$ is 355.20; Observed. 355.25 $[M+H]^+$; $^1H$ NMR (400 MHz, DMSO-$D_6$): δ 8.14 (bs, 2H), 7.65 (d, J=1.6 Hz, 1H), 6.79 (bs, 1H), 6.16 (t, J=2.0 Hz, 1H), 4.92 (d, J=5.6 Hz, 1H), 4.38 (d, J=5.2 Hz, 2H), 3.55 (d, J=5.6 Hz, 2H), 2.23 (s, 3H), 1.97 (s, 3H), 1.44 (s, 6H). HPLC purity=98.22%; XBridge C18 (4.6*150) mm, 5μ; Mobile Phase A: 10 mM ammonium bicarbonate in water; Mobile Phase B: Acetonitrile.

Example 57: 7-amino-5-(((1-(1-hydroxy-2-methyl-propan-2-yl)-1H-pyrazol-3-yl) methyl) amino)-2,3-dimethylpyrazolo[1,5-a]pyrimidine-6-carbonitrile

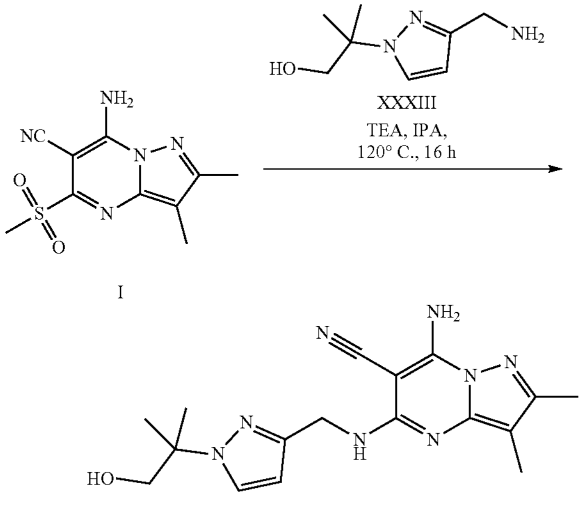

Example 57

To a stirred solution of 7-amino-2,3-dimethyl-5-(methyl sulfonyl) pyrazolo[1,5-a] pyrimidine-6-carbonitrile I (0.15 g, 0.57 mmol) and 2-(3-(aminomethyl)-1H-pyrazol-1-yl)-2-methylpropan-1-ol (0.12 g, 0.71 mmol) in 2-propanol XXXIII (5 mL), was added triethylamine (0.47 mL, 3.4 mmol) and the reaction mixture was heated at 120° C. for 16 h. The progress of the reaction was monitored by TLC analysis. After completion, the reaction mixture was diluted with water (100 ml) and extracted with ethyl acetate (100 mL×3). The organic layer was dried with $Na_2SO_4$, filtered, and evaporated under reduced pressure. The crude was purified by flash silica gel (230-400 mesh) using 0-2% methanol in DCM to afford the desired title compound Example 57 as an off-white solid. Yield: 45.0 mg (20%); LC_MS Calculated. for $C_{17}H_{22}N_8O$ is 355.20; Observed. 355.25 $[M+H]^+$; $^1H$ NMR (400 MHz, DMSO-$D_6$): δ 8.14 (bs, 2H), 7.65 (d, J=1.6 Hz, 1H), 6.79 (bs, 1H), 6.16 (t, J=2.0 Hz, 1H), 4.92 (d, J=5.6 Hz, 1H), 4.38 (d, J=5.2 Hz, 2H), 3.55 (d, J=5.6 Hz, 2H), 2.23 (s, 3H), 1.97 (s, 3H), 1.44 (s, 6H); HPLC purity=98.22%; XBridge C18 (4.6×150) mm, 5μ; Mobile Phase A: 10 mM ammonium bicarbonate in $H_2O$; Mobile Phase B: Acetonitrile.

Example 58: 7-amino-2-(difluoro methyl)-3-ethyl-5-((2-(1-(1-(hydroxymethyl) cyclopropyl)-1H-pyrazol-3-yl) ethyl) amino) pyrazolo[1,5-a]pyrimidine-6-carbonitrile

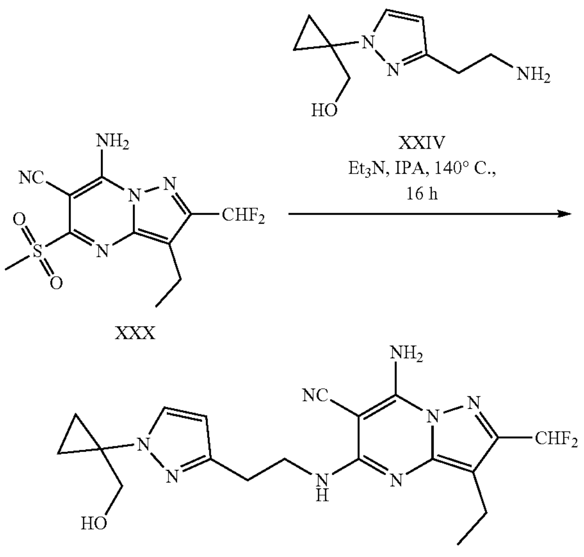

A seal tube was charged with 7-amino-2-(difluoro methyl)-3-ethyl-5-(methyl sulfonyl) pyrazolo[1,5-a] pyrimidine-6-carbonitrile (146 mg, 0.463 mmol), (1-(3-(2-aminoeth yl)-1H-pyrazol-1-yl) cyclopropyl)methanol (150 mg, 0.828 mmol) and 2-propanol (6 mL). The resulting mixture was purged with $N_2$ gas for 5 min and TEA (0.387 mL, 2.78 mmol) was added. The reaction was stirred at 140° C. for 16 h. The progress of the reaction was monitored by TLC analysis. After completion, the reaction mixture concentrated, and the residue was dissolved in water (10 mL). The resulting mixture was extracted with ethyl acetate (15 mL×2). The combined organic layer was washed with brine and dried over anhydrous sodium sulphate. The solvent was removed, and the crude material was purified by flash chromatography (combi-flash) using 20-80% ethyl acetate in n-hexane to afford the desired compound as an off-white solid. Yield: 18 mg (9.3%); LC_MS Calculated. for $C_{19}H_{23}F_2N_8O$ is 417.20; Observed. 417.20 $[M+H]^+$; $^1H$ NMR (400 MHz, DMSO-$D_6$): δ 8.45 (bs, 2H), 7.62 (s, 1H), 7.12-6.87 (m, 2H), 6.08 (s, 1H), 4.96 (bs, 1H), 3.61-3.58 (m, 4H), 2.84 (bs, 2H), 2.71-2.60 (m, 2H), 1.23-1.16 (m, 3H), 1.14-0.98 (m, 4H); HPLC purity=95.15%;)(Bridge C18 (4.6×150) mm, 5μ; Mobile Phase A: 10 mM $NH_4HCO_3$ in water; Mobile Phase B: Acetonitrile; Retention time: 11.678 min.

Example 59: 7-amino-2-(difluoro methyl)-3-ethyl-5-((2-(6-(2-(hydroxymethyl) cyclopropyl)pyridin-2-yl) ethyl)amino)pyrazolo[1,5-a]pyrimidine-6-carbonitrile

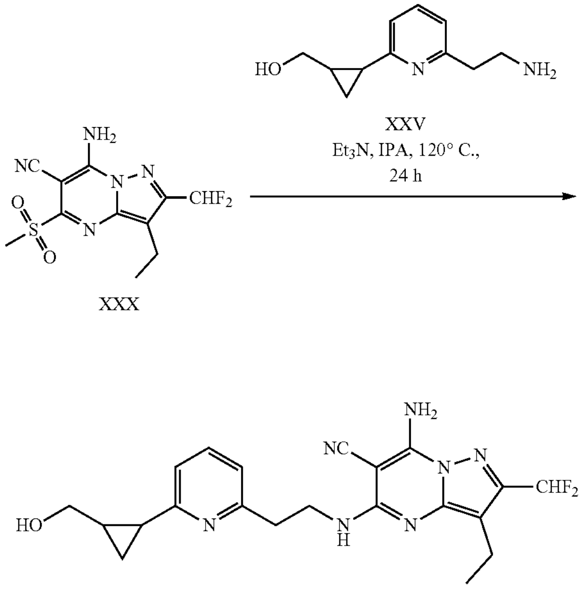

To a solution of (2-(6-(2-aminoethyl) pyridin-2-yl) cyclopropyl) methanol XXV (0.3 g, 2 mmol) and 7-amino-2-(difluoro methyl)-3-ethyl-5-(methyl sulfonyl) pyrazolo[1,5-a] pyrimidine-6-carbonitrile XXX (0.2 g, 0.8 mmol) in isopropanol (10 mL) was added triethylamine (0.7 mL, 5 mmol) and the resulting mixture was purged with $N_2$ for 10 min. The seal tube was closed tightly and heated at 140° C. for 48 h. The progress of the reaction was monitored by TLC analysis. The reaction was cooled to RT and the reaction mixture was concentrated under vacuo. To the residue was added ethyl acetate (20 mL) and water (20 mL). The organic layer was separated, washed with brine, dried over anhydrous sodium sulphate, and concentrated under vacuo to afford light brown viscous liquid. The crude compound was purified by reverse phase prep-HPLC using YMC AQUA ODS (250×20) mm. 5μ; Mobile phase A: 10 mm Ammonium bicarbonate in $H_2O$, Mobile phase B: ACN:MeOH (1:1). Yield: (50 mg, 4%). LC_MS Calculated. for $C_{12}H_{24}F_2N_7O$ is 428.20; Observed. 428.20 $[M+H]^+$. $^1H$ NMR (400 MHz, DMSO-$D_6$): δ 8.42 (bs, 2H), 7.53 (t, J=7.6 Hz, 1H), 7.18-6.91 (m, 4H), 4.57 (t, J=6.0 Hz, 1H), 3.66 (bs, 2H), 3.68-3.36 (m, 2H), 2.97 (t, J=6.8 Hz, 2H), 2.68-2.55 (m, 2H), 1.96 (bs, 1H), 1.58 (bs, 1H), 1.19 (t, J=7.2 Hz, 2H), 1.09 (bs, 1H), 1.07 (bs); HPLC Purity=96.58%, XB_9010ABC Rt=10.262 min; Chiral HPLC (two peaks); Chiral Pak IG (250×4.6) mm, 5μ; Mobile phase: A: 0.1% DEA in Hex, B: EtOH (90:10); P1=51.29%, Rt=19.022 min; P2=48.71%, Rt=21.731 min.

Example 60: 7-amino-3-ethyl-5-((2-(6-(2-(hydroxymethyl) cyclopropyl)$_{284}$yridine-2-yl) ethyl) amino)-2-methylpyrazolo[1,5-a]pyrimidine-6-carbonitrile

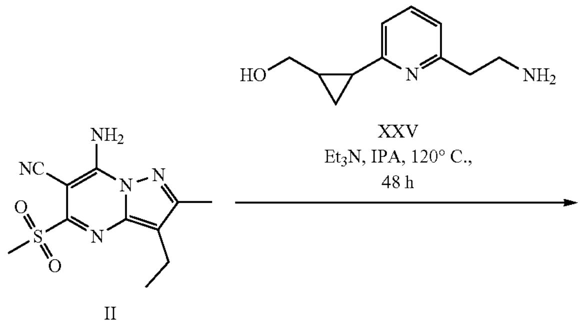

II

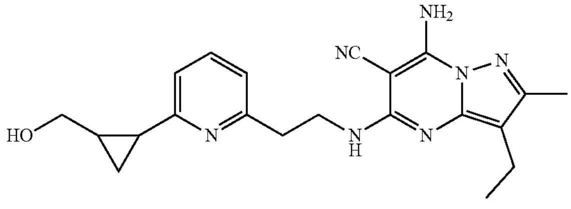

Example 60

To a solution of (2-(6-(2-aminoethyl) pyridin-2-yl) cyclopropyl) methanol XXV (344 mg, 1.79 mmol) and 7-amino-3-ethyl-2-methyl-5-(methyl sulfonyl) pyrazolo[1,5-a] pyrimidine-6-carbonitrile II (250 mg, 0.89 mmol) in isopropanol (10 mL) was added triethylamine (0.750 mL, 5.37 mmol) and the resulting mixture was purged with $N_2$ for 10 min. The seal tube was closed tightly and heated at 120° C. for 48 h. The progress of the reaction was monitored by TLC analysis. The reaction was cooled to RT and the reaction mixture was concentrated under vacuo. To the residue was added ethyl acetate (30 mL) and water (20 mL). The organic layer was separated, washed with brine, dried over anhydrous sodium sulphate, and concentrated under vacuo to afford light brown viscous liquid. The crude was purified by combi flash (230-400 mesh) column chromatography by using 0-20% ethyl acetate in n-hexane to afford the desired title compound Example 60 as an off-white solid. Yield: (45 mg, 20%). LC_MS Calculated. for $C_{21}H_{26}N_7O$ is 392.22; Observed. 392.25 $[M+H]^+$. $^1$H NMR (400 MHz, DMSO-$D_6$): δ 8.09 (bs, 2H), 7.53 (t, J=7.6 Hz, 1H), 7.05 (d, J=7.6 Hz, 1H), 6.98 (d, J=7.6 Hz, 1H), 6.68 (bs, 1H), 4.56 (t, J=5.6 Hz, 1H), 3.67-3.62 (m, 2H), 3.51-3.47 (m, 1H), 3.39-3.32 (m, 1H), 2.95 (t, J=7.2 Hz, 2H), 2.48-2.40 (m, 2H), 2.25 (s, 3H), 1.98-1.94 (m, 1H), 1.59-1.56 (m, 1H), 1.20-1.06 (m, 4H), 0.89-0.85 (m, 1H); HPLC Purity=96.79%, Rt=10.262 min; Chiral HPLC (two peaks); Chiral Pak IG (250×4.6) mm, 5μ; Mobile phase: A: 0.1% DEA In Hex, B: EtOH (90:10); P1=49.98%, Rt=26.408 min; P2=50.02%, Rt=32.475 min.

Example 61: 7-amino-3-chloro-5-((2-(4-(1-(hydroxymethyl) cyclopropyl) thiazol-2-yl) ethyl) amino)-2-methylpyrazolo[1,5-a] pyrimidine-6-carbonitrile

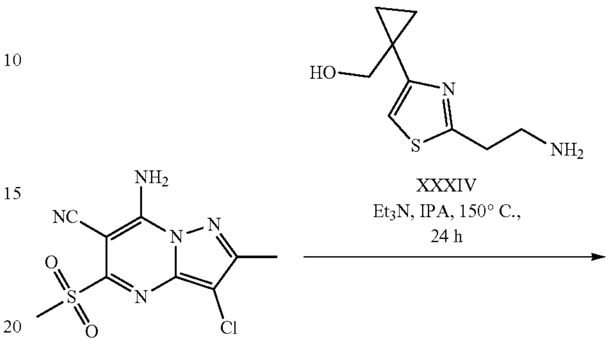

XX

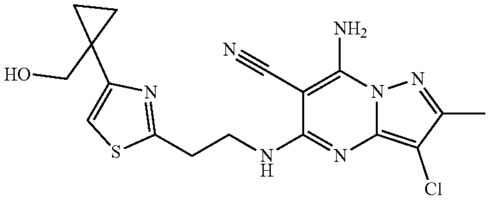

Example 61

To a stirred solution of 7-amino-3-chloro-2-methyl-5-(methyl sulfonyl) pyrazolo[1,5-a] pyrimidine-6-carbonitrile XX (0.15 g, 0.53 mmol) in isopropanol (5 mL) were added (1-(2-(2-aminoethyl) thiazol-4-yl)cyclopropyl)methanol XXXIV (0.31 g, 1.6 mmol) and TEA (0.37 mL, 2.6 mmol). The reaction mixture was stirred at 150° C. for 24 h and the progress of the reaction was monitored by TLC analysis. After completion, the reaction mixture was concentrated and to the residue was added water (15 mL). The resulting mixture was extracted with ethyl acetate (20 mL×2) and the combined organic layer was dried over anhydrous sodium sulphate. The residue obtained upon removal of the solvent was subjected to silica gel (230-400 mesh) column chromatography using (10-60%) ethyl acetate in n-hexane to afford the desired title compound Example 61 as a light brown solid. Yield: 11.3 mg (5%); LC_MS Calculated. for $C_{17}H_{18}ClN_7OS$ is 403.10; Observed. 404.15 $[M+H]^+$; $^1$H NMR (400 MHz, DMSO-$D_6$): δ 8.43 (bs, 2H), 7.16 (s, 1H), 7.10 (t, J=5.2 Hz, 1H), 4.69 (t, J=5.6 Hz, 1H), 3.71-3.65 (m, 4H), 3.22 (t, J=6.8 Hz, 2H), 2.28 (s, 3H), 0.99-0.96 (m, 2H), 0.84-0.81 (m, 2H). HPLC Purity=99.01%; INT ODS 3V-C18 (4.6×250) mm, 5μ; Mobile phase A: 0.1% Formic acid in water; Mobile phase B: Acetonitrile; Rt=11.614 min.

Example 62: 7-amino-3-ethyl-5-(2-(4-fluoro-1-(1-hydroxy-2-methylpropan-2-yl)-1H-pyrazol-3-yl) ethyl) amino)-2-methylpyrazolo[1,5-a]pyrimidine-6-carbonitrile

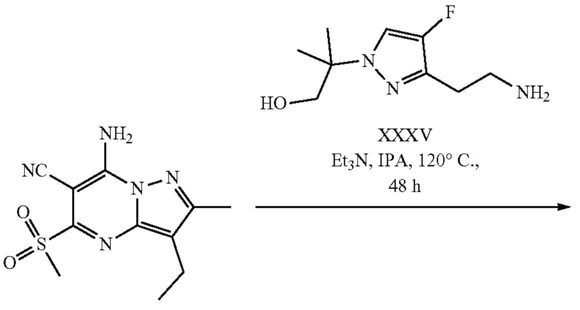

XXXV

II

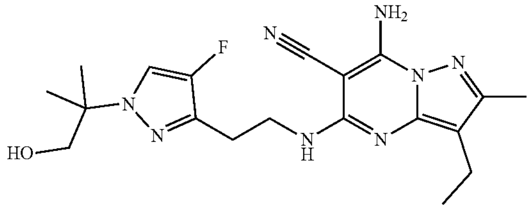

Example 62

To a stirred solution of 7-amino-3-ethyl-2-methyl-5-(methyl sulfonyl) pyrazolo[1,5-a] pyrimidine-6-carbonitrile II (250 mg, 0.895 mmol) and 2-(3-(2-aminoethyl)-4-fluoro-1H-pyrazol-1-yl)-2-methylpropan-1-ol. XXXV (350 mg, 1.74 mmol) in 2-propanol (10 mL) was added triethylamine (0.748 mL, 5.37 mmol). The resulting mixture was heated at 120° C. for 48 h. The progress of the reaction was monitored by TLC analysis. After completion, the reaction was cooled to room temperature and crude was diluted with ethyl acetate (20 mL) and water (20 mL) and mixed well. The combined organic layer was washed with brine, dried over anhydrous sodium sulphate, and concentrated under vacuum to afford light brown viscous liquid. The crude compound was purified by combi-flash silica (230-400) column chromatography by eluting with 10-50% ethyl acetate in n-hexane to afford the desired compound Example 62 as an off-white solid. Yield: 0.11 g (30%). LC_MS Calculated. for $C_{19}H_{25}FN_8O$ is 400.21; Observed. 401.25 $[M+H]^+$; $^1H$ NMR (400 MHz, DMSO-$D_6$): δ 8.10 (bs, 2H), 7.79 (d J=4.8 Hz, 1H), 6.65 (bs, 1H), 4.91-4.90 (m, 1H), 3.58-3.55 (m, 2H), 3.51-3.49 (m, 2H), 2.84-2.80 (m, 2H), 2.46-2.42 (m, 2H), 2.25 (m, 3H), 1.39 (s, 6H), 1.11 (t, J=7.60 Hz, 3H); HPLC Purity=99.09%; Rt=10.08 min;

Example 63: 7-amino-3-ethyl-5-((2-(1-((1-(hydroxymethyl) cyclopropyl)methyl)-1H-pyrazol-3-yl) ethyl)amino)-2-methylpyrazolo[1,5-a]pyrimidine-6-carbonitrile

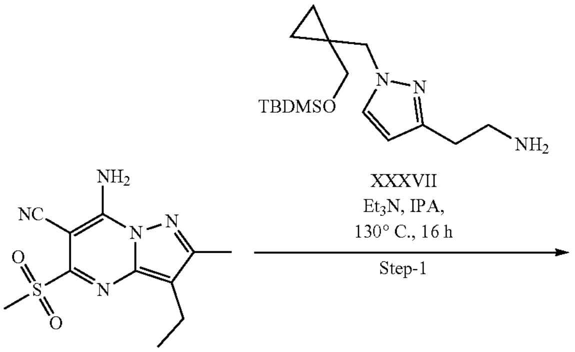

XXXVII

II

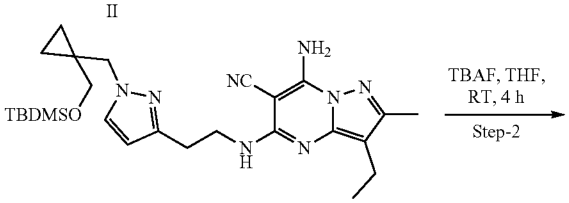

Example 63a

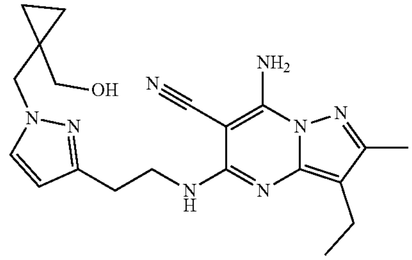

Example 63

Step-1: 7-Amino-5-((2-(1-((1-(((tert-butyl dimethyl silyl) oxy) methyl) cyclopropyl) methyl)-1H-pyrazol-3-yl) ethyl) amino)-3-ethyl-2-methylpyrazolo[1,5-a]pyrimidine-6-carbonitrile (Example 63a)

To a stirred solution of 7-amino-3-ethyl-2-methyl-5-(methyl sulfonyl) pyrazolo[1,5-a] pyrimidine-6-carbonitrile II (250 mg, 0.895 mmol) in 2-propanol (20 mL) was added 2-(1-((1-(((tert-butyl dimethyl silyl) oxy) methyl)cyclopropyl)methyl)-1H-pyrazol-3-yl)ethan-1-amine XXXVII (416 mg, 1.34 mmol) and triethylamine (624 μL, 4.48 mmol) under nitrogen. The resulting mixture was stirred at 130° C. for 16 h. The progress of the reaction was monitored by TLC analysis. After completion, the reaction mixture was cooled to room temperature and diluted with water (30 mL) then extracted with ethyl acetate (20 mL×3). The combined organic layer was washed with 25 mL of brine and passed through anhydrous sodium sulphate then concentrated under reduced pressure. The residue obtained upon removal of the solvent was subjected to silica gel (230-400 mesh) column chromatography using 0-5% MeOH in DCM to afford the desired compound Example 63a as a light-yellow solid. Yield: 0.15 g (33%). LC-MS Calculated. for $C_{26}H_{40}N_8OSi$ is 508.30; Observed. 509.35 $[M+H]^+$.

Step-2: 7-amino-3-ethyl-5-((2-(1-((1-(hydroxymethyl) cyclopropyl) methyl)-1H-pyrazol-3-yl) ethyl) amino)-2-methylpyrazolo[1,5-a]pyrimidine-6-carbonitrile To a stirred solution of 7-amino-5-((2-(1-((1-(((tert-butyldimethyl silyl)oxy)methyl)cyclopropyl)methyl)-1H-pyrazol-3-yl)ethyl) amino)-3-ethyl-2-methylpyrazolo[1,5-a] pyrimidine-6-carbonitrile Example 63a (0.150 g, 0.295 mmol) in THF (5 mL) was added TBAF (154 mg, 1.0 M in THF, 0.590 mmol) and the reaction mixture was stirred at room temperature for 4 h. The progress of the reaction was monitored by TLC analysis. After completion, the reaction mixture was diluted with water (50 mL) and extracted with ethyl DCM (30 mL×3). The combined organic layer was dried over anhydrous sodium sulphate and concentrated under vacuo to afford a desired crude compound. The residue obtained upon removal of the solvent was subjected to silica gel (230-400 mesh) column chromatography using 0-6% MeOH in DCM to afford the desired compound Example 63 as an Off-white solid. Yield: 66 mg (57%). LC-MS Calculated for $C_{20}H_{26}N_8O$ is 394.22; Observed: 395.25 $[M+H]^+$. $^1H$ NMR (400 MHz, DMSO-$D_6$): δ 8.11 (bs, 2H), 7.59 (d, J=2.0 Hz, 1H), 6.67 (t, J=5.6 Hz, 1H), 6.07 (d, J=2.0 Hz, 1H), 4.62 (t, J=5.6 Hz, 1H), 4.02 (s, 2H), 3.57 (q, J=5.6 Hz, 2H), 3.17 (d, J=5.6 Hz, 2H), 2.82 (t, J=7.6 Hz, 2H), 2.56-2.43 (m, 2H), 2.25 (s, 3H), 1.12 (t, J=7.6 Hz, 3H), 0.54-0.51 (m, 2H), 0.43-0.41 (m, 2H). HPLC: Rt=11.567 min; Purity=99.39%, INT ODS 3V-C18 (4.6×250) mm, 5μ, Mobile Phase A: 0.1% Formic acid in water, Mobile Phase B: Acetonitrile.

Example 64: 7-amino-3-chloro-5-((2-(6-(1,1-difluoro-2-hydroxyethyl) pyridin-2-yl) ethyl)amino)-2-methylpyrazolo[1,5-a]pyrimidine-6-carbonitrile

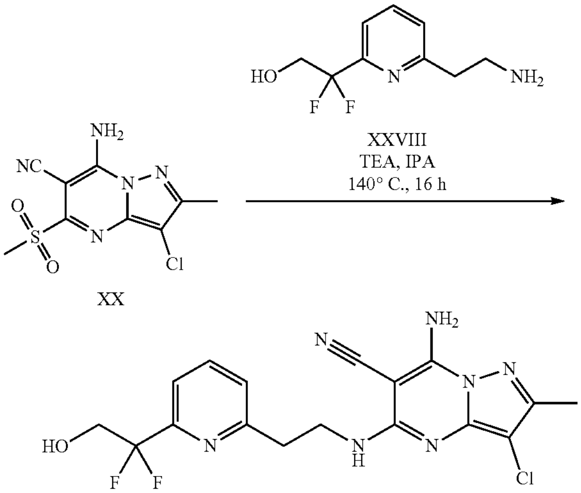

XX

Example 64

To a stirred solution of 7-amino-3-chloro-2-methyl-5-(methyl sulfonyl) pyrazolo[1,5-a] pyrimidine-6-carbonitrile XX (0.2 g, 0.7 mmol) in 2-propanol was added 2-(6-(2-Aminoethyl)pyridin-2-yl)-2,2-difluoroethan-1-ol XXXVIII (0.3 g, 1 mmol) and triethylamine (0.8 g, 7 mmol) under $N_2$ and the reaction mixture was stirred at 140° C. for 16 h. The progress of reaction was monitored by TLC analysis. After completion, reaction mixture was cooled to room temperature, diluted with water (25 mL) and extracted with ethyl acetate (20 mL×3). The combined organic phase was dried over anhydrous sodium sulphate and concentrated under reduced pressure to obtain crude product. The obtained crude material was purified by reverse phase preparative HPLC (Column: Phenomenex, Kinetic C18 (250×20) mm, 5 μm. A: 10 mm Ammonium bicarbonate in water. B: Acetonitrile) to obtain the pure desired off-white solid material. Yield: 0.05 g (8.0%). LC-MS Calculated. for $C_{17}H_{16}ClF_2N_7O$ is 407.10; Observed. 408.15 $[M+H]^+$; $^1H$ NMR (400 MHz, DMSO-$D_6$): δ 8.41 (bs, 2H), 7.89 (t, J=8.0 Hz, 1H), 7.52 (d, J=8.0 Hz, 1H), 7.45 (d, J=8.0 Hz, 1H), 7.07 (t, J=5.6 Hz, 1H), 5.49 (t, J=6.4 Hz, 1H), 4.00 (td, J=14.4, 6.8 Hz, 2H), 3.73 (q, J=6.8 Hz, 2H), 3.10 (t, J=6.8 Hz, 2H), 2.28 (s, 3H). HPLC: 97.65%, Example 65: 7-amino-3-chloro-5-((2-(6-(1-hydroxy-2-methylpropan-2-yl)pyridin-2-yl)ethyl)amino)-2-methylpyrazolo[1,5-a]pyrimidine-6-carbonitrile

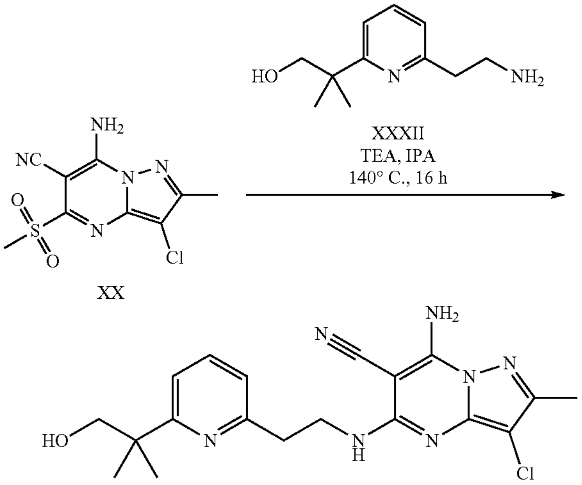

XX

Example 65

To a stirred solution of 2-(6-(2-aminoethyl) pyridin-2-yl)-2-methylpropan-1-ol XXXII (0.4 g, 2 mmol) in 2-propanol (20 mL) were added 7-amino-3-chloro-2-methyl-5-(methyl sulfonyl) pyrazolo[1,5-a] pyrimidine-6-carbonitrile XX (0.3 g, 1 mmol) and triethylamine (0.4 mL, 3 mmol) under nitrogen. The resulting mixture was stirred at 120° C. for 48 h. The progress of the reaction was monitored by TLC analysis. After completion, the reaction mixture was cooled to room temperature and diluted with water (30 mL) then extracted with ethyl acetate (25 mL×2). The combined organic layer was washed with 25 mL of brine and passed through anhydrous sodium sulphate then concentrated under reduced pressure. The residue obtained upon removal of the solvent was subjected to silica gel (230-400 mesh) column chromatography using 0-35% ethyl acetate in n-hexane to afford the desired title compound Example 65 as off-white solid. Yield: 127 mg (30%). LC-MS: calculated. for $C_{19}H_{22}ClN_7O$ is 399.15; Observed. 400.20 $[M+H]^+$; $^1H$ NMR (400 MHz, DMSO-$D_6$): δ 8.39 (bs, 2H), 7.63 (t, J=8.0 Hz, 1H), 7.22 (d, J=8.0 Hz, 1H), 7.10 (d, J=8.0 Hz, 1H), 6.97 (t, J=5.2 Hz, 1H), 4.64 (t, J=5.2 Hz, 1H), 3.73 (q, J=6.0 Hz, 2H), 3.55 (d, J=5.6 Hz, 2H), 3.03 (t, J=6.4 Hz, 2H), 2.28 (s, 3H), 1.24 (s, 6H). HPLC Purity=97.50%, Example 66: 7-amino-3-ethyl-5-((2-(4-(1-(hydroxymethyl) cyclopropyl)thiazol-2-yl)ethyl) amino)-2-methylpyrazolo[1,5-a]pyrimidine-6-carbonitrile)

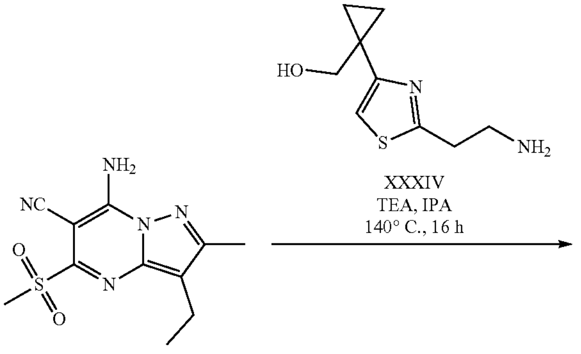

II

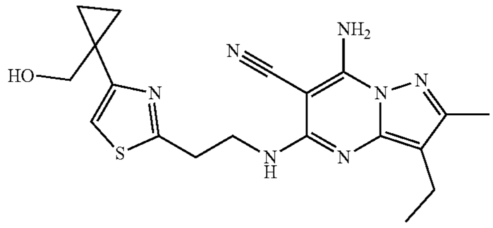

Example 66

To a stirred solution of 7-amino-3-ethyl-2-methyl-5-(methyl sulfonyl) pyrazolo[1,5-a] pyrimidine-6-carbonitrile II (0.15 g, 0.54 mmol) in isopropanol (5 mL) were added (1-(2-(2-aminoethyl) thiazol-4-yl) cyclopropyl) methanol XXXIV (0.32 g, 1.6 mmol) and TEA (0.37 mL, 2.7 mmol) in sealed tube. The reaction mixture was stirred at 120° C. for 48 h and the progress of the reaction was monitored by TLC analysis. After completion, the reaction mixture was concentrated under reduced pressure and crude was purified by flash silica gel (230-400) column chromatography using 0-35% ethyl acetate in n-hexane to afford the title compound Example 66 as a yellow sticky solid. Yield: 7.2 mg (3%). LC-MS Calculated. for $C_{19}H_{23}N_7OS$ is 397.16; Observed. 398.20 $[M+H]^+$. $^1H$ NMR (400 MHz, DMSO-$D_6$): δ 8.13 (bs, 2H), 7.15 (s, 1H), 6.79 (bs, 1H), 4.68 (bs, 1H) 3.66-3.64 (m, 4H), 3.20 (t, J=7.2 Hz, 2H), 2.45-2.43 (m, 2H), 2.25 (s, 3H), 1.12 (t, J=7.6 Hz, 4H), 0.99-0.97 (m, 3H). HPLC: 12.104 min; 98.45%, INT ODS 3V-C18 (4.6*250) mm, 5μ, Mobile Phase A: 0.1% Formic acid in water, Mobile Phase B: Acetonitrile; Flow: 1.0 mL/min.

Example 67: Synthesis of 7-amino-3-chloro-5-((2-(1-(2-(hydroxymethyl) cyclobutyl)-1H-pyrazol-3-yl) ethyl) amino)-2-methylpyrazolo[1,5-a]pyrimidine-6-carbonitrile

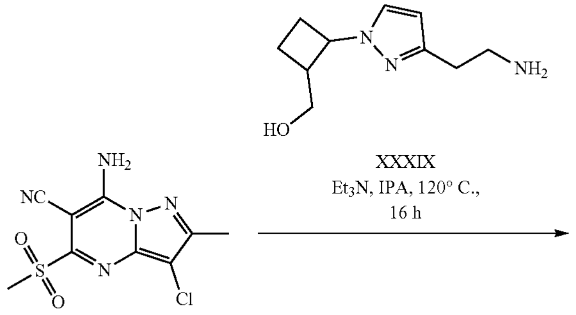

XX

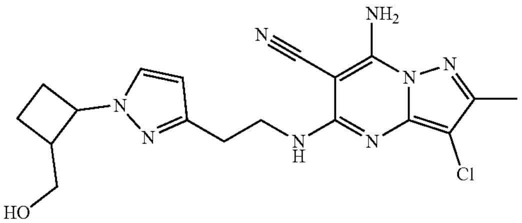

Example 67

To a stirred solution of 7-amino-3-chloro-2-methyl-5-(methyl sulfonyl) pyrazolo[1,5-a] pyrimidine-6-carbonitrile XX (2.2 g, 7.7 mmol) and (2-(3-(2-aminoethyl)-1H-pyrazol-1-yl) cyclobutyl) methanol XXXIX (1.5 g, 7.7 mmol) in 2-propanol (50 mL) was added triethylamine (6.4 mL, 46 mmol). The resulting mixture was heated at 120° C. for 16 h in seal tube. The progress of the reaction was monitored by TLC analysis. After completion, the reaction mixture was cooled to rt and concentrated in vacuum. The residue was dissolved in water (20 mL) and extracted with ethyl acetate (50 mL×3). The combined organic layer was dried over sodium sulphate, filtered, and concentrated under reduced pressure. The crude was purified by Biotage flash silica gel (230-400) column chromatography using 0-50% ethyl acetate in n-hexane to afford the desired title compound Example 67 as an off-white solid. Yield: 2.3 g, (74%); LC_MS Calculated. for $C_{18}H_{21}ClN_8O$ is 400.15; Observed. 401.30 $[M+H]^+$. $^1H$ NMR (400 MHz, DMSO-$D_6$): δ 8.40 (bs, 2H), 7.66 (d, J=1.6 Hz, 1H), 7.00 (t, J=4.8 Hz, 1H), 6.08 (d, J=2.0 Hz, 1H), 4.60 (t, J=5.2 Hz, 1H), 4.52-4.50 (m, 1H), 3.63-3.58 (m, 2H), 3.41-3.39 (m, 2H), 2.85-2.78 (m, 3H), 2.34-2.20 (m, 5H), 1.80-1.78 (m, 1H), 1.60-1.55 (m, 1H). HPLC: 10.082 min; 99.13%, Column: INT ODS 3V-C18 (4.6*250) mm, 5μ Mobile phase A: 0.1% Formic acid in water Mobile phase B: Acetonitrile, Flow: 1.0 mL/min.

Example 68: 7-amino-5-((2-(1-(1-(amino methyl) cyclopropyl)-1H-pyrazol-3-yl) ethyl) amino)-3-chloro-2-methylpyrazolo[1,5-a]pyrimidine-6-carbonitrile

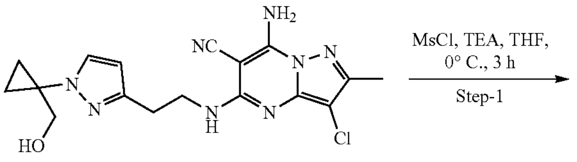

Example 37

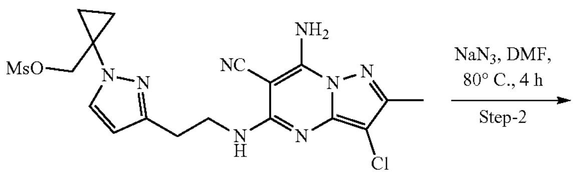

Example 68a

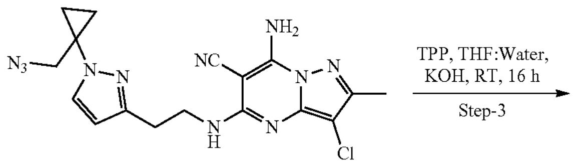

Example 68b

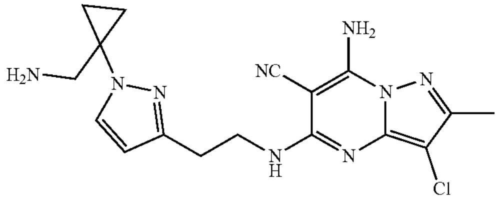

Example 68

Step-1: Synthesis of (1-(3-(2-((7-amino-3-chloro-6-cyano-2-methylpyrazolo[1,5-a] pyrimidin-5-yl) amino) ethyl)-1H-pyrazol-1-yl) cyclopropyl) methyl methane sulfonate. (Example 68a)

To a solution of 7-amino-3-chloro-5-((2-(1-(1-(hydroxymethyl) cyclopropyl)-1H-pyrazol-3-yl) ethyl) amino)-2-methylpyrazolo[1,5-a] pyrimidine-6-carbonitrile Example 37 (2.69 g, 6.95 mmol) in THF (20 mL) at 0° C. was added triethylamine (4.85 mL, 34.8 mmol) and methane sulfonyl chloride (0.6 mL, 7.65 mmol). The reaction mixture was stirred at 0° C. 3 h. The progress of the reaction was monitored by TLC analysis. After the completion, the reaction mixture was warmed to rt and diluted with $NaHCO_3$ solution (100 mL). The mixture was extracted with DCM (100 mL×3). The combined organic layer was dried over anhydrous $Na_2SO_4$, filtered and concentrated under reduced pressure. The crude compound was purified by silica gel (230-400 mesh) column chromatography using ethyl acetate in hexane (0-100%) to afford the desired compound Example 68a as a light-yellow liquid. Yield: 1.8 g, (56.0%); LC_MS Calculated. for $C_{18}H_{21}ClN_8O_3S$ is 464.11; Observed: 465.25 $[M+H]^+$.

Step-2: Synthesis of 7-amino-5-((2-(1-(1-(azidomethyl) cyclopropyl)-1H-pyrazol-3-yl) ethyl) amino)-3-chloro-2-methylpyrazolo[1,5-a] pyrimidine-6-carbonitrile (Example 68b)

To a solution of (1-(3-(2-((7-amino-3-chloro-6-cyano-2-methylpyrazolo [1,5-a] pyrimidin-5-yl) amino) ethyl)-1H-pyrazol-1-yl) cyclopropyl) methyl methane sulfonate Example 68a (1.8 g, 3.9 mmol) in N, N-dimethyl formamide (10 mL) was added sodium azide (1.0 g, 15 mmol) and heated at 80° C. for 4 h. The progress of the reaction was monitored by TLC analysis. After the completion of the reaction, reaction mixture was cooled to rt, diluted with water (30 mL), and extracted with ethyl acetate (50 mL×3). The combined organic layer was dried over anhydrous $Na_2SO_4$, filtered and concentrated under reduced pressure. The crude compound was purified by silica gel (230-400 mesh) column chromatography eluted with ethyl acetate in n-hexane (0-30%) to afford the desired product Example 68b as a light-yellow solid. Yield: 1.24 g, (77.0%); LCMS Calculated. for $C_{17}H_{18}ClN_{11}$ is 411.14; Observed: 412.3 $[M+H]^+$ $^1$HNMR (400 MHz, $CDCl_3$): δ 7.47 (d, J=2 Hz, 1H), 6.11-6.06 (m, 4H), 3.88-3.84 (m, 2H), 3.60 (s, 2H), 2.95 (t, J=6 Hz, 2H), 2.35 (s, 3H), 1.36 (t, J=6.4 Hz, 2H), 1.10 (t, J=7.2 Hz, 2H).

Step-3: 7-amino-5-((2-(1-(1-(amino methyl) cyclopropyl)-1H-pyrazol-3-yl) ethyl) amino)-3-chloro-2-methylpyrazolo[1,5-a]pyrimidine-6-carbonitrile To a solution of 7-amino-5-((2-(1-(1-(azidomethyl) cyclopropyl)-1H-pyrazol-3-yl) ethyl) amino)-3-chloro-2-methylpyrazolo[1,5-a] pyrimidine-6-carbonitrile Example 68b (0.3 g, 0.7 mmol) in THF (10 mL) and water (3 mL) was added triphenylphosphine (0.3 g, 1 mmol). The reaction mixture was stirred at for 10 min. This was followed by an addition of potassium hydroxide (0.04 g, 0.7 mmol) and stirred at rt for 16 h. The progress of the reaction was monitored by TLC analysis. After the completion of the reaction, diluted with water (20 ml) and extracted with ethyl acetate (20 mL×3). The combined organic layer was dried over anhydrous $Na_2SO_4$, filtered and concentrated under reduced pressure. The crude compound was purified by silica gel (60-120 mesh) column chromatography eluted with methanol in dichloromethane (0-10%) to afford the desired title product Example 68 as an off-white solid. Yield: 0.25 g, (83.0%); LCMS Calculated. for $C_{17}H_{20}ClN_9$ is 385.15; Observed: 386.3 $[M+H]^+$; $^1$H NMR (400 MHz, DMSO-$D_6$): δ 7.69 (d, J=2 Hz, 2H), 6.95-6.93 (m, 4H), 6.14 (d, J=2 Hz, 1H), 3.88-3.84 (m, 2H), 3.60 (s, 2H), 2.95 (t, J=6 Hz, 2H), 2.35 (s, 3H), 1.19-1.14 (m, 4H). HPLC: 7.963 min; 99.08%, INT ODS 3V-C18 (4.6*250) mm, 5μ, Mobile Phase A: 0.1% Formic acid in water, Mobile Phase B: Acetonitrile

Example 69: 7-amino-3-bromo-5-((2-(1-(1-(hydroxymethyl) cyclopropyl)-1H-pyrazol-3-yl) ethyl) amino)-2-methylpyrazolo[1,5-a]pyrimidine-6-carbonitrile

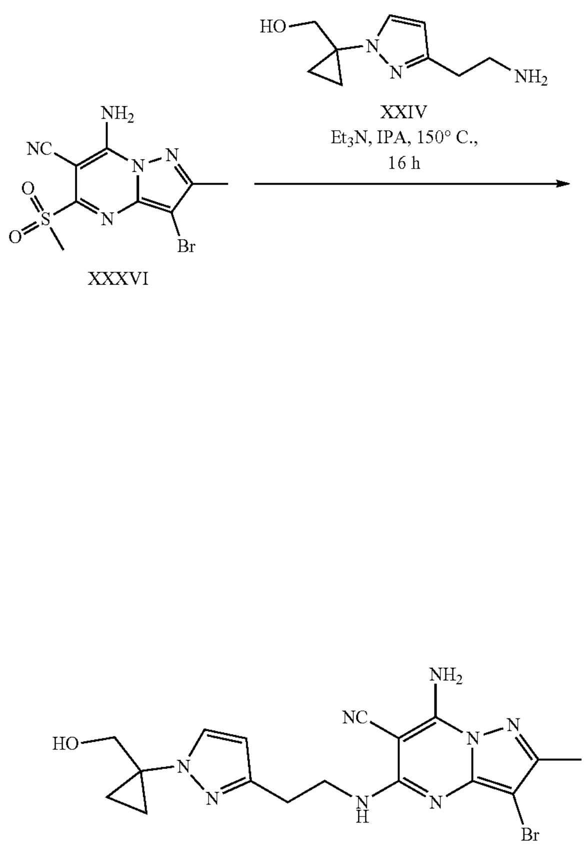

XXXVI

XXIV

Example 69

To a solution of 7-amino-3-bromo-2-methyl-5-(methyl sulfonyl) pyrazolo[1,5-a] pyrimidine-6-carbonitrile XXXVI (0.3 g, 0.91 mmol) in isopropyl alcohol (15 mL) were added (1-(3-(2-aminoethyl)-1H-pyrazol-1-yl) cyclopropyl) methanol (0.33 g, 1.82 mmol) and triethylamine (0.76 mL, 5.45 mmol) and stirred at 150° C. for 16 h. The progress of the reaction was monitored by TLC analysis. After the completion of the reaction, added water (50 mL) and extracted with ethyl acetate (2×25 mL). The combined organic layer was dried over anhydrous sodium sulphate, filtered, and concentrated under reduced pressure to afford the crude compound as a brown semi-solid. The crude compound was purified by silica gel (230-400 mesh) column chromatography with methanol in dichloromethane (0-5%) to afford the desired compound Example 69 as a brown solid. Yield: 0.1 g, (25.5%); LC_MS Calculated. for $C_{17}H_{19}BrN_8O$ is 430.08; Observed: 431.25 $[M+H]^+$. $^1H$ NMR (400 MHz, DMSO-$D_6$): δ 8.39 (bs, 2H), 7.62 (d, J=2.4 Hz, 1H), 6.95 (t, J=5.2 Hz, 1H), 6.06 (d, J=2.64 Hz, 1H), 4.88 (t, J=5.6 Hz, 1H), 3.63-3.58 (m, 4H), 2.82 (t, J=8 Hz, 2H), 2.29 (d, J=21 Hz, 3H), 1.07-0.94 (m, 4H); HPLC Purity: 10.993 min; 96.42%, INT ODS 3V-C18 (4.6*250) mm, 5μ; Mobile Phase A: 0.1% Formic acid in water, Mobile Phase B: Acetonitrile; Flow rate: 1.0 mL/min

Example 70: 7-amino-3-chloro-5-((2-(1-ethyl-2-oxo-1,2-dihydropyridin-3-yl) ethyl) amino)-2-methylpyrazolo[1,5-a]pyrimidine-6-carbonitrile

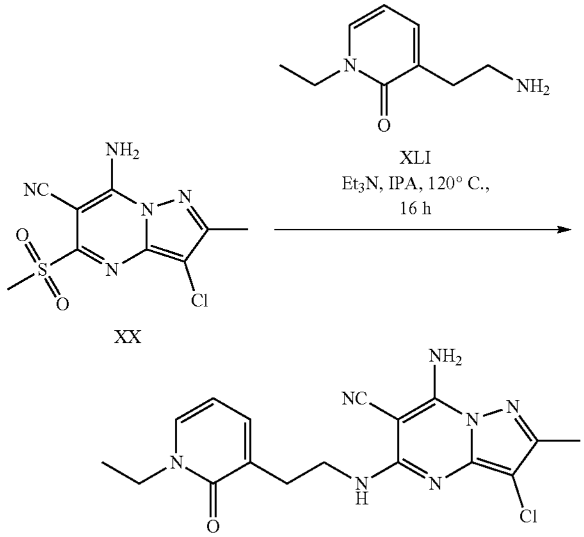

XLI

XX

Example 70

To a solution of 3-(2-aminoethyl)-1-ethylpyridin-2(1H)-one XLI (0.2 g, 0.7 mmol) in isopropyl alcohol (5 mL) were added 7-amino-3-chloro-2-methyl-5-(methyl sulfonyl) pyrazolo[1,5-a] pyrimidine-6-carbonitrile XX (0.12 g, 0.7 mmol) and triethylamine (0.5 mL, 3.50 mmol). The reaction mixture was stirred at 160° C. for 48 h. The progress of the reaction was monitored by TLC analysis. After the completion of the reaction, solids were filtered, washed with ethyl acetate (50 mL) and triturated with acetonitrile to afford the desired product as an off-white solid. Yield:0.15 g, (58.0%); LC_MS Calculated. for $C_{17}H_{18}ClN_7O$ is 371.13; Observed. 372.20 $[M+H]^+$. $^1H$ NMR (400 MHz, DMSO-$D_6$): δ 8.35 (s, 2H), 7.58-7.57 (m, 1H), 7.29 (d, J=4.4 Hz, 1H), 7.08 (t, J=5.2 Hz, 1H), 6.17 (t, J=4 Hz, 1H), 3.95-3.89 (m, 2H), 3.56-3.51 (m, 2H), 2.74 (t, J=6.4 Hz, 2H), 2.27 (s, 3H), 1.22 (t, J=8 Hz, 3H); HPLC: 95.69%.

Example 71: 7-amino-3-ethyl-5-((2-(1-(1-(hydroxymethyl) cyclopropyl)-1H-pyrazol-3-yl) ethyl) amino) pyrazolo[1,5-a] pyrimidine-6-carbonitrile

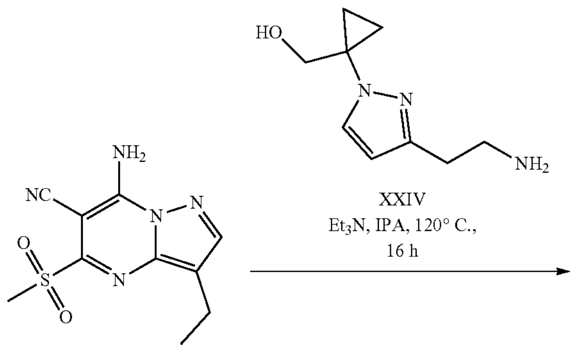

XXIV

XLII

-continued

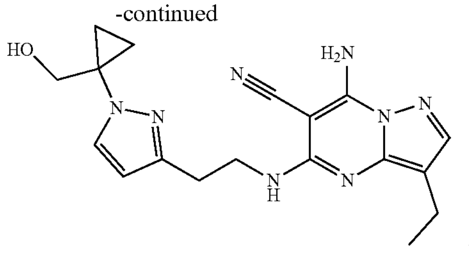

Example 71

To a solution of 7-amino-3-ethyl-5-(methyl sulfonyl) pyrazolo[1,5-a]pyrimidine-6-carbonitrile XLII (0.12 g, 0.452 mmol) in isopropyl alcohol (15 mL) were added (1-(3-(2-aminoethyl)-1H-pyrazol-1-yl)cyclopropyl)methanol XXIV (0.18 g, 0.993 mmol) and triethylamine (0.378 mL, 2.71 mmol) and the reaction mixture was stirred at 140° C. for 48 h. The progress of the reaction was monitored by TLC analysis. After the completion of the reaction, concentrated and added water (10 mL), extracted with ethyl acetate (20 mL×3). The combined organic layer was washed with brine (20 mL), dried over anhydrous sodium sulphate, and concentrated to get the crude material. The crude compound was purified by silica gel (60-120 mesh) column chromatography with ethyl acetate in n-hexane (0-60%) to afford the desired compound Example 71 as an off-white solid. Yield: 48.3 mg, (29.2%); LC_MS Calculated. for $C_{18}H_{22}N_8O$ is 366.19; Observed. 367.25 $[M+H]^+$. $^1H$ NMR (400 MHz, DMSO-$D_6$): δ 8.23 (s, 2H), 7.82 (s, 1H), 7.62 (s, 1H), 6.66 (s, 1H), 6.04 (s, 1H), 4.87 (t, J=5.6 Hz, 1H), 3.59 (t, J=5.6 Hz, 3H), 2.82 (t, J=7.2 Hz, 2H), 1.20-1.17 (m, 2H), 1.08 (d, J=6.4 Hz, 2H), 0.97-0.94 (m, 2H). HPLC: 98.98%.

Example 72: 7-amino-3-bromo-5-((2-(6-(hydroxymethyl) pyridine-2-yl) ethyl) amino)-2-methylpyrazolo[1,5-a]pyrimidine-6-carbonitrile

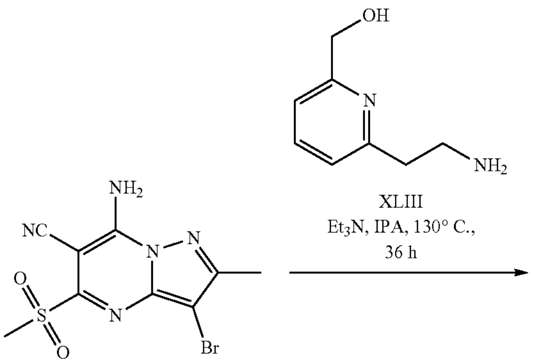

XXXVI

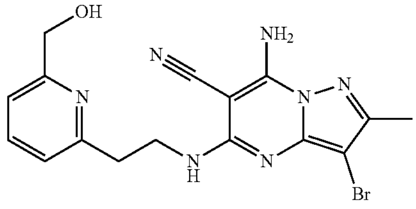

Example 72

To a solution of 7-amino-3-bromo-2-methyl-5-(methyl sulfonyl) pyrazolo[1,5-a] pyrimidine-6-carbonitrile XXXVI (0.3 g, 0.9 mmol) and (6-(2-aminoethyl) pyridin-2-yl) methanol XLIII (0.2 g, 1 mmol) in isopropyl alcohol (10 mL) was added triethylamine (0.6 mL, 5 mmol) and the reaction mixture was stirred at 130° C. for 36 h. The progress of the reaction was monitored by TLC analysis. After the completion of the reaction, the reaction mixture was cooled to rt, diluted with water (20 mL) and extracted with ethyl acetate (20 mL×3). The combined organic layer was washed with brine (10 mL), dried over anhydrous $Na_2SO_4$, filtered and concentrated under reduced pressure. The crude compound purified by silica gel (230-400 mesh) column chromatography using ethyl acetate in n-hexane (0-50%) to afford the desired compound Example 72 as an off-white solid. Yield: 21.6 mg, (5.0%); LCMS Calculated. for $C_6H_{16}BrN_7O$ is 401.06; Observed. 402.1 $[M+H]^+$. $^1H$ NMR (400 MHz, DMSO-$D_6$): δ 8.39 (s, 2H), 7.73 (t, J=8.0 Hz, 1H), 7.32 (d, J=8.0 Hz, 1H), 7.21-7.17 (m, 2H), 5.36 (t, J=4.0 Hz, 1H), 4.58 (d, J=4.0 Hz, 2H), 3.69 (d, J=4.0 Hz, 2H), 3.02 (t, J=6.4 Hz, 2H), 2.27 (s, 3H). HPLC: 95.94%.

Example 73: 7-amino-3-chloro-5-((2-(1-(1-(hydroxymethyl) cyclopropyl)-1H-pyrazol-4-yl) ethyl) amino)-2-methylpyrazolo[1,5-a] pyrimidine-6-carbonitrile

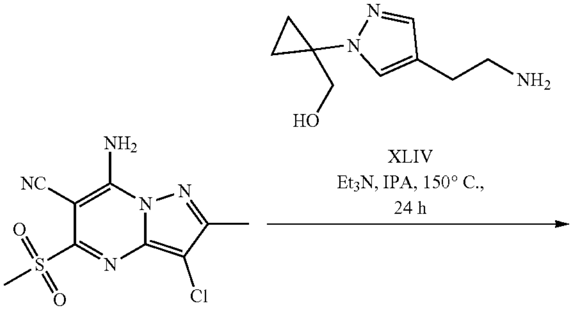

XX

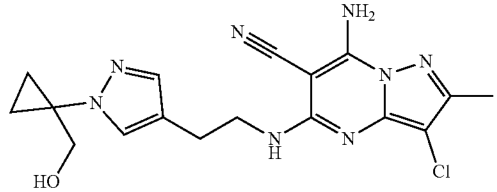

Example 73

To a solution of 7-amino-3-chloro-2-methyl-5-(methyl sulfonyl) pyrazolo[1,5-a] pyrimidine-6-carbonitrile XX (0.2 g, 0.7 mmol) in isopropanol (5 mL) was added (1-(4-(2-aminoethyl)-1H-pyrazol-1-yl)cyclopropyl)methanol XLIV (0.4 g, 2 mmol). The mixture was purged with $N_2$ gas for 5 min and triethylamine (0.5 mL, 4 mmol) was added. The reaction mixture in seal tube was heated at 150° C. for 24 h. The progress of the reaction was monitored by TLC analysis. After completion, the reaction was cooled to room temperature and the reaction mixture was concentrated under reduced pressure. The residue was dissolved in water (20 mL) and extracted with ethyl acetate (20 mL×2). The combined organic layer was given brine wash, dried over anhydrous sodium sulphate, and concentrated under vacuum to afford a light brown viscous liquid. The crude compound was purified by combi-flash silica gel (230-400) column chromatography using 10-60% ethyl acetate in n-hexane to afford the desired compound Example 73 as an off-white solid. Yield: 33 mg (11%). LC_MS Calc. for $C_{17}H_{19}ClN_8O$ is 386.13; Obs. 387.20 $[M+H]^+$; $^1H$ NMR (400 MHz, DMSO-$D_6$): 8.38 (bs, 2H), 7.57 (s, 1H), 7.29 (s, 1H), 7.01 (bs, 1H), 4.89 (bs, 1H), 3.59 (d, J=5.6 Hz, 2H), 3.51-3.45 (m, 2H), 2.69 (bs, 2H), 2.28 (s, 3H), 1.04 (bs, 2H), 0.97 (bs, 2H). HPLC: 99.30%, 8.430 min;)(Bridge C18 (4.6*150) mm, 5μ, Mobile Phase A: 10 mM ammonium bicarbonate in water, Mobile Phase B: Acetonitrile.

Example 74: 7-amino-3-(cyclopropyl methyl)-5-((2-(1-(1-(hydroxymethyl) cyclopropyl)-1H-pyrazol-3-yl) ethyl) amino)-2-methylpyrazolo[1,5-a]pyrimidine-6-carbonitrile

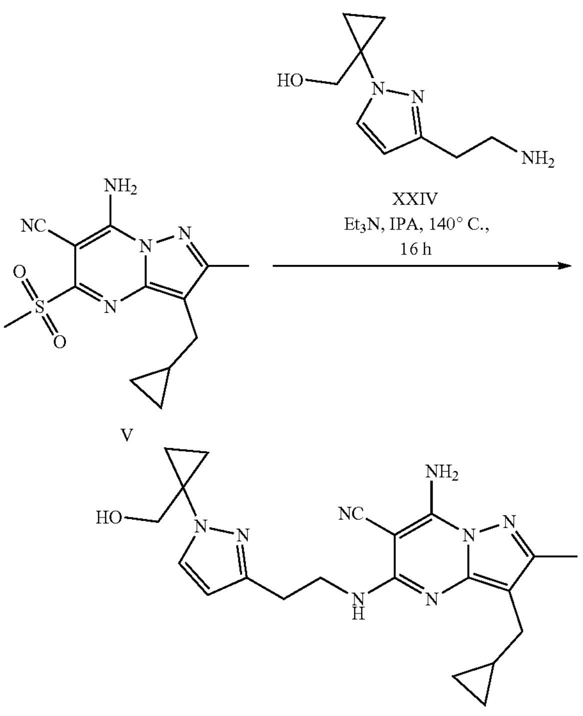

Example 74

To a solution of 7-amino-3-(cyclopropyl methyl)-2-methyl-5-(methyl sulfonyl) pyrazolo[1,5-a] pyrimidine-6-carbonitrile V (0.2 g, 0.7 mmol) and (1-(3-(2-aminoethyl)-1H-pyrazol-1-yl)cyclopropyl)methanol XXIV (0.2 g, 1 mmol) in isopropyl alcohol (10 mL) was added triethylamine (0.5 mL, 4 mmol) and the reaction mixture was stirred at 140° C. for 16 h. The progress of the reaction was monitored by TLC analysis. After the completion of the reaction, the reaction mixture was concentrated, added water (20 mL) and extracted with ethyl acetate (25 mL×3). The combined organic layer was washed with brine (25 mL), dried over anhydrous sodium sulphate, and concentrated under reduced pressure to get the crude material. The crude compound was purified by reverse phase preparative HPLC method by using Column: Inertsil (20×250 mm), 5mic. Channel A: 0.1% Formic acid in $H_2O$. Channel B: Acetonitrile: Methanol: 1:1 to afford the desired compound Example 74 as an off-white solid. Yield:0.063 g, (20.0%); LC_MS Calculated. for $C_{21}H_{26}N_8O$ is 406.22; Observed: 407.25 $[M+H]^+$. $^1H$ NMR (400 MHz, DMSO-$D_6$): δ 8.11 (s, 2H), 7.62 (s, 1H), 6.63 (bs, 1H), 6.03 (s, 1H), 4.88 (t, J=5.6 Hz, 1H), 3.6-3.53 (m, 4H), 2.81 (t, J=7.2 Hz, 2H), 2.39 (d, J=6.4 Hz, 2H), 2.27 (s, 3H), 1.08 (s, 2H), 0.96 (s, 3H), 0.35 (d, J=7.6 Hz, 2H), 0.17 (d, J=4.4 Hz, 2H). HPLC: 98.50%, 11.831 min; Column: INT ODS 3V-C18 (4.6*250) mm, 5μ; Mobile phase A: 0.1% Formic acid in water; Mobile phase B: Acetonitrile; Flow: 1.0 mL/min Example 75: 7-amino-3-chloro-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile

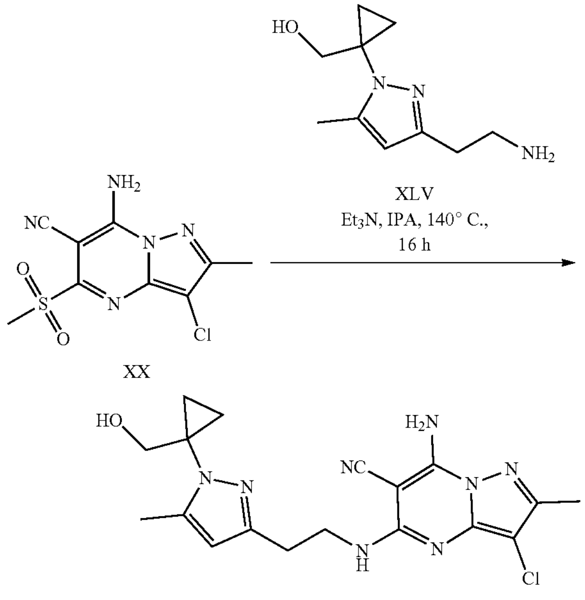

Example 75

A seal tube was charged with 7-amino-3-chloro-2-methyl-5-(methyl sulfonyl) pyrazolo[1,5-a] pyrimidine-6-carbonitrile XX (160 mg, 0.560 mmol), (1-(3-(2-aminoethyl)-5-methyl-1H-pyrazol-1-yl) cyclopropyl) methanol XLV (186 mg, 0.952 mmol) and 2-propanol (25 mL). The resulting mixture was purged with $N_2$ gas for 5 min and triethyl amine (0.47 mL, 3.36 mmol) was added. The reaction mixture was stirred at 140° C. for 16 h. The progress of reaction was monitored by TLC analysis. After completion, water (20 mL) was added, and the resulting mixture was extracted with ethyl acetate (20 mL×3). The combined organic layer was given brine wash, dried over anhydrous sodium sulphate, and concentrated to get crude material. The crude was purified by Combi-flash silica gel (230-400 mesh) column chromatography using 10-60% ethyl acetate in n-hexane to afford the desired compound Example 75 as an off-white solid. Yield: (30 mg, 13.39%); LC-MS Calculated. for $C_{18}H_{21}ClN_8O$ is 400.15; Observed: 401.20 $[M+H]^+$. $^1H$ NMR (400 MHz, DMSO-$d_6$): δ 8.39 (s, 2H), 6.91 (bs, 1H), 5.84 (s, 1H), 4.90 (bs, 1H), 3.58-3.53 (m, 4H), 2.74 (t, J=7.2 Hz, 2H), 2.30-2.26 (m, 6H), 1.03 (d, J=9.2 Hz, 4H); HPLC: 10.892 min; 97.34%, INT ODS 3V-C18 (4.6*250) mm, 5μ, Mobile Phase A: 0.1% Formic acid in water, Mobile Phase B: Acetonitrile: Flow: 1.0 mL/min Example 76: 7-amino-3-ethyl-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile

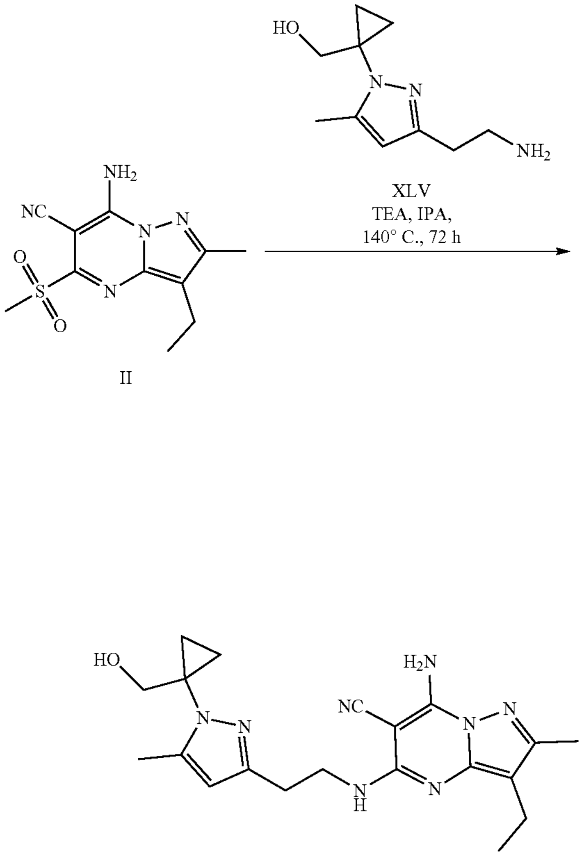

II

Example 76

A seal tube was charged with 7-amino-3-ethyl-2-methyl-5-(methyl sulfonyl) pyrazolo[1,5-a] pyrimidine-6-carbonitrile II (170 mg, 0.609 mmol), (1-(3-(2-aminoethyl)-5-methyl-1H-pyrazol-1-yl) cyclopropyl) methanol XLV (185 mg, 0.947 mmol) and 2-propanol (20 mL). The resulting mixture was purged with $N_2$ gas with vigorous stirring and triethyl amine (0.51 mL, 3.65 mmol) was added. The reaction mixture was stirred at 140° C. for 3 days and progress of the reaction was monitored by TLC analysis. After completion, the reaction was cooled to rt, and water (20 mL) was added. The mixture was extracted with ethyl acetate (15 mL×3). The combined organic layer was given brine wash and dried over anhydrous sodium sulphate. The crude material obtained upon removal of the solvent under vacuo was subjected to flash chromatography using Biotage system and 0-4% methanol in DCM as elluent to afford the desired compound Example 76 as an off-white solid. Yield: (70 mg, 29%); LC-MS Calculated for $C_{20}H_{26}N_8O$ is 394.22; Observed: 395.25 $[M^{+}+1]$. $^1$HNMR (400 MHz, DMSO-$d_6$): δ 8.09 (bs, 2H), 6.56 (bs, 1H), 5.82 (s, 1H), 4.89 (t, J=5.6 Hz, 1H), 3.54-3.51 (m, 4H), 2.73 (d, J=6.4, 2H), 2.33-2.25 (m, 6H), 1.13-1.02 (m, 7H). HPLC purity: 11.193 min; 98.87%, INT ODS 3V-C18 (4.6*250) mm, 5μ, Mobile Phase A: 0.1% Formic acid in water, Mobile Phase B: Acetonitrile.

Example 77: Racemic (+−)-7-amino-3-ethyl-5-((2-(1-(2-(hydroxymethyl) cyclobutyl)-1H-pyrazol-3-yl) ethyl) amino)-2-methylpyrazolo[1,5-a]pyrimidine-6-carbonitrile Example 78. (+)-7-amino-3-ethyl-5-((2-(1-(2-(hydroxymethyl)cyclobutyl)-1H-pyrazol-3-yl)ethyl) amino)-2-methylpyrazolo[1,5-a]pyrimidine-6-carbonitrile Example 79: (−)-7-amino-3-ethyl-5-((2-(1-(2-(hydroxymethyl)cyclobutyl)-1H-pyrazol-3-yl)ethyl) amino)-2-methylpyrazolo[1,5-a]pyrimidine-6-carbonitrile

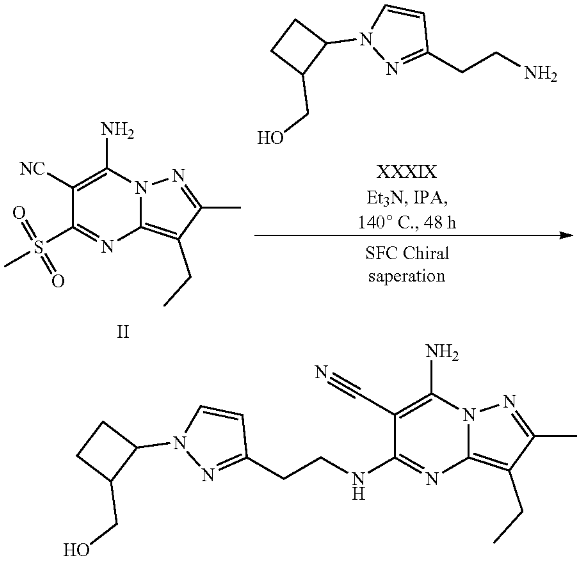

II

Example 77, Racemic (±)
Peak-1; Example 78; dextro(+) rotatory
Peak-1; Example 79; leavo(-) rotatory A stirred solution of 7-amino-3-ethyl-2-methyl-5-(methyl sulfonyl) pyrazolo[1,5-a] pyrimidine-6-carbonitrile II (20.0 g, 71.6 mmol) and (2-(3-(2-aminoethyl)-1H-pyrazol-1-yl) cyclobutyl) methanol XXXIX (28.0 g, 143 mmol) in 2-propanol (50 mL), was added triethylamine (60.0 mL, 430 mmol). The resulting reaction mixture was heated in seal tube at 140° C. for 48 h. The progress of the reaction was monitored by TLC analysis. After completion, the reaction mixture was cooled to rt and diluted with water (200 mL) and extracted with ethyl acetate (200 mL×3). The combined organic layer was washed with saturated brine solution (200 mL), dried over anhydrous $Na_2SO_4$, filtered and evaporated under reduced pressure. The crude compound was purified by combi-flash column chromatography (silica 230-400) by eluting with 0-50% ethyl acetate in n-hexane to afford the desired compound Example 77 as off-white solid. Yield: 13.9 g, (49%). LC-MS Calculated. for $C_{20}H_{26}N_8O$ is 394.22; Observed. 395.35 $[M+H]^+$. $^1$HNMR (400 MHz, DMSO-$D_6$): δ 8.11 (bs, 2H), 7.65 (m, 1H), 6.66 (bs, 1H), 6.07 (m, 1H), 4.60 (t, J=5.2 Hz, 1H), 4.54-4.47 (m, 1H), 3.58-3.57 (m, 2H), 3.42-3.39 (m, 2H), 2.84-2.81 (m, 3H), 2.47-2.41 (m, 2H), 2.34-2.18 (m, 5H), 1.83-1.76 (m, 1), 1.61-1.56 (m, 1H), 1.12 (t, J=7.6 Hz, 3H). HPLC: 11.728 min; 96.66%, Column: Column: INT ODS 3V-C18

(4.6*250) mm, 5μ Mobile phase A: 0.1% Formic acid in water Mobile phase B: Acetonitrile Flow: 1.0 mL/min.

The above racemic compound was subjected to chiral separation by SFC {The sample was dissolved in ~165 mL of Tetrahydrofuran: Methanol (1:1)}, Column Chiral Pak IG (250*21) mm, 5.0 μm; Mobile phase 75:25 (A:B). A=Liquid $CO_2$, B=0.1% Isopropyl amine in Isopropyl alcohol: Acetonitrile (1:1), Flow rate: 25 mL/min; Wavelength 254 nm to yield 6.2 g of peak 1, Example 78, $[\alpha]_D$=+43.15°, c=0.103, MeOH) and 3.9 g of peak 2, Example 79, $[\alpha]_D$=−33.63°, c=0.101, MeOH) as off-white solids, respectively.

Peak-1; Example 78: (+)-7-amino-3-ethyl-5-((2-(1-(2-(hydroxymethyl) cyclobutyl)-1H-pyrazol-3-yl) ethyl) amino)-2-methylpyrazolo[1,5-a]pyrimidine-6-carbonitrile, LCMS: Calculated. for $C_{20}H_{26}N_8O$ is 394.22; Observed. 395.35 $[M+H]^+$. $^1H$ NMR (400 MHz, DMSO-$D_6$): δ 8.10 (bs, 2H), 7.65-7.64 (m, 1H), 6.66-6.63 (m, 1H), 6.06 (m, 1H), 4.59 (m, 1H), 4.53-4.47 (m, 1H), 3.60-3.55 (m, 2H), 3.40 (m, 2H), 2.84-2.81 (m, 3H), 2.46-2.43 (m, 2H), 2.34-2.18 (m, 5H), 1.82-1.75 (m, 1H), 1.63-1.56 (m, 1H), 1.12 (t, J=7.6 Hz, 3H). HPLC: 11.711 min; 99.76%, Column: INT ODS 3V-C18 (4.6*250) mm, 5μ; Mobile phase A: 0.1% Formic acid in water Mobile phase B: Acetonitrile; Flow: 1.0 mL/min. Chiral HPLC; Column Name: Chiral Pak IG (4.6*250 mm), 5 μm; Co-Solvent Name: IPA:MeCN (1:1)+0.1% TEA; Total flow rate: 3 g/mL; % of Co-Solvent: 30; Temperature: 25° C., Back Pressure: 1500 psi.

Peak-2; Example 79; (−)-7-amino-3-ethyl-5-((2-(1-(2-(hydroxymethyl) cyclobutyl)-1H-pyrazol-3-yl) ethyl) amino)-2-methylpyrazolo[1,5-a] pyrimidine-6-carbonitrile, LC-MS Calculated: for $C_{20}H_{26}N_8O$ is 394.22; Observed: 395.35 $[M+1]^+$. $^1H$ NMR (400 MHz, DMSO-$D_6$): δ 8.10 (bs, 2H), 7.64 (m, 1H), 6.65-6.64 (bs, 1H), 6.06 (m, 1H), 4.60-4.58 (m, 1H), 4.53-4.47 (m, 1H), 3.60-3.55 (m, 2H), 3.41-3.37 (m, 2H), 2.84-2.79 (m, 3H), 2.47-2.43 (m, 2H), 2.34-2.18 (m, 5H), 1.80-1.76 (m, 1), 1.60-1.56 (m, 1H), 1.12 (t, J=7.6 Hz, 3H). HPLC: 11.721 min; 98.87%, Column: Column: INT ODS 3V-C18 (4.6*250) mm, 5μ Mobile phase A: 0.1% Formic acid in water Mobile phase B: Acetonitrile Flow: 1.0 mL/min; Chiral HPLC; Method information: Column Name: chiral Pak IG (4.6*250 mm), 5 μm; Co-Solvent Name: IPA:MeCN (1:1)+0.1% TEA; Total flow rate: 3 g/mL % of Co-Solvent: 30% Temperature: 25° C., ABPR Pressure: 1500 psi.

Example 80: 7-amino-3-ethyl-5-((2-(1-(1-(hydroxymethyl) cyclopropyl)-5-methyl-1H-pyrazol-3-yl) ethyl) amino) pyrazolo[1,5-a]pyrimidine-6-carbonitrile

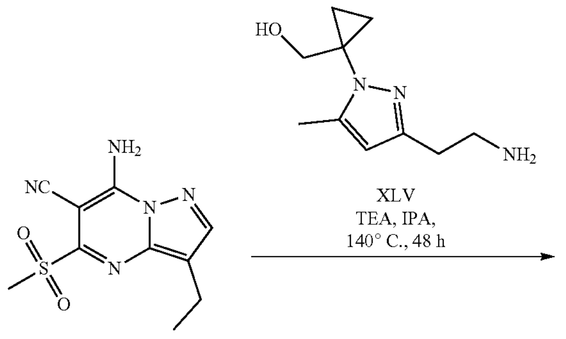

XLII

-continued

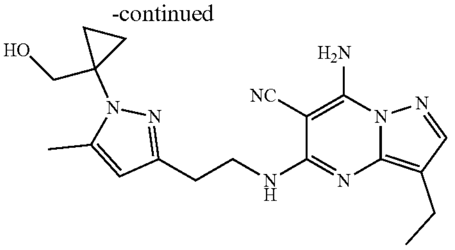

Example 80

To a stirred solution of 7-amino-3-ethyl-5-(methyl sulfonyl) pyrazolo[1,5-a] pyrimidine-6-carbonitrile XLII (150 mg, 0.565 mmol) and (1-(3-(2-aminoethyl)-5-methyl-1H-pyrazol-1-yl) cyclopropyl) methanol XLV (221 mg, 1.13 mmol) in 2-propanol (5 mL) was added triethylamine (0.474 mL, 3.39 mmol). The resulting mixture was purged with $N_2$ gas, and heated at 140° C. for 48 h. The progress of the reaction was monitored by TLC analysis. After completion, the reaction mixture was diluted with water (100 mL) and extracted with ethyl acetate (100 mL×3). The organic layer was dried over anhydrous $Na_2SO_4$, filtered and concentrated under reduced pressure. The crude was purified by combi flash silica gel (230-400 mesh) column chromatography using 0-3% MeOH in DCM to afford the desired compound Example 80 as off-white solid. Yield: (38 mg, 17.67%); LCMS Calculated. for $C_{19}H_{24}N_8O$ is 380.21; Observed: 381.35 $[M^{+}+1]$. $^1$HNMR (400 MHz, DMSO-$d_6$): δ 8.23 (bs, 2H), 7.82 (s, 1H), 6.64 (t, J=5.2 Hz, 1H), 5.82 (s, 1H), 4.90 (t, J=6.0 Hz, 1H), 3.58-3.51 (m, 4H), 2.74 (t, J=7.2 Hz, 2H), 2.30 (s, 3H), 1.19 (t, J=7.6 Hz, 3H), 1.03 (d, J=8.8 Hz, 4H). HPLC: 8.84 min; 98.79%, INT ODS 3V-C18 (4.6*250) mm, 5μ, Mobile Phase A: 0.1% Formic acid in water, Mobile Phase B: Acetonitrile

Example 81: 7-amino-3-ethyl-5-((2-(1-(1-hydroxypropan-2-yl)-1H-pyrazol-3-yl)ethyl)amino)-2-methylpyrazolo[1,5-a]pyrimidine-6-carbonitrile

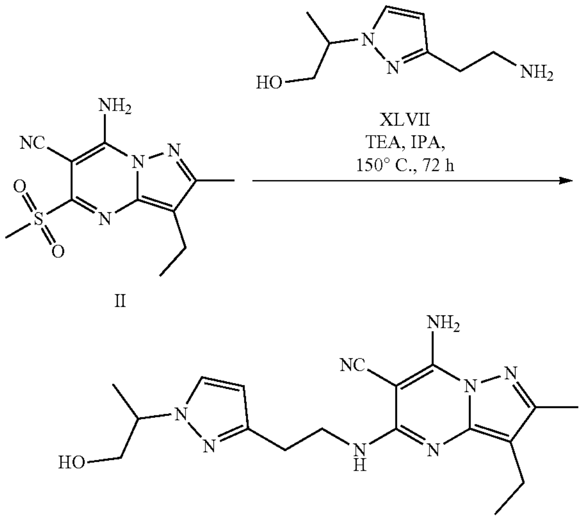

II

Example 81

In a seal tube 7-amino-3-ethyl-2-methyl-5-(methyl sulfonyl) pyrazolo[1,5-a] pyrimidine-6-carbonitrile II (120 mg, 430 μmol) and 2-(3-(2-aminoethyl)-1H-pyrazol-1-yl) propan-1-ol XLVII (109 mg, 644 μmol) were dissolved in isopropanol (15 mL) under inert atmosphere. To the reaction was added TEA (0.36 mL, 2.58 mmol) was added and the reaction mixture was stirred at 150° C. for 72 h. The progress of reaction was monitored by TLC analysis. After completion, the reaction mixture was cooled to rt and concentrated under reduced pressure. The crude material subjected to silica gel (230-400) flash column chromatography (Biotage) using 0-3% methanol in DCM to afford the desired compound Example 81 as off-white solid. Yield: 30 mg (18.9%). LC-MS Calculated. for $C_{18}H_{24}N_8O$ is 368.20; Observed.: 369.40 $[M+H]^+$. $^1H$ NMR (400 MHz, DMSO-$D_6$): δ 8.10 (bs, 2H), 7.60 (bs, 1H), 6.65 (bs, 1H), 6.05 (d, J=1.6 Hz, 1H), 4.84 (t, J=5.2 Hz, 1H), 4.26 (q, J=6.0 Hz, 1H), 3.67-3.55 (m, 4H), 2.82 (t, J=7.2 Hz, 2H), 2.47-2.45 (m, 2H), 2.25 (s, 3H), 1.36 (d, J=7.2 Hz, 3H) 1.12 (t, J=7.6 Hz, 3H). HPLC: 11.091 min; 97.12%, INT ODS 3V-C18 (4.6*250) mm, 5μ; Mobile Phase A: 0.1% Formic acid in water, Mobile Phase B: Acetonitrile; Racemic compound: Chiral HPLC: Peak-1: 18.077 min; 50.27%, Peak-2: 20.226 min; 49.73%; Column: Chiral Pak Iowa (250*4.6) mm, 5μ; Mobile phase: 0.1% TFA in Hex, B: IPA (90:10) Flow: 1.0 mL/min.

Example 82: (+−)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile Example 83: (+)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile Example 84: (−)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile

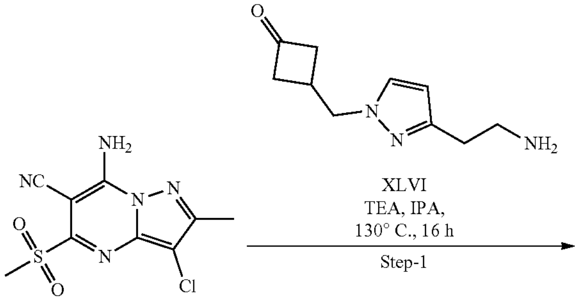

XX

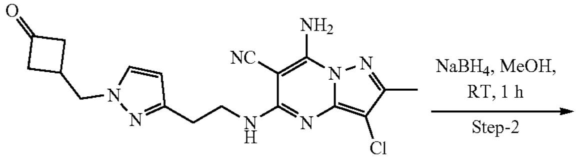

Example 82a

-continued

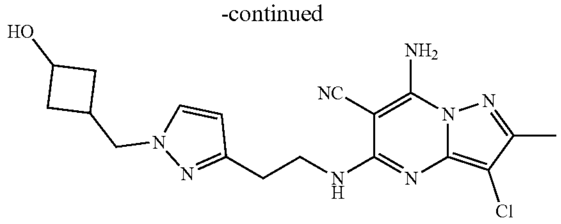

Example 82: Racemic
Example 83: Peak-1; dextro(+) rotatoty
Example 84: Peak-2; leavo(-) rotatoty Step-1: 7-amino-3-chloro-2-methyl-5-((2-(1-((3-oxocyclobutyl) methyl)-1H-pyrazol-3-yl) ethyl) amino) pyrazolo[1,5-a] pyrimidine-6-carbonitrile (Example 82a)

To a stirred solution of 7-amino-3-chloro-2-methyl-5-(methyl sulfonyl) pyrazolo[1,5-a] pyrimidine-6-carbonitrile XX (0.5 g, 2 mmol) and 3-((3-(2-aminoethyl)-1H-pyrazol-1-yl) methyl) cyclobutan-1-one XLVI (0.8 g, 4 mmol) in IPA (10 mL), in sealed tube, was added TEA (1.4 mL, 10 mmol). The reaction was stirred at 130° C. for 16 h and progress of the reaction was monitored by TLC analysis. After completion, the reaction mixture was cooled to rt and diluted with water (20 mL). The resulting mixture was extracted with ethyl acetate (20 mL×3). The combined organic layer was washed with brine, dried over anhydrous $Na_2SO_4$, filtered, and concentrated under reduced pressure. The crude compound was subjected to silica gel (230-400) combi-flash column chromatography using 0-3% methanol in DCM to afford the desired compound Example 82a as a pale-yellow solid. Yield: 0.3 g crude (43%).

Step-2: 7-amino-3-chloro-5-((2-(1-((3-hydroxycyclobutyl) methyl)-1H-pyrazol-3-yl) ethyl) amino)-2-methylpyrazolo[1,5-a] pyrimidine-6-carbonitrile (82)

To a stirred solution of 7-amino-3-chloro-2-methyl-5-((2-(1-((3-oxocyclobutyl) methyl)-1H-pyrazol-3-yl) ethyl) amino) pyrazolo[1,5-a] pyrimidine-6-carbonitrile Example 82a (0.3 g, 0.8 mmol) in methanol (5 mL) was added sodium borohydride (0.01 g, 0.4 mmol) in portions at 0° C. The resulting reaction mixture was stirred at rt for 1 h. The reaction was monitored by TLC analysis. After completion, the reaction mixture concentrated under vacuo and the residue was dissolved in water (15 mL). The mixture was extracted with DCM (10 mL×3). Combined organic layer was dried over anhydrous $Na_2SO_4$, filtered and concentrated under reduced pressure. The crude compound was purified by combi-flash column chromatography (230-400) using 0-10% methanol in DCM to afford the racemic compound Example 82 as off-white solid. Yield: 21 mg, (29%).

The above racemic compound was subjected to chiral separation by chiral HPLC separation (Chiral Pak IC (250*21) mm, 5μ Mobile phase A: 0.1% DEA In Hex, B: EtOH (90:10) Flow: 1.0 mL/min) to yield 6.2 g of peak 1 $[\alpha]_D$=+43.15°, c=0.103, MeOH) and 3.9 g of peak 2 $[\alpha]_D$=−33.63°, c=0.101, MeOH) as off-white solids, respectively.

Example 83a: Peak-1 Yield: 51 mg, (40%); LCMS Calculated. for $C_{18}H_{21}ClN_8O$ is 400.87; Observed. 401.30 $[M+H]^+$. $^1H$ NMR (400 MHz, DMSO-$D_6$): δ 8.39 (bs, 2H), 7.56 (d, J=2.0 Hz, 1H), 7.01-6.99 (bs, 1H), 6.06 (d, J=2.0 Hz, 1H), 4.98 (d, J=6.4 Hz, 1H), 4.02 (d, J=6.8 Hz, 2H), 3.93-3.88 (m, 1H), 3.62-3.57 (m, 2H), 2.80 (t, J=7.2 Hz, 2H), 2.28 (s, 3H), 2.20-2.10 (m, 3H), 1.58-1.54 (m, 2H). HPLC: 10.906 min; 99.15%, Column: Column: INT ODS 3V-C18 (4.6*250) mm, 5μ Mobile phase A: 0.1% Formic acid in water Mobile phase B: Acetonitrile Flow: 1.0 ml/min. Chiral HPLC; 19.597 min; 100%, Column: Chiral Pak IC (250*4.6) mm, 5μ, Mobile phase: A: 0.1% DEA in Hex, B: EtOH (90:10) Flow: 1.0 mL/min.

Example 84: Peak-2; Yield: 16 mg, (20%); LC_MS Calculated. for $C_{18}H_{21}ClN_8O$ is 400.87; Observed. 401.35 $[M+H]^+$. $^1H$ NMR (400 MHz, DMSO-$D_6$): δ 8.39 (bs, 2H), 7.62 (d, J=2.0 Hz, 1H), 7.01 (t, J=5.2 Hz, 1H), 6.07 (d, J=1.6 Hz, 1H), 4.97 (d, J=6.0 Hz, 1H), 4.21-4.16 (m, 1H), 4.06 (d, J=7.6 Hz, 2H), 3.62-3.57 (m, 2H), 2.82 (t, J=7.2 Hz, 2H), 2.28 (s, 3H), 2.01-1.99 (m, 2H), 1.91-1.84 (m, 2H). HPLC: 10.912 min; 98.65%, INT ODS 3V-C18 (4.6*250) mm, 5μ Mobile phase A: 0.1% Formic acid in water Mobile phase B: Acetonitrile; Flow: 1.0 mL/min. Chiral HPLC; 22.356 min; 95.90%; Chiral Pak IC (250*4.6) mm, 5μ; Mobile phase: A: 0.1% DEA In Hex, B: EtOH (90:10) Flow: 1.0 mL/min.

Example 85: 7-amino-3-ethyl-5-((2-(1-((3-hydroxy-cyclobutyl) methyl)-1H-pyrazol-3-yl) ethyl) amino)-2-methylpyrazolo[1,5-a] pyrimidine-6-carbonitrile

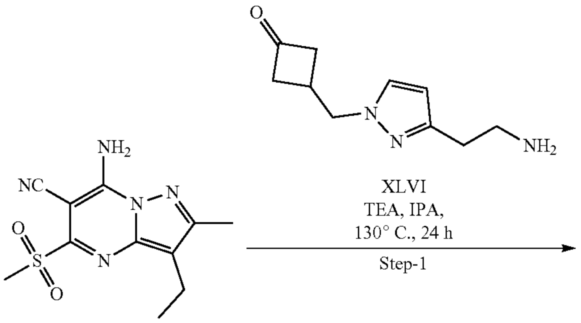

II

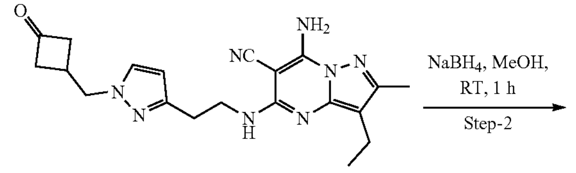

Example 85a

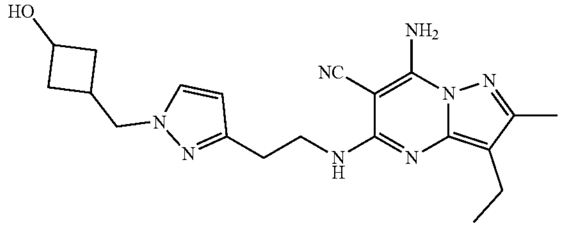

Example 85

Step-1: 7-amino-3-ethyl-2-methyl-5-((2-(1-((3-oxo-cyclobutyl) methyl)-1H-pyrazol-3-yl) ethyl) amino) pyrazolo[1,5-a] pyrimidine-6-carbonitrile (Example 85a)

To a stirred solution of 7-amino-3-ethyl-2-methyl-5-(methyl sulfonyl) pyrazolo[1,5-a] pyrimidine-6-carbonitrile II (0.5 g, 2 mmol) and 3-((3-(2-aminoethyl)-1H-pyrazol-1-yl) methyl) cyclobutan-1-one XLVI (0.8 g, 4 mmol) in IPA (10 mL), in sealed tube, was added TEA (1.4 mL, 10 mmol). The reaction mixture was stirred at 130° C. for 24 h. The progress of the reaction was monitored by TLC analysis. After completion, the reaction mixture was cooled to rt and diluted with water (20 mL). The mixture was extracted with ethyl acetate (20 mL×3). The combined organic layer was washed with brine, dried over anhydrous $Na_2SO_4$, filtered, and concentrated under reduced pressure. The crude compound was purified by combi-flash column chromatography (230-400) using 0-10% methanol in DCM to afford the desired compound Example 85a as an off-white solid. Yield: 273 mg, (39%); LC_MS Calculated. for $C_{20}H_{24}N_8O$ is 392.20; Obs. 393.35 $[M+H]^+$.

Step-2: 7-amino-3-ethyl-5-((2-(1-((3-hydroxycy-clobutyl) methyl)-1H-pyrazol-3-yl) ethyl)amino)-2-methylpyrazolo[1,5-a]pyrimidine-6-carbonitrile To a stirred solution of 7-amino-3-ethyl-2-methyl-5-((2-(1-((3-oxocyclobutyl) methyl)-1H-pyrazol-3-yl) ethyl) amino)pyrazolo[1,5-a] pyrimidine-6-carbonitrile Example 85a (0.270 g, 0.688 mmol) in methanol (5 mL) was portion wise added sodium borohydride (13.0 mg, 0.344 mmol) at 0° C. under inert atmosphere. The reaction was stirred at rt for 1 h and progress of the reaction was monitored by TLC analysis. After completion, the reaction mixture was concentrated under vacuum and the residue was diluted with water (15 mL). The mixture was extracted with DCM (10 mL×3) and the combined organic layer was dried over anhydrous $Na_2SO_4$. The solution was concentrated under reduced pressure. The crude compound was purified by combi-flash column chromatography (230-400) using 0-10% methanol in DCM to afford the desired title compound Example 85 as off-white solid. Yield: 23 mg, (19%). LC_MS Calculated. for $C_{20}H_{26}N_8O$ is 394.22; Observed. 395.40 $[M+H]^+$. $^1H$ NMR (400 MHz, DMSO-$D_6$): δ 8.10 (bs, 2H), 7.61-7.55 (m 1H), 6.66-6.62 (m, 1H), 6.05 (s, 1H), 4.98 (t, J=6.4 Hz, 1H), 4.07-4.00 (m, 2H), 3.91-3.88 (m, 1H), 3.59-3.54 (m, 2H), 2.81 (t, J=7.2 Hz, 2H), 2.46-2.43 (m, 2H), 2.24 (s, 3H), 2.20-2.10 (m, 3H), 1.92-1.88 (m, 1H), 1.58-1.54 (m, 1H), 1.12 (t, J=7.2 Hz, 3H). HPLC: 11.054 min; 96.42%; INT ODS 3V-C18 (4.6*250) mm, 5μ; Mobile phase A: 0.1% Formic acid in water Mobile phase B: Acetonitrile; Flow: 1.0 mL/min.

Example 86: 7-amino-5-((2-(1-(1-(hydroxy methyl) cyclopropyl)-5-methyl-1H-pyrazol-3-yl) ethyl) amino)-2,3-dimethylpyrazolo[1,5-a]pyrimidine-6-carbonitrile

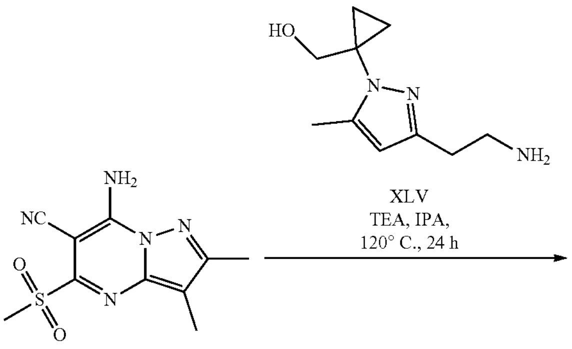

I

-continued

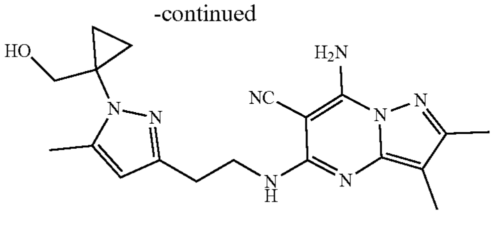

Example 86

To a stirred solution of 7-amino-2,3-dimethyl-5-(methyl sulfonyl) pyrazolo[1,5-a] pyrimidine-6-carbonitrile I (136 mg, 0.512 mmol) and (1-(3-(2-aminoethyl)-5-methyl-1H-pyrazol-1-yl) cyclopropyl) methanol XLV (200 mg, 1.02 mmol) in 2-propanol (5 mL) was added triethylamine (0.429 mL, 3.07 mmol) under inert atmosphere. The reaction mixture in seal tube was heated at 120° C. for 24 h. The progress of the reaction was monitored by TLC analysis. After completion, the reaction was cooled to room temperature and diluted with water (50 ml). The resulting mixture was extracted with ethyl acetate (50 mL×3). The combined organic layer was dried over anhydrous $Na_2SO_4$, filtered, and concentrated under reduced pressure. The crude was purified by flash column chromatography using 0-3% methanol in DCM to afford the compound Example 86 as off-white solid. Yield: 25 mg, (12.8%); LCMS Calculated. for $C_{19}H_{24}N_8O$ is 380.20; Observed. 381.35 $[M+H]^+$. $^1H$ NMR (400 MHz, DMSO-$D_6$): δ 8.10 (bs, 2H), 6.55 (t, J=5.2, 1H), 5.83 (s, 1H), 4.90 (t, J=6.0 Hz, 1H), 3.58-3.51 (m, 4H), 2.73 (t, J=7.2 Hz, 2H), 2.29 (s, 3H), 2.22 (s, 3H), 1.96 (s, 3H), 1.07-0.99 (m, 4H). HPLC: 10.03 min; 98.06%, Column: INT ODS 3V-C18 (4.6×250) mm, 5μ; 0.1% Formic acid in water: Mobile Phase B: Acetonitrile.

Example 87: 7-amino-3-chloro-2-methyl-5-((2-(1-methyl-2-oxo-1,2-dihydropyridin 3-yl) ethyl) amino) pyrazolo[1,5-a]pyrimidine-6-carbonitrile

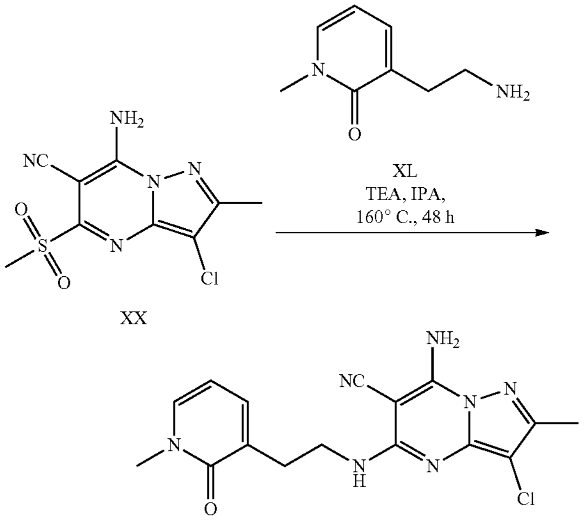

XX

Example 87

To a stirred solution of 7-amino-3-chloro-2-methyl-5-(methyl sulfonyl) pyrazolo[1,5-a] pyrimidine-6-carbonitrile XX (150 mg, 0.525 mmol) in isopropanol (5 mL) were added 3-(2-aminoethyl)-1-methylpyridin-2(1H)-one XL (160 mg, 1.05 mmol) and TEA (0.366 mL, 2.63 mmol) in a sealed tube. The resulting reaction mixture was stirred at 160° C. for 48 h. The progress of the reaction was monitored by TLC analysis. After completion the reaction mixture was cooled room temperature and precipitated solid was filtered. The solid was washed with DCM (2 mL) and diethyl ether (2 mL) to afford pure title compound Example 87 as off-white solid. Yield: 60 mg, (30%); LCMS Calculated. for $C_{16}H_{16}ClN_7O$ is 357.11; Observed. 358.25 $[M+H]^+$. $^1H$ NMR (400 MHz, DMSO-$D_6$): δ 8.33 (bs, 2H), 7.57-7.55 (m, 1H), 7.29-7.28 (m, 1H), 7.07 (t, J=5.2 Hz, 1H), 6.14 (t, J=6.8 Hz, 1H), 3.56-3.52 (m, 2H), 3.44 (s, 3H), 2.74-2.73 (m, 2H), 2.27 (s, 3H). HPLC:10.896 min; 98.54%, INT ODS 3V-C18 (4.6×250) mm, 5μ; 0.1% Formic acid in water: Mobile Phase B: Acetonitrile; Flow rate: 1.0 mL/min.

Example 88: 7-amino-3-ethyl-2-methyl-5-((2-(1-methyl-2-oxo-1,2-dihydropyridin-3-yl) ethyl) amino) pyrazolo[1,5-a]pyrimidine-6-carbonitrile

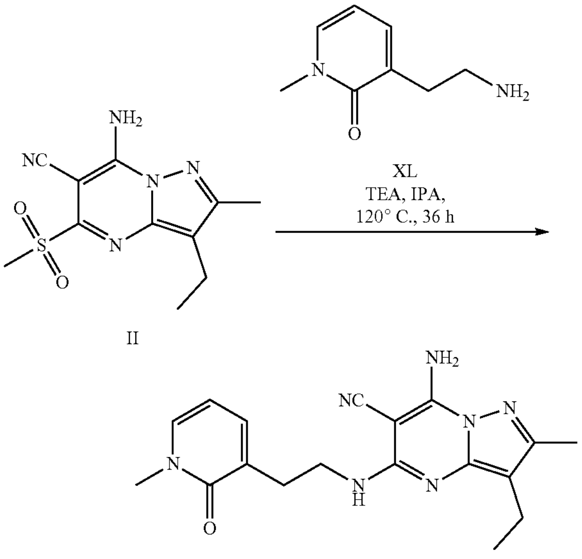

II

Example 88

To a stirred solution of 7-amino-3-ethyl-2-methyl-5-(methyl sulfonyl) pyrazolo[1,5-a] pyrimidine-6-carbonitrile II (150 mg, 0.537 mmol) in IPA (5 mL) were added 3-(2-aminoethyl)-1-methylpyridin-2(1H)-one XL (163 mg, 1.07 mmol) and TEA (0.374 ml, 2.69 mmol) in a sealed tube. The resulting reaction mixture was stirred at 160° C. for 48 hours. The progress of the reaction was monitored by TLC analysis. After completion reaction was cooled to room temperature and diluted with ethyl acetate (20 mL) and water (20 mL) and mixed well. The organic layer was separated, washed with brine, dried over anhydrous sodium sulphate, and concentrated under vacuo to afford light brown viscous liquid. The crude compound was purified by combi-flash (230-400) silica gel column chromatography using ethyl acetate in n-hexane and peak was eluted with 30% ethyl acetate in n-hexane, fraction solvent was concentrated to afford the desired compound Example 88 as an off-white solid. Yield: (84 mg, 42%); LCMS Calculated for $C_{18}H_{21}N_7O$ is 351.18; Observed. 352.30 $[M+1]^+$. $^1H$ NMR (400 MHz, DMSO-$D_6$): δ 8.049 (s, 2H), 7.567-7.546 (m, 1H), 7.271-7.255 (m, 1H), 6.705 (t, J=5.2 Hz, 1H), 6.134 (t, J=6.8 Hz, 1H), 3.541-3.494 (m, 2H), 3.437 (s, 3H), 2.737 (t, J=6.4 Hz, 2H), 2.470-2.433 (m, 2H), 2.239 (s, 3H), 1.106 (t, J=7.2 Hz, 3H). HPLC: 10.312 min; 97.38%. INT ODS 3V-C18 (4.6×250) mm, 5μ; 0.1% Formic acid in water: Mobile Phase B: Acetonitrile.

Example 89: 7-amino-3-bromo-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile

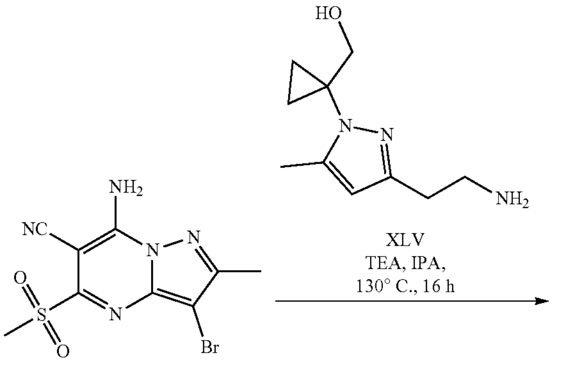

XXXVI

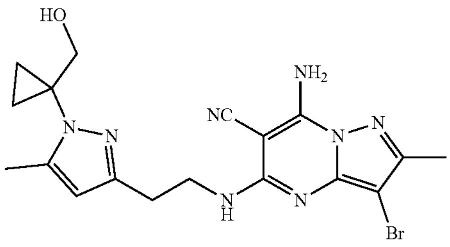

Example 89

To a solution of 7-amino-3-bromo-5-(methyl sulfonyl) pyrazolo[1,5-a] pyrimidine-6-carbonitrile XXXVI (0.5 g, 2 mmol) and (1-(3-(2-aminoethyl)-5-methyl-1H-pyrazol-1-yl) cyclopropyl) methanol XLV (0.6 g, 3 mmol) in 2-propanol (10 mL) was added triethylamine (1 mL, 9.0 mmol) and the reaction mixture was stirred at 130° C. for 16 h. The progress of the reaction was monitored by TLC analysis. After the completion, the reaction mixture was cooled to rt and diluted with water (20 mL) and extracted with ethyl acetate (20 mL×3). The combined organic layer was washed with brine (10 mL), dried over anhydrous $Na_2SO_4$, filtered and concentrated under reduced pressure. The crude compound was purified by silica gel (230-400 mesh) column chromatography using ethyl acetate in n-hexane (0-70%) to afford the desired compound Example 89 as off-white solid. Yield: 40 mg, (5.0%); LCMS Calculated for $C_{17}H_{19}BrN_8O$ is 430.09; Observed: 431.15 $[M+H]^+$. $^1$HNMR (400 MHz, DMSO-$d_6$): δ 8.48 (s, 2H), 8.04 (s, 1H), 6.99 (t, J=5.2 Hz, 1H), 5.85 (s, 1H), 4.90 (t, J=6.0 Hz, 1H), 3.61-3.51 (m, 4H), 2.763-2.670 (m, 2H), 2.31 (d, J=10 Hz, 3H), 1.03 (d, J=8.8 Hz, 4H). HPLC: 10.46 min; 98.55%, INT ODS 3V-C18 (4.6*250) mm, 5μ; Mobile Phase A: 0.1% Formic acid in water, Mobile Phase B: Acetonitrile; Flow: 1.0 mL/min Example 90: 7-amino-3-chloro-5-((2-(6-(((2-hydroxyethyl) amino) methyl) pyridin-2-yl) ethyl) amino)-2-methylpyrazolo[1,5-a]pyrimidine-6-carbonitrile

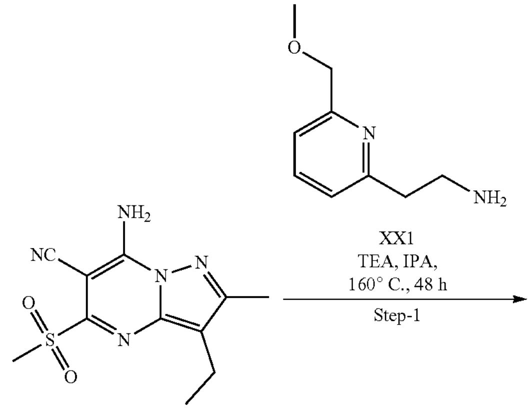

II

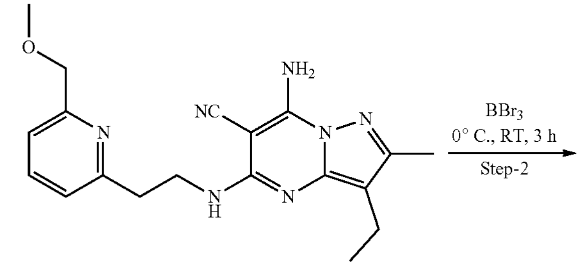

Example 90a

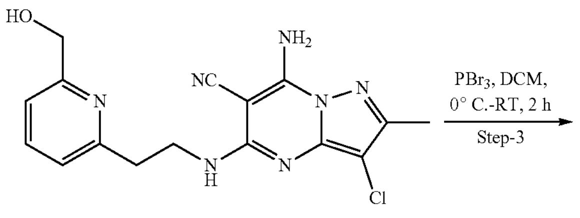

Example 37

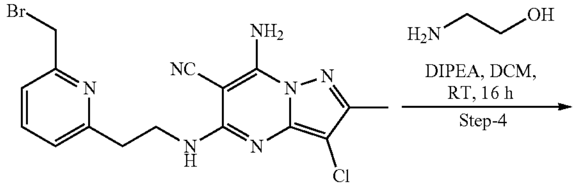

Example 90b

-continued

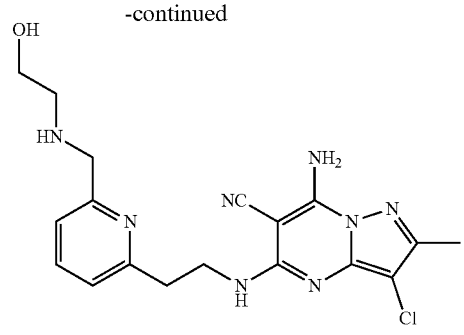

Example 90

Step-1: 7-amino-3-ethyl-5-((2-(6-(methoxymethyl) pyridin-2-yl) ethyl) amino)-2-methylpyrazolo[1,5-a] pyrimidine-6-carbonitrile (Example 90a)

To a stirred solution of 7-amino-3-ethyl-2-methyl-5-(methyl sulfonyl) pyrazolo[1,5-a] pyrimidine-6-carbonitrile II (2.0 g, 7.2 mmol) in isopropanol (40 mL) were added TEA (6.0 mL, 43 mmol) and 2-(6-(methoxymethyl) pyridin-2-yl) ethan-1-amine XXI (3.0 g, 18 mmol) and the reaction mixture was stirred at 160° C. for 48 h. The progress of the reaction was monitored by TLC analysis. After completion, the reaction mixture was concentrated under reduced pressure and the crude material was purified by silica gel (230-400) column chromatography by eluting with 0-40% ethyl acetate in n-hexane to afford the title compound Example 90a as an off-white solid. Yield: 1.3 g (50.0%); LCMS Calculated. for $C_{19}H_{23}N_7O$ is 365.20; Observed. 366.25 $[M+H]^+$; $^1H$ NMR (400 MHz, DMSO-$D_6$): δ 8.11 (bs, 2H), 7.75-7.71 (t, J=8.0 Hz, 1H), 7.26-7.19 (m, 2H), 6.95 (s, 1H), 4.51 (s, 2H), 3.69-3.65 (q, J=6.4 Hz, 2H), 3.36 (s, 3H), 3.04-3.01 (t, J=6.8 Hz, 2H), 2.50-2.43 (q, J=7.6 Hz, 2H), 2.25 (s, 3H), 1.14-1.10 (t, J=7.6 Hz, 3H).

Step-2: 7-amino-3-ethyl-5-((2-(6-(hydroxymethyl) pyridin-2-yl) ethyl) amino)-2-methylpyrazolo[1,5-a] pyrimidine-6-carbonitrile (Example 37)

A stirred solution of 7-amino-3-ethyl-5-((2-(6-(methoxymethyl) pyridin-2-yl) ethyl) amino)-2-methylpyrazolo[1,5-a] pyrimidine-6-carbonitrile Example 90a (1.3 g, 3.6 mmol) in DCM (5 mL) was cooled to 0° C. and dropwise added a solution of $BBr_3$ (0.50 mL, 5.3 mmol) in DCM (3 mL). The reaction was stirred at 0° C. for 3 h. The progress of the reaction was monitored by TLC analysis. After completion, the reaction was quenched by saturated $NaHCO_3$ solution (100 mL). The resulting mixture was extracted with DCM (200 mL×3). The combined organic layer was dried over anhydrous sodium sulphate, filtered, and concentrated under vacuo. The crude compound was purified by silica gel (230-400 mesh) column chromatography using 0-4% MeOH in dichloromethane to afford the desired compound Example 37 as an off-white solid. Yield: 0.53 g (41.0%); LCMS Calculated. for $C_{18}H_{21}N_7O$ is 351.18; Observed. 352.15 $[M+H]^+$; $^1H$ NMR (400 MHz, DMSO-$D_6$): δ 8.11 (bs, 2H), 7.72-7.70 (d, J=7.2 Hz, 1H), 7.33-7.31 (d, J=8.0 Hz, 1H), 7.15-7.13 (d, J=7.6 Hz, 1H), 6.85 (s, 1H), 5.37 (bs, 1H), 4.58-4.57 (d, J=4 Hz, 2H), 3.67-3.63 (t, J=5.6 Hz, 2H), 3.03-2.99 (t, 2H), 2.50-2.43 (q, J=7.6 Hz, 2H), 2.25 (s, 3H), 1.14-1.10 (t, J=7.6 Hz, 3H); HPLC Purity=99.32%) (Bridge C18 (4.6*150) mm, 5μ; Mobile phase A: 0.1% formic acid in $H_2O$, B: acetonitrile; Flow: 1.0 mL/min.

Step-3: 7-amino-5-((2-(6-(bromomethyl) pyridin-2-yl) ethyl) amino)-3-chloro-2-methylpyrazolo[1,5-a] pyrimidine-6-carbonitrile (Example 90b)

To a solution of 7-amino-3-chloro-5-((2-(6-(hydroxymethyl) pyridin-2-yl) ethyl) amino)-2-methylpyrazolo[1,5-a] pyrimidine-6-carbonitrile Example 90a (100 mg, 0.3 mmol) in DCM (2 mL) at 0° C. was added $PBr_3$ (0.03 mL, 0.33 mmol). The reaction mixture was stirred at rt for 2 h. The progress of the reaction was monitored by TLC analysis. After the completion, the reaction mixture was quenched with sat. $NaHCO_3$ solution (50 mL) and extracted with ethyl acetate (50 mL×3). The combined organic layer was dried over anhydrous sodium sulphate and concentrated under reduced pressure. The crude product Example 90b was taken for the next step without any further purification. Yield: 0.1 g, (84.74%); LCMS Calculated. for $C_{16}H_{15}BrClN_7$ is 419.03; Observed. 420.10 $[M+H]^+$.

Step-4: 7-amino-3-chloro-5-((2-(6-(((2-hydroxyethyl) amino) methyl) pyridin-2-yl) ethyl) amino)-2-methylpyrazolo[1,5-a] pyrimidine-6-carbonitrile To a solution of 7-amino-5-((2-(6-(bromomethyl) pyridin-2-yl) ethyl) amino)-3-chloro-2-methylpyrazolo[1,5-a] pyrimidine-6-carbonitrile Example 90b (0.1 g, 0.24 mmol) and 2-aminoethan-1-ol (0.03 g, 0.5 mmol) in DCM (4 mL) was added DIPEA (0.12 mL, 0.71 mmol). The reaction mixture was stirred at rt for 16 hours. The progress of the reaction was monitored by TLC analysis. After the completion of the reaction, the reaction mixture was quenched with water (50 mL) and extracted with ethyl acetate (50 mL×3). The combined organic layer was dried over anhydrous sodium sulphate and concentrated under reduced pressure. The crude compound was purified by PREP-HPLC (0.1% TFA in water: Acetonitrile: methanol (1:1); Inertsil ODS 3V 250*20 mm, 5.0 μm) to afford the desired product Example 90 as a yellow-solid. Yield: 23.1 mg, (24.0%); LC-MS Calculated. for $C_{18}H_{21}ClN_8O$ is 400.15; Observed. 401.25 $[M+H]^+$. $^1H$ NMR (400 MHz, DMSO-$D_6$): δ 8.60-8.00 (bs, 2H), 7.70-7.66 (t, J=8.0 Hz, 1H), 7.28-7.15 (m, 3H), 4.473 (s, 1H), 3.82 (s, 2H), 3.73-3.68 (m, 2H), 3.48-3.38 (d, J=4.8 Hz, 2H), 3.04-3.01 (t, J=6.5 Hz, 2H), 2.62-2.59 (t, J=5.6 Hz, 2H), 2.28 (s, 3H). 1.10-1.06 (m, 1H), 1.06-0.85 (m, 1H). HPLC: 7.944 min; 99.51%, INT ODS 3V-C18 (4.6*250) mm, 5μ, Mobile Phase A: 0.1% Formic acid in water, Mobile Phase B: Acetonitrile; Flow: 1.0 mL/min Example 91: 7-amino-3-ethyl-5-((2-(5-fluoro-6-(hydroxymethyl)$_{315}$yridine-2-yl) ethyl) amino)-2-methylpyrazolo[1,5-a]pyrimidine-6-carbonitrile

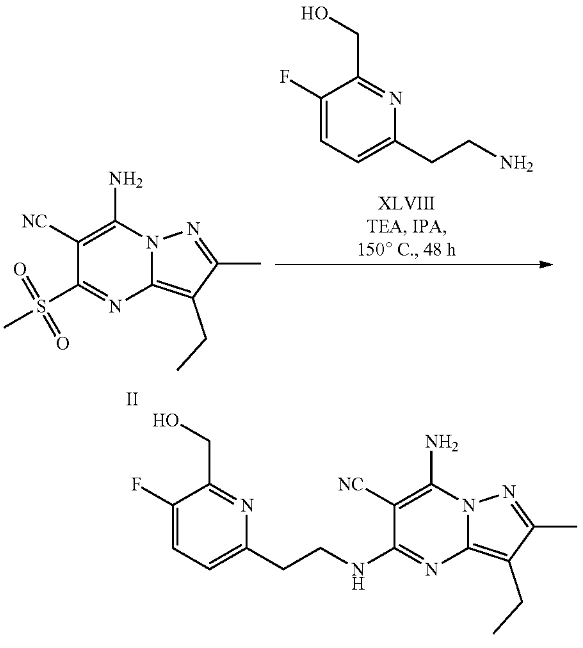

II

Example 91

To a solution of (6-(2-aminoethyl)-3-fluoropyridin-2-yl) methanol XLVIII (0.2 g, 1 mmol) and 7-amino-3-ethyl-2-methyl-5-(methyl sulfonyl) pyrazolo[1,5-a] pyrimidine-6-carbonitrile II (0.2 g, 0.7 mmol) in isopropanol (10 mL) triethylamine (0.3 mL, 2 mmol) was added. The resulting mixture was purged with $N_2$ for 10 min and heated at 150° C. for 48 h. The progress of the reaction was monitored by TLC analysis. After the completion of the reaction, the reaction mixture was cooled to rt and concentrated under reduced pressure. Added water (10 mL) and extracted with ethyl acetate (10 mL*3). The combined organic layer was separated, washed with brine, dried over anhydrous sodium sulphate, and concentrated under reduced pressure to afford the crude as a light brown viscous liquid. The crude compound Example 91 was purified by revered phase prep-HPLC; YMC AQUA ODS (250×20) mm. 5.0 microns. Mobile phase A: 10 mm Ammonium bicarbonate in $H_2O$; Mobile phase B: Acetonitrile: Methanol (1:1). Yield: 18.0 g, (7.0%); LCMS calculated for $C_{18}H_{20}FN_7O$ is 369.17; Observed. 370.25 $[M+H]^+$. $^1H$ NMR (400 MHz, DMSO-$D_6$): δ 7.88 (bs, 1H), 7.60 (t, J=9.6 Hz, 1H), 7.27 (q, J=4.8 Hz, 1H), 6.53 (bs, 1H), 5.22 (bs, 1H), 4.56 (s, 2H), 3.68-3.63 (m, 2H), 3.03 (t, J=6.8 Hz, 2H), 2.47-2.41 (m, 2H), 2.22 (s, 3H), 1.11 (t, J=7.6 Hz, 3H). HPLC: 11.64 min; 96.49%, INT ODS 3V-C18 (4.6*250) mm, 5μ, Mobile Phase A: 0.1% Formic acid in water, Mobile Phase B: Acetonitrile; Flow: 1.0 mL/min Example 92: 7-amino-3-chloro-5-((2-(1-(2-methoxyethyl)-2-oxo-1,2-dihydropyridin-3-yl) ethyl) amino)-2-methylpyrazolo[1,5-a]pyrimidine-6-carbonitrile

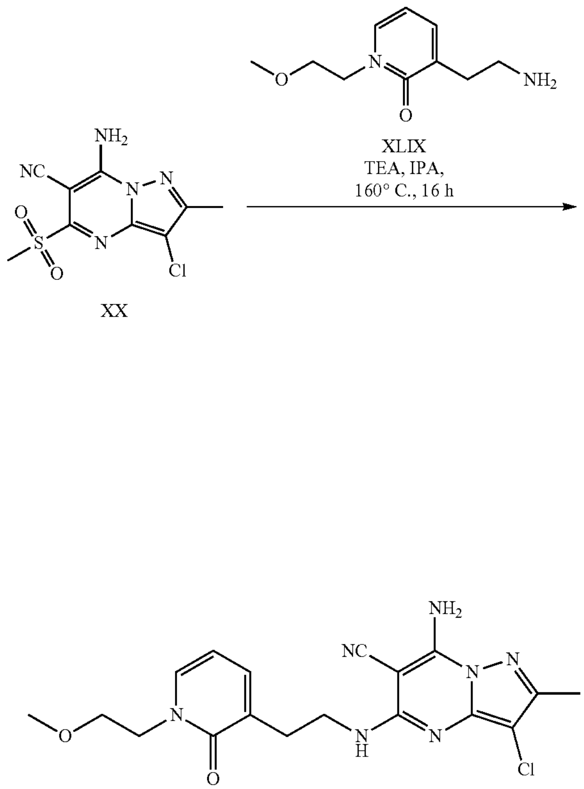

XX

Example 92

To a stirred solution of 7-amino-3-chloro-2-methyl-5-(methyl sulfonyl) pyrazolo[1,5-a] pyrimidine-6-carbonitrile XX (2 g, 7 mmol) in IPA (10 mt) was added 3-(2-aminoethyl)-1-(2-methoxyethyl) pyridin-2(1H)-one (3 g, 0.01 mol) and TEA (4 g, 6 mL, 0.04 mol) in a sealed tube. The reaction mixture was stirred at 160° C. for 16 hours and the progress of the reaction was monitored by TLC analysis. After completion, reaction mixture was allowed to room temperature and filtered the precipitated solids and then solids were washed with MeOH, diethyl ether and acetonitrile to afford the desired compound as a white solid. Yield: 1.3 g (40%); LCMS Calculated. for $C_{17}H_{20}ClN_7O_2$ is 401.14; Observed. 402.25 $[M+H]^+$; $^1H$ NMR (400 MHz, DMSO-$d_6$): δ 8.347 (bs, 2H), 7.479 (d, J=6.0 Hz, 1H), 7.293 (d, J=6.0 Hz, 1H), 7.080 (s, 1H), 6.151 (t, J=6.8 Hz, 1H), 4.076-4.052 (m, 2H), 3.602-3.538 (m, 4H), 3.227 (s, 3H), 2.765-2.734 (m, 2H) 2.270 (s, 3H). HPLC Purity=92.97%, Rt=11.332.

Example 93: 7-amino-3-chloro-5-((2-(1-(2-hydroxyethyl)-2-oxo-1,2-dihydropyridin-3-yl) ethyl) amino)-2-methylpyrazolo[1,5-a]pyrimidine-6-carbonitrile

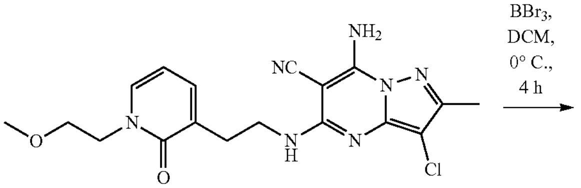

Example 92

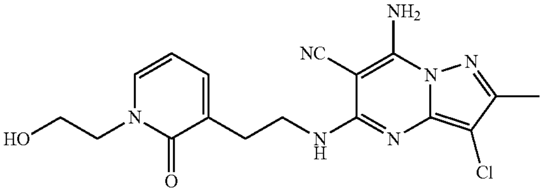

Example 93

To a stirred solution of 7-amino-3-chloro-5-((2-(1-(2-methoxyethyn-2-oxo-1,2-dihydropyridin-3-yl) ethyl) amino)-2-methylpyrazolo[1,5-a] pyrimidine-6-carbonitrile Example 92 (1.3 g, 3.2 mmol) in DCM (20 mL) was cooled to 0° C. and was added dropwise addition of BBr3 (1.2 g, 0.46 mL, 4.9 mmol). The reaction mixture was stirred at 0° C. for 4 hours. The progress of the reaction was monitored by TLC analysis. After completion, the reaction was quenched with water (50 mL) and extracted with ethyl acetate (50 ml×3). The combined organic layer was dried over anhydrous sodium sulphate and concentrated under reduced pressure. The crude residue was subjected silica gel (230-400 mesh) column chromatography using 0-10% MeOH in DCM to afford the desired compound Example 93 as a bluish solid. Yield: (850 mg, 65%); LCMS Calculated for $C_{17}H_{18}ClN_7O_2$ is 387.12; Observe: 388.25 $[M^{+}+1]$. $^{1}$HNMR (400 MHz, DMSO-$d_6$): δ 8.354 (bs, 2H), 7.490 (d, J=6.4 Hz, 1H), 7.318 (d, J=6.4 Hz, 1H), 7.116-7.093 (m, 1H), 6.153 (t, J=6.4 Hz, 1H), 4.856 (J=5.6 Hz, 1H), 3.972-3.945 (m, 2H), 3.663-3.624 (m, 2H), 3.561-3.517 (m, 2H), 2.751 (t, J=6.4 Hz, 2H), 2.271 (s, 3H). HPLC Purity=99.67%, Rt=10.122.

Example 94: 7-amino-5-((2-(1-(1-(hydroxymethyl) cyclopropyl)-1H-pyrazol-3-yl) ethyl) amino)-2-methyl-3-(trifluoromethyl) pyrazolo[1,5-a]pyrimidine-6-carbonitrile

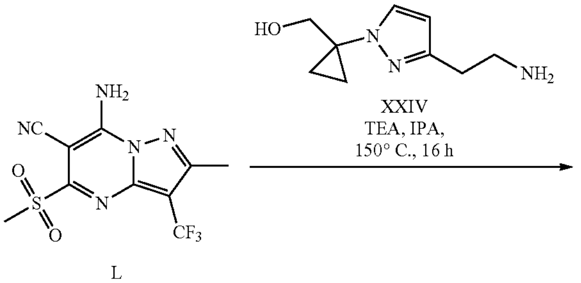

L

-continued

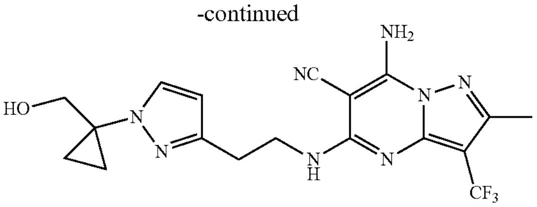

Example 94

To a stirred solution of 7-amino-2-methyl-5-(methyl sulfonyl)-3-(trifluoromethyl) pyrazolo[1,5-a] pyrimidine-6-carbonitrile L (0.17 g, 0.564 mmol) in 2-propanol (10 mL) were added (1-(3-(2-aminoethyl)-1H-pyrazol-1-yl)cyclopropyl)methanol (0.205 g, 1.13 mmol) and triethylamine (0.343 g, 3.39 mmol) at room temperature under $N_2$ atmosphere. The resulting mixture was stirred at 150° C. for 16 h. The progress of the reaction was monitored by TLC analysis. After completion, the reaction was quenched with water (5 mL) and extracted with ethyl acetate (25 mL×3). The combined organic layer was dried over anhydrous sodium sulphate and concentrated under reduced pressure. The crude residue was subjected silica gel (230-400 mesh) column chromatography using 0-3% MeOH in DCM to afford the desired compound Example 94 as a brown solid. Yield: 0.035 g (16%); LCMS Calculated. for $C_{18}H_{19}F_3N_8O$ is 420.16; Observed. 421.30 $[M+H]^{+}$; $^{1}$HNMR (400 MHz, DMSO-$D_6$): δ 8.50 (bs, 2H), 7.61 (d, J=2.0 Hz, 1H), 7.21 (t, J=5.2 Hz, 1H), 6.02 (d, J=2.0 Hz, 1H), 4.89 (t, J=6.0 Hz, 1H), 3.58-3.56 (m, 4H), 2.82-2.79 (m, 2H), 2.36 (s, 3H), 1.28-1.23 (m, 2H), 1.08-1.05 (m, 2H). HPLC Purity=94.37%; INT ODS 3V-C18 (4.6*250) mm, 5μ; Mobile phase A: 0.1% Formic acid in water; Mobile phase B: Acetonitrile; Rt=11.738.

Example 95: 7-amino-5-((2-(1-(2-(amino methyl) cyclobutyl)-1H-pyrazol-3-yl) ethyl) amino)-3-chloro-2-methylpyrazolo[1,5-a]pyrimidine-6-carbonitrile

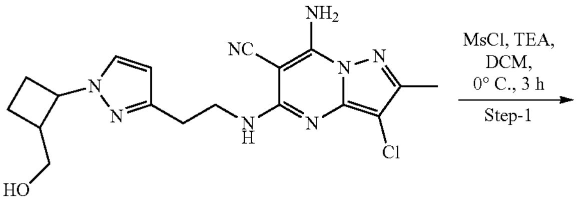

Example 67

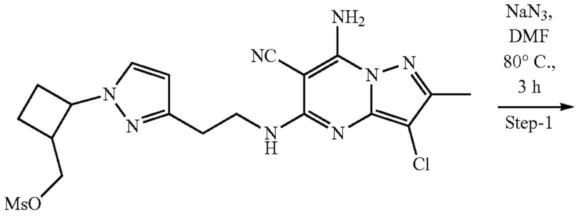

Example 95a

-continued

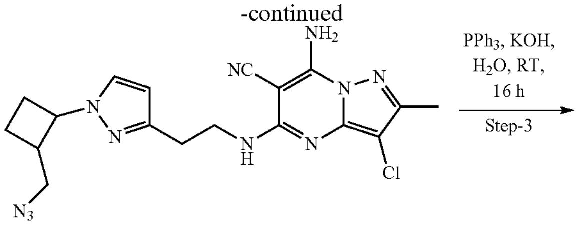

Example 95b

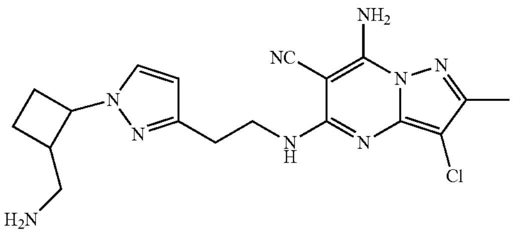

Example 95

Step-1: (2-(5-(2-((7-amino-3-chloro-6-cyano-2-methylpyrazolo[1,5-a] pyrimidin-5-yl) amino) ethyl)-1H-pyrazol-1-yl) cyclobutyl) methyl methane sulfonate (Example 95a)

To a stirred solution of 7-amino-3-chloro-5-((2-(1-(2-(hydroxymethyl) cyclobutyl)-1H-pyrazol-3-yl) ethyl) amino)-2-methylpyrazolo[1,5-a] pyrimidine-6-carbonitrile Example 67 (0.9 g, 2 mmol) in DCM (100 mL) was added triethylamine (2 mL, 10 mmol) under inert atmosphere. The resulting mixture was cooled to 0° C. and drop wise added methane sulfonyl chloride (0.2 mL, 2 mmol). The reaction mixture was stirred at 0° C. for 3 h and progress of the reaction was monitored by TLC analysis. After completion, the reaction mixture was diluted with sat. $Na_2HCO_3$ solution (100 mL) and extracted with DCM (100 mL×3). The combined organic layer was dried over anhydrous $Na_2SO_4$, filtered and concentrated under reduced pressure. The crude was purified by silica gel (mess 230-400) column chromatography using 0-50% ethyl acetate in n-hexane to afford the desired compound Example 95a as a pale-yellow solid. Yield: 0.770 g (77%). LCMS Calculated. for $C_{19}H_{23}ClN_8O_3S$ is 478.13; Observed. 479.30 [M+H]$^+$.

Step-2: 7-amino-5-((2-(1-(2-(azidomethyl) cyclobutyl)-1H-pyrazol-5-yl) ethyl) amino)-3-chloro-2-methylpyrazolo[1,5-a] pyrimidine-6-carbonitrile (Example 95b)

To a stirred solution of (2-(5-(2-((7-amino-3-chloro-6-cyano-2-methylpyrazolo[1,5-a] pyrimidin-5-yl) amino) ethyl)-1H-pyrazol-1-yl) cyclobutyl) methyl methane sulfonate Example 95a (0.9 g, 1.88 mmol) in DMF (10 mL) was added sodium azide (489 mg, 7.52 mmol) at room temperature. The reaction mixture was stirred at 80° C. for 3 h under nitrogen atmosphere. The progress of the reaction was monitored by TLC analysis. After completion, the reaction was cooled to RT and diluted with water (50 mL). The mixture was extracted with ethyl acetate (50 mL×3) and the combined organic layer was dried over anhydrous $Na_2SO_4$ before it was concentrated under reduced pressure. The crude was purified by combi flash silica gel (mess 230-400) column chromatography by using 10-40% ethyl acetate in n-hexane to afford the desired compound Example 95b as a pale-yellow solid. Yield:0.56 g (70%). LC-MS Calc. for $C_{18}H_{20}ClN_{11}$ is 425.15; Obs. 426.30 [M+H]$^+$.

Step-3: 7-amino-5-((2-(1-(2-(amino methyl) cyclobutyl)-1H-pyrazol-5-yl) ethyl) amino)-3-chloro-2-methylpyrazolo[1,5-a] pyrimidine-6-carbonitrile To a stirred solution of 7-amino-5-((2-(1-(2-(azidomethyl) cyclobutyl)-1H-pyrazol-5-yl) ethyl) amino)-3-chloro-2-methylpyrazolo[1,5-a] pyrimidine-6-carbonitrile Example 95b (0.56 g, 1.3 mmol) in THF: $H_2O$ (12 mL; 3:1) were added triphenylphosphine (0.52 g, 2.0 mmol) and potassium hydroxide (74 mg, 1.3 mmol). The resulting mixture was stirred at RT for 16 h. The progress of the reaction was monitored by TLC analysis. After completion, reaction mixture was diluted with water (10 mL) and extracted with DCM (50 mL×3). The combined organic layer was dried over anhydrous $Na_2SO_4$, filtered and concentrated under reduced pressure. The crude was purified by combi flash chromatography eluted with 0-5% methanol in DCM to afford the desired title compound Example 95 as an off-white solid. Yield: 50 mg, (10%). LCMS Calculated. for $C_{18}H_{22}ClN_9$ is 399.16; Obs. 400.30 [M+H]$^+$; $^1$HNMR (400 MHz, DMSO-$d_6$): δ 7.92 (bs, 4H), 7.69 (d, J=2.0 Hz, 1H), 7.01 (t, J=5.2 Hz, 1H), 6.14 (d, J=1.6 Hz, 1H), 4.56 (q, J=8.0 Hz, 1H), 3.63 (q, J=6.0 Hz, 2H), 2.96-2.86 (m, 5H), 2.44-2.28 (m, 5H), 2.01-1.91 (m, 1H), 1.59 (m, 1H). HPLC: 8.144 min; 99.58%, INT ODS 3V-C18 (4.6×250) mm, 5μ; 0.1% Formic acid in water: Mobile Phase B: Acetonitrile.

Example 96: 7-amino-3-ethyl-5-((2-(6-(((2-methoxyethyl) amino) methyl)$_{321}$yridine-2-yl) ethyl) amino)-2-methylpyrazolo[1,5-a]pyrimidine-6-carbonitrile

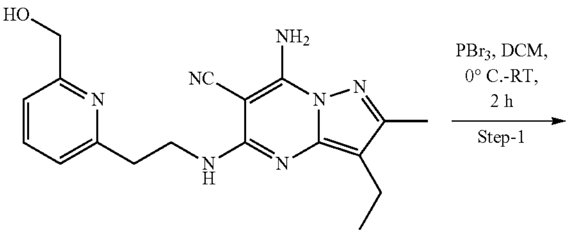

Example 45

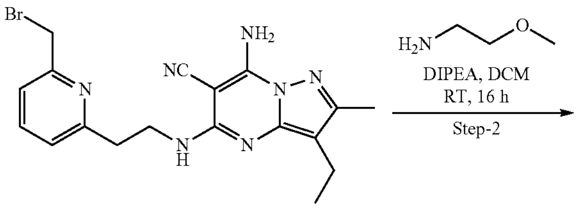

Example 96a

-continued

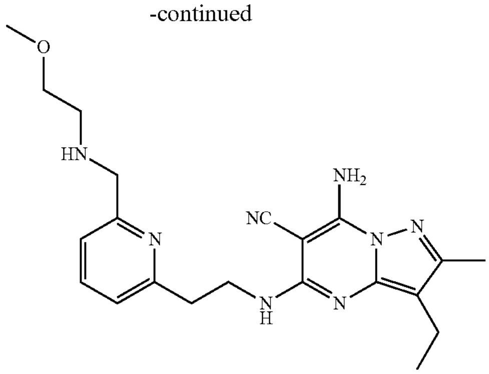

Example 96

Step-1: 7-amino-5-((2-(6-(bromomethyl) pyridin-2-yl) ethyl) amino)-3-ethyl-2-methylpyrazolo[1,5-a] pyrimidine-6-carbonitrile (Example 96a)

A solution of 7-amino-3-ethyl-5-((2-(6-(hydroxymethyl) pyridin-2-yl) ethyl) amino)-2-methylpyrazolo[1,5-a] pyrimidine-6-carbonitrile Example 45 (200 mg, 0.569 mol) in DCM (4 mL) was cooled to 0° C. and a solution of $PBr_3$ (0.161 mL, 1.71 mmol) in DCM (1 mL) was dropwise added under inert atmosphere. The reaction mixture was stirred at rt for 2 h and the progress of the reaction was monitored by TLC analysis. After completion, the reaction was quenched with sat. $NaHCO_3$ solution (10 mL) and the resulting mixture was extracted with ethyl acetate (50 mL×3). The combined organic layer was dried over anhydrous sodium sulphate and concentrated under reduced pressure. The crude was purified by silica gel (230-400 mesh) column chromatography using 0-20% ethyl acetate in n-hexane to afford the desired compound Example 96a as an off-white solid. Yield: 120 mg (50%); LCMS Calculated. for $C_{18}H_{20}BrN_7$ is 415.09; Observed. 416.30 $[M+H]^+$. $^1$HNMR (400 MHz, $CDCl_3$): δ 7.65-7.61 (m, 1H), 7.33 (d, J=8.0 Hz, 1H), 7.10 (d, J=7.6 Hz, 1H), 6.41 (bs, 1H), 6.01 (bs, 2H), 4.64 (s, 2H), 3.91-3.87 (m, 2H), 3.11 (t, J=6.0 Hz, 2H), 2.59-2.32 (m, 2H), 2.05 (s, 3H), 0.89-0.83 (m, 3H).

Step-2: 7-amino-3-ethyl-5-((2-(6-(((2-methoxyethyl) amino) methyl) pyridin-2-yl) ethyl) amino)-2-methylpyrazolo[1,5-a]pyrimidine-6-carbonitrile To a solution of 2-methoxyethan-1-amine (26.1 mg, 0.348 mmol) in DCM (4 mL) was added DIPEA (112 mg, 0.869 mmol) and the resulting mixture was stirred at rt for 10 min. To this was added a solution of 7-amino-5-((2-(6-(bromomethyl) pyridin-2-yl) ethyl) amino)-3-ethyl-2-methylpyrazolo [1,5-a] pyrimidine-6-carbonitrile Example 96 (120 mg, 0.29 mmol) in DCM (1 mL). The reaction mixture was stirred at rt for 16 h. The progress of the reaction was monitored by TLC analysis. The reaction was quenched with water (20 mL) and the resulting mixture was extracted with DCM (50 mL×3). The combined organic layer was dried over anhydrous sodium sulphate and concentrated under reduced pressure. The crude was purified by silica gel (230-400 mesh) column chromatography using 0-5% MeOH in DCM to afford the desired compound Example 96 as an off-white solid. Yield: 80 mg, (77%); LCMS Calculated. for $C_{21}H_{28}N_8O$ is 408.24; Observed.: 409.40 $[M^++1]$. $^1$H NMR (400 MHz, DMSO-$D_6$): δ 8.12 (bs, 2H), 7.76 (t, J=7.6 Hz, 1H), 7.32 (d, J=8.0 Hz, 1H), 7.25 (d, J=7.6 Hz, 1H), 6.78 (bs, 1H), 4.10 (bs, 2H), 3.72-3.69 (m, 2H), 3.53 (t, J=5.6 Hz, 2H), 3.27 (s, 3H), 3.08 (t, J=6.8 Hz, 2H), 2.97 (t, J=5.2 Hz, 2H), 2.50-2.44 (m, 2H), 2.25 (s, 3H), 1.12 (t, J=7.2 Hz, 3H); HPLC: 8.235 min; 96.75%, INT ODS 3V-C18 (4.6*250) mm, 5μ, Mobile Phase A: 0.1% Formic acid in water, Mobile Phase B: Acetonitrile.

Example 97: 7-amino-3-ethyl-5-((2-(6-(((2-hydroxyethyl) amino) methyl) pyridine-2-yl) ethyl) amino)-2-methylpyrazolo[1,5-a]pyrimidine-6-carbonitrile

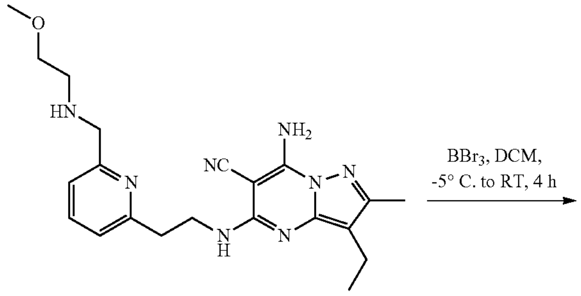

Example 96

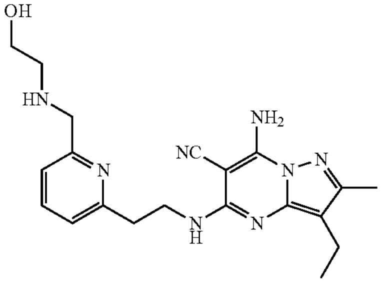

Example 97

A solution of 7-amino-3-ethyl-5-((2-(6-(((2-methoxyethyl) amino) methyl) pyridin-2-yl) ethyl)amino)-2-methylpyrazolo[1,5-a] pyrimidine-6-carbonitrile Example 96 (60 mg, 0.15 mmol) in DCM (4 mL) was cooled to −5° C. and dropwise added solution of $BBr_3$ (21 μL, 0.22 mmol) in DCM (0.5 mL). The reaction mixture was stirred at rt for 4 h. The progress of the reaction was monitored by TLC analysis. The reaction was quenched with sat. $NaHCO_3$ solution (20 mL) and the resulting mixture was extracted with DCM (50 mL×3). The combined organic layer was dried over anhydrous sodium sulphate and concentrated under reduced pressure. The crude was purified by silica gel (230-400 mesh) column chromatography using 0-10% MeOH in DCM to afford the desired compound Example 97 as an off-white solid. Yield: 20.2 mg (29%); LC-MS Calc. for $C_{20}H_{26}N_8O$ is 394.22; Obs.: 395.40 $[M^++1]$. $^1$HNMR (400 MHz, DMSO-$D_6$): δ 8.12 (bs, 2H), 7.75 (t, J=7.6 Hz, 1H), 7.34-7.23 (m, 3H), 6.79 (bs, 1H), 4.91 (bs, 1H), 4.09 (s, 2H), 3.73-3.69 (m, 2H), 3.60 (bs, 2H), 3.07 (t, J=6.8 Hz, 2H), 2.87 (t, J=5.2 Hz, 2H), 2.47-2.44 (m, 2H), 2.25 (s, 3H), 1.14 (t, J=7.2 Hz, 3H); HPLC: 7.998 min; 96.80%, INT ODS 3V-C18 (4.6*250) mm, 5μ, Mobile Phase A. 0.1% Formic acid in water, Mobile Phase B: Acetonitrile.

Example 98: 7-amino-3-chloro-5-((2-(1-(1-(((2-hydroxyethyl) amino) methyl) cyclopropyl)-1H-pyrazol-3-yl) ethyl) amino)-2-methylpyrazolo[1,5-a] pyrimidine-6-carbonitrile

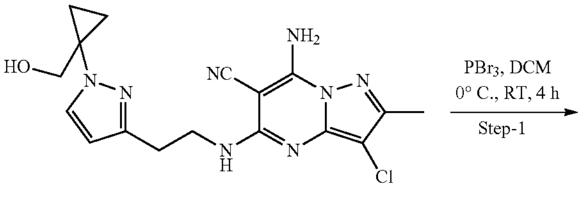

Example 37

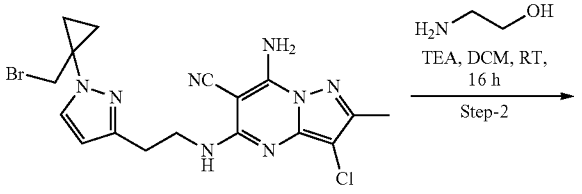

Example 98a

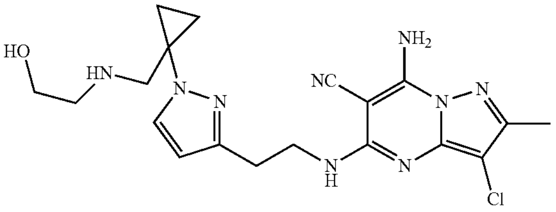

Example 98

Step-1: 7-amino-5-((2-(1-(1-(bromomethyl) cyclopropyl)-1H-pyrazol-3-yl) ethyl) amino)-3-chloro-2-methylpyrazolo[1,5-a]pyrimidine-6-carbonitrile A solution of 7-amino-3-chloro-5-((2-(1-(1-(hydroxymethyl) cyclopropyl)-1H-pyrazol-3-yl) ethyl) amino)-2-methylpyrazolo[1,5-a] pyrimidine-6-carbonitrile Example 37 (300 mg, 0.776 mmol) in DCM (10 mL) was cooled to 0° C. under inert atmosphere and $PBr_3$ (110 μL, 1.16 mmol) was added dropwise. The reaction mixture was stirred at room temperature for 4 h and the progress of reaction was monitored by TLC analysis. After completion, the reaction was cooled to 0° C. and quenched slowly with saturated sodium bicarbonate solution. The resulting mixture was extracted with DCM (10 mL×3), the combined organic layer was given brine wash, dried over anhydrous sodium sulphate, and concentrated under reduced pressure. The crude material was purified by combi flash chromatography using 10-50% ethyl acetate in n-hexane to afford the desired compound Example 98a as off-white solid. Yield: (90 mg, 25.78%); LCMS Calculated for $C_{17}H_{18}BrClN_8.05$ is 450.01; Observed: 451.20 [$M^+$+H].

Step-2: 7-amino-3-chloro-5-((2-(1-(1-(((2-hydroxyethyl) amino) methyl) cyclopropyl)-1H-pyrazol-3-yl) ethyl)amino)-2-methylpyrazolo[1,5-a]pyrimidine-6-carbonitrile To a solution of 7-amino-5-((2-(1-(1-(bromomethyl) cyclopropyl)-1H-pyrazol-3-yl) ethyl) amino)-3-chloro-2-methylpyrazolo[1,5-a] pyrimidine-6-carbonitrile Example 98a (90 mg, 0.20 mmol) in DCM (3 mL) were dropwise added DIPEA (0.10 mL, 0.60 mmol) and 2-aminoethan-1-ol (18 μL, 0.30 mmol) under inert atmosphere at rt. The reaction mixture was stirred for 16 h and the progress of the reaction was monitored by TLC analysis. Then additional 2-aminoethan-1-ol (18 μL, 0.30 mmol) was added stirring was continued for 3 days. After completion, the reaction was quenched with 10% NaOH solution (10 mL) and extracted with DCM (10 mL×3). The combined organic layer was washed brine solution, dried over anhydrous sodium sulphate, and concentrated under reduced pressure. The crude material was purified by flash chromatography (Biotage) using 0-10% methanolic ammonia (7M) in DCM to afford Example 98 as off-white solid. Yield: 25 mg (30.12%). LCMS Calculated for $C_{19}H_{24}ClN_9O$ is 429.18; Observed: 430.35 [$M^+$+1]. $^1$HNMR (400 MHz, DMSO-$D_6$): δ 8.42 (bs, 2H), 7.74 (d, J=2.0 Hz, 1H), 6.94 (t, J=5.2 Hz, 1H), 6.15 (d, J=2.0 Hz, 2H), 5.07 (bs, 1H), 3.66-3.57 (m, 4H), 3.41-3.38 (m, 2H), 2.87-2.83 (m, 4H), 2.28 (s, 3H), 1.24-1.20 (m, 4H). HPLC: 7.992 min; 99.591%, INT ODS 3V-C18 (4.6*250) mm, 5μ; Mobile Phase A: 0.1% Formic acid in water, Mobile Phase B: Acetonitrile.

Example 99: N-((1-(3-(2-((7-amino-3-chloro-6-cyano-2-methylpyrazolo[1,5-a]pyrimidin-5-yl) amino) ethyl)-1H-pyrazol-1-yl) cyclopropyl) methyl)-3-hydroxypropanamide

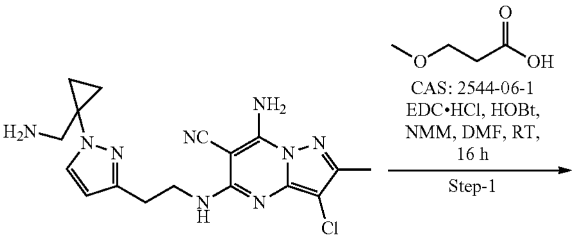

Example 68

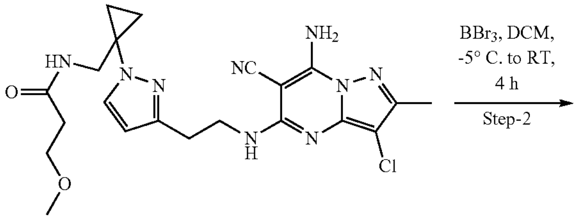

Example 99a

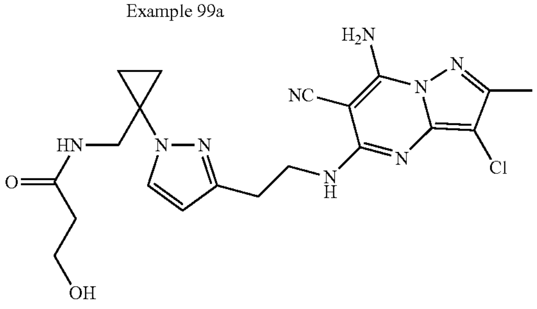

Example 99

Step-1: N-((1-(3-(2-((7-amino-3-chloro-6-cyano-2-methylpyrazolo[1,5-a] pyrimidin-5-yl) amino) ethyl)-1H-pyrazol-1-yl) cyclopropyl) methyl)-3-methoxypropanamide To a stirred solution of 7-amino-5-((2-(1-(1-(aminomethyl)cyclopropyl)-1H-pyrazol-3-yl)ethyl)amino)-3-chloro-2-methylpyrazolo[1,5-a] pyrimidine-6-carbonitrile Example 68 (0.2 g, 0.5 mmol) in DMF (5 mL) were added 3-methoxypropanoic acid (0.08 g, 0.8 mmol), N, N-diisopropylethylamine (0.2 mL, 1 mmol), 1-(3-Dimethylaminopropyl)-3-ethylcarbodiimideHydrochloride (0.1 g, 10.8 mmol) and HOBt (0.1 g, 0.8 mmol) at 0° C. under inert atmosphere. The reaction was stirred for 16 h at room temperature. Then the reaction mixture was diluted with water (50 mL) and extracted with ethyl acetate (20 mL×3). The combined organic layer was dried over anhydrous $Na_2SO_4$, filtered and concentrated under reduced pressure. The crude was purified by combi flash (230-400) column chromatography using 0-1% methanol in DCM to afford the desired compound Example 99a as off-white solid. Yield: (180 mg, 90%); LCMS Calculated for $C_{21}H_{26}ClN_9O_2$ is 471.19; Observed: 472.35 [$M^+$+1]. $^1$HNMR (400 MHz, DMSO-$D_6$): δ 8.40 (bs, 2H), 7.90 (t, J=5.6 Hz, 1H), 7.59 (s, 1H), 6.95 (t, J=5.2 Hz, 1H), 6.07 (d, J=2.0 Hz, 1H), 3.63-3.49 (m, 2H), 3.47-3.39 (m, 4H), 3.18 (t, J=5.6 Hz, 3H), 2.82 (t, J=7.2 Hz, 2H), 2.33-2.28 (m, 5H), 1.09-1.00 (m, 4H).

Step-2: N-41-(3-(2-47-amino-3-chloro-6-cyano-2-methylpyrazolo[1,5-a] pyrimidin-5-yl) amino) ethyl)-1H-pyrazol-1-yl) cyclopropyl) methyl)-3-hydroxypropanamide To a stirred solution of N-((1-(3-(2-((7-amino-3-chloro-6-cyano-2-methylpyrazolo[1,5-a] pyrimidin-5-yl) amino) ethyl)-1H-pyrazol-1-yl) cyclopropyl) methyl)-3-methoxypropanamide Example 99a (0.180 g, 0.381 mmol) in DCM (20 mL) was added $BBr_3$ (54.1 μL, 0.572 mmol) at 0° C. over a period of 5 min. The reaction mixture was stirred at rt for 16 h. The progress of the reaction was monitored by TLC analysis. After completion, the reaction was quenched with methanol 1 mL and diluted with saturated sodium bicarbonate solution (20 mL). The mixture was extracted with DCM (20 mL×3) and the combined organic layer was dried over anhydrous $Na_2SO_4$, filtered and concentrated under reduced pressure. The crude was purified by combi-flash (230-400) column chromatography using 0-5% methanol in DCM to afford the desired compound Example 99 as off-white solid. Yield: (175 mg, 37.0%); LCMS Calculated. for $C_{20}H_{24}ClN_9O_2$ is 457.17; Observed: 458.35 [$M^+$+1]. $^1$HNMR (400 MHz, DMSO-$D_6$): δ 8.41 (bs, 2H), 7.86 (t, J=5.6 Hz, 1H), 7.61 (d, J=2.0 Hz, 1H), 6.95 (t, J=5.2 Hz, 1H), 6.06 (d, J=2.0 Hz, 1H), 4.55 (t, J=5.2 Hz, 1H), 3.63-3.54 (m, 4H), 3.43 (d, J=5.6 Hz, 2H), 2.81 (t, J=7.2 Hz, 2H), 2.28 (s, 3H), 2.21 t, J=6.4 Hz, 2H), 1.09-1.00 (m, 4H); HPLC: 9.98 min; 97.70%, INT ODS 3V-C18 (4.6*250) mm, 5μ, Mobile Phase A: 0.1% Formic acid in water, Mobile Phase B: Acetonitrile.

Example 100: 7-amino-3-ethyl-5-((2-(6-(1-hydroxyethyl)$_{326}$yridine-2-yl) ethyl) amino)-2-methylpyrazolo[1,5-a]pyrimidine-6-carbonitrile

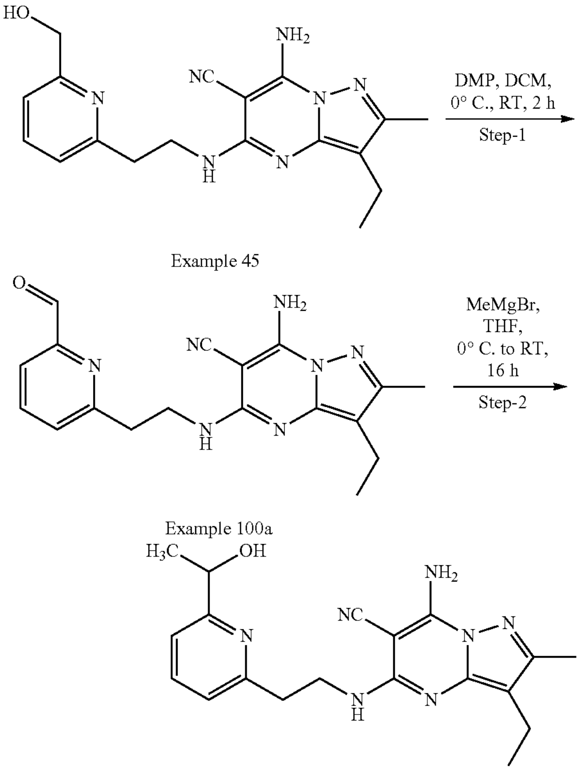

Example 45

Example 100a

Example 100

Step-1: 7-amino-3-ethyl-5-((2-(6-formylpyridin-2-yl) ethyl) amino)-2-methylpyrazolo[1,5-a] pyrimidine-6-carbonitrile A solution of 7-amino-3-ethyl-5-((2-(6-(hydroxymethyl) pyridin-2-yl) ethyl) amino)-2-methylpyrazolo[1,5-a] pyrimidine-6-carbonitrile Example 45 (200 mg, 0.57 mmol) in DCM (5 mL) was added Dess-martin periodinane (290 mg, 0.683 mmol). The reaction mixture was stirred at 0° C. for 2 h. The progress of the reaction was monitored by TLC analysis. After completion, the reaction mixture was filtered through a celite bed and washed with ethyl acetate (50 mL×2). The combined filtrates were dried over anhydrous sodium sulphate and concentrated under reduced pressure. The crude was purified by silica gel (230-400 mesh) column chromatography using 20% ethyl acetate in n-hexane to afford the desired compound Example 100a as an off-white solid. Yield: (135 mg, 67.8%); LCMS Calculated for $C_{18}H_{19}N_7O$ is 349.17; Observe: 350.35 [$M^+$+1]; $^1$HNMR (400 MHz, $CDCl_3$): δ 10.176 (s, 1H), 7.862-7.790 (m, 2H), 7.790-7.746 (m, 1H), 6.166 (s, 1H), 6.035 (s, 2H), 3.986-3.941 (m, 2H), 3.245-3.214 (t, J=6.0 Hz, 1H), 2.592-2.535 (q, J=7.6 Hz, 1H), 2.324 (s, 3H), 2.174 (s, 1H), 1.213-1.175 (t, J=7.6 Hz, 3H).

Step-2: 7-amino-3-ethyl-5-((2-(6-(1-hydroxyethyl) pyridin-2-yl) ethyl) amino)-2-methylpyrazolo[1,5-a] pyrimidine-6-carbonitrile A solution of 7-amino-3-ethyl-5-(2-(6-formylpyridin-2-yl) ethyl) amino)-2-methylpyrazolo[1,5-a] pyrimidine-6-carbonitrile Example 100a (130 mg, 0.372 mmol) in THF (3 mL) was cooled to 0° C. and added methyl magnesium bromide (0.446 mL, 1 M, 0.446 mmol). The reaction mixture was stirred at rt for 3 h. The progress of the reaction was monitored by TLC analysis. After completion, the reaction was quenched with saturated $NH_4Cl$ solution (20 mL) and extracted with ethyl acetate (50 mL×3). The combined organic layer was dried over anhydrous sodium sulphate and concentrated under reduced pressure. The crude was purified by flash silica gel chromatography using 10-50% ethyl acetate in n-hexane to afford the desired compound Example 100 as an off-white solid. Yield: (18 mg, 7%); LCMS Calculated for $C_{19}H_{23}N_7O_7$ is 365.20; Observe: 366.40 $[M^{+}+1]$. $^1H$ NMR (400 MHz, DMSO-$d_6$): δ 8.10 (s, 2H), 7.72-7.68 (t, J=7.6 Hz, 1H), 7.36-7.34 (d, J=7.6 Hz, 1H), 7.14-7.12 (d, J=7.2 Hz, 1H), 6.83 (s, H), 5.29-5.28 (t, J=4.4 Hz, 1H), 4.75 (bs, 1H), 3.67 (bs, 2H), 3.04-3.00 (m, 2H), 3.51-2.44 (m, 2H), 2.25 (s, 3H), 1.37-1.35 (d, J=6.4 Hz, 3H), 1.15-1.11 (t, J=7.6 Hz, 3H). HPLC: 8.49 min; 98.85%, INT ODS 3V-C18 (4.6*250) mm, 5μ, Mobile Phase A: 0.1% formic acid in water, Mobile Phase B: Acetonitrile:

Example 101: 7-amino-3-cyclopropyl-5-((2-(1-(1-(hydroxymethyl) cyclopropyl)-1H-pyrazol-3-yl) ethyl) amino)-2-methylpyrazolo[1,5-a]pyrimidine-6-carbonitrile

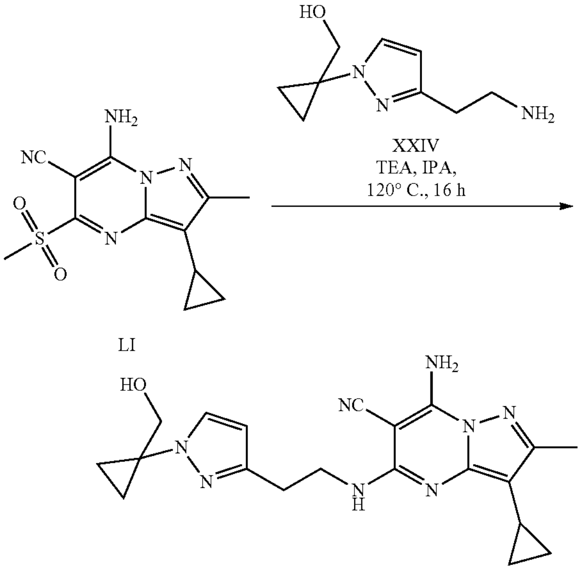

Example 101

To a stirred solution of 7-amino-3-cyclopropyl-2-methyl-5-(methyl sulfonyl) pyrazolo[1,5-a] pyrimidine-6-carbonitrile LI (0.2 g, 0.7 mmol) and (1-(3-(2-aminoethyl)-1H-pyrazol-1-yl) cyclopropyl) methanol XXIV (0.2 g, 1 mmol) in isopropanol (5 mL) in a sealed tube, was added TEA (0.3 mL, 2 mmol). The resulting reaction mixture was stirred at 120° C. for 16 h. The progress of the reaction was monitored by TLC analysis. After completion, the reaction mixture was cooled to RT and diluted with water (20 mL). The resulting mixture was extracted with ethyl acetate (20 mL×3). The combined organic layer was dried over anhydrous $Na_2SO_4$, filtered, and concentrated under reduced pressure. The crude compound was purified by combi-flash column chromatography using eluted with 0-70% ethyl acetate in n-hexane to afford the desired title compound Example 101 as off-white solid. Yield 100 mg (33%). LCMS Calculated. for $C_{20}H_{24}N_8O$ is 392.20; Observed. 393.35 $[M+1]^+$. $^1$HNMR (400 MHz, DMSO-$D_6$): δ 8.09 (bs, 2H), 7.62-7.62 (m, 1H), 6.65 (t, J=5.2 Hz, 1H), 6.06-6.05 (m, 1H), 4.88 (q, J=5.6 Hz, 1H), 3.59 (d, J=5.2 Hz, 2H) 3.55-3.50 (m, 2H), 2.80 (d, J=7.6 Hz, 2H), 2.30 (s, 3H), 1.62-1.55 (m, 1H), 1.10-1.07 (m, 2H), 1.00-0.95 (m, 4H), 0.76-0.72 (m, 2H). HPLC: 11.217 min; 99.74%, Column: INT ODS 3V-C18 (4.6*250) mm, 5μ, Mobile phase A: 0.1% Formic acid in water, Mobile phase B: Acetonitrile.

Example 102: 7-amino-2-(difluoro methyl)-3-ethyl-5-((2-(1-(2-(hydroxymethyl) cyclobutyl)-1H-pyrazol-3-yl) ethyl) amino) pyrazolo[1,5-a]pyrimidine-6-carbonitrile

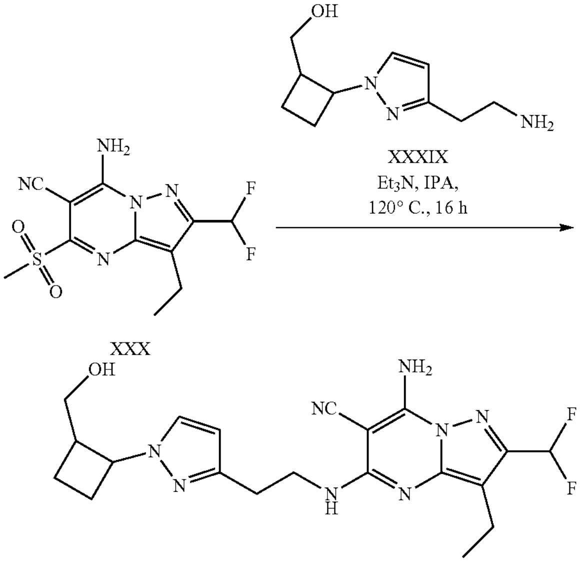

Example 102

To a stirred solution of 7-amino-2-(difluoro methyl)-3-ethyl-5-(methyl sulfonyl) pyrazolo[1,5-a] pyrimidine-6-carbonitrile XXX (0.2 g, 0.6 mmol) and (2-(3-(2-aminoethyl)-1H-pyrazol-1-yl) cyclobutyl) methanol (0.2 g, 1 mmol) in isopropanol (5 mL) in a sealed tube, was added TEA (0.3 mL, 2 mmol). The reaction mixture was stirred at 120° C. for 16 h and the progress of the reaction was monitored by TLC analysis. After completion, the reaction mixture was cooled to RT, diluted with water (20 mL) and extracted with ethyl acetate (20 mL×3). The combined organic layer was dried over anhydrous $Na_2SO_4$, filtered, and concentrated under reduced pressure. The crude compound was purified by combi-flash column chromatography using 0-50% ethyl acetate in n-hexane to afford the desired compound Example 102 as off-white solid. Yield: 0.12 g (40%). LCMS Calculated. for $C_{20}H_{24}F_2N_8O$ is 430.20; Observed. 431.35 $[M+1]^+$. $^1$HNMR (400 MHz, DMSO-$D_6$): δ 8.43 (bs, 2H), 7.65 (d, J=2.0 Hz, 1H), 7.18-6.91 (m, 2H), 6.07 (d, J=2.0 Hz, 1H), 4.60 (t, J=5.2 Hz, 1H), 4.51 (q, J=8.8 Hz, 1H), 3.63-3.58 (m, 2H), 3.41-3.36 (m, 2H), 2.86-2.77 (m, 3H), 2.63-2.58 (m, 2H), 2.33-2.20 (m, 2H), 1.83-1.76 (m, 1H), 1.61-1.56 (m, 1H), 1.16 (t, J=7.6 Hz, 3H). HPLC: 12.298 min; 98.94%, Column: INT ODS 3V-C18 (4.6*250) mm, 5μ Mobile phase A: 0.1% Formic acid in water Mobile phase B: Acetonitrile Example 103: Racemic (+-)-7-amino-5-((2-(1-(2-(hydroxymethyl) cyclobutyl)-1H-pyrazol-3-yl)ethyl) amino)-2,3-dimethylpyrazolo[1,5-a] pyrimidine-6-carbonitrile Example 104a: (+)-7-amino-5-((2-(1-(2-(hydroxymethyl) cyclobutyl)-1H-pyrazol-3-yl)ethyl)amino)-2,3-dimethylpyrazolo[1,5-a]pyrimidine-6-carbonitrile Example 104b: (−)-7-amino-5-((2-(1-(2-(hydroxymethyl)cyclobutyl)-1H-pyrazol-3-yl)ethyl)amino)-2,3-dimethylpyrazolo[1,5-a]pyrimidine-6-carbonitrile

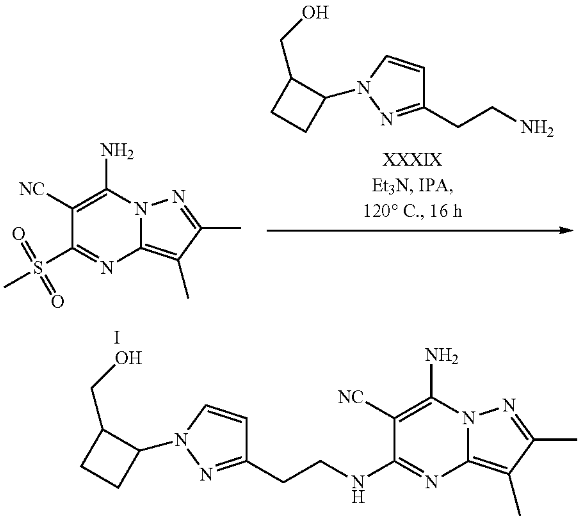

XXXIX
I

Racemic: Example 103; Racemic(±)
Peak-1: Example 104a; dextro(+) rotatory
Peak-2: Example 104b; leavo(-) rotatory To a stirred solution of 7-amino-2,3-dimethyl-5-(methyl sulfonyl) pyrazolo[1,5-a] pyrimidine-6-carbonitrile I (200 mg, 0.754 mmol) and (2-(3-(2-aminoethyl)-1H-pyrazol-1-yl) cyclobutyl) methanol XXXIX (294 mg, 1.51 mmol) in 2-propanol (10 mL) was added triethylamine (0.631 mL, 4.52 mmol). The reaction mixture was heated at 120° C. for 16 h. The progress of the reaction was monitored by TLC analysis. The reaction mixture was cooled to rt and diluted with water (20 mL) and extracted with ethyl acetate (20 mL×3). The combined organic layer was dried over in anhydrous sodium sulphate, filtered and concentrated under reduced pressure. The crude was purified by combi flash silica gel (230-400) column chromatography using 0-1% methanol in DCM to afford the desired racemic compound Example 103 as off-white solid. Yield: 0.1 g (35%). LC-MS Calculated. for $C_{19}H_{24}N_8O$ is 380.20; Observed: 381.35 $[M+H]^+$. $^1$H NMR (400 MHz, DMSO-$D_6$): δ 8.10 (bs, 2H), 7.65 (d, J=2.0 Hz, 1H), 6.63 (t, J=5.2 Hz, 1H), 6.07 (s, 1H), 4.59 (t, J=5.2 Hz, 1H), 4.54-4.47 (m, 1H), 3.61-3.56 (m, 2H), 3.41-3.37 (m, 2H), 2.84-2.77 (m, 3H), 2.34-2.27 (m, 1H), 2.22-2.18 (m, 4H), 1.96 (s, 3H), 1.83-1.76 (m, 1H), 1.63-1.53 (m, 1H). HPLC: 10.864 min; 98.31%, Column: INT ODS 3V-C18 (4.6*250) mm, 5μ, Mobile phase A: 0.1% Formic acid in water Mobile phase B: Acetonitrile.

The racemic compound Example 103 (7 g) was subjected to chiral separation by SFC {The sample was dissolved in ~115 mL of Tetrahydrofuran:Methanol (1:1)}, Column: Chiral Pak IG (250*21) mm, 5.0 μm; Mobile phase 72:28 (A:B). A=Liquid $CO_2$, B=0.1% Isopropyl amine in Isopropyl alcohol:Acetonitrile (1:1), Flow rate: 25.2 mL/min; Wavelength 254 nm to yield 2.89 g of peak 1; Example 104a; $[\alpha]_D$=+42.97°, c=0.101, MeOH) and 2.28 g of peak 2, Example 104a; $[\alpha]_D$=−35.41°, c=0.101, MeOH) as off-white solids, respectively. Absolute stereochemistry of the chiral center is unknown.

Peak-1; Example 104a; (+)-7-amino-5-((2-(1-(2-(hydroxymethyl) cyclobutyl)-1H-pyrazol-3-yl) ethyl) amino)-2,3-dimethylpyrazolo[1,5-a] pyrimidine-6-carbonitrile, LC-MS Calculated. for $C_{19}H_{24}N_8O$ is 380.20; Observed.: 381.35 $[M+H]^+$; 1H NMR (400 MHz, DMSO-$D_6$): δ 8.10 (bs, 2H), 7.65 (bs, 1H), 6.63 (m, 1H), 6.07 (bs, 1H), 4.59 (t, J=5.2 Hz, 1H), 4.52-4.98 (m, 1H), 3.60-3.58 (m, 2H), 3.41-3.39 (m, 2H), 2.84-2.81 (m, 3H), 2.32-2.22 (m, 5H), 1.96 (s, 3H), 1.80-1.78 (m, 1H), 1.60-1.55 (m, 1H). HPLC: 10.864 min; 98.31%, Column: INT ODS 3V-C18 (4.6*250) mm, 5μ Mobile phase A: 0.1% Formic acid in water Mobile phase B: Acetonitrile; Chiral HPLC: 99.37%; Rt=14.476 min; Chiral Pak IG (250*4.6) mm, 5μ Mobile phase: A: 0.1% DEA In Hex, B: IPA:MeOH (1:1) Isocratic mode: 80:20 Flow: 1.0 ml/min.

Peak-2; Example 104b; (−)-7-amino-5-((2-(1-(2-(hydroxymethyl) cyclobutyl)—1H-pyrazol-3-yl) ethyl) amino)-2,3-dimethylpyrazolo[1,5-a] pyrimidine-6-carbonitrile. LCMS Calculated. for $C_{19}H_{24}N_8O$ is 380.20; Observed. 381.35 $[M+H]^+$. $^1$H NMR (400 MHz, DMSO-$D_6$): δ 8.10 (bs, 2H), 7.65 (bs, 1H), 6.63 (m, 1H), 6.07 (bs, 1H), 4.59 (t, J=5.2 Hz, 1H), 4.52-4.98 (m, 1H), 3.60-3.58 (m, 2H), 3.41-3.39 (m, 2H), 2.84-2.81 (m, 3H), 2.32-2.22 (m, 5H), 1.96 (s, 3H), 1.80-1.78 (m, 1H), 1.60-1.55 (m, 1H). HPLC: 10.813 min; 99.40%, Column: INT ODS 3V-C18 (4.6*250) mm, 5μ Mobile phase A: 0.1% Formic acid in water Mobile phase B: Acetonitrile. Chiral HPLC: 99.35%; Rt=16.114 min; Column: Chiral Pak IG (250*4.6) mm, 5μ, Mobile phase: A: 0.1% DEA In Hex, B: IPA:MeOH (1:1), Isocratic mode: 80:20, Flow: 1.0 ml/min.

Example 105: 7-amino-5-((2-(6-(((2-hydroxyethyl) amino) methyl) pyridin-2-yl) ethyl) amino)-2,3-dimethylpyrazolo[1,5-a]pyrimidine-6-carbonitrile

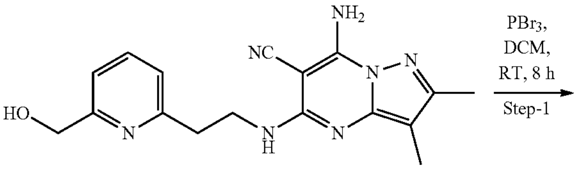

Example 44

-continued

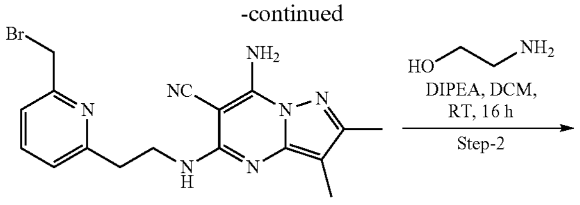

Example 105a

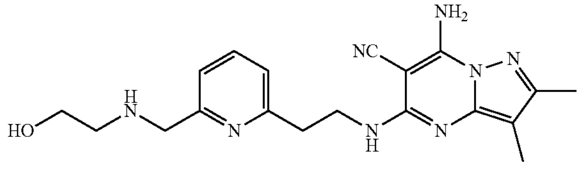

Example 105

Step-1. 7-amino-5-((2-(6-(bromomethyl) pyridin-2-yl) ethyl) amino)-2,3-dimethyl pyrazolo[1,5-a] pyrimidine-6-carbonitrile A solution of 7-amino-5-((2-(6-(hydroxymethyl) pyridin-2-yl) ethyl) amino)-2,3-dimethylpyrazolo[1,5-a] pyrimidine-6-carbonitrile Example 44 (210 mg, 0.622 mmol) in DCM (6 mL) was added $PBr_3$ (0.176 mL, 1.87 mmol) at 0° C. The reaction mixture was stirred at rt for 8 h. The progress of the reaction was monitored by TLC analysis. After completion, the reaction was quenched with sat. $NaHCO_3$ solution (30 mL) and extracted with ethyl acetate (30 mL×3). The combined organic layer was dried over anhydrous sodium sulphate and concentrated under reduced pressure to afford the title compound Example 105a as off-white solid. Yield: 0.16 g (64.25%). LCMS Calculated. for $C_{17}H_{18}BrN_7$ is 399.08; Obs. 402.30 [$M^+$+3].

Step-2: 7-amino-5-((2-(6-(((2-hydroxyethyl) amino) methyl) pyridin-2-yl) ethyl) amino)-2,3-dimethylpyrazolo[1,5-a] pyrimidine-6-carbonitrile To a stirred solution of 2-aminoethan-1-ol (29.3 mg, 0.480 mmol) in DCM (4 mL) were added DIPEA (0.280 mL, 1.20 mmol) and 7-amino-5-((2-(6-(bromomethyl) pyridin-2-yl) ethyl) amino)-2,3-dimethylpyrazolo[1,5-a] pyrimidine-6-carbonitrile Example 105a (160 mg 0.40 mmol) under inert atmosphere. The resulting mixture was stirred at rt for 16 h. The progress of the reaction was monitored by TLC analysis. After completion, reaction was quenched with water (20 mL) and extracted with DCM (50 mL×3). The combined organic layer was dried over anhydrous sodium sulphate and concentrated under reduced pressure. The crude was purified by reverse phase prep HPLC: YMC Triat C18 (250*20) mm, 5.0 μm; Mobile phase A: 10 mm Ammonium bicarbonate in water, B: Acetonitrile: Methanol (1:1) to afford the desired compound Example 105 as off-white solid. Yield: 61 mg (40%); LCMS Calculated. for $C_{19}H_{24}N_8O$ is 380.20; Observed. 381.35 $[M+H]^+$. $^1$HNMR (400 MHz, DMSO-$d_6$): δ 8.09 (bs, 2H), 7.67 (t, J=7.6 Hz, 1H), 7.26 (d, J=7.6 Hz, 1H), 7.14 (d, J=7.6 Hz, 1H), 6.84 (t, J=5.2 Hz, 1H), 4.48-4.46 (m, 1H), 3.81 (s, 2H), 3.70-3.66 (m, 2H), 3.49-3.45 (m, 3H), 3.03-2.97 (m, 2H), 2.62-2.59 (m, 2H), 2.22 (s, 3H), 1.96 (s, 3H). HPLC: 7.799 min; 98.16%, Column: INT ODS 3V-C18 (4.6*250) mm, 5μ; Mobile phase A: 0.1% Formic acid in water Mobile phase B: Acetonitrile.

Example 106: 7-amino-3-ethyl-5-((2-(1-(1-(((2-hydroxyethyl) amino) methyl) cyclopropyl)-1H-pyrazol-3-yl) ethyl) amino)-2-methylpyrazolo[1,5-a] pyrimidine-6-carbonitrile

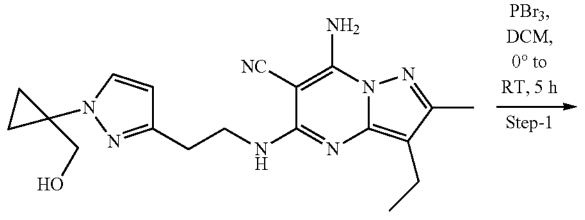

Example 39

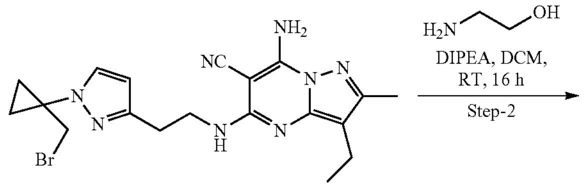

Example 106a

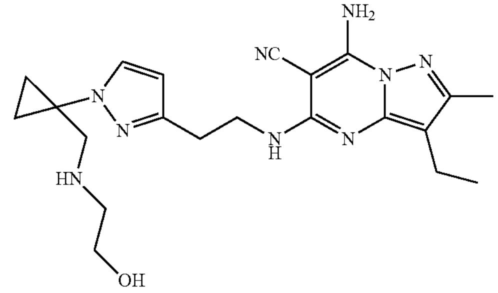

Example 106

Step-1: 7-amino-5-((2-(1-(1-(bromomethyl) cyclopropyl)-1H-pyrazol-3-yl) ethyl) amino)-3-ethyl-2-methylpyrazolo[1,5-a] pyrimidine-6-carbonitrile (Example 106a)

To a solution of 7-amino-3-ethyl-5-((2-(1-(1-(hydroxymethyl) cyclopropyl)-1H-pyrazol-3-yl) ethyl) amino)-2-methylpyrazolo[1,5-a] pyrimidine-6-carbonitrile Example 39 (500 mg, 1.31 mmol) in DCM (13 mL) was dropwise added $PBr_3$ (0.248 mL, 2.63 mmol) at 0° C. The reaction mixture was stirred at room temperature for 5 h. The progress of reaction was monitored by TLC analysis. After completion reaction mixture was cooled to 0° C. and quenched slowly with saturated sodium bicarbonate solution. The mixture was extracted with DCM (30 mL×3) and the combined organic layer was washed with brine, dried over anhydrous sodium sulphate, and concentrated under reduced pressure. Obtained solid was washed with n-pentane to afford the pure compound Example 106a as off-white solid. Yield: 390 mg (66.9%). LCMS Calculated. for $C_{19}H_{23}BrN_8$ is 442.12; Observed. 443.25 $[M+H]^+$.

Step-2: 7-amino-3-ethyl-5-((2-(1-(1-(((2-hydroxyethyl) amino) methyl) cyclopropyl)-1H-pyrazol-3-yl) ethyl) amino)-2-methylpyrazolo[1,5-a] pyrimidine-6-carbonitrile To a solution of 7-amino-5-((2-(1-(1-(bromomethyl) cyclopropyl)-1H-pyrazol-3-yl) ethyl) amino)-3-ethyl-2- methylpyrazolo[1,5-a] pyrimidine-6-carbonitrile Example 106a (200 mg, 0.451 mmol) in DCM (8 mL) were added DIPEA (0.236 mL, 1.35 mmol) and 2-aminoethan-1-ol (55.1 mg, 0.902 mmol) at RT. The resulting reaction mixture was stirred for 16 h. The progress of reaction was monitored by TLC analysis. After completion, the reaction was quenched with 10% NaOH solution (20 mL) and extracted with DCM (20 mL×3). The combined organic layer was washed with 10% NaOH solution (20 mL×6) followed by with brine. The organic layer was dried over anhydrous sodium sulphate and concentrated under reduced pressure. The crude material was purified by flash chromatography by eluting with 0-5% methanolic ammonia (7M) in DCM to afford the desired compound Example 106 as off-white solid. Yield: 50 mg (27%). LCMS Calculated. for $C_{21}H_{29}N_9O$ is 423.25; Observed. 424.40 $[M+H]^+$. $^1H$ NMR (400 MHz, DMSO-$D_6$): δ 8.08 (bs, 2H), 7.63 (m, 1H), 6.57-6.55 (m, 1H), 6.03 (m, 1H), 4.37 (t, J=4.8 Hz, 1H), 3.59-3.54 (m, 2H), 2.83-2.78 (m, 4H), 2.46-2.43 (m, 4H), 2.24 (s, 3H), 1.58 (bs, 1H), 1.13-1.07 (m, 6H), 0.94-0.91 (m, 2H). HPLC: 8.087 min; 98.52%, Column: INT ODS 3V-C18 (4.6*250) mm, 5μ; Mobile phase A: 0.1% Formic acid in water, Mobile phase B: Acetonitrile Flow: 1.0 mL/min.

Example 107: 7-amino-3-ethyl-5-((2-(1-(2-methoxyethyl)-2-oxo-1,2-dihydropyridin-3-yl) ethyl) amino)-2-methylpyrazolo[1,5-a] pyrimidine-6-carbonitrile

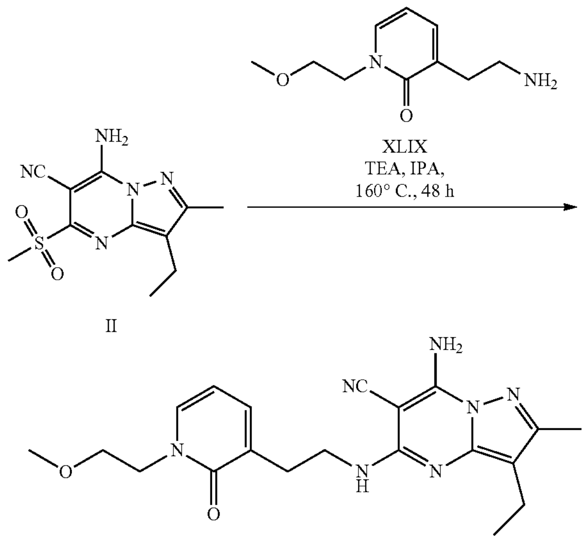

XLIX

II

Example 107

To a solution of 7-amino-3-ethyl-2-methyl-5-(methyl sulfonyl) pyrazolo[1,5-a] pyrimidine-6-carbonitrile II (0.12 g, 430 mmol) and 3-(2-aminoethyl)-1-(2-methoxyethyl) pyridin-2(1H)-one XLIX (0.253 g, 1.29 mmol) in isopropyl alcohol (4 mL) was added triethylamine (0.359 mL, 2.58 mmol) and the reaction mixture was stirred at 160° C. for 48 h. The progress of the reaction was monitored by TLC analysis. After the completion, the reaction mixture was quenched with water (50 mL) extracted with ethyl acetate (50 mL×3). The combined organic layer was dried over anhydrous sodium sulphate and concentrated under reduced pressure. The crude compound was purified by silica gel (230-400 mesh) column chromatography using 0-10% methanol in dichloromethane to afford the desired compound Example 107 as a yellow solid. Yield: 0.09 g, (53.0%); LCMS Calculated. for $C_{20}H_{25}N_7O_2$ is 395.21; Observed. 396.35 $[M+H]^+$. $^1$HNMR (400 MHz, DMSO-$D_6$): δ 8.05 (bs, 2H), 7.48 (q, J=1.6 Hz, 1H), 7.29 (d, J=5.2 Hz, 1H), 6.71 (t, J=5.2 Hz, 1H), 6.14 (t, J=6.4 Hz, 1H), 4.06 (t, J=5.6 Hz, 2H), 3.60-3.50 (m, 4H), 3.22 (s, 3H), 2.75 (t, J=6.4 Hz, 2H), 2.47 (m, 2H), 2.24 (s, 3H), 1.11 (t, J=7.6 Hz, 3H). HPLC: 10.54 min; 97.67%, Column: INT ODS 3V-C18 (4.6*250) mm, 5μ, Mobile phase A: 0.1% Formic acid in water; Mobile phase B: Acetonitrile; Flow: 1.0 mL/min Example 108: 7-amino-3-ethyl-5-((2-(1-(2-hydroxyethyl)-2-oxo-1,2-dihydropyridin-3-yl) ethyl) amino)-2-methylpyrazolo[1,5-a]pyrimidine-6-carbonitrile

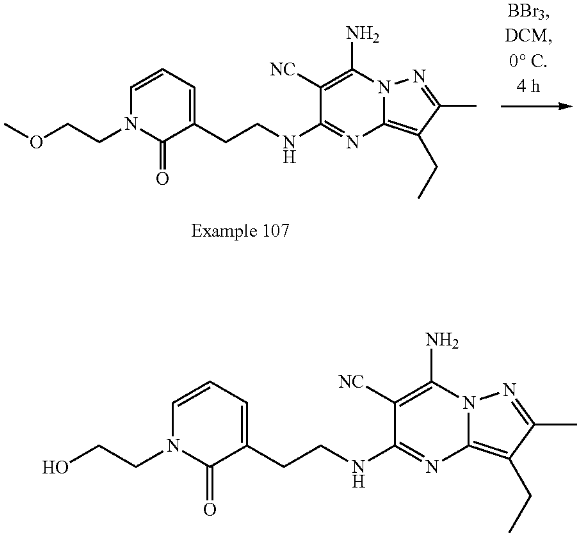

Example 107

Example 108

To a solution of 7-amino-3-ethyl-5-((2-(1-(2-methoxyethyl)-2-oxo-1,2-dihydropyridin-3-yl) ethyl) amino)-2-methylpyrazolo[1,5-a] pyrimidine-6-carbonitrile Example 107 (0.07 g, 0.18 mmol) in dichloromethane (4 mL) at 0° C. was added $BBr_3$ (0.025 mL, 0.27 mmol) and the reaction mixture was stirred at 0° C. for 4 h. The progress of the reaction was monitored by TLC analysis. After completion, the reaction mixture was quenched with $NaHCO_3$ (50 mL) and extracted with ethyl acetate (50 mL×3). The combined organic layer was dried over anhydrous sodium sulphate and concentrated under reduced pressure. The crude compound was purified by silica gel (230-400 mesh) column chromatography with 0-10% methanol in dichloromethane to afford the desired title product Example 108 as off-white solid. Yield: 0.05 g, (73.0%); LCMS Calculated. for $C_{19}H_{23}N_7O_2$ is 381.19; Observed: 382.25 $[M+H]^+$. $^1H$ NMR (400 MHz, DMSO-$D_6$): δ 8.05 (s, 2H), 7.48 (d, J=6.4 Hz, 1H), 7.29 (d, J=6.4 Hz, 1H), 6.73 (t, J=4.8 Hz, 1H), 6.14 (t, J=6.8 Hz, 1H), 4.85 (t, J=5.6 Hz, 1H), 3.95 (t, J=5.2 Hz, 1H), 3.66-3.62 (q, J=10.8 Hz, 2H), 3.54-3.49 (q, J=6.4 Hz, 2H), 2.75 (t, J=6.4 Hz, 2H), 2.48-2.42 (m, 3H), 2.24 (s, 3H), 1.11 (t, J=7.6 Hz, 3H). HPLC:98.68%.

Example 109: 7-amino-5-((2-(1-(2-(amino methyl) cyclobutyl)-1H-pyrazol-3-yl) ethyl) amino)-3-ethyl-2-methylpyrazolo[1,5-a]pyrimidine-6-carbonitrile

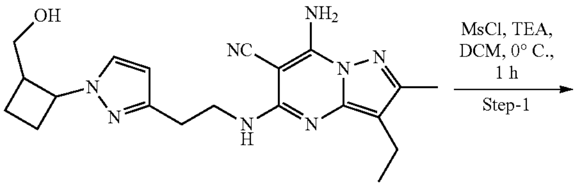

Example 78

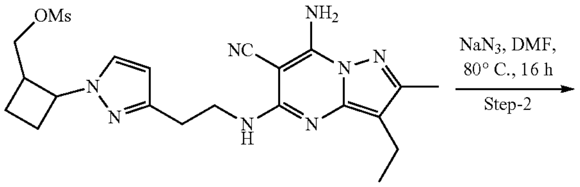

Example 109a

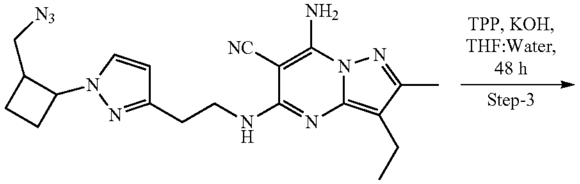

Example 109b

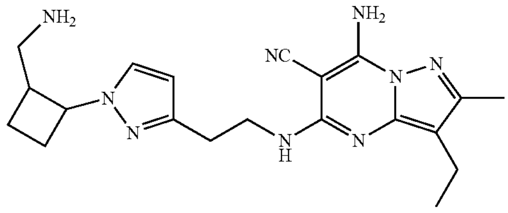

Example 109

Step-1: (2-(3-(2-((7-amino-6-cyano-3-ethyl-2-methylpyrazolo[1,5-a] pyrimidin-5-yl) amino) ethyl)-1H-pyrazol-1-yl) cyclobutyl) methyl methane sulfonate (Example 109a)

To a solution of 7-amino-3-ethyl-5-((2-(1-(2-(hydroxymethyl) cyclobutyl)-1H-pyrazol-3-yl) ethyl) amino)-2-methylpyrazolo[1,5-a] pyrimidine-6-carbonitrile Example 78 (2.0 g, 5.07 mmol) in dichloromethane (50 mL) at 0° C. were added triethylamine (3.53 mL, 25.3 mmol) and mesyl-Cl (0.474 mL, 6.08 mmol). The reaction mixture was stirred at 0° C. for 1 h. After the completion, the reaction was quenched with water (50 mL) and extracted with dichloromethane (50 mL*3). The combined organic layer was dried over $Na_2SO_4$, filtered, and concentrated under reduced pressure. The crude compound was purified by silica gel (60-120 mesh) column chromatography with ethyl acetate in n-hexane (0-10%) to afford the desired product Example 109a as a pale-yellow viscous liquid. Yield: 2.3 g, (95.83%).

Step-2: 7-amino-5-((2-(1-(2-(azidomethyl) cyclobutyl)-1H-pyrazol-3-yl) ethyl) amino)-3-ethyl-2-methylpyrazolo[1,5-a] pyrimidine-6-carbonitrile (Example 109b)

To a solution of (2-(3-(2-((7-amino-6-cyano-3-ethyl-2-methylpyrazolo[1,5-a] pyrimidin-5-yl) amino) ethyl)-1H-pyrazol-1-yl) cyclobutyl) methyl methane sulfonate Example 109a (2.30 g, 4.87 mmol) in DMF (20 mL) was added sodium azide (1.27 g, 19.5 mmol) and the reaction mixture was stirred at 80° C. for 16 h. After the completion of the reaction, the reaction mixture was cooled to rt, quenched with water (100 mL) and extracted with ethyl acetate (3×100 mL). The combined organic layer was dried over anhydrous $Na_2SO_4$, filtered and concentrated under reduced pressure. The crude compound was purified by silica gel (230-400 mesh) column chromatography with ethyl acetate in hexane (0-20%) to afford the desired product Example 109b as a pale-yellow viscous liquid. Yield:2 g, (98.0%). $^1$H NMR (400 MHz, DMSO-$D_6$): δ 8.10 (s, 2H), 7.95 (s, 1H), 7.68 (d, J=2 Hz, 1H), 6.64 (t, J=5.2 Hz, 1H), 6.09 (d, J=2 Hz, 1H), 4.53 (d, J=8.4 Hz, 1H), 3.61-3.56 (q, J=6.8 Hz, 2H), 3.45-3.43 (q, J=42 Hz, 2H), 2.99 (m, 1H), 2.83 (t, J=6.8 Hz, 2H), 2.47-2.43 (m, 2H), 2.39-2.24 (m, 5H), 1.98-1.91 (m, 1H), 1.58-1.53 (m, 1H), 1.18-1.10 (m, 3H).

Step-3: 7-amino-5-((2-(1-(2-(amino methyl) cyclobutyl)-1H-pyrazol-3-yl) ethyl) amino)-3-ethyl-2-methylpyrazolo[1,5-a] pyrimidine-6-carbonitrile To a solution of 7-amino-5-((2-(1-(2-(azidomethyl) cyclobutyl)-1H-pyrazol-3-yl) ethyl) amino)-3-ethyl-2-methylpyrazolo[1,5-a] pyrimidine-6-carbonitrile Example 109b (2.0 g, 4.8 mmol) in tetrahydrofuran (2.5 mL) and $H_2O$ (0.5 mL) were added $Ph_3P$ (1.9 g, 7.2 mmol) and potassium hydroxide (0.27 g, 4.8 mmol). The reaction mixture was stirred at rt for 48 h. The progress of the reaction was monitored by TLC analysis. After the completion of the reaction, the reaction mixture was quenched with water (100 mL) and extracted with ethyl acetate (3×100 mL). The combined organic layer was dried over anhydrous $Na_2SO_4$, filtered and concentrated under reduced pressure. The crude compound was purified by silica gel (60-120 mesh) column chromatography with methanol in dichloromethane (0-10%) to afford the desired product Example 109 as off-white solid. Yield:1.1 g, (57.89%); LCMS calculated for $C_{20}H_{27}N_9$ is 393.24; Observed: 394.40 [M+H]+. $^1$HNMR (400 MHz, DMSO-$d_6$): δ 7.68 (d, J=1.6 Hz, 1H), 6.64 (t, J=5.2 Hz, 1H), 6.06 (d, J=2 Hz, 1H), 4.45 (q, J=8 Hz, 5H), 3.58 (q, J=6 Hz, 2H), 2.81 (t, J=14 Hz, 2H), 2.66-2.55 (m, 3H), 2.47-2.43 (m, 2H), 2.33-2.25 (m, 5H), 1.83-1.73 (m, 1H), 1.52-1.48 (m, 1H), 1.12 (t, J=7.6 Hz, 3H). HPLC: 99.69%.

Example 110: 7-amino-3-ethyl-5-((2-(1-(3-hydroxypropyl)-1H-pyrazol-5-yl) ethyl) amino)-2-methylpyrazolo[1,5-a]pyrimidine-6-carbonitrile

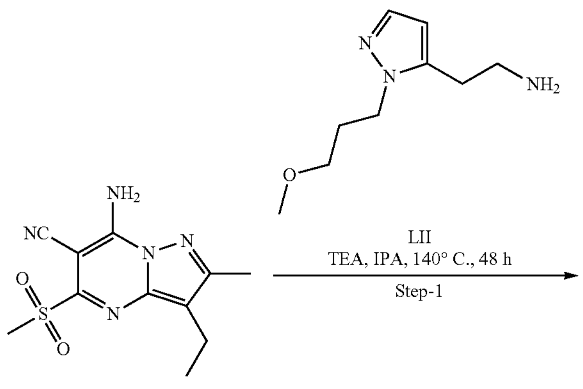

II

-continued

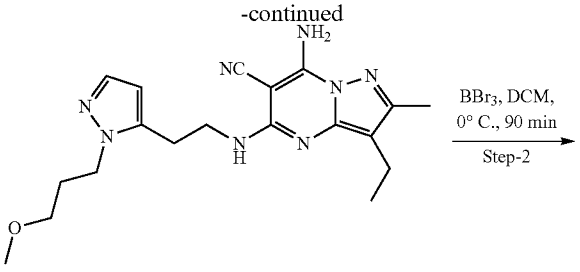

Example 110a

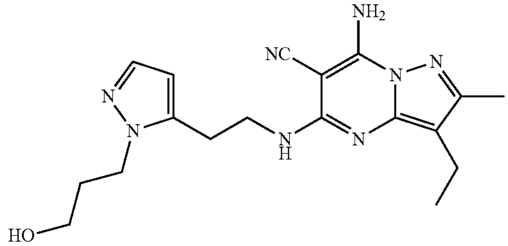

Example 110

Step-1: 7-amino-3-ethyl-5-((2-(1-(3-methoxypropyl)-1H-pyrazol-5-yl) ethyl) amino)-2-methylpyrazolo[1,5-a] pyrimidine-6-carbonitrile To a solution of 2-(1-(3-methoxypropyl)-1H-pyrazol-5-yl) ethan-1-amine LII (0.25 g, 0.90 mmol) and 7-amino-3-ethyl-2-methyl-5-(methyl sulfonyl) pyrazolo[1,5-a] pyrimidine-6-carbonitrile II (0.33 g, 1.8 mmol) in isopropyl alcohol (20 mL) was added triethylamine (0.75 mL, 5.4 mmol) and the reaction mixture was stirred at 140° C. for 48 h. The progress of the reaction was monitored by TLC analysis. After the completion of the reaction, added water (25 mL) and extracted with ethyl acetate (25 mL×3). The combined organic layer was washed with brine (20 mL), dried over anhydrous sodium sulphate, and concentrated under reduced pressure to get crude material. The crude compound was purified by silica gel (230-400 mesh) column chromatography with methanol in dichloromethane (0-5%) to afford the desired product Example 110a as off-white solid. Yield:0.14 g, (41.0%); LCMS Calculated. for $C_{19}H_{26}N_8O$ is 382.22; Observed. 383.35 $[M+H]^+$; $^1H$ NMR (400 MHz, DMSO-$D_6$): δ 8.12 (s, 2H), 7.34 (d, J=1.6 Hz 1H), 6.86 (t, J=5.6 Hz 1H), 6.06 (s, 1H), 4.10 (t, J=6.8 Hz. 3H), 3.58-3.53 (m, 2H), 3.16 (s, 3H), 2.93 (t, J=7.2 Hz, 2H), 2.50-2.44 (m, 2H), 2.25 (s, 3H), 2.25-1.94 (m, 3H), 1.12 (t, J=8.0 Hz, 3H).

Step 2: 7-amino-3-ethyl-5-((2-(1-(3-hydroxypropyl)-1H-pyrazol-5-yl) ethyl) amino)-2-methylpyrazolo[1,5-a] pyrimidine-6-carbonitrile To a solution of 7-amino-3-ethyl-5-((2-(1-(3-methoxypropyl)-1H-pyrazol-5-yl) ethyl) amino)-2-methylpyrazolo[1,5-a] pyrimidine-6-carbonitrile Example 110a (0.140 g, 0.37 mmol) in dichloromethane (4 mL) at 0° C. was added boron tribromide (0.668 mL, 0.55 mmol). The reaction mixture was stirred at rt for 90 min. The progress of the reaction was monitored by TLC analysis. After the completion of the reaction, added water (5 mL) and extracted with dichloromethane (10 mL*3). The combined organic layer was washed with brine (20 mL), dried over anhydrous sodium sulphate, and concentrated to afford the crude compound. The crude compound was purified by (230-400 mesh) column chromatography with methanol in dichloromethane (0-5%) to afford the desired product Example 110 as off-white solid. Yield:0.035 g, (26.0%); LCMS Calculated. for $C_{18}H_{24}N_8O$ is 368.21; Observed: 369.35 $[M+H]^+$. $^1H$ NMR (400 MHz, DMSO-$D_6$): δ 8.12 (s, 2H), 7.32 (d, J=1.2 Hz 1H), 6.84 (s, 1H), 6.06 (d, J=1.6 Hz, 1H), 4.53 (t, J=4.8 Hz, 1H), 4.12 (t, J=7.2 Hz, 2H), 3.56 (m, 2H), 3.38-3.36 (m, 2H), 2.94 (d, J=7.6 Hz, 2H), 2.47-2.45 (m, 2H), 2.25 (s, 3H), 1.875 (m, 2H), 1.12 (t, J=7.2 Hz, 3H): HPLC: 99.05%.

Example 111: 7-amino-3-ethyl-5-((2-(1-(3-hydroxypropyl)-1H-pyrazol-3-yl) ethyl) amino)-2-methylpyrazolo[1,5-a]pyrimidine-6-carbonitrile

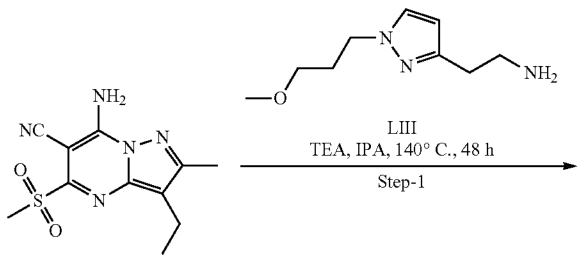

II

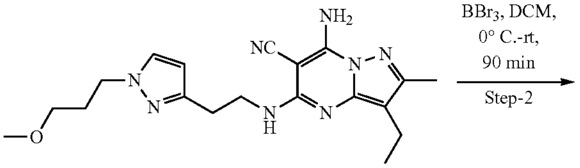

Example 111a

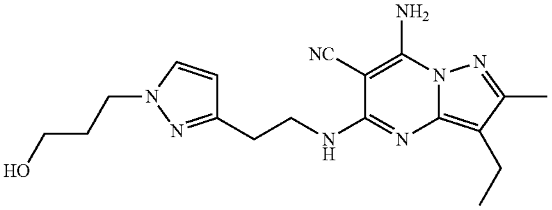

Example 111

Step-1: 7-amino-3-ethyl-5-((2-(1-(3-methoxypropyl)-1H-pyrazol-3-yl) ethyl) amino)-2-methylpyrazolo[1,5-a]pyrimidine-6-carbonitrile (Example 111a)

To a solution of 2-(1-(3-methoxypropyl)-1H-pyrazol-3-yl) ethan-1-amine LIII (0.275 g, 0.985 mmol) and 7-amino-3-ethyl-2-methyl-5-(methyl sulfonyl) pyrazolo[1,5-a] pyrimidine-6-carbonitrile II (0.36 g, 1.97 mmol) in isopropyl alcohol (25 mL) was added triethylamine (0.823 mL, 5.91 mmol) and the reaction mixture was stirred at 140° C. for 48 h. The progress of the reaction was monitored by TLC analysis. Reaction mixture was cooled to rt, added water (30 mL) and extracted with ethyl acetate (30 mL*3). The combined organic layer was washed with brine (20 mL), dried over anhydrous sodium sulphate, and concentrated under reduced pressure to get the crude material. The crude compound was purified by preparative HPLC using column: YMC, Triart, C18 (20×250) mm 5 mic. Channel A: 0.1% formic acid in water and channel B: acetonitrile to afford the desired product Example 111a as an off-white solid. Yield: 0.25 g, (66.0%); LCMS calculated for $C_{19}H_{26}N_8O$ is 382.22; Observed: 383.35 $[M+H]^+$. $^1$HNMR (400 MHz, DMSO-$d_6$): δ 8.09 (s, 2H), 7.58 (s, 1H), 6.63 (d, J=4.0 Hz, 1H), 6.06 (s, 1H), 4.07 (t, J=8.0 Hz, 2H), 3.58 (q, J=4.0 Hz, 2H), 3.33-3.21 (m, 5H), 2.82 (t, J=8.0 Hz, 2H), 2.50-2.25 (m, 5H), 1.97 (q, J=8.0 Hz, 2H), 1.12 (t, J=8.8 Hz, 3H). HPLC: 12.384 min; 99.71%, Column: INT ODS 3V-C18 (4.6*250) mm, 5μ, Mobile Phase A: 0.1% Formic acid in water, Mobile Phase B: Acetonitrile.

Step-2: 7-amino-3-ethyl-5-((2-(1-(3-hydroxypropyl)-1H-pyrazol-3-yl) ethyl) amino)-2-methylpyrazolo[1,5-a] pyrimidine-6-carbonitrile To a solution of 7-amino-3-ethyl-5-((2-(1-(3-methoxypropyl)-1H-pyrazol-3-yl) ethyl) amino)-2-methylpyrazolo[1,5-a] pyrimidine-6-carbonitrile Example 111a (0.11 g, 0.29 mmol) in dichloromethane (4 mL) at 0° C. was added boron tribromide (0.052 mL, 0.43 mmol) and stirred at rt for 90 min. The progress of the reaction was monitored by TLC analysis. After the completion of the reaction, the reaction mixture was quenched with water (10 mL) and extracted with dichloromethane (3×20 mL). The combined organic layer was washed with brine (20 mL), dried over anhydrous sodium sulphate, and concentrated to afford the crude compound. The crude compound was purified by silica gel (230-400 mesh) column chromatography with methanol in dichloromethane (0-3%) to afford the desired product Example 111 as off-white solid. Yield: 0.05 g, (47.0%); LCMS Calculated. for $C_{18}H_{24}N_8O$ is 368.21 Observed. 369.35 $[M+1]^+$. $^1$H NMR (400 MHz, DMSO-$D_6$): δ 8.10 (s, 2H), 7.58 (s, 1H), 6.64 (s, 1H), 6.05 (s, 1H), 4.54 (t, J=5.2 Hz, 1H), 4.08 (t, J=6.8 Hz, 2H), 3.57 (d, J=6 Hz, 2H), 3.37 (m, 2H), 2.82 (t, J=6.8 Hz, 2H), 2.47-2.43 (m, 2H), 2.25 (s, 3H), 1.89 (t, J=8.0 Hz, 2H), 1.12 (t, J=7.6 Hz, 3H). HPLC: 98.29%.

Example 112: 7-amino-3-chloro-5-((2-(1-(1-(2-hydroxyethyl) cyclopropyl)-1H-pyrazol-3-yl) ethyl) amino)-2-methylpyrazolo[1,5-a] pyrimidine-6-carbonitrile

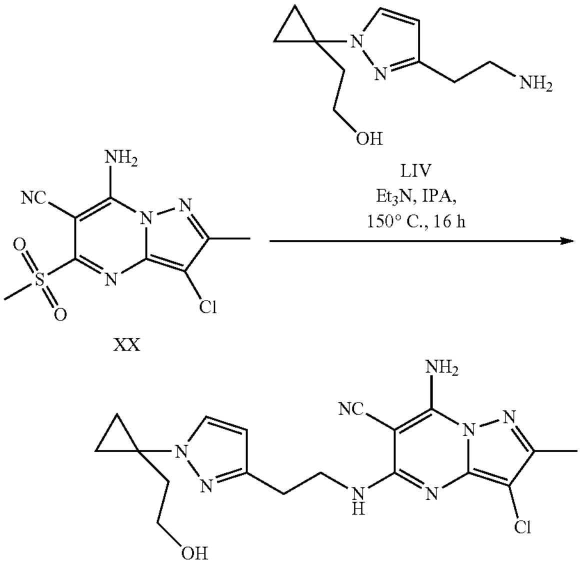

XX

Example 112

To a solution of 7-amino-3-chloro-2-methyl-5-(methyl sulfonyl) pyrazolo[1,5-a] pyrimidine-6-carbonitrile XX (0.3 g, 1.05 mmol) and 2-(1-(3-(2-aminoethyl)-1H-pyrazol-1-yl) cyclopropyl)ethan-1-ol LIV (0.41 g, 2.10 mmol) in isopropyl alcohol (10 mL) was added triethylamine (0.878 mL, 6.30 mmol) and the reaction mixture was stirred at 150° C. for 16 h. The progress of the reaction was monitored by TLC analysis. After the completion, the reaction mixture was cooled to rt, diluted with water (50 mL) and extracted with ethyl acetate (20 mL×3). The combined organic layer was dried over anhydrous $Na_2SO_4$, filtered and concentrated under reduced pressure. The crude compound was purified by silica gel (230-400 mesh) column chromatography using ethyl acetate in n-hexane (0-70%) to afford the desired product Example 112 as an off-white solid. Yield: 0.16 g, (38.0%); LCMS Calculated. for $C_{18}H_{21}ClN_8O$ is 400.15; Observed. 401.30 $[M+H]^+$. $^1$H NMR (400 MHz, DMSO-$D_6$): δ 8.39 (s, 2H), 7.62 (s, 1H), 6.92 (bs, 1H), 6.05 (s, 1H), 4.37 (t, J=4.8 Hz, 1H), 3.61-3.58 (m, 2H), 3.28-3.26 (m, 2H), 2.81 (t, J=6.8 Hz, 2H), 2.28 (s, 3H), 1.87 (t, J=7.2 Hz, 2H), 1.1 (s, 2H), 1.0 (s, 2H). HPLC: 11.102 min; 99.36%, Column: INT ODS 3V-C18 (4.6*250) mm, 5μ; Mobile phase A: 0.1% Formic acid in water; Mobile phase B: Acetonitrile; Flow: 1.0 mL/min.

Example 113: 7-amino-3-ethyl-5-((2-(1-(3-hydroxypropyl)-2-oxo-1,2-dihydropyridin-3-yl) ethyl) amino)-2-methylpyrazolo[1,5-a]pyrimidine-6-carbonitrile

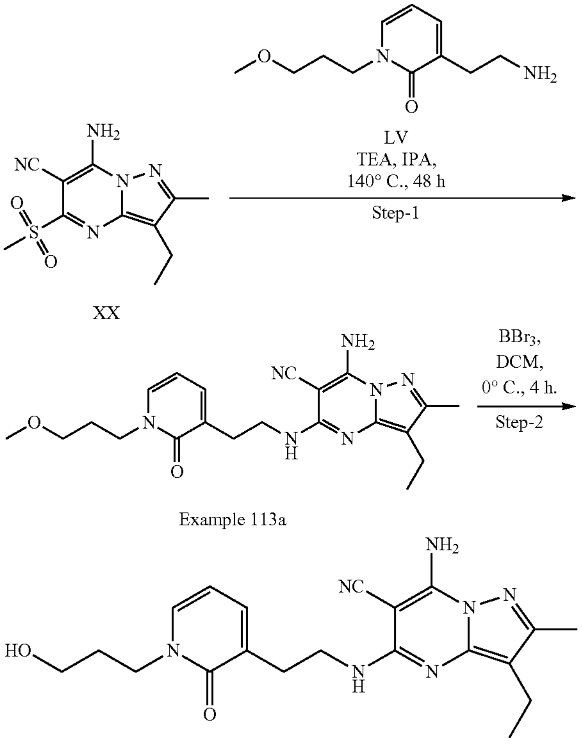

XX

Example 113a

Example 113

Step-1: 7-amino-3-ethyl-5-((2-(1-(3-methoxypropyl)-2-oxo-1,2-dihydropyridin-3-yl) ethyl) amino)-2-methylpyrazolo[1,5-a]pyrimidine-6-carbonitrile To a stirred solution of 7-amino-3-ethyl-2-methyl-5-(methyl sulfonyl) pyrazolo[1,5-a] pyrimidine-6-carbonitrile XX (300 mg, 1.07 mmol) in IPA (6 mL) were added TEA (0.898 mL, 6.44 mmol) and 3-(2-aminoethyl)-1-(3-methoxypropyl) pyridin-2(1H)-one LV (339 mg, 1.61 mmol) in a sealed tube. The reaction mixture was stirred at 140° C. for 48 h. The progress of the reaction was monitored by TLC analysis. After completion, the reaction was diluted with water (50 mL) and the resulting mixture was extracted with ethyl acetate (3×50 mL). The combined organic layer was dried over anhydrous sodium sulphate and concentrated under reduced pressure. The crude compound was purified by flash column chromatography (silica gel, 230-400) using 0-2% methanol in DCM to afford the desired product Example 113a as an off-white solid. Yield: 170 mg (38.7%); LCMS Calculated. for $C_{21}H_{27}N_7O_2$ is 409.22; Observed.: 410.35 $[M+H]^+$. $^1H$ NMR (400 MHz, DMSO-$D_6$): δ 8.05 (bs, 2H), 7.49 (d, J=6.4 Hz, 1H), 7.28 (d, J=6.4 Hz, 1H), 6.69 (bs, 1H), 6.15 (t, J=6.4 Hz, 1H), 3.92 (d, J=6.8 Hz, 2H), 3.52 (d, J=5.2 Hz, 2H), 3.29 (s, 2H), 3.21 (s, 3H), 2.74 (bs, 2H), 2.45-2.33 (m, 2H), 2.24 (s, 3H), 1.88 (d, J=6.0 Hz, 2H), 1.10 (t, J=7.2 Hz, 3H). HPLC: 10.741 min; 97.134%, Column: INT ODS 3V-C18 (4.6*250) mm, 5μ Mobile phase A: 0.1% Formic acid in water Mobile phase B: Acetonitrile, Flow: 1.0 ml/min:

Step-2: 7-amino-3-ethyl-5-((2-(1-(3-hydroxypropyl)-2-oxo-1,2-dihydropyridin-3-yl) ethyl) amino)-2-methylpyrazolo[1,5-a] pyrimidine-6-carbonitrile A stirred solution of 7-amino-3-ethyl-5-((2-(1-(3-methoxypropyl)-2-oxo-1,2-dihydropyridin-3-yl) ethyl) amino)-2-methylpyrazolo[1,5-a] pyrimidine-6-carbonitrile Example 113a (120 mg, 0.293 mmol) in DCM (10 mL) was cooled to 0° C. and dropwise added $BBr_3$ (55.4 μL, 0.586 mmol) under $N_2$ atmosphere. The resulting reaction mixture was stirred at 0° C. for 4 h. Progress of the reaction was monitored by TLC analysis. After completion, the reaction mixture was quenched with water (50 mL) and the resulting mixture was extracted with DCM (50 mL×3). The combined organic layer was dried over anhydrous sodium sulphate and concentrated under reduced pressure. The compound was purified by flash column chromatography (silica gel, 230-400) using 0-5% methanol in DCM to afford the desired compound Example 113 as an off-white solid. Yield: 21 mg (30%); LCMS Calculated. for $C_{20}H_{25}N_7O_2$ is 395.21; Observed.: 396.30 $[M+H]^+$. $^1H$ NMR (400 MHz, DMSO-$D_6$): δ 8.05 (bs, 2H), 7.51 (d, J=6.0 Hz, 1H), 7.28 (d, J=6.4 Hz, 1H), 6.71 (d, J=5.2 Hz, 1H), 4.58 (d, J=5.2 Hz, 1H), 3.94 (d, J=6.8 Hz, 2H), 3.52 (q, J=5.6 Hz, 2H), 3.41-3.36 (m, 2H), 2.74 (d, J=6.4 Hz, 2H), 2.47-2.42 (m, 2H), 2.24 (s, 3H), 1.81-1.75 (m, 2H), 1.11 (t, J=7.2 Hz, 3H). HPLC: 9.708 min; 99.24%, Column: INT ODS 3V-C18 (4.6*250) mm, 5μ, Mobile phase A: 0.1% Formic acid in water Mobile phase B: Acetonitrile, Flow: 1.0 mL/min.

Example 114: 7-amino-3-chloro-5-((2-(1-(2-(hydroxymethyl) cyclopentyl)-1H-pyrazol-3-yl) ethyl) amino)-2-methylpyrazolo[1,5-a]pyrimidine-6-carbonitrile

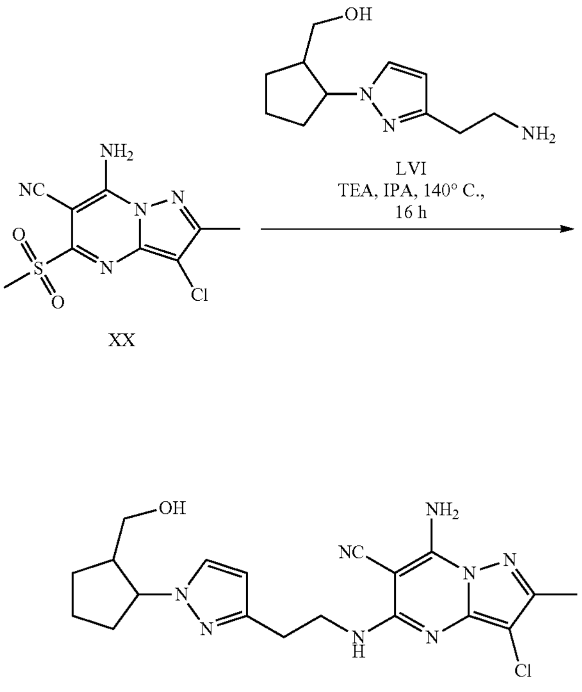

XX

Example 114

In a seal tube 7-amino-3-chloro-2-methyl-5-(methyl sulfonyl) pyrazolo[1,5-a] pyrimidine-6-carbonitrile (0.675 g, 2.36 mmol) and (2-(3-(2-aminoethyl)-1H-pyrazol-1-yl) cyclopentyl) methanol (0.89 g, 4.3 mmol) were dissolved in IPA (75 mL) at rt under inert atmosphere. To this solution TEA (1.98 mL, 14.2 mmol) was added and the resulting reaction mixture was stirred at 140° C. for 16 h. The progress of the reaction was monitored by TLC analysis. After completion, reaction mixture was cooled to room temperature, diluted with water (75 mL), and extracted with ethyl acetate (50 mL×3). The combined organic layer was washed with brine, dried over anhydrous sodium sulphate, and concentrated under reduced pressure to get crude material. The crude material was subjected to silica gel (230-400) column chromatography purification (Biotage) using 0-10% methanol in DCM to afford the desired compound as an off-white solid. Yield: 0.64 g (64.8%); LCMS Calculated. for $C_{19}H_{23}ClN_8O$ is 414.17; Observed.: 415.25 $[M+H]^+$. $^1H$ NMR (400 MHz, DMSO-$D_6$): δ 8.39 (bs, 2H), 7.62 (d, J=2.0 Hz, 1H), 6.95 (t, J=5.2 Hz, 1H), 6.07 (d, J=2.0 Hz, 1H), 4.56 (t, J=5.2 Hz, 1H), 4.35 (q, J=7.6 Hz, 1H), 3.63-3.58 (m, 2H), 3.39-3.34 (m, 1H), 3.32-3.25 (m, 1H), 2.84 (t, J=7.2 Hz, 2H), 2.31-2.25 (m, 4H), 2.05-1.93 (m, 2H), 1.91-1.82 (m, 1H), 1.80-1.72 (m, 1H), 1.65-1.55 (m, 1H), 1.51-1.42 (m, 1H). HPLC: 11.807 min; 98.02%, INT ODS 3V-C18 (4.6*250) mm, 5μ; Mobile phase A: 0.1% Formic acid in water, Mobile phase B: Acetonitrile; Flow: 1.0 mL/min: Chiral HPLC: Peak-1: 26.237 min, (48.94%); Peak-2: 28.814 min (51.06%); Chiral Pak IA (250*4.6) mm, 5μ Mobile phase: A: 0.1% DEA In n-Hex, B: EtOH (90:10) Flow: 1.0 mL/min.

Example 115: 7-amino-3-ethyl-5-((2-(1-(2-(hydroxymethyl) cyclopentyl)-1H-pyrazol-3-yl) ethyl) amino)-2-methylpyrazolo[1,5-a]pyrimidine-6-carbonitrile

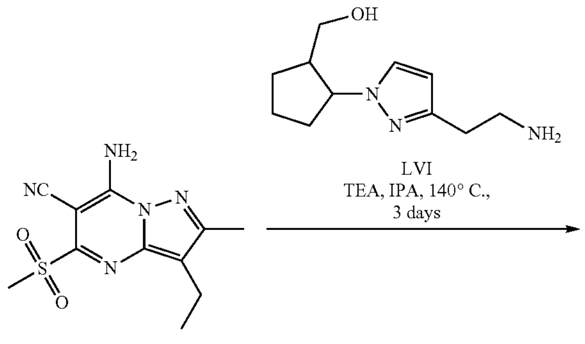

II

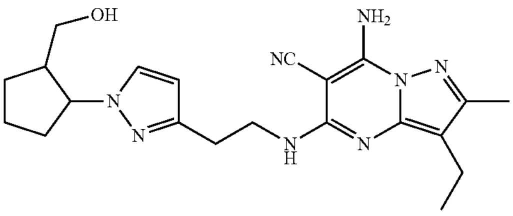

Example 115

To a stirred solution of 7-amino-3-ethyl-2-methyl-5-(methyl sulfonyl) pyrazolo[1,5-a] pyrimidine-6-carbonitrile II (275 mg, 0.985 mmol) in isopropanol (25 mL) were added (2-(3-(2-aminoethyl)-1H-pyrazol-1-yl) cyclopentyl) methanol LVI (412 mg, 1.97 mmol) and TEA (0.823 mL, 5.91 mmol) under inert atmosphere. The resulting reaction mixture was stirred at 140° C. for 3 days and the progress of the reaction was monitored by TLC analysis. After completion, reaction mixture was cooled to room temperature, diluted with water (30 mL), and extracted with ethyl acetate (30 mL×3). The combined organic layer was washed with brine, dried over anhydrous sodium sulphate, filtered, and concentrated under vacuum to get the crude. The crude was purified by combi flash silica gel (230-400) column chromatography using 0-3% methanol in DCM to afford the desired compound Example 115 as off-white solid. Yield: 0.18 g (44.8%); LCMS Calculated. for $C_{21}H_{28}N_8O$ is 408.24; Observed.: 409.40 $[M+H]^+$. $^1H$ NMR (400 MHz, DMSO-$D_6$): δ 8.09 (bs, 2H), 7.61 (bs, 1H), 6.61 (bs, 1H), 6.05 (s, 1H), 4.58 (t, J=5.2 Hz, 1H), 4.34 (q, J=7.6 Hz, 1H), 3.58-3.56 (m, 2H), 3.38-3.36 (m, 2H), 2.81 (t, J=7.2 Hz, 2H), 2.45-2.43 (m, 2H), 2.33-2.28 (m, 4H), 2.02-1.95 (m, 2H), 1.92-1.83 (m, 1H), 1.80-1.74 (m, 1H), 1.63-1.57 (m, 1H), 1.51-1.42 (m, 1H), 1.12 (t, J=7.2 Hz, 3H). HPLC: 12.204 min; 98.51%, INT ODS 3V-C18 (4.6*250) mm, 5μ; Mobile phase A: 0.1% Formic acid in water, Mobile phase B: Acetonitrile; Flow: 1.0 mL/min.

Example 116: 7-amino-3-(cyclopropyl methyl)-5-((2-(1-(2-(hydroxymethyl) cyclobutyl)-1H-pyrazol-3-yl) ethyl) amino)-2-methylpyrazolo[1,5-a]pyrimidine-6-carbonitrile

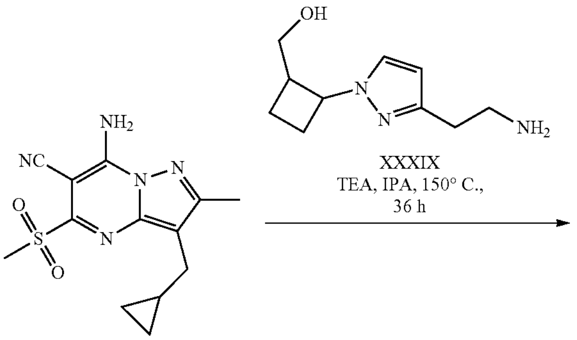

V

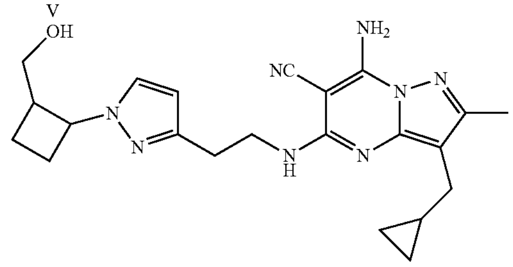

Example 116

To a stirred solution of 7-amino-3-(cyclopropyl methyl)-2-methyl-5-(methyl sulfonyl) pyrazolo[1,5-a] pyrimidine-6-carbonitrile V (0.3 g, 1 mmol), (2-(3-(2-aminoethyl)-1H-pyrazol-1-yl) cyclobutyl) methanol XXXIX (0.5 g, 2 mmol) in isopropanol (10 mL) was added triethylamine (0.8 mL, 6 mmol) at rt under inert atmosphere. The resulting mixture was stirred at 150° C. for 36 h. The progress of the reaction was monitored by TLC analysis. After completion, the reaction was cooled to rt, diluted with water (20 mL), and extracted with ethyl acetate (20 mL×3). The combined organic layer was washed with brine (20 mL), dried over anhydrous sodium sulphate, and concentrated under vacuum. Crude compound was purified by reverse phase prep-HPLC (YMC AQUA ODS (250×20) mm. 5.0μ; Mobile phase A: 10 mm ammonium bicarbonate in $H_2O$, Mobile phase B: ACN:MeOH (1:1)) to afford desired compound Example 116 as off-white solid. Yield: 110 mg (30%); LCMS Calculated. for $C_{22}H_{28}N_8O$ is 420.23; Observed.: 421.40 $[M+H]^+$. NMR (400 MHz, DMSO-$D_6$): δ 8.11 (bs, 2H), 7.64 (bs, 1H), 6.69 (t, J=5.2 Hz, 1H), 6.05 (bs, 1H), 4.59 (t, J=4.8 Hz, 1H), 4.50 (q, J=8.4 Hz, 1H), 3.60-3.54 (m, 2H), 3.42-3.34 (m, 2H), 2.84-2.80 (m, 3H), 2.40-2.18 (m, 7H), 1.79 (q, J=9.2 Hz, 1H), 1.63-1.56 (m, 1H), 0.95 (bs, 1H), 0.35 (d, J=7.6 Hz, 2H), 0.18-0.17 (m, 2H); HPLC: 12.449 min; 95.40%, INT ODS 3V-C18 (4.6*250) mm, 5μ; Mobile phase A: 0.1% Formic acid in water, Mobile phase B: Acetonitrile; Flow: 1.0 mL/min: Racemic compound: Chiral HPLC: Peak-1: 19.970 min; 49.75%, Peak-2: 23.164 min; 50.25%; Column: Chiral Pak IA (250*4.6) mm, 5μ; Mobile phase: A: 0.1% DEA In Hex, B: EtOH (90:10) Flow: 1.0 mL/min.

Example 117: 7-amino-3-chloro-5-((2-(1-(2-(((2-hydroxyethyl) amino) methyl) cyclobutyl)-1H-pyrazol-3-yl) ethyl) amino)-2-methylpyrazolo[1,5-a] pyrimidine-6-carbonitrile

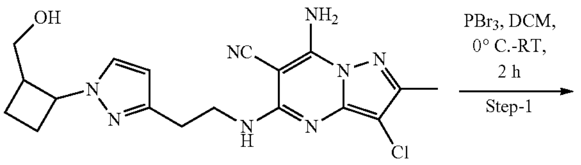

Example 67

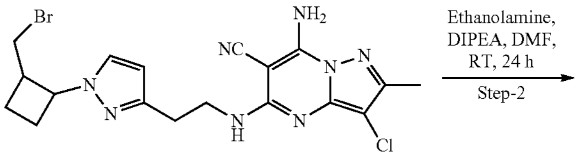

Example 117a

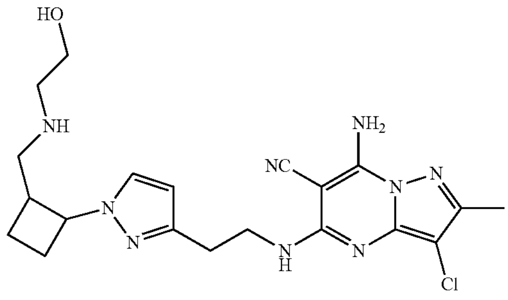

Example 117

Step-1: 7-amino-5-((2-(1-(2-(bromomethyl) cyclobutyl)-1H-pyrazol-3-yl) ethyl) amino)-3-chloro-2-methylpyrazolo[1,5-a] pyrimidine-6-carbonitrile (Example 117a)

To a solution of 7-amino-3-chloro-5-((2-(1-(2-(hydroxymethyl) cyclobutyl)-1H-pyrazol-3-yl) ethyl) amino)-2-methylpyrazolo[1,5-a] pyrimidine-6-carbonitrile Example 67 (0.2 g, 0.5 mmol) in dichloromethane (5 mL) at 0° C. was added $PBr_3$ (0.07 mL, 0.7 mmol) and the reaction mixture was stirred at rt for 2 h. The progress of the reaction was monitored by TLC analysis. After the completion of the reaction, the reaction mixture was diluted with $NaHCO_3$ (20 ml) and extracted with dichloromethane (20 mL×3). The combined organic layer was dried over anhydrous $Na_2SO_4$, filtered and concentrated under reduced pressure. The crude compound was purified by silica gel (230-400 mesh) column chromatography using ethyl acetate in n-hexane (0-70%) to afford the desired compound Example 117a as off-white solid. Yield: (0.08 g, 40%); LC-MS Calculated. for $C_{18}H_{20}BrClN_8$ is 462.07; Observed: 465.00 $[M+H]^+$. $^1H$ NMR (400 MHz, $CDCl_3$): δ 7.37 (d, J=4 Hz, 1H), 6.33 (s, 1H), 4.47 (d, J=8.8 Hz, 3H), 3.86 (q, J=4.0 Hz, 2H), 3.58-3.50 (m, 2H), 3.26 (d, J=8.0 Hz, 1H), 2.94 (t, J=4.0 Hz, 1H), 2.56 (t, J=12.0 Hz, 1H), 2.36 (d, J=10.8 Hz, 4H), 2.11 (d, J=12.0 Hz, 1H), 1.67-1.56 (m, J=8.0 Hz, 1H), 1.26 (s, 2H).

Step-2: 7-amino-3-chloro-5-((2-(1-(2-(((2-hydroxyethyl) amino) methyl) cyclobutyl)-1H-pyrazol-3-yl) ethyl) amino)-2-methylpyrazolo[1,5-a] pyrimidine-6-carbonitrile To a solution of 7-amino-5-((2-(1-(2-(bromomethyl) cyclobutyl)-1H-pyrazol-3-yl) ethyl) amino)-3-chloro-2-methylpyrazolo[1,5-a] pyrimidine-6-carbonitrile (0.08 g, 0.17 mmol) in N,N-dimethylformamide (5 mL) were added diisopropylethylamine (0.075 mL, 0.43 mmol) and 2-aminoethan-1-ol (16 mg, 0.26 mmol). The reaction mixture was stirred at rt for 24 h. The progress of the reaction was monitored by TLC analysis. After the completion of the reaction, the reaction mixture was diluted with water (20 mL) and extracted with ethyl acetate (20 mL×3). The combined organic layer was dried over anhydrous $Na_2SO_4$, filtered and concentrated under reduced pressure. The crude compound was purified by silica gel (230-400 mesh) column chromatography using ethyl acetate in n-hexane (0-70%) to afford the desired product Example 117 as off-white solid. Yield: (0.02 g, 26%); LCMS Calculated. for $C_{20}H_{26}ClN_9O$ is 443.19; Observed: 444.35 $[M+H]^+$. $^1$HNMR (400 MHz, DMSO-$d_6$): δ 8.60-8.30 (bs, 2H), 7.68 (s, 1H), 6.99 (s, 1H), 6.09 (s, 1H), 4.42 (s, 2H), 3.61 (s, 2H), 3.39-3.32 (d, J=8.0 Hz, 3H), 2.83 (s, 3H), 2.66 (d, J=8.0 Hz, 3H), 2.34-2.28 (m, 5H), 1.89 (d, J=12.0 Hz, 1H), 1.47 (d, J=8.0 Hz, 1H). HPLC: 8.168 min; 99.28%, Column: INT ODS 3V-C18 (4.6*250) mm, 5μ, Mobile phase A: 0.1% Formic acid in water; Mobile phase B: Acetonitrile; Flow: 1.0 mL/min.

Example 118: 7-amino-5-((2-(1-(2-(amino methyl) cyclopentyl)-1H-pyrazol-3-yl) ethyl) amino)-3-chloro-2-methylpyrazolo[1,5-a] pyrimidine-6-carbonitrile

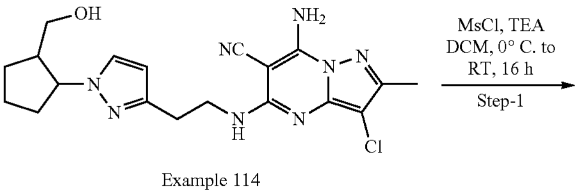

Example 114

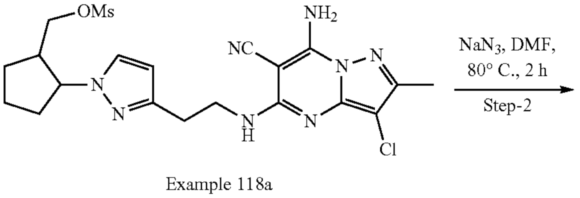

Example 118a

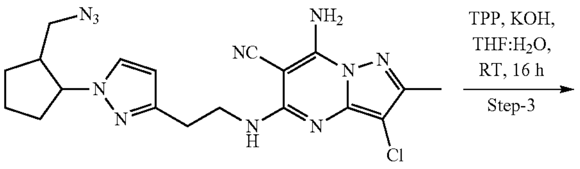

Example 118b

-continued

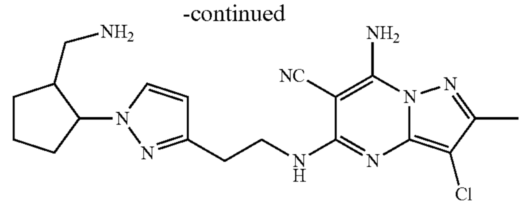

Example 118

Step-1: (2-(3-(2-((7-amino-3-chloro-6-cyano-2-methylpyrazolo[1,5-a] pyrimidin-5-yl) amino) ethyl)-1H-pyrazol-1-yl) cyclopentyl) methyl methane sulfonate (Example 118a)

To a solution of 7-amino-3-chloro-5-((2-(1-(2-(hydroxymethyl) cyclopentyl)-1H-pyrazol-3-yl) ethyl) amino)-2-methylpyrazolo[1,5-a] pyrimidine-6-carbonitrile Example 114 (0.45 g, 1.1 mmol) in dichloromethane (5 mL) was added triethylamine (0.68 mL, 4.9 mmol) and cooled to 0° C. This was followed by an addition of methane sulfonyl chloride (0.19 mL, 1.8 mmol) at 0° C. and the reaction mixture was stirred at rt for 16 h. The progress of the reaction was monitored by TLC analysis. After the completion, the reaction was quenched with water (10 mL) and extracted with dichloromethane (10 mL×3). The combined organic layer was washed with brine (10 mL), dried over anhydrous sodium sulphate, and concentrated to afford the crude compound Example 118a as a light brown thick liquid. The crude compound was taken for the next step without any further purification. Yield: 0.51 g, (95%); LCMS Calculated. for $C_{20}H_{25}ClN_8O_3S$ is 492.15; Observed: 493.30 $[M+H]^+$. $^1H$ NMR (400 MHz, $CDCl_3$): δ 7.37 (d, J=8.0 Hz, 1H), 6.09 (s, 1H), 4.39 (d, J=4.0 Hz, 1H), 4.29-4.21 (m, 1H), 3.84 (d, J=8.0 Hz, 1H), 3.32-3.23 (m, 3H), 2.80 (s, 3H), 2.35-2.30 (m, 2H), 2.21-1.74 (m, 4H), 1.35-1.25 (m, 5H).

Step-2: 7-amino-5-((2-(1-(2-(azidomethyl) cyclopentyl)-1H-pyrazol-3-yl) ethyl) amino)-3-chloro-2-methylpyrazolo[1,5-a] pyrimidine-6-carbonitrile (Example 118b)

To a solution of (2-(3-(2-((7-amino-3-chloro-6-cyano-2-methylpyrazolo[1,5-a] pyrimidin-5-yl) amino) ethyl)-1H-pyrazol-1-yl) cyclopentyl) methyl methane sulfonate Example 118a (0.68 g, 1.4 mmol) in N, N-dimethylformamide (3 mL) was added sodium azide (0.45 g, 6.9 mmol) and the reaction mixture was stirred at 80° C. for 2 h. The progress of the reaction was monitored by TLC analysis. After the completion, the reaction mixture was quenched with water (10 mL) and extracted with ethyl acetate (10 mL×3). The combined organic layer was washed with brine (10 mL), dried over anhydrous $Na_2SO_4$ and concentrated to afford the crude compound as brown liquid. The crude compound was purified by silica gel (230-400 mesh) column chromatography using 0-30% ethyl acetate in n-hexane to afford the desired product Example 118b as a pale-yellow oil. Yield: (0.10 g, 17%); LCMS Calculated. for $C_{19}H_{22}ClN_{11}$ is 439.17; Observed: 440.35 $[M+H]^+$.

Step-3: 7-amino-5-((2-(1-(2-(amino methyl) cyclopentyl)-1H-pyrazol-3-yl) ethyl) amino)-3-chloro-2-methylpyrazolo[1,5-a] pyrimidine-6-carbonitrile To a solution of 7-amino-5-((2-(1-(2-(azidomethyl) cyclopentyl)-1H-pyrazol-3-yl) ethyl) amino)-3-chloro-2-methylpyrazolo[1,5-a] pyrimidine-6-carbonitrile Example 118b (0.1 g, 0.2 mmol) in THF (3.6 mL) and water (1.2 mL) was added triphenylphosphine (0.09 g, 0.3 mmol) and the reaction mixture was stirred at rt for 10 min. This was followed by an addition of potassium hydroxide (0.034 g, 0.607 mmol) and the reaction mixture was stirred at rt for 16 h. The progress of the reaction was monitored by TLC analysis. After the completion of the reaction, the reaction mixture was quenched with water (10 mL) and extracted with ethyl acetate (20 mL×3). The combined organic layer was washed with brine (10 mL), dried over anhydrous $Na_2SO_4$ and concentrated under reduced pressure to get the crude material. The crude compound was purified by silica gel (60-120 mesh) column chromatography with methanolic ammonia in dichloromethane (0-5%) to afford the desired product Example 118 as an off-white solid. Yield: (0.05 g, 50%); LCMS Calculated. for $C_{19}H_{24}ClN_9$ is 413.18; Observed: 414.35 $[M+H]^+$. $^1H$ NMR (400 MHz, DMSO-$D_6$): δ 7.71 (d, J=4.0 Hz, 5H), 6.97 (d, J=4.0 Hz, 1H), 6.12 (d, J=4.0 Hz, 1H), 4.36 (d, J=8.0 Hz, 1H), 3.62 (d, J=8.0 Hz, 2H), 2.86-2.74 (m, 4H), 2.42 (t, J=4.0 Hz, 2H), 2.28 (s, 3H), 2.07-1.98 (m, 2H), 1.80 (d, J=8.0 Hz, 1H), 1.69 (m, 1H), 1.43 (s, 1H). HPLC: 98.32%.

Example 119: 7-amino-3-chloro-2-methyl-5-((2-(6-methylpyridin-2-yl) ethyl) amino) pyrazolo[1,5-a] pyrimidine-6-carbonitrile

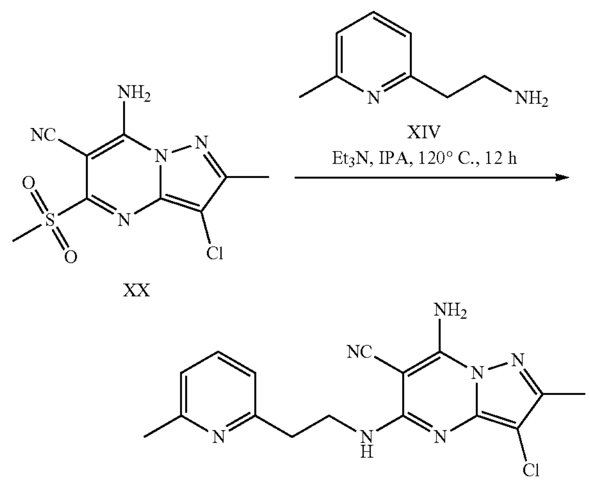

Example 119

To a solution of 7-amino-3-chloro-2-methyl-5-(methyl sulfonyl) pyrazolo[1,5-a] pyrimidine-6-carbonitrile XX (0.2 g, 0.7 mmol) and 2-(6-methylpyridin-2-yl) ethan-1-amine (0.2 g, 2 mmol) in isopropyl alcohol (10 mL) was added triethylamine XIV (0.6 mL, 4 mmol) and the reaction mixture was stirred at 120° C. for 12 h. The progress of the reaction was monitored by TLC analysis. After completion, the reaction mixture was cooled to rt, added water (20 mL) and extracted with ethyl acetate (25 mL×2). The combined organic layer was washed with brine (15 mL), dried over anhydrous sodium sulphate, and concentrated under pressure. The crude compound was purified by silica gel (230-400 mesh) column chromatography using 0-70% ethyl acetate in n-hexane to afford the desired product Example 119 as off-white solid. Yield: 0.121 g (50%); LCMS Calculated. for $C_{16}H_{16}ClN_7$ is 341.11; Observed: 342.30

$[M+H]^+$. $^1H$ NMR (400 MHz, DMSO-$D_6$): δ 8.41 (bs, 2H), 7.61 (t, J=8.0 Hz, 1H), 7.27 (bs, 1H), 7.10 (d, J=8.0 Hz, 2H), 4.0-3.67 (m, 2H), 3.00 (t, J=8.0 Hz, 2H), 2.49 (d, J=8.0 Hz, 3H), 2.28 (s, 3H). HPLC: 7.756 min; 99.21%, Column: INT ODS 3V-C18 (4.6*250) mm, 5μ, Mobile phase A: 0.1% Formic acid in water, Mobile phase B: Acetonitrile; Flow: 1.0 mL/min Example 120: 7-amino-3-chloro-5-((2-(6-ethylpyridin-2-yl) ethyl) amino)-2-methylpyrazolo[1,5-a] pyrimidine-6-carbonitrile

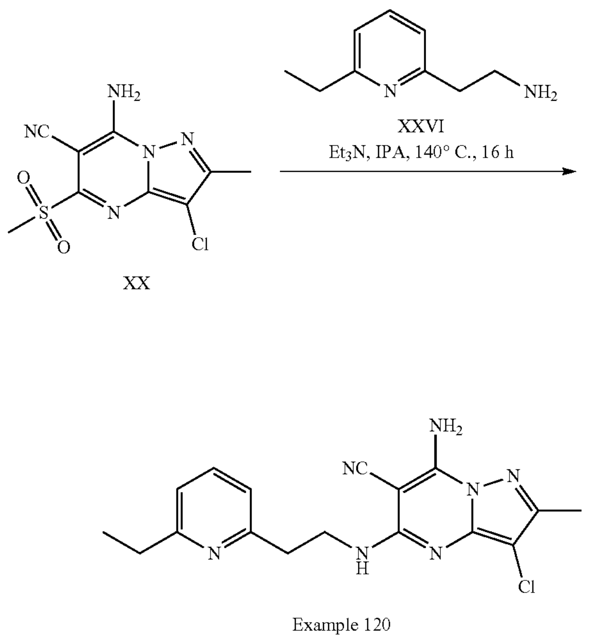

To a solution of 2-(6-ethylpyridin-2-yl) ethan-1-amine XXVI (0.2 g, 0.7 mmol) and 7-amino-3-chloro-2-methyl-5-(methyl sulfonyl) pyrazolo[1,5-a]pyrimidine-6-carbonitrile XX (0.21 g, 1.40 mmol) in isopropyl alcohol (10 mL) was added triethylamine (0.585 mL, 4.20 mmol) and the reaction mixture was stirred at 140° C. for 16 h. The progress of reaction was monitored by TLC analysis. After the completion of the reaction, the reaction mixture was cooled to rt and concentrated under reduced pressure. Added water (10 mL) and extracted with ethyl acetate (20 mL×3). The combined organic layer was washed with brine (20 mL), dried over anhydrous sodium sulphate, and concentrated under reduced pressure to get the crude material. The crude compound was purified by silica gel (60-120, mesh) column chromatography using 0-30% ethyl acetate in n-hexane to afford the desired product Example 120 as an off-white solid. Yield: 0.16 g, (63.9%); LCMS Calculated. for $C_{17}H_{18}ClN_7$ is 355.13; Observed. 356.05 $[M+H]^+$. $^1H$ NMR (400 MHz, DMSO-$D_6$): δ 8.39 (bs, 2H), 7.63 (t, J=8.0 Hz, 1H), 7.19 (bs, 1H), 7.09 (q, J=4.0 Hz, 2H), 3.71 (q, J=4.0 Hz, 2H), 3.01 (t, J=8.0 Hz, 2H), 2.74 (q, J=8.0 Hz, 2H), 2.28 (s, 3H), 1.22 (t, J=8.0 Hz, 3H). HPLC: 7.991 min; 99.61%, Column: INT ODS 3V-C18 (4.6*250) mm, 5μ, Mobile phase A: 0.1% Formic acid in water, Mobile phase B: Acetonitrile; Flow: 1.0 mL/min.

Example 121: (+−)-7-amino-3-ethyl-5-((2-(1-(4-(hydroxymethyl)tetrahydrofuran-3-yl)-1H-pyrazol-3-yl)ethyl)amino)-2-methyl pyrazolo[1,5-a]pyrimidine-6-carbonitrile Example 122a: (+)-7-amino-3-ethyl-5-((2-(1-(4-(hydroxy methyl)tetrahydrofuran-3-yl)-1H-pyrazol-3-yl)ethyl)amino)-2-methyl pyrazolo[1,5-a]pyrimidine-6-carbonitrile Example 122b: (−)-7-amino-3-ethyl-5-((2-(1-(4-(hydroxy methyl)tetrahydrofuran-3-yl)-1H-pyrazol-3-yl)ethyl)amino)-2-methyl pyrazolo[1,5-a]pyrimidine-6-carbonitrile

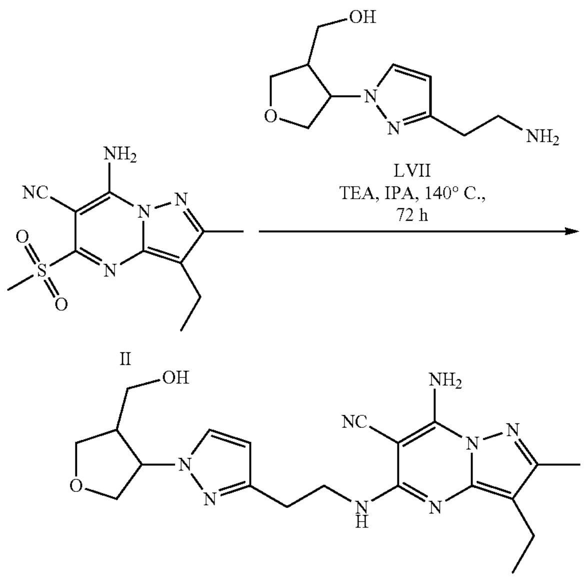

Racemic: Example 121; Racemic(±)
Peak-1: Example 122a; dextro(+) rotatory
Peak-2: Example 122b; leavo(-) rotatory To a solution of 7-amino-3-ethyl-2-methyl-5-(methyl sulfonyl) pyrazolo[1,5-a] pyrimidine-6-carbonitrile II (150 mg, 0.537 mol) and (4-(3-(2-aminoethyl)-1H-pyrazol-1-yl) tetrahydrofuran-3-yl) methanol LVII (227 mg, 1.07 mmol) in isopropanol (5 mL) was added triethylamine (449 mL, 3.22 mmol). The resulting mixture was purged with $N_2$ gas for 5 min and stirred at 140° C. for 72 h. The progress of the reaction was monitored by TLC analysis. The reaction mixture was cooled to room temperature and added water (15 mL). The resulting mixture was extracted with ethyl acetate (20 mL×3). The combined organic layer was washed with brine, dried over anhydrous sodium sulphate, and concentrated under reduced pressure. The crude material was subjected to silica gel flash column chromatography using 0-3% methanol in DCM to afford the desired compound Example 121 as an off-white solid. Yield: 0.09 g (41%); LC-MS Calculated. for $C_{20}H_{26}N_8O_2$ is 410.21; Observed. 411.35 $[M+H]^+$. $^1H$ NMR (400 MHz, DMSO-$D_6$): δ 8.10 (bs, 2H), 7.66 (d, J=1.6 Hz, 1H), 6.60 (t, J=5.2 Hz, 1H), 6.36 (d, J=1.6 Hz, 1H), 4.85 (t, J=5.2 Hz, 1H), 4.68-4.67 (m, 1H), 4.08-3.98 (m, 2H), 3.85-3.83 (m, 1H), 3.62-3.57 (m, 3H), 3.45 (bs, 2H), 2.83 (t, J=6.8 Hz, 1H) 2.66 (bs, 1H), 2.47-2.43 (m, 2H), 2.25 (s, 3H), 1.12 (t, J=7.6 Hz, 3H); HPLC: 10.899 min; 97.82%, Column: INT ODS 3V-C18 (4.6*250) mm, 5μ; Mobile phase A: 0.1% Formic acid in water, Mobile phase B: Acetonitrile Flow: 1.0 mL/min.

Further the racemic compound Example 121 was subjected to chiral SFC (Column Name: IG (21*250 mm), 5 μm; Co-Solvent Name: MeCN:MeOH 1:1 (0.1% TEA); Total flow rate: 100 mL; % of Co-Solvent: 27; Back Pressure: 100 bar) and separated in to peak-1 and peak-2.

Peak-1; Example 122a; (38 mg)

LC-MS Calc. for $C_{20}H_{26}N_8O_2$ is 410.21; Obs. 411.35 $[M+H]^+$. $^1H$ NMR (400 MHz, DMSO-$D_6$): δ 8.12 (bs, 2H), 7.67 (bs, 1H), 6.62 (bs, 1H), 6.10 (bs, 1H), 4.85 (t, J=5.2 Hz, 1H), 4.68-4.67 (m, 1H), 4.08-3.98 (m, 2H), 3.86-3.84 (m, 1H), 3.62-3.57 (m, 3H), 3.45 (bs, 2H), 2.83 (t, J=6.8 Hz, 2H), 2.66 (bs, 1H), 2.47-2.43 (m, 2H), 2.25 (s, 3H), 1.12 (t, J=7.6 Hz, 3H); HPLC: 10.899 min; 99.30%, Column: INT ODS 3V-C18 (4.6*250) mm, 5μ; Mobile phase A: 0.1% Formic acid in water, Mobile phase B: Acetonitrile Flow: 1.0 mL/min; Chiral HPLC: 7.725; 95.05%; Column Name: IG (4.6*250 mm), 5 μm; Co-Solvent Name: ACN MEOH 1:1 (0.1% TEA); Total flow rate: 3 g/mL; % of Co-Solvent: 30; Temperature: 30° C.; ABPR Pressure: 1500 psi); Specific optical rotation ($[\alpha]_D$); (c 0.1 in MeOH)=47.00.

Peak-2; Example 122a; (39 mg)

LC-MS Calc. for $C_{20}H_{26}N_8O_2$ is 410.21; Obs. 411.35 $[M+H]^+$. $^1H$ NMR (400 MHz, DMSO-$D_6$): δ 8.11 (bs, 2H), 7.67 (bs, 1H), 6.61 (bs, 1H), 6.10 (bs, 1H), 4.85 (bs, 1H), 4.68-4.67 (m, 1H), 4.08-3.99 (m, 2H), 3.86-3.84 (m, 1H), 3.62-3.59 (m, 3H), 3.45 (bs, 2H), 2.83 (t, J=6.8 Hz, 2H), 2.66 (bs, 1H), 2.47-2.43 (m, 2H), 2.25 (s, 3H), 1.12 (t, J=7.6 Hz, 3H); HPLC: 10.847 min; 98.88%, Column: INT ODS 3V-C18 (4.6*250) mm, 5μ; Mobile phase A: 0.1% Formic acid in water, Mobile phase B: Acetonitrile Flow: 1.0 mL/min; Chiral HPLC: 11.052 min; 98.61%; Column Name: IG (4.6*250 mm), 5 μm; Co-Solvent Name: ACN MEOH 1:1 (0.1% TEA); Total flow rate: 3 g/mL; % of Co-Solvent: 30; Temperature: 30° C.; ABPR Pressure: 1500 psi); Specific optical rotation ($[\alpha]_D$); (c 0.1 in MeOH)=−38.80.

Example 123: 7-amino-3-ethyl-5-((2-(1-(3-(hydroxymethyl) cyclobutyl)-1H-pyrazol-3-yl) ethyl) amino)-2-methylpyrazolo[1,5-a]pyrimidine-6-carbonitrile

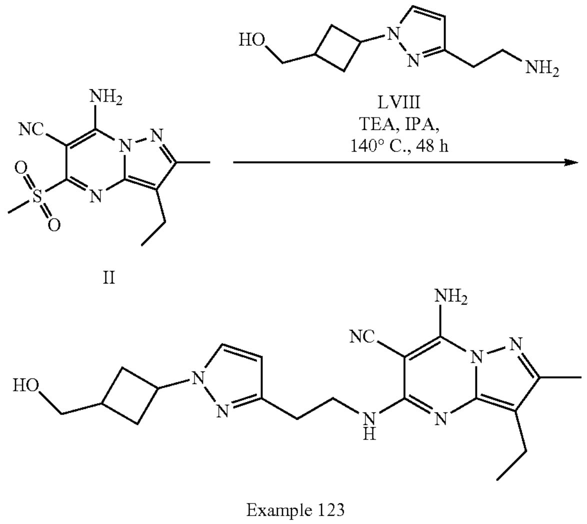

II

Example 123

To a stirred solution of 7-amino-3-ethyl-2-methyl-5-(methyl sulfonyl) pyrazolo[1,5-a] pyrimidine-6-carbonitrile II (0.2 g, 0.716 mmol) in isopropanol (10 mL) was added (3-(3-(2-aminoethyl)-1H-pyrazol-1-yl) cyclobutyl) methanol LVIII (0.3 g, 1 mmol). The mixture was purged with $N_2$ gas and triethylamine (0.5 mL, 4 mmol) was added. The resulting mixture was stirred at 140° C. for 48 h. The progress of the reaction was monitored by TLC analysis. After completion, the reaction mixture was cooled to room temperature, diluted with water (20 mL), extracted with ethyl acetate (25 mL×2). The combined organic layer was washed with brine (15 mL), dried over anhydrous sodium sulphate, and concentrated under reduced pressure. The crude product was purified by combi-flash (silica gel 230-400) column chromatography using ethyl acetate in n-hexane (0-50%) to afford the desired compound Example 123 as pale-yellow solid. Yield: 45 mg (20%); LCMS Calculated. for $C_{20}H_{26}N_8O$ is 394.22; Observed. 395.35 $[M+H]^+$; $^1H$ NMR (400 MHz, DMSO-$D_6$): δ 8.10 (bs, 2H), 7.69-7.66 (m, 1H), 6.64 (bs, 1H), 6.09-6.06 (m, 1H), 4.82 (t, J=8.0 Hz, 1H), 4.67 (bs, 1H), 3.59-3.49 (m, 5H), 2.84 (t, J=6.8 Hz, 2H), 2.45 (bs, 2H), 2.33 (bs, 2H), 2.24 (s, 3H), 2.21-2.19 (m, 2H), 1.12 (t, J=7.2 Hz, 3H). HPLC: 11.415 min; 97.651%, Column: INT ODS 3V-C18 (4.6*250) mm, 5μ; Mobile phase A: 0.1% Formic acid in water, Mobile phase B: Acetonitrile, Flow: 1.0 mL/min.

Example 124: 7-amino-3-ethyl-5-((2-(1-(1-(2-hydroxyethyl) cyclopropyl)-1H-pyrazol-3-yl) ethyl) amino)-2-methylpyrazolo[1,5-a]pyrimidine-6-carbonitrile

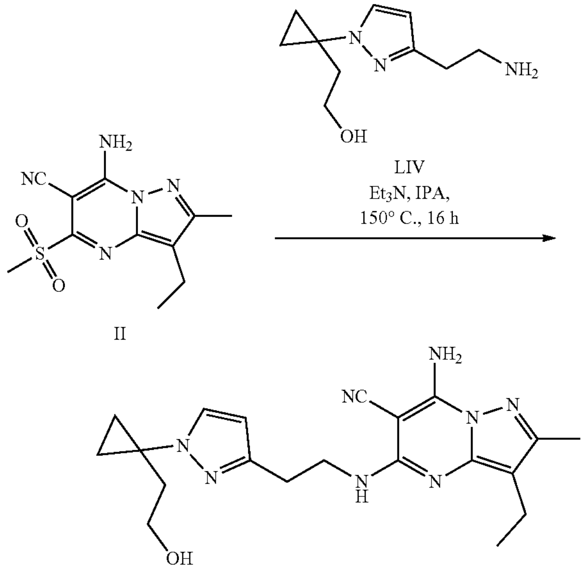

II

Example 124

To a stirred solution of 7-amino-3-ethyl-2-methyl-5-(methylsulfonyl)pyrazolo [1,5-a]pyrimidine-6-carbonitrile II (0.3 g, 1 mmol) and 2-(1-(3-(2-aminoethyl)-1H-pyrazol-1-yl)cyclopropyl)ethan-1-ol LIV (0.4 g, 2 mmol) in isopropanol (5 mL) in a sealed tube was added triethylamine (0.3 g, 3 mmol) and the reaction mixture was stirred at 150° C. for 16 h. The progress of the reaction was monitored by TLC analysis. After completion, the reaction mixture was cooled to room temperature and diluted with water (50 mL) and extracted with ethyl acetate (20 mL×3). The combined organic layer was dried over anhydrous $Na_2SO_4$ and concentrated under reduced pressure. The crude compound was subjected to silica gel (230-400 mesh) column chromatography using 0-70% ethyl acetate in n-hexane to afford the desired compound Example 124 as off-white solid. Yield: 0.12 g (30%); LCMS Calculated. for $C_{20}H_{26}N_8O$ is 394.22; Observed. 395.35 $[M^{+}+1]$. $^1$HNMR (400 MHz, DMSO-$D_6$): δ 8.09 (bs, 2H), 7.61 (s, 1H), 6.57 (s, 1H), 6.03 (s, 1H), 4.37 (t, J=6.4 Hz, 1H), 3.57 (q, J=6.4 Hz, 2H), 3.33-3.28 (m, 2H), 2.81 (t, J=6.4 Hz, 2H), 2.46-2.43 (m, 2H), 2.24 (s, 3H), 1.86 (t, J=6.4 Hz, 2H), 1.13-1.07 (m, 5H), 0.90 (s, 2H). HPLC: 11.38 min; 99.241%, INT ODS 3V-C18 (4.6*250) mm, 5μ; Mobile Phase A: 0.1% Formic acid in water, Mobile Phase B: Acetonitrile.

Example 125: 7-amino-5-((2-(1-(2-aminoethyl)-2-oxo-1,2-dihydropyridin-3-yl) ethyl) amino)-3-chloro-2-methylpyrazolo[1,5-a] pyrimidine-6-carbonitrile

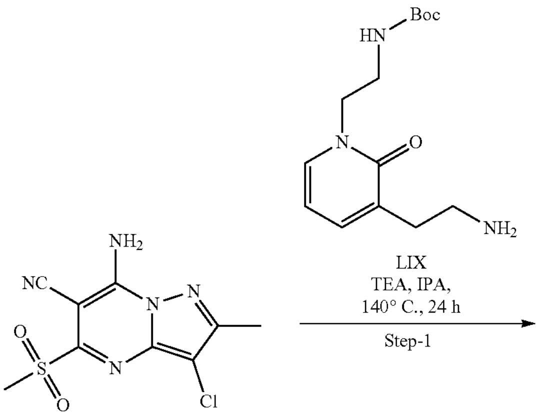

XX

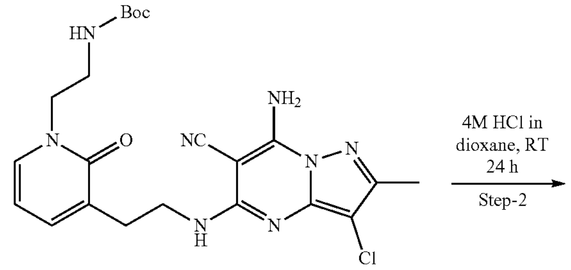

Example 125a

HCl

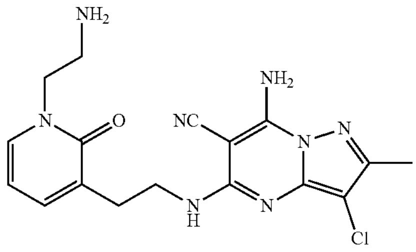

Example 125

Step-1: tert-butyl (2-(3-(2-((7-amino-3-chloro-6-cyano-2-methylpyrazolo[1,5-a] pyrimidin-5-yl) amino) ethyl)-2-oxopyridin-1(2H)-yl) ethyl) carbamate (Example 125a). To a stirred solution of 7-amino-3-chloro-2-methyl-5-(methyl sulfonyl) pyrazolo[1,5-a] pyrimidine-6-carbonitrile XX (150 mg, 0.525 mmol) in 2-propanol (5 mL) was added triethylamine (319 mg, 439 μL, 3.15 mmol) and tert-butyl (2-(3-(2-aminoethyl)-2-oxopyridin-1(2H)-yl)ethyl)carbamate LIX and the reaction mixture was stirred at 140° C. for 24 h. The progress of the reaction was monitored by TLC analysis. After completion, the reaction mixture was cooled to room temperature and precipitated solid was filtered washed with MeOH and diethyl ether to afford desired pure product Example 125a as an off-white solid. Yield: 150 mg (59%). LCMS Calculated. for $C_{22}H_{27}ClN_8O_3$ is 486.18; Observed. 487.35 $[M+H]^+$; $^1$H NMR (400 MHz, DMSO-$D_6$): δ 8.31 (bs, 2H), 7.36-7.29 (m, 2H), 7.07 (s, 1H), 6.88 (s, 1H), 6.15 (t, J=6.4 Hz, 1H), 5.14 (bs, 1H), 3.92 (s, 2H), 3.54-3.53 (m, 2H), 3.24-3.23 (m, 2H), 2.74 (t, J=6.0 Hz, 2H), 2.27 (s, 3H), 1.33 (s, 9H).

Step-2: 7-amino-((2-(2-(1-(2-aminoethyl)-2-oxo-1,2-dihydropyridin-3-yl) ethyl) amino)-3-chloro-2-methylpyrazolo[1,5-a]pyrimidine-6-carbonitrile Hydrochloride Salt To a stirred solution of tert-butyl (2-(3-(2-((7-amino-3-chloro-6-cyano-2-methylpyrazolo[1,5-a] pyrimidin-5-yl) amino) ethyl)-2-oxopyridin-1(2H)-yl) ethyl) carbamate Example 125a (150 mg, 0.308 mmol) in dioxane (5 mL) was cooled to 0° C. and was added 4.0 M hydrogen chloride in dioxane (112 mg, 770 μL, 3.08 mmol). The reaction mixture was stirred at room temperature for 24 hours. The progress of the reaction was monitored by TLC analysis. After completion, the reaction mixture was concentrated under reduced pressure and obtained solid was washed with diethyl ether (2 mL×2) to afford the title compound Example 125 as off-white solid as a HCl salt. Yield: 100 mg, (84.03%); LCMS Calculated. for $C_{17}H_{19}ClN_8O$ is 386.13; Observed: 387.35 $[M+H]^+$; $^1$H NMR (400 MHz, DMSO-$D_6$): δ 8.38 (bs, 2H), 8.09 (bs, 2H), 7.57 (bs, 1H), 7.37 (bs, 1H), 7.06 (bs, 1H), 6.25 (bs, 1H), 4.60 (bs, 2H), 4.17 (s, 2H), 3.16 (s, 2H), 2.76 (s, 2H), 2.27 (s, 3H). HPLC Purity=99.18%; Rt=7.827 min; INT ODS 3V-C18 (4.6×250) mm, 5μ; Mobile phase A: 0.1% Formic acid in water; Mobile phase B: Acetonitrile.

Example 126: 7-amino-5-((2-(1-(2-aminoethyl)-2-oxo-1,2-dihydropyridin-3-yl) ethyl) amino)-3-ethyl-2-methylpyrazolo[1,5-a] pyrimidine-6-carbonitrile

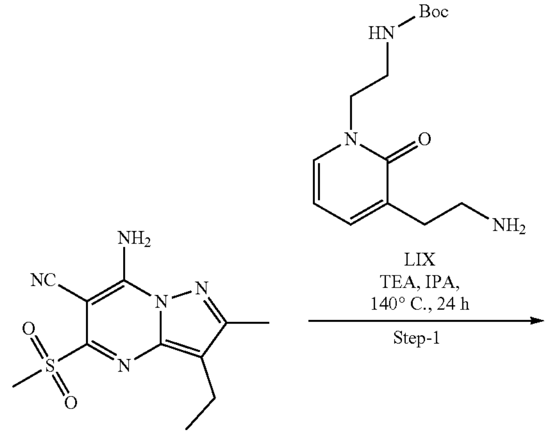

II

-continued

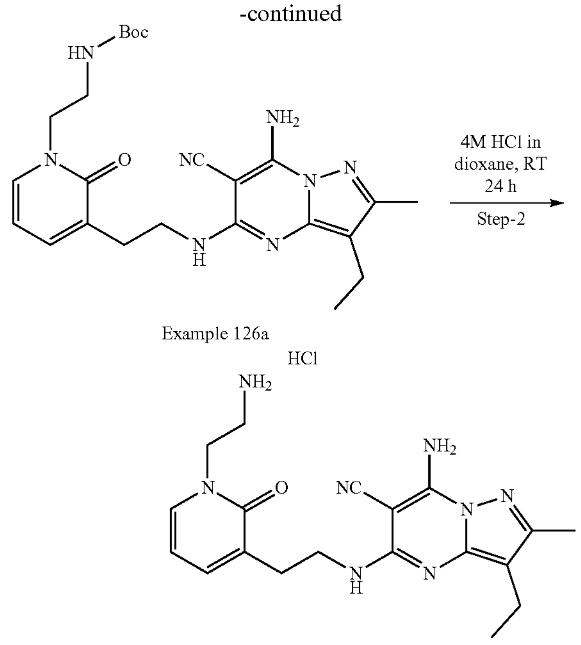

Example 126a

HCl

Example 126

Step-1: tert-Butyl (2-(3-(2-((7-amino-6-cyano-3-ethyl-2-methylpyrazolo[1,5-a] pyrimidin-5-yl) amino) ethyl)-2-oxopyridin-1(2H)-yl) ethyl) carbamate (Example 126a)

To a stirred solution of 7-amino-3-ethyl-2-methyl-5-(methylsulfonyl)pyrazolo[1,5-a]pyrimidine-6-carbonitrile II (200 mg, 0.716 mmol) in 2-propanol (5 mL) were added triethylamine (435 mg, 599 μL, 4.30 mmol) and tert-butyl (2-(3-(2-aminoethyl)-2-oxopyridin-1(2H)-yl)ethyl)carbamate LIX (423 mg, 1.50 mmol) and the reaction mixture was stirred at 140° C. for 24 h. The progress of the reaction was monitored by TLC analysis. After completion, the reaction mixture was cooled to room temperature and concentrated under reduced pressure. The residue obtained upon removal of the solvent was subjected to silica gel (230-400 mesh) column chromatography using 1-5% MeOH in DCM to afford the desired compound Example 126a as off-white solid. Yield: 180 mg (52%). LCMS Calculated. for $C_{24}H_{32}N_8O_3$ is 480.25; Observed. 481.35 $[M+H]^+$; $^1$HNMR (400 MHz, DMSO-$D_6$): δ 8.05 (s, 2H), 7.36-7.270 (m, 2H), 6.87 (s, 1H), 6.71 (s, 1H), 6.15 (t, J=6.4 Hz, 1H), 3.92 (s, 2H), 3.51 (t, J=4.8 Hz, 2H), 3.23 (d, J=4.8 Hz, 2H), 2.73 (s, 2H), 2.45 (d, J=7.6 Hz, 2H), 2.24 (s, 3H), 1.33-1.23 (m, 9H), 1.10 (t, J=7.2 Hz, 3H).

Step-2: 7-amino-5-((2-(1-(2-aminoethyl)-2-oxo-1,2-dihydropyridin-3-yl) ethyl) amino)-3-ethyl-2-methylpyrazolo[1,5-a] pyrimidine-6-carbonitrile Hydrochloride Salt To a stirred solution of tert-butyl (2-(3-(2-((7-amino-6-cyano-3-ethyl-2-methylpyrazolo[1,5-a] pyrimidin-5-yl) amino) ethyl)-2-oxopyridin-1(2H)-yl) ethyl) carbamate Example 126a (180 mg, 0.375 mmol) in dioxane (5 mL) was cooled to 0° C. and was added 4.0 M hydrogen chloride in dioxane (137 mg, 936 μL, 3.75 mmol). The reaction mixture was stirred at room temperature for 24 h. The progress of the reaction was monitored by TLC analysis. After completion, the reaction mixture was concentrated under reduced pressure and obtained solid was washed with diethyl ether (2 mL×2) to afford the title compound Example 126 as off-white solid as a HCl salt. Yield: (120 mg, 84%); LCMS Calculated. for $C_{19}H_{24}N_8O$ is 380.20; Observed. 381.35 $[M+H]^+$; $^1$HNMR (400 MHz, DMSO-$D_6$): δ 8.23 (s, 2H), 8.06 (s, 2H), 7.58 (d, J=6.0 Hz, 1H), 7.38 (d, J=6.0 Hz, 1H), 6.94 (s, 1H), 6.27 (t, J=6.0 Hz, 1H), 4.16 (s, 2H), 3.56 (m, 4H), 3.17 (d, J=4.8 Hz, 2H), 2.77 (s, 2H), 2.25 (s, 3H), 1.11 (t, J=7.2 Hz, 3H). HPLC: 97.69%.

Example 127: 7-amino-3-chloro-5-((2-(1-(4-(hydroxymethyl) tetrahydrofuran-3-yl)-1H-pyrazol-3-yl) ethyl) amino)-2-methylpyrazolo[1,5-a] pyrimidine-6-carbonitrile

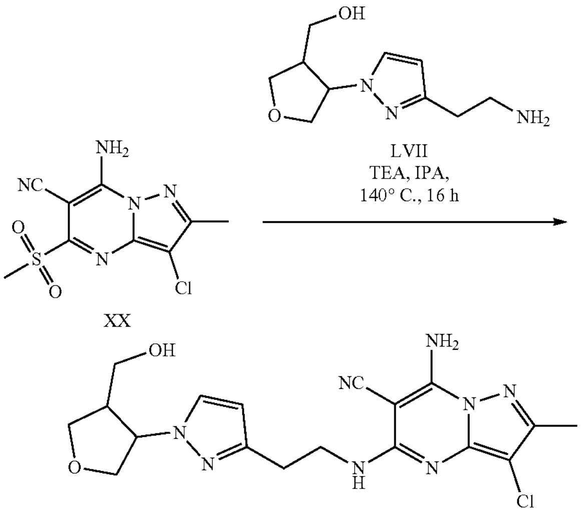

XX

Example 127

To a stirred solution of 7-amino-3-chloro-2-methyl-5-(methyl sulfonyl) pyrazolo[1,5-a] pyrimidine-6-carbonitrile XX (0.15 g, 0.53 mmol) in 2-propanol (20 mL) was added (4-(3-(2-aminoethyl)-1H-pyrazol-1-yl) tetrahydrofuran-3-yl) methanol LVII (0.20 g, 0.95 mmol). The mixture was purged with $N_2$ gas for 5 min and TEA (0.44 mL, 3.2 mmol) was added. The resulting mixture in a sela tube was stirred at 140° C. for 16 h. The progress of reaction was monitored by TLC analysis. After completion, the reaction was cooled to room temperature and the reaction mixture was diluted with water (20 mL). The mixture was extracted with ethyl acetate (25 mL×3). The combined organic layer was given brine wash, dried over anhydrous sodium sulphate, filtered, and concentrated under reduced pressure. The crude material was purified by Biotage (230-400 silica gel) using 0-3% methanol in DCM to afford the desired compound Example 127 as an off-white solid. Yield: 78 mg, (36%); LCMS Calculated. for $C_{18}H_{21}ClN_8O_2$ is 416.14; Observed.: 417.30 $[M+H]^+$. $^1$H NMR (400 MHz, DMSO-$D_6$): δ 8.40 (bs, 2H), 7.67 (s, 1H), 6.95 (bs, 1H), 6.12 (bs, 1H), 4.86 (bs, 1H), 4.69-4.68 (m, 1H), 4.08-3.99 (m, 2H), 3.86-3.83 (m, 1H), 3.62-3.59 (m, 3H), 3.45 (bs, 2H), 2.84 (t, J=7.2 Hz, 2H), 2.68 (bs, 1H), 2.28 (s, 3H). HPLC: 10.616 min; 99.62%, Column: INT ODS 3V-C18 (4.6*250) mm, 5μ Mobile phase A: 0.1% Formic acid in water Mobile phase B: Acetonitrile, Flow: 1.0 mL/min:

Example 128: 7-amino-3-ethyl-5-((2-(1-((3-hydroxycyclobutyl) methyl)-2-oxo-1,2-dihydropyridin-3-yl) ethyl)amino)-2-methylpyrazolo[1,5-a]pyrimidine-6-carbonitrile

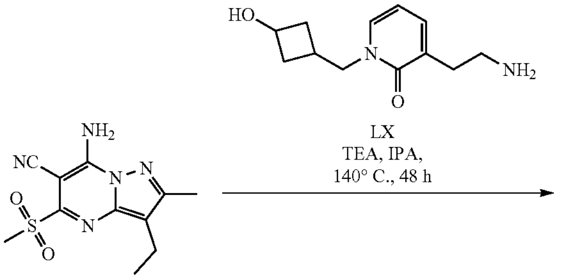

II

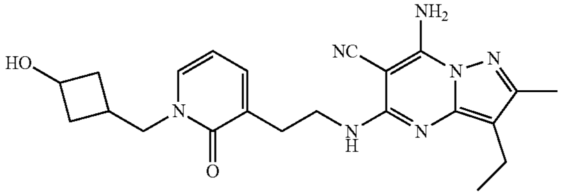

Example 128

To a stirred solution of 7-amino-3-ethyl-2-methyl-5-(methyl sulfonyl) pyrazolo[1,5-a] pyrimidine-6-carbonitrile II (200 mg, 0.716 mmol) in isopropanol (6 mL) were added TEA (0.599 mL, 4.30 mmol) and 3-(2-aminoethyl)-1-((3-hydroxycyclobutyl) methyl) pyridin-2(1H)-one LX (350 mg, 1.58 mmol) in a sealed tube. The resulting mixture was stirred at 140° C. for 48 h. The progress of the reaction was monitored by TLC analysis. After completion, the reaction was diluted with water (25 mL) and extracted with ethyl acetate (50 mL×3). The combined organic layer was dried over anhydrous sodium sulphate and concentrated under reduced pressure. The compound was purified by flash column chromatography (silica gel 230-400) by eluting with methanol in DCM (0-5%) to afford the desired compound LX as off-white solid. Yield: 15 mg (5%); LCMS Calculated. for $C_{22}H_{27}N_7O_2$ is 421.22; Observed. 422.35 $[M+H]^+$; $^1H$ NMR (400 MHz, DMSO-$D_6$): δ 8.05 (bs, 2H), 7.50 (bs, 1H), 7.26 (bs, 1H), 6.69 (bs, 1H),6.13 (bs, 1H), 5.00 (bs, 1H), 3.89 (bs, 3H), 3.51 (bs, 2H), 2.73-2.67 (m, 2H), 2.24-2.15 (m, 7H), 1.57 (bs, 2H), 1.24 (bs, 1H), 1.10 (bs, 3H). HPLC: 9.608 min; 96.45%, Column: INT ODS 3V-C18 (4.6*250) mm, 5μ; Mobile phase A: 0.1% Formic acid in water, Mobile phase B: Acetonitrile; Flow: 1.0 mL/min.

Example 129: 7-amino-5-((2-(1-(3-aminopropyl)-2-oxo-1,2-dihydropyridin-3-yl) ethyl) amino)-3-chloro-2-methylpyrazolo[1,5-a]pyrimidine-6-carbonitrile

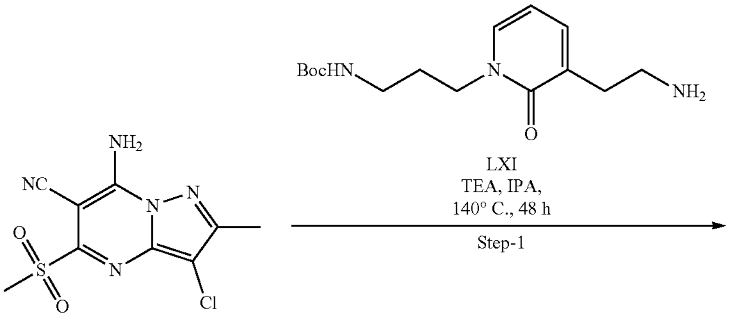

XX

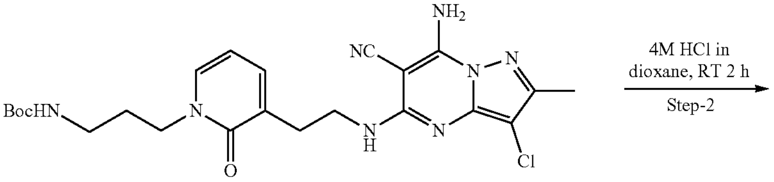

Example 129a

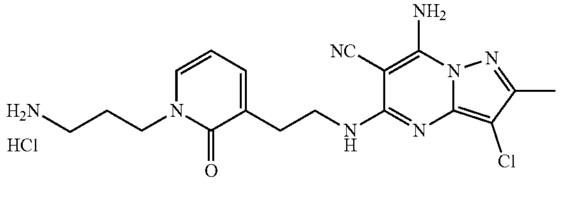

Example 129

Step-1: tert-butyl (3-(3-(2-((7-amino-3-chloro-6-cyano-2-methylpyrazolo[1,5-a] pyrimidin-5-yl) amino) ethyl)-2-oxopyridin-1(2H)-yl) propyl) carbamate (Example 129a)

To a solution of 7-amino-3-chloro-2-methyl-5-(methyl sulfonyl) pyrazolo[1,5-a] pyrimidine-6-carbonitrile XX (0.3 g, 1.05 mmol) in isopropyl alcohol (10 mL) were added triethylamine (0.878 mL, 6.30 mmol) and tert-butyl (3-(3-(2-aminoeth yl)-2-oxopyridin-1(2H)-yl) propyl) carbamate LXI (0.682 g, 2.31 mmol). The reaction mixture was stirred at 140° C. for 48 h. The progress of the reaction was monitored by TLC analysis. After completion, the reaction was cooled to rt and added water (10 mL). The mixture was extracted with ethyl acetate (50 mL×2). The combined organic layer was dried over anhydrous sodium sulphate and concentrated under reduced pressure. The crude compound was purified by silica gel (230-400 mesh) with methanol in dichloromethane (0-10%) to afford the desired product Example 129a as an off-white solid. Yield: 0.3 g, (50.0%); LCMS Calculated. for $C_{23}H_{29}ClN_8O_3$ is 500.99; Observed. 501.40 $[M+H]^+$. $^1H$ NMR (400 MHz, DMSO-$D_6$): δ 8.35 (s, 2H), 7.56 (d, J=6.4 Hz, 1H), 7.28 (d, J=6.4 Hz, 1H), 7.07 (t, J=4.8 Hz, 1H), 6.85 (s, 1H), 6.17 (t, J=6.8 Hz, 1H), 3.88 (t, J=6.8 Hz, 2H), 3.55 (t, J=6.4 Hz, 2H), 2.92 (d, J=6 Hz, 2H), 2.74 (t, J=6.8 Hz, 2H), 2.27 (s, 3H), 1.74 (t, J=6.8 Hz, 2H), 1.34 (m, 9H).

Step-2: 7-amino-5-((2-(1-(3-aminopropyl)-2-oxo-1,2-dihydropyridin-3-yl) ethyl) amino)-3-chloro-2-methylpyrazolo[1,5-a]pyrimidine-6-carbonitrile To a solution of tert-butyl (3-(3-(2-((7-amino-3-chloro-6-cyano-2-methylpyrazolo[1,5-a] pyrimidin-5-yl) amino) ethyl)-2-oxopyridin-1(2H)-yl) propyl) carbamate Example 129a (0.3 g, 0.599 mmol) in 1,4-dioxane (4 mL) was added 4 M HCl in dioxane (0.30 mL, 1.20 mmol) and stirred at rt for 2 h. The progress of the reaction was monitored by TLC analysis. After the completion, the reaction mixture was concentrated, triturated with diethyl ether and n-pentane, dried to afford the desired product Example 129 as an off-white solid. Yield: 0.125 g, (52.1%); LCMS Calculated. for $C_{18}H_{21}ClN_8O$ is 400.15; Observed: 401.3 $[M+H]^+$. $^1H$ NMR (400 MHz, DMSO-$D_6$): δ 8.38 (s, 2H), 8.16 (bs, 3H), 7.67 (s, 1H), 7.33 (s, 1H), 7.11 (s, 1H), 6.23 (s, 1H), 4.03 (s, 2H), 3.57 (s, 2H), 2.76 (s, 3H), 2.27 (s, 3H), 2.00 (s, 2H). HPLC: 7.796 min; 99.01%, Column: INT ODS 3V-C18 (4.6*250) mm, 5μ; Mobile phase A: 0.1% Formic acid in water; Mobile phase B: Acetonitrile; Flow: 1.0 mL/min.

Example 130: 7-amino-3-bromo-5-((2-(1-(2-(hydroxymethyl) cyclobutyl)-1H-pyrazol-3-yl) ethyl) amino)-2-methylpyrazolo[1,5-a]pyrimidine-6-carbonitrile

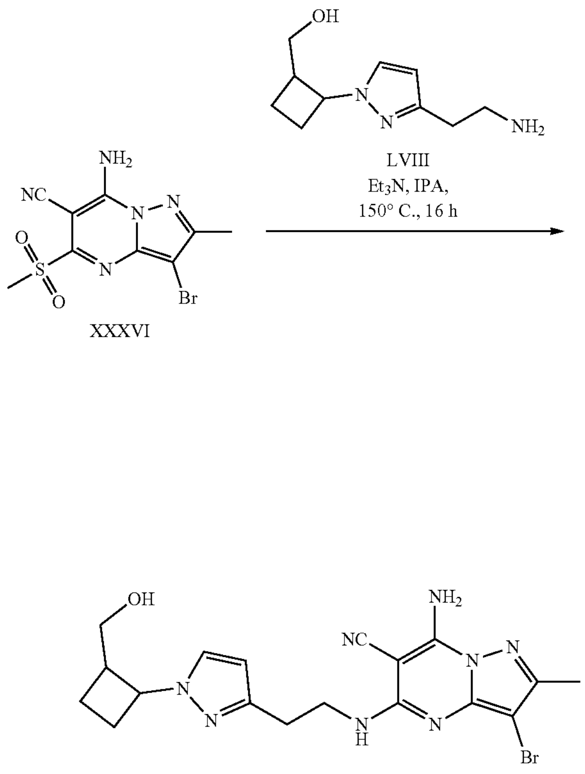

XXXVI

Example 130

To a solution of 7-amino-3-bromo-2-methyl-5-(methyl sulfonyl) pyrazolo[1,5-a] pyrimidine-6-carbonitrile XXXVI (0.17 g, 0.515 mmol) in isopropyl alcohol (10 mL) were added (2-(3-(2-aminoethyl)-1H-pyrazol-1-yl) cyclobutyl) methanol LVIII (0.201 g, 1.03 mmol) and triethylamine (0.431 mL, 3.09 mmol) and the reaction mixture was stirred at 150° C. for 16 h. The progress of the reaction was monitored by TLC analysis. After the completion, the reaction was cooled to rt, added water (50 mL) and extracted with ethyl acetate (25 mL×3). The combined organic layer was dried over anhydrous sodium sulphate, filtered, and concentrated under reduced pressure to afford the crude compound. The crude compound was purified by silica gel (60-120 mesh) column chromatography with methanol in dichloromethane (0-5%) to afford the desired product Example 130 as an off-white. Yield: 50 mg, (22%); LCMS Calculated. for $C_{18}H_{21}BrN_8O$ is 444.10; Observed. 445.25 $[M+H]^+$. $^1H$ NMR (400 MHz, DMSO-$D_6$): δ 8.39 (s, 2H), 7.66 (s, 1H), 7.00 (s, 1H), 6.09 (s, 1H), 4.60 (t, J=5.2 Hz, 1H), 4.51 (q, J=8.8 Hz, 1H), 3.61 (q, J=6.0 Hz, 2H), 3.40 (t, J=4.8 Hz, 2H), 2.83 (q, J=7.2 Hz, 3H), 2.37-2.29 (m, 2H), 2.27-2.18 (m, 1H), 1.79 (q, J=9.6 Hz, 2H), 1.58 (m, 2H). HPLC: 11.722 min; 95.47%, Column: INT ODS 3V-C18 (4.6*250) mm, 5μ; Mobile phase A: 0.1% Formic acid in water; Mobile phase B: Acetonitrile; Flow: 1.0 mL/min.

Example 131: 7-amino-2-(difluoromethyl)-3-ethyl-5-((2-(1-(2-hydroxyethyl)-2-oxo-1,2-dihydropyridin-3-yl) ethyl) amino) pyrazolo[1,5-a]pyrimidine-6-carbonitrile

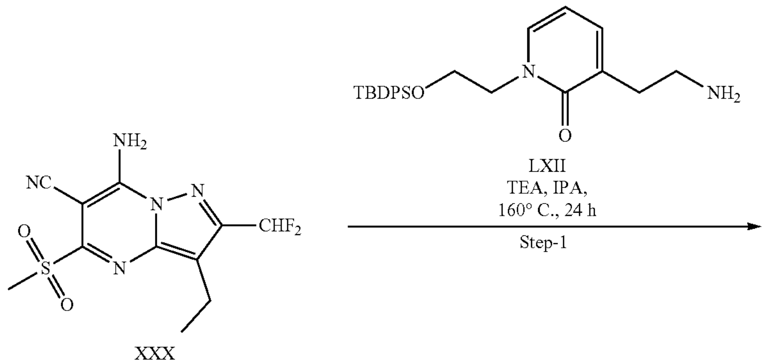

XXX

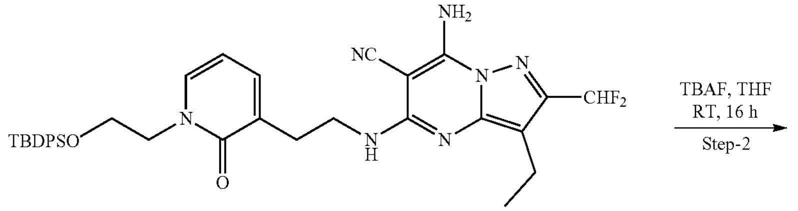

Example 131a

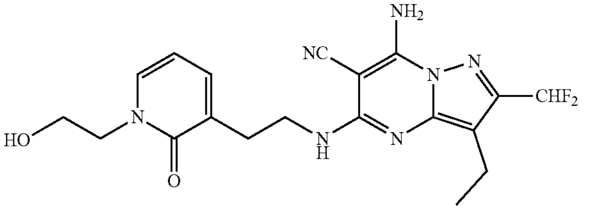

Example 131

Step-1: tert-butyl (3-(3-(2-((7-amino-3-chloro-6-cyano-2-methylpyrazolo[1,5-a] pyrimidin-5-yl) amino) ethyl)-2-oxopyridin-1(2H)-yl) propyl) carbamate (Example 131a)

To a solution of 7-amino-2-(difluoro methyl)-3-ethyl-5-(methyl sulfonyl) pyrazolo[1,5-a] pyrimidine-6-carbonitrile XXX (0.3 g, 0.951 mmol) in isopropyl alcohol (4 mL) were added 3-(2-aminoethyl)-1-(2-((tert-butyl diphenyl silyl) oxy) ethyl) pyridin-2(1H)-one LXII (0.8 g, 1.90 mmol) and triethylamine (0.796 mL, 5.71 mmol). The reaction mixture was stirred at 160° C. for 24 h. The progress of the reaction was monitored by TLC analysis. After the completion, added water (50 mL) and extracted with ethyl acetate (100 mLx3). The combined organic layer was dried over anhydrous sodium sulphate and concentrated under reduced pressure to afford the desired compound Example 131a as a pale-yellow solid. The crude compound was taken for the next step without any further purification. Yield: 0.4 g, (64%); LCMS Calculated. for $C_{35}H_{39}F_2N_7O_2Si$ is 655.29; Observed: 656.45 $[M+H]^+$.

Step-2: 7-amino-5-((2-(1-(3-aminopropyl)-2-oxo-1, 2-dihydropyridin-3-yl) ethyl) amino)-3-chloro-2-methylpyrazolo[1,5-a] pyrimidine-6-carbonitrile To a solution of 7-amino-5-((2-(1-(2-((tert-butyldiphenylsilyl)oxy)ethyl)-2-oxo-1,2-dihydropyridin-3-yl)ethyl) amino)-2-(difluoromethyl)-3-ethylpyrazolo[1,5-a]pyrimidine-6-carbonitrile Example 131a (0.4 g, 0.61 mmol) in tetrahydrofuran (10 mL) was added TBAF (1.22 mL, 1M in THF, 1.22 mmol) and the reaction mixture was stirred at rt for 16 h. The progress of the reaction was monitored by TLC analysis. After the completion of the reaction, added sat. $NaHCO_3$ (20 mL) and filtered the solid to afford the desired title product Example 131 as an off-white solid. Yield: 0.19 g, (75%); LCMS Calculated. for $C_{19}H_{21}F_2N_7O_2$ is 417.17; Observed: 418.30 $[M+H]^+$. $^1H$ NMR (400 MHz, DMSO-$d_6$): δ 8.38 (bs, 2H), 7.48-6.90 (m, 4H), 6.14 (s, 1H), 4.85 (s, 1H), 3.95 (s, 2H), 3.63-3.54 (m, 4H), 2.76 (s, 3H), 1.15 (s, 3H). HPLC: 10.959 min; 99.46%, Column: INT ODS 3V-C18 (4.6*250) mm, 5μ; Mobile phase A: 0.1% Formic acid in water; Mobile phase B: Acetonitrile; Flow: 1.0 mL/min.

Example 132: (+−)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile Example 133a: (+)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile Example 133b: (−)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile

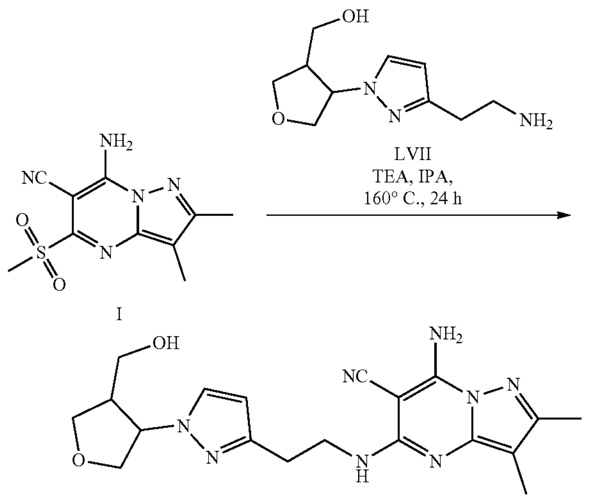

I

Racemic: Example 132; Racemic(±)
Peak-1: Example 133a; dextro(+) rotatory
Peak-2: Example 133b; leavo(-) rotatory To a solution of (4-(3-(2-aminoethyl)-1H-pyrazol-1-yl) tetrahydrofuran-3-yl) methanol LVII (0.2 g, 0.8 mmol) and 7-amino-2,3-dimethyl-5-(methyl sulfonyl) pyrazolo[1,5-a] pyrimidine-6-carbonitrile I (0.3 g, 2 mmol) in isopropyl alcohol (20 mL) was added triethylamine (0.8 mL, 6 mmol) and the reaction mixture was stirred at 140° C. for 16 h. The progress of the reaction was monitored by TLC analysis. After the completion, the reaction mixture was cooled to rt, added water (20 mL) and extracted with ethyl acetate (25 mL×3). The combined organic layer was washed with brine (25 mL), dried over anhydrous $Na_2SO_4$ and concentrated under reduced pressure to get the crude material. The crude compound was purified by silica gel (230-400 mesh) column chromatography using methanol dichloromethane (0-3%) to afford the desired product Example 132 as off-white solid. Yield: 0.3 g, (46.0%); LCMS Calculated. for $C_{19}H_{24}N_8O_2$ is 396.20; Observed: 397.35 $[M+H]^+$; $^1H$ NMR (400 MHz, DMSO-$D_6$): δ 8.11 (bs, 2H), 7.67 (d, J=2.0 Hz, 1H), 6.58 (t, J=5.2 Hz, 1H), 6.11 (d, J=2.0 Hz, 1H), 4.85 (t, J=5.2 Hz, 1H), 4.67 (m, 1H), 4.08-3.99 (m, 2H), 3.87-3.83 (m, 1H), 3.62-3.59 (m, 3H), 3.57-3.42 (m, 2H), 2.83 (t, J=8.0 Hz, 2H), 2.69-2.65 (m, 1H), 2.23 (s, 3H), 1.97 (s, 3H). HPLC: 10.060 min; 95.02%; INT ODS 3V-C18 (4.6*250) mm, 5μ; Mobile phase A: 0.1% Formic acid in water; Mobile phase B: Acetonitrile.

Further the racemic compound Example 132 was subjected to chiral SFC (Column Name: Chiral Pak IG (250*21) mm, 5μ; Mobile phase: A: 0.1% DEA In Hex, B: EtOH (70:30); Flow: 1.0 mL/min and separated into peak-1, Example 133a (and peak-2, Example 133b, Peak-1: Example 133a Yield: 37 mg. LC-MS Calculated. for $C_{19}H_{24}N_8O_2$ is 396.20; Observed: 397.35 $[M+H]^+$; $^1H$ NMR (400 MHz, DMSO-$D_6$): δ 8.11 (bs, 2H), 7.67 (bs, 1H), 6.58 (t, J=5.2 Hz, 1H), 6.12 (bs, 1H), 4.85 (t, J=5.2 Hz, 1H), 4.69-4.67 (m, 1H), 4.08-3.99 (m, 2H), 3.87-3.83 (m, 1H), 3.62-3.56 (m, 3H), 3.46-3.42 (m, 2H), 2.83 (t, J=8.0 Hz, 2H), 2.69-2.65 (m, 1H), 2.23 (s, 3H), 1.97 (s, 3H). HPLC: 9.942 min; 99.40%, INT ODS 3V-C18 (4.6*250) mm, 5μ; Mobile Phase A: 0.1% Formic acid in water, Mobile Phase B: Acetonitrile.; Chiral HPLC: 15.018 min; 100%; Column Name—Chiral Pak IG (250*4.6) mm, 5μ; Mobile phase: A: 0.1% DEA In Hex, B: EtOH (70:30) Flow: 1.0 mL/min; % of Co-Solvent: 30; Temperature: 30° C.; ABPR pressure: 1500 psi); Flow: 1.0 mL/min.

Peak-2: Example 133b); Yield: 31.6 mg. LCMS Calculated. for $C_{19}H_{24}N_8O_2$ is 396.2; Observed: 397.35 $[M+H]^+$; $^1H$ NMR (400 MHz, DMSO-$D_6$): δ 8.10 (bs, 2H), 7.67 (s, 1H), 6.58 (bs, 1H), 6.12 (s, 1H), 4.85 (t, J=5.2 Hz, 1H), 4.68 (d, J=6.0 Hz, 1H), 4.08-3.99 (m, 2H), 3.87-3.83 (m, 1H), 3.62-3.58 (m, 3H), 3.46 (bs, 2H), 2.83 (t, J=6.8 Hz, 2H), 2.67 (bs, 1H), 2.23 (s, 3H), 1.97 (s, 3H). HPLC: 9.947 min; 96.76%, INT ODS 3V-C18 (4.6*250) mm, 5μ; Mobile Phase A: 0.1% Formic acid in water, Mobile Phase B: Acetonitrile; Flow: 1.0 mL/min; Chiral HPLC: 19.618 min; 97.13%; Column Name—Chiral Pak IG (250*4.6) mm, 5μ; Mobile phase: A: 0.1% DEA In Hex, B: EtOH (70:30); Flow: 1.0 mL/min; % of Co-Solvent: 30; Temperature: 30° C.; ABPR pressure: 1500 psi).

Example 134: 2-(((2-(3-(2-((7-amino-6-cyano-3-ethyl-2-methylpyrazolo[1,5-a] pyrimidin-5-yl) amino) ethyl)-1H-pyrazol-1-yl) cyclobutyl) methyl) amino) acetamide

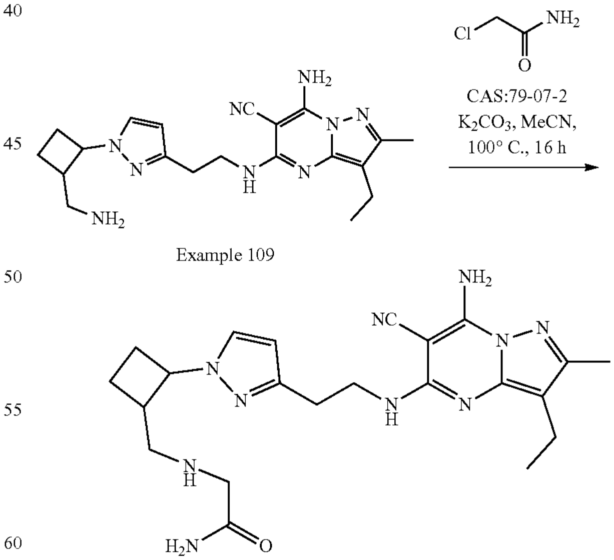

Example 109

Example 134

To a stirred solution of 7-amino-5-((2-(1-(2-(amino methyl) cyclobutyl)-1H-pyrazol-3-yl) ethyl) amino)-3-ethyl-2-methylpyrazolo[1,5-a] pyrimidine-6-carbonitrile Example 109 (150 mg, 0.381 mmol) in acetonitrile (5 mL)

was added $K_2CO_3$ (79.0 mg, 0.572 mmol) and the resulting mixture was stirred at rt for 5 min. This was followed by an addition of 2-chloroacetamide (CAS: CAS:79-07-2, 39.2 mg, 0.419 mmol) at 0° C. and the reaction mixture was stirred at 100° C. for 16 h. The progress of the reaction was monitored by TLC analysis. After completion, the reaction mixture was cooled to rt, diluted with water (20 mL) and extracted with ethyl acetate (20 mL×3). The combined organic layer was washed with brine, dried over anhydrous $Na_2SO_4$, filtered and concentrated under reduced pressure. The crude compound was subjected to silica gel (230-400) flash column chromatography using methanol in DCM (0-10%) to afford the desired compound Example 134 as an off-white solid. Yield: 25 mg (14.5%); LCMS Calculated. for $C_{23}H_{31}N_9O$ is 450.26; Observed: 449.30 $[M-H]^+$. $^1H$ NMR (400 MHz, DMSO-$D_6$): δ 8.10 (s, 2H), 7.68 (s, 1H), 7.21 (s, 1H), 7.01 (s, 1H), 6.66 (s, 1H), 6.07 (s, 1H), 4.45 (d, J=7.6 Hz, 1H), 3.48 (s, 3H), 2.96 (s, 2H), 2.83 (s, 4H), 2.38-2.24 (m, 7H), 1.89 (s, 1H), 1.48 (s, 2H), 1.12 (bs, 4H). HPLC: 8.133 min; 95.40%, INT ODS 3V-C18 (4.6*250) mm, 5μ, Mobile Phase A: 0.1% Formic acid in water, Mobile Phase B: Acetonitrile.

Example 135: 7-amino-3-ethyl-2-methyl-5-((2-(6-(2,2,2-trifluoro-1-hydroxyethyl) pyridine-2-yl) ethyl) amino) pyrazolo[1,5-a]pyrimidine-6 carbonitrile

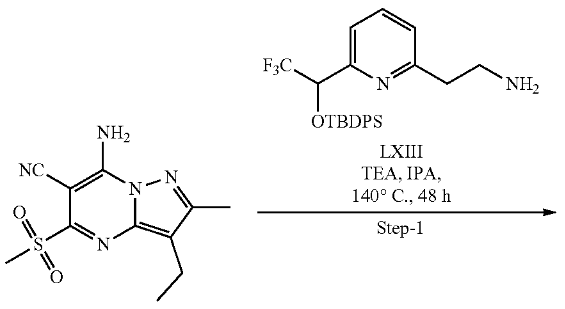

II

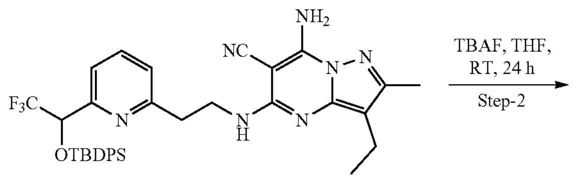

Example 135a

-continued

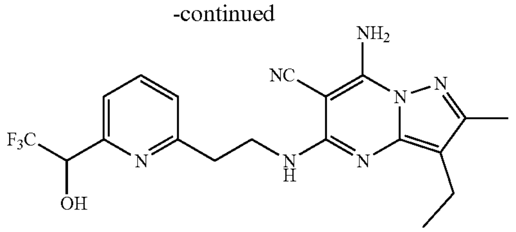

Example 135

Step-1: 7-amino-5-((2-(6-(1-((tert-butyl diphenyl silyl) oxy)-2,2,2-trifluoroethyl) pyridin-2-yl) ethyl) amino)-3-ethyl-2-methylpyrazolo[1,5-a] pyrimidine-6-carbonitrile (Example 135a)

To a stirred solution of 7-amino-3-ethyl-2-methyl-5-(methyl sulfonyl) pyrazolo[1,5-a] pyrimidine-6-carbonitrile II (0.48 g, 1.7 mmol) in isopropanol (10 mL) was added triethylamine (1.4 mL, 10 mmol) and the resulting mixture was purged with $N_2$ gas in seal tube for 5 min. This was followed by an addition of 2-(6-(1-((tert-butyl diphenyl silyl) oxy)-2,2,2-trifluoroethyl) pyridin-2-yl) ethan-1-amine LXIII (1.6 g, 3.4 mmol) and reaction mixture was stirred at 140° C. for 48 h. The progress of the reaction was monitored by TLC analysis. After completion, the reaction was cooled to rt and quenched with water (50 mL). The resulting mixture was extracted with (100 mL×3). The combined organic layer was dried over anhydrous sodium sulphate and concentrated under reduced pressure to afford the desired compound Example 135a as a pale-yellow viscous liquid. The crude was taken for next step without further purification. Yield: 1.0 g, (90.9%); LCMS Calculated. for $C_{35}H_{38}F_3N_7OSi$ Is 657.29; Observed: 656.40 $[M-H]^+$.

Step-2: 7-amino-3-ethyl-2-methyl-5-((2-(6-(2,2,2-trifluoro-1-hydroxyethyl) pyridin-2-yl) ethyl) amino) pyrazolo[1,5-a] pyrimidine-6-carbonitrile To a stirred solution of 7-amino-5-((2-(6-(1-((tert-butyl diphenyl silyl) oxy)-2,2,2-trifluoroethyl) pyridin-2-yl) ethyl) amino)-3-ethyl-2-methylpyrazolo[1,5-a] pyrimidine-6-carbonitrile Example 135a (1 g, 2 mmol) in THF (70 mL) was added TBAF (4 mL, 1M in THF, 4 mmol). The reaction mixture was stirred at rt for 24 h. The progress of the reaction was monitored by TLC analysis. After completion, the reaction was quenched with sat. $NaHCO_3$ (50 mL) and extracted with DCM (100 mL×3). The combined organic layer was dried over anhydrous sodium sulphate and concentrated under reduced pressure. The crude was purified silica gel (230-400) column chromatography using 1-5% MeOH in DCM to afford the desired compound Example 135 as an off-white solid. Yield: 400 mg (66.0%); LCMS Calculated. for $C_{19}H_{20}F_3N_7O$ is 419.17; Observed.: 420.10 $[M+H]^+$. $^1H$ NMR (400 MHz, DMSO-$D_6$): δ 8.12 (bs, 2H), 7.83 (t, J=7.6 Hz, 1H), 7.47 (d, J=8.0 Hz, 1H), 7.33 (d, J=7.6 Hz, 1H), 6.96 (d, 5.6 Hz, 1H), 6.92 (bs, 1H), 5.16 (t, J=7.2 Hz, 1H), 3.68 (t, J=4.8 Hz, 2H), 3.06 (t, J=6.4 Hz, 2H), 2.50-2.43 (m, 2H), 2.25 (s, 3H), 1.12 (t, J=7.6 Hz, 3H); HPLC Purity=98.69%, INT ODS 3V-C18 (4.6*250) mm, 5μ; Mobile Phase A: 0.1% Formic acid in water: Mobile Phase B: Acetonitrile; Retention time=12.84 min Example 136: 7-amino-5-((2-(1-(3-aminopropyl)-2-oxo-1,2-dihydropyridin-3-yl) ethyl) amino)-3-ethyl-2-methylpyrazolo[1,5-a]pyrimidine-6-carbonitrile

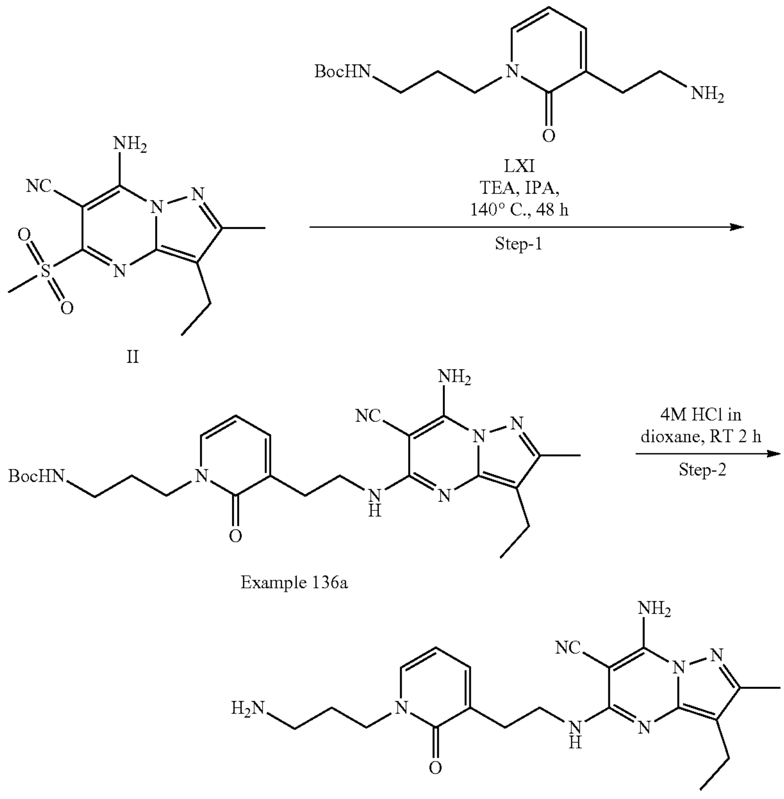

Example 136

Step-1: tert-butyl (3-(3-(2-((7-amino-6-cyano-3-ethyl-2-methylpyrazolo[1,5-a]pyrimidin-5-yl) amino) ethyl)-2-oxopyridin-1(2H)-yl) propyl) carbamate (Example 136a)

To a stirred solution of 7-amino-3-ethyl-2-methyl-5-(methyl sulfonyl) pyrazolo[1,5-a] pyrimidine-6-carbonitrile II (180 mg, 0.644 mmol) in isopropanol (6 mL) were added triethylamine (391 mg, 539 μL, 3.87 mmol) and tert-butyl (3-(3-(2-aminoethyl)-2-oxopyridin-1(2H)-yl) propyl) carbamate LXI (381 mg, 1.29 mmol) in a sealed tube. The reaction mixture was stirred at 140° C. for 48 h and the progress of the reaction was monitored by TLC analysis. After completion, water (15 mL) was added and extracted with ethyl acetate (25 mL×2). The combined organic layer was dried over anhydrous sodium sulfate and concentrated under vacuum. The compound was purified by flash column chromatography (silica gel, 230-400) using methanol in DCM (0-10%) to afford the desired compound Example 136a as an off-white solid. Yield: 95 mg (30%) LCMS Calculated. for $C_{25}H_{34}N_8O_3$ is 494.28 Observed. 495.20 $[M+H]^+$: $^1$H NMR (400 MHz, DMSO-$D_6$): δ 8.05 (bs, 2H), 7.55 (d, J=6.4 Hz, 1H), 7.27 (d, J=6.4 Hz, 1H), 6.84 (bs, 1H), 6.16 (t, J=6.8 Hz, 1H), 3.90-3.87 (m, 3H), 3.52-3.50 (m, 2H), 2.92 (d, J=6.0 Hz, 2H), 2.73 (t, J=6.4 Hz, 2H) 2.45-2.41 (m, 2H), 2.24 (s, 3H) 1.74 (t, J=6.4 Hz, 2H), 1.38 (bs, 9H), 1.10 (t, J=7.2 Hz, 3H).

Step-2: 7-amino-5-((2-(1-(3-aminopropyl)-2-oxo-1,2-dihydropyridin-3-yl) ethyl) amino)-3-ethyl-2-methylpyrazolo[1,5-a] pyrimidine-6-carbonitrile To a stirred solution of tert-butyl (3-(3-(2-((7-amino-6-cyano-3-ethyl-2-methylpyrazolo[1,5-a] pyrimidin-5-yl) amino) ethyl)-2-oxopyridin-1(2H)-yl) propyl) carbamate) Example 136a (95 mg, 0.19 mmol) in 1,4-dioxane (3 mL) at 0° C. was drop wise added 4M HCl in dioxane (9.4 μL, 0.38 mmol) under inert atmosphere. The mixture was stirred at rt for 2 h. The progress of the reaction was monitored by TLC analysis. After completion, sat. sodium bicarbonate solution (5 mL) was added and extracted with DCM (25 mL×2). The combined organic layer was dried over anhydrous sodium sulfate and concentrated under vacuum to afford the desired compound Example 136 as an off-white solid. Yield: 35 mg (46%) LCMS Calculated. for $C_{20}H_{26}N_8O$ is 394.22 $[M+H]^+$; Observed. 395.40 $[M+H]^+$; 1H NMR (400 MHz, DMSO-$D_6$): δ 8.03 (bs, 4H), 7.63 (d, J=6.0 Hz, 1H), 7.31 (d, J=6.8 Hz, 1H), 6.71 (t, J=5.2 Hz, 1H), 6.22 (t, J=6.8 Hz, 1H), 4.01 (t, J=6.8 Hz, 2H), 3.55-3.50 (m, 2H), 3.66-3.64 (m, 2H), 2.77 (t, J=6.8 Hz, 4H), 2.44-2.42 (m, 2H), 2.25 (s, 3H), 1.98 (t, J=6.8 Hz, 1H), 1.11 (t, J=7.6 Hz, 2H); HPLC Purity=98.23%, INT ODS 3V-C18 (4.6*250) mm, 5μ; Mobile Phase A: 0.1% Formic acid in water: Mobile Phase B: Acetonitrile; Retention time=7.972 min; Flow: 1.0 mL/min.

Example 137: 7-amino-3-(cyclobutylmethyl)-5-((2-(1-(1-(hydroxymethyl) cyclopropyl)-1H-pyrazol-3-yl) ethyl) amino)-2-methylpyrazolo[1,5-a]pyrimidine-6-carbonitrile

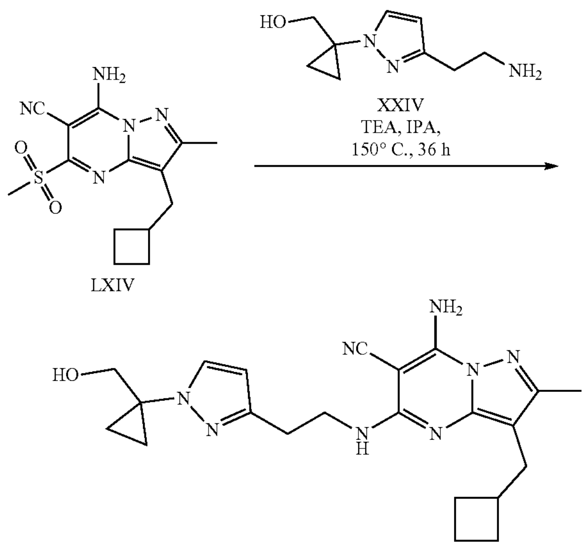

LXIV

Example 137

In a seal tube 7-amino-3-(cyclobutylmethyl)-2-methyl-5-(methyl sulfonyl) pyrazolo[1,5-a] pyridine-6carbonotrile LXIV (130 mg, 0.407 mmol) and (1-(3-(2-aminoethyl)-1H-pyrazol-1-yl) cyclopropyl) methanol XXIV (184 mg, 1.02 mmol) were dissolved in isopropanol (10 mL). To this solution TEA (0.340 mL, 2.44 mmol) was added and the reaction mixture was stirred at 150° C. for 36 h. The progress of reaction was monitored by TLC analysis. After completion, reaction was cooled to room temperature and concentrated under reduced pressure. The residue was dissolved in water (10 mL) and extracted with ethyl acetate (10 mL×3). The combined organic layer was washed with brine and dried over anhydrous sodium sulphate. The solution was concentrated under reduced pressure and crude material was purified by flash chromatography (Biotage) column using 0-5% methanol in DCM to afford the desired compound Example 137 as an off-white solid. Yield: 60 mg (35%); LCMS Calculated. for $C_{22}H_{28}N_8O$ is 420.24; Observed: 421.35 $[M+H]^+$. $^1H$ NMR (400 MHz, DMSO-$D_6$): δ 8.09 (bs, 2H), 7.62 (s, 1H), 6.64 (t, J=5.2 Hz, 1H), 6.04 (s, 1H), 4.88 (t, J=6.0 Hz, 1H), 3.60-3.54 (m, 4H), 2.81 (t, J=7.2 Hz, 2H), 2.59-2.50 (m, 3H), 2.23 (s, 3H), 1.92 (bs, 2H), 1.78-1.67 (m, 4H), 1.09 (d, J=6.8 Hz, 2H) 0.96 (t, J=4.8 Hz, 2H); HPLC Purity=97.23%, INT ODS 3V-C18 (4.6×250) mm, 5μ; Mobile Phase A: 0.1% Formic acid in water: Mobile Phase B: Acetonitrile; Retention time=12.68 min.

Example 138: 7-amino-5-((2-(1-(3-hydroxypropyl)-2-oxo-1,2-dihydropyridin-3-yl) ethyl) amino)-2,3-dimethylpyrazolo[1,5-a] pyrimidine-6-carbonitrile

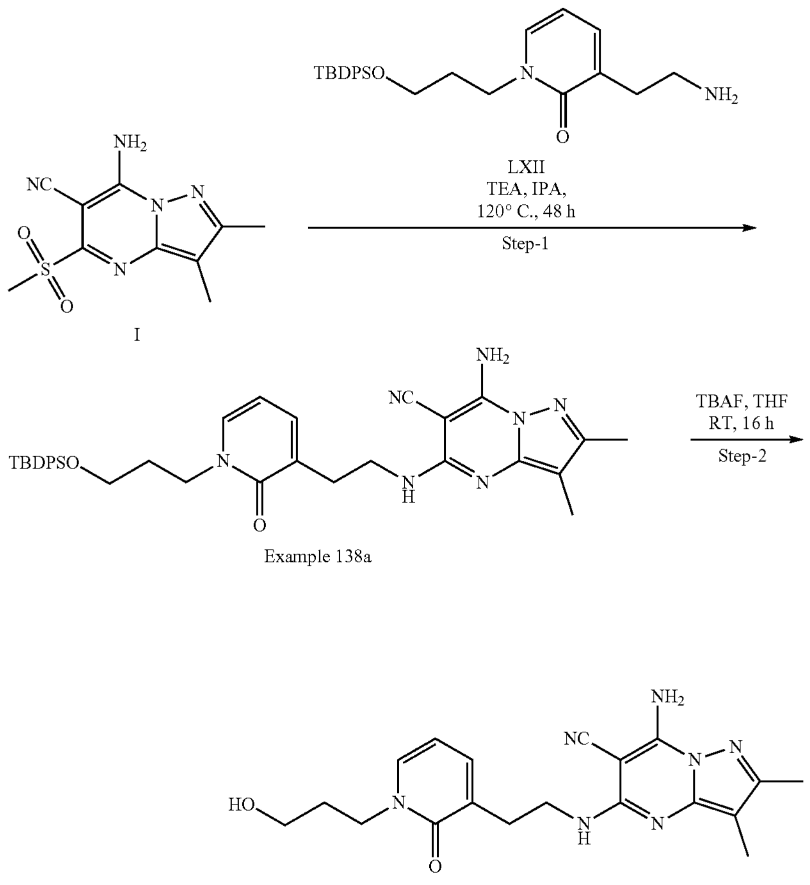

I

Example 138a

Example 138

Step-1: 7-amino-5-((2-(1-(3-((tert-butyl diphenyl silyl) oxy) propyl)-2-oxo-1,2-dihydropyridin-3-yl) ethyl) amino)-2,3-dimethylpyrazolo[1,5-a]pyrimidine-6-carbonitrile (Example 138a)

To a stirred solution of 7-amino-2,3-dimethyl-5-(methylsulfonyl)pyrazolo[1,5-a]pyrimidine-6-carbonitrile I (0.25 g, 0.94 mmol) in isopropanol (5 mL) were added triethylamine (0.57 g, 0.79 mL, 5.7 mmol) and 3-(2-aminoethyl)-1-(3-((tert-butyldiphenylsilyl)oxy)propyl)pyridin-2(1H)-one LXII (1.2 g, 2.8 mmol) and the reaction mixture was stirred at 120° C. for 48 h. The progress of the reaction was monitored by TLC analysis. After completion, the reaction mixture was cooled to room temperature and quenched with water (50 mL). The resulting mixture was extracted with ethyl acetate (25 mL×3), and the combined organic layer was dried over anhydrous sodium sulphate and concentrated under reduced pressure to afford the desired compound Example 138a as yellow liquid. Yield: (0.25 g, 43.1%); LCMS Calculated. for $C_{35}H_{41}N_7O_2Si$ is 619.31; Observed. 620.30 $[M+H]^+$; $^1$HNMR (400 MHz, $CDCl_3$): δ 7.80-7.71 (m, 2H), 7.65-7.64 (d, 2H), 7.44-7.38 (m, 8H), 7.24-7.20 (m, 2H), 6.96 (d, J=8.8 Hz, 1H), 6.10 (t, J=7.6 Hz, 1H), 4.15-4.09 (m, 2H), 3.87-3.85 (m, 2H), 3.68 (t, J=5.2 Hz, 2H), 3.08 (s, 2H), 2.79-2.76 (m, 2H), 2.05 (s, 3H), 1.97 (s, 3H), 1.08 (s, 9H).

Step-2: 7-amino-5-((2-(1-(3-hydroxypropyl)-2-oxo-1,2-dihydropyridin-3-yl) ethyl) amino)-2,3-dimethylpyrazolo[1,5-a]pyrimidine-6-carbonitrile To a stirred solution of 7-amino-5-((2-(1-(3-((tert-butyldiphenylsilyl)oxy)propyl)-2-oxo-1,2-dihydropyridin-3-yl) ethyl)amino)-2,3-dimethylpyrazolo[1,5-a]pyrimidine-6-carbonitrile Example 138a (0.25 g, 0.40 mmol) in THF (10 mL) was added TBAF (0.8 mL, 1 M in THF, 0.81 mmol) and the reaction mixture was stirred at room temperature for 16 h. The progress of the reaction was monitored by TLC analysis. After completion, the reaction mixture was quenched with saturated $NaHCO_3$ (200 mL) and extracted with DCM (300 mL×3), and the combined organic layer was dried over anhydrous sodium sulphate and concentrated under reduced pressure. The residue obtained upon removal of the solvent was subjected to silica gel (230-400 mesh) column chromatography using (1-5%) MeOH in DCM to afford the desired compound Example 138 as off-white solid. Yield: 0.080 g, (52%); LCMS Calculated. for $C_{19}H_{23}N_7O_2$ is 381.19; Observed. 382.30 $[M+H]^+$; $^1$HNMR (400 MHz, DMSO-$d_6$): δ 8.05 (s, 2H), 8.51 (d, J=6.0 Hz, 1H), 7.28 (d, J=6.0 Hz, 1H), 6.69 (s, 1H), 6.16 (t, J=6.8 Hz, 1H), 4.58 (t, J=4.8 Hz, 1H), 3.94 (t, J=6.8 Hz, 2H), 3.53 (d, J=5.6 Hz, 2H), 3.38 (s, J=5.6 Hz, 2H), 2.74 (t, J=6.4 Hz, 2H), 2.22 (s, 3H), 1.95 (s, 3H), 1.78 (t, J=6.4 Hz, 2H). HPLC: Rt=9.176 min; purity=95.99%; INT ODS 3V-C18 (4.6*250) mm, 5μ; Mobile Phase A: 0.1% Formic acid in water, Mobile Phase B: Acetonitrile.

Example 139: 7-amino-3-ethyl-5-((2-(6-(2-hydroxyethyl) pyridine-2-yl) ethyl) amino)-2-methylpyrazolo[1,5-a]pyrimidine-6-carbonitrile

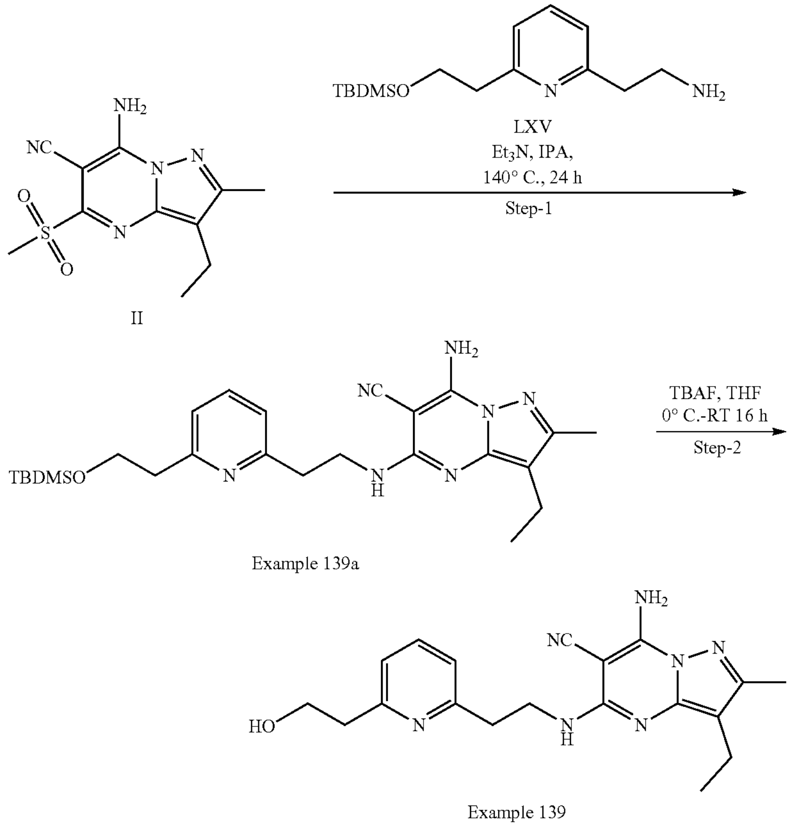

Step-1: 7-amino-5-((2-(6-(2-((tert-butyldimethylsilyl) oxy) ethyl) pyridin-2-yl) ethyl) amino)-3-ethyl-2-methylpyrazolo[1,5-a] pyrimidine-6-carbonitrile (Example 139a)

To a stirred solution of 2-(6-(2-((tert-butyldimethylsilyl) oxy) ethyl) pyridin-2-yl) ethan-1-amine LXV (0.26 g, 0.93 mmol) in 2-propanol (20 mL) was added 7-amino-3-ethyl-2-methyl-5-(methyl sulfonyl) pyrazolo[1,5-a] pyrimidine-6-carbonitrile II (0.52 g, 1.9 mmol) and triethylamine (0.28 g, 0.39 mL, 2.8 mmol) under nitrogen. The resulting mixture was stirred at 140° C. for 24 h. The progress of the reaction was monitored by TLC analysis. After completion, the reaction mixture was cooled to room temperature and diluted with water (30 mL) then extracted with ethyl acetate (45 mL×2). The combined organic layer was washed with 25 mL of brine and passed through anhydrous sodium sulphate then concentrated under reduced pressure. The residue obtained upon removal of the solvent was subjected to silica gel (230-400 mesh) column chromatography using 0-15% ethyl acetate in n-hexane to afford the desired compound Example 139a as a pale-yellow viscous liquid. Yield: 0.2 g, 40%); LCMS Calculated. for $C_{25}H_{37}N_7OSi$ is 479.28; Observed. 480.45 $[M+H]^+$; $^1$HNMR (400 MHz, $CDCl_3$): δ 7.51 (t, J=7.6 Hz, 1H), 7.08 (d, J=7.6 Hz, 1H), 7.00 (d, J=7.6 Hz, 1H), 6.44 (bs, 1H), 5.94 (bs, 2H), 4.01 (t, J=6.0 Hz, 2H), 3.87 (q, J=6.0 Hz, 2H), 3.08-3.02 (m, 4H), 2.56 (q, J=7.2 Hz, 2H), 2.32 (s, 3H), 1.19 (t, J=6.0 Hz, 3H), 0.86 (s, 9H), 0.08 (s, 6H).

Step-2: 7-amino-3-ethyl-5-((2-(6-(2-hydroxyethyl) pyridin-2-yl) ethyl) amino)-2-methylpyrazolo[1,5-a] pyrimidine-6-carbonitrile To a stirred solution of 7-amino-5-((2-(6-(2-((tert-butyldimethylsilyl) oxy) ethyl) pyridin-2-yl) ethyl) amino)-3-ethyl-2-methylpyrazolo[1,5-a] pyrimidine-6-carbonitrile Example 139a (0.20 g, 0.42 mmol) in THF (10 mL) was added TBAF (0.84 mL, 1M in THF, 0.84 mmol) and reaction mixture was stirred at room temperature for 16 h. The progress of the reaction was monitored by TLC. The reaction mixture was diluted with water (20 mL) and extracted with ethyl acetate (30 mL). The combined organic layer was dried over anhydrous sodium sulphate and concentrated under vacuo to afford a desired compound. The crude compound was washed with n-pentane (5 mL). to afford pure desired product Example 139 as an off-white solid. Yield: 0.11 g (72%); LCMS Calculated. for $C_{19}H_{23}N_7O$ is 365.19; Observed. 366.35 $[M+H]^+$; $^1$H NMR (400 MHz, DMSO-$D_6$): δ 8.10 (bs, 2H), 7.62 (t, J=7.6 Hz, 1H), 7.11-7.10 (m, 2H), 6.85 (t, J=4.8 Hz, 1H), 4.61 (bs, 1H), 3.74 (q, J=6.4 Hz, 2H), 3.66 (q, J=6.4 Hz, 2H), 3.01 (t, J=6.4 Hz, 2H), 2.88 (t, J=6.4 Hz, 2H), 2.47-2.44 (m, 2H), 2.25 (s, 3H), 1.13 (t, J=7.6 Hz, 3H). HPLC: 7.892 min; 96.98%, INT ODS 3V-C18 (4.6×150) mm, 5μ, Mobile phase A: 0.1% Formic acid in water; Mobile phase B: Acetonitrile.

Example 140: 7-amino-2,3-dimethyl-5-((2-(6-methylpyrazin-2-yl) ethyl) amino) pyrazolo[1,5-a]pyrimidine-6-carbonitrile

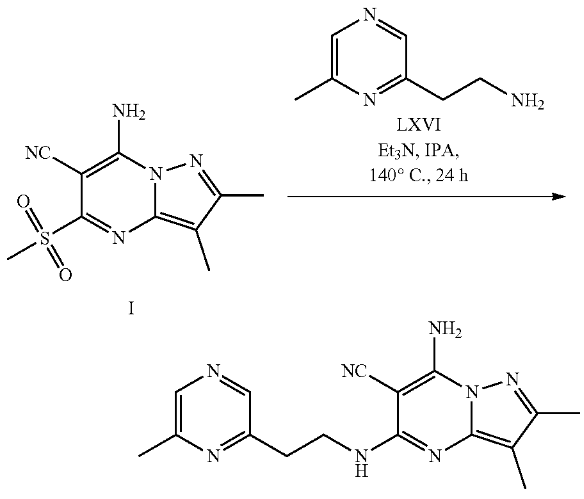

Example 140

To a stirred solution of 7-amino-2,3-dimethyl-5-(methyl sulfonyl) pyrazolo[1,5-a] pyrimidine-6-carbonitrile I (300 mg, 1.13 mmol) in 2-propanol (6 mL) was added triethylamine (687 mg, 946 μL, 6.79 mmol) and 2-(6-methylpyrazin-2-yl) ethan-1-amine LXVI (341 mg, 2.49 mmol) and the reaction mixture was stirred at 140° C. for 24 h. The progress of the reaction was monitored by TLC analysis. After completion, the reaction mixture was quenched with water (25 mL) and the resulting mixture was extracted with ethyl acetate (50 mL×3). The combined organic layer was dried over anhydrous sodium sulfate and concentrated under reduced pressure. The crude residue was subjected to silica gel (230-400) column chromatography using 0-5% methanol in DCM to afford the desired compound Example 140 as an off-white solid. Yield: (100 mg, 27%); LCMS Calculated. for $C_{16}H_{18}N_8$ is 322.16; Observed. 323.30 $[M+H]^+$; $^1$HNMR (400 MHz, DMSO-$D_6$): δ 8.35 (d, J=6.4 Hz, 2H), 8.11 (bs, 2H), 6.82 (s, 1H), 3.70 (d, J=6.4 Hz, 2H), 3.04 (t, J=6.4 Hz, 2H), 2.48 (s, 3H), 2.23 (s, 3H), 1.95 (s, 3H). HPLC: Rt=10.813 min; Purity=97.81%, INT ODS 3V-C18 (4.6×250) mm, 5μ; Mobile Phase A: 0.1% Formic acid in water, Mobile Phase B: Acetonitrile.

Example 141: 7-amino-5-((2-(1-(3-aminopropyl)-2-oxo-1,2-dihydropyridin-3-yl) ethyl) amino)-2,3-dimethylpyrazolo[1,5-a]pyrimidine-6-carbonitrile

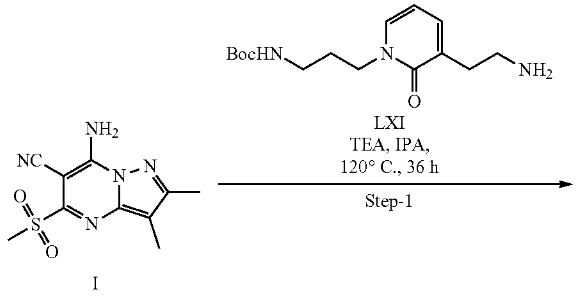

-continued

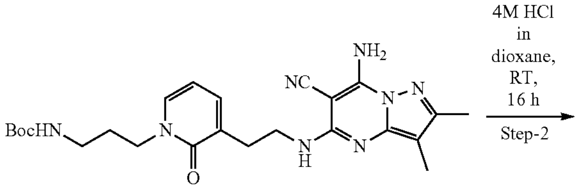

Example 141a

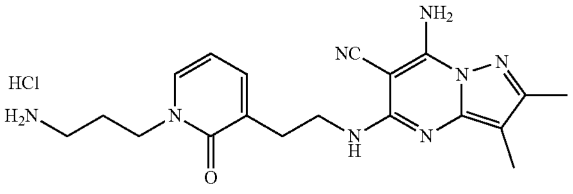

Example 141

Step-1: tert-butyl (3-(3-(2-((7-amino-6-cyano-2,3-dimethylpyrazolo[1,5-a] pyrimidin-5-yl) amino) ethyl)-2-oxopyridin-1(2H)-yl) propyl) carbamate (Example 141a)

To a stirred solution of 7-amino-2,3-dimethyl-5-(methyl sulfonyl) pyrazolo[1,5-a] pyrimidine-6-carbonitrile I (170 mg, 64 μmol) in isopropanol (5 mL) were added TEA (536 μL, 3.84 mmol) and tert-butyl (3-(3-(2-aminoethyl)-2-oxopyridin-1(2H)-yl) propyl) carbamate LXI (284 mg, 961 μmol), in a sealed tube under $N_2$ atmosphere. The reaction mixture was stirred at 120° C. for 36 h and the progress of the reaction was monitored by TLC analysis. After completion, the reaction was cooled to rt and the reaction mixture was concentrated under reduced pressure. The residue compound was purified by column chromatography (silica gel; 230-400 mesh) using 0-3% MeOH/DCM to afford the desired product Example 141a as an off-white solid. Yield: 150 mg (49%); LCMS Calculated. for $C_{24}H_{32}N_8O_3$ is 480.50; Observed. 481.40 $[M+H]^+$; $^1H$ NMR (400 MHz, DMSO-$D_6$): 8.05 (bs, 2H), 7.55 (d, J=6.0 Hz, 1H), 7.27 (d, J=5.6 Hz, 1H), 6.85 (s, 1H), 6.69 (t, J=5.2 Hz, 1H), 6.16 (t, J=6.8 Hz, 1H), 3.88 (t, J=6.8 Hz, 2H), 3.52 (q, J=6.4 Hz, 2H), 2.92 (d, J=6.0 Hz, 2H), 2.73 (t, J=6.8 Hz, 2H), 2.28 (s, 3H)), 1.98 (s, 3H), 1.73 (t, J=6.8 Hz, 2H), 1.37 (s, 9H).

Step-2: 7-amino-5-((2-(1-(3-aminopropyl)-2-oxo-1, 2-dihydropyridin-3-yl) ethyl) amino)-2,3-dimethylpyrazolo[1,5-a] pyrimidine-6-carbonitrile: Hydrochloride Salt A solution of tert-butyl (3-(3-(2-((7-amino-6-cyano-2,3-dimethylpyrazolo[1,5-a] pyrimidin-5-yl) amino) ethyl)-2-oxopyridin-1(2H)-yl) propyl) carbamate Example 141a (150 mg, 312 μmol) in 1-4-dioxane (5 mL) was cooled to 0° C. and added hydrogen chloride in dioxane (780 μL, 4 molar, 3.12 mmol). The reaction mixture was stirred at rt for 16 h and the progress of the reaction was monitored by TLC analysis. After completion, the reaction mixture concentrated under reduced pressure and solid obtained was washed with diethyl ether (2 mL×2) to afford the desire product Example 141 as an off-white solid. Yield: 74.1 mg (57%); LCMS Calculated. for $C_{17}H_{19}N_7$ is 380.20; Observed. 381.35 $[M+H]^+$; $^1H$ NMR (400 MHz, DMSO-$D_6$): 8.35 (bs, 2H), 7.96 (bs, 3H), 7.67 (d, J=6.0 Hz, 1H), 7.39 (d, J=6.0 Hz, 1H), 6.28 (t, J=6.8 Hz, 1H), 4.03 (t, J=6.4 Hz, 2H), 3.54 (d, J=6.4 Hz, 2H), 2.76 (t, J=6.8 Hz, 4H), 2.24 (s, 3H), 2.03-1.96 (m, 5H); HPLC: 7.617 min; 95.87%; INT ODS 3V-C18 (4.6*250) mm, 5μ; Mobile phase A: 0.1% Formic acid in water, Mobile phase B: Acetonitrile; Flow: 1.0 mL/min.

Example 142: 7-amino-3-ethyl-2-methyl-5-((2-(1-(2-(methylthio)ethyl)-2-oxo-1,2-dihydropyridin-3-yl)ethyl)amino)pyrazolo[1,5-a]pyrimidine-6-carbonitrile

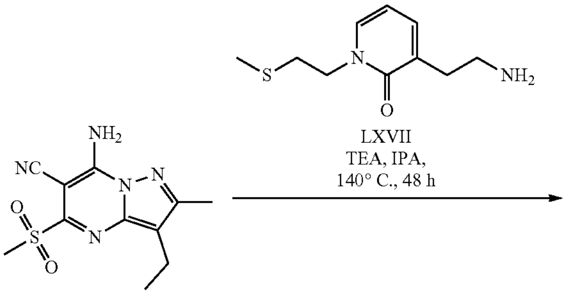

II

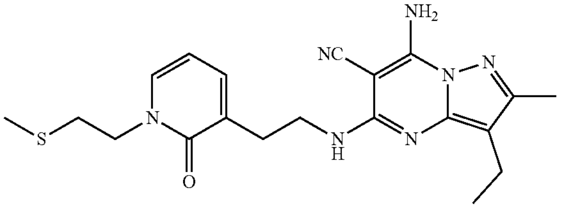

Example 142

To a stirred solution of 7-amino-3-ethyl-2-methyl-5-(methyl sulfonyl) pyrazolo[1,5-a] pyrimidine-6-carbonitrile II (4 g, 0.01 mol) in IPA (50 mL) were added TEA (12.5 mL, 0.09 mol) and 3-(2-aminoethyl)-1-(2-(methylthio) ethyl) pyridin-2(1H)-one LXVII (7 g, 0.03 mol), in a sealed tube. The reaction mixture was stirred at 140° C. for 48 h. The progress of the reaction was monitored by TLC analysis. After completion, the reaction was cooled to RT and water (50 mL) was added. The resulting mixture was extracted with ethyl acetate (100 mL×3). The combined organic layer was dried over anhydrous sodium sulphate, filtered, and concentrated under reduced pressure to obtained crude compound. The crude compound was purified by flash column chromatography (silica gel, 230-400) using 0-5% methanol in DCM to afford the desired compound as a yellow solid. Yield: 2.0 g (30%); LCMS Calculated. for $C_{20}H_{25}N_7OS$ is 411.18; Observed. 412.25 $[M+H]^+$. $^1H$ NMR (400 MHz, DMSO-$D_6$): δ 8.04 (bs, 2H), 7.58 (d, J=5.2 Hz, 1H), 7.31 (s, J=4.8 Hz, 1H), 6.70 (s, 1H), 6.17 (s, 1H), 4.07 (s, 2H), 3.52 (s, 2H), 2.75-2.67 (m, 4H), 2.44 (d, J=7.2 Hz, 2H), 2.23 (s, 3H), 2.06 (s, 3H), 1.67 (d, J=6.4 Hz, 3H). HPLC: 11.96 min; 99.401%, INT ODS 3V-C18 (4.6*250) mm, 5μ; Mobile Phase A: 0.1% Formic acid in water, Mobile Phase B: Acetonitrile; Flow: 1.0 mL/min.

Example 143: Racemic (+−)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile Example 144a: (+)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile Example 144b: (−)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile

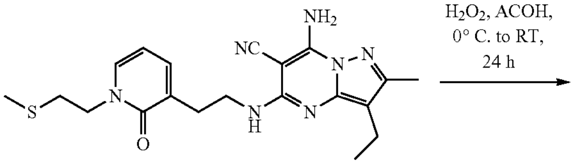

Example 142

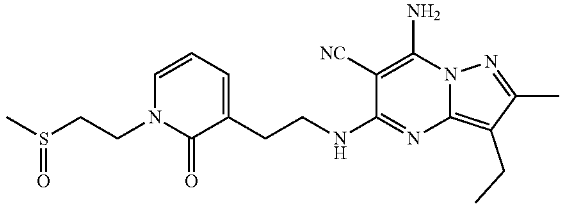

Racemic: Example 143; Racemic(±)
Peak-1: Example 144a, dextro(+) rotatory
Peak-2: Example 144b, leavo(-) rotatory A solution of 7-amino-3-ethyl-2-methyl-5-((2-(1-(2-(methylthio) ethyl)-2-oxo-1,2-dihydropyridin-3-yl) ethyl) amino) pyrazolo[1,5-a] pyrimidine-6-carbonitrile Example 142 (0.230 g, 0.559 mmol) and in acetic acid (5 mL) was cooled to 0° C. and added $H_2O_2$ (205 μL, 6.71 mmol). The reaction mixture was stirred at rt for 24 h. The progress of the reaction was monitored by TLC analysis. After completion, the reaction was quenched with sat. $NaHCO_3$ solution (20 mL) and extracted with ethyl acetate (100 mL×3). The combined organic layer was concentrated under reduced pressure. The crude compound was purified by column chromatography (silica gel 230-400 mesh) using 0-3% MeOH/DCM to afford the desired compound Example 143 as an off-white solid. Yield: 180 mg (75%); LCMS Calculated. for $C_{20}H_{25}N_7O_2S$ is 427.18; Observed. 428.30 $[M+H]^+$. $^1H$ NMR (400 MHz, DMSO-$D_6$): δ 8.04 (bs, 2H), 7.56 (d, J=6.0 Hz, 1H), 7.31 (d, J=5.6 Hz, 1H), 6.67 (s, 1H), 6.21 (d, J=6.4 Hz, 1H), 4.33 (t, J=6.0 Hz, 1H), 4.15 (t, J=6.4 Hz, 1H), 3.51 (d, J=4.4 Hz, 2H), 3.22 (m, 2H), 3.06-3.02 (m, 1H), 2.75 (s, 2H), 2.60 (s, 2H), 2.49-2.41 (m, 2H), 2.23 (s, 3H), 1.10 (t, J=6.8 Hz, 3H); HPLC: 9.537 min; 99.04%, INT ODS 3V-C18 (4.6*250) mm, 5μ; Mobile Phase A: 0.1% Formic acid in water, Mobile Phase B: Acetonitrile; Flow: 1.0 mL/min.

Further the racemic compound Example 143 was subjected to chiral SFC (column IC (21*250 mm), 5 μm; Co-Solvent Name: MeOH, % of Co-Solvent: 40; ABPR Pressure: 1500 psi) and separated into peak-1 Example 144a and peak-2 Example 144b Absolute stereochemistry of the chiral center is unknown Peak1: Example 144a Yield:16.2 mg; LCMS Calculated. for $C_{20}H_{25}N_7O_2S$ is 427.18; Observed. 428.30 $[M+H]^+$. $^1H$ NMR (400 MHz, DMSO-$D_6$): δ 8.07 (bs, 2H), 7.56 (q, J=1.6 Hz, 1H), 7.32 (q, J=1.6 Hz, 1H), 6.70 (t, J=5.2 Hz, 1H), 6.21 (t, J=6.8 Hz, 1H), 4.36-4.30 (m, 1H), 4.15-4.14 (m, 1H), 3.52 (q, J=6.4 Hz, 2H), 3.26-3.16 (m, 1H), 3.07-2.99 (m, 1H), 2.75 (t, J=6.8 Hz, 2H), 2.60 (s, 3H), 2.45-2.42 (m, 2H), 2.24 (s, 3H), 1.10 (t, J=7.6 Hz, 3H); HPLC: 9.468 min; 99.20%, INT ODS 3V-C18 (4.6*250) mm, 5μ; Mobile Phase A: 0.1% Formic acid in water, Mobile Phase B: Acetonitrile.; Chiral HPLC: 8.582 min; 100%; Column Name-IC (4.6*250 mm), 5 μm; Co-Solvent Name: MeOH; Total flow rate: 3 g/mL; % of Co-Solvent: 40; Temperature: 30° C.; ABPR pressure: 1500 psi); Specific optical rotation ($[\alpha]_D$); (c 0.1 in MeOH) =75.62. Peak-2: Example 144b Yield:16.2 mg. LCMS Calculated. for $C_{20}H_{25}N_7O_2S$ is 427.18; Observed. 428.30 $[M+H]^+$. $^1H$NMR (400 MHz, DMSO-$D_6$): δ 8.06 (bs, 2H), 7.57 (d, J=6.0 Hz, 1H), 7.32 (d, J=6.0 Hz, 1H), 6.69 (bs, 1H), 6.21 (t, J=6.8 Hz, 1H), 4.34-4.32 (m, 1H), 4.18-4.16 (m, 1H), 3.53-3.52 (m, 2H), 3.26-3.21 (m, 1H), 3.06-3.10 (m, 1H), 2.77 (bs, 2H), 2.60 (s, 3H), 2.45-2.42 (m, 2H), 2.24 (s, 3H), 1.11 (t, J=7.6 Hz, 3H); HPLC: 9.436 min; 97.05%, INT ODS 3V-C18 (4.6*250) mm, 5μ; Mobile Phase A: 0.1% Formic acid in water, Mobile Phase B: Acetonitrile; Chiral HPLC: 9.293 min; 97.46%; Column Name-IC (4.6*250 mm), 5 μm; Co-Solvent Name: MeOH; Total flow rate: 3 g/mL; % of Co-Solvent: 40; Temperature: 30° C.; ABPR pressure: 1500 psi); Specific optical rotation ($[\alpha]_D$); (c 0.1 in MeOH)=−48.96.

Example 145: N-(3-(3-(2-((7-amino-6-cyano-3-ethyl-2-methylpyrazolo[1,5-a]pyrimidin-5-yl) amino) ethyl)-2-oxopyridin-1(2H)-yl) propyl) acetamide

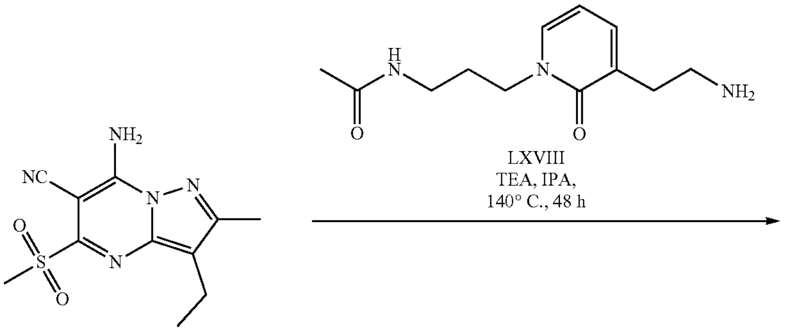

II

-continued

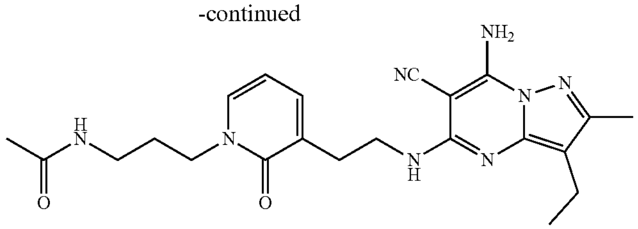

Example 145

To a stirred solution of 7-amino-3-ethyl-2-methyl-5-(methyl sulfonyl) pyrazolo[1,5-a] pyrimidine-6-carbonitrile II (100 mg, 358 μmol) in IPA (6 mL) were added TEA (299 μL, 2.15 mmol) and N-(3-(3-(2-aminoethyl)-2-oxopyridin-1(2H)-yl) propyl) acetamide LXVIII (212 mg, 895 μmol) in a sealed tube under $N_2$ atmosphere. The reaction mixture was stirred at 140° C. for 48 h and the progress of the reaction was monitored by TLC analysis. After completion, the reaction was cooled to rt and quenched with water (50 mL). The resulting mixture was extracted with ethyl acetate (50 mL×3). The combined organic layer was dried over anhydrous sodium sulfate and concentrated under reduced pressure. The crude compound was purified by flash column chromatography (silica gel, 230-400) using methanol in DCM (0-5%) to afford the desired compound Example 145 as an off-white solid. Yield: 120 mg (77%); LCMS Calculated. for $C_{22}H_{28}N_8O_2$ is 436.23 Observed. 437.40 $[M+H]^+$. $^1H$ NMR (400 MHz, DMSO-$d_6$): δ 8.05 (bs, 2H), 7.85 (s, 1H), 7.56 (d, J=6.4 Hz, 1H), 7.27 (d, J=6.4 Hz, 1H), 6.72 (s, 1H), 6.17 (t, J=6.8 Hz, 1H), 3.89 (t, J=6.4 Hz, 2H), 3.52 (d, J=5.2 Hz, 2H), 3.03 (q, J=6.4 Hz, 2H), 2.74 (t, J=6.0 Hz, 2H), 2.43 (t, J=7.2 Hz, 2H), 2.24 (s, 3H), 1.80-1.74 (m, 5H), 1.11 (t, J=7.2 Hz, 3H); HPLC: 9.668 min; 98.89%; INT ODS 3V-C18 (4.6*250) mm, 5μ; Mobile phase A: 0.1% Formic acid in water Mobile phase B: Acetonitrile; Flow: 1.0 mL/min.

Example 146: 7-amino-5-((2-(1-(1-(amino methyl) cyclopropyl)-1H-pyrazol-3-yl) ethyl) amino)-3-ethyl-2-methylpyrazolo[1,5-a]pyrimidine-6-carbonitrile

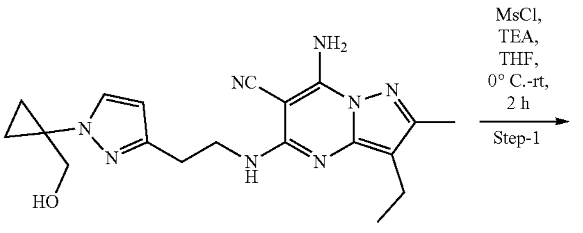

Example 39

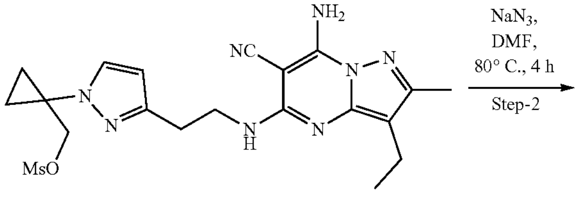

Example 146a

-continued

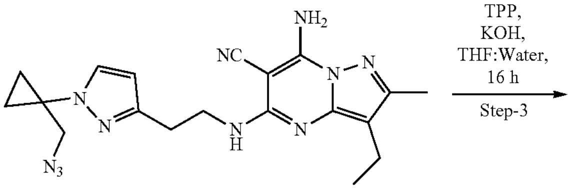

Example 146b

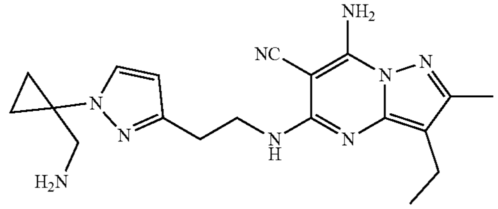

Example 146

Step-1: (1-(3-(2-47-amino-6-cyano-3-ethyl-2-methylpyrazolo[1,5-a] pyrimidin-5-yl) amino) ethyl)-1H-pyrazol-1-yl) cyclopropyl) methyl methane sulfonate (Example 146a)

To a solution of 7-amino-3-ethyl-5-((2-(1-(1-(hydroxymethyl) cyclopropyl)-1H-pyrazol-3-yl) ethyl) amino)-2-methylpyrazolo[1,5-a] pyrimidine-6-carbonitrile Example 39 (1.0 g, 2.6 mmol) in THF (20 mL) triethylamine (1.1 mL, 7.9 mmol) was added and the reaction mixture was cooled to 0° C. under $N_2$ atmosphere. Then methane sulfonyl chloride (0.53 mL, 5.3 mmol) was added dropwise, and the reaction mixture was stirred at rt for 2 h. The progress of reaction was monitored by TLC analysis. After completion, the reaction mixture was quenched with water (30 mL) and extracted with DCM (30 mL×3). The combined organic was given brine wash, dried over anhydrous sodium sulphate, filtered, and concentrated under reduced pressure to get crude material. The crude product obtained was purified by combi-flash chromatography (230-400) using 0-50% ethyl acetate in n-hexane to afford the desired compound Example 146a as a pale-yellow semi-solid. Yield: 0.459 g (38.3%); LCMS Calculated. for $C_{20}H_{26}N_8O_3S$ is 458.18; Observed. 459.30 $[M+H]^+$.

Step-2: 7-amino-5-((2-(1-(1-(azidomethyl) cyclopropyl)-1H-pyrazol-3-yl) ethyl) amino)-3-ethyl-2-methylpyrazolo[1,5-a] pyrimidine-6-carbonitrile (Example 146b)

To a solution of (1-(3-(2-((7-amino-6-cyano-3-ethyl-2-methylpyrazolo[1,5-a] pyrimidin-5-yl)amino)ethyl)-1H- pyrazol-1-yl)cyclopropyl)methyl methane sulfonate Example 146a (450 mg, 0.98 mmol) in DMF (2 mL) sodium azide (319 mg, 4.91 mmol) was added and the reaction mixture was stirred at 80° C. for 4 h. Progress of reaction was monitored by TLC analysis. After completion, the reaction mixture was quenched with water (20 mL) and extracted with ethyl acetate (30 mL×3). The combined organic layer was washed with brine and dried over anhydrous sodium sulphate. The solution was concentrated under reduced pressure to afford the desired compound Example 146b as a light brown viscous liquid. The crude product was taken for the next step without further purification. Yield: 477 mg (Crude); LCMS Calculated. for $C_{19}H_{23}N_{11}$ is 405.21; Observed. 406.35 $[M+H]^+$.

Step-3: 7-amino-5-((2-(1-(1-(amino methyl) cyclopropyl)-1H-pyrazol-3-yl) ethyl) amino)-3-ethyl-2-methylpyrazolo[1,5-a] pyrimidine-6-carbonitrile To a solution of 7-amino-5-((2-(1-(1-(azidomethyl) cyclopropyl)-1H-pyrazol-3-yl) ethyl) amino)-3-ethyl-2-methylpyrazolo[1,5-a] pyrimidine-6-carbonitrile Example 146b (390 mg, 0.96 mmol) in THF: $H_2O$ (8.0 mL; 3:1) $Ph_3P$ (378 mg, 1.44 mmol) was added, and the reaction mixture was stirred for 10 minutes at RT under inert atmosphere. Then potassium hydroxide (54.0 mg, 0.96 mmol) was added, and the reaction mixture was stirred at RT for 16 h. Progress of reaction was monitored by TLC analysis. After completion, the reaction mixture was quenched with water (20 mL) and extracted with ethyl acetate (30 mL×3). The combined organic layer was washed with brine and dried over anhydrous sodium sulphate. The mixture was concentrated under reduced pressure to get crude material. The crude was purified by flash silica gel column chromatography (Biotage) using 0-5% methanolic ammonia (7M) in DCM afford the desired compound Example 146 as a light green semi solid. Yield: 280 mg (76.71%); LCMS Calculated. for $C_{19}H_{25}N_9$ is 379.22; Observed. 380.40 $[M+H]^+$. $^1H$ NMR (400 MHz, DMSO-$D_6$): δ 8.15 (bs, 2H), 7.64 (d, J=2.0 Hz, 1H), 6.57 (t, J=5.2 Hz, 1H), 6.05 (d, J=2.4 Hz, 1H), 3.56 (q, J=5.6 Hz, 2H), 2.83-2.80 (m, 5H), 2.55-2.50 (m, 2H), 2.49-2.43 (m, 2H), 2.25 (s, 3H), 1.12 (t, J=7.2 Hz, 3H), 1.05-1.02 (m, 2H), 0.98-0.93 (m, 2H); HPLC: 7.967 min; 99.45%, Column: INT ODS 3V-C18 (4.6*250) mm, 5μ; Mobile phase A: 0.1% Formic acid in water, Mobile phase B: Acetonitrile Flow: 1.0 mL/min.

Example 147: N-((1-(3-(2-((7-amino-6-cyano-3-ethyl-2-methylpyrazolo[1,5-a]pyrimidin-5-yl) amino) ethyl)-1H-pyrazol-1-yl) cyclopropyl) methyl) acetamide

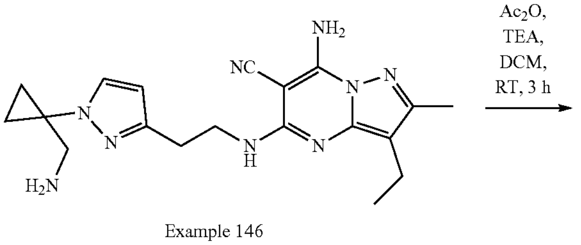

Example 146

-continued

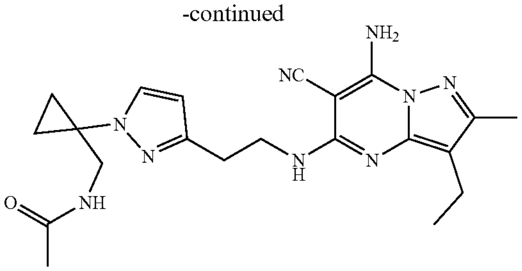

Example 147

To a solution of 7-amino-5-((2-(1-(1-(amino methyl) cyclopropyl)-1H-pyrazol-3-yl) ethyl) amino)-3-ethyl-2-methylpyrazolo[1,5-a] pyrimidine-6-carbonitrile Example 146 (50 mg, 0.13 mmol) in DCM (1 mL), TEA (46 μL, 0.33 mmol) was added. This was followed by an addition of solution of acetic anhydride (12 μL, 0.13 mmol) in DCM (0.5 mL). The resulting mixture was stirred at room temperature for 3 h and progress of the reaction was monitored by TLC analysis. After completion, the reaction was quenched with cold water (10 mL) and extracted with DCM (10 mL×3). The combined organic layer was washed with brine and dried over anhydrous sodium sulphate. The solution was concentrated, and the residue was washed with diethyl ether to afford the desired product Example 147 as an off-white solid. Yield: 30 mg (53.57%); LCMS Calculated. for $C_{21}H_{27}H_9O$ is 421.23; Observed. 422.40 $[M+H]^+$. $^1H$ NMR (400 MHz, DMSO-$D_6$): δ 8.10 (bs, 2H), 7.87 (bs, 1H), 7.60 (d, J=1.6 Hz, 1H), 6.59 (t, J=5.6 Hz, 1H), 6.05 (d, J=2.0 Hz, 1H), 3.60-3.55 (m, 2H), 3.42-3.33 (m, 2H), 2.81 (t, J=7.2 Hz, 2H), 2.47-2.43 (m, 2H), 2.25 (s, 3H), 1.77 (s, 3H), 1.37-1.08 (m, 5H), 1.02 (bs, 2H); HPLC: 10.766 min; 95.29%, Column: INT ODS 3V-C18 (4.6*250) mm, 5μ; Mobile phase A: 0.1% Formic acid in water, Mobile phase B: Acetonitrile; Flow: 1.0 mL/min.

Example 148: 7-amino-5-((2-(1-(1-(2-aminoethyl) cyclopropyl)-1H-pyrazol-3-yl) ethyl) amino)-3-ethyl-2-methylpyrazolo[1,5-a] pyrimidine-6-carbonitrile

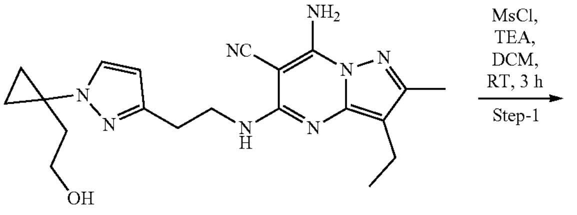

Example 124

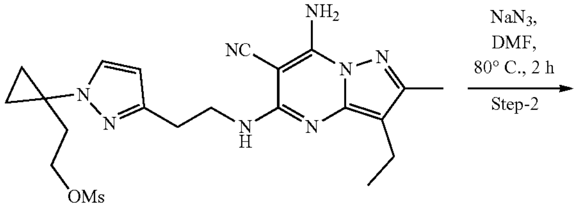

Example 148a

-continued

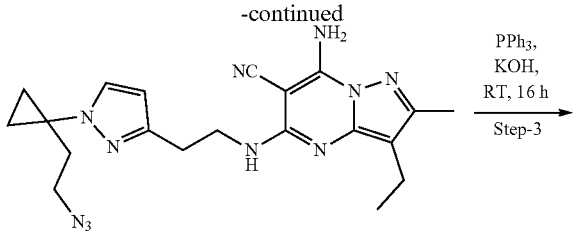

Example 148b

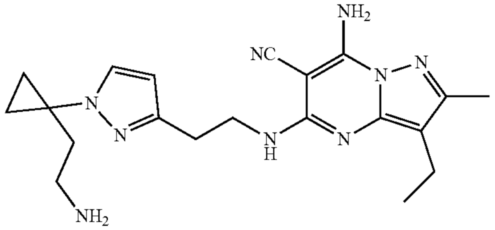

Example 148

Step-1: 2-(1-(3-(2-((7-amino-6-cyano-3-ethyl-2-methylpyrazolo[1,5-a] pyrimidin-5-yl) amino) ethyl)-1H-pyrazol-1-yl) cyclopropyl) ethyl methane sulfonate (148a)

To a stirred solution of 7-amino-3-ethyl-5-((2-(1-(1-(2-hydroxyethyl) cyclopropyl)-1H-pyrazol-3-yl) ethyl) amino)-2-methylpyrazolo[1,5-a] pyrimidine-6-carbonitrile Example 124 (860 mg, 2.18 mmol) in DCM (100 mL) was added triethylamine (1.52 mL, 10.9 mmol) under $N_2$ atmosphere. The resulting mixture was cooled to 0° C. and methane sulfonyl chloride (0.187 mL, 2.40 mmol) was added dropwise over the period of 10 min. The reaction was stirred at 0° C. for 3 h. The progress of the reaction was monitored by TLC analysis. After completion, the reaction mixture was diluted with sat. $NaHCO_3$ solution (50 mL) and extracted with DCM (50 mL×3). The combined organic layer was dried over anhydrous $Na_2SO_4$, filtered and concentrated under reduced pressure. The crude compound was subjected to silica gel (230-400) combi-flash column chromatography using 0-50% ethyl acetate in n-hexane to afford the desired compound Example 148a as a pale-yellow solid. Yield: 197 mg (19%); LCMS Calculated. for $C_{21}H_{28}N_8O_3S$ is 472.20; Observed. 473.30 $[M+H]^+$.

Step-2: 7-amino-5-((2-(1-(1-(2-azidoethyl) cyclopropyl)-1H-pyrazol-3-yl) ethyl) amino)-3-ethyl-2-methylpyrazolo[1,5-a] pyrimidine-6-carbonitrile (Example 148b)

To a stirred solution of 2-(1-(3-(2-((7-amino-6-cyano-3-ethyl-2-methylpyrazolo[1,5-a] pyrimidin-5-yl) amino) ethyl)-1H-pyrazol-1-yl) cyclopropyl) ethyl methane sulfonate Example 148a (197 mg, 0.417 mmol) in DMF (5 mL) was added sodium azide (108 mg, 1.67 mmol). The reaction was stirred at 80° C. for 2 h and the progress of the reaction was monitored by TLC analysis. After completion, the reaction mixture was diluted with water (20 mL) and extracted with ethyl acetate (20 mL×3). The combined organic layer was dried over anhydrous $Na_2SO_4$, filtered and concentrated under reduced pressure. The crude compound was subjected to silica gel (230-400) combi-flash column chromatography using 0-40% ethyl acetate in n-hexane to afford the desired compound Example 148b as an off-white solid. Yield: 90 mg (51%); LCMS Calculated. for $C_{20}H_{25}N_{11}$ is 419.23; Observed. 420.30 $[M+H]^+$.

Step-3: 7-amino-5-((2-(1-(1-(2-aminoethyl) cyclopropyl)-1H-pyrazol-3-yl) ethyl) amino)-3-ethyl-2-methylpyrazolo[1,5-a] pyrimidine-6-carbonitrile To a stirred solution of 7-amino-5-((2-(1-(1-(2-azidoethyl) cyclopropyl)-1H-pyrazol-3-yl) ethyl) amino)-3-ethyl-2-methylpyrazolo[1,5-a] pyrimidine-6-carbonitrile Example 148b (90 mg, 0.21 mmol) in THF: $H_2O$ (8 mL; 3:1) was added triphenylphosphine (84 mg, 0.32 mmol) and stirred for 10 min at rt. This was followed by an addition of KOH (12 mg, 0.21 mmol) under nitrogen atmosphere. The reaction was stirred at rt for 16 h. After completion, the reaction mixture was diluted with water (10 mL) and extracted with DCM (50 mL×3). The combined organic layer was dried over anhydrous $Na_2SO_4$, filtered and concentrated under reduced pressure. The crude was purified by combi-flash column chromatography using 0-5% methanol in DCM to afford the desired compound Example 148 as an off-white solid. Yield: 70 mg (83%); LCMS Calculated. for $C_{20}H_{27}N_9$ is 393.23; Observed. 394.35 $[M+H]^+$. $^1H$ NMR (400 MHz, DMSO-$D_6$): δ 7.65 (bs, 1H), 6.55 (bs, 1H), 6.04 (s, 1H), 3.58-3.57 (m, 3H), 2.81 (t, J=6.8 Hz, 2H), 2.47-2.40 (m, 4H), 2.25 (s, 3H), 1.82-1.76 (m, 3H), 1.14-1.08 (m, 5H), 0.98 (s, 1H), 0.93 (s, 2H); HPLC: 8.143 min; 98.92%, Column: INT ODS 3V-C18 (4.6*250) mm, 5μ; Mobile phase A: 0.1% Formic acid in water, Mobile phase B: Acetonitrile; Flow: 1.0 mL/min.

Example 149: N-(2-(1-(3-(2-((7-amino-6-cyano-3-ethyl-2-methylpyrazolo[1,5-a]pyrimidin-5-yl) amino) ethyl)-1H-pyrazol-1-yl) cyclopropyl) ethyl) acetamide (Example 149)

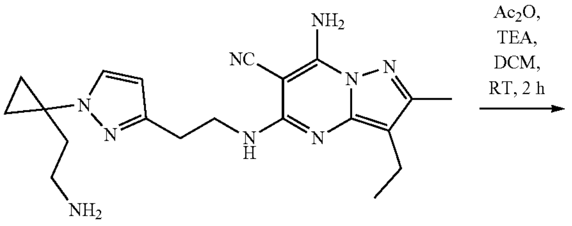

Example 148

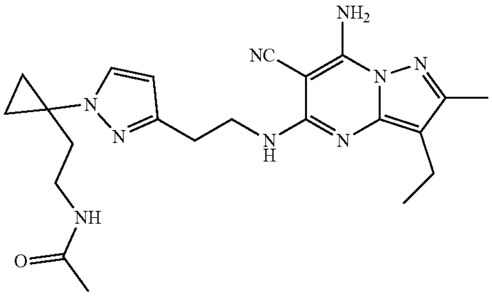

Example 149

To a stirred solution of 7-amino-5-((2-(1-(1-(2-aminoethyl) cyclopropyl)-1H-pyrazol-3-yl) ethyl) amino)-3-ethyl-2-methylpyrazolo[1,5-a] pyrimidine-6-carbonitrile Example 148 (50 mg, 0.13 mmol) in DCM (10 mL) were added triethylamine (35 μL, 0.25 mmol) and acetic anhydride (18 μL, 0.19 mmol) under inert atmosphere. The reaction mixture was stirred at rt for 2 h and the progress of the reaction was monitored by TLC analysis. After completion, the reaction mixture was diluted with water (20 mL) and extracted with DCM (20 mL×3). The organic layer was dried over anhydrous $Na_2SO_4$, filtered and concentrated under reduced pressure. The crude compound was subjected to silica gel (230-400) combi-flash column chromatography using 0-10% methanol in DCM to afford the desired compound Example 149 as an off-white solid. Yield: 10 mg (18%); LCMS Calculated. for $C_{22}H_{29}N_9O$ is 435.25; Observed. 436.40 $[M+H]^+$. $^1H$ NMR (400 MHz, DMSO-$D_6$): δ 8.10 (bs, 2H), 7.68 (bs, 2H), 6.59 (bs, 1H), 6.05 (bs, 1H), 3.58-3.57 (m, 2H), 2.94-2.92 (m, 2H), 2.82 (bs, 2H), 2.25 (s, 3H), 1.83 (bs, 2H), 1.74 (s, 3H), 1.14-1.09 (m, 5H), 2.01 (s, 2H); HPLC: 11.045 min; 99.30%, Column: INT ODS 3V-C18 (4.6*250) mm, 5μ; Mobile phase A: 0.1% Formic acid in water, Mobile phase B: Acetonitrile Flow: 1.0 mL/min.

Example 150: 7-amino-3-ethyl-5-((2-(6-(2-hydroxyethoxy)$_{386}$yridine-2-yl) ethyl) amino)-2-methylpyrazolo[1,5-a] pyrimidine-6-carbonitrile

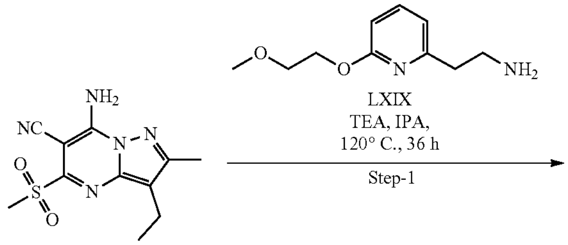

II

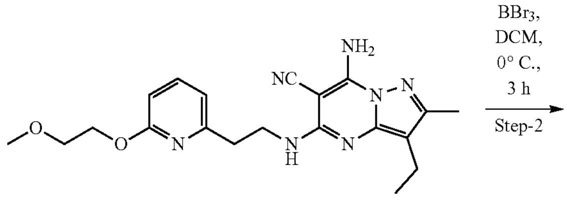

Example 150a

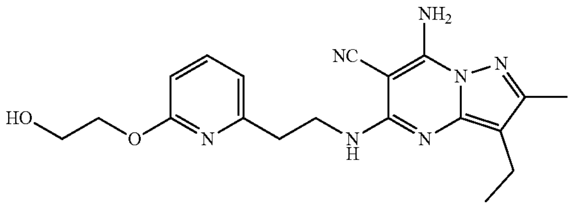

Example 150

Step-1: 7-amino-3-ethyl-5-((2-(6-(2-methoxyethoxy) pyridin-2-yl) ethyl) amino)-2-methylpyrazolo[1,5-a] pyrimidine-6-carbonitrile (Example 150a)

To a stirred solution of 2-(6-(2-methoxyethoxy)-1,6-dihydropyridin-2-yl) ethan-1-amine LXIX (0.3 g, 2 mmol) in isopropanol (10 mL) were added 7-amino-3-ethyl-2-methyl-5-(methyl sulfonyl) pyrazolo[1,5-a] pyrimidine-6-carbonitrile II (0.5 g, 2 mmol) and triethylamine (0.4 mL, 3 mmol). The reaction was stirred at 120° C. for 16 h. After completion, the reaction mixture was cooled to rt and diluted with water (50 mL). The mixture was extracted with ethyl acetate (100 mL×3). The combined organic layer was dried over anhydrous $Na_2SO_4$, filtered and concentrated under reduced pressure. The crude was purified by combi flash silica gel (230-400) column chromatography using 0-50% ethyl acetate in n-hexane to afford the desired compound Example 150a as an off-white solid. Yield: 0.35 g (58%); LCMS Calculated. for $C_{20}H_{25}N_7O_2$ is 395.21; Observed. $[M+H]^+$. $^1H$ NMR (400 MHz, DMSO-$D_6$): δ 7.49 (t, J=7.6 Hz, 1H), 6.74 (d, J=7.6 Hz, 1H), 6.67 (d, J=8.0 Hz, 1H), 5.98 (s, 2H), 5.73 (s, 1H), 4.56 (t, J=4.8 Hz, 2H), 3.87 (q, J=6.0 Hz, 2H), 3.45 (s, 3H), 3.02 (t, J=6.4 Hz, 2H) 2.56 (q, J=7.2 Hz, 2H), 2.32 (s, 3H), 1.19 (t, J=7.6 Hz, 3H).

Step-2: 7-amino-3-ethyl-5-((2-(6-(2-hydroxyethoxy) pyridin-2-yl) ethyl) amino)-2-methylpyrazolo[1,5-a] pyrimidine-6-carbonitrile To a stirred solution of 7-amino-3-ethyl-5-((2-(6-(2-methoxyethoxy) pyridin-2-yl) ethyl) amino)-2-methylpyrazolo[1,5-a] pyrimidine-6-carbonitrile Example 150a (250 mg, 0.632 mmol) in DCM (20 mL) was added $BBr_3$ (65.7 μL, 0.695 mmol). The reaction was stirred at 0° C. for 3 h and the reaction was monitored by TLC analysis. After completion, the reaction mixture was diluted with saturated $NaHCO_3$ solution (10 mL) and extracted with DCM (20 mL×3). The combined organic layer was dried over anhydrous $Na_2SO_4$, filtered and concentrated under reduced pressure. The crude was purified by combi flash silica gel (230-400) column chromatography using 0-5% methanol in DCM to afford the desired compound Example 150 as an off-white solid. Yield: 150 mg (62%); LCMS Calculated. for $C_{19}H_{23}N_7O_2$ is 381.19; Observed. 382.30 $[M+H]^+$. $^1H$ NMR (400 MHz, DMSO-$D_6$): δ 8.09 (bs, 2H), 7.61 (t, J=7.6 Hz, 1H), 6.83 (t, J=7.6 Hz, 1H), 6.63 (t, J=8.0 Hz, 2H), 4.79 (t, J=5.6 Hz, 1H), 4.29 (t, J=8.0 Hz, 1H), 3.73-3.65 (m, 4H), 2.95 (t, J=7.2 Hz, 2H) 2.47-2.43 (m, 2H), 2.25 (s, 3H), 1.13 (t, J=7.6 Hz, 3H); HPLC: 11.872 min; 98.65%, Column: INT ODS 3V-C18 (4.6*250) mm, 5μ; Mobile phase A: 0.1% Formic acid in water, Mobile phase B: Acetonitrile Flow: 1.0 mL/min.

Example 151: 7-amino-5-((2-(1-(1-(2-aminoethyl) cyclopropyl)-1H-pyrazol-3-yl) ethyl) amino)-3-chloro-2-methylpyrazolo[1,5-a]pyrimidine-6-carbonitrile

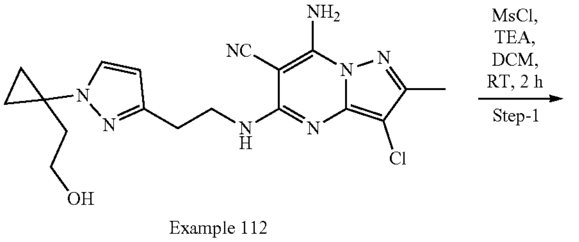

Example 112

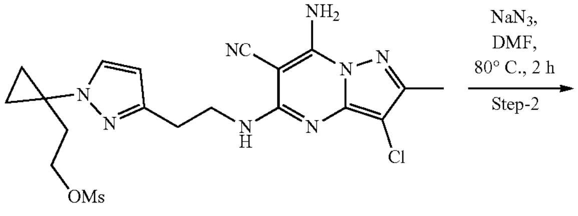

Example 151a

-continued

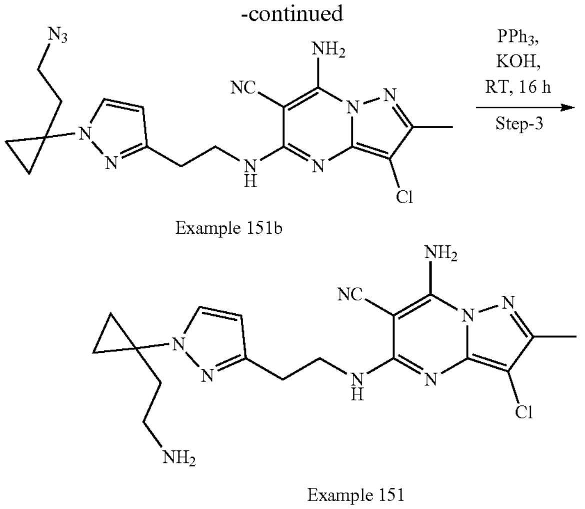

Example 151b

Example 151

Step-1: 2-(1-(3-(2-((7-amino-3-chloro-6-cyano-2-methylpyrazolo[1,5-a] pyrimidin-5-yl) amino) ethyl)-1H-pyrazol-1-yl) cyclopropyl) ethyl methane sulfonate (Example 151a)

To a stirred solution of 7-amino-3-chloro-5-((2-(1-(1-(2-hydroxyethyl) cyclopropyl)-1H-pyrazol-3-yl) ethyl) amino)-2-methylpyrazolo[1,5-a] pyrimidine-6-carbonitrile Example 112 (460 mg, 1.15 mmol) in DCM (50 mL) was slowly added triethylamine (0.800 mL, 5.74 mmol) and the resulting mixture was cooled to 0° C. under inert atmosphere. This was followed by a dropwise addition of solution of methane sulfonyl chloride (0.098 mL, 1.26 mmol) in DCM (1 mL) over 10 min. The progress of the reaction was monitored by TLC analysis. After completion, to the reaction was diluted with $NaHCO_3$ solution (50 mL) and extracted with DCM (50 ml×3). The combined organic layer was washed with brine, dried over anhydrous $Na_2SO_4$, filtered and concentrated under reduced pressure to afford the desired compound Example 151a as a pale-yellow viscous liquid. The crude compound was taken for the next step without purification. Yield: 0.5 g (90%); LCMS Calculated. for $C_{19}H_{23}ClN_8O_3S$ is 478.13; Observed. 479.25 $[M+H]^+$.

Step-2: 7-amino-5-((2-(1-(1-(2-azidoethyl) cyclopropyl)-1H-pyrazol-3-yl) ethyl) amino)-3-chloro-2-methylpyrazolo[1,5-a] pyrimidine-6-carbonitrile (151b)

To a stirred solution of 2-(1-(3-(2-((7-amino-3-chloro-6-cyano-2-methylpyrazolo [1,5-a] pyrimidin-5-yl) amino) ethyl)-1H-pyrazol-1-yl) cyclopropyl) ethyl methane sulfonate Example 151a (500 mg, mmol) in DMF (5 mL) was added sodium azide (271 mg, 4.18 mmol) and the reaction mixture was stirred at 80° C. for 2 h. The progress of the reaction was monitored by TLC analysis. After completion, the reaction mixture was cooled to rt and diluted with water (20 mL). The mixture was extracted with ethyl acetate (20 mL×3). The combined organic layer was dried over anhydrous $Na_2SO_4$, filtered and concentrated under reduced pressure. The crude compound was purified by combi-flash silica gel (230-400) column chromatography using 0-30% ethyl acetate in n-hexane to afford the desired compound Example 151b as a pale-yellow viscous liquid. Yield: 0.135 g (30%); LCMS Calculated. for $C_{18}H_{20}ClN_{11}$ is 425.16; Observed. 426.25 $[M+H]^+$.

Step-3: 7-amino-5-((2-(1-(1-(2-aminoethyl) cyclopropyl)-1H-pyrazol-3-yl) ethyl) amino)-3-chloro-2-methylpyrazolo[1,5-a] pyrimidine-6-carbonitrile To a stirred solution of 7-amino-5-((2-(1-(1-(2-azidoethyl) cyclopropyl)-1H-pyrazol-3-yl) ethyl) amino)-3-chloro-2-methylpyrazolo[1,5-a] pyrimidine-6-carbonitrile Example 151b (135 mg, 0.317 mmol) in THF: water (8 mL; 3:1) was added triphenylphosphine (83.1 mg, 0.317 mmol) and stirred at rt for 10 min. This was followed by addition of KOH (26.7 mg, 0.475 mmol) under nitrogen atmosphere. The reaction mixture was stirred at rt for 16 h and progress of the reaction was monitored by TLC analysis. After completion, the reaction mixture was diluted with water (10 mL) and extracted with DCM (50 mL×3). The combined organic layer was dried over anhydrous $Na_2SO_4$, filtered and concentrated under reduced pressure. The crude compound was purified by silica-gel (230-400) Biotage column chromatography using methanol in DCM (0-15%) to afford the desired compound Example 151 as an off-white solid. Yield: 35 mg (27%); LCMS Calculated. for $C_{18}H_{22}ClN_9$ is 399.16; Observed. 400.15 $[M+H]^+$. $^1H$ NMR (400 MHz, DMSO-$D_6$): δ 7.98 (bs, 4H), 7.74 (d, J=2.0 Hz, 1H), 6.96 (t, J=5.2 Hz, 1H), 6.11 (d, J=2.4 Hz, 1H), 3.64-3.59 (m, 2H), 2.83 (t, J=7.2 Hz, 2H), 2.72-2.68 (m, 2H), 2.28 (s, 3H), 2.01-1.97 (m, 2H), 1.16-1.14 (m, 2H), 0.98-0.95 (m, 2H); HPLC: 8.050 min; 99.35%, Column: INT ODS 3V-C18 (4.6*250) mm, 5μ; Mobile phase A: 0.1% Formic acid in water, Mobile phase B: Acetonitrile; Flow: 1.0 mL/min.

Example 152: 7-amino-5-((2-(6-(2-hydroxyethyl) 390yridine-2-yl) ethyl) amino)-2,3-dimethylpyrazolo [1,5-a]pyrimidine-6-carbonitrile

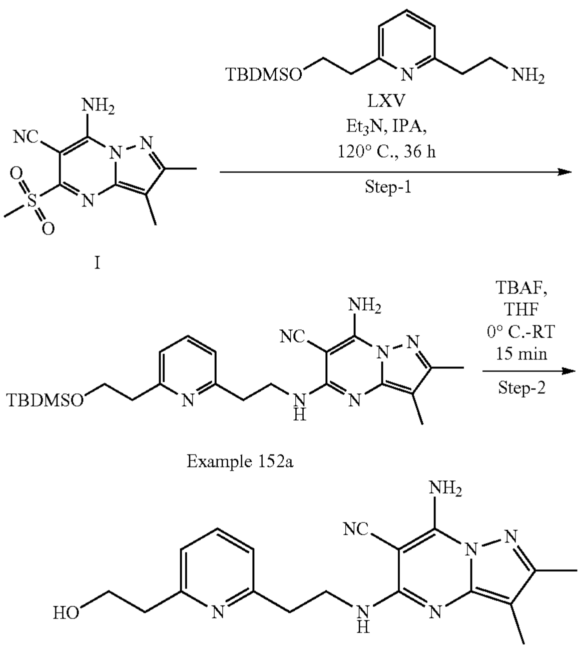

I

Example 152a

Example 152

Step-1: 7-amino-5-((2-(6-(2-((tert-butyl dimethyl silyl) oxy) ethyl) pyridin-2-yl) ethyl) amino)-2,3-dimethylpyrazolo[1,5-a] pyrimidine-6-carbonitrile (Example 152a)

To stirred solution of 7-amino-2,3-dimethyl-5-(methyl sulfonyl) pyrazolo[1,5-a] pyrimidine-6-carbonitrile (0.2 g, 0.7 mmol) and 2-(6-(2-((tert-butyl dimethyl silyl) oxy) ethyl) pyridin-2-yl) ethan-1-amine LXV in isopropanol (5 mL) was added TEA (0.6 mL, 4 mmol) at room temperature under inert atmosphere. The resulting reaction mixture was stirred at 120° C. for 36 h. The progress of the reaction was monitored by TLC analysis. After completion, the reaction was cooled to room temperature diluted with water (100 mL). The resulting mixture was extracted with ethyl acetate (20 mL×2). The combined organic layers were dried over anhydrous sodium sulphate and concentrated under reduced pressure to afford Example 152a as a light-yellow viscous liquid. The crude compound was taken for the next step without further purification. Yield: 0.120 g (crude).

Step-2: 7-amino-5-((2-(6-(2-hydroxyethyl) pyridin-2-yl) ethyl) amino)-2,3-dimethylpyrazolo[1,5-a] pyrimidine-6-carbonitrile To a stirred solution of 7-amino-5-((2-(6-(2-((tert-butyldimethylsilyl) oxy) ethyl) pyridin-2-yl) ethyl) amino)-2,3-dimethylpyrazolo [1,5-a] pyrimidine-6-carbonitrile Example 152a (0.09 g, 0.2 mmol) in THF (10 mL) was added TBAF (0.3 mL, 1M in THF, 0.3 mmol) at 0° C. under $N_2$ and stirred it at room temperature for 15 min. The progress of the reaction was monitored by TLC analysis. After completion, reaction mixture was diluted with water (20 mL) and extracted with DCM (15 mL×3). The combined organic layer was dried over anhydrous sodium sulphate and concentrated under reduced pressure to afford a brown viscous liquid. The crude compound was purified by combi flash chromatography by eluted with 0-4% methanol in DCM to get the desired compound Example 152 as an off-white solid. Yield: 30 mg (42%); LCMS Calculated. for $C_{18}H_{21}N_7O$ is 351.18; Observed. 352.30 $[M+H]^+$. $^1H$ NMR (400 MHz, DMSO-$D_6$): δ 8.12 (bs, 3H), 7.43 (bs, 2H), 6.86 (bs, 1H), 5.12-4.50 (bs, 1H), 3.75-3.73 (m, 4H), 3.16-3.00 (m, 4H), 2.22 (s, 3H), 1.93 (m, 3H); HPLC: 7.50 min; 98.09%, Column: INT ODS 3V-C18 (4.6*250) mm, 5μ; Mobile phase A: 0.1% Formic acid in water, Mobile phase B: Acetonitrile; Flow: 1.0 mL/min.

Example 153: 7-amino-3-ethyl-2-methyl-5-((2-(1-(3-(methylthio) propyl)-2-oxo-1,2-dihydropyridin-3-yl) ethyl) amino)pyrazolo[1,5-a]pyrimidine-6-carbonitrile

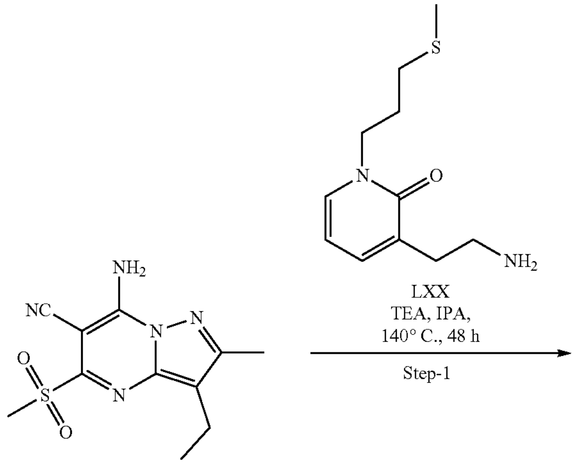

II

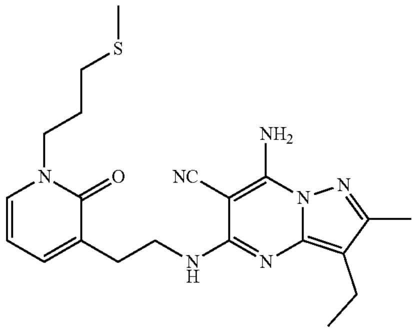

Example 153

To a solution of 7-amino-3-ethyl-2-methyl-5-(methyl sulfonyl)pyrazolo[1,5-a] pyrimidine-6-carbonitrile II (0.5 g, 1.79 mmol) in isopropyl alcohol (10 mL) were added triethylamine (1.50 mL, 10.7 mmol) and 3-(2-aminoethyl)-1-(3-(methylthio) propyl) pyridin-2(1H)-one LXX (0.891 g, 3.94 mmol). The reaction mixture was stirred at 140° C. for 48 h. The progress of the reaction was monitored by TLC analysis. After the completion, the reaction mixture was concentrated under reduced pressure to get the crude material. The crude compound was purified by silica gel (230-400 mesh) column chromatography with ethyl acetate in dichloromethane (0-50%) to afford the desired product Example 153 as an off-white solid. Yield: 0.4 g, (52.0%); LCMS Calculated. for $C_{21}H_{27}N_7OS$ is 425.19; Observed: 426 $[M+H]^+$. $^1H$ NMR (400 MHz, DMSO-$D_6$): δ 8.05 (bs, 2H), 7.54-7.52 (m, 1H), 7.28 (d, J=4.8 Hz, 1H), 6.70 (s, 1H), 6.16 (t, J=6.8 Hz, 1H), 3.95 (t, J=6.8 Hz, 2H), 3.51 (t, J=5.6 Hz, 2H), 2.74 (t, J=6.8 Hz, 2H), 2.47-2.413 (m, 4H), 2.24 (s, 3H), 2.04 (s, 3H), 1.91 (m, 2H), 1.10 (t, J=7.6 Hz, 3H); HPLC: 11.682 min; 97.14%, Column: INT ODS 3V-C18 (4.6*250) mm, 5μ; Mobile phase A: 0.1% Formic acid in water; Mobile phase B: Acetonitrile; Flow: 1.0 mL/min.

Example 154a: (−)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a]pyrimidine-6-carbonitrile Example 154b: (+)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a]pyrimidine-6-carbonitrile

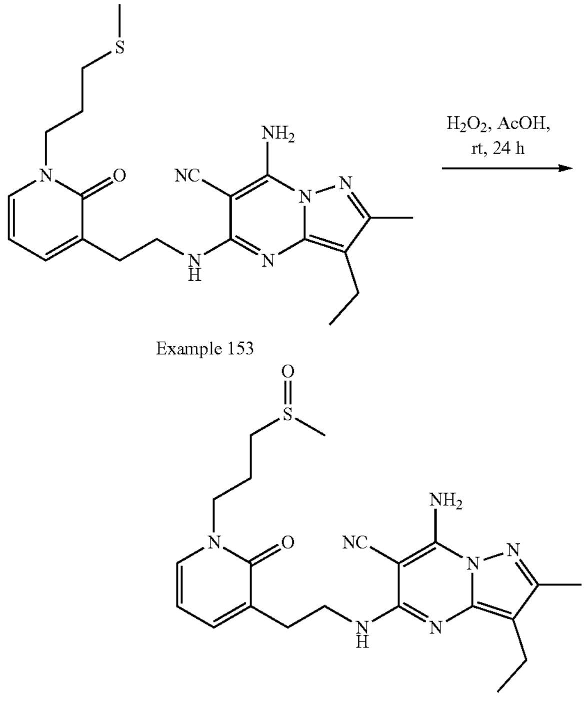

Example 153

Peak-1: Example 154a; leavo(-) rotator
Peak-2: Example 154b; dextro(+) rotatory

To a solution of 7-amino-3-ethyl-2-methyl-5-((2-(1-(3-(methylthio) propyl)-2-oxo-1,2-dihydropyridin-3-yl) ethyl) amino) pyrazolo[1,5-a] pyrimidine-6-carbonitrile Example 153 (0.490 g, 1.15 mmol) in acetic acid (5 mL) at 0° C. was added $H_2O_2$ (0.635 mL, 20.7 mmol). The reaction mixture was stirred at rt for 24 h. The progress of the reaction was monitored by TLC analysis. After the completion of the reaction, added $NaHCO_3$ (50 mL) and extracted with ethyl acetate (200 mL×3). The combined organic layer was dried over anhydrous sodium sulphate, filtered and concentrated. The crude compound was purified by silica gel (230-400 mesh) column chromatography with methanol in dichloromethane (0-10%) to afford the desired racemic product as an off-white solid. Yield:0.4 g, (78.0%); LCMS Calculated. for $C_{21}H_{27}N_7O_2S$ is 441.19; Observed: 442 $[M+H]^+$. $^1H$ NMR (400 MHz, DMSO-$D_6$): δ 8.05 (s, 2H), 7.57 (d, J=6.0 Hz, 1H), 7.29 (d, J=5.6 Hz, 1H), 6.71 (s, 1H), 6.18 (t, J=6.4 Hz, 1H), 4.01 (s, 2H), 3.52 (d, J=4.8 Hz, 2H), 2.75-2.65 (m, 3H), 2.45-2.43 (m, 6H), 2.24 (s, 3H), 2.04-2.01 (m, 2H), 1.11 (t, J=7.2 Hz, 3H); HPLC: 9.406 min; 99.57%, Column: INT ODS 3V-C18 (4.6*250) mm, 5μ, Mobile phase A: 0.1% Formic acid in water; Mobile phase B: Acetonitrile; Flow: 1.0 mL/min.

Further the above racemic compound was subjected to chiral SFC (Column Name: Chiral Pak IC (21*250 mm), 5 μm; Co-Solvent Name: MeOH: n-hexane (1:1)+0.1% TEA; Total flow rate: 3 g/mL; % of Co-Solvent: 35; Back Pressure: 1500 psi; and separated into peak-1 Example 154a and peak-2 Example 154b Peak-1; Example 154a: (39 mg) LCMS Calculated. for $C_{21}H_{27}N_7O_2S$ is 441.19; Observed. 442.35 $[M+H]^+$. $^1H$ NMR (400 MHz, DMSO-$D_6$): δ 8.06 (bs, 2H), 7.57 (bs, 1H), 7.28 (bs, 1H), 6.72 (bs, 1H), 6.18 (bs, 1H), 4.01 (bs, 2H), 3.52 (bs, 2H), 2.75 (bs, 3H), 2.66 (bs, 4H), 2.33 (bs, 2H), 2.24 (s, 3H), 2.02 (bs, 2H), 1.11 (bs, 3H); HPLC: 9.410 min; 99.56%, Column: INT ODS 3V-C18 (4.6*250) mm, 5μ; Mobile phase A: 0.1% Formic acid in water; Mobile phase B: Acetonitrile; Flow: 1.0 mL/min; Chiral HPLC: 34.165 min; 98.46%; Column Name: IG (4.6*250 mm), 5 μm; Co-Solvent Name: EtOH:MeOH 1:1 (0.1% DEA); Total flow rate: 3 g/mL; % of Co-Solvent: 40; Temperature:30° C. ABPR Pressure: 1500 psi; Specific optical rotation ($[\alpha]_D$); (c 0.1 in MeOH)=−20.59

Peak-2; Example 154b; (39 mg)

LCMS Calculated. for $C_{21}H_{27}N_7O_2S$ is 441.19; Observed. 442.35 $[M+H]^+$. $^1H$ NMR (400 MHz, DMSO-$D_6$): δ 8.04 (bs, 2H), 7.58-7.56 (m, 1H), 7.29 (d, J=5.2 Hz, 1H), 6.69 (bs, 1H), 6.18 (t, J=6.4 Hz, 1H), 4.03-3.99 (m, 2H), 3.52 (q, J=6.4 Hz, 2H), 2.78-2.73 (m, 2H), 2.68-2.63 (m, 1H), 2.52-2.5 (m, 4H), 2.47-2.41 (m, 2H), 2.24 (s, 3H), 2.02 (m, 2H), 1.1 (t, J=7.6 Hz, 3H); HPLC: 9.408 min; 99.12%, Column: INT ODS 3V-C18 (4.6*250) mm, 5μ; Mobile phase A: 0.1% Formic acid in water; Mobile phase B: Acetonitrile; Flow: 1.0 ml/min; Chiral HPLC: 44.033 min; 95.30%; Column Name: IG (4.6*250 mm), 5 μm; Co-Solvent Name: EtOH:MeOH (0.1% DEA); Total flow rate: 3 g/mL; % of Co-Solvent:40; Temperature: 30° C.; ABPR Pressure: 1500 psi; Specific optical rotation ($[\alpha]_D$); (c 0.1 in MeOH)=+23.05.

Example 155: 7-amino-3-ethyl-5-((2-(6-(3-hydroxypropyl) pyridin-2-yl) ethyl) amino)-2-methylpyrazolo[1,5-a]pyrimidine-6-carbonitrile

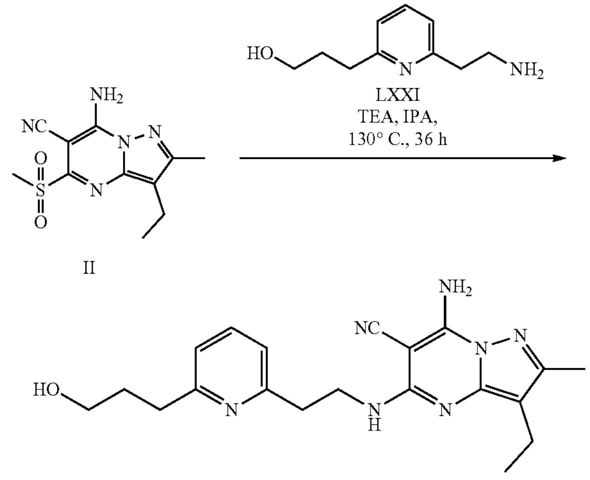

Example 155

To a stirred solution of 7-amino-3-ethyl-2-methyl-5-(methyl sulfonyl) pyrazolo[1,5-a] pyrimidine-6-carbonitrile II (0.3 g, 1 mmol) in 2-propanol (20 mL) was added 3-(6-(2-aminoethyl) pyridin-2-yl) propan-1-ol LXXI (0.7 g, 4 mmol) and triethylamine (0.7 g, 0.9 mL, 6 mmol) under nitrogen.

The resulting mixture was stirred at 130° C. for 36 h. The progress of the reaction was monitored by TLC analysis. After completion, the reaction mixture was cooled to room temperature and diluted with water (30 mL) then extracted with ethyl acetate (45 mL×3). The combined organic layer was dried over anhydrous sodium sulphate and concentrated under reduced pressure. The residue obtained upon removal of the solvent was subjected to silica gel (230-400 mesh) column chromatography using 0-5% MeOH in DCM to afford the desired compound Example 155 as an off-white solid. Yield: (0.028 g, 7%); LCMS Calculated. for $C_{20}H_{25}N_7O$ is 379.21; Observed. 380.35 $[M+H]^+$; $^1H$ NMR (400 MHz, DMSO-$D_6$): δ 8.10 (bs, 2H), 7.61 (t, J=7.6 Hz, 1H), 7.07 (d, J=7.6 Hz, 2H), 6.86 (t, J=5.2 Hz, 1H), 4.46 (t, J=5.2 Hz, 1H), 3.67 (q, J=6.8 Hz, 2H), 3.44 (q, J=6.8 Hz, 2H), 3.00 (t, J=6.8 Hz, 2H), 2.75 (t, J=6.8 Hz, 2H), 2.47-2.43 (m, 2H), 2.25 (s, 3H), 1.81 (quint, J=6.8 Hz, 2H), 1.12 (t, J=6.8 Hz, 3H). HPLC: Rt=7.837 min; Purity=99.59%, INT ODS 3V-C18 (4.6×250) mm, 5μ, Mobile phase A: 0.1% Formic acid in water; Mobile phase B: Acetonitrile.

Example 156: 7-amino-5-((2-(1-(3-hydroxypropyl)-2-oxo-1,2-dihydropyridin-3-yl) ethyl) amino)-2-methyl-3-propylpyrazolo[1,5-a]pyrimidine-6-carbonitrile

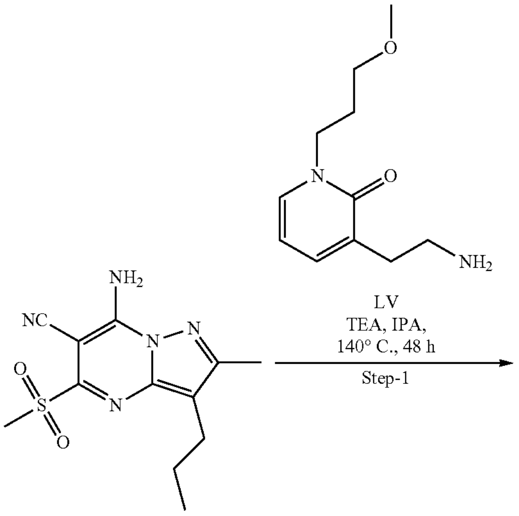

LXXII

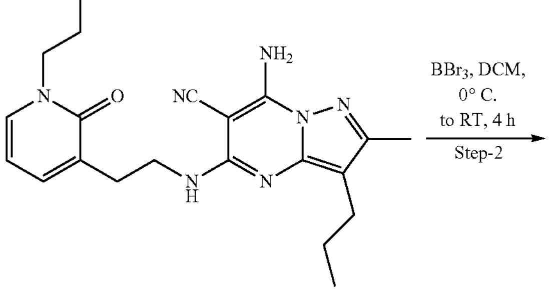

Example 156a

-continued

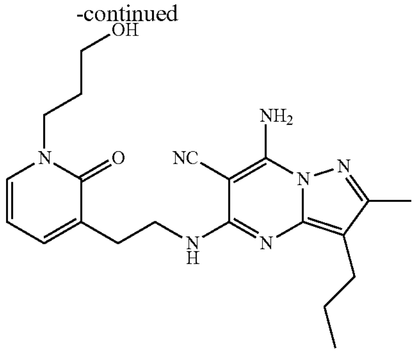

Example 156

Step-1: 7-amino-5-((2-(1-(3-methoxypropyl)-2-oxo-1,2-dihydropyridin-3-yl) ethyl) amino)-2-methyl-3-propylpyrazolo[1,5-a] pyrimidine-6-carbonitrile (Example 156a)

To a stirred solution of 7-amino-2-methyl-5-(methyl sulfonyl)-3-propylpyrazolo [1,5-a] pyrimidine-6-carbonitrile LXXII (250 mg, 852 μmol) and 3-(2-aminoethyl)-1-(3-methoxypropyl) pyridin-2(1H)-one LV (394 mg, 1.87 mmol) in isopropanol (5 mL) was added TEA (0.713 mL, 5.11 mmol) under inert atmosphere in a sealed tube. The reaction mixture was stirred at 140° C. for 48 h and progress of the reaction was monitored by TLC analysis. After completion, the reaction was cooled to rt and the reaction mixture was diluted with water (10 mL). The resulting mixture was extracted with ethyl acetate (50 mL×3) and the combined organic layer was dried over anhydrous sodium sulfate. The solution was concentrated under reduced pressure. The crude compound was purified by flash column chromatography (silica gel, 230-400; 10 g) using 0-5% methanol in DCM to afford the desired compound Example 156a as an off-white solid. Yield: 136 mg (36.0%); LCMS Calculated. for $C_{22}H_{29}N_7O_2$ is 423.52; Observed. 424.35 $[M+H]^+$. $^1H$ NMR (400 MHz, DMSO-$D_6$): δ 8.06 (bs, 2H), 7.66 (d, J=6.4 Hz, 1H), 7.27 (d, J=6.4 Hz, 1H), 6.71 (s, 1H), 6.15 (t, J=6.4 Hz, 1H), 3.92 (t, J=6.4 Hz, 2H), 3.50 (d, J=5.2 Hz, 2H), 3.30 (t, J=12.4 Hz, 2H), 3.21 (s, 3H), 2.70 (d, J=26.8 Hz, 2H), 2.40-2.23 (m, 5H), 1.87 (t, J=6.8 Hz, 2H), 1.53 (q, J=6.8 Hz, 2H), 0.86 (t, J=7.2 Hz, 3H).

Step-4: 7-amino-3-ethyl-5-((2-(6-(3-hydroxypropyl) pyridin-2-yl) ethyl) amino)-2-methylpyrazolo[1,5-a] pyrimidine-6-carbonitrile To a solution of 7-amino-5-((2-(1-(3-methoxypropyl)-2-oxo-1,2-dihydropyridin-3-yl) ethyl) amino)-2-methyl-3-propylpyrazolo[1,5-a] pyrimidine-6-carbonitrile Example 156a (130 mg, 307 μmol) in DCM (15 mL) at 0° C. was dropwise added $BBr_3$ (43.5 μL, 460 μmol) under $N_2$ atmosphere. The reaction mixture was stirred at 0° C. for 4 h and progress of the reaction was monitored by TLC analysis. After completion, the reaction was quenched with sat. $NaHCO_3$ solution (20 mL), and the resulting mixture was extracted with DCM (100 mL×3). The combined organic layer was dried over anhydrous sodium sulphate and concentrated under reduced pressure. The crude compound was purified by flash silica gel column chromatography using 0-5% methanol in DCM to afford the desired compound Example 156 as an off-white solid. Yield: 20 mg (16.0%);

LCMS Calculated. for $C_{21}H_{27}N_7O_2$ is 409.22; Observed. 410.35 $[M+H]^+$. $^1H$ NMR (400 MHz, DMSO-$D_6$): δ 8.05 (bs, 2H), 7.51 (d, J=5.2 Hz, 1H), 7.27 (d, J=5.6 Hz, 1H), 6.72 (s, 1H), 6.16 (t, J=6.8 Hz, 1H), 4.58 (s, 1H), 3.94 (t, J=6.4 Hz, 2H), 3.48 (q, J=6.8 Hz, 2H), 3.38 (t, J=5.2 Hz, 2H), 2.74 (t, J=6.8 Hz, 2H), 2.41 (d, J=7.2 Hz, 2H), 2.23 (s, 3H), 1.78 (p, J=6.4 Hz, 2H), 1.58-1.49 (m, 2H), 0.86 (t, J=7.6 Hz, 3H). HPLC: 10.555 min; 98.04%, Column: INT ODS 3V-C18 (4.6*250) mm, 5μ; Mobile phase A: 0.1% Formic acid in water, Mobile phase B: Acetonitrile; Flow: 1.0 mL/min.

Example 157: 7-amino-5-((2-(6-(hydroxymethyl) $_{397}$yridine-2-yl) ethyl) amino)-2-methyl-3-propylpyrazolo[1,5-a]pyrimidine-6-carbonitrile

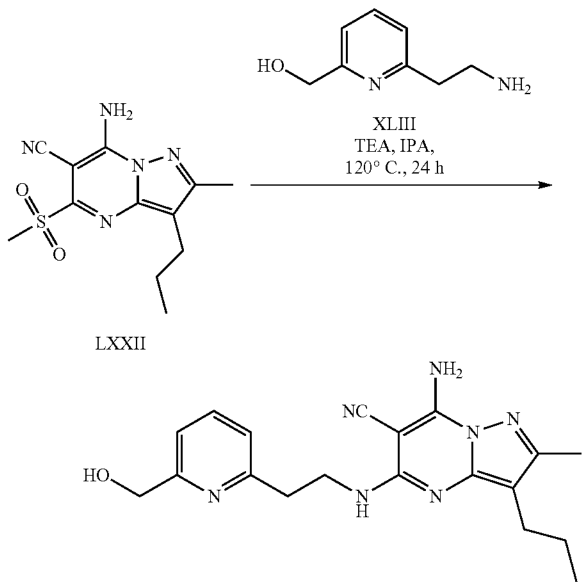

LXXII

Example 157

To a stirred solution of 7-amino-2-methyl-5-(methyl sulfonyl)-3-propylpyrazolo[1,5-a] pyrimidine-6-carbonitrile LXXII (0.2 g, 682 μmol) and (6-(2-aminoethyl) pyridin-2-yl) methanol XLIII (311 mg, 2.05 mmol) in isopropanol (10 mL) was added triethyl amine (570 μL, 4.09 mmol) under inert atmosphere. The resulting mixture in a sealed tube was stirred at 140° C. for 24 h. The progress of the reaction was monitored by TLC analysis. After completion, the reaction was cooled to rt and water (100 mL) was added. The resulting mixture was extracted with ethyl acetate (100 mL×3). The combined organic layer was dried over anhydrous sodium sulphate and concentrated under reduced pressure. The crude was purified by silica gel (230-400) column chromatography using 0-5% MeOH in DCM to afford the desired compound Example 157 as an off-white solid. Yield: 120 mg (48%); LCMS Calculated. for $C_{19}H_{23}N_7O$ is 365.20; Observed. 366.35 $[M+H]^+$. $^1H$ NMR (400 MHz, DMSO-$D_6$): δ 8.11 (bs, 2H), 7.72 (t, J=7.6 Hz, 1H), 7.31 (d, J=8.0 Hz, 1H), 7.13 (d, J=7.6 Hz, 1H), 6.87 (bs, 1H), 5.37 (t, J=5.6 Hz, 1H), 4.58 (d, J=5.2 Hz, 2H), 3.65 (d, J=7.6 Hz, 2H), 3.01 (t, J=6.4 Hz, 2H), 2.43 (t, J=6.8 Hz, 2H), 2.24 (s, 3H), 1.56 (q, J=6.8 Hz, 2H) 0.87 (t, J=6.8 Hz, 3H); HPLC: 8.609 min; 99.43%, Column: INT ODS 3V-C18 (4.6*250) mm, 5μ; Mobile phase A: 0.1% Formic acid in water, Mobile phase B: Acetonitrile Flow: 1.0 mL/min.

Example 158: 7-amino-5-((2-(1-(1-(hydroxymethyl) cyclopropyl)-1H-pyrazol-3-yl) ethyl) amino)-2-methyl-3-propylpyrazolo[1,5-a]pyrimidine-6-carbonitrile

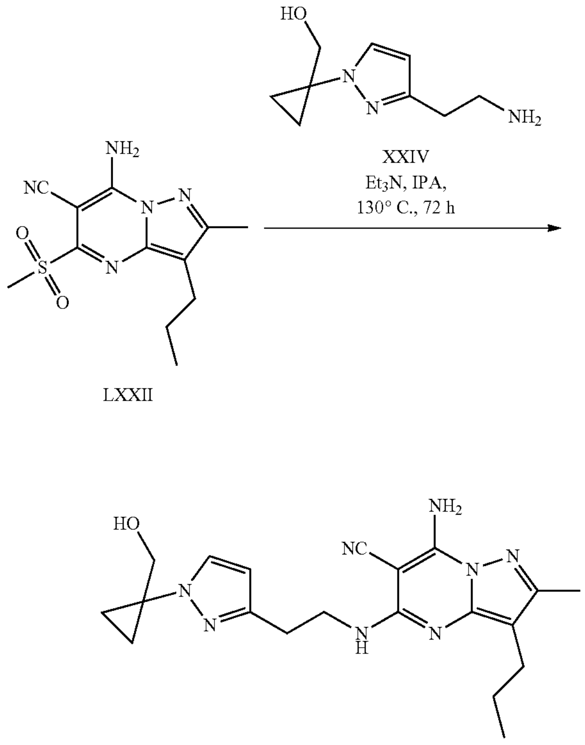

LXXII

Example 158

To a stirred solution of (1-(3-(2-aminoethyl)-1H-pyrazol-1-yl)cyclopropyl)methanol XXIV (232 mg, 1.28 mmol) and 7-amino-2-methyl-5-(methylsulfonyl)-3-propylpyrazolo[1,5-a]pyrimidine-6-carbonitrile LXXII (150 mg, 511 μmol) in isopropanol (10 mL), in a sealed tube, was added triethylamine (214 μL, 1.53 mmol) and the reaction mixture was stirred at 140° C. for 3 days. The progress of the reaction was monitored by TLC analysis. After completion, the reaction mixture was cooled to rt and diluted with water (50 mL). The resulting mixture was extracted with ethyl acetate (20 mL×3) and the combined organic layer was dried over anhydrous $Na_2SO_4$. The solvent was removed under reduced pressure. The crude compound was subjected to silica gel (230-400) combi-flash column chromatography using 0-3% methanol in DCM to afford the desired compound Example 158 as an off-white solid. Yield: 130 mg (64.0%); LCMS Calculated. for $C_{20}H_{26}N_8O$ is 394.22; Observed. 395.35 $[M+H]^+$. $^1H$ NMR (400 MHz, DMSO-$D_6$): δ 8.10 (bs, 2H), 7.61 (s, 1H), 6.61 (s, 1H), 6.03 (s, 1H), 4.88 (s, 1H), 3.57 (q, J=5.2 Hz, 4H), 2.80 (s, 2H), 2.42 (s, 2H), 2.23 (s, 3H), 1.56 (t, J=6.8 Hz, 2H), 1.07 (s, 2H), 0.96 (s, 2H), 0.86 (t, J=6.8 Hz, 3H); HPLC: 11.706 min; 99.15%, Column: INT ODS 3V-C18 (4.6*250) mm, 5μ; Mobile phase A: 0.1% Formic acid in water, Mobile phase B: Acetonitrile; Flow: 1.0 mL/min.

Example 159a: (+)-7-amino-3-ethyl-5-((2-(6-(1-hydroxyethyl) pyridin-2-yl) ethyl) amino)-2-methylpyrazolo[1,5-a]pyrimidine-6-carbonitrile Example 159b: (−)-7-amino-3-ethyl-5-((2-(6-(1-hydroxyethyl) pyridine-2-yl) ethyl) amino)-2-methylpyrazolo[1,5-a]pyrimidine-6-carbonitrile

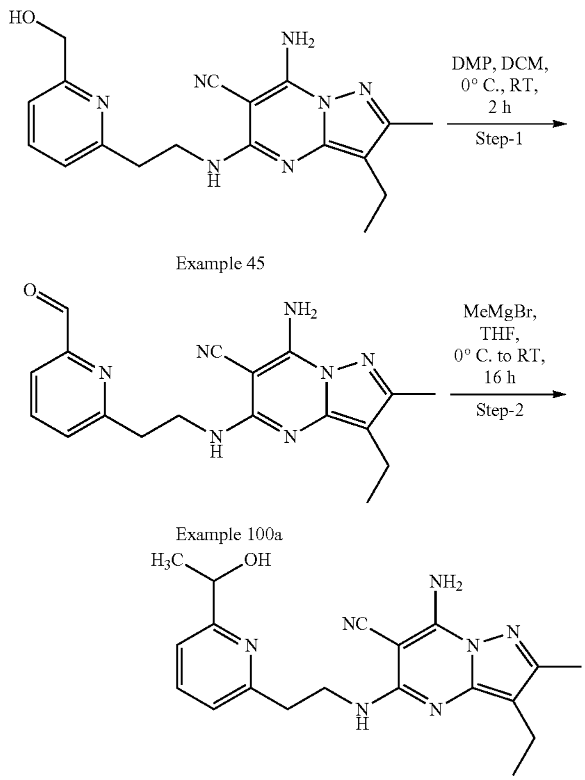

Example 45

Example 100a

Racemic: Example 100; Racemic (±)
Peak-1: Example 159a; dextro (+) rotatory
Peak-2: Example 159b; leavo (-) rotatory Step-1: 7-amino-3-ethyl-5-((2-(6-formylpyridin-2-yl) ethyl) amino)-2-methylpyrazolo[1,5-a] pyrimidine-6-carbonitrile (Example 100a)

To a stirred solution of 7-amino-3-ethyl-5-((2-(6-(hydroxymethyl) pyridin-2-yl) ethyl) amino)-2-methylpyrazolo [1,5-a] pyrimidine-6-carbonitrile Example 45 (200 mg, 0.57 mmol) in DCM (5 mL) under inert atmosphere was added dess-martin periodinane (290 mg, 0.683 mmol). The reaction mixture was stirred at 0° C. for 2 h. The progress of the reaction was monitored by TLC analysis. After completion, the reaction mixture was filtered through a celite bed and washed with ethyl acetate (50 mL×2). The combined filtrates were dried over anhydrous sodium sulphate and concentrated under reduced pressure. The crude was purified by silica gel (230-400 mesh) column chromatography using 20% ethyl acetate in n-hexane to afford the desired compound Example 100a as an off-white solid. Yield: 135 mg (67.8%); LCMS Calculated. for $C_{18}H_{19}N_7O$ is 349.17; Observed.: 350.35 $[M+H]^+$; $^1H$ NMR (400 MHz, $CDCl_3$): 10.17 (s, 1H), 7.86-7.79 (m, 2H), 7.42 (q, J=0.8 Hz, 1H), 6.17 (s, 1H), 6.03 (s, 2H), 3.96 (q, J=6.0 Hz, 2H), 3.23 (t, J=6.0 Hz, 2H), 2.56 (q, J=7.6 Hz, 2H), 2.32 (s, 3H), 1.19 (t, J=8.0 Hz, 3H).

Step-2: 7-amino-3-ethyl-5-((2-(6-(1-hydroxyethyl) pyridin-2-yl) ethyl) amino)-2-methylpyrazolo[1,5-a] pyrimidine-6-carbonitrile (Example 100)

A solution of 7-amino-3-ethyl-5-((2-(6-formylpyridin-2-yl) ethyl) amino)-2-methylpyrazolo[1,5-a] pyrimidine-6-carbonitrile Example 100a (130 mg, 0.372 mmol) in THF (3 mL) was cooled to 0° C. and added methyl magnesium bromide (0.446 mL, 1 M in THF, 0.446 mmol). The reaction mixture was stirred at rt for 3 h. The progress of the reaction was monitored by TLC analysis. After completion, the reaction was quenched with saturated $NH_4Cl$ solution (20 mL) and extracted with ethyl acetate (50 mL×3). The combined organic layer was dried over anhydrous sodium sulphate and concentrated under reduced pressure. The crude was purified by flash silica gel chromatography using 10-50% ethyl acetate in n-hexane to afford the desired compound Example 100 as an off-white solid. Yield: (18 mg, 7%); LCMS Calculated. for $C_{19}H_{23}N_7O_7$ is 365.20; Observed. 366.40 $[M+H]^+$; $^1H$ NMR (400 MHz, DMSO-$D_6$): δ 8.10 (bs, 2H), 7.70 (t, J=7.2 Hz, 1H), 7.34 (d, J=7.6 Hz, 1H), 7.13 (d, J=7.2 Hz, 1H), 6.82 (bs, 1H), 5.29 (d, J=3.2 Hz, 1H), 4.75 (t, J=5.6 Hz, 1H), 3.68 (d, J=5.6 Hz, 2H), 3.02 (t, J=6.0 Hz, 2H), 2.45 (t, J=7.6 Hz, 2H), 2.25 (s, 3H), 1.36 (d, J=6.0 Hz, 3H), 1.13 (t, J=7.2 Hz, 3H). HPLC: 8.497 min; 98.85%, INT ODS 3V-C18 (4.6*250) mm, 5μ, Mobile Phase A: 0.1% formic acid in water, Mobile Phase B: Acetonitrile; Flow: 1.0 mL/min.

Further the racemic compound (example 100)—2.50 g was subjected to chiral SFC purification (Column Name: Chiralpak IC (21*250 mm), 5 μm; Co-Solvent Name: Methanol:IPA (1:1)+0.1% TEA; % of Co-Solvent: 25%; Temperature: 25° C.; Flow: 1.0 mL/min to separate the diastereomers named as Peak-1 Example 159a; and Peak-2; Example 159b;

Peak-1; Example 159a; (Yield: 708 mg, LC-MS Calc. for $C_{19}H_{23}N_7O$ is 365.20; Obs. 366.30 $[M+H]^+$; $^1H$ NMR (400 MHz, DMSO-$D_6$): δ 8.10 (bs, 2H), 7.70 (t, J=7.2 Hz, 1H), 7.34 (d, J=7.6 Hz, 1H), 7.13 (d, J=7.2 Hz, 1H), 6.82 (bs, 1H), 5.29 (d, J=3.2 Hz, 1H), 4.75 (t, J=5.6 Hz, 1H), 3.68 (d, J=5.6 Hz, 2H), 3.02 (t, J=6.0 Hz, 2H), 2.45 (t, J=7.6 Hz, 2H), 2.24 (s, 3H), 1.36 (d, J=6.0 Hz, 3H), 1.13 (t, J=7.2 Hz, 3H). HPLC: 8.354 min; 99.38%, Column: INT ODS 3V-C18 (4.6*250) mm, 5μ Mobile phase A: 0.1% Formic acid in water Mobile phase B: Acetonitrile; Chiral HPLC: 100%; Rt=5.692 min Column Name: Chiralpak IC (4.6*250 mm), 5 μm; Co-Solvent Name: Methanol:IPA (1:1)+0.1% TEA; Total flow rate: 3 g/mL, % of Co-Solvent: 25%; Temperature: 25° C.; ABPR Pressure: 1500 psi; Specific optical rotation: +36.63.

Peak-2; Example 159b; Yield: 711 mg, LCMS Calculated. for $C_{19}H_{23}N_7O$ is 365.20; Observed. 366.30 $[M+H]^+$; $^1H$ NMR (400 MHz, DMSO-$D_6$): δ 8.10 (bs, 2H), 7.70 (t, J=7.2 Hz, 1H), 7.34 (d, J=7.6 Hz, 1H), 7.13 (d, J=7.2 Hz, 1H), 6.82 (bs, 1H), 5.29 (d, J=3.2 Hz, 1H), 4.75 (t, J=5.6 Hz, 1H), 3.68 (d, J=5.6 Hz, 2H), 3.02 (t, J=6.0 Hz, 2H), 2.45 (t, J=7.6 Hz, 2H), 2.24 (s, 3H), 1.36 (d, J=6.0 Hz, 3H), 1.13 (t, J=7.2 Hz, 3H). HPLC: 8.360 min; 99.10%; Column: INT ODS 3V-C18 (4.6*250) mm, 5μ; Mobile phase A: 0.1% Formic acid in water, Mobile phase B: Acetonitrile; Chiral HPLC: 96.20%; Rt=6.173 min Column Name: Chiralpak IC (4.6*250 mm), 5 μm; Co-Solvent Name: Methanol:IPA (1:1)+0.1% TEA, Total flow rate: 3 g/mL, % of Co-Solvent: 25%; Temperature: 25° C., ABPR Pressure: 1500 psi; Specific optical rotation: −16.070.

Example 160a: (+) 7-amino-5-((2-(1-(4-(hydroxymethyl) tetrahydrofuran-3-yl)-1H-pyrazol-3-yl) ethyl) amino)-2-methyl-3-propylpyrazolo[1,5-a]pyrimidine-6-carbonitrile Example 160b: (−) 7-amino-5-((2-(1-(4-(hydroxymethyl) tetrahydrofuran-3-yl)-1H-pyrazol-3-yl) ethyl) amino)-2-methyl-3-propylpyrazolo[1,5-a]pyrimidine-6-carbonitrile

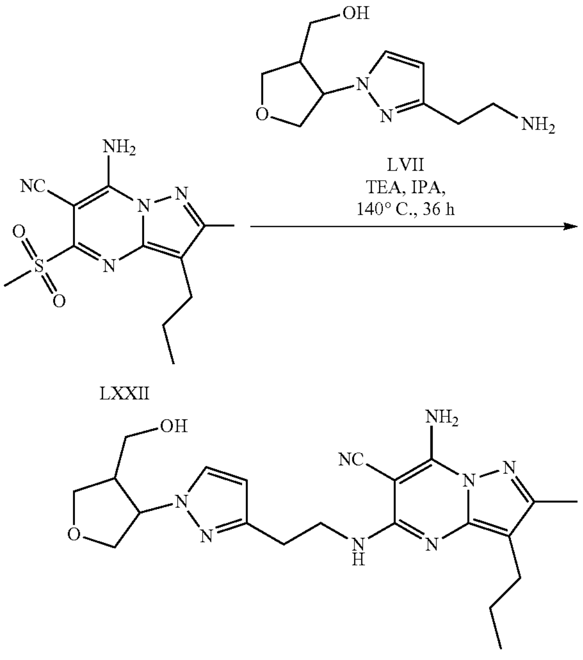

Peak-1: Example 160a; dextro (+) rotatory
Peak-2: Example 160b; leavo (-) rotatory In a 50 mL seal tube, 7-amino-2-methyl-5-(methyl sulfonyl)-3-propylpyrazolo[1,5-a] pyrimidine-6-carbonitrile LXXII (230 mg, 0.784 mmol) and (4-(3-(2-aminoethyl)-1H-pyrazol-1-yl) tetrahydrofuran-3-yl) methanol LVII (199 mg, 0.941 mmol) were dissolved in isopropanol (15 mL). The mixture was purged with $N_2$ gas for 5 min. To this was added TEA (0.656 mL, 4.70 mmol) was added and the reaction mixture was stirred at 140° C. for 3 days. The progress of reaction was monitored by TLC analysis. After completion, the reaction mixture was cooled to room temperature and added water (20 mL). The resulting mixture was extracted with ethyl acetate (25 mL×3). The combined organic layer was washed with brine and dried over anhydrous sodium sulphate. The solution was concentrated under reduced pressure to get crude material. The crude material was subjected to silica gel column chromatography purification using 0-3% methanol in DCM to afford the desired compound as an off-white solid. Yield: 0.12 g (36.0%).

Further the racemic compound was subjected to chiral SFC purification (Column: Chiral Pak IG (250*21) mm, 5μ; Co-Solvent Name: MeCN:MeOH (1:1)+0.1% TEA; Total flow rate: 3 g/mL; % of Co-Solvent: 30; Temperature: 30° C.; ABPR Pressure: 1500 psi and isolated the diastereomers as peak-1; Example 160a; and peak-2; Example 160b;

Peak-1; Example 160a; Yield: 22 mg. LCMS Calculated. for $C_{21}H_{28}N_8O_2$ is 424.51; Observed.: 425.35 $[M+H]^+$; $^1H$ NMR (400 MHz, DMSO-$D_6$): δ 8.08 (bs, 2H), 7.66 (d, J=1.6 Hz, 1H), 6.61 (bs, 1H), 6.08 (d, J=1.6 Hz, 1H), 4.84 (t, J=4.8 Hz, 1H), 4.67 (q, J=4.8 Hz, 1H), 4.07-3.98 (m, 2H), 3.85 (q, J=4.0 Hz, 1H), 3.62-3.53 (m, 3H), 3.46 (q, J=6.8 Hz, 2H), 2.83 (t, J=7.2 Hz, 2H), 2.66 (q, J=6.0 Hz, 1H), 2.42 (t, J=7.2 Hz, 2H), 2.23 (s, 3H), 1.55 (q, J=7.2 Hz, 2H), 0.86 (t, J=7.2 Hz, 3H). HPLC: 11.559 min; 99.57%, Column: INT ODS 3V-C18 (4.6*250) mm, 5μ; Mobile phase A: 0.1% Formic acid in water Mobile phase B: Acetonitrile; Chiral HPLC: 98.37%; Rt=6.704 min; Chiral Pak IG (250*4.6) mm, 5μ; Mobile phase MeCN:MeOH (1:1)+0.1% TEA, Total flow rate: 3 g/mL, % of Co-Solvent: 30, Temperature: 30° C., ABPR Pressure: 1500 psi.

Peak-2; Example 160b; Yield: 19.5 mg. LCMS Calculated. for $C_{21}H_{28}N_8O_2$ is 424.51; Observed. 425.35 $[M+H]^+$; $^1H$ NMR (400 MHz, DMSO-$D_6$): δ 8.08 (bs, 2H), 7.66 (d, J=2.0 Hz, 1H), 6.61 (bs, 1H), 6.07 (d, J=2.0 Hz, 1H), 4.83 (t, J=5.2 Hz, 1H), 4.67 (q, J=6.4 Hz, 1H), 4.07-3.98 (m, 2H), 3.84 (q, J=4.0 Hz, 1H), 3.62-3.53 (m, 2H), 3.45 (q, J=2.4 Hz, 2H), 2.83 (t, J=7.2 Hz, 2H), 2.67 (s, 1H), 2.42 (t, J=7.2 Hz, 2H), 2.24 (s, 3H), 1.56 (q, J=7.2 Hz, 2H), 0.86 (t, J=7.2 Hz, 3H). HPLC: 11.561 min; 99.45%, Column: INT ODS 3V-C18 (4.6*250) mm, 5μ; Mobile phase A: 0.1% Formic acid in water, Mobile phase B: Acetonitrile; Chiral HPLC: 98.84%; Rt=8.492 min; Chiral Pak IG (250*4.6) mm, 5μ, Mobile phase: MeCN:MeOH (1:1)+0.1% TEA; Total flow rate: 3 g/mL; % of Co-Solvent: 30; Temperature: 30° C.; ABPR Pressure: 1500 psi.

Example 161: 7-amino-3-ethyl-2-methyl-5-((2-(1-(3-(methylthio) propyl)-1H-pyrazol-3-yl)ethyl) amino)pyrazolo[1,5-a]pyrimidine-6-carbonitrile

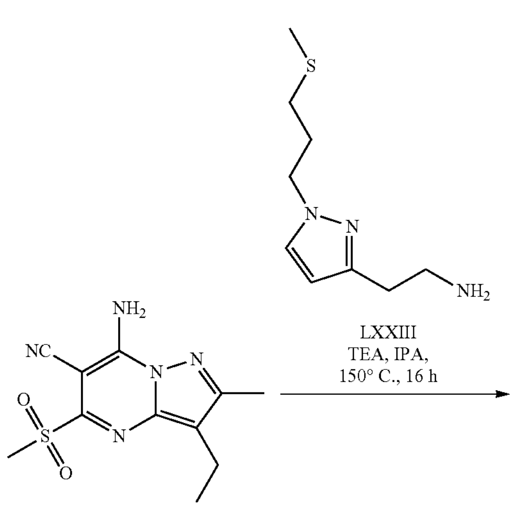

II

-continued

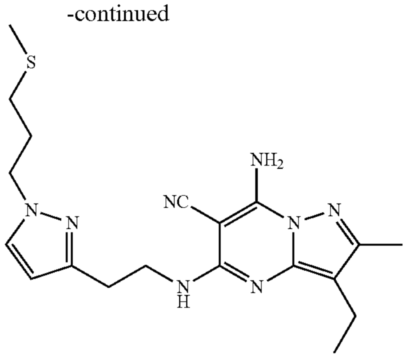

Example 161

In a seal tube, to a solution of 7-amino-3-ethyl-2-methyl-5-(methyl sulfonyl) pyrazolo[1,5-a] pyrimidine-6-carbonitrile II (500 mg, 1.79 mmol) and 2-(1-(3-(methylthio) propyl)-1H-pyrazol-3-yl) ethan-1-amine LXXIII (892 mg, 4.48 mmol) in isopropanol (10 mL) was added triethylamine (1.50 mL, 10.7 mmol) at rt under nitrogen. The resulting reaction mixture was stirred at 150° C. for 16 h and progress of the reaction was monitored by TLC analysis. After completion, the reaction was cooled to rt and diluted with water (50 mL). The mixture was extracted with ethyl acetate (2×25 mL). The combined organic layer was dried over anhydrous sodium sulphate, filtered, and concentrated under reduced pressure. The crude material was purified by combi flash (silica gel 230-400) column chromatography using 0-1% methanol in DCM to afford the desired compound Example 161 as an off-white solid. Yield: 350 mg (44.9%); LCMS Calculated. for $C_{19}H_{26}N_8S$ is 398.20; Observed. 399.35; $[M+H]^+$. $^1H$ NMR (400 MHz, DMSO-$D_6$): δ 8.10 (bs, 2H), 7.61 (d, J=1.6 Hz, 1H), 6.64 (t, J=5.2 Hz, 1H), 6.07 (bs, 1H), 4.11 (t, J=6.8 Hz, 2H), 3.57 (q, J=6.4 Hz, 2H), 2.82 (t, J=6.8 Hz, 2H), 2.46-2.43 (m, 2H), 2.38 (t, J=6.8 Hz, 2H), 2.25 (s, 3H), 2.03-2.00 (m, 5H), 1.12 (t, J=7.2 Hz, 3H); HPLC: 13.280 min; 99.11%, Column: INT ODS 3V-C18 (4.6*250) mm, 5μ; Mobile phase A: 0.1% Formic acid in water, Mobile phase B: Acetonitrile; Flow: 1.0 mL/min.

Example 162a: (−)-7-amino-3-ethyl-2-methyl-5-((2-(1-(3-(methyl sulfinyl) propyl)-1H-pyrazol-3-yl) ethyl) amino)pyrazolo[1,5-a]pyrimidine-6-carbonitrile Example 162b: (+)-7-amino-3-ethyl-2-methyl-5-((2-(1-(3-(methylsulfinyl)propyl)-1H-pyrazol-3-yl)ethyl) amino)pyrazolo[1,5-a]pyrimidine-6-carbonitrile

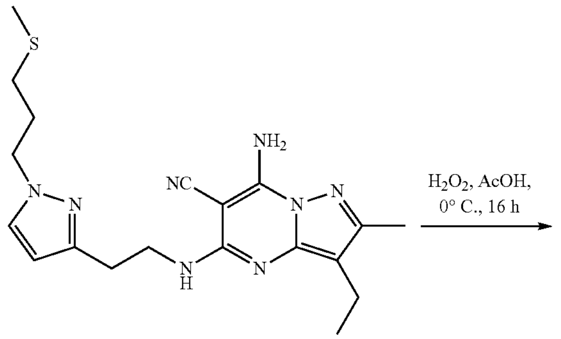

Example 161

-continued

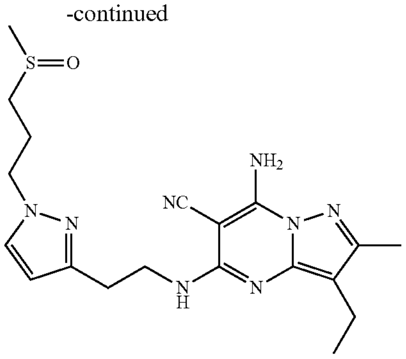

Peak-1: Example 162a; leavo (-) rotatory
Peak-2: Example 162b; dextro (+) rotatory To a solution of 7-amino-3-ethyl-2-methyl-5-((2-(1-(3-(methylthio) propyl)-1H-pyrazol-3-yl) ethyl) amino) pyrazolo[1,5-a] pyrimidine-6-carbonitrile Example 161 (310 mg, 0.778 mmol) in acetic acid (5 mL) was dropwise added $H_2O_2$ (9.53 mL, 3% Wt, 9.33 mmol) at 0° C. under nitrogen atmosphere. The resulting mixture was stirred at rt for 16 h and the progress of the reaction was monitored by TLC analysis. After completion, reaction mixture was cooled to rt and added water (50 mL). The mixture was extracted with ethyl acetate (25 mL×2). The combined organic layer was dried over anhydrous sodium sulphate, filtered, and concentrated under reduced pressure. The crude material was triturated with diethyl ether and dried to afford the desired compound as an off-white solid. Yield: 0.35 g (95.9%).

Further, the racemic compound was subjected to chiral SFC purification using Chiral pack IA (21*250 mm), 5 μm. Co-Solvent Name: EtOH:MeOH 1:1 (TEA 0.1%);

Total flow rate: 3 g/mL; % of Co-Solvent: 30, and resolved the enantiomers identified as peak-1 Example 162a; (and peak-2; Example 162b.

Peak-1; Example 162a: (39 mg)

LC-MS Calc. for $C_{19}H_{26}N_8OS$ is 414.19; Obs. 415.30 $[M+H]^+$. $^1H$ NMR (400 MHz, DMSO-$D_6$): δ 8.11 (bs, 2H), 7.65 (s, 1H), 6.65 (bs, 1H), 6.09 (s, 1H), 4.16 (t, J=6.4 Hz, 2H), 3.57 (q, J=6.4 Hz, 2H), 2.83 (t, J=7.2 Hz, 2H), 2.73-2.56 (m, 3H), 2.50-2.43 (m, 4H), 2.25 (s, 3H), 2.12 (t, J=7.2 Hz, 2H), 1.12 (t, J=7.2 Hz, 3H); HPLC: 10.354 min; 99.50%, Column: INT ODS 3V-C18 (4.6*250) mm, 5μ; Mobile phase A: 0.1% Formic acid in water, Mobile phase B: Acetonitrile Flow: 1.0 mL/min; Chiral HPLC: 12.297 min; 100%; Column Name: IA (4.6*250 mm), 5 μm; Co-Solvent Name: MeOH; Total flow rate: 3 g/mL; % of Co-Solvent: 30; Temperature: 30° C.; ABPR Pressure: 1500 psi); Specific optical rotation ($[\alpha]_D$); (c 0.1 in MeOH), −21.359.

Peak-2; Example 162b: (39 mg)

LC-MS Calc. for $C_{19}H_{26}N_8OS$ is 414.19; Obs. 415.35 $[M+H]^+$. $^1H$ NMR (400 MHz, DMSO-$D_6$): δ 8.11 (bs, 2H), 7.64 (d, J=2.0 Hz, 1H), 6.65 (m, 1H), 6.08 (d, J=2.0 Hz, 1H), 4.16 (t, J=6.4 Hz, 2H), 3.57 (d, J=5.6 Hz, 2H), 2.83 (t, J=6.8 Hz, 2H), 2.68-2.56 (m, 3H), 2.50-2.43 (m, 4H), 2.25 (s, 3H), 2.14-2.10 (m, 2H), 1.12 (t, J=7.2 Hz, 3H); HPLC: 10.343 min; 99.03%, Column: INT ODS 3V-C18 (4.6*250) mm, 5μ; Mobile phase A: 0.1% Formic acid in water, Mobile phase B: Acetonitrile; Flow: 1.0 mL/min; Chiral HPLC: 18.799 min; 100%; Column Name: IA (4.6*250 mm), 5 μm; Co-Solvent Name: MeOH; Total flow rate: 3 g/mL; % of Co-Solvent: 30; Temperature: 30° C.; ABPR Pressure: 1500 psi); Specific optical rotation ([α]$_D$); (c 0.1 in MeOH)=26.47.

Example 163a: (−)-7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a]pyrimidine-6-carbonitrile Example 163b: (+)-7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a]pyrimidine-6-carbonitrile

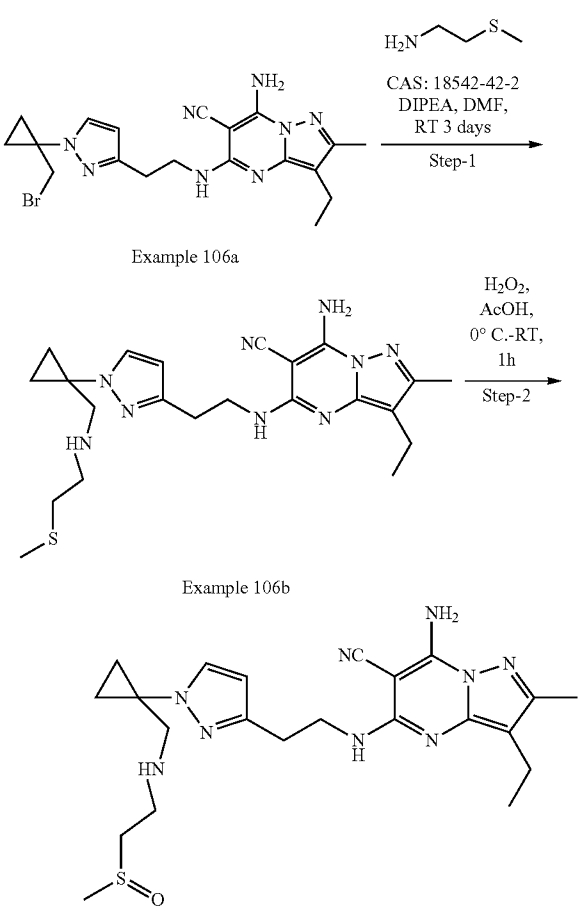

Example 106a

Example 106b

Peak-1: Example 163a; leavo (-) rotatory
Peak-2: Example 163b; dextro (+) rotatory Step-1: 7-amino-3-ethyl-2-methyl-5-((2-(1-(1-(((2-(methylthio) ethyl) amino) methyl) cyclopropyl)-1H-pyrazol-3-yl) ethyl) amino) pyrazolo[1,5-a] pyrimidine-6-carbonitrile (Example 106b)

To a solution of 7-amino-5-((2-(1-(1-(bromomethyl) cyclopropyl)-1H-pyrazol-3-yl) ethyl) amino)-3-ethyl-2-methylpyrazolo[1,5-a] pyrimidine-6-carbonitrile Example 106a (426 mg, 0.961 mmol) in DMF (5 mL) under inert atmosphere were added DIPEA (0.502 mL, 2.88 mmol) and 2-(methylthio) ethan-1-amine (0.180 mL, 1.92 mmol). The resulting reaction mixture was stirred at rt for 3 days and progress of reaction was monitored by TLC analysis. After completion, the reaction mixture was diluted with water (20 mL) and extracted with ethyl acetate (30 mL×3). The combine organic layer was washed with brine, dried over anhydrous sodium sulphate, and concentrated under reduced pressure. The crude material was purified by flash silica gel column chromatography (Biotage) using 0-5% methanol in DCM to afford the desired compound Example 106b as an off-white solid. Yield: 390 mg (89.9%) LCMS Calculated. for $C_{22}H_{31}N_9S$ is 453.24; Observed. 454.35 $[M+H]^+$. $^1H$ NMR (400 MHz, DMSO-$D_6$): δ 7.45 (bs, 1H), 6.06 (bs, 1H), 5.97 (bs, 2H), 5.61 (bs, 1H), 3.80-3.78 (m, 2H), 2.98-2.94 (m, 4H), 2.78-2.76 (m, 2H), 2.57-2.54 (m, 4H), 2.32 (s, 3H), 2.04 (s, 3H), 1.27 (bs, 3H), 1.18 (t, J=7.2 Hz, 3H), 1.02 (bs, 2H).

Step-2: 7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a] pyrimidine-6-carbonitrile A solution of 7-amino-3-ethyl-2-methyl-5-((2-(1-(1-(((2-(methylthio) ethyl) amino) methyl) cyclopropyl)-1H-pyrazol-3-yl) ethyl) amino) pyrazolo[1,5-a] pyrimidine-6-carbonitrile Example 106b (392 mg, 0.864 mmol) in acetic acid (8 mL) was cooled to 0° C. and dropwise added $H_2O_2$ (11.8 mL, 3% wt, 10.4 mmol). The resultant mixture was stirred at rt for 1 h and progress of the reaction was monitored by TLC analysis. After completion, reaction mixture was cooled to 0° C. and quenched with saturated sodium bicarbonate solution (till effervescence stops). The mixture was extracted with DCM (50 mL×6) and combine organic layer was washed with water (20 mL) followed by with brine. The organic layer was dried over anhydrous sodium sulphate and concentrated under reduced pressure. The crude material was purified by flash silica gel column chromatography (Biotage) using 0-5% methanol in DCM to afford the desired compound as an off-white solid. Yield: 0.27 g (66.6%). Further the racemic compound was subjected to chiral SFC purification (Column Name: Column Name: Chiralpak IC (21*250 mm), 5 μm; Co-Solvent Name: MeOH; Total flow rate: 3 g/mL; % of Co-Solvent: 30; Temperature: 30° C., ABPR Pressure: 1500 psi, and separated in to peak-1; Example 163a; and peak-2; Example 163b.

Peak-1; Example 163a; (39 mg)

LCMS: Calculated. for $C_{22}H_{31}N_9OS$ is 469.23; Observed. 470.35 $[M+H]^+$. $^1H$ NMR (400 MHz, DMSO-$D_6$): δ 8.08 (bs, 2H), 7.65 (bs, 1H), 6.55 (bs, 1H), 6.04 (bs, 1H), 3.58-3.56 (m, 2H), 2.88-2.60 (m, 8H), 2.47-2.42 (m, 5H), 2.25 (s, 3H), 1.87 (bs, 1H), 1.14-1.08 (m, 5H), 0.94 (bs, 2H). HPLC: 7.945 min; 98.91%, Column: INT ODS 3V-C18 (4.6*250) mm, 5μ; Mobile phase A: 0.1% Formic acid in water, Mobile phase B: Acetonitrile; Flow: 1.0 mL/min; Chiral HPLC: 13.070 min; 100%; Column Name: Chiral Pak IC (4.6*250 mm), 5 μm; Co-Solvent Name: MeOH; Total flow rate: 3 g/mL; % of Co-Solvent: 30; Temperature: 30° C.; ABPR Pressure: 1500 psi); Specific optical rotation ([α]$_D$); (c 0.1 in MeOH)=−37.00.

Peak-2; Example 163b; (39 mg)

LC-MS: Calculated. for $C_{22}H_{31}N_9OS$ is 469.23; Observed. 470.35 $[M+H]^+$. $^1H$ NMR (400 MHz, DMSO-$D_6$): δ 8.08 (bs, 2H), 7.65 (bs, 1H), 6.55 (bs, 1H), 6.04 (bs, 1H), 3.57 (bs, 2H), 2.99-2.67 (m, 8H), 2.49-2.79 (m, 5H), 2.25 (s, 3H), 1.86 (bs, 1H), 1.13-1.08 (m, 5H), 0.94 (bs, 2H). HPLC: 7.950 min; 99.28%, Column: INT ODS 3V-C18 (4.6*250) mm, 5μ; Mobile phase A: 0.1% Formic acid in water, Mobile phase B: Acetonitrile Flow: 1.0 mL/min;

Chiral HPLC: 14.490 min; 95.87%; Column Name: Chiral Pak IC (4.6*250 mm), 5 μm; Co-Solvent Name: MeOH; Total flow rate: 3 g/mL; % of Co-Solvent: 30; Temperature: 30° C.; ABPR Pressure: 1500 psi); Specific optical rotation ([α]$_D$); (c 0.1 in MeOH)=+36.40.

Example 164: 7-amino-2-methyl-5-((2-(6-methylpyridin-2-yl) ethyl) amino)-3-propylpyrazolo[1,5-a]pyrimidine-6-carbonitrile

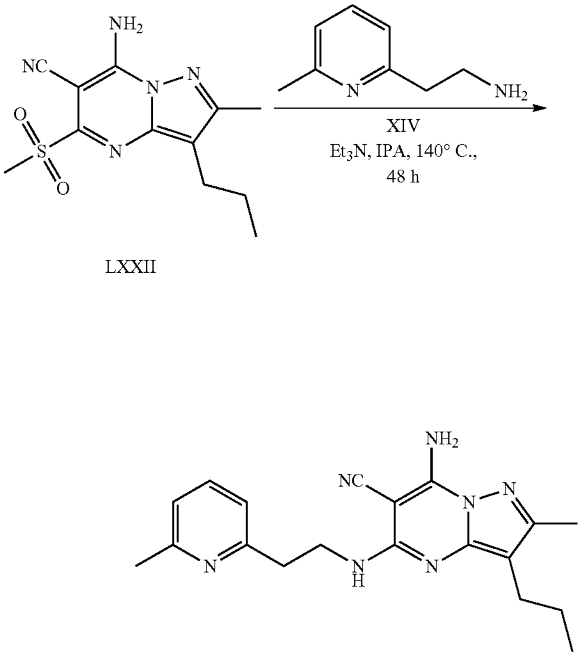

Example 164

To a stirred solution of 2-(6-methylpyridin-2-yl) ethan-1-amine XIV (279 mg, 2.05 mmol) and 7-amino-2-methyl-5-(methyl sulfonyl)-3-propylpyrazolo[1,5-a] pyrimidine-6-carbonitrile LXXII (300 mg, 1.02 mmol) in IPA (15 mL) was added triethylamine (0.855 mL, 6.14 mmol). The resulting mixture was stirred at 140° C. for 48 h. The progress of the reaction was monitored by TLC analysis. After completion, the reaction was cooled to rt and diluted with water (50 mL). The resulting mixture was extracted with ethyl acetate (150 mL×3). The combined organic layer was dried over anhydrous sodium sulphate, filtered, and concentrated under reduced pressure to afford the crude brown semi-solid. The crude material was purified by flash silica gel (Biotage) column chromatography using 0-3% MeOH in DCM to afford the desired compound Example 164 as a light brown solid. Yield: 230 mg (64.4%); LCMS Calculated, for $C_{19}H_{23}N_7$ is 349.20; Observed. 350.35 $[M+H]^+$. $^1$H NMR (400 MHz, DMSO-D$_6$): δ 8.11 (bs, 2H), 7.60 (t, J=8.0 Hz, 1H), 7.08 (t, J=6.4 Hz, 2H), 6.94 (d, J=5.2 Hz, 1H), 3.65 (q, J=6.8 Hz, 2H), 2.99 (t, J=7.2, 2H), 2.47 (s, 3H), 2.43 (t, J=6.8, 2H), 2.24 (s, 3H), 1.55 (q, J=6.8 Hz, 2H), 0.87 (t, J=7.2 Hz, 3H); HPLC: 8.220 min; 98.88%, Column: INT ODS 3V-C18 (4.6*250) mm, 5μ; Mobile phase A: 0.1% Formic acid in water, Mobile phase B: Acetonitrile; Flow: 1.0 mL/min.

Example 165a: (+)-7-amino-5-((2-(1-(2-(hydroxymethyl) cyclobutyl)-1H-pyrazol-3-yl) ethyl) amino)-2-methyl-3-propylpyrazolo[1,5-a]pyrimidine-6-carbonitrile

Example 165a: (−)-7-amino-5-((2-(1-(2-(hydroxymethyl) cyclobutyl)-1H-pyrazol-3-yl) ethyl) amino)-2-methyl-3-propylpyrazolo[1,5-a]pyrimidine-6-carbonitrile

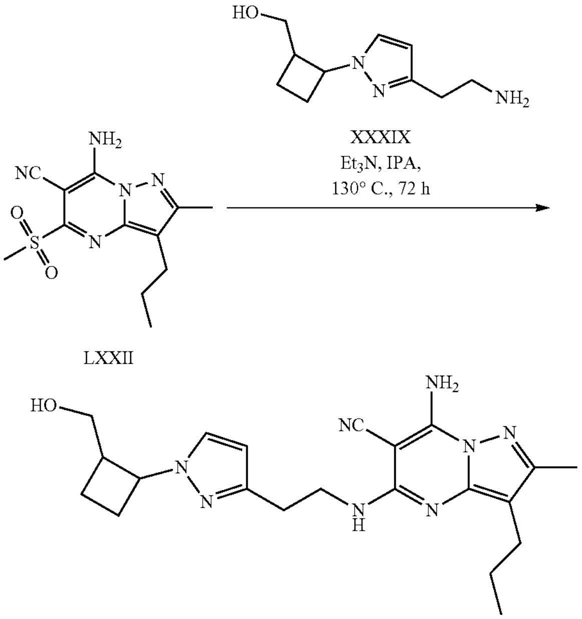

Peak-1: Example 165a; dextro (+) rotatory
Peak-2: Example 165b; leavo (-) rotatory To a solution of 7-amino-2-methyl-5-(methyl sulfonyl)-3-propylpyrazolo[1,5-a] pyrimidine-6-carbonitrile LXXII (0.5 g, 1.70 mmol) and (2-(3-(2-aminoethyl)-1H-pyrazol-1-yl) cyclobutyl) methanol XXXIX (0.67 g, 3.41 mmol) in isopropyl alcohol (15 mL) was added triethylamine (0713 mL, 5.11 mmol) and the reaction mixture was stirred at 130° C. for 72 h. The progress of the reaction was monitored by TLC analysis. After the completion of the reaction, the reaction mixture was diluted with water (20 ml) and extracted with ethyl acetate (20 mL×3). The combined organic layer was dried over anhydrous $Na_2SO_4$, filtered and concentrated under reduced pressure. The crude compound was purified by silica gel (230-400 mesh) column chromatography with ethyl acetate in hexane (0-70%) to afford the desired product as an off-white solid. Yield: 0.172 g, (25.0%).

Further the racemic compound was subjected to chiral SFC purification (Column Name: IG (21*250 mm), 5 μm; Co-Solvent Name: EtOH:IPA+0.1% TEA; Total flow rate: 3 g/mL; % of Co-Solvent:30; Temperature: 30° C.; ABPR Pressure: 1500 psiand) to separate into peak-1; Example 165a and peak-2; Peak-2; Example 165b; (39 mg)

Peak-1; Example 165a; (39 mg)

LCMS Calculated. for $C_{21}H_{28}N_8O$ is 408.24; Observed. 409.4 $[M+H]^+$. $^1$H NMR (400 MHz, DMSO-D$_6$): δ 8.11 (bs, 2H), 7.65 (bs, 1H), 6.69 (bs, 1H), 6.10 (bs, 1H), 4.61-4.59 (m, 1H), 4.50 (d, J=8.4 Hz, 1H), 3.56 (d, J=5.6 Hz, 2H), 3.41-3.90 (m, 2H), 2.82 (t, J=6.8 Hz, 3H), 2.42 (t, J=7.2 Hz, 2H), 2.32-2.21 (m, 5H), 1.79 (d, J=9.6 Hz, 1H), 1.56 (m, 3H), 0.86 (t, J=7.2 Hz, 3H); HPLC: 12.404 min; 99.46%, Column: INT ODS 3V-C18 (4.6*250) mm, 5μ; Mobile phase A: 0.1% Formic acid in water; Mobile phase B: Acetonitrile; Flow: 1.0 mL/min; Chiral HPLC: 5.319 min; 100%; Column Name: IG (4.6*250 mm), 5 μm; Co-Solvent Name: EtOH:IPA+0.1% TEA; Total flow rate: 3 g/mL; % of Co-Solvent: 30; Temperature:30° C.; ABPR Pressure: 1500 psi; Specific optical rotation ($[\alpha]_D$); (c 0.1 in MeOH)=+ 43.98

Peak-2; Example 165b; (39 mg)

LC-MS Calculated. for $C_{21}H_{28}N_8O$ is 408.24; Observed. 409.4 $[M+H]^+$. $^1H$ NMR (400 MHz, DMSO-$D_6$): δ 8.11 (bs, 2H), 7.65 (bs, 1H), 6.69 (bs, 1H), 6.10 (bs, 1H), 4.61 (bs, 1H), 4.54-4.48 (q, J=8.8 Hz, 1H), 3.5 (d, J=6.0 Hz, 2H), 3.4 (s, 2H), 2.82 (t, J=6.4 Hz, 3H), 2.42 (t, J=7.2 Hz, 2H), 2.32-2.18 (m, 5H), 1.79 (q, J=8.4 Hz, 1H), 1.57 (m, 3H), 0.86 (t, J=7.2 Hz, 3H); HPLC: 12.407 min; 99.32%, Column: INT ODS 3V-C18 (4.6*250) mm, 5μ; Mobile phase A: 0.1% Formic acid in water; Mobile phase B: Acetonitrile; Flow: 1.0 mL/min; Chiral HPLC: 5.712 min; 96.58%; Column Name: IG (4.6*250 mm), 5μ; Co-Solvent Name: EtOH:IPA+0.1% TEA; Total flow rate: 3 g/mL; % of Co-Solvent: 30; Temperature: 30° C.; ABPR Pressure: 1500 psi; Specific optical rotation ($[\alpha]_D$); (c 0.1 in MeOH)=−27.72.

Example 166: (R)-7-amino-3-ethyl-2-methyl-5-((2-(6-(((tetrahydrofuran-3-yl) oxy) methyl) pyridine-2-yl) ethyl) amino) pyrazolo[1,5-a]pyrimidine-6-carbonitrile

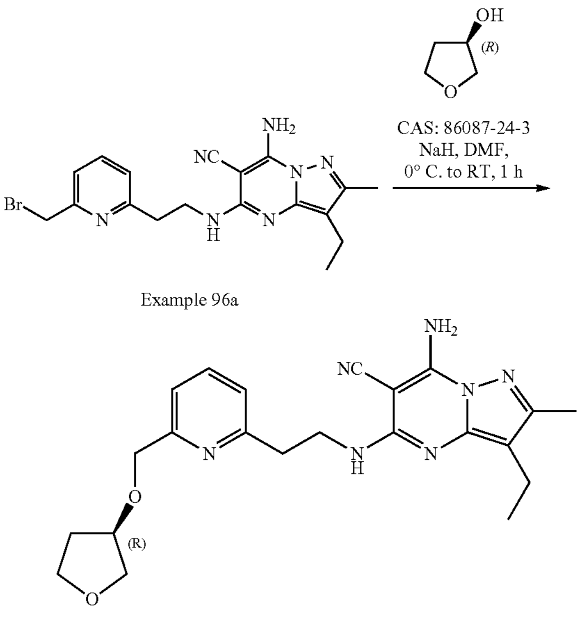

Example 96a

Example 166

To a solution of (R)-tetrahydrofuran-3-ol (CAS:86087-24-3, 0.038 mg, 0.434 mmol) in DMF (10 mL) at 0° C. was added sodium hydride (10 mg, 0.434 mmol) and the mixture was stirred under inert atmosphere for 5 min. This was followed by dropwise addition of solution of 7-amino-5-((2-(6-(bromomethyl) pyridin-2-yl) ethyl) amino)-3-ethyl-2-methylpyrazolo[1,5-a] pyrimidine-6-carbonitrile. Example 96a (0.18 g, 434 mmol) in DMF (1 mL). The reaction mixture was stirred at rt for 1 h and progress of the reaction was monitored by TLC analysis. After completion, the reaction mixture was quenched with water (20 mL) and extracted with ethyl acetate (30 mL×3). The combined organic layer was dried over anhydrous sodium sulphate and concentrated under reduced pressure. The crude compound was purified by silica gel (230-400 mesh) column chromatography using ethyl acetate in n-hexane (0-30%) to afford the desired product Example 166 as off-white solid. Yield: 0.045 g, (24.0%); LCMS Calculated. for $C_{22}H_{27}N_7O_2$ is 421.22; Observed: 422 $[M+H]^+$. NMR (400 MHz, DMSO-$D_6$): δ 8.12 (bs, 2H), 7.73 (t, J=7.6 Hz, 1H), 7.26 (d, J=7.6 Hz, 1H), 7.19 (d, J=7.2 Hz, 1H), 6.87 (bs, 1H), 4.57 (t, J=14.8 Hz, 2H), 4.26 (bs, 1H), 3.79-3.75 (m, 2H), 3.68 (t, J=7.2 Hz, 4H), 3.026 (t, J=6 Hz, 2H), 2.48-2.45 (m, 2H), 2.33-2.25 (m, 3H), 1.97 (d, J=4.0 Hz, 2H), 1.14-1.06 (m, 3H); HPLC: 10.260 min; 98.27%, Mobile phase A: 0.1% Formic acid in water; Mobile phase B: Acetonitrile; Flow: 1.0 mL/min; Chiral HPLC: 5.602 min; 100.00%; Column Name: IC (4.6*250 mm), 5 μm; Co-Solvent Name: EtOH; Total flow rate: 3 g/mL; % of Co-Solvent: 30; Temperature: 30° C.; ABPR Pressure: 1500 psi; Specific optical rotation ($[\alpha]_D$): (c 0.1 in MeOH)=−0.784.

Example 167: (+7-amino-3-ethyl-5-((2-(1-(4-(hydroxymethyl) tetrahydrofuran-3-yl)-5-methyl-1H-pyrazol-3-yl) ethyl) amino)-2-methylpyrazolo[1,5-a] pyrimidine-6-carbonitrile

Example 168: (+)-7-amino-3-ethyl-5-((2-(1-(4-(hydroxy methyl) tetrahydrofuran-3-yl)-1H-pyrazol-3-yl) ethyl) amino)-2-methyl pyrazolo[1,5-a]pyrimidine-6-carbonitrile

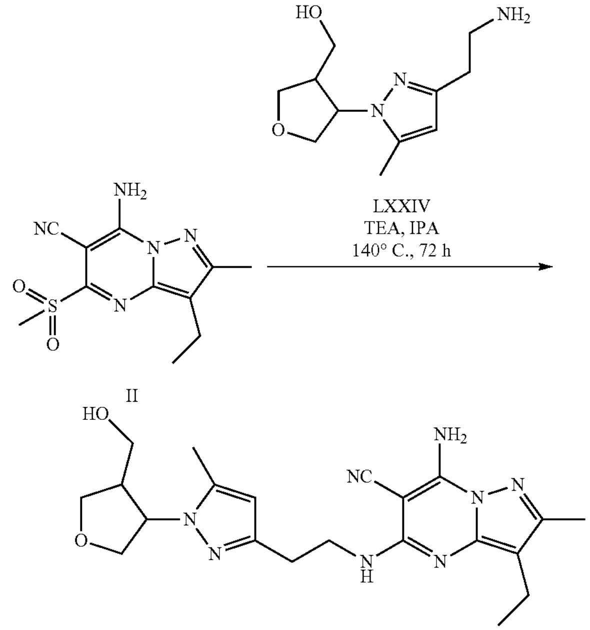

II

Example 167: Peak-1: Levo (-) rotatory
Example 168: Peak-2: Dextro (+) rotatory

To a stirred solution of 7-amino-3-ethyl-2-methyl-5-(methyl sulfonyl) pyrazolo[1,5-a] pyrimidine-6-carbonitrile II (0.5 g, 1.18 mmol) in 2-propanol (5 mL) were added (4-(3-(2-aminoethyl)-5-methyl-1H-pyrazol-1-yl) tetrahydrofuran-3-yl) methanol LXXIV (0.6 g, 2.66 mmol) and triethylamine (1.5 mL, 10.76 mmol). The reaction mixture in seal tube was stirred at 140° C. for 48 h. The progress of the reaction was monitored by TLC analysis. After the completion, the reaction mixture was cooled and diluted with water (20 mL). The mixture was extracted with ethyl acetate (20 mL×3). The combined organic layer was dried over anhydrous $Na_2SO_4$, filtered and concentrated under reduced pressure. The crude compound was purified by silica gel (230-400 mesh) column chromatography with ethyl acetate in n-hexane (10-50%) to afford the desired product as an off-white solid. Yield: 0.3 g, (59.7%). The racemic compound (0.3 g) was subjected to chiral separation by SFC {The sample was dissolved in 4.5 mL of tetrahydrofuran: methanol (1:1)}, column: chiral Pak IG (250*21) mm, 5.0 μm; mobile phase 82:18 (A:B).A=Liquid $CO_2$, B=0.1% triethyl amine in acetonitrile: methanol (1:1), Flow rate:18 mL/min; Wavelength 254 nm; to yield 56 mg of peak 1; Example 167: $[\alpha]_D$=−27.00°, c=0.1, MeOH) and 58 mg of peak 2; Example 168 $[\alpha]_D$+33.00°, c=0.1, MeOH) as off-white solids, respectively.

Peak-1; Example 167: LCMS Calculated. for $C_{21}H_{28}N_8O_2$ is 425.23; Observed. 425.40 $[M+H]^+$. $^1H$ NMR (400 MHz, DMSO-$D_6$): δ 8.11 (bs, 2H), 6.56 (t, J=4.8 Hz, 1H), 5.88 (s, 1H), 6.12 (s, 1H), 4.83 (t, J=5.2 Hz, 1H), 4.65-4.61 (m, 1H), 4.05 (q, J=8.0 Hz, 2H), 3.81 (t, J=8.4 Hz, 1H), 3.64 (t, J=5.2 Hz, 1H), 3.55-3.52 (m, 2H), 3.41 (t, J=5.6 Hz, 2H), 2.76 (t, J=7.2 Hz, 2H), 2.72-2.67 (m, 1H), 2.47-2.43 (m, 1H), 2.25 (s, 3H), 2.23 (s, 3H), 1.12 (t, J=7.6 Hz, 3H); HPLC: 11.220 min; 97.97%, Column: INT ODS 3V-C18 (4.6*250) mm, 5μ; Mobile phase A: 0.1% Formic acid in water; Mobile phase B: Acetonitrile; Flow: 1.0 mL/min; Chiral HPLC: 18.698 min; 100%; Column Name: IG (4.6*250 mm), 5 μm; Co-Solvent Name: MeCN:MeOH+0.1% DEA; Total flow rate: 3 g/mL; % of Co-Solvent: 20; Temperature: 30° C.; ABPR Pressure: 1500 psi.

Peak-2; Example 168: LCMS Calculated. for $C_{21}H_{28}N_8O_2$ is 425.23; Observed. 425.40 $[M+H]^+$. $^1H$ NMR (400 MHz, DMSO-$D_6$): δ 8.12 (bs, 2H), 6.55 (bs, 1H), 5.89 (s, 1H), 6.12 (s, 1H), 4.83 (bs, 1H), 4.64-4.62 (m, 1H), 4.05 (q, J=8.0 Hz, 2H), 3.82 (t, J=6.4 Hz, 1H), 3.65-3.62 (m, 1H), 3.55-3.52 (m, 2H), 3.41 (bs, 2H), 2.76 (t, J=6.8 Hz, 2H), 2.75-2.69 (m, 1H), 2.47-2.43 (m, 1H), 2.25 (s, 3H), 2.23 (s, 3H), 1.12 (t, J=7.6 Hz, 3H); HPLC: 11.218 min; 98.62%, Column: INT ODS 3V-C18 (4.6*250) mm, 5μ; Mobile phase A: 0.1% Formic acid in water; Mobile phase B: Acetonitrile; Flow: 1.0 mL/min; Chiral HPLC: 22.260 min; 99.13%; Column Name: IG (4.6*250 mm), 5 μm; Co-Solvent Name: MeCN:MeOH+0.1% DEA; Total flow rate: 3 g/mL; % of Co-Solvent: 20; Temperature: 30° C.; ABPR Pressure: 1500 psi.

Biological Activity

Inhibition of cAMP in HEK

Adenosine A2A receptors and Adenosine A2B receptors induce the production of cAMP when activated/stimulated by an agonist like adenosine or 5'-(N-Ethylcarboxamido) adenosine (NECA). A Time-Resolved Fluorescence Energy Transfer (TR-FRET) assay was used to show the inhibition of this cAMP production in HEK cells upon treatment with compounds of the Formula I of the present disclosure.

Determination of Adenosine 2a Receptor (A2aR) and Adenosine 2b (A2bR) Receptor Antagonism IC50 Using 5'-(N-Ethylcarboxamido) Adenosine (NECA) as Agonist HEK-293 cells expressing A2A receptor (#ES-011-C) or A2B receptor (#ES 013-C) were obtained from PerkinElmer. Cells were maintained in DMEM medium supplemented with 10% FBS and 200 μg/mL of G418 at 37° C. and 5% $CO_2$. The cells were cultured in antibiotic free medium for a period of 16-20 hours prior to the assay. All subsequent steps of the assay are performed at room temperature (22-24° C.). The cells were harvested at about 80% confluency by gentle flushing with PBS, recovered by centrifugation and resuspended in stimulation buffer at the concentration of $5.0\times10^6$ cells/mL. About 800-1000 cells per well were pre-incubated for 10 minutes with the compounds of the present invention before adding the agonist NECA at 5 nM for $A_2A$ and 30 nM for $A_2B$ corresponding to their respective $EC_{90}$ for a total stimulation time of 30 minutes.

The $IC_{50}$ s of compounds of Formula I were determined by assessing the cAMP levels using the Lance Ultra cAMP Kit (PerkinElmer, TRF0263) on white 384 well plates (Corning 3572). The assays were conducted in a stimulation buffer containing 1×DMEM, 5 mM HEPES, 0.1% BSA stabilizer and 20-30 μM Rolipram. Serial dilutions of compounds were made in stimulation buffer to achieve a final concentration of high micromolar (10 μM to 0.08 nM) in the reaction volume of 10 μL. The total reaction volume was 10 μL (5 μL of cells, 2.5 μL of antagonist and 2.5 μL of agonist). The stimulation was ended, and the reaction completed by adding 5 μL of 4× Eu-cAMP tracer working solution and 5 μL of 4× ULight-anti-cAMP working solution. The TR-FRET signal was measured after 1-hour incubation using a Tecan M1000 reader.

Determination of Adenosine 2a Receptor ($A_{2a}R$) and Adenosine 2b ($A_{2b}R$) Receptor Antagonism $IC_{50}$ Using High Concentration of Adenosine (30 μm) to Mimic the Pathological Conditions HEK-293 cells expressing A2A receptor (#ES-011-C) or $A_{2B}$ receptor (#ES 013-C) were obtained from PerkinElmer. Cells were maintained in DMEM medium supplemented with 10% FBS and 200 μg/mL of G418 at 37° C. and 5% CO2. The cells were cultured in antibiotic free medium for a period of 16-20 hours prior to the assay. All subsequent steps of the assay are performed at room temperature (22-24° C.). The cells were harvested at about 80% confluency by gentle flushing with PBS, recovered by centrifugation and resuspended in stimulation buffer at the concentration of 5.0×106 cells/mL. About 1500 cells per well were pre-incubated for 10 minutes with the compounds of the present invention before adding the agonist Adenosine at a high concentration (30 μM) for a total stimulation time of 30 minutes. The IC50 s of compounds of formula (I) were determined by assessing the cAMP levels using the Lance Ultra cAMP Kit (PerkinElmer, TRF0263) on white 384 well plates (Corning 3572). The assays were conducted in a stimulation buffer containing 1×DMEM, 5 mM HEPES, 2% Human serum albumin (HSA), 100 μM Rolipram and 30 μM erythro-9-(2-hydroxy-3-nonyl) adenine (EHNA). Serial dilutions of compounds were made in stimulation buffer to achieve a final concentration of high micromolar in a reaction volume of 10 μL. The total reaction volume was 10 μL (5 μL of cells, 2.5 μL of antagonist and 2.5 μL of agonist). ZM241385 and AB928 were used as reference compounds. The stimulation was ended, and the reaction completed by adding 5 μL of 4× Eu-cAMP tracer working solution and 5 μL of 4× ULight-anti-cAMP working solution. The TR FRET signal was measured after 1-hour incubation using a Tecan M1000 or a PerkinElmer Victor Nivo plate reader.

Results:

IC50 s of the antagonists of Formula (I) against $A_{2a}$ and $A_{2b}$ receptor expressing HEK-293 cells are presented in Table 1

TABLE 1

| Example | $A_{2A}$R $IC_{50}$ (nM) (@5 nM NECA) | $A_{2B}$R $IC_{50}$ (nM) (@30 nM NECA) | $A_{2A}$R $IC_{50}$ (nM) (@30 µM Adenosine) | $A_{2B}$R $IC_{50}$ (nM) (@30 µM Adenosine) |
|---|---|---|---|---|
| 1 | 10 | 1326 | ND | ND |
| 2 | 2.0 | 547 | ND | ND |
| 3 | 1014 | >3000 | ND | ND |
| 4 | 25 | 1374 | ND | ND |
| 5 | 0.15 | 0.87 | ND | ND |
| 6 | 6.6 | >3000 | ND | ND |
| 7 | 0.59 | >3000 | ND | ND |
| 8 | 46 | 1683 | ND | ND |
| 9 | ND | 1131 | ND | ND |
| 10 | 2.3 | 41 | ND | ND |
| 11 | 6.8 | 43 | ND | ND |
| 12 | 0.9 | 3.7 | ND | ND |
| 13 | 0.25 | 3.4 | 300 | 2319 |
| 14 | 1 | 7 | ND | ND |
| 15 | ND | 102 | ND | ND |
| 16 | 2 | 53 | ND | ND |
| 17 | 0.15 | 0.87 | 260 | 2378 |
| 18 | 5.5 | 9.5 | ND | ND |
| 19 | 2.1 | 36 | ND | ND |
| 20 | ND | 4 | ND | ND |
| 21 | 3.9 | 13 | ND | ND |
| 22 | 2.5 | 2.2 | ND | ND |
| 23 | 11 | 130 | ND | ND |
| 24 | ND | 2.5 | ND | ND |
| 25 | 0.2 | 14 | ND | ND |
| 26 | 2.9 | 0.83 | ND | ND |
| 27 | ND | 654 | ND | ND |
| 28 | 31 | 17 | ND | ND |
| 29 | 1 | 18 | ND | ND |
| 30 | ND | 4.5 | ND | ND |
| 31 | 0.73 | 51 | ND | ND |
| 32 | 0.5 | 7.3 | 452 | 2126 |
| 33 | 0.38 | 0.97 | 206 | 1423 |
| 34 | 0.4 | 6 | 160 | ND |
| 35 | 0.92 | 16 | ND | ND |
| 36 | 0.8 | 22 | 250 | ND |
| 37 | 0.12 | 7 | 78 | 1767 |
| 38 | 0.1 | 4.4 | 178 | ND |
| 39 | 0.23 | 0.94 | 120 | 1833 |
| 40 | <0.1 | 3.6 | 260 | 2378 |
| 41 | 0.88 | 73 | ND | ND |
| 42 | 0.88 | 76 | ND | ND |
| 43 | 2.3 | 123 | ND | ND |
| 44 | 1.3 | 2.3 | ND | ND |
| 45 | 0.58 | 2.9 | 935 | 650 |
| 46 | 1.9 | ND | ND | ND |
| 47 | 7.2 | ND | ND | ND |
| 48 | 2.2 | 51 | 7659 | ND |
| 49 | 0.3 | 6 | 635 | 4260 |
| 50 | 0.2 | 3.6 | 2161 | 2367 |
| 51 | 0.17 | 2.1 | 348 | 1287 |
| 52 | 0.54 | 29.3 | ND | ND |
| 53 | 0.3 | 27 | ND | ND |
| 54 | 0.74 | 5 | ND | ND |
| 55 | 0.74 | 8.6 | 250 | 3789 |
| 56 | 3.3 | 11 | ND | ND |
| 57 | 13 | 100 | ND | ND |
| 58 | 0.22 | 4.7 | 756 | 12208 |
| 59 | ND | 9 | 1083 | ND |
| 60 | ND | 0.94 | 211 | ND |
| 61 | <1 | 24 | 574 | ND |
| 62 | 5 | 42 | ND | ND |
| 63 | ND | 7.3 | 810 | 2798 |
| 64 | ND | 11 | 284 | 9075 |
| 65 | <1 | 27 | 227 | 15000 |
| 66 | 5 | 21 | ND | ND |
| 67 | 0.1 | ND | 50 | 1881 |
| 68 | ND | ND | 161 | 9382 |
| 69 | ND | ND | 68 | 2053 |
| 70 | ND | ND | 125 | >15000 |
| 71 | ND | ND | 158 | 2820 |
| 72 | ND | ND | 362 | 3116 |
| 73 | ND | ND | >15000 | >15000 |
| 74 | ND | ND | 398 | 1076 |
| 75 | ND | ND | 43 | 7147 |

TABLE 1-continued

| Example | $A_{2A}$R $IC_{50}$ (nM) (@5 nM NECA) | $A_{2B}$R $IC_{50}$ (nM) (@30 nM NECA) | $A_{2A}$R $IC_{50}$ (nM) (@30 µM Adenosine) | $A_{2B}$R $IC_{50}$ (nM) (@30 µM Adenosine) |
|---|---|---|---|---|
| 76 | ND | ND | 50 | 1593 |
| 77 | 0.1 | 2 | 81 | 700 |
| 78 | ND | ND | 200 | 798 |
| 79 | <0.1 | 2 | 88 | 586 |
| 80 | ND | 12 | 83 | 3804 |
| 81 | ND | 3.6 | 63 | 1054 |
| 82 | ND | 7 | 110 | 2338 |
| 83 | ND | ND | 109 | 2646 |
| 84 | ND | ND | 102 | 4245 |
| 85 | ND | 3 | 211 | 1070 |
| 86 | 0.2 | 19 | 43 | 2554 |
| 87 | ND | ND | 80 | 1764 |
| 88 | ND | ND | 286 | 1298 |
| 89 | ND | ND | 66 | 2371 |
| 90 | ND | ND | 77 | 1830 |
| 91 | ND | ND | 628 | 1617 |
| 92 | ND | ND | 79 | 5645 |
| 93 | ND | ND | 50 | 1227 |
| 94 | ND | ND | 104 | 10000 |
| 95 | 1.2 | 53 | 112 | 1060 |
| 96 | ND | ND | 456 | ND |
| 97 | ND | ND | 451 | 1428 |
| 98 | ND | ND | 100 | >15000 |
| 99 | ND | ND | 69 | 20000 |
| 100 | ND | ND | 139 | 1007 |
| 101 | ND | ND | 2100 | >15000 |
| 102 | ND | ND | 804 | 8301 |
| 103 | ND | ND | 100 | 2592 |
| 104a | ND | ND | 88 | 2262 |
| 104b | ND | ND | 102 | 2607 |
| 105 | ND | ND | ND | 3869 |
| 106 | ND | ND | 75 | 4388 |
| 107 | ND | ND | 224 | 1548 |
| 108 | ND | ND | 392 | 1074 |
| 109 | ND | ND | 402 | 723 |
| 110 | ND | ND | >15000 | >15000 |
| 111 | ND | ND | 666 | 2383 |
| 112 | ND | ND | 84 | 10829 |
| 113 | ND | ND | 187 | 1051 |
| 114 | ND | ND | 96 | 4384 |
| 115 | 0.3 | 9 | 117 | 829 |
| 116 | ND | ND | 427 | 2100 |
| 117 | ND | ND | 66 | 3061 |
| 118 | ND | ND | 78 | 7849 |
| 119 | ND | ND | 260 | 3412 |
| 120 | ND | ND | 529 | 8630 |
| 121 | ND | ND | 245 | 895 |
| 122a | ND | ND | 289 | 707 |
| 122b | ND | ND | 130 | 521 |
| 123 | ND | ND | 405 | 1580 |
| 124 | ND | ND | 126 | 2219 |
| 125 | ND | ND | 767 | >15000 |
| 126 | ND | ND | 1885 | 3551 |
| 127 | ND | ND | 161 | 2171 |
| 128 | ND | ND | 368 | 1110 |
| 129 | ND | ND | 237 | 5664 |
| 130 | ND | ND | 280 | 5880 |
| 131 | ND | ND | 1457 | >15000 |
| 132 | ND | ND | 248 | ND |
| 133a | ND | ND | 554 | 6685 |
| 133b | ND | ND | 136 | 6073 |
| 134 | ND | ND | 475 | 2509 |
| 135 | ND | ND | 1312 | 2216 |
| 136 | ND | ND | 506 | 2613 |
| 137 | ND | ND | 820 | >15000 |
| 138 | ND | ND | 88 | 2048 |
| 139 | ND | ND | 165 | 482 |
| 140 | ND | ND | 6019 | >15000 |
| 141 | ND | ND | 679 | 4749 |
| 142 | ND | ND | 141 | 1665 |
| 143 | ND | ND | 667 | 1340 |
| 144a | ND | ND | 327 | 821 |
| 144b | ND | ND | 254 | 815 |
| 145 | ND | ND | 294 | 1125 |
| 146 | ND | ND | 255 | 2469 |

TABLE 1-continued

| Example | $A_{2A}R$ $IC_{50}$ (nM) (@5 nM NECA) | $A_{2B}R$ $IC_{50}$ (nM) (@30 nM NECA) | $A_{2A}R$ $IC_{50}$ (nM) (@30 μM Adenosine) | $A_{2B}R$ $IC_{50}$ (nM) (@30 μM Adenosine) |
|---|---|---|---|---|
| 147 | ND | ND | 363 | 9076 |
| 148 | ND | ND | 161 | 2736 |
| 149 | ND | ND | 43 | 988 |
| 150 | ND | ND | 1153 | 1626 |
| 151 | ND | ND | 95 | 4614 |
| 152 | ND | ND | 209 | 1788 |
| 153 | ND | ND | 195 | 1193 |
| 154a | ND | ND | 1055 | 1544 |
| 154b | ND | ND | 1010 | 1411 |
| 155 | ND | ND | 181 | 429 |
| 156 | ND | ND | 750 | 2954 |
| 157 | ND | ND | 1669 | 2934 |
| 158 | ND | ND | 805 | 3347 |
| 159a | ND | ND | 139 | 911 |
| 159b | ND | ND | 457 | 1022 |
| 160a | ND | ND | 579 | 1931 |
| 160b | ND | ND | 341 | 1252 |
| 161 | ND | ND | 2768 | 3965 |
| 162a | ND | ND | 1881 | 5793 |
| 162b | ND | ND | 1233 | 2725 |
| 163a | ND | ND | 72 | 11129 |
| 163b | ND | ND | 82 | 12177 |
| 164 | ND | ND | 8258 | >15000 |
| 165a | ND | ND | 2164 | >15000 |
| 165b | ND | ND | 1535 | 9157 |
| 166 | ND | ND | 1424 | 466 |
| 167 | ND | ND | 100 | 700 |
| 168 | ND | ND | 90 | 650 |
| ZM241385 | 3.5 | ND | 27296 | 16745 |

ND—not determined.

From Table 1, it can be observed that the compounds of the present disclosure exhibit very potent antagonism against both adenosine 2aR and 2bR with sub nanomolar to nanomolar potency under the physiological condition of adenosine agonist (NECA). It also evident from Table-1 is that the compound of the present invention also demonstrates very potent functional antagonism against adenosine 2aR and 2bR with nanomolar to micromolar potency under high adenosine concentrations (30 μM) which mimics the pathological disease conditions. Hence the compounds present disclosure demonstrates superior dual antagonism compared to reference adenosine antagonist (ZM241385)

Cytokine Restoration in Human PBMCS

The representative compounds of Formula (I) are of interest due to their potent dual functional antagonism of adenosine 2a and 2b receptors through inhibition of cyclic AMP in HEK 293 cells. The ability of the invention compounds disclosed herein to restore the cytokines (IL-2 and TNF-α) release under adenosine agonist (NECA) environment evaluated using human Peripheral blood mononuclear cells (PBMCs).

PBMC Isolation

Peripheral blood was collected from healthy adult individuals in vacutainer tube. Peripheral blood mononuclear cells (PBMCs) were isolated via density gradient centrifugation, which uses Ficoll (Histopaque buffer) combined with short, low-speed centrifugation, to separate different cell populations. Diluted defibrinated blood was layered on a Ficoll and centrifuged at 1800 rpm for 20 minutes at 22° C. Differential migration of cells during centrifugation results in the formation of layers containing different cell types. The bottom layer contains erythrocytes. Remaining cells (i.e., lymphocytes, monocytes, and platelets) that are not dense enough to penetrate the Ficoll media layers (densities of 1.0770 g/ml), forms a buffy coat at the interface between the upper plasma layer and the Ficoll media layer. After carefully collected the buffy coat excess of platelets, Ficoll and plasma were removed by washing it with isotonic sterile phosphate buffered saline (PBS) and resulting cell pellet was resuspended in RPMI media with 5% FBS an P/S. The isolated PBMCs were allowed to be conditioned for an hour at 37° C. in a $CO_2$ incubator. These cells were subsequently used for specific downstream assay.

Cytokine Restoration Assay in Human PBMCs

Isolated PBMC ($3\times10^5$ cells/200 μl) were plated in in 96 well microtiter plate in RPMI media with 5% FBS in presence of 100 units of penicillin plus 100 μg/ml streptomycin. NECA was added at a final concentration of 5 μM, control wells were maintained without NECA suppression (i.e., no NECA control). The assay plates were incubated at 37° C. for 4 hours in a $CO_2$ incubator. Various concentrations of test compounds were added into respective wells in triplicates. Pre-washed anti CD3/28 Dynabeads (2.5 μL) was added for CD4 and CD8 + T-cell stimulation (to obtain a bead-to-cell ratio of 1:1). The assay plate was incubated at 37° C. in 5% $CO_2$ and 20% ambient $O_2$ maximum for 48 hours. At the end of 48 hours, the activated PBMC were harvested, and culture supernatants were used directly for further analysis.

Forty-eight hours post treatment, 15 μL of cell-free supernatant was collected and assayed for secreted IL2 using the human Interleukin 2 (hIL2)—LANCE Ultra Detection Kit (Perkin Elmer). Similarly, level of soluble Tumor Necrosis Factor alpha (TNFα) was determined using human TNFα LANCE Ultra Detection Kit (Perkin Elmer). T-FRET signal was measured with Tecan spark multimode plate reader. Data was analyzed by graph-pad prism9. $EC_{50}$ s of the compounds of Formula (I) in restoration of cytokine release under adenosine agonist from the human PBMCS are presented in Table 2

TABLE 2

| Example | IL-2 restoration $EC_{50}$ (nM) | TNF-α restoration $EC_{50}$ (nM) |
|---|---|---|
| 13 | 5.5 | 5.2 |
| 39 | 4.2 | 2.3 |
| 79 | 2.2 | 1.4 |
| 122b | 1.4 | 1.2 |
| 155 | 3.6 | 3.2 |
| ZM241385 | 200 | 60.5 |

hERG Inhibition Assay

To test if the compounds of Formula I has any safety risk by inhibiting cardiac ion channel, particularly the potassium channel (Ikr, hERG), compounds were tested using electrophysiological assays to evaluate its potential activity on hERG ion channel. The representative compounds of formula I were tested for inhibition of the human ether a go-go related gene (hERG) K+ channel using Qpatch HTX automated electrophysiology. 6-Point concentration-response curves were generated using three-fold serial dilutions from a maximum final test concentration of 300 μM and the results are presented in Table 3.

Compounds were solubilised to 100 mM in DMSO before dilution in HBPS to 100 μM. 6-Point concentration-response curves were generated using 3.16-fold serial dilutions from the top test concentration. Electrophysiological recordings were made from a Chinese Hamster Ovary cell line stably expressing the full-length hERG potassium channel. Single cell ionic currents were measured in whole-cell patch clamp configuration at room temperature (21-23° C.) using the Qpatch HTX platform (Sophion). Intracellular solution contained (mM): 120 KF, 20 KCl, 10 EGTA, 10 HEPES and was buffered to pH 7.3. The extracellular solution (HEPES-buffered physiological saline, HBPS) contained (mM): 145 NaCl, 4 KCl, 2 $CaCl_2$, 1 $MgCl_2$, 10 HEPES, 10 glucose, buffered to pH7.4. Cells were clamped at a holding potential of −80 mV. Cells were stepped to +20 mV for 2 s then −40 mV for 3 s before returning to the holding potential. This sweep was repeated 10 times at 10 s intervals. hERG currents were measured from the tail step and referenced to the holding current. Compounds were then incubated for 2 minutes prior to a second measurement of ion channel current using an identical pulse train.

TABLE 3 hERG $IC_{50}$ values

| Example | hERG $IC_{50}$ (μM) |
|---|---|
| 13 | >100 |
| 39 | >100 |
| 79 | >100 |
| 122b | >100 |
| 155 | >100 |
| Cisapride | 0.14 |

Plasma Protein Binding Assay:

Protein binding is measured using the equilibrium dialysis technique. Compound is added to 10% plasma giving a concentration of 10 μM and dialysed with isotonic buffer for 18 hours at 37° C. The plasma and buffer solutions are analysed using generic LC UV/MS and the first apparent binding constant for the compound derived. The binding constant is then used to determine the % free in 100% plasma The percentage of plasma bound/unbound fraction preparation was calculated as follows $$\% \text{ Unbound} = 100 * \frac{F_C}{T_C}$$

$$\% \text{ Recovery} = 100 * \frac{(F_C + T_C)}{T_O}$$

where, $T_c$=Total plasma concentration was determined by the calculated concentration on the plasma side of the chamber $F_c$=Total plasma concentration was determined by the calculated concentration on the buffer side of the chamber $T_o$=Total compound concentration determined before analysis.

TABLE 4

Multi Species (Mice; Rat; Dog & Human) Plasma Protein binding of Example 13, Example 122b, Example 39

| Species | Example 13 | Example 122b | Example 39 |
|---|---|---|---|
| mouse, CD-1 | 90.67 | ND | 87.52 |
| rat, Sprague-Dawley | 90.36 | 86.07 | 75.14 |
| dog, Beagle | 91.00 | 84.99 | 84.44 |
| human | 95.00 | 88.33 | 90.87 |

ND: Not determined

In Vitro In Vivo Extrapolation (IVIVE) of Clearance in Multiple Species (Rat/Dog & Human) & Prediction of Human Pharmacokinetic (PK) Parameters Well stirred model was used for predicting human CL using human hepatocyte Clint and free fraction (fu) in human plasma. Liver blood flow rates, liver weights, hepatocellularity and in vitro in vivo correlation/extrapolation (IVIVC/E) templates routinely employed (Smith et al., Pharmacokinetics and Metabolism in Drug Design, Methods and Principles in Medicinal Chemistry Volume 13, 2004 Wiley—VCH, Weinheim, Germany) were used for prediction.

Briefly, thawed cryopreserved hepatocytes was transferred into the pre-warmed (maintained at 37° C.) buffer medium, and hepatocytes was mixed by gently inverting the tube 3 times. The cell suspension was centrifuged at 50×g room temperature for 5 min. The supernatant was discarded, and cell pellet was loosened by gently swirling the centrifuge tube. The hepatocytes were resuspended in 2 mL pre-warmed buffer. The total cell count was determined and the number of viable cells by trypan blue dye exclusion method. The acceptable cell viability at the beginning of the assay was ~85%. The hepatocyte suspension was diluted with the buffer to attain a final concentration of 1 million cells/mL ($1*10^6$ cells/mL).

The stock (10 mM) solution of test compounds and positive controls was prepared in dimethyl sulfoxide (DMSO). Subsequently, sub stock (1 mM) solutions were prepared by diluting 10 μL of 10 mM stock solution with 90 mL of DMSO. The final working stock (1 μM) solutions were prepared by diluting 2 μL of sub stock solution with 1998 μL of incubation media. For the assay, working stock solution (1 μM) was spiked into hepatocyte incubation mixture to obtain a final concentration of 0.5 μM. Final organic content in the assay was <0.1%.

The stability assay was conducted in duplicate (n=2). Manually 200 μL of diluted hepatocyte suspension ($1*10^6$ cells/mL) was added to each well of a 48 well plate. 200 μL of test compound (1 μM) prepared was added in the incubation medium to each of the wells containing hepatocytes. Final concentration of hepatocytes and test compound in the assay were $0.5*10^6$ cells/mL (0.5 million cells/mL) and 0.5 μM, respectively. The 48 well plate was placed in an incubator maintained at 37° C., 5% $CO_2$ atmosphere and 95% relative humidity. The hepatocyte mixture was incubated for 120 mins with constant shaking at 250 rpm. At each time point (0, 5, 10, 15, 30, 60, 90 and 120 mins), 50 μL aliquot of hepatocyte mixture was added into 96 deep well plate and precipitated with 200 μL of acetonitrile containing internal standard. The samples were vortex mixed and centrifuged for 10 mins at 4000 rpm. Post centrifugation, the supernatant (100 μL) was separated and transfer to a fresh 96 well plate and diluted with 100 μL of water. The samples were analyzed using LCMS/MS method.

The metabolic stability was expressed as the percentage of parent remaining is calculated from the peak area ratio of NCE remaining after incubation (tx) compared to the time zero ($t_0$) incubation. The percentage of parent test compound remaining at each time point was calculated by comparing the peak area ratio of test compound after incubation (tx) with peak area of time zero ($t_0$) incubation. Similarly, half-life (t½) was calculated using following equation:

$$\text{In-vitro } T_{1/2} = \frac{0.693}{K_{el}}$$

The intrinsic clearance (Clint) was calculated using the following equations:

$$CL_{int} = \frac{0.693}{K_{el}} \times \frac{\mu L \text{ of incubation}}{K_{el} \times \text{Number of cells/incubation}} \times \text{no of } \frac{\text{cells}}{\text{gram}} \text{ liver}$$

Scaling factors to represent hypocellularity million cells/gm liver and liver/kg body wt.

TABLE 5

Metabolic stability and Intrinsic Clearance of Example 122b, Example 13 and Example 39 determined from Rat; Dog and Human in-vitro hepatocytes assay

| | Rat | | Dog | | Human | |
|---|---|---|---|---|---|---|
| Compounds | CLint (µl/min/ 10^6) | CLint T1/2 | CLint (µl/min/ 10^6) | CLint T1/2 | CLint (µl/min/ 10^6) | CLint T1/2 |
| Example 122b | 4.7 | 216 | <4.1 | >240 | <4.1 | >240 |
| Example 13 | 34 | 29 | 9.5 | 107 | <8.2 | >120 |
| Example 39 | <8.2 | >120 | 10.8 | 92 | <8.2 | >120 |

TABLE 6

Invitro-In vivo Extrapolation (IVIVE) of intrinsic clearance ($CL_{int}$) of Example 122b, Example 13 and Example 39 determined using Rat, Dog and Human hepatocytes

| Compound | Species | Hepatocyte Clint (µl/min/$10^6$) | Predicted $CL_h$ (mL/min/ kg) | Total $CL_{systemic}$ in plasma (mL/min/ kg) | Vss (L/kg) | T1/2 (hr) (IV bolus) | % F |
|---|---|---|---|---|---|---|---|
| Example 122b | Rat | 4.7 | 16 | 78 | 1.6 | 0.33 | 21 |
| | Dog | <4.1 | 10 | ND | ND | ND | ND |
| | Human | <4.1 | 8.6 | ND | ND | ND | ND |
| Example 13 | Rat | 34 | 41 | 69 | 1.4 | 0.41 | <1 |
| | Dog | 9.5 | 17 | 33 | 1.8 | 0.77 | 25 |
| | Human | <8.2 | 12 | ND | ND | ND | ND |
| Example 39 | Rat | <8.2 | 23 | 90 | 2.4 | 1.2 | 27 |
| | Dog | 10.8 | 18 | 52 | 2.0 | 0.45 | 25 |
| | Human | <8.2 | 12 | ND | ND | ND | ND |

ND: Not determined

Cell Based Permeability/Efflux Caco-2 Assay:

The intestinal permeability of the compounds is critical for good oral absorption and hence it was determined using Caco-2 assay.

Briefly, Permeability in a Caco-2 monolayer was determined at 10 µM. High density Caco-2 cells were obtained with fluent monolayer with trans epithelial electrical resistance (TEER) values greater than 350 ohm·$cm^2$ in the assay at 21 days of culture in 24 or 96 well insert plates. TEER was measured both before and after performing all the transport experiments. $P_{app}$ was measured in apical A to basolateral B direction. Transport buffer, 800 µL Hanks balanced salt sodium (HBSS) (pH 7.4) consisting of 10 mM HEPES without proteins was first dispensed to the basal side of the monolayer. The assay was then initiated by adding 200 µL, of compound solution to the apical side (all test compounds were diluted in HBSS, pH 6.5, with 1% DMSO as co-solvent). Two µL and 200 µL of samples were withdrawn before and at 45- and 120-min post addition of test compound, from the apical donor compartment and the base lateral receiver compartment, respectively. The transwell plates were kept for 120 min of incubation time at 37° C., 5% $CO_2$, 95% relative humidity. At the end of incubation, sample solutions from both donor and receiver wells were mixed with acetonitrile containing internal standard (IS) immediately. Samples were analyzed including starting dosing solution, donor solution, and receiver solution by LC/MS/MS (API-4500). Concentrations of test compound was expressed as area ratio of analytes versus internal standard (IS).

A passive permeability was determined by complete chemical inhibition of the three major efflux transporters, ABCB1 (P-gp), ABCG2 (BCRP) and ABCG2 (MRP2) in Caco-2 cells using a cocktail of chemical inhibitors quinidine (P-gp), sulfasalazine (BCRP) and benzbromarone (MRP2)

The mean apparent permeability ($P_{app}$, X $10^{-6}$ nm/sec) is calculated as follows $$Papp = \frac{dq}{dt} \times \frac{1}{Co} \times \frac{1}{A}$$

Where dq/dt=rate of transport (rate of transport of compound in the receiver compartment), Co=initial concentration in the donor compartment, A=surface area of the effective filter membrane. Plot the cumulative amount of transported drug against time to obtain rate transport.

The percent recovery was calculated using the following equation $$\% \text{ Recovery} = \frac{\text{Total compound in donor and receiver chamber at the end of experiment}}{\text{Initial amount of compound loaded in donor chamber}} \times 100$$

$$\text{Efflux ratio} = \frac{P_{app} \text{ values in } B \rightarrow A}{P_{app} \text{ values in } A \rightarrow B}$$

Efflux ratio>2.0 suggest that the compound is subjected to apical efflux and provides evidence for involvement of one or more transport pathways in the transport of test compound.

TABLE 7

Bi-directional permeability of Example 122b, Example 13 and Example 39 measured in the CaCo-2 assay

| Properties | Example 122b | Example 13 | Example 39 |
|---|---|---|---|
| A – B permeability × $10^{-6}$ cm/s | 14.4 | 58.0 | 18.4 |
| B – A permeability × $10^{-6}$ cm/s | 15.9 | 19.5 | 18.5 |

Pharmacokinetic Studies of Example 13, Example 122b and Example 39 in Mice, Rats, and Dogs Intravenous (i.v) and Oral formulations for pharmacokinetic (PK) studies was formulated in different vehicles and excipients to achieve the desirable solubility for intravenous and Oral routes of administration.

Appropriate amount of the test compound was weighed and dissolved in required volume of the vehicles, followed by vertexing for a few seconds to dissolve the compound. Then the solution (or) suspension was sonicated at room temperature for 5 minutes to obtain a visually clear solution and or homogenous suspension. All the formulations were prepared freshly at room temperature before dosing. All these formulations were observed to be stable at room temperature for more than 24 hours. The formulation details of each of the compound tested was given in the Table 8.

Rodent (Mice & Rat) Pharmacokinetic (PK) Studies

The rodent pharmacokinetic studies were carried out in male Sprague-Dawley (SD) rats (8-12 weeks of age, weighing 280±20 g at the time of dosing) and CD1 mice (8-12 weeks of age, weighing 30-35 g body weight at the time of dosing) to estimate the plasma clearance, volume of distribution and terminal half-life, area under curve (AUC) and peak plasma concentration ($C_{max}$) and time of peak plasma concentration ($T_{max}$) following intravenous and oral routes of administration. The detailed experimental design is described in the Table 8 below.

Rats were anaesthetized by Isoflurane anaesthesia. The jugular and femoral veins of rat were cannulated, and the study was performed 48 h post cannulation. At each time point about 100 μL, of rat blood was collected from the jugular vein into a labelled microfuge tube containing 200 mM $K_2$EDTA solution (20 μL, per mL of blood) and equivalent volume of heparinized saline was replaced following sample collection. Similarly, 25 μL, of mice blood was collected from the saphenous vein into a labelled microfuge tube containing 200 mM $K_2$EDTA solution Serial blood sampling method was used for blood collection. Blood samples were collected at pre-dose, 0.25 h, 0.5, 1, 2, 4, 6, 8 and 24-hours post dose. The blood samples were processed to obtain the plasma samples within 30 min of scheduled sampling time. All plasma samples were stored −70° C. until bioanalysis.

Non-Rodent (Dog) PK Study:

The dog PK study was carried out in male Beagle dogs of minimum 10 Kg body weight to estimate the plasma clearance, volume of distribution and terminal half-life, area under curve (AUC) and peak plasma concentration ($C_{max}$), time of peak plasma concentration ($T_{max}$) and absolute bioavailability (% F) following intravenous and oral routes of administration. The detailed experimental design is provided in Table-8.

TABLE 8

Pharmacokinetic Study design of Example 13, Example 122b and Example 39 in Mice, Rats and Dogs

| Test item | Species/Strain/ Gender | Route/ condition | Dose (mg/kg) | Dose volume (mL/kg) | Formulation details |
|---|---|---|---|---|---|
| Example 13 | Rat/SD/Male | IV bolus/Fed | 3 | 2 | 5% w/v ascorbic acid in water, pH adjusted to ~4.1 using 8.4% NaHCO3 |
| | Rat/SD/Male | Oral/Fasted | 100 | 10 | 5% Ascorbic acid:10% TPGS:6% Solutol:5% Poloxamer:water q.s |
| | Mice/CD1/Male | Subcutaneous/Fed | 5 | 5 | 5% w/v ascorbic acid in water + 15% TPGS |

TABLE 8-continued

Pharmacokinetic Study design of Example 13, Example 122b and Example 39 in Mice, Rats and Dogs

| Test item | Species/Strain/ Gender | Route/ condition | Dose (mg/kg) | Dose volume (mL/kg) | Formulation details |
|---|---|---|---|---|---|
| | Mice/CD1/Male | Oral/Fasted | 30 | 10 | 10% v/v DMSO:5% v/v Ethanol:15% v/v TPGS in water:Saline q.s |
| | Dog/Beagle/Male | IV bolus/Fed | 3 | 2 | 5% w/v L-Ascorbic Acid in water, pH adjusted to 4 using 8.4% w/v sodium bicarbonate (NaHCO3) |
| | Dog/Beagle/Male | Oral/Fasted | 10 | 5 | 10% v/v Dimethyl sulfoxide (DMSO):5% v/v Ethanol:15% v/v TPGS in water:70% v/v sterile Saline. |
| Example 39 | Mice/CD1/Male | IV bolus/Fed | 15 | 5 | 15% v/v DMSO:25% v/v PEG400:10% v/v Ethanol:50% v/v Normal saline |
| | Mice/CD1/Male | Oral/Fasted | 30 | 10 | 10% v/v DMSO:30% v/v PEG400:10% v/v Ethanol:5% v/v tween80:45% v/v Saline |
| | Mice/CD1/Male | Oral/Fasted | 30 | 10 | 10% v/v DMSO:5% v/v Ethanol:15% v/v TPGS in water:70% v/v normal saline |
| | Rat/SD/Male | IV bolus/Fed | 15 | 5 | 15% v/v DMSO + 25% v/v PEG400 + 10% v/v Ethanol + 50% v/v Normal saline |
| | Rat/SD/Male | Oral/Fasted | 100 | 10 | 10% v/v DMSO:30% v/v PEG400:10% v/v Ethanol:5% v/v tween80:45% v/v Saline |
| | Dog/Beagle/Male | IV bolus/Fed | 3 | 2 | 20% v/v N, N-Dimethyl acetamide (DMA):10% v/v PEG400:70% v/v sterile saline. |
| | Dog/B eagle/Male | Oral/Fasted | 10 | 5 | 10% v/v DMSO:5% v/v Ethanol:15% v/v TPGS in water:70% v/v Saline. |

TABLE 8-continued

| Pharmacokinetic Study design of Example 13, Example 122b and Example 39 in Mice, Rats and Dogs | | | | | |
|---|---|---|---|---|---|
| Test item | Species/Strain/ Gender | Route/ condition | Dose (mg/kg) | Dose volume (mL/kg) | Formulation details |
| Example 122b | Mice/CD1/Male | Oral/Fasted | 100 | 10 | 10% v/v DMSO:5% v/v Ethanol:15% v/v TPGS in water:Saline q.s |
| | Rat/SD/Male | IV bolus/Fed | 5 | 2 | 10% v/v DMSO:5% v/v Solutol HS:20% v/v PEG400:Saline q.s |
| | Rat/SD/Male | Oral/Fasted | 30 | 10 | 10% v/v DMSO:5% v/v Ethanol:15% v/v TPGS in water:Saline q.s |

Briefly, Example 13 and Example 39 was administered to a group of 3 non-naïve male dogs. The first set of 3 animals received an intravenous administration and following a washout period of 7 days, received an oral administration of Example 13. Following a further 7-day washout the animals will then repeat the intravenous and oral dosing regimen with an administration of Example 39. Blood samples (1 mL) was collected from the jugular vein by venepuncture into tubes containing K2EDTA anticoagulant at the following sampling times:

IV: Predose, 0.083 (5 min), 0.25, 0.5, 1, 2, 4, 8 and 24 hrs post-dose.

PO: Predose, 0.25, 0.5, 1, 2, 4, 8 and 24 hrs post-dose.

Immediately following collection blood samples was inverted to ensure mixing with anticoagulant and placed on wet ice. As soon as practically possible samples were centrifuged (3000 rpm, 10 min, at 4° C.) and the resultant plasma decanted into appropriately labelled polypropylene tubes in 96-well plate format and stored in a freezer set to maintain a temperature of ≤−65° C., until analysis.

Plasma samples were analysed for a fit-for purpose LC-MS/MS method with a lower limit of quantification. The pharmacokinetic parameters were calculated using the non-compartmental analysis tool of validated Phoenix® WinNonlin® software (Certara, USA version 8.4) with linear up and log down method for estimating AUC.

All animals in intravenous (IV bolus) group were under fed state and animals in oral groups were fasted overnight (min 12 hr) before dose administration and food was provided 4 h post dose administration. All animals were received water ad libitum during the study period. The mean (±SD) pharmacokinetic parameters of Example 13, Example 122b & Example 39 following IV bolus and Oral dose administration in Mice/Rat and Dog is provided in Table-9.

TABLE 9

| Mean (±SD) Pharmacokinetic Parameters of Example 12, Example 122b and Example 39 following IV bolus and Oral dose administration in Mice, Rat and Dog | | | | | | | | | | | |
|---|---|---|---|---|---|---|---|---|---|---|---|
| Compound | Species | Route | Dose mg/k | Co*/ ng/m | $T_{ma}$ h | $AUC_{0-t}$ h*ng/m | $AUC_{0-}$ h*ng/m | CL mL/min/ | $V_{ss}$ L/K | $t_{1/2}$ h | % F |
| Example 13 | Mice | p.o | 30 | 236 ± | 0.2 | 138 ± | 148 ± | | ND | | |
| | | s.c | 10 | 1346 | 0.5 | 1504 ± | 1539 ± | | ND | | |
| | Rat | i.v | 3 | 2242 | — | 728 ± | 730 ± | 69 ± 9.0 | 1.4 | 0.4 | <1 |
| | | p.o | 10 | 4.2 ± | 0.2 | 3.7 ± | — | ND | | | |
| | Dog | i.v | 3 | 2899 | NA | 1497 ± | 1526 ± | 33 ± 3.6 | 1.75 | 0.7 | 25 ± 11 |
| | | p.o | 10 | 839 ± | 0.5 | 1253 ± | 1319 ± | ND | | | |
| Example 39 | Mice | i.v | 15 | 2236 | NA | 4498 ± | 4503 | 58 ± 14 | 1.0 | 0.9 | 15 |
| | | p.o | 30 | 3300 | 0.2 | 1360 ± | 1364 ± | ND | | | |
| | Rat | i.v | 15 | 8676 | NA | 2831 ± | 2835 ± | 90 ± 15 | 2.4 | 1.2 | 27 ± 13 |
| | | p.o | 100 | 4103 | 0.2 | 5152 ± | 5344 ± | ND | | | |
| | Dog | i.v | 3 | 1352 | NA | 929 ± | 975 ± | 52 ± 8.7 | 2.0 | 0.4 | 25 |
| | | p.o | 10 | 618 | 0.5 | 756 | 827 | ND | | | |
| | | p.o | 30 | 201 ± | 0.5 | 382 ± | ND | ND | | | |
| Example 122b | Mice | p.o | 100 | 1378 | 0.2 | 10504 | 10524 | ND | | | |
| | Rat | i.v | 5 | 4169 | NA | 1098 ± | 1104 ± | 78 ± 17 | 1.58 | 0.3 | |
| | | p.o | 30 | 983 ± | 0.5 | 1415 ± | 1440 ± | ND | | | 21 |

*Co is reported only for IV parameters; NA: Not applicable; ND: Not determined; #Median Good bioavailability of 25% observed in dogs for example 13 and 39. Total systemic clearance of Example 13 is equivalent to that of hepatic clearance and High volume of distribution, 3× of total body water (TBW). Whereas Example 39 had 1.7× higher clearance than hepatic clearance and high volume of distribution (3.3×TBW). Rapid absorption post administration with $T_{max}$ of 0.5 h and similar $C_{max}$ at 10 mg/kg dose level for both the compounds In rats & mice, total CL is similar to hepatic clearance for Example 13 and 1.6× high for Example 39. Highly distributed (2× than TBW). 27% bioavailability for Example 39 and <5% for Example 13 in rats was observed. High oral exposure in mice was observed for Example 39 than Example 13.

Following subcutaneous (SC) dose administration of example 13 in mice, the exposure was 32× higher than the oral route. It indicates that absorption from subcutaneous route results in significantly higher exposures than oral route of administration for example 13 in mice. Overall, the pharmacokinetic studies of representative compounds of Formula I indicates the compounds amenable for both parenteral and peroral route of administration for treating disease conditions.

In mice at 100 mg/kg post oral dose administration, Example 122b have demonstrated very good exposure ($AUC_{0-t}$, 10504 ng·h/mL) and C. (13787 ng/mL) with $T_{max}$ of 0.25 hr.

In rats at 30 mg/kg post oral administration Example 122b had achieved good exposure and with an absolute bioavailability of 21%. Total plasma systemic clearance (CL) following IV bolus administration for Example 122b was 1.3× higher than hepatic blood flow, similarly Volume of distribution ($V_{ss}$) was 2.5 higher than total body water indicating that the compound was e highly distributed.

In Vivo Efficacy of Example 13 on CT-26 Syngeneic Colon Cancer Mice Model

CT-26 syngeneic model of colon cancer in BALB/c is an established model and has been reported widely in literature for screening of compounds in efficacy studies for immune-oncology therapeutics.

CT-26 Cell line expansion and sub-culturing: CT26 (CT26·WT, ATCC® CRL-2638) is an N-nitroso-N-methylurethane-(NNMU) induced, undifferentiated colon carcinoma cell line derived from Mus musculus, mouse colon tissue. Cells were cultured using standard techniques in RPMI 1640 with 10% FBS and 1× penicillin—streptomycin solution at 37° C. with 5% $CO_2$ in a suitable incubator. Cell density was determined using a hemocytometer upon harvest and the cells were prepared in 100 μL of cold PBS in a microfuge tube and kept on ice until use for inoculations.

Mice: All animal studies were conducted in accordance with an Institutional Animal Care and Use Committee. 6- to 8-week-old Balb/c mice were typically housed in sterilized suspended standard, polysulfone cages, with stainless steel top grills having facilities for holding pelleted food and drinking water in polycarbonate bottles with stainless steel sipper tubes and environment enrichment objects in the vivarium for two weeks prior to tumor cell injection. The same conditions were maintained throughout the subsequent tumor engraftment and treatment evaluation.

Tumor engraftment: All animals were inoculated with $5\times10^5$/mouse in 100 μL subcutaneously in the lower right flank. Tumor growth was monitored twice a week from Day 4 onwards using a calibrated digital vernier caliper and the tumor volume calculated using the formula, tumor volume (mm3)=length×(width) 2/2. Once tumor volume reaches 100±50 $mm^3$ on Day 12, all animals were randomized into respective treatment groups as per study plan. See Table 1 for details regarding the setup and dosing of animals. Tumor volume at the time of randomization was 90 $mm^3$ There was no statistical significance in tumor volume at the time of treatment initiation. Post randomization, animals were treated with the test substance for 21 days. The average tumor volume/size in the treatment group allowed to reach up to 2500 $mm^3$, beyond this tumor size the animals to be sacrificed humanely as per general guidelines. The efficacy experimental design summarized in Table 10.

Formulation and administration: Formulations were prepared with the components listed in Table 11 every day and mixed well before dosing each time and administered orally. The anti PD-1 antibody was administered via the intraperitoneal route.

TABLE 10

Efficacy experimental design

| Group | Treatment | n | dose (mg/kg) | Route | Regimen | Duration |
|---|---|---|---|---|---|---|
| 1 | Vehicle | 10 | 10 ml/kg | PO | BID | Day 1 to Day 21 |
| 3 | PD-1 Antibody | 8 | 5 | IP | Every 3 days | Day 1 to Day 21 |
| 4 | Example 13 | 10 | 1 | PO | TID | Day 1 to Day 21 |
| 5 | Example 13 | 10 | 3 | PO | TID | Day 1 to Day 21 |
| 6 | Example 13 | 10 | 10 | PO | TID | Day 1 to Day 21 |
| 7 | Example 13 | 10 | 30 | PO | TID | Day 1 to Day 21 |

TID: Dosed three times in a day at 4 h interval (ex 9.00 am, 01.00 pm and 05.00 pm)
BID:] Dosed two times in a day at ~8 h interval (ex 9.00 am and 05.00 pm)
Example 13 and vehicle were dosed by oral route every day from Day 1 to Day 21.
Anti-mouse PD-1 antibody was dosed by IP route every three days

TABLE 11

Formulations used for the efficacy studies

| Treatment | Vehicle |
|---|---|
| Example 13 | 30% Gelucire 44/14 + 10% Solutol HS-15 + 30% Propylene Glycol in saline |
| Anti-mouse PD-1 Antibody (Bioxcel, USA) | PBS pH 7.4 |
| Vehicle | 30% Gelucire 44/14 + 10% Solutol HS-15 + 30% Propylene Glycol in saline |

The in vivo efficacy effect of Example-13 on Tumor volume is summarized in FIG. 1. Data is represented as Mean±SEM n=4-10, *$p<0.05$ Vs Vehicle, One-Way ANOVA followed by Dunnett's multiple comparison test. All animals injected with CT-26 increased tumor volume, vehicle treatment group from Day 11 onwards showed increased tumor volume compared to other treatment groups. EXAMPLE-13 treatment showed trend towards decrease in tumor volume from Day 11 onwards till the end of study period that is till Day 22. While the 1 mg/kg, PO, TID did not show significant change in tumor volume the 3 mg/kg, 10 mg/kg, and 30 mg/kg, PO, TID groups showed 35%, 35%, and 48% respective decrease in tumor volume by day 22. Significant decrease in tumor volume was observed on Day 18 and Day 22 compared to vehicle treatment. PD-1 antibody dosed at 5 mg/kg; IP (every 3 days) control treatment group showed trend towards decrease in tumor volume, 29% and 25% respectively, however not statistically significant compared to vehicle treatment.

Biomarker (Granzyme-B) Analysis in Tumour Samples from the Efficacy Studies

On Day 22, the animals from the efficacy study above were euthanized by overdose of gaseous anaesthesia and tumor samples were collected and their weights were recorded before evaluating for Granzyme-B by FACs analysis.

Figure 2:
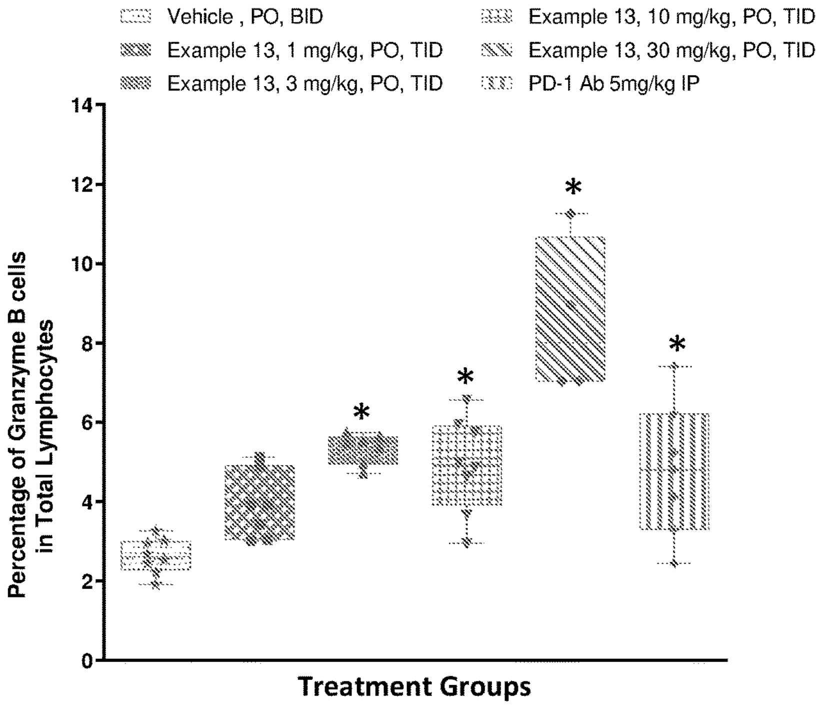
FIG. 2 depicts Tumor Granzyme B expression compared to vehicle treatment in accordance with an implementation of the present disclosure.

Approximately 100 mg of tissue samples were homogenized, and the single cell suspensions were fixed and permeabilized using Miltenyi Biotec and BD kit-based reagents before staining with anti-Granzyme-B antibodies. Cells were subjected to FACS analysis while using isotype controls to ensure the specific binding of antibody and unstained cells as a negative control. The result obtained were analyzed using Flow Jo software and represented in FIG. 2.

Example-13, 30 mg/kg TID treatment group showed significant increase in tumor Granzyme B expression as compared to vehicle treatment and anti-PD1 antibody treatment groups. Granzyme B is expressed in the granules of cytotoxic T lymphocytes and NK cells and is an important protein that is implicated in its ability to bring about apoptosis. Significant increase in Granzyme B expression in tumor tissue indicates the probable mechanism that inhibits tumor growth on treatment with the test compounds belonging to compounds of Formula (I) having dual adenosine 2a and 2b receptor functional antagonism

ADVANTAGES OF THE PRESENT INVENTION

The present disclosure provides a new class of heterocyclic compounds of Formula I its pharmaceutically acceptable salts, complexes, hydrates, solvates, tautomers, polymorphs, stereoisomers, racemates, pharmaceutically active derivatives thereof. The present disclosure provides a new class of heterocyclic compounds of Formula I for use as a medicament. The compounds of Formula I act as antagonists for adenosine receptors and particularly adenosine $A_{2a}R$ and $A_{2b}R$ receptors. The compounds of Formula I can be widely used in the treatment of proliferative disorders, diseases, condition, cancer or immune related diseases mediated by the adenosine receptors.

The compounds of the present disclosure also shown to restore the cytokine release (IL-2 and TNF-α) under adenosine agonist background in human PBMC indicates the confirmation of immune activation via adenosine $A_{2a}R$ and $A_{2b}R$ receptors functional antagonism.

The compounds of the present disclosure exhibit high degree of selectivity against hERG channel and may be devoid of cardio toxicity in animal and human The compounds of the present disclosure demonstrates desirable pharmacokinetic profile in rat and efficacious in CT-26 syngeneic colon cancer mice model thus confirming in vivo proof of principle in animal through adenosine $A_{2a}R$ and $A_{2b}R$ receptors functional antagonism.

The present disclosure also provides a pharmaceutical composition comprising the compounds of Formula I with additional therapeutic agents. The present disclosure further provides a schematic synthetic preparation process for the compounds of Formula I.

We claim:

1. A compound of Formula I

Formula I

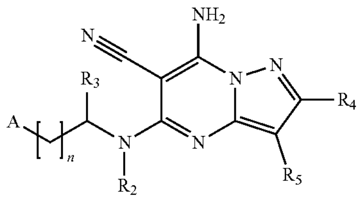

or its pharmaceutically acceptable salts, tautomers, stereoisomers, or racemates, wherein:

A is selected from

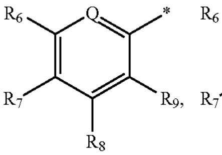
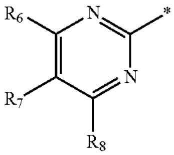
,
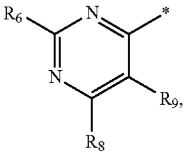
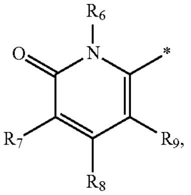
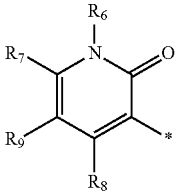
,
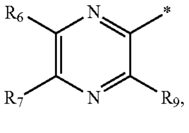
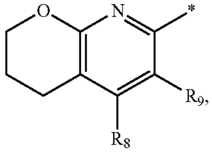
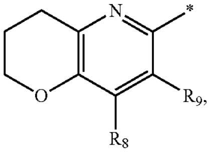
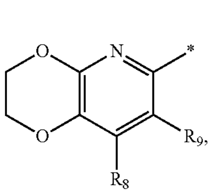
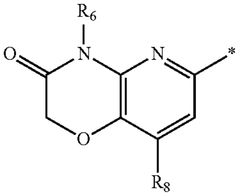
,
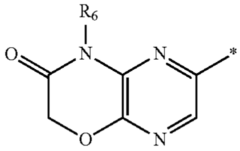
,
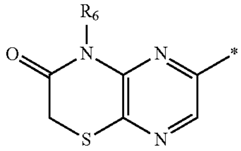
,
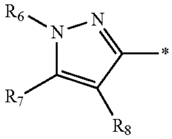
,
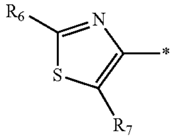
,
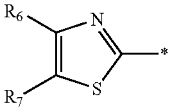
,
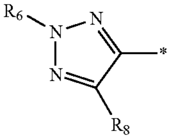
,
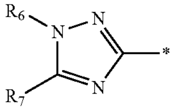

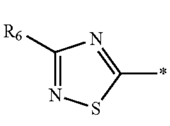
, and
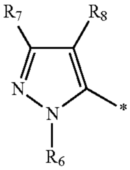
, wherein:

Q is N or $CR_1$;

$R_1$ is cyano, hydrogen, halogen, $C_{1-6}$ alkyl, or $C_{1-6}$ alkoxy;

$R_2$ is hydrogen or $C_{1-6}$ alkyl;

$R_3$ is hydrogen or $C_{1-6}$ alkyl;

$R_4$ and $R_5$ are independently hydrogen, halogen, cyano, $C_{1-6}$ alkyl, $C_{3-6}$ cycloalkyl, $C_{1-6}$ alkoxy, $C_{1-6}$ haloalkyl, or $C_{1-6}$ haloalkoxy, wherein $C_{1-6}$ alkyl is optionally substituted with one or more groups selected from $C_{3-6}$ cycloalkyl and $C_{1-6}$ alkoxy $R_6$ is hydrogen, $C_{1-6}$ alkyl, $C_{1-6}$ haloalkyl, $C_{1-6}$ alkoxy, $C_{1-6}$ alkylhydroxy, $C_{1-6}$ aminoalkyl, $C_{3-6}$ cycloalkyl, Y—CO—NH—$R_{13}$, —Y—Z, or $C_{1-10}$ heterocyclyl, wherein $C_{1-6}$ alkyl, $C_{1-6}$ alkoxy, $C_{3-6}$ cycloalkyl, $C_{1-6}$ haloalkyl, $C_{1-6}$ aminoalkyl, $C_{1-6}$ alkylhydroxy, or $C_{1-10}$ heterocyclyl is optionally substituted with one or more groups selected from halogen, hydroxyl, amine, $C_{1-6}$ alkoxy, $C_{3-6}$ cycloalkyl, $C_{1-6}$ alkylhydroxy, $C_{1-6}$ aminoalkyl, $C_{1-6}$ haloalkoxy, and $C_{1-10}$ heterocyclyl, wherein $C_{3-6}$ cycloalkyl or $C_{1-6}$ aminoalkyl is optionally further substituted with one or more groups independently selected from halogen, hydroxyl, $C_{1-6}$ alkylhydroxy, —C(O)$C_{1-6}$ alkyl, —C(O)$NH_2$, and —C(O)—$C_{1-6}$ alkylhydroxy;

Y is $C_{1-6}$ alkyl or $C_{3-6}$ cycloalkyl;

Z is —$SO_2NH_2$, —$SO_2CH_3$, —$SOCH_3$, —$SCH_3$, $CH_2$—NH—($C_{1-6}$ alkyl)-$SOCH_3$, —$CONH_2$, —CONH($C_{1-6}$ alkyl), —$SO_2$NH($C_{1-6}$ alkyl), CON($C_{1-6}$ alkyl)$_2$, or —NHCO($C_{1-6}$ alkyl);

$R_{13}$ is hydrogen, $C_{1-6}$ alkyl, or $C_{3-6}$ cycloalkyl;

$R_7$, $R_8$, $R_9$, and $R_{9a}$ are independently hydrogen, halogen, cyano, $C_{1-6}$ alkyl, $C_{3-6}$ cycloalkyl, or $C_{1-6}$ alkoxy and n is 0, 1, or 2.

2. The compound of claim 1, or its pharmaceutically acceptable salts, tautomers, stereoisomers, or racemates, or wherein the compound is selected from the group consisting of:

(1) 7-amino-2,3-dimethyl-5-{[1-(6-methylpyridin-2-yl)ethyl]amino}pyrazolo[1,5-a]pyrimidine-6-carbonitrile;
(2) 7-amino-2,3-dimethyl-5-{[(1S)-1-(6-methylpyridin-2-yl)ethyl]amino}pyrazolo[1,5-a]pyrimidine-6-carbonitrile;
(3) (R)-7-Amino-3-ethyl-2-methyl-5-((1-(pyridin-2-yl) ethyl) amino) pyrazolo[1,5-a]pyrimidine-6-carbonitrile;
(4) (S)-7-Amino-3-ethyl-2-methyl-5-((1-(pyridin-2-yl) ethyl) amino) pyrazolo[1,5-a]pyrimidine-6-carbonitrile;
(5) (S)-7-Amino-3-ethyl-2-methyl-5-((1-(6-methylpyridin-2-yl) ethyl) amino) pyrazolo [1,5-a]pyrimidine-6-carbonitrile;
(6) 7-amino-2,3-dimethyl-5-{[(6-methylpyridin-2-yl) methyl]amino}pyrazolo[1,5-a]pyrimidine-6-carbonitrile;
(7) 7-amino-5-{[(6-ethylpyridin-2-yl)methyl]amino}-2,3-dimethylpyrazolo[1,5-a]pyrimidine-6-carbonitrile;
(8) 7-amino-2,3-dimethyl-5-{methyl[(6-methylpyridin-2-yl)methyl]amino}pyrazolo[1,5-a]pyrimidine-6-carbonitrile;
(9) 7-amino-5-({[6-(2-hydroxypropan-2-yl)pyridin-2-yl]methyl}amino)-2,3-dimethylpyrazolo[1,5-a]pyrimidine-6-carbonitrile;
(10) 7-Amino-2,3-dimethyl-5-((2-(5-methylpyridin-2-yl) ethyl) amino) pyrazolo[1,5-a]pyrimidine-6-carbonitrile;
(11) 7-amino-5-((2-(5-fluoropyridin-2-yl)ethyl)amino)-2,3-dimethylpyrazolo[1,5-a]pyrimidine-6-carbonitrile;
(12) 7-amino-5-((2-(6-methoxypyridin-2-yl)ethyl) amino)-2,3-dimethylpyrazolo[1,5-a]pyrimidine-6-carbonitrile;
(13) 7-amino-5-((2-(6-methylpyridin-2-yl)ethyl)amino)-2,3-dimethylpyrazolo[1,5-a]pyrimidine-6-carbonitrile;
(14) 7-amino-2,3-dimethyl-5-{[1-(6-methylpyridin-2-yl) propan-2-yl]amino}pyrazolo[1,5-a]pyrimidine-6-carbonitrile;
(15) 7-amino-2,3-dimethyl-5-{[1-(6-methylpyridin-2-yl) propan-2-yl]amino}pyrazolo[1,5-a]pyrimidine-6-carbonitrile;
(16) 7-amino-5-({2-[6-(2-hydroxypropan-2-yl)pyridin-2-yl]ethyl}amino)-2,3-dimethylpyrazolo[1,5-a]pyrimidine-6-carbonitrile;
(17) 7-Amino-3-ethyl-2-methyl-5-((2-(6-methylpyridin-2-yl) ethyl) amino) pyrazolo[1,5-a]pyrimidine-6-carbonitrile;
(18) 7-Amino-3-ethyl-2-methyl-5-((2-(5-methylpyridin-2-yl) ethyl) amino) pyrazolo[1,5-a]pyrimidine-6-carbonitrile;
(19) 7-Amino-3-ethyl-5-((2-(5-methoxypyridin-2-yl) ethyl) amino)-2-methylpyrazolo [1,5-a]pyrimidine-6-carbonitrile;
(20) 7-Amino-3-ethyl-5-((2-(6-methoxypyridin-2-yl) ethyl) amino)-2-methylpyrazolo [1,5-a]pyrimidine-6-carbonitrile;
(21) 7-Amino-3-ethyl-5-((2-(5-fluoropyridin-2-yl) ethyl) amino)-2-methylpyrazolo[1,5-a]pyrimidine-6-carbonitrile;
(22) 7-Amino-3-ethyl-2-methyl-5-((1-(pyridin-2-yl) propan-2-yl) amino) pyrazolo[1,5-a]pyrimidine-6-carbonitrile;
(23) 7-Amino-3-ethyl-2-methyl-5-((1-(pyridin-2-yl) propan-2-yl) amino) pyrazolo[1,5-a]pyrimidine-6-carbonitrile;
(24) 7-Amino-3-ethyl-2-methyl-5-((1-(6-methylpyridin-2-yl) propan-2-yl) amino) pyrazolo[1,5-a]pyrimidine-6-carbonitrile;
(25) 7-amino-3-ethyl-5-({2-[6-(2-hydroxypropan-2-yl) pyridin-2-yl]ethyl}amino)-2-methylpyrazolo[1,5-a]pyrimidine-6-carbonitrile;
(26) 7-amino-3-(cyclopropylmethyl)-2-methyl-5-((2-(6-methylpyridin-2-yl)ethyl) amino) pyrazolo[1,5-a]pyrimidine-6-carbonitrile;
(27) 7-amino-3-(isopropylmethyl)-2-methyl-5-((2-(6-methylpyridin-2-yl)ethyl) amino) pyrazolo[1,5-a]pyrimidine-6-carbonitrile;
(28) 7-amino-3-(isopropyl)-2-methyl-5-((2-(6-methylpyridin-2-yl)ethyl) amino) pyrazolo[1,5-a]pyrimidine-6-carbonitrile;
(29) 7-amino-5-{[2-(1-ethyl-1H-pyrazol-3-yl)ethyl] amino}-2,3-dimethylpyrazolo[1,5-a]pyrimidine-6-carbonitrile;
(30) 7-amino-3-ethyl-5-{[2-(1-ethyl-1H-pyrazol-3-yl) ethyl]amino}-2-methylpyrazolo[1,5-a]pyrimidine-6-carbonitrile;
(31) 7-amino-5-({2-[1-(1-hydroxy-2-methylpropan-2-yl)-1H-pyrazol-3-yl]ethyl}amino)-2,3-dimethylpyrazolo [1,5-a]pyrimidine-6-carbonitrile;
(32) 7-amino-3-ethyl-5-((2-(1-(1-hydroxy-2-methylpropan-2-yl)-1H-pyrazol-3-yl) ethyl) amino)-2-methylpyrazolo[1,5-a]pyrimidine-6-carbonitrile;
(33) 7-amino-3-chloro-5-((2-(6-(hydroxymethyl) pyridin-2-yl) ethyl) amino)-2-methylpyrazolo[1,5-a]pyrimidine-6-carbonitrile;
(34) 7-amino-3-chloro-5-((2-(6-(1-(hydroxymethyl) cyclopropyl) pyridin-2-yl) ethyl) amino)-2-methylpyrazolo[1,5-a]pyrimidine-6-carbonitrile;
(35) 7-amino-3-chloro-5-((2-(1-(2-hydroxyethyl)-1H-pyrazol-3-yl) ethyl) amino)-2-methylpyrazolo[1,5-a] pyrimidine-6-carbonitrile;
(36) 7-amino-3-chloro-5-((2-(1-(1-hydroxy-2-methylpropan-2-yl)-1H-pyrazol-3-yl) ethyl) amino)-2-methylpyrazolo[1,5-a]pyrimidine-6-carbonitrile;

(37) 7-amino-3-chloro-5-((2-(1-(1-(hydroxymethyl) cyclopropyl)-1H-pyrazol-3-yl) ethyl) amino)-2-methylpyrazolo[1,5-a]pyrimidine-6-carbonitrile;

(38) 7-amino-3-chloro-5-((2-(6-(2-(hydroxymethyl) cyclopropyl) pyridin-2-yl) ethyl) amino)-2-methylpyrazolo[1,5-a]pyrimidine-6-carbonitrile;

(39) 7-amino-3-ethyl-5-((2-(1-(1-(hydroxymethyl) cyclopropyl)-1H-pyrazol-3-yl) ethyl) amino)-2-methylpyrazolo[1,5-a]pyrimidine-6-carbonitrile;

(40) amino-5-((2-(6-ethylpyridin-2-yl) ethyl) amino)-2,3-dimethylpyrazolo [1,5-a]pyrimidine-6-carbonitrile;

(41) 7-amino-5-((2-(3-fluoro-6-methylpyridin-2-yl) ethyl) amino)-2,3-dimethylpyrazolo[1,5-a]pyrimidine-6-carbonitrile;

(42) 7-amino-2-ethyl-3-methyl-5-((2-(6-methylpyridin-2-yl) ethyl) amino)pyrazolo[1,5-a]pyrimidine-6-carbonitrile;

(43) 7-amino-2-ethyl-5-((2-(6-(2-hydroxypropan-2-yl) pyridin-2-yl)ethyl)amino)-3-methylpyrazolo[1,5-a]pyrimidine-6-carbonitrile;

(44) 7-amino-5-((2-(6-(hydroxymethyl) pyridin-2-yl) ethyl) amino)-2,3-dimethylpyrazolo [1,5-a]pyrimidine-6-carbonitrile;

(45) 7-amino-3-ethyl-5-((2-(6-(hydroxymethyl) pyridin-2-yl) ethyl)amino)-2-methylpyrazolo[1,5-a]pyrimidine-6-carbonitrile;

(46) 7-amino-3-(cyclopropyl methyl)-5-((2-(6-(hydroxymethyl) pyridin-2-yl) ethyl)amino)-2-methylpyrazolo[1,5-a]pyrimidine-6-carbonitrile;

(47) 7-amino-2-cyclopropyl-5-((2-(6-(2-hydroxypropan-2-yl) pyridin-2-yl) ethyl)amino)-3-methylpyrazolo[1,5-a]pyrimidine-6-carbonitrile;

(48) 7-amino-2-(difluoromethyl)-3-ethyl-5-((2-(1-(1-hydroxy-2-methylpropan-2-yl)-1H-pyrazol-3-yl) ethyl) amino)pyrazolo[1,5-a]pyrimidine-6-carbonitrile;

(49) 7-amino-5-((2-(6-(1-(hydroxymethyl) cyclopropyl) pyridin-2-yl) ethyl)amino)-2,3-dimethylpyrazolo[1,5-a]pyrimidine-6-carbonitrile;

(50) 7-amino-3-ethyl-5-((2-(6-(1-(hydroxymethyl) cyclopropyl) pyridin-2-yl) ethyl)amino)-2-methylpyrazolo [1,5-a]pyrimidine-6-carbonitrile;

(51) 7-amino-5-((2-(6-(2-(hydroxymethyl) cyclopropyl) pyridin-2-yl) ethyl)amino)-2,3-dimethylpyrazolo[1,5-a]pyrimidine-6-carbonitrile;

(52) 7-amino-3-ethyl-5-((2-(6-(1-hydroxy-2-methylpropan-2-yl) pyridin-2-yl) ethyl) amino)-2-methylpyrazolo[1,5-a]pyrimidine-6-carbonitrile;

(53) 7-amino-5-((2-(6-(1-hydroxy-2-methylpropan-2-yl) pyridin-2-yl) ethyl) amino)-2,3-dimethylpyrazolo[1,5-a]pyrimidine-6-carbonitrile;

(54) 7-amino-3-ethyl-5-((2-(1-(2-hydroxyethyl)-1H-pyrazol-3-yl) ethyl) amino)-2-methylpyrazolo[1,5-a] pyrimidine-6-carbonitrile;

(55) 7-amino-5-((2-(1-(1-(hydroxymethyl) cyclopropyl)-1H-pyrazol-3-yl) ethyl) amino)-2,3-dimethylpyrazolo [1,5-a]pyrimidine-6-carbonitrile;

(56) 7-amino-2-(difluoro methyl)-3-ethyl-5-((2-(6-(hydroxymethyl) pyridin-2-yl) ethyl) amino) pyrazolo[1,5-a]pyrimidine-6-carbonitrile;

(57) 7-amino-5-(((1-(1-hydroxy-2-methylpropan-2-yl)-1H-pyrazol-3-yl) methyl) amino)-2,3-dimethylpyrazolo[1,5-a]pyrimidine-6-carbonitrile;

(58) 7-amino-2-(difluoro methyl)-3-ethyl-5-((2-(1-(1-(hydroxymethyl) cyclopropyl)-1H-pyrazol-3-yl) ethyl) amino) pyrazolo[1,5-a]pyrimidine-6-carbonitrile;

(59) 7-amino-2-(difluoro methyl)-3-ethyl-5-((2-(6-(2-(hydroxymethyl) cyclopropyl) pyridin-2-yl) ethyl) amino) pyrazolo[1,5-a]pyrimidine-6-carbonitrile;

(60) 7-amino-3-ethyl-5-((2-(6-(2-(hydroxymethyl) cyclopropyl) pyridin-2-yl) ethyl) amino)-2-methylpyrazolo [1,5-a]pyrimidine-6-carbonitrile;

(61) 7-amino-3-chloro-5-((2-(4-(1-(hydroxymethyl) cyclopropyl) thiazol-2-yl) ethyl) amino)-2-methylpyrazolo[1,5-a]pyrimidine-6-carbonitrile;

(62) 7-amino-3-ethyl-5-((2-(4-fluoro-1-(1-hydroxy-2-methylpropan-2-yl)-1H-pyrazol-3-yl) ethyl) amino)-2-methylpyrazolo[1,5-a]pyrimidine-6-carbonitrile;

(63) 7-amino-3-ethyl-5-((2-(1-((1-(hydroxymethyl) cyclopropyl) methyl)-1H-pyrazol-3-yl) ethyl) amino)-2-methylpyrazolo[1,5-a]pyrimidine-6-carbonitrile;

(64) 7-amino-3-chloro-5-((2-(6-(1,1-difluoro-2-hydroxyethyl) pyridin-2-yl) ethyl) amino)-2-methylpyrazolo[1,5-a]pyrimidine-6-carbonitrile;

(65) 7-amino-3-chloro-5-((2-(6-(1-hydroxy-2-methylpropan-2-yl) pyridin-2-yl) ethyl) amino)-2-methylpyrazolo[1,5-a]pyrimidine-6-carbonitrile;

(66) 7-amino-3-ethyl-5-((2-(4-(1-(hydroxymethyl) cyclopropyl) thiazol-2-yl) ethyl) amino)-2-methylpyrazolo [1,5-a]pyrimidine-6-carbonitrile;

(67) 7-amino-3-chloro-5-((2-(1-(2-(hydroxymethyl) cyclobutyl)-1H-pyrazol-3-yl) ethyl) amino)-2-methylpyrazolo[1,5-a]pyrimidine-6-carbonitrile;

(68) 7-amino-5-((2-(1-(1-(amino methyl) cyclopropyl)-1H-pyrazol-3-yl) ethyl) amino)-3-chloro-2-methylpyrazolo[1,5-a]pyrimidine-6-carbonitrile;

(69) 7-amino-3-bromo-5-((2-(1-(1-(hydroxymethyl) cyclopropyl)-1H-pyrazol-3-yl) ethyl) amino)-2-methylpyrazolo[1,5-a]pyrimidine-6-carbonitrile;

(70) 7-amino-3-chloro-5-((2-(1-ethyl-2-oxo-1,2-dihydropyridin-3-yl) ethyl) amino)-2-methylpyrazolo[1,5-a] pyrimidine-6-carbonitrile;

(71) 7-amino-3-ethyl-5-((2-(1-(1-(hydroxymethyl) cyclopropyl)-1H-pyrazol-3-yl) ethyl) amino) pyrazolo[1,5-a]pyrimidine-6-carbonitrile;

(72) 7-amino-3-bromo-5-((2-(6-(hydroxymethyl) pyridine-2-yl) ethyl) amino)-2-methylpyrazolo[1,5-a]pyrimidine-6-carbonitrile;

(73) 7-amino-3-chloro-5-((2-(1-(1-(hydroxymethyl) cyclopropyl)-1H-pyrazol-4-yl) ethyl) amino)-2-methylpyrazolo[1,5-a]pyrimidine-6-carbonitrile;

(74) 7-amino-3-(cyclopropyl methyl)-5-((2-(1-(1-(hydroxymethyl) cyclopropyl)-1H-pyrazol-3-yl) ethyl) amino)-2-methylpyrazolo[1,5-a]pyrimidine-6-carbonitrile;

(75) 7-amino-3-chloro-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile;

(76) 7-amino-3-ethyl-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile;

(77) N-((1-(3-(2-((7-amino-3-chloro-6-cyano-2-methylpyrazolo[1,5-a]pyrimidin-5-yl) amino) ethyl)-1H-pyrazol-1-yl) cyclopropyl) methyl) acetamide;

(78) (+)-7-amino-3-ethyl-5-((2-(1-(2-(hydroxymethyl)cyclobutyl)-1H-pyrazol-3-yl)ethyl)amino)-2-methylpyrazolo[1,5-a]pyrimidine-6-carbonitrile;

(79) (−)-7-amino-3-ethyl-5-((2-(1-(2-(hydroxymethyl)cyclobutyl)-1H-pyrazol-3-yl)ethyl) amino)-2-methylpyrazolo[1,5-a]pyrimidine-6-carbonitrile;

(80) 7-amino-3-ethyl-5-((2-(1-(1-(hydroxymethyl) cyclopropyl)-5-methyl-1H-pyrazol-3-yl) ethyl) amino) pyrazolo[1,5-a]pyrimidine-6-carbonitrile;

(81) 7-amino-3-ethyl-5-((2-(1-(1-hydroxypropan-2-yl)-1H-pyrazol-3-yl) ethyl) amino)-2-methylpyrazolo[1,5-a]pyrimidine-6-carbonitrile;

(82) (+−)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile;

(83) (+)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile;

(84) (−)-7-amino-3-chloro-5-((2-(1-((3-hydroxycyclobutyl) methyl)-1H-pyrazol-3-yl) ethyl) amino)-2-methylpyrazolo[1,5-a]pyrimidine-6-carbonitrile (83b);

(85) 7-amino-3-ethyl-5-((2-(1-((3-hydroxycyclobutyl) methyl)-1H-pyrazol-3-yl) ethyl) amino)-2-methylpyrazolo[1,5-a]pyrimidine-6-carbonitrile;

(86) 7-amino-5-((2-(1-(1-(hydroxy methyl) cyclopropyl)-5-methyl-1H-pyrazol-3-yl) ethyl) amino)-2,3-dimethylpyrazolo[1,5-a]pyrimidine-6-carbonitrile;

(87) 7-amino-3-chloro-2-methyl-5-((2-(1-methyl-2-oxo-1,2-dihydropyridin 3-yl) ethyl) amino) pyrazolo[1,5-a]pyrimidine-6-carbonitrile;

(88) 7-amino-3-ethyl-2-methyl-5-((2-(1-methyl-2-oxo-1,2-dihydropyridin-3-yl) ethyl) amino) pyrazolo[1,5-a]pyrimidine-6-carbonitrile;

(89) 7-amino-3-bromo-5-((2-(1-(1-(hydroxymethyl) cyclopropyl)-5-methyl-1H-pyrazol-3-yl) ethyl) amino)-2-methylpyrazolo[1,5-a]pyrimidine-6-carbonitrile;

(90) 7-amino-3-chloro-5-((2-(6-(((2-hydroxyethyl) amino) methyl) pyridin-2-yl) ethyl) amino)-2-methylpyrazolo[1,5-a]pyrimidine-6-carbonitrile;

(91) 7-amino-3-ethyl-5-((2-(5-fluoro-6-(hydroxymethyl) pyridine-2-yl) ethyl) amino)-2-methylpyrazolo[1,5-a]pyrimidine-6-carbonitrile;

(92) 7-amino-3-chloro-5-((2-(1-(2-methoxyethyl)-2-oxo-1,2-dihydropyridin-3-yl) ethyl) amino)-2-methylpyrazolo[1,5-a]pyrimidine-6-carbonitrile;

(93) 7-amino-3-chloro-5-((2-(1-(2-hydroxyethyl)-2-oxo-1,2-dihydropyridin-3-yl) ethyl) amino)-2-methylpyrazolo[1,5-a]pyrimidine-6-carbonitrile;

(94) 7-amino-5-((2-(1-(1-(hydroxymethyl) cyclopropyl)-1H-pyrazol-3-yl) ethyl) amino)-2-methyl-3-(trifluoromethyl) pyrazolo[1,5-a]pyrimidine-6-carbonitrile;

(95) 7-amino-5-((2-(1-(2-(amino methyl) cyclobutyl)-1H-pyrazol-3-yl) ethyl) amino)-3-chloro-2-methylpyrazolo [1,5-a]pyrimidine-6-carbonitrile;

(96) 7-amino-3-ethyl-5-((2-(6-(((2-methoxyethyl) amino) methyl) pyridine-2-yl) ethyl) amino)-2-methylpyrazolo [1,5-a]pyrimidine-6-carbonitrile;

(97) 7-amino-3-ethyl-5-((2-(6-(((2-hydroxyethyl) amino) methyl) pyridine-2-yl) ethyl) amino)-2-methylpyrazolo [1,5-a]pyrimidine-6-carbonitrile;

(98) 7-amino-3-chloro-5-((2-(1-(1-(((2-hydroxyethyl) amino) methyl) cyclopropyl)-1H-pyrazol-3-yl) ethyl) amino)-2-methylpyrazolo[1,5-a]pyrimidine-6-carbonitrile;

(99) N-((1-(3-(2-((7-amino-3-chloro-6-cyano-2-methylpyrazolo[1,5-a]pyrimidin-5-yl) amino) ethyl)-1H-pyrazol-1-yl) cyclopropyl) methyl)-3-hydroxypropanamide;

(100) 7-amino-3-ethyl-5-((2-(6-(1-hydroxyethyl) pyridine-2-yl) ethyl) amino)-2-methylpyrazolo[1,5-a]pyrimidine-6-carbonitrile;

(101) 7-amino-3-cyclopropyl-5-((2-(1-(1-(hydroxymethyl) cyclopropyl)-1H-pyrazol-3-yl) ethyl) amino)-2-methylpyrazolo[1,5-a]pyrimidine-6-carbonitrile;

(102) 7-amino-2-(difluoro methyl)-3-ethyl-5-((2-(1-(2-(hydroxymethyl) cyclobutyl)-1H-pyrazol-3-yl) ethyl) amino) pyrazolo[1,5-a]pyrimidine-6-carbonitrile;

(103) (+−)-7-amino-5-((2-(1-(2-(hydroxymethyl) cyclobutyl)-1H-pyrazol-3-yl)ethyl)amino)-2,3-dimethylpyrazolo[1,5-a]pyrimidine-6-carbonitrile;

(104a) (+)-7-amino-5-((2-(1-(2-(hydroxymethyl) cyclobutyl)-1H-pyrazol-3-yl)ethyl)amino)-2,3-dimethylpyrazolo[1,5-a]pyrimidine-6-carbonitrile;

(104b) (−)-7-amino-5-((2-(1-(2-(hydroxymethyl)cyclobutyl)-1H-pyrazol-3-yl)ethyl)amino)-2,3-dimethylpyrazolo[1,5-a]pyrimidine-6-carbonitrile (104b);

(105) 7-amino-5-((2-(6-(((2-hydroxyethyl) amino) methyl) pyridin-2-yl) ethyl) amino)-2,3-dimethylpyrazolo[1,5-a]pyrimidine-6-carbonitrile;

(106) 7-amino-3-ethyl-5-((2-(1-(1-(((2-hydroxyethyl) amino) methyl) cyclopropyl)-1H-pyrazol-3-yl) ethyl) amino)-2-methylpyrazolo[1,5-a]pyrimidine-6-carbonitrile;

(107) 7-amino-3-ethyl-5-((2-(1-(2-methoxyethyl)-2-oxo-1,2-dihydropyridin-3-yl) ethyl) amino)-2-methylpyrazolo[1,5-a]pyrimidine-6-carbonitrile;

(108) 7-amino-3-ethyl-5-((2-(1-(2-hydroxyethyl)-2-oxo-1,2-dihydropyridin-3-yl) ethyl) amino)-2-methylpyrazolo[1,5-a]pyrimidine-6-carbonitrile;

(109) 7-amino-5-((2-(1-(2-(amino methyl) cyclobutyl)-1H-pyrazol-3-yl) ethyl) amino)-3-ethyl-2-methylpyrazolo[1,5-a]pyrimidine-6-carbonitrile;

(110) 7-amino-3-ethyl-5-((2-(1-(3-hydroxypropyl)-1H-pyrazol-5-yl) ethyl) amino)-2-methylpyrazolo[1,5-a] pyrimidine-6-carbonitrile;

(111) 7-amino-3-ethyl-5-((2-(1-(3-hydroxypropyl)-1H-pyrazol-3-yl) ethyl) amino)-2-methylpyrazolo[1,5-a] pyrimidine-6-carbonitrile;

(112) 7-amino-3-chloro-5-((2-(1-(1-(2-hydroxyethyl) cyclopropyl)-1H-pyrazol-3-yl) ethyl) amino)-2-methylpyrazolo[1,5-a]pyrimidine-6-carbonitrile;

(113) 7-amino-3-ethyl-5-((2-(1-(3-hydroxypropyl)-2-oxo-1,2-dihydropyridin-3-yl) ethyl) amino)-2-methylpyrazolo[1,5-a]pyrimidine-6-carbonitrile;

(114) 7-amino-3-chloro-5-((2-(1-(2-(hydroxymethyl) cyclopentyl)-1H-pyrazol-3-yl) ethyl) amino)-2-methylpyrazolo[1,5-a]pyrimidine-6-carbonitrile;

(115) 7-amino-3-ethyl-5-((2-(1-(2-(hydroxymethyl) cyclopentyl)-1H-pyrazol-3-yl) ethyl) amino)-2-methylpyrazolo[1,5-a]pyrimidine-6-carbonitrile;

(116) 7-amino-3-(cyclopropyl methyl)-5-((2-(1-(2-(hydroxymethyl) cyclobutyl)-1H-pyrazol-3-yl) ethyl) amino)-2-methylpyrazolo[1,5-a]pyrimidine-6-carbonitrile;

(117) 7-amino-3-chloro-5-((2-(1-(2-(((2-hydroxyethyl) amino) methyl) cyclobutyl)-1H-pyrazol-3-yl) ethyl) amino)-2-methylpyrazolo[1,5-a]pyrimidine-6-carbonitrile;

(118) 7-amino-5-((2-(1-(2-(amino methyl) cyclopentyl)-1H-pyrazol-3-yl) ethyl) amino)-3-chloro-2-methylpyrazolo[1,5-a]pyrimidine-6-carbonitrile;

(119) 7-amino-3-chloro-2-methyl-5-((2-(6-methylpyridin-2-yl) ethyl) amino) pyrazolo[1,5-a]pyrimidine-6-carbonitrile;

(120) 7-amino-3-chloro-5-((2-(6-ethylpyridin-2-yl) ethyl) amino)-2-methylpyrazolo[1,5-a]pyrimidine-6-carbonitrile;

(121) (+−)-7-amino-3-ethyl-5-((2-(1-(4-(hydroxymethyl) tetrahydrofuran-3-yl)-1H-pyrazol-3-yl)ethyl)amino)-2-methyl pyrazolo[1,5-a]pyrimidine-6-carbonitrile;

(122a) (+)-7-amino-3-ethyl-5-((2-(1-(4-(hydroxy methyl) tetrahydrofuran-3-yl)-1H-pyrazol-3-yl)ethyl)amino)-2-methyl pyrazolo[1,5-a]pyrimidine-6-carbonitrile;

(122b) (−)-7-amino-3-ethyl-5-((2-(1-(4-(hydroxy methyl) tetrahydrofuran-3-yl)-1H-pyrazol-3-yl)ethyl)amino)-2-methyl pyrazolo[1,5-a]pyrimidine-6-carbonitrile;

(123) (−)-7-amino-3-ethyl-5-((2-(1-(4-(hydroxy methyl) tetrahydrofuran-3-yl)-1H-pyrazol-3-yl)ethyl)amino)-2-methyl pyrazolo[1,5-a]pyrimidine-6-carbonitrile;

(124) 7-amino-3-ethyl-5-((2-(1-(3-(hydroxymethyl) cyclobutyl)-1H-pyrazol-3-yl) ethyl) amino)-2-methylpyrazolo[1,5-a]pyrimidine-6-carbonitrile;

(125) 7-amino-3-ethyl-5-((2-(1-(1-(2-hydroxyethyl) cyclopropyl)-1H-pyrazol-3-yl) ethyl) amino)-2-methylpyrazolo[1,5-a]pyrimidine-6-carbonitrile;

(126) 7-amino-5-((2-(1-(2-aminoethyl)-2-oxo-1,2-dihydropyridin-3-yl) ethyl) amino)-3-ethyl-2-methylpyrazolo[1,5-a]pyrimidine-6-carbonitrile;

(127) 7-amino-3-chloro-5-((2-(1-(4-(hydroxymethyl) tetrahydrofuran-3-yl)-1H-pyrazol-3-yl) ethyl) amino)-2-methylpyrazolo[1,5-a]pyrimidine-6-carbonitrile;

(128) 7-amino-3-ethyl-5-((2-(1-((3-hydroxycyclobutyl) methyl)-2-oxo-1,2-dihydropyridin-3-yl) ethyl) amino)-2-methylpyrazolo[1,5-a]pyrimidine-6-carbonitrile;

(129) 7-amino-5-((2-(1-(3-aminopropyl)-2-oxo-1,2-dihydropyridin-3-yl) ethyl) amino)-3-chloro-2-methylpyrazolo[1,5-a]pyrimidine-6-carbonitrile;

(130) 7-amino-3-bromo-5-((2-(1-(2-(hydroxymethyl) cyclobutyl)-1H-pyrazol-3-yl) ethyl) amino)-2-methylpyrazolo[1,5-a]pyrimidine-6-carbonitrile;

(131) 7-amino-2-(difluoromethyl)-3-ethyl-5-((2-(1-(2-hydroxyethyl)-2-oxo-1,2-dihydropyridin-3-yl) ethyl) amino) pyrazolo[1,5-a]pyrimidine-6-carbonitrile;

(132) (+−)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile;

(133a) (+)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile;

(133b) (−)-7-amino-5-((2-(1-(4-(hydroxymethyl) tetrahydrofuran-3-yl)-1H-pyrazol-3-yl) ethyl) amino)-2,3-dimethylpyrazolo[1,5-a]pyrimidine-6-carbonitrile;

(134) 2-(((2-(3-(2-((7-amino-6-cyano-3-ethyl-2-methylpyrazolo[1,5-a]pyrimidin-5-yl) amino) ethyl)-1H-pyrazol-1-yl) cyclobutyl) methyl) amino) acetamide;

(135) 7-amino-3-ethyl-2-methyl-5-((2-(6-(2,2,2-trifluoro-1-hydroxyethyl) pyridine-2-yl) ethyl) amino) pyrazolo [1,5-a]pyrimidine-6 carbonitrile;

(136) 7-amino-5-((2-(1-(3-aminopropyl)-2-oxo-1,2-dihydropyridin-3-yl) ethyl) amino)-3-ethyl-2-methylpyrazolo[1,5-a]pyrimidine-6-carbonitrile;

(137) 7-amino-3-(cyclo butyl methyl)-5-((2-(1-(1-(hydroxymethyl) cyclopropyl)-1H-pyrazol-3-yl) ethyl) amino)-2-methylpyrazolo[1,5-a]pyrimidine-6-carbonitrile;

(138) 7-amino-5-((2-(1-(3-hydroxypropyl)-2-oxo-1,2-dihydropyridin-3-yl) ethyl) amino)-2,3-dimethylpyrazolo[1,5-a]pyrimidine-6-carbonitrile;

(139) 7-amino-3-ethyl-5-((2-(6-(2-hydroxyethyl) pyridine-2-yl) ethyl) amino)-2-methylpyrazolo[1,5-a]pyrimidine-6-carbonitrile;

(140) 7-amino-2,3-dimethyl-5-((2-(6-methylpyrazin-2-yl) ethyl) amino) pyrazolo[1,5-a]pyrimidine-6-carbonitrile;

(141) 7-amino-5-((2-(1-(3-aminopropyl)-2-oxo-1,2-dihydropyridin-3-yl) ethyl) amino)-2,3-dimethylpyrazolo [1,5-a]pyrimidine-6-carbonitrile;

(142) 7-amino-3-ethyl-2-methyl-5-((2-(1-(2-(methylthio) ethyl)-2-oxo-1,2-dihydropyridin-3-yl) ethyl) amino) pyrazolo[1,5-a]pyrimidine-6-carbonitrile;

(143) (+−)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile;

(144a) (+)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile;

(144b) (−)7-amino-3-ethyl-2-methyl-5-((2-(1-(2-(methyl sulfinyl) ethyl)-2-oxo-1,2-dihydropyridin-3-yl) ethyl) amino) pyrazolo[1,5-a]pyrimidine-6-carbonitrile;

(145) N-(3-(3-(2-((7-amino-6-cyano-3-ethyl-2-methylpyrazolo[1,5-a]pyrimidin-5-yl) amino) ethyl)-2-oxopyridin-1(2H)-yl) propyl) acetamide;

(146) 7-amino-5-((2-(1-(1-(amino methyl) cyclopropyl)-1H-pyrazol-3-yl) ethyl) amino)-3-ethyl-2-methylpyrazolo[1,5-a]pyrimidine-6-carbonitrile;

(147) N-((1-(3-(2-((7-amino-6-cyano-3-ethyl-2-methylpyrazolo[1,5-a]pyrimidin-5-yl) amino) ethyl)-1H-pyrazol-1-yl) cyclopropyl) methyl) acetamide;

(148) 7-amino-5-((2-(1-(1-(2-aminoethyl) cyclopropyl)-1H-pyrazol-3-yl) ethyl) amino)-3-ethyl-2-methylpyrazolo[1,5-a]pyrimidine-6-carbonitrile;

(149) N-(2-(1-(3-(2-((7-amino-6-cyano-3-ethyl-2-methylpyrazolo[1,5-a]pyrimidin-5-yl) amino) ethyl)-1H-pyrazol-1-yl) cyclopropyl) ethyl) acetamide;

(150) 7-amino-3-ethyl-5-((2-(6-(2-hydroxyethoxy) pyridine-2-yl) ethyl) amino)-2-methylpyrazolo[1,5-a]pyrimidine-6-carbonitrile;

(151) 7-amino-5-((2-(1-(1-(2-aminoethyl) cyclopropyl)-1H-pyrazol-3-yl) ethyl) amino)-3-chloro-2-methylpyrazolo[1,5-a]pyrimidine-6-carbonitrile;

(152) 7-amino-5-((2-(6-(2-hydroxyethyl) pyridine-2-yl) ethyl) amino)-2,3-dimethylpyrazolo[1,5-a]pyrimidine-6-carbonitrile;

(153) 7-amino-3-ethyl-2-methyl-5-((2-(1-(3-(methylthio) propyl)-2-oxo-1,2-dihydropyridin-3-yl) ethyl) amino) pyrazolo[1,5-a]pyrimidine-6-carbonitrile;

(154a) (−)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a]pyrimidine-6-carbonitrile;

(154b) (+)-7-amino-3-ethyl-2-methyl-5-((2-(1-(3-(methyl sulfinyl) propyl)-2-oxo-1,2-dihydropyridin-3-yl) ethyl) amino) pyrazolo[1,5-a]pyrimidine-6-carbonitrile;

(155) 7-amino-3-ethyl-5-((2-(6-(3-hydroxypropyl) pyridin-2-yl) ethyl) amino)-2-methylpyrazolo[1,5-a]pyrimidine-6-carbonitrile;

(156) 7-amino-5-((2-(1-(3-hydroxypropyl)-2-oxo-1,2-dihydropyridin-3-yl) ethyl) amino)-2-methyl-3-propylpyrazolo[1,5-a]pyrimidine-6-carbonitrile;

(157) 7-amino-5-((2-(6-(hydroxymethyl) pyridine-2-yl) ethyl) amino)-2-methyl-3-propylpyrazolo[1,5-a]pyrimidine-6-carbonitrile;

(158) 7-amino-5-((2-(1-(1-(hydroxymethyl) cyclopropyl)-1H-pyrazol-3-yl) ethyl) amino)-2-methyl-3-propylpyrazolo[1,5-a]pyrimidine-6-carbonitrile;

(159a) (+)-7-amino-3-ethyl-5-((2-(6-(1-hydroxyethyl) pyridin-2-yl) ethyl) amino)-2-methylpyrazolo[1,5-a] pyrimidine-6-carbonitrile;

(159b) (−)-7-amino-3-ethyl-5-((2-(6-(1-hydroxyethyl) pyridine-2-yl) ethyl) amino)-2-methylpyrazolo[1,5-a] pyrimidine-6-carbonitrile;

(160a) (+) 7-amino-5-((2-(1-(4-(hydroxymethyl) tetrahydrofuran-3-yl)-1H-pyrazol-3-yl) ethyl) amino)-2-methyl-3-propylpyrazolo[1,5-a]pyrimidine-6-carbonitrile;

(160b) (−) 7-amino-5-((2-(1-(4-(hydroxymethyl) tetrahydrofuran-3-yl)-1H-pyrazol-3-yl) ethyl) amino)-2-methyl-3-propylpyrazolo[1,5-a]pyrimidine-6-carbonitrile;

(161) 7-amino-3-ethyl-2-methyl-5-((2-(1-(3-(methylthio) propyl)-1H-pyrazol-3-yl) ethyl) amino) pyrazolo[1,5-a]pyrimidine-6-carbonitrile;

(162a) (−)-7-amino-3-ethyl-2-methyl-5-((2-(1-(3-(methyl sulfinyl) propyl)-1H-pyrazol-3-yl) ethyl) amino) pyrazolo[1,5-a]pyrimidine-6-carbonitrile;

(162b) (+)-7-amino-3-ethyl-2-methyl-5-((2-(1-(3-(methylsulfinyl)propyl)-1H-pyrazol-3-yl)ethyl)amino)pyrazolo[1,5-a]pyrimidine-6-carbonitrile;

(163a) (−)-7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a]pyrimidine-6-carbonitrile;

(163b) (+)-7-amino-3-ethyl-2-methyl-5-((2-(1-(1-(((2-(methyl sulfinyl) ethyl) amino) methyl) cyclopropyl)-1H-pyrazol-3-yl) ethyl) amino) pyrazolo[1,5-a]pyrimidine-6-carbonitrile;

(164) 7-amino-2-methyl-5-((2-(6-methylpyridin-2-yl) ethyl) amino)-3-propylpyrazolo[1,5-a]pyrimidine-6-carbonitrile;

(165a) (+)-7-amino-5-((2-(1-(2-(hydroxymethyl) cyclobutyl)-1H-pyrazol-3-yl) ethyl) amino)-2-methyl-3-propylpyrazolo[1,5-a]pyrimidine-6-carbonitrile;

(165b) (−)-7-amino-5-((2-(1-(2-(hydroxymethyl) cyclobutyl)-1H-pyrazol-3-yl) ethyl) amino)-2-methyl-3-propylpyrazolo[1,5-a]pyrimidine-6-carbonitrile;

(166) (R)-7-amino-3-ethyl-2-methyl-5-((2-(6-(((tetrahydrofuran-3-yl) oxy) methyl) pyridine-2-yl) ethyl) amino) pyrazolo[1,5-a]pyrimidine-6-carbonitrile;

(167) (−)-7-amino-3-ethyl-5-((2-(1-(4-(hydroxymethyl) tetrahydrofuran-3-yl)-5-methyl-1H-pyrazol-3-yl) ethyl) amino)-2-methylpyrazolo[1,5-a]pyrimidine-6-carbonitrile; and (168) (+)-7-amino-3-ethyl-5-((2-(1-(4-(hydroxy methyl) tetrahydrofuran-3-yl)-1H-pyrazol-3-yl) ethyl) amino)-2-methyl pyrazolo[1,5-a]pyrimidine-6-carbonitrile.

3. A medicament comprising a compound of claim 1.

4. The compound of claim 1, its pharmaceutically acceptable salts, tautomers, stereoisomers, or racemates, wherein the compound is an antagonist of adenosine 2a receptor ($A_{2a}R$), adenosine 2b receptor ($A_{2b}R$) or a combination of adenosine 2a receptor ($A_{2a}R$) and adenosine 2b receptor ($A_{2b}R$).

5. A method for preparing a compounds of Formula I of claim 1, its pharmaceutically acceptable salts, tautomers, stereoisomers, or racemates, the method comprising reacting a compound of Formula (A), and a compound of Formula (B) in the presence of a base to obtain the compound of Formula I,

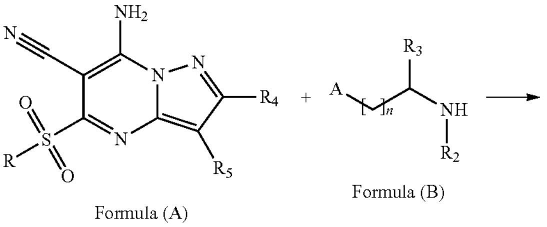

Formula (A) Formula (B)

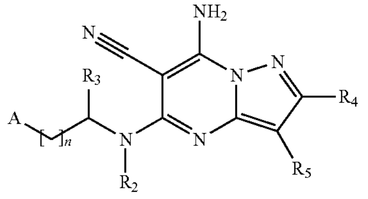

Formula I wherein:

R is $C_{1-6}$ alkyl, $C_{3-6}$ cycloalkyl, $C_{5-10}$ aryl, $C_{2-10}$ heteroaryl, or $C_{1-10}$ heterocyclyl; and $R_2$, $R_3$, $R_4$, and $R_5$ are the same as defined in claim 1.

6. The method of claim 5, wherein the base is triethylamine, diisopropylethylamine, pyridine, sodium carbonate, potassium carbonate, sodium hydroxide, potassium tertiary-butoxide potassium tertiarybutoxide, sodium hydride, lithium bis(trimethylsilyl)amide (LiHAMIDS), N-diisopropylethylamine, or combinations thereof.

7. The method of claim 5, wherein the method is carried out in the presence of a solvent selected from isopropanol, methanol, n-butanol, dichloromethane, tetrahydrofuran, dimethylformaide, n-methylpyrrolidone, Dimethyl sulfoxide, water, dioxane, acetonitrile, or combinations thereof.

8. A pharmaceutical composition comprising a compound of Formula I of claim 1, and one or more additional therapeutic agent.

9. The composition of claim 8, wherein the one or more additional therapeutic agent is chemotherapeutic agent or immune checkpoint inhibitors, wherein the chemotherapeutic agent is phosphoinositide 3-kinase inhibitor (PI3K) inhibitor, tyrosine kinase inhibitor, signal transducer and activator of transcription 3 (Stat-3) inhibitor, topoisomerase inhibitors, Protein kinase B (AKT) inhibitor, c-Jun N-terminal kinase (JNK1/K2) inhibitors, hypoxia-inducible factor 1 alpha (HIF-1a) inhibitor, extracellular signal-regulated kinase (ERK) inhibitor, poly ADP ribose polymerase-1 ((PARP-1) inhibitor, cisplatin, or oxaplatin, and wherein the immune checkpoint inhibitor is programmed death-1 (PD-1) inhibitor, programmed death-ligand i (PD-L1) inhibitor, anti-PD1 antibody, anti-PD-L1 antibody, cytotoxic T-lymphocyte-associated protein 4 (CTLA4)inhibitor, anti-CTLA4 antibody, T cell immunoglobulin and ITIM domain (TIGIT) inhibitor, ecto-nucleoside triphosphate diphosphohydrolase 1(E-NTPDase, CD39) inhibitor, or ecto-5'-nucleotidase(Ecto5'NTase, CD79) inhibitor.

10. A method for treating colon cancer, comprising administering to a subject suffering from colon cancer, a therapeutically effective amount of the compound of Formula I of claim 1.

* * * * *